US009517264B2

United States Patent
Fachini et al.

(10) Patent No.: US 9,517,264 B2
(45) Date of Patent: Dec. 13, 2016

(54) HUMAN FGF RECEPTOR AND β-KLOTHO BINDING PROTEINS

(75) Inventors: Roger Fachini, Thousand Oaks, CA (US); Ian Foltz, Burnaby (CA); Seog Joon Han, Simi Valley, CA (US); Susie Miki Harris, Newbury Park, CA (US); Shaw-Fen Sylvia Hu, Thousand Oaks, CA (US); Chadwick Terence King, North Vancouver (CA); Yang Li, Mountain View, CA (US); Ji Lu, Thousand Oaks, CA (US); Mark Leo Michaels, Encino, CA (US); Jeonghoon Sun, San Diego, CA (US)

(73) Assignee: AMGEN INC., Thousand Oaks, CA (US)

( * ) Notice: Subject to any disclaimer, the term of this patent is extended or adjusted under 35 U.S.C. 154(b) by 292 days.

(21) Appl. No.: 13/641,041

(22) PCT Filed: Apr. 13, 2011

(86) PCT No.: PCT/US2011/032333
§ 371 (c)(1),
(2), (4) Date: Feb. 1, 2013

(87) PCT Pub. No.: WO2011/130417
PCT Pub. Date: Oct. 20, 2011

(65) Prior Publication Data
US 2013/0129725 A1 May 23, 2013

Related U.S. Application Data

(60) Provisional application No. 61/324,691, filed on Apr. 15, 2010, provisional application No. 61/392,859, filed on Oct. 13, 2010.

(51) Int. Cl.
*A61K 39/395* (2006.01)
*C07K 16/28* (2006.01)
*C07K 16/40* (2006.01)

(52) U.S. Cl.
CPC ....... *A61K 39/3955* (2013.01); *C07K 16/2863* (2013.01); *C07K 16/40* (2013.01); *C07K 2317/21* (2013.01); *C07K 2317/32* (2013.01); *C07K 2317/75* (2013.01); *C07K 2317/92* (2013.01); *C07K 2319/75* (2013.01)

(58) Field of Classification Search
None
See application file for complete search history.

(56) References Cited

U.S. PATENT DOCUMENTS

| | | | |
|---|---|---|---|
| 3,773,919 A | 11/1973 | Boswell et al. |
| 4,179,337 A | 12/1979 | Davis et al. |
| 4,301,144 A | 11/1981 | Iwashita et al. |
| 4,376,110 A | 3/1983 | David et al. |
| 4,496,689 A | 1/1985 | Mitra |
| 4,619,794 A | 10/1986 | Hauser |
| 4,640,835 A | 2/1987 | Shimizu et al. |
| 4,670,417 A | 6/1987 | Iwasaki et al. |
| 4,791,192 A | 12/1988 | Nakagawa et al. |
| 4,816,567 A | 3/1989 | Cabilly et al. |
| 4,892,538 A | 1/1990 | Aebischer et al. |
| 4,945,050 A | 7/1990 | Sanford et al. |

(Continued)

FOREIGN PATENT DOCUMENTS

AU 567572 B2 11/1987
EP 0036676 A1 9/1981
(Continued)

OTHER PUBLICATIONS

Ito al. (Journal of Clinical Investigation, 115(8): 2202-2208, 2005).*
Mariuzza et al. (Annu. Rev. Biophys. Biophys. Chem. 1987; 16: 139-159).*
Zhao et al. (Crit. Rev. Biotechnol., 36(2):276-289, 2016).*
McCarthy et al. (J. Immunol. Methods, 251(1-2): 137-149, 2001).*
Nishimura et al. (2000), "Identification of a novel FGF, FGF-21, preferentially expressed in the liver(I)." Biochim Biophys Acta 21: 203-6.
Plotnikov et al. (1999), "Structural Basis for FGF Receptor Dimerization and Activation" Cell 98: 641-650.
Riechmann et al., 1988, "Reshaping human antibodies for therapy" Nature 332: 323-27.
Sidman et al., 1983, "Controlled release of macromolecules and pharmaceuticals from synthetic polypeptides based on glutamic acid" Biopolymers 22: 547-56.
Trouiller, et al. (2006), "MSH2 is essential for the preservation of genome integrity and prevents homeologous recombination in the moss *Physcomitrella patens*" Nucleic Acids Research vol. 34, (1): 232-242.

(Continued)

*Primary Examiner* — Brad Duffy
*Assistant Examiner* — Nelson B Moseley, II

(57) ABSTRACT

The present invention provides compositions and methods relating to or derived from antigen binding proteins and antigen binding protein-FGF21 fusions that specifically bind to β-Klotho, or β-Klotho and one or more of FGFR1c, FGFR2c, FGFR3c, and FGFR4. In some embodiments the antigen binding proteins and antigen binding protein-FGF21 fusions induce FGF21-like signaling. In some embodiments, an antigen binding protein or antigen binding protein-FGF21 fusion antigen binding component is a fully human, humanized, or chimeric antibody, binding fragments and derivatives of such antibodies, and polypeptides that specifically bind to β-Klotho, or β-Klotho and one or more of FGFR1c, FGFR2c, FGFR3c, and FGFR4. Other embodiments provide nucleic acids encoding such antigen binding proteins and antigen binding protein-FGF21 fusions, and fragments and derivatives thereof, and polypeptides, cells comprising such polynucleotides, methods of making such antigen binding proteins and antigen binding protein-FGF21 fusions, and fragments and derivatives thereof, and polypeptides, and methods of using such antigen binding proteins and antigen binding protein-FGF21 fusions, fragments and derivatives thereof, and polypeptides, including methods of treating or diagnosing subjects suffering from type 2 diabetes, obesity, NASH, metabolic syndrome and related disorders or conditions.

41 Claims, 27 Drawing Sheets

(56) References Cited

U.S. PATENT DOCUMENTS

| | | |
|---|---|---|
| 4,970,154 A | 11/1990 | Chang |
| 5,011,472 A | 4/1991 | Aebischer et al. |
| 5,106,627 A | 4/1992 | Aebischer et al. |
| 5,217,889 A | 6/1993 | Roninson et al. |
| 5,229,501 A | 7/1993 | Keifer |
| 5,234,784 A | 8/1993 | Aslam et al. |
| 5,252,714 A | 10/1993 | Harris et al. |
| 5,272,071 A | 12/1993 | Chappel |
| 5,288,855 A | 2/1994 | Bergonzoni |
| 5,364,791 A | 11/1994 | Vegeto et al. |
| 5,489,743 A | 2/1996 | Robinson et al. |
| 5,545,807 A | 8/1996 | Surani et al. |
| 5,557,032 A | 9/1996 | Mak |
| 5,585,089 A | 12/1996 | Queen et al. |
| 5,589,362 A | 12/1996 | Bujard et al. |
| 5,593,875 A | 1/1997 | Wurm et al. |
| 5,635,399 A | 6/1997 | Kriegler et al. |
| 5,650,298 A | 7/1997 | Bujard et al. |
| 5,654,168 A | 8/1997 | Bujard et al. |
| 5,670,323 A | 9/1997 | Nova |
| 5,672,510 A | 9/1997 | Eglitis et al. |
| 5,676,954 A | 10/1997 | Brigham |
| 5,679,559 A | 10/1997 | Kim et al. |
| 5,693,762 A | 12/1997 | Queen et al. |
| 5,707,632 A | 1/1998 | Williams |
| 5,811,234 A | 9/1998 | Roninson et al. |
| 6,133,426 A | 10/2000 | Gonzalez et al. |
| 6,150,098 A | 11/2000 | Zhang |
| 6,214,795 B1 | 4/2001 | Benjamin |
| 6,255,454 B1 | 7/2001 | Keifer |
| 6,350,593 B1 | 2/2002 | Williams |
| 6,355,440 B1 | 3/2002 | Williams |
| 6,384,191 B1 | 5/2002 | Williams |
| 6,548,634 B1 | 4/2003 | Ballinger |
| 6,579,850 B1 | 6/2003 | Nabeshima |
| 6,639,063 B1 | 10/2003 | Edwards |
| 6,716,626 B1 | 4/2004 | Itoh |
| 6,844,168 B1 | 1/2005 | Keifer |
| 7,259,248 B2 | 8/2007 | Itoh |
| 7,288,406 B2 | 10/2007 | Bogin |
| 7,381,804 B2 | 6/2008 | Osslund |
| 7,408,047 B1 | 8/2008 | Thomason |
| 7,491,697 B2 | 2/2009 | Beals |
| 7,531,304 B2 | 5/2009 | Bange |
| 7,563,769 B2 | 7/2009 | Bogin |
| 7,645,857 B2 | 1/2010 | Zhou |
| 7,667,005 B2 | 2/2010 | Nabeshima |
| 7,678,890 B2 | 3/2010 | Bosch |
| 7,695,938 B2 | 4/2010 | Thomason |
| 7,696,153 B2 | 4/2010 | Nissen et al. |
| 7,696,172 B2 | 4/2010 | Thomason |
| 7,700,558 B2 | 4/2010 | Thomason |
| 7,704,952 B2 | 4/2010 | Thomason |
| 7,727,742 B2 | 6/2010 | Thomason |
| 7,741,078 B2 | 6/2010 | Imamura |
| 7,879,323 B2 | 2/2011 | Thomason |
| 7,887,799 B2 | 2/2011 | Thomason |
| 2001/0012628 A1 | 8/2001 | Agarwal et al. |
| 2002/0081663 A1 | 6/2002 | Conklin |
| 2002/0164713 A1 | 11/2002 | Itoh |
| 2003/0220246 A1 | 11/2003 | Conklin |
| 2004/0018499 A1 | 1/2004 | Lal |
| 2004/0185494 A1 | 9/2004 | Itoh |
| 2004/0259780 A1 | 12/2004 | Glasebrook |
| 2005/0037457 A1 | 2/2005 | Itoh |
| 2005/0176631 A1 | 8/2005 | Heuer |
| 2005/0187150 A1 | 8/2005 | Mohammadi |
| 2006/0223114 A1 | 10/2006 | Stemmer |
| 2007/0036806 A1 | 2/2007 | Glaesner |
| 2007/0128619 A1 | 6/2007 | Itoh |
| 2007/0142278 A1 | 6/2007 | Beals |
| 2007/0237768 A1 | 10/2007 | Glaesner |
| 2007/0238657 A1 | 10/2007 | Itoh |
| 2007/0265200 A1 | 11/2007 | Glaesner |
| 2007/0293430 A1 | 12/2007 | Frye |
| 2007/0299007 A1 | 12/2007 | Frye |
| 2008/0071065 A1 | 3/2008 | Thomason |
| 2008/0071066 A1 | 3/2008 | Thomason |
| 2008/0103096 A1 | 5/2008 | Frye |
| 2008/0242607 A1 | 10/2008 | DeFrees |
| 2008/0248959 A1 | 10/2008 | DeFrees |
| 2008/0253992 A1 | 10/2008 | DeFrees |
| 2008/0255040 A1 | 10/2008 | DeFrees |
| 2008/0255045 A1 | 10/2008 | Cujec |
| 2008/0261236 A1 | 10/2008 | Kuro-o |
| 2008/0261875 A1 | 10/2008 | Etgen |
| 2008/0274958 A1 | 11/2008 | DeFrees |
| 2009/0074776 A1 | 3/2009 | Itoh |
| 2009/0118190 A1 | 5/2009 | Beals |
| 2009/0123462 A1 | 5/2009 | Bange |
| 2009/0192087 A1 | 7/2009 | Glass |
| 2009/0305986 A1 | 12/2009 | Belouski |
| 2010/0158911 A1 | 6/2010 | Williams |
| 2010/0158914 A1 | 6/2010 | Desnoyers |
| 2010/0184665 A1 | 7/2010 | Suzuki |
| 2010/0226921 A1 | 9/2010 | Thomason |
| 2010/0233169 A1 | 9/2010 | Thomason |
| 2010/0310566 A1 | 12/2010 | Thomason |
| 2011/0003302 A1 | 1/2011 | Thomason |
| 2011/0008347 A1 | 1/2011 | Ullrich et al. |

FOREIGN PATENT DOCUMENTS

| | | |
|---|---|---|
| EP | 0058481 A1 | 8/1982 |
| EP | 0088046 A2 | 9/1983 |
| EP | 0133988 A2 | 3/1985 |
| EP | 0143949 A1 | 6/1985 |
| EP | 0154316 A2 | 9/1985 |
| EP | 0401384 A1 | 12/1990 |
| EP | 0505500 A1 | 9/1992 |
| EP | 0545343 A1 | 6/1993 |
| EP | 0315456 B1 | 6/1994 |
| EP | 0546073 B1 | 9/1997 |
| EP | 2060270 A2 | 5/2009 |
| EP | 2163626 A1 | 3/2010 |
| WO | 90/04036 A1 | 4/1990 |
| WO | 91/09955 A1 | 7/1991 |
| WO | 91/10425 A1 | 7/1991 |
| WO | 91/10470 A1 | 7/1991 |
| WO | 91/10741 A1 | 7/1991 |
| WO | 93/15722 A1 | 8/1993 |
| WO | 94/02602 A1 | 2/1994 |
| WO | 94/20069 A1 | 9/1994 |
| WO | 94/28122 A1 | 12/1994 |
| WO | 95/05452 A2 | 2/1995 |
| WO | 95/34670 A2 | 12/1995 |
| WO | 96/11953 A1 | 4/1996 |
| WO | 96/32478 A1 | 10/1996 |
| WO | 96/33735 A1 | 10/1996 |
| WO | 96/37609 A1 | 11/1996 |
| WO | 96/40958 A1 | 12/1996 |
| WO | 96/41865 A1 | 12/1996 |
| WO | 97/31899 A1 | 9/1997 |
| WO | 97/34631 A1 | 9/1997 |
| WO | 99/10494 A2 | 3/1999 |
| WO | 00/18921 A2 | 4/2000 |
| WO | 00/24782 A2 | 5/2000 |
| WO | 00/54813 A2 | 9/2000 |
| WO | 01/18172 A2 | 3/2001 |
| WO | 01/18209 A1 | 3/2001 |
| WO | 01/32678 A1 | 5/2001 |
| WO | 01/36640 A2 | 5/2001 |
| WO | 01/38357 A2 | 5/2001 |
| WO | 01/49849 A1 | 7/2001 |
| WO | 01/72957 A2 | 10/2001 |
| WO | 03/011213 A2 | 2/2003 |
| WO | 03/059270 A2 | 7/2003 |
| WO | 2004/044011 A2 | 5/2004 |
| WO | 2004/110472 A2 | 12/2004 |
| WO | 2005/037235 A2 | 4/2005 |
| WO | 2005/061712 A1 | 7/2005 |
| WO | 2005/072769 A1 | 8/2005 |
| WO | 2005/091944 A2 | 10/2005 |
| WO | 2005/113606 A2 | 12/2005 |

(56) References Cited

FOREIGN PATENT DOCUMENTS

| WO | 2006/095559 | | 1/2006 |
|---|---|---|---|
| WO | 2006/028595 | A2 | 3/2006 |
| WO | 2006/028714 | A1 | 3/2006 |
| WO | 2006/050247 | A2 | 5/2006 |
| WO | 2006/065582 | A2 | 6/2006 |
| WO | 2006/078463 | A2 | 7/2006 |
| WO | 2006/130527 | | 12/2006 |
| WO | 2007/055789 | A2 | 5/2007 |
| WO | 2007/100695 | A2 | 9/2007 |
| WO | 2008/011633 | A2 | 1/2008 |
| WO | 2008/121563 | A2 | 10/2008 |
| WO | 2008/151258 | A2 | 12/2008 |
| WO | 2008/153705 | A2 | 12/2008 |
| WO | 2009/020802 | A2 | 2/2009 |
| WO | 2009149171 | A2 | 12/2009 |
| WO | 2010006214 | A1 | 1/2010 |
| WO | 2010/129503 | | 11/2010 |

OTHER PUBLICATIONS

Verhoeyen et al., 1988, "Reshaping human antibodies: grafting an antilysozyme activity" Science 239: 1534-36.
Wente et al. (2006), "Fibroblast Growth Factor-21 Improves Pancreatic Beta-Cell Function and Survival by Activation of Extracellular Signal-Regulated Kinase ½ and Akt Signaling Pathways" Diabetes 55: 2470-2478.
Wischke & Schwendeman, 2008, "Principles of encapsulating hydrophobic drugs in PLA/PLGA microparticles" Int. J. Pharm. 364: 298-327.
Xu et al., (2009) "Fibroblast Growth Factor 21 Reverses Hepatic Steatosis, Increases Energy Expenditure, and Improves Insulin Sensitivity in Diet-Induced Obese Mice" Diabetes 58(1):250-9.
Yie et al., 2009, "FGF21 N- and C-termini play different roles in receptor interaction and activation" FEBS Lett. 583:19-24.
Faham, S. et al., (1998) "Diversity does make a difference: fibroblast growth factor-heparin interactions," Curr. Opin. Struct. Biol. 8(5): 578-586.
GenBank Acc. No. AB006136.
GenBank Acc. No. AQ175436.
GenBank Acc. No. AV050323.
GenBank Acc. No. BAA99415.
GenBank Acc. No. BAA99416.
GenBank Acc. No. NP_061986.
GenBank Acc. No. Q9NSA1.
Ghielli et al. (1998), "Regeneration processes in the kidney after acute injury: role of infiltrating cells," Exp. Nephrol. 6: 502-507.
Hoppenreijs et al. (1996), "Corneal endothelium and growth factors," Surv. Ophthalmol. 41: 155-64.
Hu et al., (1998), "FGF-18, a novel member of the fibroblast growth factor family, stimulates hepatic and intestinal proliferation," Mol. Cell. Biol. 18(10): 6063-6074.
Itoh and Ornitz (2004), "Evolution of the FGF and FGFR gene families," Trends in Genetics 20(11): 563-569.
Kaufman et al. (1999), "Transgenic analysis of a 100-kb human beta-globin cluster-containing DNA fragment propagated as a bacterial artificial chromosome." Blood 94: 3178-3184.
Kennell (1971), "Principles and practices of nucleic acid hybridization," Progr. Nucl. Acid Res. Mol. Biol. 11: 259-301.
Kornmann et al. (1998), "Role of fibroblast growth factors and their receptors in pancreatic cancer and chronic pancreatitis." Pancreas 17: 169-75.
Parthiban et al. (2007), "Computational modeling protein mutant stability: analysis and optimization of statistical potentials and structural features reveal insights into prediction model development," BMC Struct. Biol. 7:54.
Ledley (1996), "Pharmaceutical Approach to Somatic Gene Therapy." Pharm. Res. 13(11): 1595-1614.
Lewis et al. (1997), "Angiogenesis by gene therapy: a new horizon for myocardial revascularization?" Cardiovasc. Res. 35: 490-497.

Liu et al. (2007), "FGF18 is required for early chondrocyte proliferation, hypertrophy and vascular invasion of the growth plate." Dev. Biol. 302: 80-91.
Mahairas et al. (1999), "Sequence-tagged connectors: a sequence approach to mapping and scanning the human genome." PNAS 96(17): 9739-9744.
Mikkelsen (1993), "Interpreting sequence motifs: a cautionary note," Trends Genet. 9(5): 159.
Nakamura et al. (1995), "The murine lymphotoxin-beta receptor cDNA: isolation by the signal sequence trap and chromosomal mapping," Genomics 30(2): 312-19.
Ngo et al. (1994), "Computational complexity, protein structure prediction, and the Levinthal paradox," in The Protein Folding Problem and Tertiary Structure Prediction. Merz & Le Grand ed., Birkhauser: Boston, pp. 491-495.
Niyogi (1969), "The influence of chain length and base composition on the specific association of oligoribonucleotides with denatured deoxyribonucleic acid." J. Biol. Chem. 244(6): 1576-81.
Peu and Pittelkow (1996), "Growth factors in hair organ development and the hair growth cycle." Dermatol. Clin. 14:559-72.
Phillips (2001), "The challenge of gene therapy and DNA delivery." J. Pharm. Pharmacology 53: 1169-1174.
Francis et al. (1992), "Protein modification and fusion proteins," Focus on Growth Factors 3:4-10.
Podolsky (1997), "Healing the epithelium: solving the problem from two sides," J. Gastroenterol. 32: 122-6.
Polejaeva et al. (2000), "New advances in somatic cell nuclear transfer: application in transgenesis," Theriogenology 53(1): 117-26.
Plotnikov et al. (2000), "Crystal Structures of Two FGF-FGFR Complexes Reveal the Determinants of Ligand-Receptor Specificity," Cell 101: 413-24.
Ratajczak (1997), "Fibroblast growth factors and early hemopoietic cell development." Leuk. Lymphoma 27: 221-9.
Rulicke et al. (2000), "Germ line transformation of mammals by pronuclear microinjection," Exp. Physiol. 85(6): 589-601.
Skolnick et al. (2000), "From genes to protein structure and function: novel applications of computational approaches in the genomic era," Trends Biotechnol. 18(1): 34-39.
Smallwood et al. (1996), "Fibroblast Growth Factor (FGF) homologous factors: new members of the FGF family implicated in nervous system development", PNAS 93: 9850-9857.
Smith et al. (1997), "The challenges of genome sequence annotation or 'the devil is in the details,'" Nat. Biotechnol. 15(12): 1222-23.
Verma et al. (1997), "Gene therapy—promises,problems and prospects." Nature 389: 239-242.
Wang et al. (1999), "Rapid analysis of gene expression (RAGE) facilitates universal expression profiling." Nuc. Acids Res. 27: 4609-4618.
Webster (1997), "Growth factors and myelin regeneration in multiple sclerosis," Mult. Scler. 3:113-20.
Yamaoka and Itakura (1999), "Development of pancreatic islets (review)." Int. J. Mol. Med. 3: 247-61.
The ADHR consortium (2000), "Autosomal dominant hypophosphataemic rickets is associated with mutations in FGF23." Nature Genetics 26: 345-348.
Arner et al. (2008) "FGF21 attenuates lipolysis in human adipocytes—A possible link to improved insulin sensitivity" FEBS Letters 582: 1725-1730.
Artuc et al. (1999), "Mast cells and their mediators in cutaneous wound healing—active participants or innocent bystanders?" Exp. Dermatol. 8: 1-16.
Bayer et al., 1990, "Protein biotinylation" Meth. Enz. 184: 138-63.
Beck and Podolsky (1999), "Growth factors in inflammatory bowel disease." Inflamm. Bowel Dis. 5: 44-60.
Bishop (1996), "Chromosomal insertion of foreign DNA," Reprod. Nutr. Dev. 36(6): 607-18.
Bork et al. (1996), "Go hunting in sequence databases but watch out for the traps," Trends Genet. 12(10): 425-27.
Bork et al. (1998), "Predicting functions from protein sequences—where are the bottlenecks?" Nature Genetics 18(4): 313-18.
Bork (2000), "Powers and pitfalls in sequence analysis: the 70% hurdle," Genome Res. 10(4): 398-400.

(56) References Cited

OTHER PUBLICATIONS

Branch (1998), "A good antisense molecule is hard to find." Trends Biochem Sci. 23(2): 45-50.
Brenner (1999), "Errors in genome annotation," Trends Genet. 15(4): 132-33.
Brodeur et al., Monoclonal Antibody Production Techniques and Applications 51-63 (Marcel Dekker, Inc., 1987).
Bruggermann et al., (1993), "Designer mice: the production of human antibody repertoires in transgenic animals" Year in Immuno. 7: 33.
Capon et al., (1989), "Designing CD4 immunoadhesins for AIDS therapy" Nature 337: 525-31.
Debernardez Clark E., (1998), "Refolding of recombinant proteins" Curr. Opin. Biotechnol. 9: 157-63.
Cunha et al. (1996), "Keratinocyte growth factor as mediator of mesenchymal-epithelial interactions in the development of androgen target organs." Semin Cell Dev Biol 7: 203-210.
Ausubel, et al., Current Protocols in Molecular Biology (Ausubel et al., eds., Green Publishers Inc. and Wiley and Sons 1994).
Dailey, et al. (2005). "Mechanisms underlying differential responses to FGF signaling," Cytokine & Growth Factor Reviews 16: 233-247.
Doerks et al. (1998), "Protein annotation: detective work for function prediction," Trends Genet. 14(6): 248-50.
Ebadi et al. (1997). "Neurotrophins and their receptors in nerve injury and repair," Neurochem. Int. 30: 347-74.
Econs and McEnery (1997) "Autosomal dominant hypophosphatemic rickets/osteomalacia: clinical characterization of a novel renal phosphate-wasting disorder," J Clin Endocrinol Metab 82:674-681.
Ellison et al., (1982), "The nucleotide sequence of a human immunoglobulin Cy1 gene" Nucleic Acids Res. 10:4071-9).
Eppstein, et al., (1985) "Biological activity of liposome-encapsulated murine interferon y is mediated by a cell membrane receptor" Proc. Natl. Acad. Sci. U.S.A. 82:3688-92.
Freiberg & Zhu, (2004) "Polymer microspheres for controlled drug release" Int. J. Pharm. 282:1-18.
Galzie Z. et al. (1997), "Fibroblast Growth Factors and their Receptors", Biochemistry and Cell Biology 75(6):669-685.
Goldfarb (1996), "Functions of fibroblast growth factors in vertebrate development," Cytokine Growth Factor Rev. 7(4): 311-325.
Hoogenboom et al., 1992, "By-passing immunisation. Human antibodies from synthetic repertoires of germline VH gene segments rearranged in vitro" J. Mol. Biol. 227: 381.
Hsu et al. (1999). "Heparin is Essential for a Single Keratinocyte Growth Factor Molecule to Bind and Form a Complex with Two Molecules of the Extracellular Domain of its Receptor," Biochemistry 38: 2523-34.
Hull et al (1997), "Healing with basic fibroblast growth factor is associated with reduced indomethacin induced relapse in a human model of gastric ulceration," Gut 40: 204-10.
Eswarakumar, et al. (2005) "Cellular signaling by fibroblast growth factor receptors" Cytokine & Growth Factor Reviews 16: 139-149.
Ishibashi et al., 2005, "Is arginine a protein-denaturant?" Protein Expr. Purif. 42: 1-6.
Jakobovits et al., 1993, "Analysis of homozygous mutant chimeric mice: deletion of the immunoglobulin heavy-chain joining region blocks B-cell development and antibody production" Proc. Natl. Acad. Sci. U.S.A. 90: 2551-55.
Jakobovits et al., 1993, "Germ-line transmission and expression of a human-derived yeast artificial chromosome" Nature 362: 255-58.
Jones et al., 1986, "Replacing the complementarity-determining regions in a human antibody with those from a mouse" Nature 321: 522-25.
Kurosu et al. (2007). "Tissue-specific Expression of Beta-Klotho and Fibroblast Growth Factor (FGF) Receptor Isoforms Determines Metabolic Activity of FGF19 and FGF21," J. Biol. Chem. 282(37): 26687-26695.
Kharitonenkov et al. (2008), "Fibroblast Growth Factor-21 as a Therapeutic Agent for Metabolic Diseases" Biodrugs 22 1: 37-44.

Kharitonenkov et al. (2007), "The metabolic state of diabetic monkeys is regulated by FGF-21" Endocrinology DOI:10.1210/en.2006-1168.
Kharitonenkov et al. (2005), "FGF-21 as a novel metabolic regulator." J. Clin. Invest. 115: 1627-1635.
Kohler et al., 1975, "Continuous cultures of fused cells secreting antibody of predefined specificity" Nature 256: 495-97.
Kozbor, 1984, "A human hybrid myeloma for production of human monoclonal antibodies" J. Immunol. 133: 3001.
Laemmli, 1970, "Cleavage of structural proteins during the assembly of the head of bacteriophage T4" Nature 227: 680-85.
Langer et al., 1981, "Biocompatibility of polymeric delivery systems for macromolecules" J. Biomed. Mater. Res. 15: 267-277.
Langer et al., 1982. "Controlled release of macromolecules" Chem. Tech. 12: 98-105.
Mannall et al., 2007, "Factors affecting protein refolding yields in a fed-batch and batch-refolding system" Biotechnol. Bioeng. 97: 1523-34.
Marks et al., 1991, "By-passing immunization. Human antibodies from V-gene libraries displayed on phage" J. Mol. Biol. 222: 581-597.
Mohammadi, et al. (2005), "Structural basis for fibroblast growth factor receptor activation" Cytokine & Growth Factor Reviews 16: 107-137.
Morrison et al., 1985, "Chimeric human antibody molecules: mouse antigen-binding domains with human constant region domains" Proc. Natl. Acad. Sci. U.S.A. 81: 6851-55.
Moyers et al. (2007), "Molecular Determinants of FGF-21 Activity-Synergy and Cross-Talk with PPARγ Signaling" J. Cell. Phys. 210: 1-6.
Beenken, Andrew and Mohammadi, Moosa (2009), "The FGF family: biology, pathophysiology and therapy," Nature Reviews 8:235-253.
R&D Systems, Catalog No. MAB3738, Lot No. XRU02 (2007), "Monoclonal anti-human/mouse Klotho Beta antibody," XP-002624719.
Suzuki, Masashi et al. (2008) "Beta-klotho is required for fibroblast growth factor (FGF) 21 signaling through FGF receptor (FGFR) 1c and FGFR3c," Mol. Endocr. 22(4):1006-1014.
Li, Xiaofan, et al. (2009) "Inhibition of lipolysis may contribute to the acute regulation of plasma FFA and glucose by FGF21 in ob/ob mice," FEBS Letters 583: 323-03234.
Wu, Xinle et al. (2008) "C-terminal tail of FGF19 determines its specificity toward klothe co-receptors," J. Biol. Chem. 283 (48): 33304-33309.
Wu, Xinle et al. (2007) "Co-receptor requirement for fibroblast growth factor-19 signaling." J. Biol. Chem. 282 (40): 29069-29072.
Wu, Xinle et al. (2009) "Selective activation of FGFR4 by an FGF19 variant does not improve glucose metabolism in ob/ob mice," PNAS 106 (34): 14379-14384.
Wu, Xinle et al. (2010) "Separating mitogenic and metabolic activities of fibroblast growth factor 19 (FGF19)," PNAS 107 (32): 14158-14163.
Xu, Jing et al. (2009) "Acute glucose-lowering and insulin-sensitizing action of FGF21 in insulin-resistant mouse models-association with liver and adipose tissue effects," Am. J. Physiol. Endocrinol. Metab. 297: E1105-E1114.
Ogawa et al. (2007). "Beta-klotho is required for metabolic activity of fibroblast growth factor 21." PNAS 104(18) 7432-7437.
Rudolph et al., 1997, "Folding proteins," Protein Function: A Practical Approach (Creighton, ed., New York, IRL Press) 57-99.
Sambrook, et al. Molecular Cloning: A Laboratory Manual (Cold Spring Harbor Laboratory Press, 1989).
Zola, Monoclonal Antibodies: A Manual of Techniques 147-158 (CRC Press, Inc., 1987).
Wu, X. et al. (2010) "FGF19 induced hepatocyte proliferation is mediated through FGFR4 activation," J. Biol. Chem. 285:5165.
Fukumoto, Seji, (2008) "Actions and mode of actions of FGF19 subfamily members," Endocr. J. 55:23-31.
Goetz et al., "Molecular Insights into the Klotho-Dependent. Endocrine Mode of Action of Fibroblast Growth Factor 19 Subfamily Members" Molecular and Cellular Biology. May 2007, vol. 27, No. 9, pp. 3417-3428.

(56) References Cited

OTHER PUBLICATIONS

Kharitonenkov et al. (2007), "The metabolic state of diabetic monkeys is regulated by FGF-21" Endocrinology 148:774-781.
Ogawa, Y., et al. (2007) "Beta-Klotho is required for metabolic activity of fibroblast growth factor 21," Proc. Natl. Acad. Sci. USA 104:7432-7437.
Schlessinger, J. et al., "Crystal Structure of a Ternary FGF-FGFR-Heparin Complex Reveals a Dual Role for Heparin in FGFR Binding and Dimerization," Mol. Cell 6:743-50 (2000).
Shinji et al., "Impaired negative feedback suppression of bile acid syntheses in mice lacking βKlotho", Journal of Clinical Investigation, 115/8, pp. 2202-2208, Aug. 1, 2005.

* cited by examiner

FIG.1A

```
                       1                                                  50
hu FGFR1     (1)   MWSWKCLLFWAVLVTATLCTARPAPTLPEQAQPWGAPVEVESFLVHPGDL
muFGFR1      (1)   MWGWKCLLFWAVLVTATLCTARPAPTLPEQAQPWSVPVEVESLLVHPGDL
Consensus    (1)   MW WKCLLFWAVLVTATLCTARPAPTLPEQAQPWG PVEVES LVHPGDL
                      51                                                100
hu FGFR1    (51)   LQLRCRLRDDVQSINWLRDGVQLAESNRTRITGEEVEVQDSIPADSGLYA
muFGFR1     (51)   LQLRCRLRDDVQSINWLRDGVQLVESNRTRITGEEVEVRDSVPADSGLYA
Consensus   (51)   LQLRCRLRDDVQSINWLRDGVQL ESNRTRITGEEVEV DSIPADSGLYA
                     101                                                150
hu FGFR1   (101)   CVTSSPSGSDTTYFSVNVSDALPSSEDDDDDDDSSSEEKETDNTKPNRMP
muFGFR1    (101)   CVTSSPSGSDTTYFSVNVSDALPSSEDDDDDDSSSEEKETDNTKPNRRP
Consensus  (101)   CVTSSPSGSDTTYFSVNVSDALPSSEDDDDDDDSSSEEKETDNTKPNR P
                     151                                                200
hu FGFR1   (151)   VAPYWTSPEKMEKKLHAVPAAKTVKFKCPSSGTPNPTLRWLKNGKEFKPD
muFGFR1    (151)   VAPYWTSPEKMEKKLHAVPAAKTVKFKCPSSGTPNPTLRWLKNGKEFKPD
Consensus  (151)   VAPYWTSPEKMEKKLHAVPAAKTVKFKCPSSGTPNPTLRWLKNGKEFKPD
                     201                                                250
hu FGFR1   (201)   HRIGGYKVRYATWSIIMDSVVPSDKGNYTCIVENEYGSINHTYQLDVVER
muFGFR1    (201)   HRIGGYKVRYATWSIIMDSVVPSDKGNYTCIVENEYGSINHTYQLDVVER
Consensus  (201)   HRIGGYKVRYATWSIIMDSVVPSDKGNYTCIVENEYGSINHTYQLDVVER
                     251                                                300
hu FGFR1   (251)   SPHRPILQAGLPANKTVALGSNVEFMCKVYSDPQPHIQWLKHIEVNGSKI
muFGFR1    (251)   SPHRPILQAGLPANKTVALGSNVEFMCKVYSDPQPHIQWLKHIEVNGSKI
Consensus  (251)   SPHRPILQAGLPANKTVALGSNVEFMCKVYSDPQPHIQWLKHIEVNGSKI
                     301                                                350
hu FGFR1   (301)   GPDNLPYVQILKTAGVNTTDKEMEVLHLRNVSFEDAGEYTCLAGNSIGLS
muFGFR1    (301)   GPDNLPYVQILKTAGVNTTDKEMEVLHLRNVSFEDAGEYTCLAGNSIGLS
Consensus  (301)   GPDNLPYVQILKTAGVNTTDKEMEVLHLRNVSFEDAGEYTCLAGNSIGLS
                     351                                                400
hu FGFR1   (351)   HHSAWLTVLEALEERPAVMTSPLYLEIIIYCTGAFLISCMLGSVITYKMK
muFGFR1    (351)   HHSAWLTVLEALEERPAVMTSPLYLEIIIYCTGAFLISCMLGSVITYKMK
Consensus  (351)   HHSAWLTVLEALEERPAVMTSPLYLEIIIYCTGAFLISCMLGSVITYKMK
                     401                                                450
hu FGFR1   (401)   SGTKKSDFHSQMAVHKLAKSIPLRRQVTVSADSSASMNSGVLLVRPSRLS
muFGFR1    (401)   SGTKKSDFHSQMAVHKLAKSIPLRRQVTVSADSSASMNSGVLLVRPSRLS
Consensus  (401)   SGTKKSDFHSQMAVHKLAKSIPLRRQVTVSADSSASMNSGVLLVRPSRLS
                     451                                                500
hu FGFR1   (451)   SSGTPMLAGVSEYELPEDPRWELPRDRLVLGKPLGEGCFGQVVLAEAIGL
muFGFR1    (451)   SSGTPMLAGVSEYELPEDPRWELPRDRLVLGKPLGEGCFGQVVLAEAIGL
Consensus  (451)   SSGTPMLAGVSEYELPEDPRWELPRDRLVLGKPLGEGCFGQVVLAEAIGL
                     501                                                550
hu FGFR1   (501)   DKDKPNRVTKVAVKMLKSDATEKDLSDLISEMEMMKMIGKHKNIINLLGA
muFGFR1    (501)   DKDKPNRVTKVAVKMLKSDATEKDLSDLISEMEMMKMIGKHKNIINLLGA
Consensus  (501)   DKDKPNRVTKVAVKMLKSDATEKDLSDLISEMEMMKMIGKHKNIINLLGA
                     551                                                600
hu FGFR1   (551)   CTQDGPLYVIVEYASKGNLREYLQARRPPGLEYCYNPSHNPEEQLSSKDL
muFGFR1    (551)   CTQDGPLYVIVEYASKGNLREYLQARRPPGLEYCYNPSHNPEEQLSSKDL
Consensus  (551)   CTQDGPLYVIVEYASKGNLREYLQARRPPGLEYCYNPSHNPEEQLSSKDL
                     601                                                650
hu FGFR1   (601)   VSCAYQVARGMEYLASKKCIHRDLAARNVLVTEDNVMKIADFGLARDIHH
muFGFR1    (601)   VSCAYQVARGMEYLASKKCIHRDLAARNVLVTEDNVMKIADFGLARDIHH
Consensus  (601)   VSCAYQVARGMEYLASKKCIHRDLAARNVLVTEDNVMKIADFGLARDIHH
```

FIG.1B

```
                 651                                                      700
hu FGFR1   (651) IDYYKKTTNGRLPVKWMAPEALFDRIYTHQSDVWSFGVLLWEIFTLGGSP
  muFGFR1  (651) IDYYKKTTNGRLPVKWMAPEALFDRIYTHQSDVWSFGVLLWEIFTLGGSP
Consensus  (651) IDYYKKTTNGRLPVKWMAPEALFDRIYTHQSDVWSFGVLLWEIFTLGGSP
                 701                                                      750
hu FGFR1   (701) YPGVPVEELFKLLKEGHRMDKPSNCTNELYMMMRDCWHAVPSQRPTFKQL
  muFGFR1  (701) YPGVPVEELFKLLKEGHRMDKPSNCTNELYMMMRDCWHAVPSQRPTFKQL
Consensus  (701) YPGVPVEELFKLLKEGHRMDKPSNCTNELYMMMRDCWHAVPSQRPTFKQL
                 751                               800
hu FGFR1   (751) VEDLDRIVALTSNQEYLDLSIPLDQYSPSFPDTRSSTCSSGEDSVFSHEP
  muFGFR1  (751) VEDLDRIVALTSNQEYLDLSIPLDQYSPSFPDTRSSTCSSGEDSVFSHEP
Consensus  (751) VEDLDRIVALTSNQEYLDLSIPLDQYSPSFPDTRSSTCSSGEDSVFSHEP
                 801         822
hu FGFR1   (801) LFEEPCLFRHPAQLANGGLKRR
  muFGFR1  (801) LFEEPCLFRHPTQLANSGLKRR
Consensus  (801) LFEEPCLFRHP QLAN GLKRR
```

FIG. 2A

```
                         1                                                      50
hu beta Klotho     (1)   MKPGCAAGSPGNEWIFFSSDEITTRYRNTMSNGLQRSVLLSALILLRAV
mu beta klotho     (1)   MKTGCAAGSPGNEWIFFSSDERNESSKTMSNRLQPSALLSALFLLRAV
       Consensus   (1)   MK GCAAGSPGNEWIFFSSDE TR R TMSN ALQRS ILSA ILLRAV 51                                                    100
hu beta Klotho    (51)   TGFSGDGRATWSINPNFTRSQLFLYDTFPKNFLWGTGALQTGSSH
mu beta klotho    (51)   TGFSGDGRAWDKQTVFPNRSQLFLIDTFPKNFSWGLGIAFQVEGSR
       Consensus  (51)   TGFSGDGKAIW   SPVN SQLFLYDTFPKNF WGIGTGA QVEGSW 101                                                   150
hu beta Klotho   (101)   RKDGSMPIWDHFIHNYSSENGSIDSYIFLEKDLSALDFIGVSFYQ
mu beta klotho   (101)   KTDGRPIWDPIGPIGNGTDRSLSVIFKDLLADLDSFYQ
       Consensus (101)   K DGKGPSIWD FIHSHLK V  T SSDSYIFLEKDL ALDFIGVSFYQ 151                                                   200
hu beta Klotho   (151)   FSISWPRLFPDGIVTVANRRQIYSTLLQESTIVETPTVLYHWDLPL
mu beta klotho   (151)   FSISWPRLFPNGTVAAVNQGLRYRALLDAVIRNIEPIVTLYHWDLPL
       Consensus (151)   FSISWPRLFP G V  NA GL YY  LLDALVLRNIEPIVTLYHWDLPL 201                                                   250
hu beta Klotho   (201)   ALQRKGGWKNDTIYATCFGDRVKYWITTHNEYVPMHG
mu beta klotho   (201)   TLQEEIGGWKNATIDATCFGDRVKTIRNEPIVIHHG
       Consensus (201)   LQE YGGWKN TIIDIFNDYATYCFQ FGDRVKYWITIHNPYLVAWHGF 251                                                   300
hu beta Klotho   (251)   GTGMHAPGEKGNATVTGHLIKAHSKVWHNYDKNFRPHQKWLSITL
mu beta klotho   (251)   GTGMHAPGEKGSTAVTGHLIKAHSKVWHNDKNFRPHQKWLSIH
       Consensus (251)   GTGMHAPGEKGNL AVYTVGHNLIKAHSKVWHNY   FRPHQKWLSITL 301                                                   350
hu beta Klotho   (301)   GSHWIEPNRTMDTFKQQSMVSVLGWPLARDGDYPEGKKLF
mu beta klotho   (301)   GSHWIEPNRMDIQRRSVLGWANRQGDYEFNG---
       Consensus (301)   GSHWIEPNRSDN DI  CQ SM SVLGWFANPIHGDGDYPE MK  A
```

FIG. 2B

```
                    351                                                              400
hu beta Klotho (351) PIFSEEEHHMCPQDFPSFQRNMTFLLNIAKKNSYNIRLYRRNAL
mu beta klotho (349) PEFSEEEKEFQCPADMFAFSGPNHIPSNHLVNSSSNINKSQVL
     Consensus (351) MIP FSEAEK EMRGTADFFAFSGPNWFKP NTM KMGQNVSNLR  L 401                                                              450
hu beta Klotho (401) NWIKEENPNFRLL(DWPDTSSNMKNFSDQNELLP
mu beta klotho (399) NWIKEDDPQLSGWFTDSYKEDTTAIYMMHPIKNQNQATFP
     Consensus (401) NWIKLEY P ILIAENGWFTDS IKTEDTTAIYMMKNFL QVLQAIK D 451                                                              500
hu beta Klotho (451) EIRVFGYTAWSLLDGFEWQDAYTIRRGLFYVDFNSKQERKPKSSAHYYK
mu beta klotho (449) EIRVFGYTAMELLDGFEWQDAYVTTRGLFYVDFNSEQKERKPKSSAYYY
     Consensus (451) EIRVFGYTAWSLLDGFEWQDAYT RRGLFYVDFNS QKERKPKSSAHYYK 501                                                              550
hu beta Klotho (501) QIIPPSQKESTPVQCPQDFPSMQYTESVKPESVASPQFNM
mu beta klotho (499) QITQTPTLKRPPSWGTSSTLKPFTVSSPCLPHH
     Consensus (501) QII DNGF LKESTPDM G FPCDFSWGVTESVLKPE  SSPQFSDFHL 551                                                              600
hu beta Klotho (551) YVWHATNRLITNKIMKEGRLKTRPRDNIKQAMKTHPRA
mu beta klotho (549) NRVTRNRLKREIMKELKEYGPDSIEMNTREPEKHQSPA
     Consensus (551) YVWN TGNRLLHRVEGVLKTRPAQCTDEV IKK LEMLAKMKVTHY FA 601                                                              650
hu beta Klotho (601) LDWASHPTEMSAYMQAAHYCVKGCSAKTMETTPLR
mu beta klotho (599) LDWTSLPTDSKVNRGVLPLTCVSEAKLQQFPPTHLLD
     Consensus (601) LDW SILPTGNLS VNRQ LRYYRCVVSEGLKLGI  MVTLYHPTHAHLG 651                                                              700
hu beta Klotho (651) LPELLIHDMHPSTKEPAMRGFQLVKNEPTHEPRLS
mu beta klotho (649) LPLELSGONLRMTAKFQDIARLFREDGLVKLMITNEPRLSN
     Consensus (651) LP PLL A GWLN  YA AFQ YA LCF ELGDLVKLMITNEPNRLSDI
```

FIG. 2C

```
hu beta Klotho  (701) YHKGHTYGQHNIKPLAMRRLLDWIPSQRGAVQSIRAWVEEI
mu beta klotho  (699) YHNSDITRAAHNISAQVHLLDPMFVQHQAVSLECHALBHH
Consensus       (701) YNRS NDTY AAHNLLIHA W LYDRQFRP Q GAVSLSLH DWAEPA
                       751                                        800
hu beta Klotho  (751) NPADSHWKASREFLOBIAWFADPITEDFPAMBHERGLSS
mu beta klotho  (749) HDEVISHWKAERKLOEIANFAKBLEKDEVNELIASNWRGLSS
Consensus       (751) NPF DSHWKAAERFLQFEIAWFADPLFKTGDYPA MKEYIASK RGLSS
                       801                                        850
hu beta Klotho  (801) SALPRLISEADRRLLKIDCAIHHTRTREBEOLAGSRYDIELVEG
mu beta klotho  (799) SVLPFTAKESR KGTVDPYALHHTTRVN KQLNTNRSVLEELEE
Consensus       (801) S LPR T  E RLLKGTVDF ALNHFTRFVIH QL  R  ADRDIQFL
                       851                                        900
hu beta Klotho  (851) QDITRLSSPSRLAVIPWGVRKLLRWIKNIGMOI TASGIDDQALEDD
mu beta klotho  (849) QDITRLSSPSRLAVTPWGVRKLLARNTRDTYTANCIDDLAEDD
Consensus       (851) QDITRLSSPSRLAV PWGVRKLL WIRRNY D DYITA GIDD ALEDD
                       901                                        950
hu beta Klotho  (901) RRRYZGENIEVKATLIKYYACYAFLABEKSPREGFTSDFK
mu beta klotho  (899) QRKYLEKYLEALKAYLIDKIKCYAEKTEHSKPREGFTSDH
Consensus       (901) IRKYYL KYLQE LKAYLIDKVRTKGYYAFKL EEKSKPRFGFFTSDFK
                       951                                       1000
hu beta Klotho  (951) AKSSICIETNKPSSRGFFENSSSRCSTQENTVSLPFYQKEPLIPL
mu beta klotho  (949) AKGSIQEDVSKISSSLPAENRSPACGQPAEDTFSCSPLVEKKLIFF
Consensus       (951) AKSSIQFY KLISS G P EN S  C Q  E TDCTIC PLV KKPLIF
                      1001                                       1045
hu beta Klotho (1001) GCFFFTVIJIGLATORQFKFTWKTIQHTPLKKGKRVYS-
mu beta klotho  (999) CCIFISHLANHIRTTHHQENPEMLQNIEEGHSRVFS
Consensus      (1001) GCCF STL LLLSI IF  QHRRMF KAKNLQ IPLKKG  V
```

AM-1 Parental-Unstained

AM-1 /bKlotho +FGFR1 pool 3 - Unstained

CHO/bKlotho+FGFR1 pool 5- Unstained

AM-1 parental + Alexa647-FGF21
DB120707-AM1 Unstained

AM-1 /bKlotho +FGFR1 pool 3 + Alexa647-FGF21
DB120707-Pool3 Sort

CHO/bKlotho + FGFR1 pool 5 + Alexa647-FGF21
DB120707-Pool5 Sort

FIG. 4

DPSPTLPEQAQPWGAPVEVESFLVHPGDLLQLRCRLRDDVQSINWLRDGVQL
AESNRTRITGEEVEVQDSVPADSGLYACVTSSPSGSDTTYFSVNVSDALPSS
EDDDDDDSSSEEKETDNTKPNRMPVAPYWTSPEKMEKKLHAVPAAKTVKFK
CPSSGTPNPTLRWLKNGKEFKPDHRIGGYKVRYATWSIIMDSVVPSDKGNYT
CIVENEYGSINHTYQLDVVERSPHRPILQAGLPANKTVALGSNVEFMCKVYS
DPQPHIQWLKHIEVNGSKIGPDNLPYVQILKTAGVNTTDKEMEVLHLRNVSF
EDAGEYTCLAGNSIGLSHHSAWLTVLEALEERPAVMTSPLY*ggggg*dkthtc
ppcpapellggpsvflfppkpkdtlmisrtpevtcVvvdvshedpevkfnwy
vdgvevhnaktkpreeqynstyrvvsvltvlhqdwlngkeyKckvsnkalpa
piektiskakgqprepqvytlppsrdeltknqvsltclvkgfypsdiavewE
sngqpennykttppvldsdgsfflyskltvdksrwqqgnvfscsvmhealhn
hytqkslslspgk

FIG. 5

FSGDGRAI WSKNPNFTPV NESQLFLYDT FPKNFEWGIG TGALQVEGSW
KKDGKGPSIW DHFIHTHLKN VSSTNGSSDS YIFLEKDLSA LDFIGVSFYQ
FSTSWPRLFP DGIVTVANAK GLQYSTLLD ALVLRNTEPI VTLYHWDLPL
ALQEKYGGWK NDTIIDIFND YATYCFQMFG DRVKVWITIH NPYLVAWHGY
GTGMHAPGEK GNLAAVYTVG HNLIKAHSKV WHNYNTHFRP HQKGWLSITL
GSHWIEPNRS ENTMDIFKCQ QSMVSVLQWF ANPIHGDGDY PEGMRKKLFS
VLPIFSEAEK HEMRGTADFF AFSFGPNNFK PLNTMAKMGQ NVSLNLREAL
NWIKLEYNNP RILIAENGWF TDSRVKTEDT TAIYMMKNFL SQVLQAIRLD
EIRVFGYTAW SLLDGFEWQD AYTIRRGLFY VDFNSKQKER KPKSSAHYYK
QIRENGFSL KESTPDVQGQ FPCDFSWGVT ESVLKPESVA SSPQFSDPHL
YVWNATGNRL LHRVEGVRLK TRPAQCTDFV NIKKQLEMLA RMKVTHYRFA
LDWASVLPTG NLSAVNRQAL RYRCVVSEG LKLGTSAMVT LYYPTHAHLG
LPEPLLHADG WLNPSTAEAF QAYAGLCFQE LGDLVKLWIT INEPNRLSDI
VNRSGNDTYG AAHNLLVAHA LAWRLYDRQF RPSQRGAVSL SLHADWAEPA
NPYADSHWRA AERFLQFEIA WFAEPLFKTG DYPAAMREYI ASKHRRGLSS
SAIPRLTEAE RRLLKGTVDF CALNHFTTRF VMHEQLAGSR YDSDRDIQFL
QDITRLSSPT RLAVIPWGVR KLLRWVRRNY GDMDIYITAS GIDDQALEDD
RLRKYYLGKY LQEVLKAYLI DKVRIKGYYA FKLLAEEKSKP RFGFFTSDFK
AKSSIQFYNK VISSRGFPFE NSSSRCSQTQ ENTECTVCLE LVQKKP
ggggdkthtcppcpapellggpsvflfppkpkdtlmisrtpevtcvvvdvshe
dpevkfnwyvdgvevhnaktkpreeqynstYrvvsvltvlhqdwlngkeykckv
snkalpapiektiskakgqprepqvytlppsrdeltknqvsltclvkgfypsdi
avewesngqpennyktppvldsdgsfflyskltvdksrwqqgnvfscsvmhea
lhnhytqkslslspgk 1. Mol. wt. markers
2. Heterodimer, non-reducing
3. Stds
4. Heterodimer, reducing
5. Mol. wt. markers

FIG. 7

| Line | Clone | pI (Q->pyroGlu, desK)/isotype |
|---|---|---|
| 10H3(=3E10) | 1 | 8.42/IgG2_K |
| 1A2 | 1 | 8.16/IgG2_K |
| 1B5 | 1 | 8.44/IgG2_K |
| 3B4 | 1 | 8.44/IgG2_K |
| 9D10 | 1 | 8.59/IgG2_L |
| 3F4 | 1 | 8.15/IgG2_L |
| 1C10 | 1 | 8.44/IgG2_L |
| 2G10 | 1 | 8.76/IgG2_L |
| 8F9 | 1 | 8.6/IgG2_L |

| Sensor | IgG | $k_d$ [1/s] | $k_a$ [1/Ms] | $K_D$ [M] | $K_D$ [nM] |
|---|---|---|---|---|---|
| A1 | 1A2.1 | 3.34E-05 | 1.56E+04 | 2.14E-09 | 2.14 |
| B1 | 1B5.1 | 6.13E-05 | 1.06E+05 | 5.78E-10 | 0.58 |
| C1 | 2G10.1 | 3.49E-05 | 2.71E+05 | 1.29E-10 | 0.13 |
| D1 | 3B4.1 | 1.13E-04 | 1.86E+04 | 6.08E-09 | 6.08 |
| E1 | 3E10.1 | 7.87E-05 | 1.32E+05 | 5.97E-10 | 0.60 |
| F1 | 3F4.1 | 7.41E-05 | 2.64E+05 | 2.81E-10 | 0.28 |
| G1 | 8F9.1 | 5.75E-05 | 1.36E+05 | 4.22E-10 | 0.42 |
| H1 | 9D10.1 | 4.76E-05 | 1.60E+05 | 2.98E-10 | 0.30 |
| A2 | 10H3.1 | 8.03E-05 | 1.43E+05 | 5.63E-10 | 0.56 |

FIG. 11

| Ab ID | | Kd (nM) |
|---|---|---|
| 3B4.1 | Kappa | 6.08 |
| 1A2.1 | Kappa | 2.14 |
| 1B5.1 | Kappa | 0.58 |
| 10H3.1 | Kappa | 0.56 |
| 9D10.1 | Lambda | 0.30 |
| 2G10.1 | Lambda | 0.13 |
| 3F4.1 | Lambda | 0.28 |
| 8F9.1 | Lambda | 0.42 |

FIG. 12

| Pb ID | aa sequences | Kd (nM) | ELISA | Agretopes |
|---|---|---|---|---|
| Rm26 | EWYCGVLFNCQQ | 1.02 | Hu: ++<br>Mu: ++<br>Other:- | 0 |
| Rm27 | HFGCGVIFNCVSD | 1.08 | Hu: ++<br>Mu: ++<br>Other:- | 0 |
| Rm33 | WELCASGYGWCYHL | 3.00 | Hu: ++<br>Mu: ++<br>Other:- | 0 |
| Rm37 | APSCKSYIGFGLYHCWDG | 8.19 | Hu: ++<br>Mu: ++<br>Other:- | 0 |
| Rm40 | HFKCGMGLFECADP | 1.44 | Hu: ++<br>Mu: ++<br>Other:- | 0 |
| SR4 | YQAWGYYV | 0.46 | Hu: ++<br>Mu: ++<br>Other:- | 0 |

FIG. 13A
HUMAN
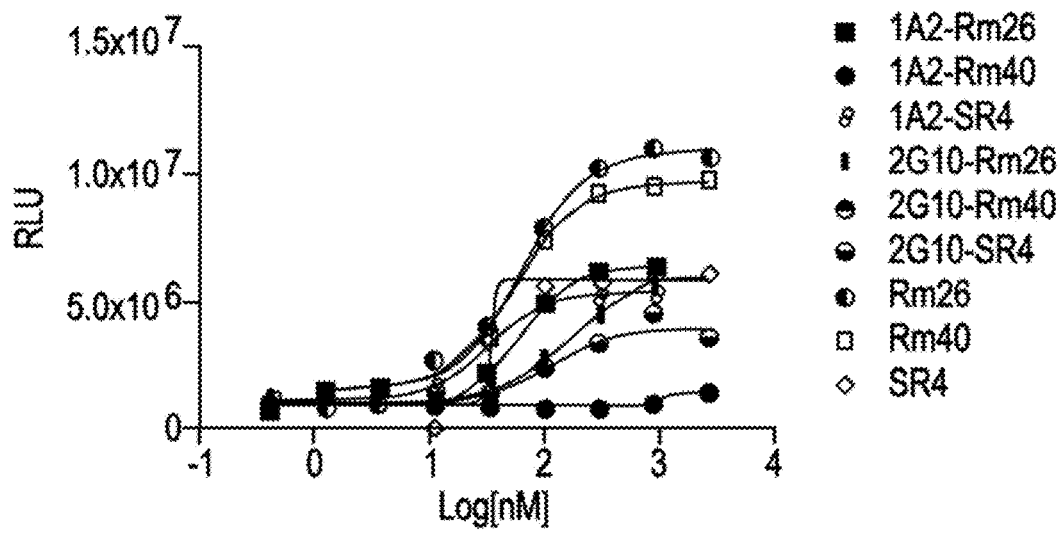
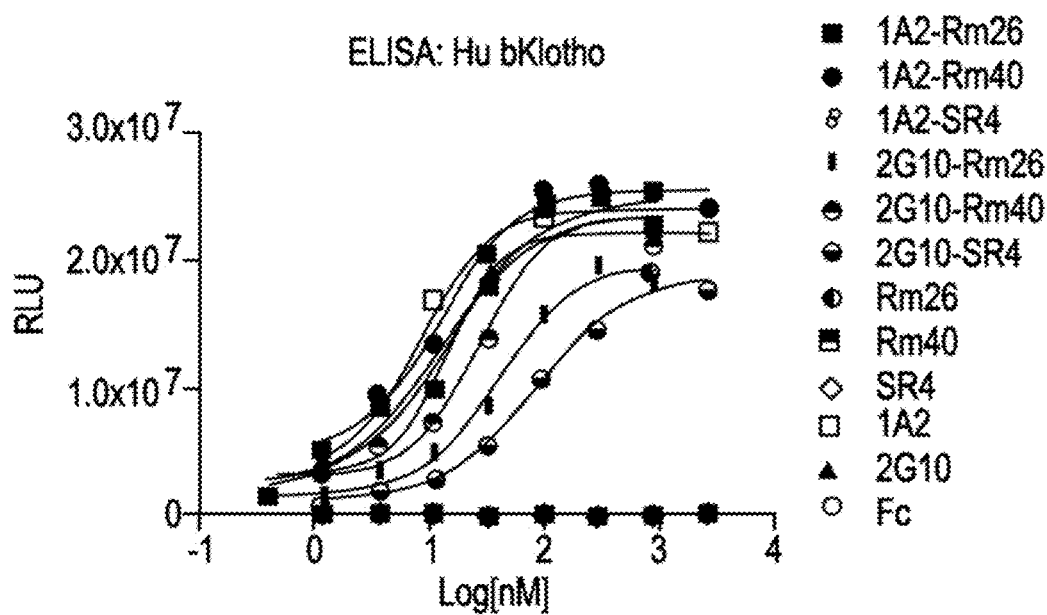

FIG. 13B
MURINE
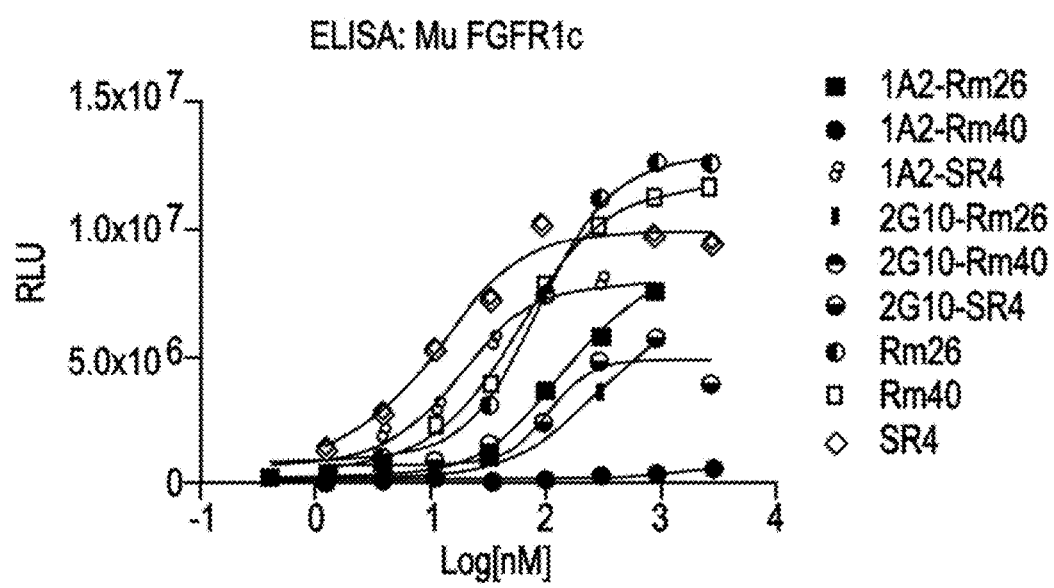
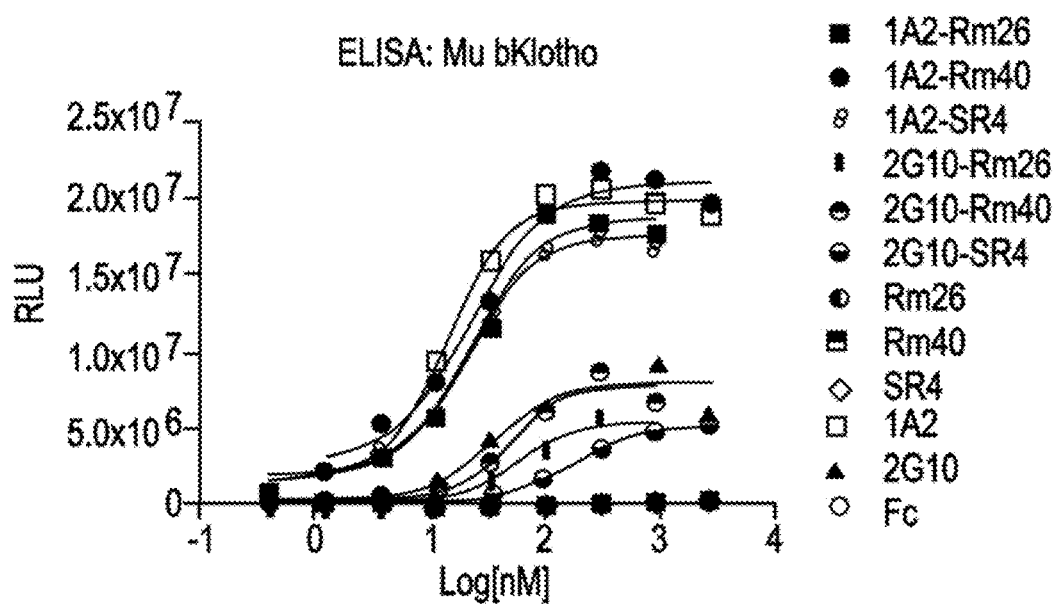

FIG. 14
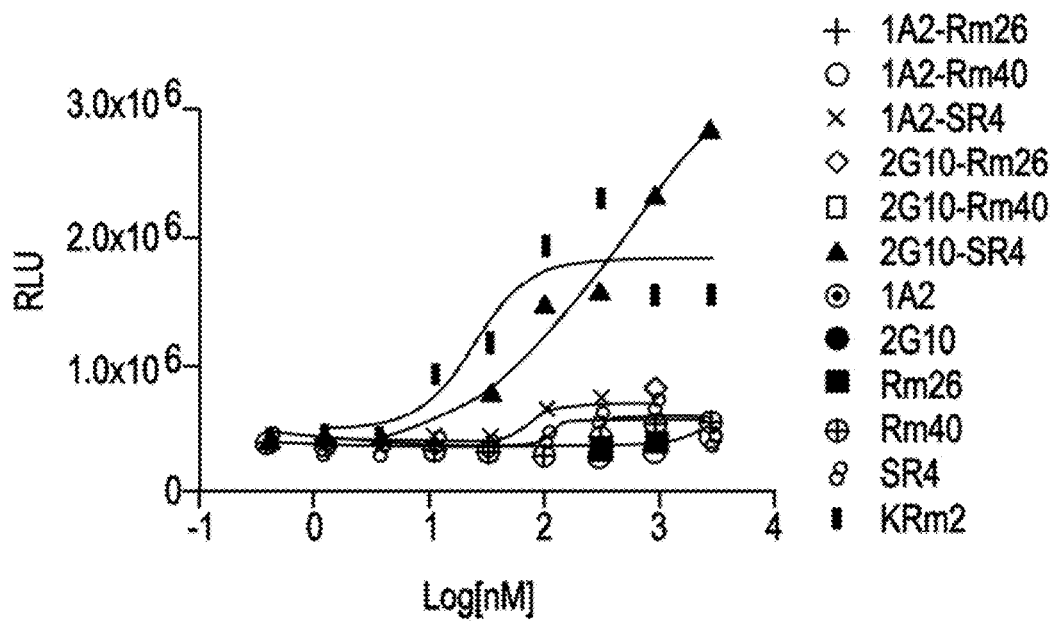
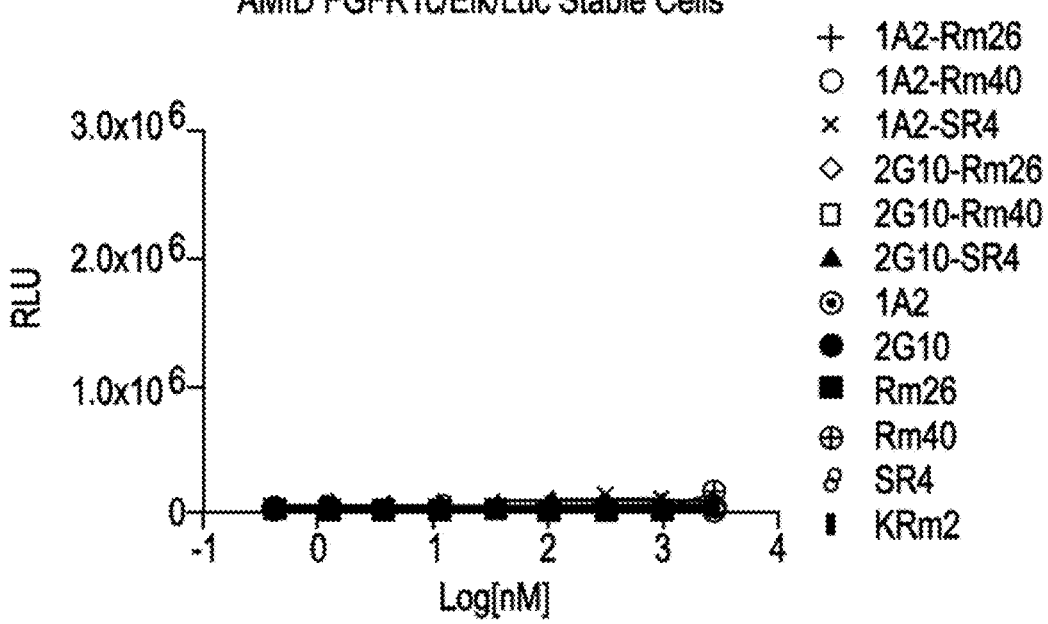

FIG. 15
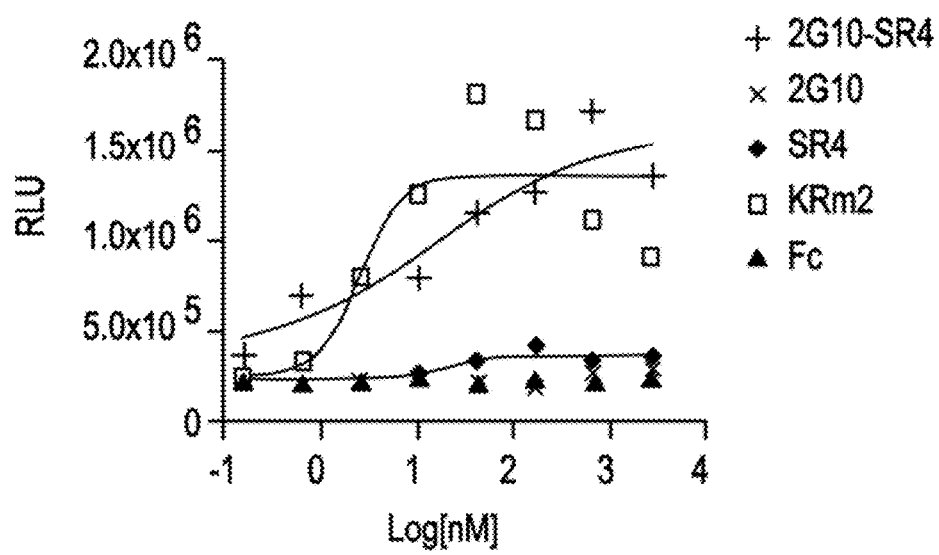
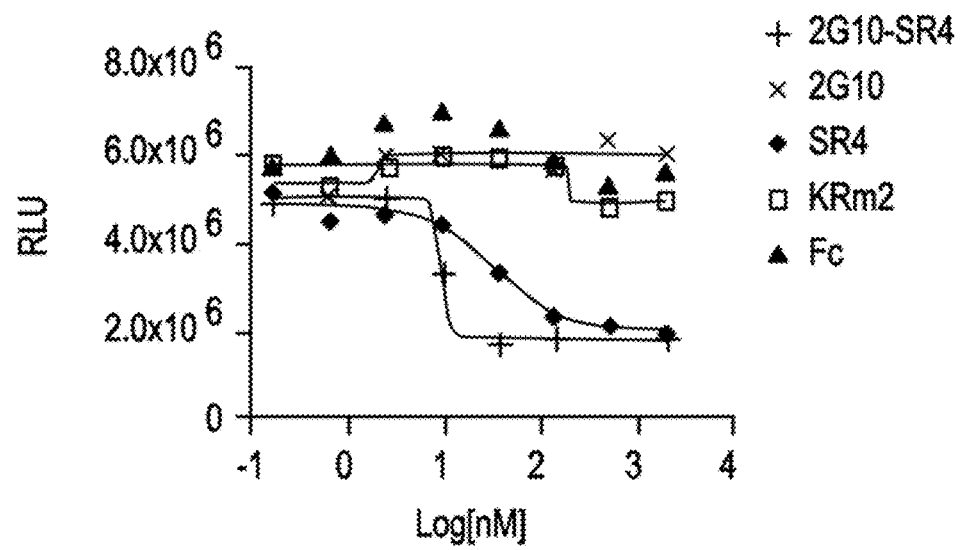

ELISA: Hu bKlotho

+ 2G10-6G4S-FGF21 (#1)
■ FGF21-15G4S-2G10 (#2)
※ 2G10-9G4S-FGF21 (#3)
♦ FGF21-12G4S-2G10 (#4)
□ FGF21-9G4S-2G10 (#5)
▲ 2G10-15G4S-FGF21 (#6)
∗ FGF21-6G4S-2G10 (#7)
✧ 2G10-12G4S-FGF21 (#8)
× 2G10
○ FC

HUMAN FGF RECEPTOR AND β-KLOTHO BINDING PROTEINS

This application is a National Phase Application under U.S.C. §371 of PCT/US2011/032333 filed Apr. 13, 2011 which claims the benefit of U.S. Provisional Application No. 61/324,691 filed Apr. 15, 2010 and U.S. Provisional Application No. 61/392,859 filed Oct. 13, 2010, all of which are incorporated by reference in their entirety.

SEQUENCE LISTING

The instant application contains a Sequence Listing which has been submitted via EFS-Web and is hereby incorporated by reference in its entirety. Said text copy, created on Oct. 10, 2012, is named A-1554-WO-PCT.txt and is 315 KB in size.

FIELD OF THE INVENTION

The present disclosure relates to nucleic acid molecules encoding antigen binding proteins that bind to β-Klotho or β-Klotho and one or more of FGFR1c, FGFR2c, FGFR3c, and FGFR4. The present disclosure also provides antigen binding proteins that bind to β-Klotho or β-Klotho and one or more of FGFR1c, FGFR2c, FGFR3c and FGFR4 that induce FGF21-like signaling, as well as pharmaceutical compositions comprising antigen binding proteins that bind to β-Klotho or β-Klotho and one or more of FGFR1c, FGFR2c, FGFR3c, and FGFR4, including antigen binding proteins that induce FGF21-like signaling, and methods for treating metabolic disorders using such nucleic acids, polypeptides, or pharmaceutical compositions. Diagnostic methods using the antigen binding proteins are also provided.

BACKGROUND

Fibroblast Growth Factor 21 (FGF21) is a secreted polypeptide that belongs to a subfamily of Fibroblast Growth Factors (FGFs) that includes FGF19, FGF21, and FGF23 (Itoh et al., (2004) *Trend Genet.* 20:563-69). FGF21 is an atypical FGF in that it is heparin independent and functions as a hormone in the regulation of glucose, lipid, and energy metabolism.

It is highly expressed in liver and pancreas and is the only member of the FGF family to be primarily expressed in liver. Transgenic mice overexpressing FGF21 exhibit metabolic phenotypes of slow growth rate, low plasma glucose and triglyceride levels, and an absence of age-associated type 2 diabetes, islet hyperplasia, and obesity. Pharmacological administration of recombinant FGF21 protein in rodent and primate models results in normalized levels of plasma glucose, reduced triglyceride and cholesterol levels, and improved glucose tolerance and insulin sensitivity. In addition, FGF21 reduces body weight and body fat by increasing energy expenditure, physical activity, and metabolic rate. Experimental research provides support for the pharmacological administration of FGF21 for the treatment of type 2 diabetes, obesity, dyslipidemia, and other metabolic conditions or disorders in humans.

FGF21 is a liver derived endocrine hormone that stimulates glucose uptake in adipocytes and lipid homeostasis through the activation of its receptor. Interestingly, in addition to the canonical FGF receptor, the FGF21 receptor also comprises the membrane associated β-Klotho as an essential cofactor. Activation of the FGF21 receptor leads to multiple effects on a variety of metabolic parameters.

In mammals, FGFs mediate their action via a set of four FGF receptors, FGFR1-4, that in turn are expressed in multiple spliced variants, e.g., FGFR1c, FGFR2c, FGFR3c and FGFR4. Each FGF receptor contains an intracellular tyrosine kinase domain that is activated upon ligand binding, leading to downstream signaling pathways involving MAPKs (Erk1/2), RAF1, AKT1 and STATs. (Kharitonenkov et al., (2008) *BioDrugs* 22:37-44). Several reports suggested that the "c"-reporter splice variants of FGFR1-3 exhibit specific affinity to β-Klotho and could act as endogenous receptor for FGF21 (Kurosu et al., (2007) *J. Biol. Chem.* 282:26687-26695); Ogawa et al., (2007) *Proc. Natl. Acad. Sci. USA* 104:7432-7437); Kharitonenkov et al., (2008) *J. Cell Physiol.* 215:1-7). In the liver, which abundantly expresses both β-Klotho and FGFR4, FGF21 does not induce phosphrylation of MAPK albeit the strong binding of FGF21 to the β-Klotho-FGFR4 complex. In 3T3-L1 cells and white adipose tissue, FGFR1 is by far the most abundant receptor, and it is therefore most likely that FGF21's main functional receptors in this tissue are the β-Klotho-FGFR1c complexes.

The present disclosure provides a human (or humanized) antigen binding protein, such as a monoclonal antibody, that induces FGF21-like signaling, e.g., an antigen binding protein that mimics the function of FGF21. Such an antibody is a molecule with FGF21-like activity and selectivity but with added therapeutically desirable characteristics typical for an antibody such as protein stability, lack of immunogenicity, ease of production and long half-life in vivo.

SUMMARY

An isolated antigen binding protein is provided. In one embodiment the antigen binding protein comprises an amino acid sequence selected from the group consisting of: (a) a light chain CDR3 comprising a sequence selected from the group consisting of: (i) a light chain CDR3 sequence that differs by no more than two amino acid additions, substitutions, deletions, and combinations thereof, from a CDR3 sequence of L1-L11, SEQ ID NOs:17-27; (ii) MQAX$_1$EFPWT (SEQ ID NO: 174); (iii) GTWDSSLSX$_2$VX$_3$ (SEQ ID NO: 175); (iv) QQYDNLFT (SEQ ID NO: 122); (v) QQYGSAPLT (SEQ ID NO: 123); (vi) VLYMGSGIWV (SEQ ID NO: 124); (vii) ETWDSSLSAGV (SEQ ID NO: 127); wherein X$_1$ is L or I; X$_2$ is V or A; and X$_3$ is V or A; (b) a heavy chain CDR3 sequence comprising a sequence selected from the group consisting of: (i) a heavy chain CDR3 sequence that differs by no more than one amino acid additions, substitutions, deletions, and combinations thereof, from a CDR3 sequence of H1-H11, SEQ ID NOs:28-38; (ii) GWFDX$_6$ (SEQ ID NO: 178); (iii) GTSFDY (SEQ ID NO: 99); (iv) YGGSFDY (SEQ ID NO: 100); (v) MVYVLDY (SEQ ID NO: 101); (vi) VAGPFDF (SEQ ID NO: 102); wherein X$_6$ is Y, I or F; and (c) the light chain CDR3 sequence of (a) and the heavy chain CDR3 sequence of (b) and the Fc sequence of (c) and wherein the antigen binding protein specifically binds β-Klotho.

In a further embodiment the antigen binding protein comprises (a) a light chain CDR1 sequence selected from the group consisting of: (i) a light chain CDR1 sequence that differs by no more than two amino acid additions, substitutions, deletions, and combinations thereof, from a CDR1 sequence of L1-L11, SEQ ID NOs:17-27; (ii) RSSQSLVX$_{22}$YX$_{23}$DGNTYLS (SEQ ID NO: 177); (iii) SGSSSNIGNNYVS (SEQ ID NO: 107); (iv) QASQDINNYLN (SEQ ID NO: 108); (v) RASQSVSGNYLA (SEQ ID NO: 109); (vi) GVSSGSVSTRYYPS (SEQ ID NO: 110); wherein $X_{22}$ is H or absent; and $X_{23}$ is S or absent; (b) a light chain CDR2 sequence selected from the group consisting of: (i) a light chain CDR2 sequence that differs by no more than two amino acid additions, substitutions, deletions, and combinations thereof, from a CDR2 sequence of L1-L11, SEQ ID NOs:17-27; (ii) KISNRFS (SEQ ID NO: 112); (iii) DNNX$_4$RPX$_5$ (SEQ ID NO: 176); (iv) DTSNLET (SEQ ID NO: 114); (v) GASSRAT (SEQ ID NO: 115); (vi) STNTRSS (SEQ ID NO: 116); wherein $X_4$ is K, N or R; and $X_5$ is S or absent; and (c) a heavy chain CDR1 sequence selected from the group consisting of: (i) a heavy chain CDR1 sequence that differs by no more than three amino acid additions, substitutions, deletions, and combinations thereof, from a CDR1 sequence of H1-H11, SEQ ID NOs:28-38; (ii) $X_{19}YX_{20}MX_{21}$ wherein $X_{19}$ is A, G, R, S, T, or I; $X_{20}$ is Y, G or A; and $X_{21}$ is H or S; (d) a heavy chain CDR2 selected from the group consisting of: (i) a heavy chain CDR2 sequence that differs by no more than five amino acid additions, substitutions, and/or deletions from a CDR2 sequence of H1-H11, SEQ ID NOs:28-38; (ii) WINPX$_7$SGGTNSAQKFQG (SEQ ID NO: 179); (iii) VIX$_8$X$_9$DGX$_{10}$X$_{11}$X$_{12}$YYADSVKG (SEQ ID NO: 180); (iv) X$_{13}$ISGX$_{14}$GX$_{15}$X$_{16}$TYYADSVKG (SEQ ID NO: 181); (v) VIX$_{17}$YDGRNKYX$_{18}$ADSVKG (SEQ ID NO: 182); wherein $X_7$ is N or Y; $X_8$ is W or G; $X_9$ is F or Y; $X_{10}$ is R or S; $X_{11}$ is N or Y; $X_{12}$ is Q or K; $X_{13}$ is A or D; $X_{14}$ is S or R; $X_{15}$ is V or G; $X_{16}$ is S or Y; $X_{17}$ is W or S; and $X_{18}$ is Y or H; (e) the light chain CDR1 of (a) and the light chain CDR2 of (b); (f) the light chain CDR1 of (a) and the heavy chain CDR1 of (c); (g) the light chain CDR1 of (a) and the heavy chain CDR2 of (d); (h) the light chain CDR1 (b) and the heavy chain CDR1 of (c); (i) the heavy chain CDR1 of (c) and the heavy chain CDR2 of (d); (j) the light chain CDR2 of (b) and the heavy chain CDR2 of (d); (k) the light chain CDR1 of (a), the light chain CDR2 of (b), and the heavy chain CDR1 of (c); (l) the light chain CDR2 of (b), the heavy CDR1 of (c), and the heavy chain CDR2 of (d); (m) the light chain CDR1 of (a), the heavy chain CDR1 of (c), and the heavy chain CDR2 of (d); or (n) the light chain CDR1 of (a), the light chain CDR2 of (b), the heavy chain CDR2 of (c), and the heavy chain CDR2 of (d), wherein said antigen binding protein specifically binds β-Klotho.

In an additional embodiment, the antigen binding protein comprises (a) a light chain variable domain comprising; (i) a light chain CDR1 sequence selected from SEQ ID NOs: 106-111; (ii) a light chain CDR2 sequence selected from SEQ ID NOs:112-119; (iii) a light chain CDR3 sequence selected from SEQ ID NOs:120-127; and (b) a heavy chain variable domain comprising: (i) a heavy chain CDR1 sequence selected from SEQ ID NOs:83-88; (ii) a heavy chain CDR2 sequence selected from SEQ ID NOs:89-97; and (iii) a heavy chain CDR3 sequence selected from SEQ ID NOs:98-105; or (c) the light chain variable domain of (a) and the heavy chain variable domain of (b), wherein the antigen binding protein specifically binds β-Klotho.

In still a further embodiment, the antigen binding protein comprises: (a) a light chain variable domain sequence selected from the group consisting of: (i) amino acids having a sequence at least 80% identical to a light chain variable domain sequence selected from L1-L11, SEQ ID NOs:17-27; (ii) a sequence of amino acids encoded by a polynucleotide sequence that is at least 80% identical to a polynucleotide sequence encoding the light chain variable domain sequence of L1-L11, SEQ ID NOs:17-27; (b) a heavy chain variable domain sequence selected from the group consisting of: (i) a sequence of amino acids that is at least 80% identical to a heavy chain variable domain sequence of H1-H11 of SEQ ID NOs:28-38; (ii) a sequence of amino acids encoded by a polynucleotide sequence that is at least 80% identical to a polynucleotide sequence encoding the heavy chain variable domain sequence of H1-H11, SEQ ID NOs:28-38; or (c) the light chain variable domain of (a) and the heavy chain variable domain of (b); wherein the antigen binding protein specifically binds β-Klotho.

In another embodiment the isolated antigen binding protein of claim 5, comprising either: (a) a light chain variable domain sequence selected from the group consisting of: L1-L11 of SEQ ID NOs:17-27; (b) a heavy chain variable domain sequence selected from the group consisting of: H1-H11 of SEQ ID NOs: 28-38; or (c) the light chain variable domain of (a) and the heavy chain variable domain of (b), wherein the antigen binding protein specifically binds to β-Klotho.

The light chain variable domain and a heavy chain variable domain can be selected from the group of combinations consisting of: L1H1, L2H2, L3H3, L4H4, L5H5, L6H6, L7H7, L8H8, L9H9, L10H10 and L11H11, wherein the antigen binding protein specifically binds to β-Klotho.

In some embodiments the antigen binding protein further comprises: (a) the light chain constant sequence of SEQ ID NO: 13; (b) the light chain constant sequence of SEQ ID NO:15; (c) the heavy chain constant sequence of SEQ ID NO: 9; or (d) the light chain constant sequence of SEQ ID NO: 13 or SEQ ID NO: 15 and the heavy chain constant sequence of SEQ ID NO: 9.

The antigen binding protein of can be selected from the group consisting of a human antibody, a humanized antibody, chimeric antibody, a monoclonal antibody, a polyclonal antibody, a recombinant antibody, an antigen-binding antibody fragment, a single chain antibody, a diabody, a triabody, a tetrabody, a Fab fragment, an F(fa')$_x$ fragment, a domain antibody, an IgD antibody, an IgE antibody, and IgM antibody, and IgG1 antibody, and IgG2 antibody, and IgG3 antibody, and IgG4 antibody, and IgG4 antibody having at least one mutation in the hinge region.

Also provided is an antigen binding protein that, when bound to β-Klotho: (a) binds to β-Klotho with substantially the same Kd as a reference antibody; (b) induces FGF21-like signaling of 10% or greater than the signaling induced by a wild-type FGF21 standard comprising the mature form of SEQ ID NO:2 as measured in an ELK-luciferase reporter assay; (c) exhibits an EC50 of 10 nM or less of FGF21-like signaling in an assay selected from the group consisting of: (i) a FGFR1c/βKlotho-mediated in vitro recombinant cell-based assay; (d) exhibits an EC50 of less than 10 nM of agonistic activity on FGFR1c in the presence of βKlotho in an in vitro recombinant FGFR1c receptor mediated reporter assay; and (e) an EC50 of greater than 1 μM of agonistic activity on FGFR1c in the absence of βKlotho in an in vitro recombinant FGFR1c receptor mediated reporter assay; (f) competes for binding with a reference antibody to β-Klotho, wherein the reference antibody comprises a combination of light chain and heavy chain variable domain sequences selected from the group consisting of L1H1, L2H2, L3H3, L4H4, L5H5, L6H6, L7H7, L8H8, L9H9, L10H10 and L11H11.

Also provided is a polypeptide comprising a sequence selected from the group consisting of: TRLWKYWV (SEQ ID NO: 184); RRLYIFWE (SEQ ID NO: 185); YKAW-GYYV (SEQ ID NO: 186); YQAWGYYV (SEQ ID NO: 187); YQAWGYLV (SEQ ID NO: 188); YQAWGYFV (SEQ ID NO: 189); FTWVFWNV (SEQ ID NO: 190); YQVWGYFV (SEQ ID NO: 191); YKWLKWNL (SEQ ID NO: 192); RRLYIFEW (SEQ ID NO: 193); WAERGG (SEQ ID NO: 194); GGWAVGRI (SEQ ID NO: 195); YKYLVFWV (SEQ ID NO: 196); YKYLSYWV (SEQ ID NO: 197); YKTAWYWK (SEQ ID NO: 198); YVFHKWWV (SEQ ID NO: 199); YVFYLWWK (SEQ ID NO: 200); YRWLHWHV (SEQ ID NO: 201); YKFLFWHA (SEQ ID NO: 202); RRQWGFWV (SEQ ID NO: 203); YSAWSFWV (SEQ ID NO: 204); LARWGFWV (SEQ ID NO: 205); YDAWGYWV (SEQ ID NO: 206); WRKYYHFWVS (SEQ ID NO: 207); KRLYGLFWYD (SEQ ID NO: 208); KKHWSSLFFE (SEQ ID NO: 209); KAWPYSWEAV (SEQ ID NO: 210); EWYCGVLFNCQQ (SEQ ID NO: 211); HFGCGVIFNCVSD (SEQ ID NO: 212); WELCASGYGWCYLH (SEQ ID NO: 213); APSCKSYIGFGLYHCWDG (SEQ ID NO: 214); and HFKCGMGLFECADP (SEQ ID NO: 215).

Also provided is an antigen binding protein heavy chain comprising a peptide that specifically binds to one or more of FGFR1c, FGFR2c, FGFR3c, FGFR4. In one embodiment the antigen binding protein heavy chain comprises a peptide sequence selected from the group consisting of: TRLWKYWV (SEQ ID NO: 184); RRLYIFWE (SEQ ID NO: 185); YKAWGYYV (SEQ ID NO: 186); YQAWGYYV (SEQ ID NO: 187); YQAWGYLV (SEQ ID NO: 188); YQAWGYFV (SEQ ID NO: 189); FTWVFWNV (SEQ ID NO: 190); YQVWGYFV (SEQ ID NO: 191); YKWLKWNL (SEQ ID NO: 192); RRLYIFEW (SEQ ID NO: 193); WAERGG (SEQ ID NO: 194); GGWAVGRI (SEQ ID NO: 195); YKYLVFWV (SEQ ID NO: 196); YKYLSYWV (SEQ ID NO: 197); YKTAWYWK (SEQ ID NO: 198); YVFHKWWV (SEQ ID NO: 199); YVFYLWWK (SEQ ID NO: 200); YRWLHWHV (SEQ ID NO: 201); YKFLFWHA (SEQ ID NO: 202); RRQWGFWV (SEQ ID NO: 203); YSAWSFWV (SEQ ID NO: 204); LARWGFWV (SEQ ID NO: 205); YDAWGYWV (SEQ ID NO: 206); WRKYYHFWVS (SEQ ID NO: 207); KRLYGLFWYD (SEQ ID NO: 208); KKHWSSLFFE (SEQ ID NO: 209); KAWPYSWEAV (SEQ ID NO: 210); EWYCGVLFNCQQ (SEQ ID NO: 211); HFGCGVIFNCVSD (SEQ ID NO: 212); WELCASGYGWCYLH (SEQ ID NO: 213); APSCKSYIGFGLYHCWDG (SEQ ID NO: 214); and HFKCGMGLFECADP (SEQ ID NO: 215). The antigen binding protein heavy chain can comprise a CH2 loop, a CH3 loop or both a CH2 and a CH3 loop. In various embodiments the heavy chain comprises a CH3 loop, and the CH3 loop can comprise the peptide. In other embodiments the heavy chain comprises a CH2 loop and the CH2 loop can comprise the peptide.

In still another embodiment an antigen binding protein can comprise the heavy chain comprising the peptide and in a further embodiment the antigen binding protein's heavy chain comprises a heavy chain CDR3 sequence comprising a sequence selected from the group consisting of: (i) a heavy chain CDR3 sequence that differs by no more than one amino acid additions, substitutions, deletions, and combinations thereof, from a CDR3 sequence of H1-H11, SEQ ID NOs:28-38; (ii) GWFDX$_6$ (SEQ ID NO: 178); (iii) GTSFDY (SEQ ID NO: 99); (iv) YGGSFDY (SEQ ID NO: 100); (v) MVYVLDY (SEQ ID NO: 101); (vi) VAGPFDF (SEQ ID NO: 102); wherein X$_6$ is Y, I or F; and wherein the antigen binding protein specifically binds to β-Klotho and one or more of FGFR1c, FGFR2c, FGFR3c, FGFR4.

In an additional embodiment the antigen binding protein further comprises: (a) a heavy chain CDR1 sequence selected from the group consisting of: (i) a heavy chain CDR1 sequence that differs by no more than three amino acid additions, substitutions, deletions, and combinations thereof, from a CDR1 sequence of H1-H11, SEQ ID NOs: 28-38; (ii) X$_{19}$YX$_{20}$MX$_{21}$ wherein X$_{19}$ is A, G, R, S, T, or I; X$_{20}$ is Y, G or A; and X$_{21}$ is H or S; (b) a heavy chain CDR2 selected from the group consisting of: (i) a heavy chain CDR2 sequence that differs by no more than five amino acid additions, substitutions, and/or deletions from a CDR2 sequence of H1-H11, SEQ ID NOs:28-38; (ii) WINPX$_7$SGGTNSAQKFQG (SEQ ID NO: 179); (iii) VIX$_8$X$_9$DGX$_{10}$X$_{11}$X$_{12}$YYADSVKG (SEQ ID NO: 180); (iv)X$_{13}$ISGX$_{14}$GX$_{15}$X$_{16}$TYYADSVKG (SEQ ID NO: 181); (v) VIX$_{17}$YDGRNKYX$_{18}$ADSVKG (SEQ ID NO: 182) wherein X$_7$ is N or Y; X$_8$ is W or G; X$_9$ is F or Y; X$_{10}$ is R or S X$_{11}$ is N or Y; X$_{12}$ is Q or K; X$_{13}$ is A or D; X$_{14}$ is S or R; X$_{15}$ is V or G; X$_{16}$ is S or Y; X$_{17}$ is W or S; and X$_{18}$ is Y or H; and wherein the antigen binding protein specifically binds to β-Klotho and one or more of FGFR1c, FGFR2c, FGFR3c, FGFR4. In another embodiment the antigen binding protein comprises (a) a heavy chain variable domain comprising: (i) a heavy chain CDR1 sequence selected from SEQ ID NOs:83-88; (ii) a heavy chain CDR2 sequence selected from SEQ ID NOs:89-97; and (iii) a heavy chain CDR3 sequence selected from SEQ ID NOs: 98-105; or wherein the antigen binding protein specifically binds to β-Klotho and one or more of FGFR1c, FGFR2c, FGFR3c, FGFR4. In still another embodiment the antigen binding protein comprises (a) a heavy chain variable domain sequence selected from the group consisting of: (i) a sequence of amino acids that is at least 80% identical to a heavy chain variable domain sequence of H1-H11 of SEQ ID NOs:28-38; (ii) a sequence of amino acids encoded by a polynucleotide sequence that is at least 80% identical to a polynucleotide sequence encoding the heavy chain variable domain sequence of H1-H11, SEQ ID NOs: 28-38; wherein the antigen binding protein specifically binds to β-Klotho and one or more of FGFR1c, FGFR2c, FGFR3c, FGFR4. The isolated antigen binding protein can comprise: (a) a heavy chain variable domain sequence selected from the group consisting of: H1-H11, SEQ ID NOs:28-38; wherein the antigen binding protein specifically binds to β-Klotho and one or more of FGFR1c, FGFR2c, FGFR3c, FGFR4.

Also provided is an isolated antigen binding protein that specifically binds to β-Klotho or β-Klotho and one or more of FGFR1c, FGFR2c, FGFR3c, and FGFR4. In one embodiment the heavy chain of the antigen binding protein comprises a sequence selected from the group consisting of: TRLWKYWV (SEQ ID NO: 184); RRLYIFWE (SEQ ID NO: 185); YKAWGYYV (SEQ ID NO: 186); YQAWGYYV (SEQ ID NO: 187); YQAWGYLV (SEQ ID NO: 188); YQAWGYFV (SEQ ID NO: 189); FTWVFWNV (SEQ ID NO: 190); YQVWGYFV (SEQ ID NO: 191); YKWLKWNL (SEQ ID NO: 192); RRLYIFEW (SEQ ID NO: 193); WAERGG (SEQ ID NO: 194); GGWAVGRI (SEQ ID NO: 195); YKYLVFWV (SEQ ID NO: 196); YKYLSYWV (SEQ ID NO: 197); YKTAWYWK (SEQ ID NO: 198); YVFHKWWV (SEQ ID NO: 199); YVFYLWWK (SEQ ID NO: 200); YRWLHWHV (SEQ ID NO: 201); YKFLFWHA (SEQ ID NO: 202); RRQWGFWV (SEQ ID NO: 203); YSAWSFWV (SEQ ID NO: 204); LARWGFWV (SEQ ID NO: 205); YDAWGYWV (SEQ ID NO: 206); WRKYYHFWVS (SEQ ID NO: 207); KRLYGLFWYD (SEQ ID NO: 208); KKHWSSLFFE (SEQ ID NO: 209); KAWPYSWEAV (SEQ ID NO: 210); EWYCGVLFNCQQ (SEQ ID NO: 211); HFGCGVIFNCVSD (SEQ ID NO: 212); WELCASGYGWCYLH (SEQ ID NO: 213); APSCKSYIGFGLYHCWDG (SEQ ID NO: 214); and HFKCGMGLFECADP (SEQ ID NO: 215).

In a further embodiment the antigen binding protein comprises an amino acid sequence selected from the group consisting of: (a) a light chain CDR3 comprising a sequence selected from the group consisting of: (i) a light chain CDR3 sequence that differs by no more than two amino acid additions, substitutions, deletions, and combinations thereof, from a CDR3 sequence of L1-L11, SEQ ID NOs:17-27; (ii) MQAX$_1$EFPWT (SEQ ID NO: 174); (iii) GTWDSSLSX$_2$VX$_3$ (SEQ ID NO: 175); (iv) QQYDNLFT (SEQ ID NO: 122); (v) QQYGSAPLT (SEQ ID NO: 123); (vi) VLYMGSGIWV (SEQ ID NO: 124); (vii) ETWDSSLSAGV (SEQ ID NO: 127); wherein X$_1$ is L or I; X$_2$ is V or A; and X$_3$ is V or A; (b) a heavy chain CDR3 sequence comprising a sequence selected from the group consisting of: (i) a heavy chain CDR3 sequence that differs by no more than one amino acid additions, substitutions, deletions, and combinations thereof, from a CDR3 sequence of H1-H11, SEQ ID NOs:28-38; (ii) GWFDX$_6$ (SEQ ID NO: 178); (iii) GTSFDY (SEQ ID NO: 99); (iv) YGGSFDY (SEQ ID NO: 100); (v) MVYVLDY (SEQ ID NO: 101); (vi) VAGPFDF (SEQ ID NO: 102); wherein X$_6$ is Y, I or F; (c) the light chain CDR3 sequence of (a) and the heavy chain CDR3 sequence of (b) and the Fc sequence of (c) and wherein the antigen binding protein specifically binds β-Klotho or β-Klotho and one or more of FGFR1c, FGFR2c, FGFR3c, and FGFR4.

In another embodiment the antigen binding protein comprises either: (a) a light chain CDR1 sequence selected from the group consisting of: (i) a light chain CDR1 sequence that differs by no more than two amino acid additions, substitutions, deletions, and combinations thereof, from a CDR1 sequence of L1-L11, SEQ ID NOs:27-37; (ii) RSSQSLVX$_{22}$YX$_{23}$DGNTYLS (SEQ ID NO: 177) (iii) SGSSSNIGNNYVS (SEQ ID NO: 107); (iv) QASDIN-NYLN (SEQ ID NO: 108); (v) RASQSVSGNYLA (SEQ ID NO: 109); (vi) GVSSGSVSTRYYPS (SEQ ID NO: 110); wherein X$_{22}$ is H or absent; and X$_{23}$ is S or absent; (b) a light chain CDR2 sequence selected from the group consisting of: (i) a light chain CDR2 sequence that differs by no more than two amino acid additions, substitutions, deletions, and combinations thereof, from a CDR2 sequence of L1-L11, SEQ ID NOs:17-27; (ii) KISNRFS (SEQ ID NO: 112); (iii) DNNX$_4$RPX$_5$ (SEQ ID NO: 176); (iv) DTSNLET (SEQ ID NO: 114); (v) GASSRAT (SEQ ID NO: 115); (vi) STNTRSS (SEQ ID NO: 116); wherein X$_4$ is K, N or R; and X$_5$ is S or absent; (c) a heavy chain CDR1 sequence selected from the group consisting of: (i) a heavy chain CDR1 sequence that differs by no more than three amino acid additions, substitutions, deletions, and combinations thereof, from a CDR1 sequence of H1-H11, SEQ ID NOs:28-38; (ii) X$_{19}$YX$_{20}$MX$_{21}$ wherein X$_{19}$ is A, G, R, S, T, or I; X$_{20}$ is Y, G or A; and X$_{21}$ is H or S; (d) a heavy chain CDR2 selected from the group consisting of: (i) a heavy chain CDR2 sequence that differs by no more than five amino acid additions, substitutions, and/or deletions from a CDR2 sequence of H1-H11, SEQ ID NOs:28-38; (ii) WINPX$_7$SGGTNSAQKFQG (SEQ ID NO: 179) (iii) VIX$_8$X$_9$DGX$_{10}$X$_{11}$X$_{12}$YYADSVKG; (SEQ ID NO: 180); (iv) X$_{13}$ISGX$_{14}$GX$_{15}$X$_{16}$TYYADSVKG (SEQ ID NO: 181); (v) VIX$_{17}$YDGRNKYX$_{18}$ADSVKG (SEQ ID NO: 182); wherein X$_7$ is N or Y; X$_8$ is W or G; X$_9$ is F or Y; X$_{10}$ is R or S; X$_{11}$ is N or Y; X$_{12}$ is Q or K; X$_{13}$ is A or D; X$_{14}$ is S or R; X$_{15}$ is V or G; X$_{16}$ is S or Y; X$_{17}$ is W or S; and X$_{18}$ is Y or H; (e) the light chain CDR1 of (a) and the light chain CDR2 of (b); (f) the light chain CDR1 of (a) and the heavy chain CDR1 of (c); (g) the light chain CDR1 of (a) and the heavy chain CDR2 of (d); (h) the light chain CDR1 (b) and the heavy chain CDR1 of (c); (i) the heavy chain CDR1 of (c) and the heavy chain CDR2 of (d); (j) the light chain CDR2 of (b) and the heavy chain CDR2 of (d); (k) the light chain CDR1 of (a), the light chain CDR2 of (b), and the heavy chain CDR1 of (c); (l) the light chain CDR2 of (b), the heavy CDR1 of (c), and the heavy chain CDR2 of (d); (m) the light chain CDR1 of (a), the heavy chain CDR1 of (c), and the heavy chain CDR2 of (d); or (n) the light chain CDR1 of (a), the light chain CDR2 of (b), the heavy chain CDR2 of (c), and the heavy chain CDR2 of (d), wherein said antigen binding protein specifically binds to β-Klotho or β-Klotho and one or more of FGFR1c, FGFR2c, FGFR3c, and FGFR4.

In a further embodiment the antigen binding protein comprises (a) a light chain variable domain comprising; (i) a light chain CDR1 sequence selected from SEQ ID NOs: 106-111; (ii) a light chain CDR2 sequence selected from SEQ ID NOs:112-119; (iii) a light chain CDR3 sequence selected from SEQ ID NOs:120-127; and (b) a heavy chain variable domain comprising: (i) a heavy chain CDR1 sequence selected from SEQ ID NOs:83-88; (ii) a heavy chain CDR2 sequence selected from SEQ ID NOs:89-97; and (iii) a heavy chain CDR3 sequence selected from SEQ ID NOs:98-105; or (c) the light chain variable domain of (a) and the heavy chain variable domain of (b), wherein the antigen binding protein specifically binds β-Klotho and one or more of FGFR1c, FGFR2c, FGFR3c, and FGFR4.

In yet another embodiment the antigen binding protein comprises (a) a light chain variable domain sequence selected from the group consisting of: (i) amino acids having a sequence at least 80% identical to a light chain variable domain sequence selected from L1-L11, SEQ ID NOs:17-27; (ii) a sequence of amino acids encoded by a polynucleotide sequence that is at least 80% identical to a polynucleotide sequence encoding the light chain variable domain sequence of L1-L11, SEQ ID NOs:17-27; (b) a heavy chain variable domain sequence selected from the group consisting of: (i) a sequence of amino acids that is at least 80% identical to a heavy chain variable domain sequence of H1-H11 of SEQ ID NOs:28-38; (ii) a sequence of amino acids encoded by a polynucleotide sequence that is at least 80% identical to a polynucleotide sequence encoding the heavy chain variable domain sequence of H1-H11, SEQ ID NOs: 28-38; or (c) the light chain variable domain of (a) and the heavy chain variable domain of (b); wherein the antigen binding protein specifically binds to β-Klotho or β-Klotho and one or more of FGFR1c, FGFR2c, FGFR3c, and FGFR4.

In a further embodiment the antigen binding protein comprises (a) a light chain variable domain sequence selected from the group consisting of: L1-L11 of SEQ ID NOs:17-27; (b) a heavy chain variable domain sequence selected from the group consisting of: H1-H11 of SEQ ID NOs:28-38; or (c) the light chain variable domain of (a) and the heavy chain variable domain of (b), wherein the antigen binding protein specifically binds to β-Klotho or β-Klotho and one or more of FGFR1c, FGFR2c, FGFR3c, and FGFR4.

In still another embodiment the light chain variable domain and a heavy chain variable domain of the antigen binding protein are selected from the group of combinations consisting of: L1H1, L2H2, L3H3, L4H4, L5H5, L6H6, L7H7, L8H8, L9H9, L10H10 and L11H11 wherein the antigen binding protein specifically binds to β-Klotho and one or more of FGFR1c, FGFR2c, FGFR3c, and FGFR4.

In a further embodiment the antigen binding protein comprises (a) the light chain constant sequence of SEQ ID NO: 13; (b) the light chain constant sequence of SEQ ID NO:15; (c) the heavy chain constant sequence of SEQ ID NO: 9; or (d) the light chain constant sequence of SEQ ID NO: 13 or SEQ ID NO: 15 and the heavy chain constant sequence of SEQ ID NO: 9.

In embodiments the antigen binding protein of can be selected from the group consisting of a human antibody, a humanized antibody, chimeric antibody, a monoclonal antibody, a polyclonal antibody, a recombinant antibody, an antigen-binding antibody fragment, a single chain antibody, a diabody, a triabody, a tetrabody, a Fab fragment, an F(fa')$_x$ fragment, a domain antibody, an IgD antibody, an IgE antibody, and IgM antibody, and IgG1 antibody, and IgG2 antibody, and IgG3 antibody, and IgG4 antibody, and IgG4 antibody having at least one mutation in the hinge region.

Also provided is an antigen binding protein that, when bound to β-Klotho: (a) binds to β-Klotho with substantially the same Kd as a reference antibody; (b) induces FGF21-like signaling of 10% or greater than the signaling induced by a wild-type FGF21 standard comprising the mature form of SEQ ID NO:2 as measured in an ELK-luciferase reporter assay; (c) exhibits an EC50 of 10 nM or less of FGF21-like signaling in an assay selected from the group consisting of: (i) a FGFR1c/βKlotho-mediated in vitro recombinant cell-based assay; (d) exhibits an EC50 of less than 10 nM of agonistic activity on FGFR1c in the presence of βKlotho in an in vitro recombinant FGFR1c receptor mediated reporter assay; and (e) an EC50 of greater than 1 µM of agonistic activity on FGFR1c in the absence of βKlotho in an in vitro recombinant FGFR1c receptor mediated reporter assay; (f) competes for binding with a reference antibody to β-Klotho, wherein the reference antibody comprises a combination of light chain and heavy chain variable domain sequences selected from the group consisting of L1H1, L2H2, L3H3, L4H4, L5H5, L6H6, L7H7, L8H8, L9H9, L10H10 and L11H11. The disclosed antigen binding proteins can be of therapeutic use and in embodiments, the antigen binding proteins, when bound to β-Klotho or β-Klotho and one or more of FGFR1c, FGFR2c, FGFR3c, and FGFR4 (a) lower blood glucose in an animal model; (b) lower serum lipid levels in an animal model; or (c) (a) and (b).

Pharmaceutical compositions comprising the disclosed antigen binding protein in admixture with a pharmaceutically acceptable carrier thereof are also provided. In one embodiment, the pharmaceutical composition can comprise an additional active agent that is selected from the group consisting of a radioisotope, radionuclide, a toxin, or a therapeutic and a chemotherapeutic group.

A method of producing an antigen binding protein that specifically binds to β-Klotho or β-Klotho and one or more of FGFR1c, FGFR2c, FGFR3c, and FGFR4 is provided. In one embodiment the method comprises incubating the disclosed host cell under conditions that allow it to express the antigen binding protein.

A method of preventing or treating a condition in a subject in need of such treatment is also provided. In one embodiment, the method comprises administering a therapeutically effective amount of a disclosed pharmaceutical composition to the subject, wherein the condition is treatable by lowering blood glucose. The condition can be selected from, e.g., type 2 diabetes, obesity, dyslipidemia, NASH, cardiovascular disease, and metabolic syndrome.

Generally, a method of preventing or treating a condition in a subject in need of such treatment, wherein the condition is treatable by lowering blood glucose. In one embodiment the method comprises administering a therapeutically effective amount of a pharmaceutical composition disclosed herein to the subject. The condition can be selected from, e.g., type 2 diabetes, obesity, dyslipidemia, NASH, cardiovascular disease, and metabolic syndrome.

One embodiment includes expression systems, including cell lines, for the production of antigen binding proteins that bind to β-Klotho or β-Klotho and one or more of FGFR1c, FGFR2c, FGFR3c, and FGFR4, and methods for diagnosing and treating diseases related to human FGF21.

In yet another aspect, the isolated antigen-binding protein can compete for binding to one or more of the human or non-human forms of β-Klotho or β-Klotho and one or more of FGFR1c, FGFR2c, FGFR3c, and FGFR4, e.g., the extracellular portion(s) of β-Klotho, FGFR1c, FGFR2c, FGFR3c, or FGFR4, with one of the disclosed antigen binding proteins.

In one embodiment, the isolated antigen binding protein is effective to lower plasma glucose levels, lower circulating triglycerides, cholesterol levels, improve lipoprotein abnormality and substantially improve cardiovascular risk factor profile, when administered to a patient with type 2 diabetes or other metabolic diseases.

In another aspect the isolated antigen binding protein specifically or selectively binds to β-Klotho, e.g., human β-Klotho, and in another aspect the isolated antigen binding protein binds to β-Klotho, e.g., β-Klotho, and induces FGF21-like signaling.

In another aspect the isolated antigen binding protein specifically or selectively binds to β-Klotho or β-Klotho and one or more of FGFR1c, FGFR2c, FGFR3c, and FGFR4 and induces FGF21-like signaling.

In another aspect, the isolated antigen-binding protein specifically or selectively binds to β-Klotho or β-Klotho and one or more of FGFR1c, FGFR2c, FGFR3c, and FGFR4, and does not specifically or selectively bind to α-Klotho, FGFR2c, FGFR3c, or FGFR4.

In another aspect the isolated antigen binding protein specifically or selectively binds to a complex comprising β-Klotho, e.g., human β-Klotho, and FGFR1c, e.g., human FGFR1c, and in another aspect the isolated antigen binding protein binds to such a complex and induces FGF21-like signaling.

In a further aspect, also provided are isolated nucleic acid molecules that encode the antigen binding proteins disclosed herein. In some instances, the isolated nucleic acid molecules are operably-linked to a control sequence.

In another aspect, also provided are expression vectors and host cells transformed or transfected with the expression vectors that comprise the aforementioned isolated nucleic acid molecules that encode the antigen binding proteins disclosed herein.

In another aspect, also provided are methods of preparing antigen binding proteins that specifically or selectively bind β-Klotho or β-Klotho and one or more of FGFR1c, FGFR2c, FGFR3c, FGFR4 and includes the step of preparing the antigen binding protein from a host cell that secretes the antigen binding protein.

Other embodiments further provide a method for treating or preventing a condition associated with FGF21 in a patient, comprising administering to a patient an effective amount of at least one isolated antigen-binding protein. In one embodiment, the condition is diabetes, in another embodiment the condition is obesity and in another embodiment the condition is dyslipidemia.

Also provided is an antigen binding protein-FGF21 fusion. In one embodiment the antigen binding protein-FGF21 fusion comprises (a) an antigen binding component; and (b) an FGF21 component. The antigen binding protein-FGF21 fusion can comprise any of the antigen binding component provided herein. In some embodiments the FGF21 component of the antigen binding protein-FGF21 fusion comprises at least 25 consecutive residues of SEQ ID NO:341. In other embodiments the FGF21 component of the antigen binding protein-FGF21 fusion comprises one of (a) SEQ ID NO:342 and (b) SEQ ID NO:343. The antigen binding protein-FGF21 fusion can further comprise a linker. In yet another embodiment the antigen binding protein-FGF21 fusion (a) the antigen binding component comprises 2G10; and (b) an FGF21 component selected from the group consisting of (i) SEQ ID NO: 342; and (ii) SEQ ID NO: 343. In one embodiment of the antigen binding protein-FGF21 fusion the antigen binding component is joined to the FGF21 component by a linker selected from the group consisting of $(G_4S)_3$, (SEQ ID NO: 336) $(G_4S)_6$ (SEQ ID NO: 337), $(G_4S)_9$ (SEQ ID NO: 338), $(G_4S)_{12}$ (SEQ ID NO: 339) and $(G_4S)_{15}$ (SEQ ID NO: 340). In still another embodiment the FGF21 component is joined to the heavy chain of the 2G10 antigen binding component. In particular embodiments the heavy chain of the antigen binding protein-FGF21 fusion comprises an amino acid sequence selected from the group consisting of SEQ ID NOs:316, 320, 322, 324, 326, 318, 328, 330, 332 and 334. Alternatively the FGF21 component can be joined to the light chain of the 2G10 antigen binding component.

The provided antigen binding protein-FGF21 fusions can have various biological activities. In some embodiments, an antigen binding protein-FGF21 fusion can, when bound to β-Klotho, or β-Klotho and one or more of FGFR1c, FGFR2c, FGFR3c, and FGFR4: (a) lower blood glucose in an animal model; (b) lower serum lipid levels in an animal model; or c) both (a) and (b).

Also provided is an isolated nucleic acid encoding the light chain, the heavy chain or both of the antigen binding component of an antigen binding protein-FGF21 fusion, wherein the sequence is selected from L1-L11, SEQ ID NOs:17-27; H1-H11, SEQ ID NOs: 28-38, and SEQ ID NOs: 316, 320, 322, 324, 326, 318, 328, 330, 332 and 334. Expression vectors comprising the disclosed nucleic acids, as well as isolated cells comprising the disclosed nucleic acids and expression vectors comprising the nucleic acids are also provided.

Also provided is a pharmaceutical composition comprising an antigen binding protein-FGF21 fusion disclosed herein, further comprising a pharmaceutically acceptable carrier. A method of preventing or treating a condition in a subject in need of such treatment is provided, and in one embodiment comprises administering a therapeutically effective amount of a pharmaceutical composition comprising an antigen binding protein-FGF21 fusion to the subject, wherein the condition is treatable by lowering blood glucose. In various embodiments the condition is selected from type 2 diabetes, obesity, dyslipidemia, NASH, cardiovascular disease, and metabolic syndrome.

These and other aspects will be described in greater detail herein. Each of the aspects provided can encompass various embodiments provided herein. It is therefore anticipated that each of the embodiments involving one element or combinations of elements can be included in each aspect described, and all such combinations of the above aspects and embodiments are expressly considered. Other features, objects, and advantages of the disclosed antigen binding proteins and associated methods and compositions are apparent in the detailed description that follows.

BRIEF DESCRIPTION OF THE DRAWINGS

FIG. 1a-1b is an alignment showing the sequence homology between human FGFR1c (GenBank Accession No P11362; SEQ ID NO: 305) and murine FGFR1c (GenBank Accession No NP_034336; SEQ ID NO: 306); various features are highlighted, including the signal peptide, transmembrane sequence, heparin binding region and a protein kinase domain, and a consensus sequence (SEQ ID NO: 307) is provided.

FIG. 2a-2c is an alignment showing the sequence homology between human β-Klotho (GenBank Accession No NP_783864; SEQ ID NO: 308) and murine β-Klotho (GenBank Accession No NP_112457; SEQ ID NO: 309); various features are highlighted, including the transmembrane sequence and two glycosyl hydrolase domains, and a consensus sequence (SEQ ID NO: 310) is provided.

FIG. 4 is a sequence (SEQ ID NO: 311) showing an immunogen used to generate antigen binding proteins comprising the extracellular domain (ECD) of human FGFR1c fused to an IgG1 Fc via a $Gly_5$ linker (SEQ ID NO: 304); the FGFR1c component is in capitals, the linker is italic and underlined and the Fc is in lower case letters.

FIG. 5 is a sequence (SEQ ID NO: 312) showing an immunogen used to generate antigen binding proteins comprising the extracellular domain (ECD) of human β-Klotho fused to an IgG1 Fc via a $Gly_5$ linker (SEQ ID NO: 304); the β-Klotho component is in capitals, the linker is italic and underlined and the Fc is in lower case letters.

FIG. 7 is a table showing the calculated pI for β-Klotho binding proteins 10H3, 1A2, 1B5, 3B4, 9D10, 3F4, 1C10, 2G10 and 8F9.

FIG. 8 is an alignment showing some of the structural features identified in the heavy and light chains of some of the disclosed β-Klotho binding proteins. Light chain sequences disclosed as residues 1-112 of SEQ ID NO: 23, residues 1-112 of SEQ ID NO: 24, residues 1-112 of SEQ ID NO: 22, residues 1-112 of SEQ ID NO: 17, residues 1-110 of SEQ ID NO: 26, residues 1-110 of SEQ ID NO: 27, SEQ ID NO: 313, residues 1-110 of SEQ ID NO: 25 and residues 1-110 of SEQ ID NO: 18. Heavy chain sequences disclosed as residues 1-118 of SEQ ID NO: 34, residues 1-118 of SEQ ID NO: 35, residues 1-118 of SEQ ID NO: 33, residues 1-118 of SEQ ID NO: 28, SEQ ID NO: 314, residues 1-120 of SEQ ID NO: 38, residues 1-120 of SEQ ID NO: 37, residues 1-120 of SEQ ID NO: 36 and residues 1-120 of SEQ ID NO: 29.

FIGS. 9A and 9B depict the results of binding studies performed on the antigen binding proteins 1A2, 1B5, 2G10, 3B4, 3E10, 3F4, 8F9, 9D10 and 10H3; FIG. 9A is a series of traces from binding assays demonstrating the binding of the β-Klotho binding proteins to β-Klotho; FIG. 9B is a table showing the binding constants generated in the binding assays.

FIG. 11 is a table summarizing the binding properties of the β-Klotho-binding antigen binding proteins 3B4, 1A2, 1B5, 10H3, 9D10, 2G10, 3F4 and 8F9.

FIG. 12 is a table summarizing the sequences and properties of FGFR1c-binding peptides Rm26 (SEQ ID NO: 211), Rm27 (SEQ ID NO: 212), Rm33 (SEQ ID NO: 213), Rm37 (SEQ ID NO: 214), Rm40 (SEQ ID NO: 215) and SR4 (SEQ ID NO: 187).

FIG. 13 is a series of plots depicting the results of a series of binding assays that demonstrate that the bispecific antigen binding proteins 1A2-Rm26, 1A2-SR4, 2G10-Rm26, 2G10-Rm40, 2G10-SR4 bind to both human an murine β-Klotho and FGFR1c, that the antigen binding proteins 1A2-Rm40 and 2G10-Rm40 bind to both human and murine β-Klotho and that the peptides Rm26, Rm40 and SR4 bind to human and murine FGFR1c.

FIG. 14 is a series of plots depicting the results of a series of luciferase assays performed on antigen binding proteins 1A2-Rm26, 1A2-Rm40, 1A2-SR4, 2G10-Rm26, 2G10Rm40, 2G10SR4, the antigen binding proteins 1A2 and 2G10, and the peptides Rm26, Rm40, SR4 and KRm2, demonstrating that bispecific antigen binding protein 2G10-SR4 showed agonistic activities in β-Klotho/FGFR1c cell line, but not in a FGFR1c cell line; the left panel shows the results of a luciferase assay using AMID reporter cells expressing b-Klotho and FGFR1c shows agonist activity of 2G10-SR4, and the right panel shows the results of a luciferase assay using AMID reporter cells expressing FGFR1c.

FIG. 15 is a series of plots depicting the results of a series of luciferase assays that demonstrate that bispecific antigen binding protein 2G10-SR4 showed agonistic (left panel) and antagonistic activity (right panel) in a β-Klotho/FGFR1c cell line; the left panel shows the results of a luciferase assay using AMID reporter cells expressing β-Klotho and FGFR1c and demonstrating the agonist activity of 2G10-SR4, and the right panel shows that when incubated along with 3 nM FGF21, 2G10-SR4 and SR4 demonstrated antagonistic activity.

DETAILED DESCRIPTION

Figure 3A:
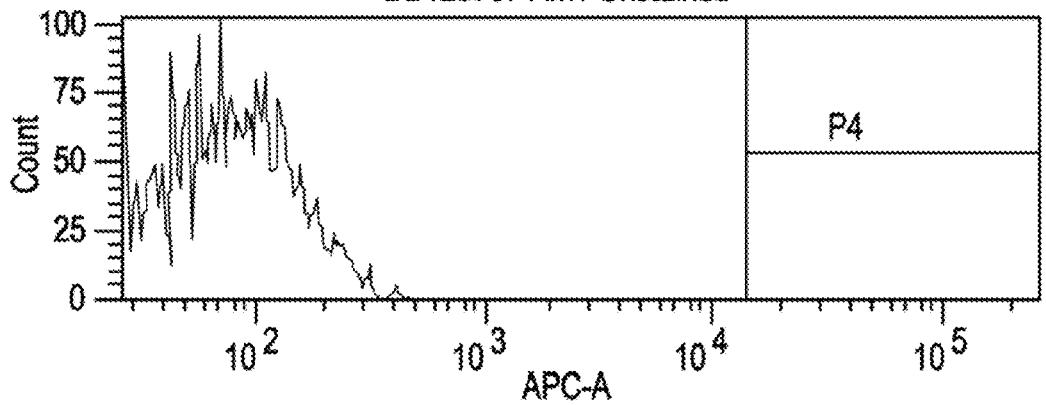
FIG. 3 is a flow cytometry profile of cells stained with FGF21-Alexa 647 that were used as an immunogen to generate antigen binding proteins; the figure shows the expression level of an FGF21R (a complex comprising FGFR1c and β-Klotho) and binding to FGF21.
Figure 3B:
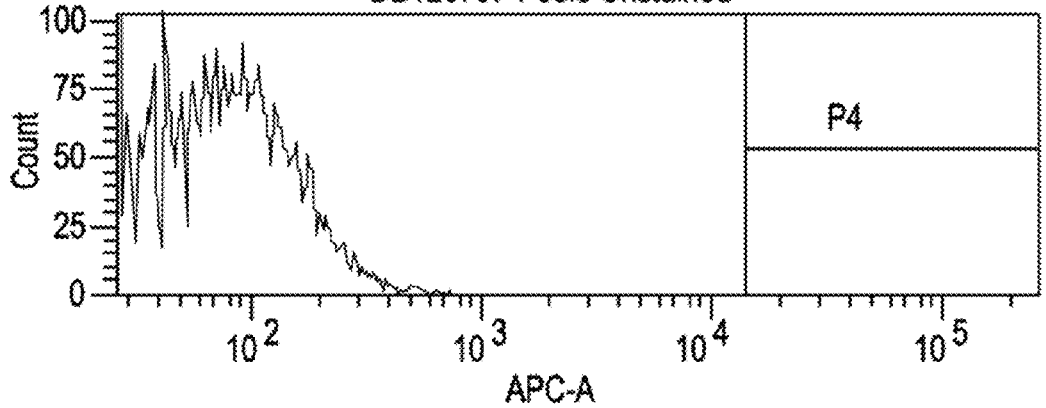
Figure 3C:
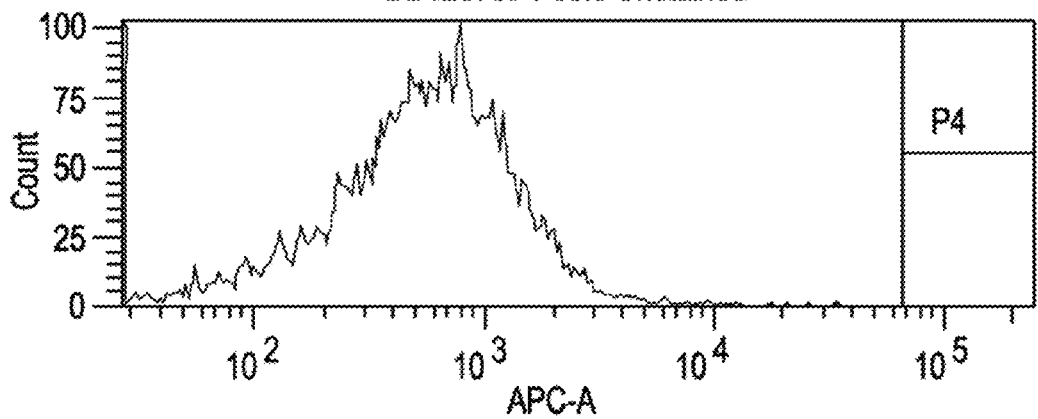
Figure 3D:
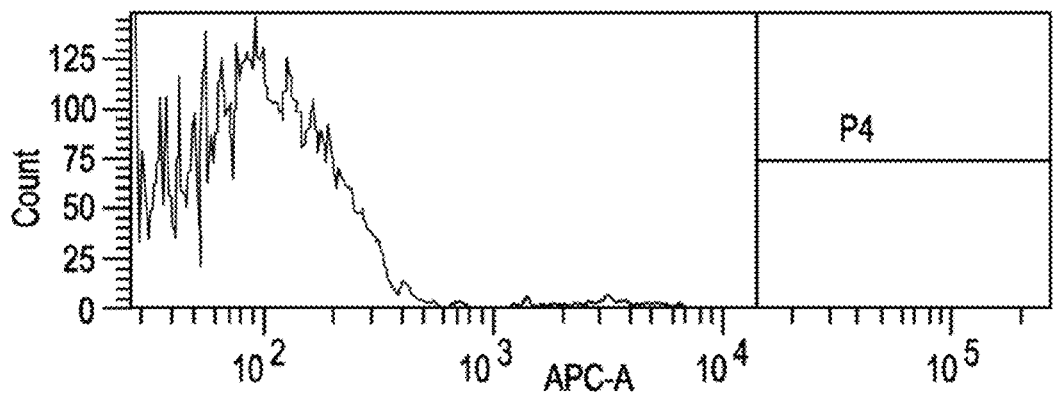
Figure 3E:
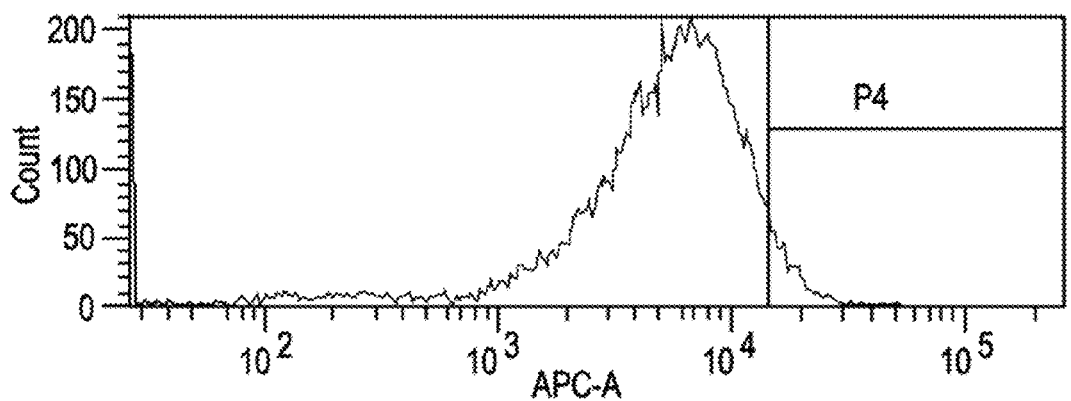
Figure 3F:
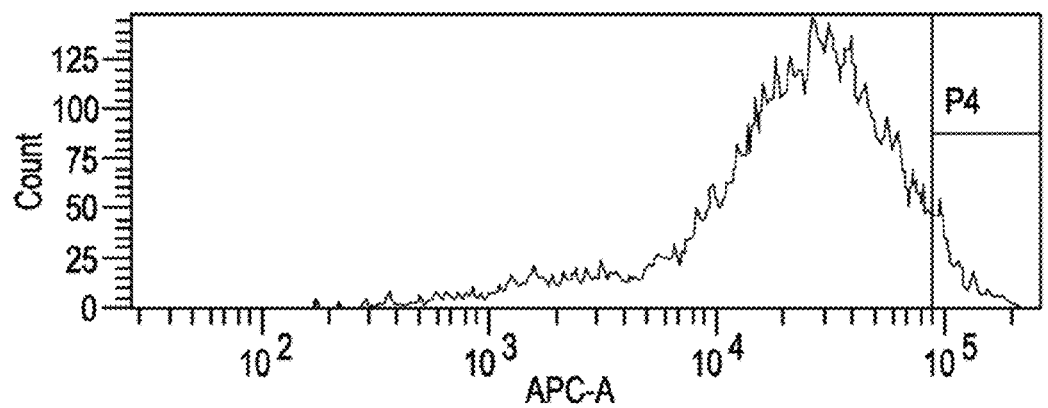

The section headings used herein are for organizational purposes only and are not to be construed as limiting the subject matter described.

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular.

Generally, nomenclatures used in connection with, and techniques of, cell and tissue culture, molecular biology, immunology, microbiology, genetics and protein and nucleic acid chemistry and hybridization described herein are those well known and commonly used in the art. The methods and techniques of the present application are generally performed according to conventional methods well known in the art and as described in various general and more specific references that are cited and discussed throughout the present specification unless otherwise indicated. See, e.g., Sambrook et al., Molecular Cloning: A Laboratory Manual, 3rd ed., Cold Spring Harbor Laboratory Press, Cold Spring Harbor, N.Y. (2001), Ausubel et al., Current Protocols in Molecular Biology, Greene Publishing Associates (1992), and Harlow and Lane Antibodies: A Laboratory Manual Cold Spring Harbor Laboratory Press, Cold Spring Harbor, N.Y. (1990), which are incorporated herein by reference. Enzymatic reactions and purification techniques are performed according to manufacturer's specifications, as commonly accomplished in the art or as described herein. The terminology used in connection with, and the laboratory procedures and techniques of, analytical chemistry, synthetic organic chemistry, and medicinal and pharmaceutical chemistry described herein are those well known and commonly used in the art. Standard techniques can be used for chemical syntheses, chemical analyses, pharmaceutical preparation, formulation, and delivery, and treatment of patients.

It should be understood that the instant disclosure is not limited to the particular methodology, protocols, and reagents, etc., described herein and as such can vary. The terminology used herein is for the purpose of describing particular embodiments only, and is not intended to limit the scope of the present disclosure.

Other than in the operating examples, or where otherwise indicated, all numbers expressing quantities of ingredients or reaction conditions used herein should be understood as modified in all instances by the term "about." The term "about" when used in connection with percentages can mean±5%, e.g., 1%, 2%, 3%, 4% or 5%.

DEFINITIONS

As used herein, the terms "a" and "an" mean "one or more" unless specifically stated otherwise.

An "antigen binding protein" is a protein comprising a portion that specifically binds to an antigen and, optionally, a scaffold or framework portion that allows the antigen binding portion to adopt a conformation that promotes binding of the antigen binding protein to the antigen. Examples of antigen binding proteins include a human antibody, a humanized antibody; a chimeric antibody; a recombinant antibody; a single chain antibody; a diabody; a triabody; a tetrabody; a Fab fragment; a F(ab')2 fragment; an IgD antibody; an IgE antibody; an IgM antibody; an IgG1 antibody; an IgG2 antibody; an IgG3 antibody; or an IgG4 antibody, and fragments thereof. The antigen binding protein can comprise, for example, an alternative protein scaffold or artificial scaffold with grafted CDRs or CDR derivatives. Such scaffolds include, but are not limited to, antibody-derived scaffolds comprising mutations introduced to, for example, stabilize the three-dimensional structure of the antigen binding protein as well as wholly synthetic scaffolds comprising, for example, a biocompatible polymer. See, e.g., Korndorfer et al., 2003, *Proteins: Structure, Function, and Bioinformatics,* 53(1):121-129 (2003); Roque et al., *Biotechnol. Prog.* 20:639-654 (2004). In addition, peptide antibody mimetics ("PAMs") can be used, as well as scaffolds based on antibody mimetics utilizing fibronection components as a scaffold.

An antigen binding protein can have, for example, the structure of a naturally occurring immunoglobulin. An "immunoglobulin" is a tetrameric molecule. In a naturally occurring immunoglobulin, each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as kappa and lambda light chains. Heavy chains are classified as mu, delta, gamma, alpha, or epsilon, and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. See generally, Fundamental Immunology, Ch. 7 (Paul, W., ed., 2$^{nd}$ ed. Raven Press, N.Y. (1989)) (incorporated by reference in its entirety for all purposes). The variable regions of each light/heavy chain pair form the antibody binding site such that an intact immunoglobulin has two binding sites.

Naturally occurring immunoglobulin chains exhibit the same general structure of relatively conserved framework regions (FR) joined by three hypervariable regions, also called complementarity determining regions or CDRs. From N-terminus to C-terminus, both light and heavy chains comprise the domains FR1, CDR1, FR2, CDR2, FR3, CDR3 and FR4. The assignment of amino acids to each domain is in accordance with the definitions of Kabat et al. in Sequences of Proteins of Immunological Interest, 5$^{th}$ Ed., US Dept. of Health and Human Services, PHS, NIH, NIH Publication no. 91-3242, 1991. As desired, the CDRs can also be redefined according an alternative nomenclature scheme, such as that of Chothia (see Chothia & Lesk, 1987, *J. Mol. Biol.* 196:901-917; or Chothia et al., 1989, *Nature* 342:878-883).

An antigen binding protein or antigen binding protein-FGF21 fusion is said to "specifically bind" its target antigen when the dissociation constant ($K_D$) is $\leq 10^{-8}$ M. The antigen binding protein or antigen binding protein-FGF21 fusion specifically binds antigen with "high affinity" when the $K_D$ is $\leq 5 \times 10^{-9}$ M, and with "very high affinity" when the $K_D$ is $\leq 5 \times 10^{-10}$ M. In one embodiment, an antigen binding protein or antigen binding protein-FGF21 fusion will bind to β-Klotho (for example human β-Klotho) or β-Klotho and one or more of FGFR1c, FGFR2c, FGFR3c or FGFR4, (for example, human β-Klotho, human FGFR1c, human FGFR2c, human FGFR3c, or human FGFR4), with a $K_D$ of between about $10^{-7}$ M and $10^{-12}$ M, and in yet another embodiment the antigen binding proteins or antigen binding protein-FGF21 fusions will bind with a $K_D \leq 5 \times 10^{-9}$ M.

As used herein the term "antigen binding protein-FGF21 fusion" means a polypeptide comprising (a) an antigen binding protein component comprising an "antigen binding protein," as defined herein, that specifically binds to β-Klotho or to a β-Klotho and one or more of FGFR1c, FGFR2c, FGFR3c or FGFR4; and (b) an FGF21 component comprising FGF21 or a fragment thereof. The β-Klotho polypeptide can be derived from any species, for example human, mouse or rat. Similarly, the FGF21 polypeptide can be derived from any speicies, for example human, mouse or rat. The antigen binding protein can comprise any antigen binding protein that specifically binds to β-Klotho, including the antigen binding proteins described herein in Tables 1-3 and 6.

The FGF21 polypeptide component can comprise a truncated form of the full length (SEQ ID NO:2) or mature (SEQ ID NO: 341) FGF21 polypeptide sequence. The FGF21 polypeptide sequence can be truncated at the C-terminus, the N-terminus or both the C-terminus and can range in length from 180 or fewer amino acids to 25 or more amino acids, for example 180, 179, 178, 177, 176, 175, 174, 173, 172, 171, 170, 169, 168, 167, 166, 165, 160, 155, 150, 145, 140, 135, 130, 125, 120, 115, 110, 105, 100, 95, 90, 85, 80, 75, 70, 65, 60, 55, 50, 45, 40, 35, 30 or 25 amino acids.

A linker can be employed to join the antigen bindin protein component to the FGF21 component. Any convenient linker can be employed, for example a linker of the form $(Gly_xSer)_y$ (SEQ ID NO: 335), wherein x and y are independently 1, 2, 3, 4, 5, 6, 7, 8, 9, 10, 11, 12, 13, 14, 15 or more. Specific examples of linkers include $(G_4S)_3$ (SEQ ID NO: 336), (G4S)$_6$ (SEQ ID NO: 337), (G$_4$S)$_9$ (SEQ ID NO: 338), (G$_4$S)$_{12}$ (SEQ ID NO: 339), and (G4S)$_{1-5}$ (SEQ ID NO: 340).

Specific examples of antigen binding protein-FGF21 fusions include human FGF21 (1-169)-(G$_4$S)$_{3-2}$G10 (SEQ ID NO:316), human FGF21 (1-169)-(G$_4$S)$_{6-2}$G10 (SEQ ID NO:320), human FGF21 (1-169)-(G$_4$S)$_{9-2}$G10 (SEQ ID NO:322), human FGF21 (1-169)-(G4S)$_{12}$-2G10 (SEQ ID NO:324), human FGF21 (1-169)-(G$_4$S)$_{15}$-2G10 (SEQ ID NO:326), 2G10-(G$_4$S)$_3$-human FGF21 (1-170) (SEQ ID NO:318), 2G10-(G$_4$S)$_6$-human FGF21 (1-170) (SEQ ID NO:328), 2G10-(G$_4$S)$_9$-human FGF21 (1-170) (SEQ ID NO:330), 2G10-(G$_4$S)$_{12}$-human FGF21 (1-170) (SEQ ID NO:332), and 2G10-(G$_4$S)$_{15}$-human FGF21 (1-170) (SEQ ID NO:334).

The FGF21 component of a fusion can be joined to the antigen binding component of the fusion at either the N-terminus of the heavy or light chain of the antigen binding component or at the C-terminus of the heavy chain of the antigen binding component. The two components can be joined via a linker sequence or they can be directly fused together. A fusion can optionally comprise an N-terminal methionine, which may be introduced as a consequence of expression in a non-mammalian expression system.

An "antibody" refers to an intact immunoglobulin or to an antigen binding portion thereof that competes with the intact antibody for specific binding, unless otherwise specified. Antigen binding portions can be produced by recombinant DNA techniques or by enzymatic or chemical cleavage of intact antibodies. Antigen binding portions include, inter alia, Fab, Fab', F(ab')$_2$, Fv, domain antibodies (dAbs), fragments including complementarity determining regions (CDRs), single-chain antibodies (scFv), chimeric antibodies, diabodies, triabodies, tetrabodies, and polypeptides that contain at least a portion of an immunoglobulin that is sufficient to confer specific antigen binding to the polypeptide.

A Fab fragment is a monovalent fragment having the V$_L$, V$_H$, C$_L$ and C$_H$1 domains; a F(ab')$_2$ fragment is a bivalent fragment having two Fab fragments linked by a disulfide bridge at the hinge region; a Fd fragment has the V$_H$ and C$_H$1 domains; an Fv fragment has the V$_L$ and V$_H$ domains of a single arm of an antibody; and a dAb fragment has a V$_H$ domain, a V$_L$ domain, or an antigen-binding fragment of a V$_H$ or V$_L$ domain (U.S. Pat. Nos. 6,846,634, 6,696,245, US App. Pub. No. 05/0202512, 04/0202995, 04/0038291, 04/0009507, 03/0039958, Ward et al., Nature 341:544-546 (1989)).

A single-chain antibody (scFv) is an antibody in which a V$_L$ and a V$_H$ region are joined via a linker (e.g., a synthetic sequence of amino acid residues) to form a continuous protein chain wherein the linker is long enough to allow the protein chain to fold back on itself and form a monovalent antigen binding site (see, e.g., Bird et al., Science 242:423-26 (1988) and Huston et al., 1988, Proc. Natl. Acad. Sci. USA 85:5879-83 (1988)). Diabodies are bivalent antibodies comprising two polypeptide chains, wherein each polypeptide chain comprises V$_H$ and V$_L$ domains joined by a linker that is too short to allow for pairing between two domains on the same chain, thus allowing each domain to pair with a complementary domain on another polypeptide chain (see, e.g., Holliger et al., 1993, Proc. Natl. Acad. Sci. USA 90:6444-48 (1993), and Poljak et al., Structure 2:1121-23 (1994)). If the two polypeptide chains of a diabody are identical, then a diabody resulting from their pairing will have two identical antigen binding sites. Polypeptide chains having different sequences can be used to make a diabody with two different antigen binding sites. Similarly, tribodies and tetrabodies are antibodies comprising three and four polypeptide chains, respectively, and forming three and four antigen binding sites, respectively, which can be the same or different.

Complementarity determining regions (CDRs) and framework regions (FR) of a given antibody can be identified using the system described by Kabat et al. in Sequences of Proteins of Immunological Interest, 5th Ed., US Dept. of Health and Human Services, PHS, NIH, NIH Publication no. 91-3242, 1991. One or more CDRs can be incorporated into a molecule either covalently or noncovalently to make it an antigen binding protein. An antigen binding protein can incorporate the CDR(s) as part of a larger polypeptide chain, can covalently link the CDR(s) to another polypeptide chain, or can incorporate the CDR(s) noncovalently. The CDRs permit the antigen binding protein to specifically bind to a particular antigen of interest.

An antigen binding protein can have one or more binding sites. If there is more than one binding site, the binding sites can be identical to one another or can be different. For example, a naturally occurring human immunoglobulin typically has two identical binding sites, while a "bispecific" or "bifunctional" antibody has two different binding sites.

The term "human antibody" includes all antibodies that have one or more variable and constant regions derived from human immunoglobulin sequences. In one embodiment, all of the variable and constant domains are derived from human immunoglobulin sequences (a fully human antibody). These antibodies can be prepared in a variety of ways, examples of which are described below, including through the immunization with an antigen of interest of a mouse that is genetically modified to express antibodies derived from human heavy and/or light chain-encoding genes.

A humanized antibody has a sequence that differs from the sequence of an antibody derived from a non-human species by one or more amino acid substitutions, deletions, and/or additions, such that the humanized antibody is less likely to induce an immune response, and/or induces a less severe immune response, as compared to the non-human species antibody, when it is administered to a human subject. In one embodiment, certain amino acids in the framework and constant domains of the heavy and/or light chains of the non-human species antibody are mutated to produce the humanized antibody. In another embodiment, the constant domain(s) from a human antibody are fused to the variable domain(s) of a non-human species. In another embodiment, one or more amino acid residues in one or more CDR sequences of a non-human antibody are changed to reduce the likely immunogenicity of the non-human antibody when it is administered to a human subject, wherein the changed amino acid residues either are not critical for immunospecific binding of the antibody to its antigen, or the changes to the amino acid sequence that are made are conservative changes, such that the binding of the humanized antibody to the antigen is not significantly worse than the binding of the non-human antibody to the antigen. Examples of how to make humanized antibodies can be found in U.S. Pat. Nos. 6,054,297, 5,886,152 and 5,877,293.

The term "chimeric antibody" refers to an antibody that contains one or more regions from one antibody and one or more regions from one or more other antibodies, such as the CDR or the CH2, CH3, or Fc regions. In one embodiment, one or more of the CDRs are derived from a human antibody that binds human or mouse β-Klotho or β-Klotho and one or more of FGFR1c, FGFR2c, FGFR3c and FGFR4. In another embodiment, all of the CDRs are derived from a human antibody that binds human or mouse β-Klotho or β-Klotho and one or more of FGFR1c, FGFR2c, FGFR3c and FGFR4. In another embodiment, the CDRs from more than one human antibody that binds human or mouse β-Klotho or β-Klotho and one or more of FGFR1c, FGFR2c, FGFR3c and FGFR4 are mixed and matched in a chimeric antibody. For instance, a chimeric antibody can comprise a CDR1 from the light chain of a first human antibody that binds human or mouse β-Klotho or β-Klotho and one or more of FGFR1c, FGFR2c, FGFR3c and FGFR4, a CDR2 and a CDR3 from the light chain of a second human antibody that binds human or mouse β-Klotho or β-Klotho and one or more of FGFR1c, FGFR2c, FGFR3c and FGFR4, or the CDRs from the heavy chain from a third human antibody that binds human or mouse β-Klotho or β-Klotho and one or more of FGFR1c, FGFR2c, FGFR3c and FGFR4, which can be joined to an $C_H2$, $C_H3$ or Fc region from yet another antibody or another source. Further, the framework regions can be derived from one of the same antibodies that bind human or mouse β-Klotho or β-Klotho and one or more of FGFR1c, FGFR2c, FGFR3c and FGFR4, from one or more different antibodies, such as a human antibody, or from a humanized antibody. In one example of a chimeric antibody, a portion of the heavy and/or light chain is identical with, homologous to, or derived from an antibody from a particular species or belonging to a particular antibody class or subclass, while the remainder of the chain(s) is/are identical with, homologous to, or derived from an antibody or antibodies from another species or belonging to another antibody class or subclass. Also included are fragments of such antibodies that exhibit the desired biological activity (e.g., the ability to specifically bind β-Klotho).

The term "light chain" includes a full-length light chain and fragments thereof having sufficient variable region sequence to confer binding specificity. A full-length light chain includes a variable region domain, $V_L$, and a constant region domain, $C_L$. The variable region domain of the light chain is at the amino-terminus of the polypeptide. Light chains include kappa chains and lambda chains.

The term "heavy chain" includes a full-length heavy chain and fragments thereof having sufficient variable region sequence to confer binding specificity. A full-length heavy chain includes a variable region domain, $V_H$, and three constant region domains, $C_HL$ $C_H2$, and $C_H3$. The $V_H$ domain is at the amino-terminus of the polypeptide, and the $C_H$ domains are at the carboxyl-terminus, with the $C_H3$ being closest to the carboxy-terminus of the polypeptide. Heavy chains can be of any isotype, including IgG (including IgG1, IgG2, IgG3 and IgG4 subtypes), IgA (including IgA1 and IgA2 subtypes), IgM and IgE.

The term "immunologically functional fragment" (or simply "fragment") of an antigen binding protein, e.g., an antibody or immunoglobulin chain (heavy or light chain), as used herein, is an antigen binding protein comprising a portion (regardless of how that portion is obtained or synthesized) of an antibody that lacks at least some of the amino acids present in a full-length chain but which is capable of specifically binding to an antigen. Such fragments are biologically active in that they bind specifically to the target antigen and can compete with other antigen binding proteins, including intact antibodies, for specific binding to a given epitope. In one aspect, such a fragment will retain at least one CDR present in the full-length light or heavy chain, and in some embodiments will comprise a single heavy chain and/or light chain or portion thereof. These biologically active fragments can be produced by recombinant DNA techniques, or can be produced by enzymatic or chemical cleavage of antigen binding proteins, including intact antibodies. Immunologically functional immunoglobulin fragments include, but are not limited to, Fab, Fab', $F(ab')_2$, Fv, domain antibodies and single-chain antibodies, and can be derived from any mammalian source, including but not limited to human, mouse, rat, camelid or rabbit. It is contemplated further that a functional portion of the antigen binding proteins disclosed herein, for example, one or more CDRs, could be covalently bound to a second protein or to a small molecule to create a therapeutic agent directed to a particular target in the body, possessing bifunctional therapeutic properties, or having a prolonged serum half-life.

An "Fc" or "Fc region" comprises one or two heavy chain fragments, and can comprise the $C_H2$ and/or $C_H3$ domains of an antibody. When two heavy chain fragments are present, the two heavy chain fragments are held together by two or more disulfide bonds and by hydrophobic interactions of the $C_H3$ domains. An Fc region can be naturally occurring (e.g., a Fc region derived from an IgG1, IgG2, IgG3, IgG4, IgE, IgA, etc) or can be an engineered sequence comprising one or more (e.g., 1, 2, 3, 4, 5, 6, 7, 8, 9, 10, 11, 12, 13, 14, 15, 16, 17, 18, 19, 20, etc) mutations, deletions or insertions introduced into a naturally occurring heavy chain fragment or fragments that make up an Fc sequence.

An "Fab' fragment" contains one light chain and a portion of one heavy chain that contains the $V_H$ domain and the $C_H1$ domain and also the region between the $C_H1$ and $C_H2$ domains, such that an interchain disulfide bond can be formed between the two heavy chains of two Fab' fragments to form an $F(ab')_2$ molecule.

An "$F(ab')_2$ fragment" contains two light chains and two heavy chains containing a portion of the constant region between the $C_H1$ and $C_H2$ domains, such that an interchain disulfide bond is formed between the two heavy chains. A $F(ab')_2$ fragment thus is composed of two Fab' fragments that are held together by a disulfide bond between the two heavy chains.

The "Fv region" comprises the variable regions from both the heavy and light chains, but lacks the constant regions.

A "domain antibody" is an immunologically functional immunoglobulin fragment containing only the variable region of a heavy chain or the variable region of a light chain. In some instances, two or more $V_H$ regions are covalently joined with a peptide linker to create a bivalent domain antibody. The two $V_H$ regions of a bivalent domain antibody can target the same or different antigens.

A "bivalent antigen binding protein" or "bivalent antibody" comprises two antigen binding sites. In some instances, the two binding sites have the same antigen specificities. Bivalent antigen binding proteins and bivalent antibodies can be bispecific, see, e.g., infra.

A "multispecific antigen binding protein" or "multispecific antibody" is one that targets more than one antigen or epitope.

A "bispecific," "dual-specific" or "bifunctional" antigen binding protein or antibody is a hybrid antigen binding protein or antibody, respectively, having two different antigen binding sites. Bispecific antigen binding proteins and antibodies are a species of multispecific antigen binding protein or multispecific antibody and can be produced by a variety of methods including, but not limited to, fusion of hybridomas, linking an Fc to a Fab' fragment or linking of Fab' fragments. See, e.g., Songsivilai and Lachmann, 1990, *Clin. Exp. Immunol.* 79:315-321; Kostelny et al., 1992, *J. Immunol.* 148:1547-1553. The two binding sites of a bispecific antigen binding protein or antibody will bind to two different epitopes, which can reside on the same or different protein targets.

The terms "FGF21-like signaling" and "induces FGF21-like signaling," when applied to an antigen binding protein of the present disclosure (including bispecific antigen binding proteins), means that the antigen binding protein mimics, or modulates, the in vivo biological effect induced by the binding of FGF21 to an FGF receptor (e.g., FGFR1c, FGFR2c, FGFR3c or FGFR4) and β-Klotho, and induces a biological response that otherwise would result from FGF21 binding to an FGF receptor (e.g., FGFR1c, FGFR2c, FGFR3c or FGFR4) and β-Klotho in vivo. In assessing the binding and specificity and induction of a biological response of an antigen binding protein, e.g., an antibody or immunologically functional fragment thereof, an antibody or fragment is deemed to induce a biological response when the response is equal to or greater than 5%, and preferably equal to or greater than 10%, 15%, 20%, 25%, 30%, 35%, 40%, 45%, 50%, 55%, 60%, 65%, 70%, 75%, 80%, 85%, 90% or 95%, of the activity of a wild type FGF21 standard comprising the mature form of SEQ ID NO:2 (i.e., the mature form of the human FGF21 sequence) and has the following properties: exhibiting an efficacy level of equal to or more than 5% of an FGF21 standard, with an EC50 of equal to or less than 100 nM, e.g., 90 nM, 80 nM, 70 nM, 60 nM, 50 nM, 40 nM, 30 nM, 20 nM or 10 nM in (1) the recombinant FGF21 receptor mediated luciferase-reporter cell assay of Examples 5 and 11 and (2) ERK-phosphorylation in the recombinant FGF21 receptor mediated cell assay of Examples 5 and 11. The "potency" of an antigen binding protein is defined as exhibiting an EC50 of equal to or less than 100 nM, e.g., 90 nM, 80 nM, 70 nM, 60 nM, 50 nM, 40 nM, 30 nM, 20 nM, 10 nM and preferably less than 10 nM of the antigen binding protein in the following assays: (1) the recombinant FGF21 receptor mediated luciferase-reporter cell assay of Examples 5 and 11 (2) the ERK-phosphorylation in the recombinant FGF21 receptor mediated cell assay of Examples 5 and 11.

It is noted that some of the antigen binding proteins and antigen binding protein-FGF21 fusions of the present disclosure may not induce FGF21-mediated signaling at therapeutically-applicable levels, nor is this property necessarily desirable in all circumstances. Nevertheless, antigen binding proteins and antigen binding protein-FGF21 fusions that do not induce FGF21-mediated signaling form aspects of the present disclosure and may be useful as diagnostic reagents or in other applications.

The term "polynucleotide" or "nucleic acid" includes both single-stranded and double-stranded nucleotide polymers. The nucleotides comprising the polynucleotide can be ribonucleotides or deoxyribonucleotides or a modified form of either type of nucleotide. Said modifications include base modifications such as bromouridine and inosine derivatives, ribose modifications such as 2',3'-dideoxyribose, and internucleotide linkage modifications such as phosphorothioate, phosphorodithioate, phosphoroselenoate, phosphorodiselenoate, phosphoroanilothioate, phoshoraniladate and phosphoroamidate.

The term "oligonucleotide" means a polynucleotide comprising 200 or fewer nucleotides. In some embodiments, oligonucleotides are 10 to 60 bases in length. In other embodiments, oligonucleotides are 12, 13, 14, 15, 16, 17, 18, 19, or 20 to 40 nucleotides in length. Oligonucleotides can be single stranded or double stranded, e.g., for use in the construction of a mutant gene. Oligonucleotides can be sense or antisense oligonucleotides. An oligonucleotide can include a label, including a radiolabel, a fluorescent label, a hapten or an antigenic label, for detection assays. Oligonucleotides can be used, for example, as PCR primers, cloning primers or hybridization probes.

An "isolated nucleic acid molecule" means a DNA or RNA of genomic, mRNA, cDNA, or synthetic origin or some combination thereof which is not associated with all or a portion of a polynucleotide in which the isolated polynucleotide is found in nature, or is linked to a polynucleotide to which it is not linked in nature. For purposes of this disclosure, it should be understood that "a nucleic acid molecule comprising" a particular nucleotide sequence does not encompass intact chromosomes. Isolated nucleic acid molecules "comprising" specified nucleic acid sequences can include, in addition to the specified sequences, coding sequences for up to ten or even up to twenty other proteins or portions thereof, or can include operably linked regulatory sequences that control expression of the coding region of the recited nucleic acid sequences, and/or can include vector sequences.

Unless specified otherwise, the left-hand end of any single-stranded polynucleotide sequence discussed herein is the 5' end; the left-hand direction of double-stranded polynucleotide sequences is referred to as the 5' direction. The direction of 5' to 3' addition of nascent RNA transcripts is referred to as the transcription direction; sequence regions on the DNA strand having the same sequence as the RNA transcript that are 5' to the 5' end of the RNA transcript are referred to as "upstream sequences;" sequence regions on the DNA strand having the same sequence as the RNA transcript that are 3' to the 3' end of the RNA transcript are referred to as "downstream sequences."

The term "control sequence" refers to a polynucleotide sequence that can affect the expression and processing of coding sequences to which it is ligated. The nature of such control sequences can depend upon the host organism. In particular embodiments, control sequences for prokaryotes can include a promoter, a ribosomal binding site, and a transcription termination sequence. For example, control sequences for eukaryotes can include promoters comprising one or a plurality of recognition sites for transcription factors, transcription enhancer sequences, and transcription termination sequence. "Control sequences" can include leader sequences and/or fusion partner sequences.

The term "vector" means any molecule or entity (e.g., nucleic acid, plasmid, bacteriophage or virus) used to transfer protein coding information into a host cell.

The term "expression vector" or "expression construct" refers to a vector that is suitable for transformation of a host cell and contains nucleic acid sequences that direct and/or control (in conjunction with the host cell) expression of one or more heterologous coding regions operatively linked thereto. An expression construct can include, but is not limited to, sequences that affect or control transcription, translation, and, if introns are present, affect RNA splicing of a coding region operably linked thereto.

As used herein, "operably linked" means that the components to which the term is applied are in a relationship that allows them to carry out their inherent functions under suitable conditions. For example, a control sequence in a vector that is "operably linked" to a protein coding sequence is ligated thereto so that expression of the protein coding sequence is achieved under conditions compatible with the transcriptional activity of the control sequences.

The term "host cell" means a cell that has been transformed, or is capable of being transformed, with a nucleic acid sequence and thereby expresses a gene of interest. The term includes the progeny of the parent cell, whether or not the progeny is identical in morphology or in genetic make-up to the original parent cell, so long as the gene of interest is present.

The term "transduction" means the transfer of genes from one bacterium to another, usually by bacteriophage. "Transduction" also refers to the acquisition and transfer of eukaryotic cellular sequences by replication-defective retroviruses.

The term "transfection" means the uptake of foreign or exogenous DNA by a cell, and a cell has been "transfected" when the exogenous DNA has been introduced inside the cell membrane. A number of transfection techniques are well known in the art and are disclosed herein. See, e.g., Graham et al., (1973) *Virology* 52:456; Sambrook et al., (2001) Molecular Cloning: A Laboratory Manual, supra; Davis et al., (1986) *Basic Methods in Molecular Biology*, Elsevier; Chu et al., (1981) Gene 13:197. Such techniques can be used to introduce one or more exogenous DNA moieties into suitable host cells.

The term "transformation" refers to a change in a cell's genetic characteristics, and a cell has been transformed when it has been modified to contain new DNA or RNA. For example, a cell is transformed where it is genetically modified from its native state by introducing new genetic material via transfection, transduction, or other techniques. Following transfection or transduction, the transforming DNA can recombine with that of the cell by physically integrating into a chromosome of the cell, or can be maintained transiently as an episomal element without being replicated, or can replicate independently as a plasmid. A cell is considered to have been "stably transformed" when the transforming DNA is replicated with the division of the cell.

The terms "polypeptide" or "protein" are used interchangeably herein to refer to a polymer of amino acid residues. The terms also apply to amino acid polymers in which one or more amino acid residues is an analog or mimetic of a corresponding naturally occurring amino acid, as well as to naturally occurring amino acid polymers. The terms can also encompass amino acid polymers that have been modified, e.g., by the addition of carbohydrate residues to form glycoproteins, or phosphorylated. The disclosed polypeptides and proteins can be produced by a naturally-occurring and non-recombinant cell; or they can is produced by a genetically-engineered or recombinant cell, and comprise molecules having the amino acid sequence of the native protein, or molecules having deletions from, additions to, and/or substitutions of one or more amino acids of the native sequence. The terms "polypeptide" and "protein" encompass antigen binding proteins and antigen binding protein-FGF21 fusions that specifically or selectively bind β-Klotho and antigen binding proteins and antigen binding protein-FGF21 fusions that bind (i) one or more of FGFR1c, FGFR2c, FGFR3c or FGFR4 and (ii) β-Klotho, or sequences that have deletions from, additions to, and/or substitutions of one or more amino acids of an antigen binding protein or antigen binding protein-FGF21 fusion that specifically or selectively binds to β-Klotho or both FGFR1c and β-Klotho. The term "polypeptide fragment" refers to a polypeptide that has an amino-terminal deletion, a carboxyl-terminal deletion, and/or an internal deletion as compared with the full-length protein. Such fragments can also contain modified amino acids as compared with the full-length protein. In certain embodiments, fragments are about five to 500 amino acids long. For example, fragments can be at least 5, 6, 8, 10, 14, 20, 50, 70, 100, 110, 150, 200, 250, 300, 350, 400, or 450 amino acids long. Useful polypeptide fragments include immunologically functional fragments of antibodies, including binding domains. In the case of an antigen binding protein or antigen binding protein-FGF21 fusion that specifically binds to β-Klotho or β-Klotho and one or more of FGFR1c, FGFR2c, FGFR3c and FGFR4, useful fragments include but are not limited to a CDR region, a variable domain of a heavy or light chain, a portion of an antibody chain or just its variable region including two CDRs, and the like.

The term "isolated protein" means that a subject protein (1) is free of at least some other proteins with which it would normally be found, (2) is essentially free of other proteins from the same source, e.g., from the same species, (3) is expressed by a cell from a different species, (4) has been separated from at least about 50 percent of polynucleotides, lipids, carbohydrates, or other materials with which it is associated in nature, (5) is operably associated (by covalent or noncovalent interaction) with a polypeptide with which it is not associated in nature, or (6) does not occur in nature. Typically, an "isolated protein" constitutes at least about 5%, at least about 10%, at least about 25%, or at least about 50% of a given sample. Genomic DNA, cDNA, mRNA or other RNA, of synthetic origin, or any combination thereof can encode such an isolated protein. Preferably, the isolated protein is substantially free from proteins or polypeptides or other contaminants that are found in its natural environment that would interfere with its therapeutic, diagnostic, prophylactic, research or other use.

A "variant" of a polypeptide (e.g., an antigen binding protein, antigen binding protein-FGF21 fusion or an antibody) comprises an amino acid sequence wherein one or more amino acid residues are inserted into, deleted from and/or substituted into the amino acid sequence relative to another polypeptide sequence. Variants include fusion proteins.

A "derivative" of a polypeptide is a polypeptide (e.g., an antigen binding protein, antigen binding protein-FGF21 fusion or an antibody) that has been chemically modified in some manner distinct from insertion, deletion, or substitution variants, e.g., via conjugation to another chemical moiety.

The term "naturally occurring" as used throughout the specification in connection with biological materials such as polypeptides, nucleic acids, host cells, and the like, refers to materials which are found in nature.

"Antigen binding region" means a protein, or a portion of a protein, that specifically binds a specified antigen, e.g., β-Klotho or both β-Klotho and one of FGFR1c, FGFR2c, FGFR3c and FGFR4. For example, that portion of an antigen binding protein or antigen binding protein-FGF21 fusion that contains the amino acid residues that interact with an antigen and confer on the antigen binding protein or antigen binding protein-FGF21 fusion its specificity and affinity for the antigen is referred to as "antigen binding region." An antigen binding region typically includes one or more "complementary binding regions" ("CDRs"). Certain antigen binding regions also include one or more "framework" regions. A "CDR" is an amino acid sequence that contributes to antigen binding specificity and affinity.

"Framework" regions can aid in maintaining the proper conformation of the CDRs to promote binding between the antigen binding region and an antigen.

In certain aspects, recombinant antigen binding proteins and antigen binding protein-FGF21 fusions that bind to β-Klotho or β-Klotho and one or more of FGFR1c, FGFR2c, FGFR3c and FGFR4 are provided. In this context, a "recombinant protein" is a protein made using recombinant techniques, i.e., through the expression of a recombinant nucleic acid as described herein. Methods and techniques for the production of recombinant proteins are well known in the art.

The term "compete" when used in the context of antigen binding proteins and antigen binding protein-FGF21 fusions (e.g., neutralizing antigen binding proteins, neutralizing antibodies, agonistic antigen binding protein or agonistic antibodies) that compete for the same epitope means competition between antigen binding proteins or antigen binding protein-FGF21 fusions is determined by an assay in which the antigen binding protein or antigen binding protein-FGF21 fusion (e.g., antibody or immunologically functional fragment thereof) under test prevents or inhibits specific binding of a reference antigen binding protein or antigen binding protein-FGF21 fusion (e.g., a ligand, or a reference antibody) to a common antigen (e.g., FGFR1c, FGFR2c, FGFR3c, FGFR4, β-Klotho or a fragment thereof). Numerous types of competitive binding assays can be used, for example: solid phase direct or indirect radioimmunoassay (RIA), solid phase direct or indirect enzyme immunoassay (EIA), sandwich competition assay (see, e.g., Stahli et al., (1983) *Methods in Enzymology* 9:242-253); solid phase direct biotin-avidin EIA (see, e.g., Kirkland et al., (1986) *J. Immunol.* 137:3614-3619) solid phase direct labeled assay, solid phase direct labeled sandwich assay (see, e.g., Harlow and Lane, (1988) *Antibodies, A Laboratory Manual*, Cold Spring Harbor Press); solid phase direct label RIA using 1-125 label (see, e.g., Morel et al., (1988) *Molec. Immunol.* 25:7-15); solid phase direct biotin-avidin EIA (see, e.g., Cheung, et al., (1990) *Virology* 176:546-552); and direct labeled RIA (Moldenhauer et al., (1990) *Scand. J. Immunol.* 32:77-82). Typically, such an assay involves the use of purified antigen bound to a solid surface or cells bearing either of these, an unlabelled test antigen binding protein or antigen binding protein-FGF21 fusion and a labeled reference antigen binding protein or antigen binding protein-FGF21 fusion. Competitive inhibition is measured by determining the amount of label bound to the solid surface or cells in the presence of the test antigen binding protein or antigen binding protein-FGF21 fusion. Usually the test antigen binding protein or antigen binding protein-FGF21 fusion is present in excess. Antigen binding proteins or antigen binding protein-FGF21 fusions identified by competition assay (competing antigen binding proteins) include antigen binding proteins and antigen binding protein-FGF21 fusions binding to the same epitope as the reference antigen binding proteins or antigen binding protein-FGF21 fusions and antigen binding proteins or antigen binding protein-FGF21 fusions binding to an adjacent epitope sufficiently proximal to the epitope bound by the reference antigen binding protein or antigen binding protein-FGF21 fusion for steric hindrance to occur. Additional details regarding methods for determining competitive binding are provided in the examples herein. Usually, when a competing antigen binding protein is present in excess, it will inhibit specific binding of a reference antigen binding protein or antigen binding protein-FGF21 fusion to a common antigen by at least 40%, 45%, 50%, 55%, 60%, 65%, 70% or 75%. In some instance, binding is inhibited by at least 80%, 85%, 90%, 95%, or 97% or more.

The term "antigen" refers to a molecule or a portion of a molecule capable of being bound by a selective binding agent, such as an antigen binding protein or antigen binding protein-FGF21 fusion (including, e.g., an antibody or immunological functional fragment thereof), and additionally is capable of being used in an animal to produce antibodies capable of binding to that antigen. An antigen can possess one or more epitopes that are capable of interacting with different antigen binding proteins, e.g., antibodies.

The term "epitope" is the portion of a molecule that is bound by an antigen binding protein or antigen binding protein-FGF21 fusion (for example, an antibody). The term includes any determinant capable of specifically binding to an antigen binding protein or antigen binding protein-FGF21 fusion, such as an antibody. An epitope can be contiguous or non-contiguous (e.g., (i) in a single-chain polypeptide, amino acid residues that are not contiguous to one another in the polypeptide sequence but that within in context of the molecule are bound by the antigen binding protein or antigen binding protein-FGF21 fusion, or (ii) in a multimeric receptor comprising two or more individual components, e.g., FGFR1c, FGFR2c, FGFR3c or FGFR4, and β-Klotho, amino acid residues that are present on one or more of the individual components, but which are still bound by the antigen binding protein or antigen binding protein-FGF21 fusion). In certain embodiments, epitopes can be mimetic in that they comprise a three dimensional structure that is similar to an epitope used to generate the antigen binding protein or antigen binding protein-FGF21 fusion, yet comprise none or only some of the amino acid residues found in that epitope used to generate the antigen binding protein or antigen binding protein-FGF21 fusion. Most often, epitopes reside on proteins, but in some instances can reside on other kinds of molecules, such as nucleic acids. Epitope determinants can include chemically active surface groupings of molecules such as amino acids, sugar side chains, phosphoryl or sulfonyl groups, and can have specific three dimensional structural characteristics, and/or specific charge characteristics. Generally, antigen binding proteins or antigen binding protein-FGF21 fusions specific for a particular target antigen will preferentially recognize an epitope on the target antigen in a complex mixture of proteins and/or macromolecules.

The term "identity" refers to a relationship between the sequences of two or more polypeptide molecules or two or more nucleic acid molecules, as determined by aligning and comparing the sequences. "Percent identity" means the percent of identical residues between the amino acids or nucleotides in the compared molecules and is calculated based on the size of the smallest of the molecules being compared. For these calculations, gaps in alignments (if any) must be addressed by a particular mathematical model or computer program (i.e., an "algorithm"). Methods that can be used to calculate the identity of the aligned nucleic acids or polypeptides include those described in *Computational Molecular Biology*, (Lesk, A. M., ed.), (1988) New York: Oxford University Press; Biocomputing Informatics and Genome Projects, (Smith, D. W., ed.), 1993, New York: Academic Press; Computer Analysis of Sequence Data, Part I, (Griffin, A. M., and Griffin, H. G., eds.), 1994, New Jersey: Humana Press; von Heinje, G., (1987) Sequence Analysis in Molecular Biology, New York: Academic Press; Sequence Analysis Primer, (Gribskov, M. and Devereux, J., eds.), 1991, New York: M. Stockton Press; and Carillo et al., (1988) *SIAM J. Applied Math.* 48:1073.

In calculating percent identity, the sequences being compared are aligned in a way that gives the largest match between the sequences. The computer program used to determine percent identity can be, for example, the GCG program package, which includes GAP (Devereux et al., (1984) *Nucl. Acid Res.* 12:387; Genetics Computer Group, University of Wisconsin, Madison, Wis.). The computer algorithm GAP is used to align the two polypeptides or polynucleotides for which the percent sequence identity is to be determined. The sequences are aligned for optimal matching of their respective amino acid or nucleotide (the "matched span", as determined by the algorithm). A gap opening penalty (which is calculated as 3× the average diagonal, wherein the "average diagonal" is the average of the diagonal of the comparison matrix being used; the "diagonal" is the score or number assigned to each perfect amino acid match by the particular comparison matrix) and a gap extension penalty (which is usually 1/10 times the gap opening penalty), as well as a comparison matrix such as PAM 250 or BLOSUM 62 are used in conjunction with the algorithm. In certain embodiments, a standard comparison matrix (see, Dayhoff et al., (1978) *Atlas of Protein Sequence and Structure* 5:345-352 for the PAM 250 comparison matrix; Henikoff et al., (1992) *Proc. Natl. Acad. Sci. U.S.A.* 89:10915-10919 for the BLOSUM 62 comparison matrix) is also used by the algorithm.

Recommended parameters for determining percent identity for polypeptides or nucleotide sequences using the GAP program are the following:

Algorithm: Needleman et al., 1970, *J. Mol. Biol.* 48:443-453;

Comparison matrix: BLOSUM 62 from Henikoff et al., 1992, supra;

Gap Penalty: 12 (but with no penalty for end gaps)

Gap Length Penalty: 4

Threshold of Similarity: 0

Certain alignment schemes for aligning two amino acid sequences can result in matching of only a short region of the two sequences, and this small aligned region can have very high sequence identity even though there is no significant relationship between the two full-length sequences. Accordingly, the selected alignment method (e.g., the GAP program) can be adjusted if so desired to result in an alignment that spans at least 50 contiguous amino acids of the target polypeptide.

As used herein, "substantially pure" means that the described species of molecule is the predominant species present, that is, on a molar basis it is more abundant than any other individual species in the same mixture. In certain embodiments, a substantially pure molecule is a composition wherein the object species comprises at least 50% (on a molar basis) of all macromolecular species present. In other embodiments, a substantially pure composition will comprise at least 80%, 85%, 86%, 87%, 88%, 89%, 90%, 95%, 96%, 97%, 98% or 99% of all macromolecular species present in the composition. In other embodiments, the object species is purified to essential homogeneity wherein contaminating species cannot be detected in the composition by conventional detection methods and thus the composition consists of a single detectable macromolecular species.

The terms "treat" and "treating" refer to any indicia of success in the treatment or amelioration of an injury, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. For example, certain methods presented herein successfully treat diabetes, obesity and dyslipidemia, either prophylactically or as an acute treatment, and/or decrease plasma glucose levels and circulating triglyceride and cholesterol levels and/or ameliorate a symptom associated with type 2 diabetes, obesity or dyslipidemia.

An "effective amount" is generally an amount sufficient to reduce the severity and/or frequency of symptoms, eliminate the symptoms and/or underlying cause, prevent the occurrence of symptoms and/or their underlying cause, and/or improve or remediate the damage that results from or is associated with diabetes, obesity or dyslipidemia. In some embodiments, the effective amount is a therapeutically effective amount or a prophylactically effective amount. A "therapeutically effective amount" is an amount sufficient to remedy a disease state (e.g., diabetes, obesity or dyslipidemia) or symptoms, particularly a state or symptoms associated with the disease state, or otherwise prevent, hinder, retard or reverse the progression of the disease state or any other undesirable symptom associated with the disease in any way whatsoever. A "prophylactically effective amount" is an amount of a pharmaceutical composition that, when administered to a subject, will have the intended prophylactic effect, e.g., preventing or delaying the onset (or reoccurrence) of diabetes, obesity or dyslipidemia, or reducing the likelihood of the onset (or reoccurrence) of diabetes, obesity or dyslipidemia or associated symptoms. The full therapeutic or prophylactic effect does not necessarily occur by administration of one dose, and can occur only after administration of a series of doses. Thus, a therapeutically or prophylactically effective amount can be administered in one or more administrations.

The term "amino acid" is employed per its normal meaning in the art. The twenty naturally-occurring amino acids and their abbreviations follow conventional usage. See, e.g., Immunology-A Synthesis, $2^{nd}$ Edition, (E. S. Golub and D. R. Green, eds.), Sinauer Associates: Sunderland, Mass. (1991), incorporated herein by reference for any purpose. Stereoisomers (e.g., D-amino acids) of the twenty conventional amino acids, unnatural or non-naturally occurring amino acids such as α-,α-disubstituted amino acids, N-alkyl amino acids, and other unconventional amino acids can also be suitable components for polypeptides and are included in the term "amino acid." Examples of non-naturally amino acids (which can be substituted for any naturally-occurring amino acid found in any sequence disclosed herein, as desired) include: 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine, and other similar amino acids and imino acids (e.g., 4-hydroxyproline). In the polypeptide notation used herein, the left-hand direction is the amino-terminal (or "N-terminal") direction and the right-hand direction is the carboxyl-terminal (or "C-terminal") direction, in accordance with standard usage and convention. The term "amino acid" also encompasses non-naturally occurring amino acids. A non-limiting list of examples of non-naturally occurring amino acids that can be inserted into an antigen binding protein or antigen binding protein-FGF21 fusion sequence or substituted for a wild-type residue in an antigen binding sequence includes β-amino acids, homoamino acids, cyclic amino acids and amino acids with derivatized side chains. Examples include (in the L-form or D-form; abbreviated as in parentheses): citrulline (Cit), homocitrulline (hCit), Nα-methylcitrulline (NMeCit), Nα-methylhomocitrulline (Nα-MeHoCit), ornithine (Orn), Nα-Methylornithine (Nα-MeOrn or NMeOrn), sarcosine (Sar), homolysine (hLys or hK), homoarginine (hArg or hR), homoglutamine (hQ), Nα-methylarginine (NMeR), Nα-methylleucine (Nα-MeL or NMeL), N-methylhomolysine (NMeHoK), Nα-methylglutamine (NMeQ), norleucine (Nle), norvaline (Nva), 1,2,3,4-tetrahydroisoquinoline (Tic), Octahydroindole-2-carboxylic acid (Oic), 3-(1-naphthyl) alanine (1-Nal), 3-(2-naphthyl)alanine (2-Nal), 1,2,3,4-tetrahydroisoquinoline (Tic), 2-indanylglycine (IgI), para-iodophenylalanine (pI-Phe), para-aminophenylalanine (4AmP or 4-Amino-Phe), 4-guanidino phenylalanine (Guf), glycyllysine (abbreviated "K(Nε-glycyl)" or "K(glycyl)" or "K(gly)"), nitrophenylalanine (nitrophe), aminophenylalanine (aminophe or Amino-Phe), benzylphenylalanine (benzylphe), γ-carboxyglutamic acid (γ-carboxyglu), hydroxyproline (hydroxypro), p-carboxyl-phenylalanine (Cpa), α-aminoadipic acid (Aad), Nα-methyl valine (NMeVal), N-α-methyl leucine (NMeLeu), Nα-methylnorleucine (NMeNle), cyclopentylglycine (Cpg), cyclohexylglycine (Chg), acetylarginine (acetylarg), α,β-diaminopropionoic acid (Dpr), α,γ-diaminobutyric acid (Dab), diaminopropionic acid (Dap), cyclohexylalanine (Cha), 4-methyl-phenylalanine (MePhe), β,β-diphenyl-alanine (BiPhA), aminobutyric acid (Abu), 4-phenyl-phenylalanine (or biphenylalanine; 4Bip), α-amino-isobutyric acid (Aib), beta-alanine, beta-aminopropionic acid, piperidinic acid, aminocaprioic acid, aminoheptanoic acid, aminopimelic acid, desmosine, diaminopimelic acid, N-ethylglycine, N-ethylaspargine, hydroxylysine, allo-hydroxylysine, isodesmosine, allo-isoleucine, N-methylglycine, N-methylisoleucine, N-methylvaline, 4-hydroxyproline (Hyp), γ-carboxyglutamate, ε-N,N,N-trimethyllysine, ε-N-acetyllysine, O-phosphoserine, N-acetylserine, N-formylmethionine, 3-methylhistidine, 5-hydroxylysine, ω-methylarginine, 4-Amino-O-Phthalic Acid (4APA), and other similar amino acids, and derivatized forms of any of those specifically listed.

General Overview

FGF21 is a secreted polypeptide that is a member of a subfamily of fibroblast growth factors (FGFs). Transgenic mice overexpressing FGF21 exhibit metabolic phenotypes of slow growth rate, low plasma glucose as well as triglyceride levels, and an absence of age-associated type 2 diabetes, islet hyperplasia, and obesity. Pharmacological administration of recombinant FGF21 protein in diabetic rodent models, results in normalized levels of plasma glucose, reduced triglyceride and cholesterol levels, improved glucose tolerance and insulin sensitivity. In addition, FGF21 reduces body weight and body fat by increasing energy expenditure, physical activity, and metabolic rate.

It has been suggested that a complex comprising β-klotho and fibroblast growth factor recptor 1c (FGFR1c) can elicit an in vivo effect similar to the effect induced by FGF21. Based on this observation bispecific antibodies and antigen binding protein-FGF21 fusions were designed based on an immunoglobulin (IgG) scaffold. The disclosed bispecific antigen binding proteins bind specifically to β-klotho via the Fab regions and also to FGFR1c via the $C_H3$ loop of the Fc region. The antigen binding protein-FGF21 fusions provided herein comprise or the antigen binding protein component and a FGF21 component; the antigen binding protein component binds to β-Klotho via the Fab regions of the antigen binding component and associates with FGFR1c, FGFR2c, FGFR3c and/or FGFR4 via the FGF21 component of the fusion. In another embodiment, the antigen binding protein component of an antigen binding protein-FGF21 fusion can associate with FGFR1c, FGFR2c, FGFR3c and/or FGFR4 via the Fab regions of the antigen binding component and with β-Klotho via the FGF21 component of the fusion. The specificity of an antigen binding protein-FGF21 fusion will depend on whether the N- or C-terminal of the FGF21 component is truncated and on the specificity of the antigen binding component.

In the antigen binding proteins disclosed herein the β-klotho binding sites are positioned on the Fab domains, which are then joined to an Fc region comprising FGFR1c-binding peptides situated in the CH3 loop of the Fc region.

Antigen binding proteins that bind β-Klotho or β-Klotho and one or more of FGFR1c, FGFR2c, FGFR3c, and FGFR4, are provided herein, as well as antigen binding protein-FGF21 fusions. A unique property of the antigen binding proteins and antigen binding protein-FGF21 fusions disclosed herein is the agonistic nature of these proteins, specifically the ability to induce FGF21-like signaling, in the case of antigen binding proteins by binding to β-Klotho via the Fab region and associating with FGFR1c via the peptide inserted in the native Fc region and in the case of in the case of antigen binding protein-FGF21 fusions by associating with either (a) β-Klotho via the Fab region of the antigen binding protein component and with FGFR1c, FGFR2c, FGFR3c, and/or FGFR4 via the FGF21 component or (b) FGFR1c, FGFR2c, FGFR3c and/or FGFR4 via the Fab region of the antigen binding protein component and β-Klotho via the FGF21 component.

More remarkably and specifically, some of the antigen binding proteins and antigen binding protein-FGF21 fusions disclosed herein induce FGF21-like signaling in several in vitro cell-based assays, including the ELK-luciferase reporter assay of Examples 5 and 11 under the following conditions (1) the binding to and activity of the FGF21 receptor is β-Klotho dependent; (2) the activity is selective to FGFR1c/β-Klotho complex; (3) the binding to the FGFR1c/β-Klotho triggers FGF21-like signaling pathways and (4) the potency (EC50) is comparable to a wild-type FGF21 standard comprising the mature form of SEQ ID NO:2, as measured in the following cell-based assays: (1) the recombinant FGF21 receptor mediated luciferase-reporter cell assay of Examples 5 and 11; and (2) the ERK-phosphorylation in the recombinant FGF21 receptor mediated cell assay of Examples 5 and 11. The disclosed antigen binding proteins and antigen binding protein-FGF21 fusions, therefore, are expected to exhibit activities in vivo that are consistent with the natural biological function of FGF21. This property makes the disclosed antigen binding proteins and antigen binding protein-FGF21 fusions viable therapeutics for the treatment of metabolic diseases such as type 2 diabetes, obesity, dyslipidemia, NASH, cardiovascular disease, metabolic syndrome and broadly any disease or condition in which it is desirable to mimic or augment the in vivo effects of FGF21.

The antigen binding proteins and antigen binding protein-FGF21 fusions provided are polypeptides into which one or more complementarity determining regions (CDRs), as described herein, are embedded and/or joined. In some antigen binding proteins, the CDRs are embedded into a "framework" region, which orients the CDR(s) such that the proper antigen binding properties of the CDR(s) is achieved. In general, the antigen binding proteins and antigen binding protein-FGF21 fusions that are provided can facilitate or enhance the interaction between FGFR1c and β-Klotho, and can substantially induce FGF21-like signaling.

Certain antigen binding proteins and antigen binding protein-FGF21 fusions described herein are antibodies or are derived from antibodies. In certain embodiments, the polypeptide structure of the antigen binding proteins is based on antibodies, including, but not limited to, monoclonal antibodies, bispecific antibodies, minibodies, domain antibodies, synthetic antibodies (sometimes referred to herein as "antibody mimetics"), chimeric antibodies, humanized antibodies, human antibodies, antibody fusions (sometimes referred to herein as "antibody conjugates"), and fragments thereof. The various structures are further described herein below.

The antigen binding proteins and antigen binding protein-FGF21 fusions provided herein have been demonstrated to bind to β-Klotho or β-Klotho and one or more of FGFR1c, FGFR2c, FGFR3c, and FGFR4, and particularly the human forms of FGFR1c and/or β-Klotho to varying degrees. The antigen binding proteins and antigen binding protein-FGF21 fusions that are provided mimic the natural in vivo biological activity of FGF21. As a consequence, the antigen binding proteins and antigen binding protein-FGF21 fusions provided herein are capable of activating FGF21-like signaling activity to varying degrees. In particular, antigen binding proteins and antigen binding protein-FGF21 fusions binding to these epitopes can have one or more of the following activities in vivo: induction of FGF21-like signal transduction pathways, lowering blood glucose levels, lowering circulating lipid levels, improving metabolic parameters and other physiological effects induced in vivo by the formation of the ternary complex of FGFR1c, β-Klotho and FGF21, for example in conditions such as type 2 diabetes, obesity, dyslipidemia, NASH, cardiovascular disease, and metabolic syndrome.

The antigen binding proteins and antigen binding protein-FGF21 fusions that are disclosed herein have a variety of utilities. Some of the antigen binding proteins and antigen binding protein-FGF21 fusions, for instance, are useful in specific binding assays, in the affinity purification of FGFR1c and/or β-Klotho, in particular human FGFR1c and/β-Klotho, or ligands of these proteins, and in screening assays to identify other agonists of FGF21-like signalling activity.

The antigen binding proteins and antigen binding protein-FGF21 fusions that specifically bind β-Klotho or β-Klotho and one or more of FGFR1c, FGFR2c, FGFR3c, and FGFR4 that are disclosed herein can be used in a variety of treatment applications, as explained herein. For example, certain antigen binding proteins and antigen binding protein-FGF21 fusions are useful for treating conditions associated with FGF21-like signaling processes in a patient, such as reducing, alleviating, or treating type 2 diabetes, obesity, dyslipidemia, NASH, cardiovascular disease, and metabolic syndrome. Other uses for the antigen binding proteins and antigen binding protein-FGF21 fusions include, for example, diagnosis of diseases or conditions associated with β-Klotho, FGFR1c, FGFR2c, FGFR3c, FGFR4 or FGF21, and screening assays to determine the presence or absence of these molecules. The antigen binding proteins and antigen binding protein-FGF21 fusions described herein may be useful in treating conditions, symptoms and/or the pathology associated with decreased FGF21-like signalling activity. Exemplary conditions include, but are not limited to, diabetes, obesity, NASH and dyslipidemia.

FGF21

The antigen binding proteins and antigen binding protein-FGF21 fusions disclosed herein can induce FGF21-mediated signaling, as defined herein, to varying degrees. In vivo, the mature form of FGF21 is the active form of the molecule. The nucleotide sequence encoding full length FGF21 is provided; the nucleotides encoding the signal sequence are underlined.

(SEQ ID NO: 1)
<u>ATG GAC TCG GAC GAG ACC GGG TTC GAG CAC TCA GGA</u>

<u>CTG TGG GTT TCT GTG CTG GCT GGT CTT CTG CTG GGA</u>

<u>GCC TGC CAG GCA</u> CAC CCC ATC CCT GAC TCC AGT CCT

CTC CTG CAA TTC GGG GGC CAA GTC CGG CAG CGG TAC

CTC TAC ACA GAT GAT GCC CAG CAG ACA GAA GCC CAC

CTG GAG ATC AGG GAG GAT GGG ACG GTG GGG GGC GCT

GCT GAC CAG AGC CCC GAA AGT CTC CTG CAG CTG AAA

GCC TTG AAG CCG GGA GTT ATT CAA ATC TTG GGA GTC

AAG ACA TCC AGG TTC CTG TGC CAG CGG CCA GAT GGG

GCC CTG TAT GGA TCG CTC CAC TTT GAC CCT GAG GCC

TGC AGC TTC CGG GAG CTG CTT CTT GAG GAC GGA TAC

AAT GTT TAC CAG TCC GAA GCC CAC GGC CTC CCG CTG

CAC CTG CCA GGG AAC AAG TCC CCA CAC CGG GAC CCT

GCA CCC CGA GGA CCA GCT CGC TTC CTG CCA CTA CCA

GGC CTG CCC CCC GCA CCC CCG GAG CCA CCC GGA ATC

CTG GCC CCC CAG CCC CCC GAT GTG GGC TCC TCG GAC

CCT CTG AGC ATG GTG GGA CCT TCC CAG GGC CGA AGC

CCC AGC TAC GCT TCC TGA

The amino acid sequence of full length FGF21 is provided; the amino acids that make up the signal sequence are underlined:

(SEQ ID NO: 2)
<u>M D S D E T G F E H S G L W V S V L A G L L L G A C Q A</u> H P I P D S S

P L L Q F G G Q V R Q R Y L Y T D D A Q Q T E A H L E I R E D G T V

G G A A D Q S P E S L L Q L K A L K P G V I Q I L G V K T S R F L C Q

R P D G A L Y G S L H F D P E A C S F R E L L L E D G Y N V Y Q S E A

H G L P L H L P G N K S P H R D P A P R G P A R F L P L P G L P P A P P

E P P G I L A P Q P P D V G S S D P L S M V G P S Q G R S P S Y A S

Thus, the mature form of FGF21 comprises the amino acid sequence:

(SEQ ID NO: 341)
HPIPDSSPLLQFGGQVRQRYLYTDDAQQTEAHLEI
REDGTVGGAADQSPESLLQLKALKPGVIQILGVKT
SRFLCQRPDGALYGSLHFDPEACSFRELLLEDGYN
VYQSEAHGLPLHLPGNKSPHRDPAPRGPARFLPLP
GLPPAPPEPPGILAPQPPDVGSSDPLSMVGPSQGRS
PSYAS

A truncated form of FGF21 comprising residues 1-169 comprises the amino acid sequence:

(SEQ ID NO: 342)
HPIPDSSPLLQFGGQVRQRYLYTDDAQQTEAHLEIREDGTVGGAADQS
PESLLQLKALKPGVIQILGVKTSRFLCQRPDGALYGSLHFDPEACSFRE
LLLEDGYNVYQSEAHGLPLHLPGNKSPHRDPAPRGPARFLPLPGLPPA
PPEPPGILAPQPPDVGSSDPLSMV

A truncated form of FGF21 comprising residues 1-170 comprises the amino acid sequence:

(SEQ ID NO: 343)
HPIPDSSPLLQFGGQVRQRYLYTDDAQQTEAHLEIREDGTVGGAADQS
PESLLQLKALKPGVIQILGVKTSRFLCQRPDGALYGSLHFDPEACSFRE
LLLEDGYNVYQSEAHGLPLHLPGNKSPHRDPAPRGPARFLPLPGLPPA
PPEPPGILAPQPPDVGSSDPLSMVG

FGF21 can exist in at least two different forms, which differ from one another at position 146 (underlined and in bold in SEQ ID NO: 341 above); in one form the residue at this position is a proline as in SEQ ID NO:341 and in another form it is a leucine. Throughout the present disclosure, unless indicated otherwise, the term FGF21 encompasses these and any other known or discovered isoforms of SEQ ID NO:341).

As described herein, an FGF21 can also include fragments. As used herein, the terms are used interchangeably to mean a protein, in particular and unless otherwise specified, a human protein, that upon association with β-Klotho and FGFR1c, FGFR2c, FGFR3c and/or FGFR4 induces FGF21-like signaling activity.

FGFR1c

The antigen binding proteins and the antigen binding protein component of the antigen binding protein-FGF21 fusions disclosed herein bind to or associate with FGFR1c, in particular human FGFR1c, when associated with β-Klotho, to varying degrees. The nucleotide sequence encoding human FGFR1c (GenBank Accession Number NM_023110) is provided:

(SEQ ID NO: 3)
ATGTGGAGCTGGAAGTGCCTCCTCTTCTGGGCTGTGCTGGTCACAG

CCACACTCTGCACCGCTAGGCCGTCCCCGACCTTGCCTGAACAAGC

CCAGCCCTGGGGAGCCCCTGTGGAAGTGGAGTCCTTCCTGGTCCAC

CCCGGTGACCTGCTGCAGCTTCGCTGTCGGCTGCGGGACGATGTGC

AGAGCATCAACTGGCTGCGGGACGGGGTGCAGCTGGCGGAAAGCA

ACCGCACCCGCATCACAGGGGAGGAGGTGGAGGTGCAGGACTCCG

TGCCCGCAGACTCCGGCCTCTATGCTTGCGTAACCAGCAGCCCCTC

GGGCAGTGACACCACCTACTTCTCCGTCAATGTTTCAGATGCTCTCC

CCTCCTCGGAGGATGATGATGATGATGATGACTCCTCTTCAGAGGA

GAAAGAAACAGATAACACCAAACCAAACCGTATGCCCGTAGCTCC

ATATTGGACATCACCAGAAAAGATGGAAAAGAAATTGCATGCAGT

GCCGGCTGCCAAGACAGTGAAGTTCAAATGCCCTTCCAGTGGGACA

CCAAACCCAACACTGCGCTGGTTGAAAAATGGCAAAGAATTCAAA

CCTGACCACAGAATTGGAGGCTACAAGGTCCGTTATGCCACCTGGA

GCATCATAATGGACTCTGTGGTGCCCTCTGACAAGGGCAACTACAC

CTGCATTGTGGAGAATGAGTACGGCAGCATCAACCACACATACCA

GCTGGATGTCGTGGAGCGGTCCCCTCACCGGCCCATCCTGCAAGCA

GGGTTGCCCGCCAACAAAACAGTGGCCCTGGGTAGCAACGTGGAG

TTCATGTGTAAGGTGTACAGTGACCCGCAGCCGCACATCCAGTGGC

TAAAGCACATCGAGGTGAATGGGAGCAAGATTGGCCCAGACAACC

TGCCTTATGTCCAGATCTTGAAGACTGCTGGAGTTAATACCACCGA

CAAAGAGATGGAGGTGCTTCACTTAAGAAATGTCTCCTTTGAGGAC

GCAGGGGAGTATACGTGCTTGGCGGGTAACTCTATCGGACTCTCCC

ATCACTCTGCATGGTTGACCGTTCTGGAAGCCCTGGAAGAGAGGCC

GGCAGTGATGACCTCGCCCCTGTACCTGGAGATCATCATCTATTGC

ACAGGGGCCTTCCTCATCTCCTGCATGGTGGGGTCGGTCATCGTCT

ACAAGATGAAGAGTGGTACCAAGAAGAGTGACTTCCACAGCCAGA

TGGCTGTGCACAAGCTGGCCAAGAGCATCCCTCTGCGCAGACAGGT

AACAGTGTCTGCTGACTCCAGTGCATCCATGAACTCTGGGGTTCTT

CTGGTTCGGCCATCACGGCTCTCCTCCAGTGGGACTCCCATGCTAG

CAGGGGTCTCTGAGTATGAGCTTCCCGAAGACCCTCGCTGGGAGCT

GCCTCGGGACAGACTGGTCTTAGGCAAACCCCTGGGAGAGGGCTG

CTTTGGGCAGGTGGTGTTGGCAGAGGCTATCGGGCTGGACAAGGA

CAAACCCAACCGTGTGACCAAAGTGGCTGTGAAGATGTTGAAGTC

-continued
```
GGACGCAACAGAGAAAGACTTGTCAGACCTGATCTCAGAAATGGA

GATGATGAAGATGATCGGGAAGCATAAGAATATCATCAACCTGCT

GGGGGCCTGCACGCAGGATGGTCCCTTGTATGTCATCGTGGAGTAT

GCCTCCAAGGGCAACCTGCGGGAGTACCTGCAGGCCCGGAGGCCC

CCAGGGCTGGAATACTGCTACAACCCCAGCCACAACCCAGAGGAG

CAGCTCTCCTCCAAGGACCTGGTGTCCTGCGCCTACCAGGTGGCCC

GAGGCATGGAGTATCTGGCCTCCAAGAAGTGCATACACCGAGACC

TGGCAGCCAGGAATGTCCTGGTGACAGAGGACAATGTGATGAAGA

TAGCAGACTTTGGCCTCGCACGGGACATTCACCACATCGACTACTA

TAAAAAGACAACCAACGGCCGACTGCCTGTGAAGTGGATGGCACC

CGAGGCATTATTTGACCGGATCTACACCCACCAGAGTGATGTGTGG

TCTTTCGGGGTGCTCCTGTGGGAGATCTTCACTCTGGGCGGCTCCCC

ATACCCCGGTGTGCCTGTGGAGGAACTTTTCAAGCTGCTGAAGGAG

GGTCACCGCATGGACAAGCCCAGTAACTGCACCAACGAGCTGTAC

ATGATGATGCGGGACTGCTGGCATGCAGTGCCCTCACAGAGACCCA

CCTTCAAGCAGCTGGTGGAAGACCTGGACCGCATCGTGGCCTTGAC

CTCCAACCAGGAGTACCTGGACCTGTCCATGCCCCTGGACCAGTAC

TCCCCCAGCTTTCCCGACACCCGGAGCTCTACGTGCTCCTCAGGGG

AGGATTCCGTCTTCTCTCATGAGCCGCTGCCCGAGGAGCCCTGCCT

GCCCCGACACCCAGCCCAGCTTGCCAATGGCGGACTCAAACGCCG

CTGA.
```

The amino acid sequence of human FGFR1c (GenBank Accession Number NP_075598) is provided:

(SEQ ID NO: 4)
```
MWSWKCLLFWAVLVTATLCTARPSPTLPEQAQPWGAPVEVESFLVHP

GDLLQLRCRLRDDVQSINWLRDGVQLAESNRTRITGEEVEVQDSVPA

DSGLYACVTSSPSGSDTTYFSVNVSDALPSSEDDDDDDSSSEEKETD

NTKPNRMPVAPYWTSPEKMEKKLHAVPAAKTVKFKCPSSGTPNPTLR

WLKNGKEFKPDHRIGGYKVRYATWSIIMDSVVPSDKGNYTCIVENEY

GSINHTYQLDVVERSPHRPILQAGLPANKTVALGSNVEFMCKVYSDPQ

PHIQWLKHIEVNGSKIGPDNLPYVQILKTAGVNTTDKEMEVLHLRNVS

FEDAGEYTCLAGNSIGLSHHSAWLTVLEALEERPAVMTSPLYLEIIIYC

TGAFLISCMVGSVIVYKMKSGTKKSDFHSQMAVHKLAKSIPLRRQVT

VSADSSASMNSGVLLVRPSRLSSSGTPMLAGVSEYELPEDPRWELPRD

RLVLGKPLGEGCFGQVVLAEAIGLDKDKPNRVTKVAVKMLKSDATE

KDLSDLISEMEMMKMIGKHKNIINLLGACTQDGPLYVIVEYASKGNLR

EYLQARRPPGLEYCYNPSHNPEEQLSSKDLVSCAYQVARGMEYLASK

KCIHRDLAARNVLVTEDNVMKIADFGLARDIHHIDYYKKTTNGRLPV

KWMAPEALFDRIYTHQSDVWSFGVLLWEIFTLGGSPYPGVPVEELFKL

LKEGHRMDKPSNCTNELYMMMRDCWHAVPSQRPTFKQLVEDLDRIV
```

-continued
```
ALTSNQEYLDLSMPLDQYSPSFPDTRSSTCSSGEDSVFSHEPLPEEPCL

PRHPAQLANGGLKRR.
```

The antigen binding proteins and the antigen binding protein component of the antigen binding protein-FGF21 fusions described herein bind or associate with the extracellular portion of FGFR1c to varying degrees which, in some embodiments, may be bound to or associated with β-Klotho. An example of an extracellular region of FGFR1c is:

(SEQ ID NO: 5)
```
MWSWKCLLFWAVLVTATLCTARPSPTLPEQAQPWGAPVEVESFLVHPGD

LLQLRCRLRDDVQSINWLRDGVQLAESNRTRITGEEVEVQDSVPADSGL

YACVTSSPSGSDTTYFSVNVSDALPSSEDDDDDDSSSEEKETDNTKPN

RMPVAPYWTSPEKMEKKLHAVPAAKTVKFKCPSSGTPNPTLRWLKNGKE

FKPDHRIGGYKVRYATWSIIMDSVVPSDKGNYTCIVENEYGSINHTYQL

DVVERSPHRPILQAGLPANKTVALGSNVEFMCKVYSDPQPHIQWLKHIE

VNGSKIGPDNLPYVQILKTAGVNTTDKEMEVLHLRNVSFEDAGEYTCLA

GNSIGLSHHSAWLTVLEALEERPAVMTSPLY.
```

As described herein, FGFR1c proteins can also include fragments. As used herein, the terms are used interchangeably to mean a receptor, in particular and unless otherwise specified, a human receptor, that upon association with β-Klotho and FGF21 induces FGF21-like signaling activity.

The term FGFR1c also includes post-translational modifications of the FGFR1c amino acid sequence, for example, possible N-linked glycosylation sites. Thus, the antigen binding proteins can bind to or be generated from proteins glycosylated at one or more of the positions.

β-Klotho

The antigen binding proteins and the antigen binding protein component of the antigen binding protein-FGF21 fusions disclosed herein bind to the extracellular domain of β-Klotho to varying degrees, in particular to human β-Klotho. The nucleotide sequence encoding full-length human β-Klotho (GenBank Accession Number NM_175737) is provided:

(SEQ ID NO: 6)
```
ATGAAGCCAGGCTGTGCGGCAGGATCTCCAGGGAATGAATGGATT

TTCTTCAGCACTGATGAAATAACCACACGCTATAGGAATACAATGT

CCAACGGGGATTGCAAAGATCTGTCATCCTGTCAGCACTTATTCT

GCTACGAGCTGTTACTGGATTCTCTGGAGATGGAAGAGCTATATGG

TCTAAAAATCCTAATTTTACTCCGGTAAATGAAAGTCAGCTGTTTCT

CTATGACACTTTCCCTAAAAACTTTTTCTGGGGTATTGGGACTGGA

GCATTGCAAGTGGAAGGGAGTTGGAAGAAGGATGGAAAAGGACCT

TCTATATGGGATCATTTCATCCACACACACCTTAAAAATGTCAGCA

GCACGAATGGTTCCAGTGACAGTTATATTTTCTGGAAAAAGACTT

ATCAGCCCTGGATTTTATAGGAGTTTCTTTTTATCAATTTTCAATTT

CCTGGCCAAGGCTTTTCCCCGATGGAATAGTAACAGTTGCCAACGC

AAAAGGTCTGCAGTACTACAGTACTCTTCTGGACGCTCTAGTGCTT
```

-continued

```
AGAAACATTGAACCTATAGTTACTTTATACCACTGGGATTTGCCTTT
GGCACTACAAGAAAAATATGGGGGTGGAAAAATGATACCATAAT
AGATATCTTCAATGACTATGCCACATACTGTTTCCAGATGTTTGGG
GACCGTGTCAAATATTGGATTACAATTCACAACCCATATCTAGTGG
CTTGGCATGGGTATGGGACAGGTATGCATGCCCCTGGAGAGAAGG
GAAATTTAGCAGCTGTCTACACTGTGGACACAACTTGATCAAGGC
TCACTCGAAAGTTTGGCATAACTACAACACACATTTCCGCCCACAT
CAGAAGGGTTGGTTATCGATCACGTTGGGATCTCATTGGATCGAGC
CAAACCGGTCGGAAAACACGATGGATATATTCAAATGTCAACAAT
CCATGGTTTCTGTGCTTGGATGGTTTGCCAACCCTATCCATGGGAT
GGCGACTATCCAGAGGGGATGAGAAAGAAGTTGTTCTCCGTTCTAC
CCATTTTCTCTGAAGCAGAAGCATGAGATGAGAGGCACAGCTG
ATTTCTTTGCCTTTTCTTTTGGACCCAACAACTTCAAGCCCCTAAAC
ACCATGGCTAAAATGGGACAAAATGTTTCACTTAATTTAAGAGAAG
CGCTGAACTGGATTAAACTGGAATACAACAACCCTCGAATCTTGAT
TGCTGAGAATGGCTGGTTCACAGACAGTCGTGTGAAAACAGAAGA
CACCACGGCCATCTACATGATGAAGAATTTCCTCAGCCAGGTGCTT
CAAGCAATAAGGTTAGATGAAATACGAGTGTTTGGTTATACTGCCT
GGTCTCTCCTGGATGGCTTTGAATGGCAGGATGCTTACACCATCCG
CCGAGGATTATTTTATGTGGATTTTAACAGTAAACAGAAAGAGCGG
AAACCTAAGTCTTCAGCACACTACTACAAACAGATCATACGAGAA
AATGGTTTTCTTTAAAAGAGTCCACGCCAGATGTGCAGGGCCAGT
TTCCCTGTGACTTCTCCTGGGGTGTCACTGAATCTGTTCTTAAGCCC
GAGTCTGTGGCTTCGTCCCCACAGTTCAGCGATCCTCATCTGTACGT
GTGGAACGCCACTGGCAACAGACTGTTGCACCGAGTGGAAGGGGT
GAGGCTGAAAACACGACCCGCTCAATGCACAGATTTTGTAAACATC
AAAAAACAACTTGAGATGTTGGCAAGAATGAAAGTCACCCACTAC
CGGTTTGCTCTGGATTGGGCCTCGGTCCTTCCCACTGGCAACCTGTC
CGCGGTGAACCGACAGGCCCTGAGGTACTACAGGTGCGTGGTCAG
TGAGGGGCTGAAGCTTGGCATCTCCGCGATGGTCACCCTGTATTAT
CCGACCCACGCCCACCTAGGCCTCCCCGAGCCTCTGTTGCATGCCG
ACGGGTGGCTGAACCCATCGACGGCCGAGGCCTTCCAGGCCTACG
CTGGGCTGTGCTTCCAGGAGCTGGGGACCTGGTGAAGCTCTGGAT
CACCATCAACGAGCCTAACCGGCTAAGTGACATCTACAACCGCTCT
GGCAACGACACCTACGGGGCGGCGCACAACCTGCTGGTGGCCCAC
GCCCTGGCCTGGCGCCTCTACGACCGGCAGTTCAGGCCCTCACAGC
GCGGGGCCGTGTCGCTGTCGCTGCACGCGGACTGGGCGGAACCCG
CCAACCCCTATGCTGACTCGCACTGGAGGGCGGCCGAGCGCTTCCT
GCAGTTCGAGATCGCCTGGTTCGCCGAGCCGCTCTTCAAGACCGGG
GACTACCCCGCGGCCATGAGGGAATACATTGCCTCCAAGCACCGA
```

```
CGGGGGCTTTCCAGCTCGGCCCTGCCGCGCCTCACCGAGGCCGAAA
GGAGGCTGCTCAAGGGCACGGTCGACTTCTGCGCGCTCAACCACTT
CACCACTAGGTTCGTGATGCACGAGCAGCTGGCCGGCAGCCGCTAC
GACTCGGACAGGGACATCCAGTTTCTGCAGGACATCACCCGCCTGA
GCTCCCCCACGCGCCTGGCTGTGATTCCCTGGGGGGTGCGCAAGCT
GCTGCGGTGGGTCCGGAGGAACTACGGCGACATGGACATTTACATC
ACCGCCAGTGGCATCGACGACCAGGCTCTGGAGGATGACCGGCTC
CGGAAGTACTACCTAGGGAAGTACCTTCAGGAGGTGCTGAAAGCA
TACCTGATTGATAAAGTCAGAATCAAAGGCTATTATGCATTCAAAC
TGGCTGAAGAGAAATCTAAACCCAGATTTGGATTCTTCACATCTGA
TTTTAAAGCTAAATCCTCAATACAATTTTACAACAAAGTGATCAGC
AGCAGGGCTTCCCTTTTGAGAACAGTAGTTCTAGATGCAGTCAGA
CCCAAGAAAATACAGAGTGCACTGTCTGCTTATTCCTTGTGCAGAA
GAAACCACTGATATTCCTGGGTTGTTGCTTCTTCTCCACCCTGGTTC
TACTCTTATCAATTGCCATTTTTCAAAGGCAGAAGAGAAGAAAGTT
TTGGAAAGCAAAAAACTTACAACACATACCATTAAAGAAAGGCAA
GAGAGTTGTTAGCTAA.
```

The amino acid sequence of full length human β-Klotho (GenBank Accession Number NP_783864) is provided:

(SEQ ID NO: 7)
MKPGCAAGSPGNEWIFFSTDEITTRYRNTMSNGGLQRSVILSALILLRA

VTGFSGDGRAIWSKNPNFTPVNESQLFLYDTFPKNFFWGIGTGALQVE

GSWKKDGKGPSIWDHFIHTHLKNVSSTNGSSDSYIFLEKDLSALDFIGV

SFYQFSISWPRLFPDGIVTVANAKGLQYYSTLLDALVLRNIEPIVTLYH

WDLPLALQEKYGGWKNDTIIDIFNDYATYCFQMFGDRVKYWITIHNP

YLVAWHGYGTGMHAPGEKGNLAAVYTVGHNLIKAHSKVWHNYNTH

FRPHQKGWLSITLGSHWIEPNRSENTMDIFKCQQSMVSVLGWFANPIH

GDGDYPEGMRKKLFSVLPIFSEAEKHEMRGTADFFAFSFGPNNFKPLN

TMAKMGQNVSLNLREALNWIKLEYNNPRILIAENGWFTDSRVKTEDT

TAIYMMKNFLSQVLQAIRLDEIRVFGYTAWSLLDGFEWQDAYTIRRGL

FYVDFNSKQKERKPKSSAHYYKQIIRENGFSLKESTPDVQGQFPCDFS

WGVTESVLKPESVASSPQFSDPHLYVWNATGNRLLHRVEGVRLKTRP

AQCTDFVNIKKQLEMLARMKVTHYRFALDWASVLPTGNLSAVNRQA

LRYYRCVVSEGLKLGISAMVTLYYPTHAHLGLPEPLLHADGWLNPST

AEAFQAYAGLCFQELGDLVKLWITINEPNRLSDIYNRSGNDTYGAAHN

LLVAHALAWRLYDRQFRPSQRGAVSLSLHADWAEPANPYADSHWRA

AERFLQFEIAWFAEPLFKTGDYPAAMREYIASKHRRGLSSSALPRLTEA

ERRLLKGTVDFCALNHFTTRFVMHEQLAGSRYDSDRDIQFLQDITRLS

SPTRLAVIPWGVRKLLRWVRRNYGDMDIYITASGIDDQALEDDRLRK

-continued
```
YYLGKYLQEVLKAYLIDKVRIKGYYAFKLAEEKSKPRFGFFTSDFKAK

SSIQFYNKVISSRGFPPENSSSRCSQTQENTECTVCLFLVQKKPLIFLG

CCFFSTLVLLLSIAIFQRQKRRKFWKAKNLQHIPLKKGKRVVS.
```

An example of an extracellular region of β-Klotho is:

```
                                          (SEQ ID NO: 8)
MKPGCAAGSPGNEWIFFSTDEITTRYRNTMSNGGLQRSVILSALILLRA

VTGFSGDGRAIWSKNPNFTPVNESQLFLYDTFPKNFFWGIGTGALQVEG

SWKKDGKGPSIWDHFIHTHLKNVSSTNGSSDSYIFLEKDLSALDFIGVS

FYQFSISWPRLFPDGIVTVANAKGLQYYSTLLDALVLRNIEPIVTLYHW

DLPLALQEKYGGWKNDTIIDIFNDYATYCFQMFGDRVKYWITIHNPYLV

AWHGYGTGMHAPGEKGNLAAVYTVGHNLIKAHSKVWHNYNTHFRPHQKG

WLSITLGSHWIEPNRSENTMDIFKCQQSMVSVLGWFANPIHGDGDYPEG

MRKKLFSVLPIFSEAEKHEMRGTADFFAFSFGPNNFKPLNTMAKMGQNV

SLNLREALNWIKLEYNNPRILIAENGWFTDSRVKTEDTTAIYMMKNFLS

QVLQAIRLDEIRVFGYTAWSLLDGFEWQDAYTIRRGLFYVDFNSKQKER

KPKSSAHYYKQIIRENGFSLKESTPDVQGQFPCDFSWGVTESVLKPESV

ASSPQFSDPHLYVWNATGNRLLHRVEGVRLKTRPAQCTDFVNIKKQLEM

LARMKVTHYRFALDWASVLPTGNLSAVNRQALRYYRCVVSEGLKLGISA

MVTLYYPTHAHLGLPEPLLHADGWLNPSTAEAFQAYAGLCFQELGDLVK

LWITINEPNRLSDIYNRSGNDTYGAAHNLLVAHALAWRLYDRQFRPSQR

GAVSLSLHADWAEPANPYADSHWRAAERFLQFEIAWFAEPLFKTGDYPA

AMREYIASKHRRGLSSSALPRLTEAERRLLKGTVDFCALNHFTTRFVMH

EQLAGSRYDSDRDIQFLQDITRLSSPTRLAVIPWGVRKLLRWVRRNYGD

MDIYITASGIDDQALEDDRLRKYYLGKYLQEVLKAYLIDKVRIKGYYAF

KLAEEKSKPRFGFFTSDFKAKSSIQFYNKVISSRGFPPENSSSRCSQTQ

ENTECTVCLFLVQKKP.
```

As described herein, β-Klotho proteins can also include fragments. As used herein, these terms are used interchangeably to mean a co-receptor, in particular and unless otherwise specified, a human co-receptor, that upon association with FGFR1c, FGFR2c, FGFR3c or FGFR4 and FGF21 induces FGF21-like signaling activity.

The term β-Klotho also includes post-translationally modified forms of the β-Klotho amino acid sequence, for example, glycosylation at N-linked glycosylation sites. Thus, the antigen binding proteins and antigen binding protein-FGF21 fusions can bind to or be generated from proteins glycosylated at one or more of these positions.

Antigen Binding Proteins and Antigen Binding Protein-FGF21 Fusions that Specifically Bind β-Klotho or β-Klotho and One or More of FGFR1c, FGFR2c, FGFR3c, FGFR4c A variety of antigen binding proteins and antigen binding protein-FGF21 fusions useful for modulating FGF21-like signaling are provided. These agents include, for instance, antigen binding proteins and antigen binding protein-FGF21 fusions that contain an antigen binding domain (e.g., single chain antibodies, domain antibodies, immunoadhesions, and polypeptides with an antigen binding region) and specifically bind to β-Klotho or, when a FGFR-binding peptide is present, both β-Klotho and one or more of FGFR1c, FGFR2c, FGFR3c or FGFR4, in particular human FGFR1c, FGFR2c, FGFR3c or FGFR4 and human β-Klotho. Some of the agents are useful, for example, in mimicking the signaling effect generated in vivo by the association of an FGF receptor (e.g., FGFR1c, FGFR2c, FGFR3c or FGFR4) with β-Klotho and with FGF21, and can thus be used to enhance or modulate one or more activities associated with FGF21-like signaling.

In general, the antigen binding proteins and the antigen binding protein component of the antigen binding protein-FGF21 fusions that are provided typically comprise one or more CDRs as described herein (e.g., 1, 2, 3, 4, 5 or 6) and can also comprise a FGFR-binding peptide. In some instances, the antigen binding protein or the antigen binding protein component of an antigen binding protein-FGF21 fusion comprises (a) a polypeptide structure and (b) one or more CDRs that are inserted into and/or joined to the polypeptide structure. The polypeptide structure can take a variety of different forms. For example, the polypeptide structure can be, or comprise, the framework of a naturally occurring antibody, or fragment or variant thereof, or can be completely synthetic in nature. Examples of various antigen binding protein structures and the antigen binding protein component of antigen binding protein-FGF21 fusions are further described herein. In particular embodiments, the polypeptide structure of an antigen binding protein or the antigen binding protein component of an antigen binding protein-FGF21 fusion comprises a FGFR-binding peptide, which can be integrated at any point in the heavy chain, such as in the CH2 and CH3 loops.

In certain embodiments, the polypeptide structure of the antigen binding proteins and the antigen binding protein component of antigen binding protein-FGF21 fusions is an antibody or is derived from an antibody, including, but not limited to, monoclonal antibodies, bispecific antibodies, minibodies, domain antibodies, synthetic antibodies (sometimes referred to herein as "antibody mimetics"), chimeric antibodies, humanized antibodies, antibody fusions (sometimes referred to as "antibody conjugates"), and portions or fragments of each, respectively. In some instances, the antigen binding protein is an immunological fragment of an antibody (e.g., a Fab, a Fab', a F(ab')$_2$, or a scFv). The polypeptide structure of an antigen binding protein can comprise a CH3 region, which has been further engineered to comprise a peptide component that is not normally found in the wild-type CH3 sequence, such as a FGFR-binding peptide. Alternatively, an antigen binding protein-FGF21 fusion can comprise a truncated form of FGF21 fused to an antigen binding protein. These various structures are further described and defined herein.

Certain of the antigen binding proteins and the antigen binding protein component of antigen binding protein-FGF21 fusions provided herein specifically bind to β-Klotho β-Klotho and one or more of FGFR1c, FGFR2c, FGFR3c, and FGFR4. In one embodiment, an antigen binding protein or the antigen binding protein component of antigen binding protein-FGF21 fusion specifically binds to both human FGFR1c comprising the amino acid sequence of SEQ ID NO:5 (the extracellular region of FGFR1c) and human β-Klotho comprising the amino acid sequence of SEQ ID NO:8 (the extracellular region of β-Klotho), and in another embodiment an antigen binding protein or the antigen binding protein component of antigen binding protein-FGF21 fusion specifically binds to both human FGFR1c comprising the amino acid sequence of SEQ ID NO:5 and human β-Klotho having the amino acid sequence of SEQ ID NO:8 and the antigen binding protein or antigen binding protein- FGF21 fusion induces FGF21-like signaling. It is noted that, an antigen binding protein or antigen binding protein-FGF21 fusion of the present disclosure can, but need not, induce FGF21-like signaling and still form an aspect of the dislosed invention.

Antigen Binding Protein and Antigen Binding Protein-FGF21 Fusion Structure

Some of the antigen binding proteins and antigen binding protein components of antigen binding protein-FGF21 fusions that specifically bind β-Klotho or β-Klotho and one or more of FGFR1c, FGFR2c, FGFR3c, and FGFR4 that are provided herein comprise a structure typically associated with naturally occurring antibodies. The structural units of these antibodies typically comprise one or more tetramers, each composed of two identical couplets of polypeptide chains, though some species of mammals also produce antibodies having only a single heavy chain. In a typical antibody, each pair or couplet includes one full-length "light" chain (in certain embodiments, about 25 kDa) and one full-length "heavy" chain (in certain embodiments, about 50-70 kDa). Each individual immunoglobulin chain is composed of several "immunoglobulin domains", each consisting of roughly 90 to 110 amino acids and expressing a characteristic folding pattern. These domains are the basic units of which antibody polypeptides are composed. The amino-terminal portion of each chain typically includes a variable domain that is responsible for antigen recognition. The carboxy-terminal portion is more conserved evolutionarily than the other end of the chain and is referred to as the "constant region" or "C region". Human light chains generally are classified as kappa and lambda light chains, and each of these contains one variable domain and one constant domain. Heavy chains are typically classified as mu, delta, gamma, alpha, or epsilon chains, and these define the antibody's isotype as IgM, IgD, IgG, IgA, and IgE, respectively. IgG has several subtypes, including, but not limited to, IgG1, IgG2, IgG3, and IgG4. IgM subtypes include IgM, and IgM2. IgA subtypes include IgA1 and IgA2. In humans, the IgA and IgD isotypes contain four heavy chains and four light chains; the IgG and IgE isotypes contain two heavy chains and two light chains; and the IgM isotype contains five heavy chains and five light chains. The heavy chain C region typically comprises one or more domains that can be responsible for effector function. The number of heavy chain constant region domains will depend on the isotype. Each IgG heavy chain, for example, contains three C region domains known as $C_H1$, $C_H2$ and $C_H3$. The antibodies that are provided can have any of these isotypes and subtypes. In certain embodiments, an antigen binding protein or antigen binding protein component of an antigen binding protein-FGF21 fusion that specifically binds to β-Klotho or β-Klotho and one or more of FGFR1c, FGFR2c, FGFR3c or FGFR4 is an antibody of the IgG1, IgG2, or IgG4 subtype, and which can comprise an FGFR-binding peptide integrated into the constant region of the heavy chain(s).

In full-length light and heavy chains, the variable and constant regions are joined by a "J" region of about twelve or more amino acids, with the heavy chain also including a "D" region of about ten more amino acids. See, e.g., Fundamental Immunology, 2nd ed., Ch. 7 (Paul, W., ed.) 1989, New York: Raven Press (hereby incorporated by reference in its entirety for all purposes). The variable regions of each light/heavy chain pair typically form the antigen binding site.

One example of an IgG2 heavy chain constant domain of an exemplary monoclonal antibody, which comprises wild type CH2 and CH3 loops, that specifically binds β-Klotho or β-Klotho and one or more of FGFR1c, FGFR2c, FGFR3c, and FGFR4 has the amino acid sequence:

```
                                             (SEQ ID NO: 9)
ASTKGPSVFPLAPSSKSTSGGTAALGCLVKDYFPEPVTVSWNSGALTS

GVHTFPAVLQSSGLYSLSSVVTVPSSSLGTQTYICNVNHKPSNTKVDK

KVEPKSCDKTHTCPPCPAPELLGGPSVFLFPPKPKDTLMISRTPEVTCV

VVDVSHEDPEVKFNWYVDGVEVHNAKTKPREEQYQSTYRVVSVLTV

LHQDWLNGKEYKCKVSNKALPAPIEKTISKAKGQPREPQVYTLPPSRD

ELTKNQVSLTCLVKGFYPSDIAVEWESNGQPENNYKTTPPVLDSDGSF

FLYSKLTVDKSRWQQGNVFSCSVMHEALHNHYTQKSLSLSPGK.
``` which is encoded by the nucleotide sequence:

```
                                             (SEQ ID NO: 10)
gcctccaccaagggcccatcggtcttccccctggcgcctgctccaggagcacctccgagagcacagcggcc ctgggctgcctggtcaaggactacttccccgaaccggtgacggtgtcgtggaactcaggcgctctgaccagcg gcgtgcacaccttcccagctgtcctacagtcctcaggactctactccctcagcagcgtggtgaccgtgccctcca gcaacttcggcacccagacctacacctgcaacgtagatcacaagcccagcaacaccaaggtggacaagaca gttgagcgcaaatgttgtgtcgagtgcccaccgtgcccagcaccacctgtggcaggaccgtcagtcttcctcttc cccccaaaacccaaggacaccctcatgatctcccggacccctgaggtcacgtgcgtggtggtggacgtgagc cacgaagaccccgaggtccagttcaactggtacgtggacggcgtggaggtgcataatgccaagacaaagcca cgggaggagcagttcaacagcacgttccgtgtggtcagcgtcctcaccgttgtgcaccaggactggctgaacg gcaaggagtacaagtgcaaggtctccaacaaaggcctcccagcccccatcgagaaaaccatctccaaaacca aagggcagccccgagaaccacaggtgtacaccctgcccccatcccgggaggagatgaccaagaaccaggt cagcctgacctgcctggtcaaaggcttctaccccagcgacatcgccgtggagtgggagagcaatgggcagcc ggagaacaactacaagaccacacctcccatgctggactccgacggctccttcttcctctacagcaagctcaccg tggacaagagcaggtggcagcaggggaacgtcttctcatgctccgtgatgcatgaggctctgcacaaccacta cacgcagaagagcctctccctgtctccgggtaaa
```

In another aspect, a heavy chain of any isotype can but need not comprise a FGFR-binding peptide, which can be integrated into the constant region of the heavy chain. Any FGFR-binding peptide can be inserted into a heavy chain, including those FGFR-binding peptides disclosed herein, for example in Table 4A. The FGFR-binding peptide can be integrated into any region of the heavy chain constant region, including the CH2 or CH3 loop regions of the heavy chain. Examples of heavy chains that comprise a FGFR-binding peptide are listed in Table 5A.

One particular example of a IgG2 heavy chain comprising a FGFR-binding peptide has the amino acid sequence:

(SEQ ID NO: 11)
QVQLVESGGGVVQPGRSLRLSCAASRFSFSRYGMHWVRQAPGKGLE

WVAVIWFDGRNQYYADSVKGRFTISRDNSKNTLFLQMNSLRVEDTAV

YYCARDHPVVGTSFDYWGQGTLVTVSSASTKGPSVFPLAPSSKSTSGG

TAALGCLVKDYFPEPVTVSWNSGALTSGVHTFPAVLQSSGLYSLSSVV

TVPSSSLGTQTYICNVNHKPSNTKVDKKVEPKSCDKTHTCPPCPAPELL

GGPSVFLFPPKPKDTLMISRTPEVTCVVVDVSHEDPEVKFNWYVDGVE

VHNAKTKPREEQYQSTYRVVSVLTVLHQDWLNGKEYKCKVSNKALP

APIEKTISKAKGQPREPQVYTLPPSRDELGGCYQAWGYYVCGGTKNQ

VSLTCLVKGFYPSDIAVEWESNGQPENNYKTTPPVLDSDGSFFLYSKL

TVDKSRWQQGNVFSCSVMHEALHNHYTQKSLSLSPGK;

which is encoded by the nucleotide sequence:

(SEQ ID NO: 12)
caggtgcagttggtggagtctgggggaggcgtggtccagcctggggaggtccctgagactctcctgtgcagcgt ctagattctccttcagtagatatggcatgcactgggtccgccaggctccaggcaaggggctggagtgggtggc agttatatggtttgatggaagaaatcaatactatgcagactccgtgaaggggcgattcaccatctccagagacaat tccaagaatacgctgtttctgcaaatgaacagcctgagagtcgaggacacggctgtgtattactgtgcgagagat cacccagtagttggtacgagctttgactactggggccagggaaccctggtcaccgtctctagtgcctccaccaa gggcccatcggtcttccccctggcaccctcctccaagagcacctctggggggcacagcggccctgggctgcct ggtcaaggactacttccccgaaccggtgacggtgtcgtggaactcaggcgccctgaccagcggcgtgcacac cttcccggctgtcctacagtcctcaggactctactccctcagcagcgtggtgaccgtgccctccagcagctttggg cacccagacctacatctgcaacgtgaatcacaagcccagcaacaccaaggtggacaagaaagttgagcccaa atcttgtgacaaaactcacacatgcccaccgtgcccagcacctgaactcctggggggaccgtcagtcttcctctt ccccccaaaacccaaggacaccctcatgatctcccggacccctgaggtcacatgcgtggtggtggacgtgag ccacgaagaccctgaggtcaagttcaactggtacgtggacggcgtggaggtgcataatgccaagacaaagcc gcggaggagcagtaccagagcacgtaccgtgtggtcagcgtcctcaccgtcctgcaccaggactggctgaa tggcaaggagtacaagtgcaaggtctccaacaaagccctcccagcccccatcgagaaaaccatcccaaagcc caaagggcagccccgagaaccacaggtgtacaccctgcccccatcccgggatgagctgggtggttgctacca ggcctggggctactacgtgtgcggtggtaccaagaaccaggtcagcctgacctgcctggtcaaaggcttctatc ccagcgacatcgccgtggagtgggagagcaatgggcagccggagaacaactacaagaccacgcctcccgt gctggactccgacggctccttcttcctctatagcaagctcaccgtggacaagagcaggtggcagcaggggaac gtcttctcatgctccgtgatgcatgaggctctgcacaaccactacacgcagaagagcctctccctgtctccgggt aaa One example of a kappa light constant domain of an exemplary monoclonal antibody that binds β-Klotho or β-Klotho and one or more of FGFR1c, FGFR2c, FGFR3c, and FGFR4 has the amino acid sequence:

(SEQ ID NO: 13)
RTVAAPSVFIFPPSDEQLKSGTASVVCLLNNFYPREAKVQWKVDNAL

QSGNSQESVTEQDSKDSTYSLSSTLTLSKADYEKHKVYACEVTHQGLS

SPVTKSFNRGEC.

which is encoded by the nucleotide sequence:

(SEQ ID NO: 14)
cgtacggtggctgcaccatctgtcttcatcttcccgccatctgatgagcag ttgaaatctggaactgcctctgttgtgtgcctgctgaataacttctatccc agagaggccaaagtacagtggaaggtggataacgccctccaatcgggtaac tcccaggagagtgtcacagagcaggacagcaaggacagcacctacagcctc agcagcaccgctacgctgagcaaagcagactacgagaaacacaaagtctac gcctgcgaagtcacccatcagggcctgagctcgcccgtcacaaagagcttc aacaggggagagtgt One example of a lambda light constant domain of an exemplary monoclonal antibody that binds β-Klotho or β-Klotho and one or more of FGFR1c, FGFR2c, FGFR3c, and FGFR4 has the amino acid sequence:

```
                                                              (SEQ ID NO: 15)
GQPKANPTVTLFPPSSEELQANKATLVCLISDFYPGAVTVAWKADGSP

VKAGVETTKPSKQSNNKYAASSYLSLTPEQWKSHRSYSCQVTHEGST

VEKTVAPTECS
``` which is encoded by the nucleotide sequence:

```
                                                              (SEQ ID NO: 16)
ggtcagcccaaggccaacccactgtcactctgttcccgccctcctctgaggagctccaagccaacaaggcca cactagtgtgtctgatcagtgacttctacccgggagctgtgacagtggcctggaaggcagatggcagccccgtc aaggcgggagtggagaccaccaaaccctccaaacagagcaacaacaagtacgcggccagcagctacctga gcctgacgcccgagcagtggaagtcccacagaagctacagctgccaggtcacgcatgaagggagcaccgtg gagaagacagtggcccctacagaatgttca
```

Variable regions of immunoglobulin chains generally exhibit the same overall structure, comprising relatively conserved framework regions (FR) joined by three hypervariable regions, more often called "complementarity determining regions" or CDRs. The CDRs from the two chains of each heavy chain/light chain pair typically are aligned by the framework regions to form a structure that binds specifically with a specific epitope on the target protein (e.g., β-Klotho or β-Klotho and one or more of FGFR1c, FGFR2c, FGFR3c, and FGFR4). From N-terminal to C-terminal, naturally-occurring light and heavy chain variable regions both typically conform with the following order of these elements: FR1, CDR1, FR2, CDR2, FR3, CDR3 and FR4. A numbering system has been devised for assigning numbers to amino acids that occupy positions in each of these domains. This numbering system is defined in Kabat Sequences of Proteins of Immunological Interest (1987 and 1991, NIH, Bethesda, Md.), or Chothia & Lesk, 1987, *J. Mol. Biol.* 196:901-917; or Chothia et al., 1989, *Nature* 342:878-883, or AHo any of which can be employed to describe the regions of the disclosed antigen binding proteins.

The various heavy chain and light chain variable regions provided herein are depicted in Tables 2A and 2B. Each of these variable regions can be attached to the disclosed heavy and light chain constant regions to form a complete antibody heavy and light chain, respectively. Further, each of the heavy and light chain sequences can be combined to form a complete antibody structure. It should be understood that the heavy chain and light chain variable regions provided herein can also be attached to other constant domains having different sequences than the exemplary sequences listed above.

Specific examples of some of the full length light and heavy chains of the antibodies that are provided and their corresponding amino acid sequences are summarized in Tables 1A and 1B. Table 1A shows exemplary light chain sequences, and Table 1B shows exemplary heavy chain sequences. The heavy chains presented in Table 1B do not comprise a FGFR-binding peptide; heavy chains comprising a FGFR-binding peptide are presented in Table 5A.

TABLE 1A

Exemplary Antibody Light Chain Sequences

| SEQ ID NO: | Designation | Contained in Clone | Amino Acid Sequence |
|---|---|---|---|
| 17 | L1 | 1A2 | DIVMTQTPLSSPVTLGQPASISCRSSQSLVYSDGNTY LSWLQQRPGQPPRLLIYKISNRFSGVPDRFSGSGAGT DFTLKISRVEADDVGIYYCMQAIEFPWTFGQGTQVEI KRTVAAPSVFIFPPSDEQLKSGTASVVCLLNNFYPRE AKVQWKVDNALQSGNSQESVTEQDSKDSTYSLSST LTLSKADYEKHKVYACEVTHQGLSSPVTKSFNRGEC |
| 18 | L2 | 2G10 | QSVLTQPPSVSAAPGQKVTVSCSGSSSNIGNNYVSW YQQLPGTAPKLLIYDNNKRPSGIPDRFSGSKSGTSAT LGITGLQTGDEAEYYCGTWDSSLSVVAFGGGTKLT VLGQPKANPTVTLFPPSSEELQANKATLVCLISDFYP GAVTVAWKADGSPVKAGVETTKPSKQSNNKYAAS SYLSLTPEQWKSHRSYSCQVTHEGSTVEKTVAPTEC S |
| 19 | L3 | 14E8 | DIQMTQSPSSLSASVGDRVTITCQASQDINNYLNWY QQKLGKAPKLLIYDTSNLETGVPSRFSGSGFGTDFTF TISSLQPEDIATYYCQQYDNLFTGQGTRLEIKRTVA APSVFIFPPSDEQLKSGTASVVCLLNNFYPREAKVQ WKVDNALQSGNSQESVTEQDSKDSTYSLSSTLTLSK ADYEKHKVYACEVTHQGLSSPVTKSFNRGEC |

TABLE 1A-continued

Exemplary Antibody Light Chain Sequences

| SEQ ID NO: | Designation | Contained in Clone | Amino Acid Sequence |
|---|---|---|---|
| 21 | L5 | 25B10 | QTVVTQEPSFSVSPGGTVTLTCGVSSGSVSTRYYPS WYQQTPGQAPRTLINSTNTRSSGVPDRFSGSILGNKA ALTITGAQADDESDYFCVLYMGSGIWVFGGGTKLT VLGQPKANPTVTLFPPSSEELQANKATLVCLISDFYP GAVTVAWKADGSPVKAGVETTKPSKQSNNKYAAS SYLSLTPEQWKSHRSYSCQVTHEGSTVEKTVAPTEC S |
| 22 | L6 | 3B4 | DIVMTQTPLSSPVTLGQPASISCRSSQSLVHYDGNT YLSWLQQRPGQPPRLLIYKISNRFSGVPDRFSGSGA GTDFTLKISRVEAEDVGIYYCMQALEFPWTFGQGT KVEIKRTVAAPSVFIFPPSDEQLKSGTASVVCLLNNF YPREAKVQWKVDNALQSGNSQESVTEQDSKDSTY SLSSTLTLSKADYEKHKVYACEVTHQGLSSPVTKSF NRGEC |
| 23 | L7 | 1B5 | DIVMTQTPLTSPVTLGQPASISCRSSQSLVHYDGNT YLSWLQQRPGQPPRLLIYKISNRFSGVPDRFSGSGA GTDFTLKISRVEAEDVGIYYCMQALEFPWTFGQGT KVEIKRTVAAPSVFIFPPSDEQLKSGTASVVCLLNNF YPREAKVQWKVDNALQSGNSQESVTEQDSKDSTY SLSSTLTLSKADYEKHKVYACEVTHQGLSSPVTKSF NRGEC |
| 24 | L8 | 10H3 | DIVMTQTPLSSPVTLGQPASISCRSSQSLVHYDGNTY LSWLQQRPGQPPRLLIYKISNRFSGVPDRFSGSGAGT DFTLKISRVAAEDVGIYYCMQALEFPWTFGQGTKVE IKRTVAAPSVFIFPPSDEQLKSGTASVVCLLNNFYPR EAKVQWKVDNALQSGNSQESVTEQDSKDSTYSLSS TLTLSKADYEKHKVYACEVTHQGLSSPVTKSFNRGE C |
| 25 | L9 | 9D10 | QSVLTQPPSVSAAPGQKVTISCSGSSSNIGNNYVSWY QQLPGTAPKLLIYDNNRRPSGIPDRFSGSKSGTSATL GITGLQTGDEADYYCGTWDSSLSAVVFGGGTKLTV LGQPKANPTVTLFPPSSEELQANKATLVCLISDFYPG AVTVAWKADGSPVKAGVETTKPSKQSNNKYAASS YLSLTPEQWKSHRSYSCQVTHEGSTVEKTVAPTECS |
| 26 | L10 | 3F4 | QSVLTQPPSVSAAPGQKVTISCSGSSSNIGNNYVSWY QQLPGTAPKLLIYDNNNRPSGIPDRFSGSKSGTSATL GITGLQTGDEADYYCETWDSSLSAGVFGGGTKLTV LGQPKANPTVTLFPPSSEELQANKATLVCLISDFYPG AVTVAWKADGSPVKAGVETTKPSKQSNNKYAASS YLSLTPEQWKSHRSYSCQVTHEGSTVEKTVAPTECS |
| 27 | L11 | 8F9 | QSVLTQPPSVSAAPGQKVTISCSGSSSNIGNNYVSWY QQLPGTAPKLLIYDNNKRPSGIPDRFSGSKSGTSATL GITGLQTGDEADYYCGTWDSSLSAVVFGGGTKLTV LGQPKANPTVTLFPPSSEELQANKATLVCLISDFYPG AVTVAWKADGSPVKAGVETTKPSKQSNNKYAASS YLSLTPEQWKSHRSYSCQVTHEGSTVEKTVAPTECS |

TABLE 1B

Exemplary Antibody Heavy Chain Sequences

| SEQ ID NO: | Designation | Contained in Clone | Sequence |
|---|---|---|---|
| 28 | H1 | 1A2 | QVQLVQSGAEVKKPGASVKVSCKASGYTFTGYY MHWVRQAPGQGLEWMGWINPNSGGTNSAQKFQ GRVTMTRDTSISTAYMELSRLRSDDTAVYYCARD ATSGWFDYWGQGTLVTVSSASTKGPSVFPLAPSSK STSGGTAALGCLVKDYFPEPVTVSWNSGALTSGV HTFPAVLQSSGLYSLSSVVTVPSSSLGTQTYICNVN HKPSNTKVDKKVEPKSCDKTHTCPPCPAPELLGGP SVFLFPPKPKDTLMISRTPEVTCVVVDVSHEDPEV KFNWYVDGVEVHNAKTKPREEQYQSTYRVVSVL TVLHQDWLNGKEYKCKVSNKALPAPIEKTISKAK |

TABLE 1B-continued

Exemplary Antibody Heavy Chain Sequences

| SEQ ID NO: | Designation | Contained in Clone | Sequence |
|---|---|---|---|
| | | | GQPREPQVYTLPPSRDELTKNQVSLTCLVKGFYPS DIAVEWESNGQPENNYKTTPPVLDSDGSFFLYSKL TVDKSRWQQGNVFSCSVMHEALHNHYTQKSLSLS PGK |
| 29 | H2 | 2G10 | QVQLVESGGGVVQPGRSLRLSCAASRFSFSRYGM HWVRQAPGKGLEWVAVIWFDGRNQYYADSVKG RFTISRDNSKNTLFLQMNSLRVEDTAVYYCARDHP VVGTSFDYWGQGTLVTVSSASTKGPSVFPLAPSSK STSGGTAALGCLVKDYFPEPVTVSWNSGALTSGV HTFPAVLQSSGLYSLSSVVTVPSSSLGTQTYICNVN HKPSNTKVDKKVEPKSCDKTHTCPPCPAPELLGGP SVFLFPPKPKDTLMISRTPEVTCVVVDVSHEDPEV KFNWYVDGVEVHNAKTKPREEQYQSTYRVVSVL TVLHQDWLNGKEYKCKVSNKALPAPIEKTISKAK GQPREPQVYTLPPSRDELTKNQVSLTCLVKGFYPS DIAVEWESNGQPENNYKTTPPVLDSDGSFFLYSKL TVDKSRWQQGNVFSCSVMHEALHNHYTQKSLSLS PGK |
| 30 | H3 | 14E8 | QVQLVESGGGVVQPGRSLRLSCAASGFTFSSYGM HWVRQAPGKGLEWVAVIGYDGSYKYYADSVKGR FTISRDNSKNTLYLQMNSLRAEDTAVYYCARDGS NWNYGGSFDYWGQGTLVTVSSASTKGPSVFPLAP SSKSTSGGTAALGCLVKDYFPEPVTVSWNSGALTS GVHTFPAVLQSSGLYSLSSVVTVPSSSLGTQTYICN VNHKPSNTKVDKKVEPKSCDKTHTCPPCPAPELLG GPSVFLFPPKPKDTLMISRTPEVTCVVVDVSHEDPE VKFNWYVDGVEVHNAKTKPREEQYQSTYRVVSV LTVLHQDWLNGKEYKCKVSNKALPAPIEKTISKA KGQPREPQVYTLPPSRDELTKNQVSLTCLVKGFYP SDIAVEWESNGQPENNYKTTPPVLDSDGSFFLYSK LTVDKSRWQQGNVFSCSVMHEALHNHYTQKSLSL SPGK |
| 32 | H5 | 25B10 | EVQLLESGGGLVQPEGSLRLSCAASGFTFSIYAMS WVRQAPGKGLEWVSDISGRGGYTYYADSVKGRF TISRDNSKNTLYLQMNSLRADDTAVYYCAKDRSI AVAGPFDFWGQGTLVTVSSASTKGPSVFPLAPSSK STSGGTAALGCLVKDYFPEPVTVSWNSGALTSGV HTFPAVLQSSGLYSLSSVVTVPSSSLGTQTYICNVN HKPSNTKVDKKVEPKSCDKTHTCPPCPAPELLGGP SVFLFPPKPKDTLMISRTPEVTCVVVDVSHEDPEV KFNWYVDGVEVHNAKTKPREEQYQSTYRVVSVL TVLHQDWLNGKEYKCKVSNKALPAPIEKTISKAK GQPREPQVYTLPPSRDELTKNQVSLTCLVKGFYPS DIAVEWESNGQPENNYKTTPPVLDSDGSFFLYSKL TVDKSRWQQGNVFSCSVMHEALHNHYTQKSLSLS PGK |
| 33 | H6 | 3B4 | QVQLVQSGAEVKKPGASVKVSCKASGYTFTAYY MHWVRQAPGQGLEWMGWINPNSGGTNSAQKFQ GRVTMTRDTSIRTAYMELSWLRSDDTAVYYCARD ATSGWFDIWGQGTPVTVSSASTKGPSVFPLAPCSR STSESTAALGCLVKDYFPEPVTVSWNSGALTSGVH TFPAVLQSSGLYSLSSVVTVPSSNFGTQTYTCNVD HKPSNTKVDKTVERKCCVECPPCPAPPVAGPSVFL FPPKPKDTLMISRTPEVTCVVVDVSHEDPEVQFNW YVDGVEVHNAKTKPREEQFNSTFRVVSVLTVVHQ DWLNGKEYKCKVSNKGLPAPIEKTISKTKGQPREP QVYTLPPSREEMTKNQVSLTCLVKGFYPSDIAVEW ESNGQPENNYKTTPPMLDSDGSFFLYSKLTVDKSR WQQGNVFSCSVMHEALHNHYTQKSLSLSPGK |
| 34 | H7 | 1B5 | QVQLVQSGAEVKKPGASVKVSCKASGYTFTAYY MHWVRQAPGQGLEWMGWINPNSGGTNSAQKFQ GRVTMTRDTSIRTAYMELSWLRSDDTAVYYCARD ATSGWFDFWGQGTPVTVSSASTKGPSVFPLAPCSR STSESTAALGCLVKDYFPEPVTVSWNSGALTSGVH TFPAVLQSSGLYSLSSVVTVPSSNFGTQTYTCNVD HKPSNTKVDKTVERKCCVECPPCPAPPVAGPSVFL FPPKPKDTLMISRTPEVTCVVVDVSHEDPEVQFNW YVDGVEVHNAKTKPREEQFNSTFRVVSVLTVVHQ DWLNGKEYKCKVSNKGLPAPIEKTISKTKGQPREP |

TABLE 1B-continued

Exemplary Antibody Heavy Chain Sequences

| SEQ ID NO: | Designation | Contained in Clone | Sequence |
|---|---|---|---|
| | | | QVYTLPPSREEMTKNQVSLTCLVKGFYPSDIAVEW ESNGQPENNYKTTPPMLDSDGSFFLYSKLTVDKSR WQQGNVFSCSVMHEALHNHYTQKSLSLSPGK |
| 35 | H8 | 10H3 | QVQLVQSGAEVRKPGASVKVSCKASGYTFTAYY MHWVRQAPGQGLEWMGWINPYSGGTNSAQKFQ GRVTMTRDTSISTAYMELSWLRSDDTAVYYCARD ATSGWFDFWGQGTLVTVSSASTKGPSVFPLAPCSR STSESTAALGCLVKDYFPEPVTVSWNSGALTSGVH TFPAVLQSSGLYSLSSVVTVPSSNFGTQTYTCNVD HKPSNTKVDKTVERKCCVECPPCPAPPVAGPSVFL FPPKPKDTLMISRTPEVTCVVVDVSHEDPEVQFNW YVDGVEVHNAKTKPREEQFNSTFRVVSVLTVVHQ DWLNGKEYKCKVSNKGLPAPIEKTISKTKGQPREP QVYTLPPSREEMTKNQVSLTCLVKGFYPSDIAVEW ESNGQPENNYKTTPPMLDSDGSFFLYSKLTVDKSR WQQGNVFSCSVMHEALHNHYTQKSLSLSPGK |
| 36 | H9 | 9D10 | QVQLVESGGGVVQPGRSLRLSCAASGFTFRSYGM HWVRQAPGKGLEWVAVIWYDGRNEYYADSVKG RFTISRDNSKNTLYLRMNSLRAEDTAVYYCARDH PVAGTSFDYWGQGTLVTVSSASTKGPSVFPLAPCS RSTSESTAALGCLVKDYFPEPVTVSWNSGALTSGV HTFPAVLQSSGLYSLSSVVTVPSSNFGTQTYTCNV DHKPSNTKVDKTVERKCCVECPPCPAPPVAGPSVF LFPPKPKDTLMISRTPEVTCVVVDVSHEDPEVQFN WYVDGVEVHNAKTKPREEQFNSTFRVVSVLTVVH QDWLNGKEYKCKVSNKGLPAPIEKTISKTKGQPRE PQVYTLPPSREEMTKNQVSLTCLVKGFYPSDIAVE WESNGQPENNYKTTPPMLDSDGSFFLYSKLTVDK SRWQQGNVFSCSVMHEALHNHYTQKSLSLSPGK |
| 37 | H10 | 3F4 | QVQLVESGGGVVQPGRSLRLSCAASGFIFRSYGMH WVRQAPGKGLEWVAVISYDGSNKYYADSVKGRF TISRDNSKNTLYLQMNSLRAEDTAVYYCARDHPV AGTSFDYWGQGTLVTVSSASTKGPSVFPLAPCSRS TSESTAALGCLVKDYFPEPVTVSWNSGALTSGVHT FPAVLQSSGLYSLSSVVTVPSSNFGTQTYTCNVDH KPSNTKVDKTVERKCCVECPPCPAPPVAGPSVFLF PPKPKDTLMISRTPEVTCVVVDVSHEDPEVQFNWY VDGVEVHNAKTKPREEQFNSTFRVVSVLTVVHQD WLNGKEYKCKVSNKGLPAPIEKTISKTKGQPREPQ VYTLPPSREEMTKNQVSLTCLVKGFYPSDIAVEWE SNGQPENNYKTTPPMLDSDGSFFLYSKLTVDKSR WQQGNVFSCSVMHEALHNHYTQKSLSLSPGK |
| 38 | H11 | 8F9 | QVQLVESGGGVVQPGRSLRLSCAASGFTFSSYGM HWVRQAPGKGLEWVAVIWYDGRNKYHADSVKG RFTISRDNSKNTLYLQMNSLRAEDTAVYYCARDH PVAGTSFDYWGQGTLVTVSSASTKGPSVFPLAPCS RSTSESTAALGCLVKDYFPEPVTVSWNSGALTSGV HTFPAVLQSSGLYSLSSVVTVPSSNFGTQTYTCNV DHKPSNTKVDKTVERKCCVECPPCPAPPVAGPSVF LFPPKPKDTLMISRTPEVTCVVVDVSHEDPEVQFN WYVDGVEVHNAKTKPREEQFNSTFRVVSVLTVVH QDWLNGKEYKCKVSNKGLPAPIEKTISKTKGQPRE PQVYTLPPSREEMTKNQVSLTCLVKGFYPSDIAVE WESNGQPENNYKTTPPMLDSDGSFFLYSKLTVDK SRWQQGNVFSCSVMHEALHNHYTQKSLSLSPGK |

Again, each of the exemplary heavy chains (H1, H2, H3 etc.) listed in Table 1B, or alternatively each of the exemplary heavy chains comprising a FGFR-binding protein listed in Table 5A can be combined with any of the exemplary light chains shown in Table 1A to form an antibody. Examples of such combinations include H1 combined with any of L1 through L11; H2 combined with any of L1 through L11; H3 combined with any of L1 through L11, any heavy chain comprising a FGFR-binding peptide (e.g., those shown in Table 5) combined with any of L1 through L11, any heavy chain comprising a FGFR-binding peptide (e.g., those shown in Table 5) combined with any of L1 through L11, and so on. In some instances, the antibodies include at least one heavy chain and one light chain from those listed in Tables 1A, 1B and 5A. In some instances, the antibodies comprise two different heavy chains and two different light chains listed in Tables 1A, 1B and 5A. In other instances, the antibodies contain two identical light chains and two identical heavy chains. As an example, an antibody or immunologically functional fragment thereof can include two H1 heavy chains and two L1 light chains, or two H2 heavy chains and two L2 light chains, or two H3 heavy chains and two L3 light chains and other similar combinations of pairs of light chains and pairs of heavy chains as listed in Tables 1A, 1B and 5A.

Other antigen binding proteins and the antigen binding protein component of the antigen binding protein-FGF21 fusions that are provided herein comprise variants of antibodies formed by combination of the heavy and light chains shown in Tables 1A, 1B and 5A and comprise light and/or heavy chains that each have at least 70%, 75%, 80%, 85%, 90%, 95%, 96%, 97%, 98% or 99°A identity to the amino acid sequences of these chains. In some instances, such antibodies include at least one heavy chain and one light chain, whereas in other instances the variant forms contain two identical light chains and two identical heavy chains.

Variable Domains of Antigen Binding Proteins and the Antigen Binding Protein Component of Antigen Binding Protein-FGF21 Fusions Also provided are antigen binding proteins and the antigen binding protein components of antigen binding protein-FGF21 fusions that contain an antibody heavy chain variable region selected from the group consisting of $V_H1$-$V_H11$ as shown in Table 2B and/or an antibody light chain variable region selected from the group consisting of $V_L1$-$V_L11$ as shown in Table 2A, and immunologically functional fragments, derivatives, muteins and variants of these light chain and heavy chain variable regions.

Antigen binding proteins and antigen binding protein-FGF21 fusions of this type can generally be designated by the formula "$V_Hx/V_Ly$," where "x" corresponds to the number of heavy chain variable regions and "y" corresponds to the number of the light chain variable regions.

TABLE 2A

Exemplary Antibody Variable Light ($V_L$) Chains

| Contained in Clone | Designation | SEQ ID NO. | Amino Acid Sequence |
|---|---|---|---|
| 1A2 | $V_L1$ | 39 | DIVMTQTPLSSPVTLGQPASISCRSSQSLVYSDGNT YLSWLQQRPGQPPRLLIYKISNRFSGVPDRFSGSGA GTDFTLKISRVEADDVGIYYCMQAIEFPWTFGQGT QVEIKR |
| 2G10 | $V_L2$ | 40 | QSVLTQPPSVSAAPGQKVTVSCSGSSSNIGNNYVS WYQQLPGTAPKLLIYDNNKRPSGIPDRFSGSKSGT SATLGITGLQTGDEAEYYCGTWDSSLSVVAFGGG TKLTVLG |
| 14E8 | $V_L3$ | 41 | DIQMTQSPSSLSASVGDRVTITCQASQDINNYLNW YQQKLGKAPKLLIYDTSNLETGVPSRFSGSGFGTD FTFTISSLQPEDIATYYCQQYDNLFTFGQGTRLEIK R |
| 25B10 | $V_L5$ | 43 | QTVVTQEPSFSVSPGGTVTLTCGVSSGSVSTRYYPS WYQQTPGQAPRTLINSTNTRSSGVPDRFSGSILGN KAALTITGAQADDESDYFCVLYMGSGIWVFGGGT KLTVLG |
| 3B4 | $V_L6$ | 44 | DIVMTQTPLSSPVTLGQPASISCRSSQSLVHYDGNT YLSWLQQRPGQPPRLLIYKISNRFSGVPDRFSGSGA GTDFTLKISRVEAEDVGIYYCMQALEFPWTFGQGT KVEIK |
| 1B5 | $V_L7$ | 45 | DIVMTQTPLTSPVTLGQPASISCRSSQSLVHYDGNT YLSWLQQRPGQPPRLLIYKISNRFSGVPDRFSGSGA GTDFTLKISRVEAEDVGIYYCMQALEFPWTFGQGT KVEIK |
| 10H3 | $V_L8$ | 46 | DIVMTQTPLSSPVTLGQPASISCRSSQSLVHYDGNT YLSWLQQRPGQPPRLLIYKISNRFSGVPDRFSGSGA GTDFTLKISRVAAEDVGIYYCMQALEFPWTFGQG TKVEIK |
| 9D10 | $V_L9$ | 47 | QSVLTQPPSVSAAPGQKVTISCSGSSSNIGNNYVS WYQQLPGTAPKLLIYDNNRRPSGIPDRFSGSKSGT SATLGITGLQTGDEADYYCGTWDSSLSAVVFGGG TKLTVL |
| 3F4 | $V_L10$ | 48 | QSVLTQPPSVSAAPGQKVTISCSGSSSNIGNNYVS WYQQLPGTAPKLLIYDNNNRPSGIPDRFSGSKSGT SATLGITGLQTGDEADYYCETWDSSLSAGVFGGG TKLTVL |
| 8F9 | $V_L11$ | 49 | QSVLTQPPSVSAAPGQKVTISCSGSSSNIGNNYVS WYQQLPGTAPKLLIYDNNKRPSGIPDRFSGSKSGT SATLGITGLQTGDEADYYCGTWDSSLSAVVFGGG TKLTVL |

TABLE 2B

Exemplary Antibody Variable Heavy (V$_H$) Chains

| Contained in Clone | Designation | SEQ ID NO. | Amino Acid Sequence |
|---|---|---|---|
| 1A2 | V$_H$1 | 50 | QVQLVQSGAEVKKPGASVKVSCKASGYTFTGYY MHWVRQAPGQGLEWMGWINPNSGGTNSAQKFQ GRVTMTRDT SISTAYMELSRLRSDDTAVYYCARD ATSGWFDYWGQGTLVTVSS |
| 2G10 | V$_H$2 | 51 | QVQLVESGGGVVQPGRSLRLSCAASRFSFSRYGM HWVRQAPGKGLEWVAVIWFDGRNQYYADSVKG RFTISRDNSKNTLFLQMNSLRVEDTAVYYCARDHP VVGTSFDYWGQGTLVTVSS |
| 14E8 | V$_H$3 | 52 | QVQLVESGGGVVQPGRSLRLSCAASGFTFSSYGM HWVRQAPGKGLEWVAVIGYDGSYKYYADSVKG RFTISRDNSKNTLYLQMNSLRAEDTAVYYCARDG SNWNYGGSFDYWGQGTLVTVSS |
| 25B10 | V$_H$5 | 54 | EVQLLESGGGLVQPEGSLRLSCAASGFTFSIYAMS WVRQAPGKGLEWVSDISGRGGYTYYADSVKGRF TISRDNSKNTLYLQMNSLRADDTAVYYCAKDRSI AVAGPFDFWGQGTLVTVSS |
| 3B4 | V$_H$6 | 55 | QVQLVQSGAEVKKPGASVKVSCKASGYTFTAYY MHWVRQAPGQGLEWMGWINPNSGGTNSAQKFQ GRVTMTRDTSIRTAYMELSWLRSDDTAVYYCARD ATSGWFDIWGQGTPVTVSS |
| 1B5 | V$_H$7 | 56 | QVQLVQSGAEVKKPGASVKVSCKASGYTFTAYY MHWVRQAPGQGLEWMGWINPNSGGTNSAQKFQ GRVTMTRDTSIRTAYMELSWLRSDDTAVYYCARD ATSGWFDFWGQGTPVTVSS |
| 10H3 | V$_H$8 | 57 | QVQLVQSGAEVRKPGASVKVSCKASGYTFTAYY MHWVRQAPGQGLEWMGWINPYSGGTNSAQKFQ GRVTMTRDTSISTAYMELSWLRSDDTAVYYCARD ATSGWFDFWGQGTLVTVSS |
| 9D10 | V$_H$9 | 58 | QVQLVESGGGVVQPGRSLRLSCAASGFTFRSYGM HWVRQAPGKGLEWVAVIWYDGRNEYYADSVKG RFTISRDNSKNTLYLRMNSLRAEDTAVYYCARDH PVAGTSFDYWGQGTLVTVSS |
| 3F4 | V$_H$10 | 59 | QVQLVESGGGVVQPGRSLRLSCAASGFIFRSYGM HWVRQAPGKGLEWVAVISYDGSNKYYADSVKGR FTISRDNSKNTLYLQMNSLRAEDTAVYYCARDHP VAGTSFDYWGQGTLVTVSS |
| 8F9 | V$_H$11 | 60 | QVQLVESGGGVVQPGRSLRLSCAASGFTFSSYGM HWVRQAPGKGLEWVAVIWYDGRNKYHADSVKG RFTISRDNSKNTLYLQMNSLRAEDTAVYYCARDH PVAGTSFDYWGQGTLVTVSS |

TABLE 2C

Coding Sequence for Antibody Variable Light (V$_L$) Chains

| Contained in Clone | Designation | SEQ ID NO. | Coding Sequence |
|---|---|---|---|
| 1A2 | V$_L$1 | 61 | gatattgtgatgacccagactccactctcctcacctgtcacccttggacagccgg cctccatctcctgcaggtctagtcaaagctcgtatacagtgatggaaacaccta cttgagttggcttcagcagaggccaggccagcctccaagactcctaatttataag atttctaaccggttctctggggtcccagacagattcagtggcagtggggcaggg acagatttcacactgaaaatcagcagggtggaagctgacgatgtcgggattatt actgcatgcaagctatagaatttccgtggacgttcggccaagggacccaggtg gaaatcaaacgt |
| 2G10 | V$_L$2 | 62 | cagtctgtgttgacgcagccgccctcagtgtctgcggccccaggacagaaggt caccgtctcctgctctggaagcagctccaacattgggaataattatgtatcctggt accagcaactcccaggaacagccccaaactcctcatttatgacaataataagc gaccctcaggggattcctgaccgattctctggctccaagtctggcacgtcagcca ccctgggcatcaccggactccagactggggacgaggccgagtattactgcgg |

TABLE 2C-continued

Coding Sequence for Antibody Variable Light (V$_L$) Chains

| Contained in Clone | Designation | SEQ ID NO. | Coding Sequence |
|---|---|---|---|
| | | | aacatgggatagcagcctgagtgttgtggcattcggcggagggaccaagctga ccgtcctaggt |
| 14E8 | V$_L$3 | 63 | gacatccagatgacccagtctccatcctccctgtctgcatctgtaggagacaga gtcaccatcacttgccaggcgagtcaggacattaacaattatttaaattggtatca gcagaaactagggaaagcccctaagctcctgatctacgatacatccaatttgga aacagggtcccatcaaggttcagtggaagtggatttgggacagattttactttc accatcagcagcctgcagcctgaagatattgcaacatattactgtcaacagtatg ataatctcttccacttcggccaagggacacgactggagattaaacgt |
| 25B10 | V$_L$5 | 65 | cagactgtggtgacccaggagccatcgttctcagtgtccctggagggacagt cacactcacttgtggcgtgagctctggctcagtctctactaggtactaccccagct ggtaccagcagacccaggccaggctccacgcacgctcatcaacagcacaaa cactcgctcttctggggtccctgatcgcttctctggctccatccttgggaacaaag ctgccctcaccatcacgggggcccaggcagatgatgaatctgattatttctgtgt gctgtatatgggtagtggcatttgggtgttcggcggagggaccaagctgaccgt cctaggt |
| 3B4 | V$_L$6 | 66 | gatattgtgatgacccagactccactctcctcacctgtcacccttggacagccgg cctccatctcctgcaggtctagtcaaagcctcgttcactatgatggaaacacctac ttgagttggcttcagcagaggccaggccagcctccaagactcctaatttataaga tttctaaccggttctctggggtcccagacagattcagtggcagtggggcaggga cagatttcacactgaaaatcagcagggtggaagctgaggatgtcgggatttatta ctgcatgcaagctctagaatttccgtggacgttcggccaagggaccaaggtgg aaatcaaa |
| 1B5 | V$_L$7 | 67 | gatattgtgatgacccagactccactcacctcacctgtcacccttggacagccgg cctccatctcctgcaggtctagtcaaagcctcgttcactatgatggaaacacctac ttgagttggcttcagcagaggccaggccagcctccaagactcctaatttataaga tttctaaccggttctctggggtcccagacagattcagtggcagtggggcaggga cagatttcacactgaaaatcagcagggtggaagctgaggatgtcgggatttatta ctgcatgcaagctctagaatttccgtggacgttcggccaagggaccaaggtgg aaatcaaa |
| 10H3 | V$_L$8 | 68 | gatattgtgatgacccagactccactctcctcacctgtcacccttggacagccgg cctccatctcctgcaggtctagtcaaagcctcgttcactatgatggaaacacctac ttgagttggcttcagcagaggccaggccagcctccaagactcctaatttataaga tttctaaccggttctctggggtcccagacagattcagtggcagtggggcaggga cagatttcacactgaaaatcagcagggtggcagctgaggatgtcgggatttatta ctgcatgcaagctctagaatttccgtggacgttcggccaagggaccaaggtgg aaatcaaa |
| 9D10 | V$_L$9 | 69 | cagtctgtgttgacgcagccgccctcagtgtctgcggccccaggacagaaggt caccatctcctgctctggaagcagctccaacattgggaataattatgtatcctggt accagcagctcccagggacagcccccaaactcctcatttatgacaataataggc gacccctcagggattcctgaccgattctctggctccaagtctggcacgtcagcca ccctgggcatcaccggactccagactggggacgaggccgattattactgcgga acatgggatagcagcctgagtgctgtggtgttcggcggagggaccaagctga ccgtccta |
| 3F4 | V$_L$10 | 70 | cagtctgtgttgacgcagccgccctcagtgtctgcggccccaggacagaaggt caccatctcctgctctggaagcagctccaacattgggaataattatgtatcctggt accagcagctcccaggaacagcccccaaactcctcatttatgacaataataacc gacccctcagggattcctgaccgattctctggctccaagtctggcacgtcagcca ccctgggcatcaccggactccagactggggacgaggccgattattactgcgaa acatgggatagcagcctgagtgctggggtgttcggcggagggaccaagctga ccgtccta |
| 8F9 | VL11 | 71 | cagtctgtgttgacgcagccgccctcagtgtctgcggccccaggacagaaggt caccatctcctgctctggaagcagctccaacattgggaataattatgtatcctggt accagcaactcccaggaacagcccccaaactcctcatttatgacaataataagc gacccctcagggattcctgaccgattctctggctccaagtctggcacgtcagcca ccctgggcatcaccggactccagactggggacgaggccgattattactgcgga acttgggatagcagcctgagtgctgtggtattcggcggagggaccaagctgac cgtccta |

TABLE 2D

Coding Sequence for Antibody Variable Heavy ($V_H$) Chains

| Contained in Clone | Designation | SEQ ID NO. | Coding Sequence |
|---|---|---|---|
| 1A2 | $V_H1$ | 72 | caggtgcaactggtgcagtctggggctgaggtgaagaagcctggggcctcag tgaaggtctcctgcaaggatctggatacaccttcaccggctactatatgcactg ggtgcgacaggcccctggacaagggcttgagtggatgggatggatcaaccct aacagtggtggcacaaactctgcacagaagtttcagggcagggtcaccatgac cagggacacgtccatcagcacagcctacatggagctgagcaggctgagatct gacgacacggccgtgtattactgtgcaagagatgcgaccagtggctggtttgac tactggggccagggaaccctggtcaccgtctctagt |
| 2G10 | $V_H2$ | 73 | caggtgcagttggtggagtctggggggagcgcgtggtccagcctggggaggtccc tgagactctcctgtgcagcgtctagattctccttcagtagatatggcatgcactgg gtccgccaggctccaggcaaggggctggagtgggtggcagttatatggtttga tggaagaaatcaatactatgcagactccgtgaaggggcgattcaccatctccag agacaattccaagaatacgctgtttctgcaaatgaacagcctgagagtcgagga cacggctgtgtattactgtgcgagagatcacccagtagttggtacgagctttgac tactggggccagggaaccctggtcaccgtctctagt |
| 14E8 | $V_H3$ | 74 | caggtgcaactggtggagtctgggggaggcgtggtccagcctggggaggtccc tgagactctcctgtgcagcgtctggattcaccttcagtagctatggcatgcactgg gtccgccaggctccaggcaaggggctggagtgggtggcagttatatagggtatg atggaagttataaatactatgcagactccgtgaagggccgattcaccatctccag agacaattccaagaacacgctatatctgcaaatgaacagcctgagagccgagg acacggctgtgtattactgtgcgagagatgggtctaactggaactacgggggtt cttttgactactggggccagggaaccctggtcaccgtctctagt |
| 25B10 | $V_H5$ | 76 | gaggtgcagctgttggagtctgggggaggcttggtacagccggaggggtccc tgagactctcctgtgcagcctctggattcacctttagcatctatgccatgagctgg gtccgccaggctccaggaaggggctggagtgggtctcagatattagtggtcg tggtggttacacatactacgcagactccgtgaagggccggttcaccatctccag agacaattccaagaacacgctgtatctgcaaatgaacagcctgagagccgacg acacggccgtatattactgtgcgaaagatcggagtatagcagtggctggtcctt tgacttctggggccagggaaccctggtcaccgtctctagt |
| 3B4 | $V_H6$ | 77 | caggtgcagctggtgcagtctggggctgaggtgaagaagcctggggcctcag tgaaggtctcctgcaaggcttctggatacaccttcaccgcctactatatgcactgg gtgcgacaggcccctggacaagggcttgagtggatgggatggatcaaccct acagtggtggcacaaactctgcacagaagtttcagggcagggtcaccatgacc agggacacgtccatcagaacagcctacatggagttgagctggctgagatctga cgacacggccgtgtattattgtgcgagagatgcgaccagtggctggtttgacat ctggggccagggaaccccggtcaccgtctcctca |
| 1B5 | $V_H7$ | 78 | caggtgcagctggtgcagtctggggctgaggtgaagaagcctggggcctcag tgaaggtctcctgcaaggcttctggatacaccttcaccgcctactatatgcactgg gtgcgacaggcccctggacaagggcttgagtggatgggatggatcaaccct acagtggtggcacaaactctgcacagaagtttcagggcagggtcaccatgacc agggacacgtccatcagaacagcctacatggagttgagctggctgagatctga cgacacggccgtgtattactgtgcgagagatgcgaccagtggctggtttgactt ctggggccagggaaccccggtcaccgtctcctca |
| 10H3 | $V_H8$ | 79 | caggtgcagctggtgcagtctggggctgaggtgaggaagcctggggcctcag tgaaggtctcctgcaaggcttctggatacaccttcaccgcctactatatgcactgg gtgcgacaggcccctggacaagggcttgagtggatgggatggatcaaccctta cagtggtggcacaaactctgcacagaagtttcagggcagggtcaccatgacca gggacacgtccatcagcacagcctacatggagttgagctggctgagatctgac gacacggccgtgtattactgtgcgagagatgcgaccagtggctggtttgacttct ggggccagggaaccctggtcaccgtctcctca |
| 9D10 | $V_H9$ | 80 | caggtgcagctggtggagtctggggggaggcgtggtccagcctggggaggtccc tgagactctcctgcgcagcgtctggattcaccttcagaagctatggcatgcactg ggtccgccaggctccaggcaaggggctggagtgggtggcagttatatggtatg atggaaggaatgaatactatgcagactccgtgaagggccgattcaccatctcca gagacaattccaagaatacgctgtatctgcgaatgaacagtctgagagccgag gacacggctgtgtattactgtgcgagagatcacccagtagctggtacgagcttt gactactggggccagggaaccctggtcaccgtctcctca |
| 3F4 | $V_H10$ | 81 | caggtgcagctggtggagtctggggggcggcgtggtccagcctggggaggtccc tgagactctcctgtgcagcctctggattcatcttcaggagctatggcatgcactgg gtccgccaggctccaggcaaggggctggagtgggtggcagttatatcatatga tggaagtaataaatactatgcagactccgtgaagggccgattcaccatctccag agacaattccaagaacacgctgtatctgcaaatgaacagcctgagagctgagg acacggctgtctattactgtgcgagagatcacccagtggctggtacctcctttga ctactggggccagggaaccctggtcaccgtctcctca |
| 8F9 | $V_H11$ | 82 | caggtgcagctggtggagtctgggggaggcgtggtccagcctggggaggtccc tgagactctcctgtgcagcgtctggattcaccttcagtagctatggcatgcactgg |

TABLE 2D-continued

Coding Sequence for Antibody Variable Heavy (V_H) Chains

| Contained in Clone | Designation | SEQ ID NO. | Coding Sequence |
|---|---|---|---|
| | | | gtccgccaggctccaggcaaggggctggagtgggtggcagtcatatggtatg |
| | | | atggaagaaataaataccatgcagactccgtgaagggccgattcaccatctcca |
| | | | gagacaattccaagaacacgctatatctgcaaatgaacagcctgagagccgag |
| | | | gacacggctgtgtattactgtgcgagagatcacccagtagctggtacgagcttt |
| | | | gactactggggccagggaaccctggtcaccgtctcctca |

Each of the heavy chain variable regions listed in Table 2B can be combined with any of the light chain variable regions shown in Table 2A to form an antigen binding protein or the antigen binding protein component of an antigen binding protein-FGF21 fusion. Examples of such combinations include $V_H1$ combined with any of $V_L1$-$V_L11$; $V_H2$ combined with any of $V_L1$-$V_L11$; $V_H3$ combined with any of $V_L1$-$V_L11$; and so on.

In some instances, the antigen binding protein or the antigen binding protein component of an antigen binding protein-FGF21 fusion includes at least one heavy chain variable region and/or one light chain variable region from those listed in Tables 2A and 2B. In some instances, the antigen binding protein or the antigen binding protein component of an antigen binding protein-FGF21 fusion includes at least two different heavy chain variable regions and/or light chain variable regions from those listed in Table 2B. An example of such an antigen binding protein or the antigen binding protein component of an antigen binding protein-FGF21 fusion comprises (a) one $V_H1$, and (b) one of $V_H2$-$V_H11$. Another example comprises (a) one $V_H2$, and (b) one of $V_H1$ or $V_H3$-$V_H11$. Again another example comprises (a) one $V_H3$, and (b) one of $V_H1$, $V_H2$, or $V_H5$ or $V_H11$, etc.

Again another example of such an antigen binding protein or the antigen binding protein component of an antigen binding protein-FGF21 fusion comprises (a) one $V_L1$, and (b) one of $V_L2$-$V_L11$. Again another example of such an antigen binding protein or the antigen binding protein component of an antigen binding protein-FGF21 fusion comprises (a) one $V_L2$, and (b) one of $V_L1$, or $V_L3$-$V_L11$, etc. Again another example of such an antigen binding protein or the antigen binding protein component of an antigen binding protein-FGF21 fusion comprises (a) one $V_L3$, and (b) one of $V_L1$, $V_L2$, or $V_L4$-$V_L11$, etc.

The various combinations of heavy chain variable regions can be combined with any of the various combinations of light chain variable regions.

In other instances, the antigen binding protein or the antigen binding protein component of an antigen binding protein-FGF21 fusion contains two identical light chain variable regions and/or two identical heavy chain variable regions. As an example, the antigen binding protein or the antigen binding protein component of an antigen binding protein-FGF21 fusion can be an antibody or immunologically functional fragment that includes two light chain variable regions and two heavy chain variable regions in combinations of pairs of light chain variable regions and pairs of heavy chain variable regions as listed in Tables 2A and 2B.

Some antigen binding proteins and antigen binding protein-FGF21 fusion antigen binding protein components that are provided comprise a heavy chain variable domain comprising a sequence of amino acids that differs from the sequence of a heavy chain variable domain selected from $V_H1$-$V_H11$ at only 1, 2, 3, 4, 5, 6, 7, 8, 9, 10, 11, 12, 13, 14 or 15 amino acid residues, wherein each such sequence difference is independently either a deletion, insertion or substitution of one amino acid, with the deletions, insertions and/or substitutions resulting in no more than 15 amino acid changes relative to the foregoing variable domain sequences. The heavy chain variable region in some antigen binding proteins and some antigen binding protein components of antigen binding protein-FGF21 fusions comprise a sequence of amino acids that has at least 70%, 75%, 80%, 85%, 90%, 95%, 97% or 99% sequence identity to the amino acid sequences of the heavy chain variable region of $V_H1$-$V_H11$.

Certain antigen binding proteins and antigen binding protein-FGF21 fusion antigen binding protein components comprise a light chain variable domain comprising a sequence of amino acids that differs from the sequence of a light chain variable domain selected from $V_L1$-$V_L11$ at only 1, 2, 3, 4, 5, 6, 7, 8, 9, 10, 11, 12, 13, 14 or 15 amino acid residues, wherein each such sequence difference is independently either a deletion, insertion or substitution of one amino acid, with the deletions, insertions and/or substitutions resulting in no more than 15 amino acid changes relative to the foregoing variable domain sequences. The light chain variable region in some antigen binding proteins and antigen binding protein-FGF21 fusion antigen binding protein components comprise a sequence of amino acids that has at least 70%, 75%, 80%, 85%, 90%, 95%, 97% or 99% sequence identity to the amino acid sequences of the light chain variable region of $V_L1$-$V_L11$.

In additional instances, antigen binding proteins and antigen binding protein-FGF21 fusion antigen binding protein components comprise the following pairings of light chain and heavy chain variable domains: $V_L1$ with $V_H1$, $V_L2$ with $V_H2$, $V_L3$ with $V_H3$, $V_L4$ with $V_H4$, $V_L5$ with $V_H5$, $V_L6$ with $V_H6$, $V_L7$ with $V_H7$, $V_L8$ with $V_H8$, $V_L9$ with $V_H9$, $V_L10$ with $V_H10$, $V_L11$ with $V_H11$. In some instances, the antigen binding proteins and antigen binding protein-FGF21 fusion antigen binding protein components in the above pairings can comprise amino acid sequences that have 70%, 75%, 80%, 85%, 90%, 95%, 96%, 97%, 98% or 99% sequence identity with the specified variable domains.

Still other antigen binding proteins and antigen binding protein components of an antigen binding protein-FGF21 fusions, e.g., antibodies or immunologically functional fragments, include variant forms of a variant heavy chain and a variant light chain as just described.

Antigen Binding Protein and Antigen Binding Protein-FGF21 Fusion Antigen Binding Protein Component CDRs The antigen binding proteins and antigen binding protein components of antigen binding protein-FGF21 fusions disclosed herein are polypeptides into which one or more CDRs are grafted, inserted and/or joined. An antigen binding protein or antigen binding protein component of an antigen binding protein-FGF21 fusion can have 1, 2, 3, 4, 5 or 6 CDRs. An antigen binding protein or antigen binding protein component of an antigen binding protein-FGF21 fusion thus can have, for example, one heavy chain CDR1 ("CDRH1"), and/or one heavy chain CDR2 ("CDRH2"), and/or one heavy chain CDR3 ("CDRH3"), and/or one light chain CDR1 ("CDRL1"), and/or one light chain CDR2 ("CDRL2"), and/or one light chain CDR3 ("CDRL3"). Some antigen binding proteins and antigen binding protein-FGF21 fusion antigen binding protein components include both a CDRH3 and a CDRL3. Specific heavy and light chain CDRs are identified in Tables 3A and 3B, respectively.

Complementarity determining regions (CDRs) and framework regions (FR) of a given antibody can be identified using any of the numbering systems known to those of skill in the art, such as the system described by Kabat et al. in Sequences of Proteins of Immunological Interest, 5th Ed., US Dept. of Health and Human Services, PHS, NIH, NIH Publication no. 91-3242, 1991, see also Chothia and Lesk, 1987, *J. Mol. Biol.* 196:901-917; Chothia et al., 1989, *Nature* 342: 877-883. Certain antigen binding proteins and antigen binding protein-FGF21 fusion antigen binding protein components that are disclosed herein comprise one or more amino acid sequences that are identical or have substantial sequence identity to the amino acid sequences of one or more of the CDRs presented in Table 3A (CDRHs) and Table 3B (CDRLs).

TABLE 3A

Exemplary CDRH Sequences

| CloneNO: | SEQ ID NO: | Contained in Reference | Designation | Sequence |
|---|---|---|---|---|
| 1A2 | 83 | $V_H1$ | CDRH1-1 | GYYMH |
| 2G10 | 84 | $V_H2$ | CDRH1-2 | RYGMH |
| 14E8 | 85 | $V_H3$ | CDRH1-3 | SYGMH |
| 25B10 | 87 | $V_H5$ | CDRH1-5 | IYAMS |
| 3B4 | 88 | $V_H6$ | CDRH1-6 | AYYMH |
| 1B5 | 88 | $V_H7$ | CDRH1-7 | AYYMH |
| 10H3 | 88 | $V_H8$ | CDRH1-8 | AYYMH |
| 9D10 | 85 | $V_H9$ | CDRH1-9 | SYGMH |
| 3F4 | 85 | $V_H10$ | CDRH1-10 | SYGMH |
| 8F9 | 85 | $V_H11$ | CDRH1-11 | SYGMH |
| 1A2 | 89 | $V_H1$ | CDRH2-1 | WINPNSGGTNSAQKFQG |
| 2G10 | 90 | $V_H2$ | CDRH2-2 | VIWFDGRNQYYADSVKG |
| 14E8 | 91 | $V_H3$ | CDRH2-3 | VIGYDGSYKYYADSVKG |
| 25B10 | 93 | $V_H5$ | CDRH2-5 | DISGRGGYTYYADSVKG |
| 3B4 | 89 | $V_H6$ | CDRH2-6 | WINPNSGGTNSAQKFQG |
| 1B5 | 89 | $V_H7$ | CDRH2-7 | WINPNSGGTNSAQKFQG |
| 10H3 | 94 | $V_H8$ | CDRH2-8 | WINPYSGGTNSAQKFQG |
| 9D10 | 95 | $V_H9$ | CDRH2-9 | VIWYDGRNEYYADSVKG |
| 3F4 | 96 | $V_H10$ | CDRH2-10 | VISYDGSNKYYADSVKG |
| 8F9 | 97 | $V_H11$ | CDRH2-11 | VIWYDGRNKYHADSVKG |
| 1A2 | 98 | $V_H1$ | CDRH3-1 | GWFDY |
| 2G10 | 99 | $V_H2$ | CDRH3-2 | GTSFDY |
| 14E8 | 100 | $V_H3$ | CDRH3-3 | YGGSFDY |
| 25B10 | 102 | $V_H5$ | CDRH3-5 | VAGPFDF |
| 3B4 | 103 | $V_H6$ | CDRH3-6 | GWFDI |
| 1B5 | 104 | $V_H7$ | CDRH3-7 | GWFDF |
| 10H3 | 104 | $V_H8$ | CDRH3-8 | GWFDF |
| 9D10 | 105 | $V_H9$ | CDRH3-9 | GTSFDY |
| 3F4 | 105 | $V_H10$ | CDRH3-10 | GTSFDY |
| 8F9 | 105 | $V_H11$ | CDRH3-11 | GTSFDY |

TABLE 3B

Exemplary CDRL Sequences

| CloneNO: | SEQ ID NO: | Contained in Reference | Designation | Sequence |
|---|---|---|---|---|
| 1A2 | 106 | $V_L1$ | CDRL1-1 | RSSQSLVYSDGNTYLS |
| 2G10 | 107 | $V_L2$ | CDRL1-2 | SGSSSNIGNNYVS |
| 14E8 | 108 | $V_L3$ | CDRL1-3 | QASQDINNYLN |
| 25B10 | 110 | $V_L5$ | CDRL1-5 | GVSSGSVSTRYYPS |
| 3B4 | 111 | $V_L6$ | CDRL1-6 | RSSQSLVHYDGNTYLS |
| 1B5 | 111 | $V_L7$ | CDRL1-7 | RSSQSLVHYDGNTYLS |
| 10H3 | 111 | $V_L8$ | CDRL1-8 | RSSQSLVHYDGNTYLS |
| 9D10 | 107 | $V_L9$ | CDRL1-9 | SGSSSNIGNNYVS |
| 3F4 | 107 | $V_L10$ | CDRL1-10 | SGSSSNIGNNYVS |
| 8F9 | 107 | $V_L11$ | CDRL1-11 | SGSSSNIGNNYVS |
| 1A2 | 112 | $V_L1$ | CDRL2-1 | KISNRFS |
| 2G10 | 113 | $V_L2$ | CDRL2-2 | DNNKRP |
| 14E8 | 114 | $V_L3$ | CDRL2-3 | DTSNLET |
| 25B10 | 116 | $V_L5$ | CDRL2-5 | STNTRSS |
| 3B4 | 112 | $V_L6$ | CDRL2-6 | KISNRFS |
| 1B5 | 112 | $V_L7$ | CDRL2-7 | KISNRFS |
| 10H3 | 112 | $V_L8$ | CDRL2-8 | KISNRFS |
| 9D10 | 117 | $V_L9$ | CDRL2-9 | DNNRRPS |
| 3F4 | 118 | $V_L10$ | CDRL2-10 | DNNNRPS |
| 8F9 | 119 | $V_L11$ | CDRL2-11 | DNNKRPS |
| 1A2 | 120 | $V_L1$ | CDRL3-1 | MQAIEFPWT |

TABLE 3B-continued

Exemplary CDRL Sequences

| CloneNO: | SEQ ID NO: | Contained in Reference | Designation | Sequence |
|---|---|---|---|---|
| 2G10 | 121 | $V_L2$ | CDRL3-2 | GTWDSSLSVVA |
| 14E8 | 122 | $V_L3$ | CDRL3-3 | QQYDNLFT |
| 25B10 | 124 | $V_L5$ | CDRL3-5 | VLYMGSGIWV |
| 3B4 | 125 | $V_L6$ | CDRL3-6 | MQALEFPWT |
| 1B5 | 125 | $V_L7$ | CDRL3-7 | MQALEFPWT |
| 10H3 | 125 | $V_L8$ | CDRL3-8 | MQALEFPWT |
| 9D10 | 126 | $V_L9$ | CDRL3-9 | GTWDSSLSAVV |
| 3F4 | 127 | $V_L10$ | CDRL3-10 | ETWDSSLSAGV |
| 8F9 | 126 | $V_L11$ | CDRL3-11 | GTWDSSLSAVV |

TABLE 3C

Coding Sequences for CDRHs

| CloneNO: | SEQ ID NO: | Contained in Reference | Designation | Sequence |
|---|---|---|---|---|
| 1A2 | 128 | $V_H1$ | CDRH1-1 | ggctactatatgcac |
| 2G10 | 129 | $V_H2$ | CDRH1-2 | agatatggcatgcac |
| 14E8 | 130 | $V_H3$ | CDRH1-3 | agctatggcatgcac |
| 25B10 | 132 | $V_H5$ | CDRH1-5 | atctatgccatgagc |
| 3B4 | 133 | $V_H6$ | CDRH1-6 | gcctactatatgcac |
| 1B5 | 133 | $V_H7$ | CDRH1-7 | gcctactatatgcac |
| 10H3 | 133 | $V_H8$ | CDRH1-8 | gcctactatatgcac |
| 9D10 | 130 | $V_H9$ | CDRH1-9 | agctatggcatgcac |
| 3F4 | 130 | $V_H10$ | CDRH1-10 | agctatggcatgcac |
| 8F9 | 130 | $V_H11$ | CDRH1-11 | agctatggcatgcac |
| 1A2 | 134 | $V_H1$ | CDRH2-1 | tggatcaaccctaacagtggtggcacaaactctgcacagaagtttcagggc |
| 2G10 | 135 | $V_H2$ | CDRH2-2 | ttatatggtttgatggaagaaatcaatactatgcagactccgtgaagggg |
| 14E8 | 136 | $V_H3$ | CDRH2-3 | gttatagggtatgatggaagttataaatactatgcagactccgtgaagggc |
| 25B10 | 138 | $V_H5$ | CDRH2-5 | gatattagtggtcgtggtggttacacatactacgcagactccgtgaagggc |
| 3B4 | 134 | $V_H6$ | CDRH2-6 | tggatcaaccctaacagtggtggcacaaactctgcacagaagtttcagggc |
| 1B5 | 134 | $V_H7$ | CDRH2-7 | tggatcaaccctaacagtggtggcacaaactctgcacagaagtttcagggc |
| 10H3 | 139 | $V_H8$ | CDRH2-8 | tggatcaacccttacagtggtggcacaaactctgcacagaagtttcagggc |
| 9D10 | 140 | $V_H9$ | CDRH2-9 | gttatatggtatgatggaaggaatgaatactatgcagactccgtgaagggc |
| 3F4 | 141 | $V_H10$ | CDRH2-10 | gttatatcatatgatggaagtaataaatactatgcagactccgtgaagggc |
| 8F9 | 142 | $V_H11$ | CDRH2-11 | gtcatatggtatgatggaagaaataaataccatgcagactccgtgaagggc |
| 1A2 | 143 | $V_H1$ | CDRH3-1 | ggctggtttgactac |
| 2G10 | 144 | $V_H2$ | CDRH3-2 | ggtacgagctttgactac |
| 14E8 | 145 | $V_H3$ | CDRH3-3 | tacggggttcttttgactac |
| 25B10 | 147 | $V_H5$ | CDRH3-5 | gtggctggtcctttgacttc |
| 3B4 | 148 | $V_H6$ | CDRH3-6 | ggctggtttgacatc |
| 1B5 | 149 | $V_H7$ | CDRH3-7 | ggctggtttgacttc |
| 10H3 | 149 | $V_H8$ | CDRH3-8 | ggctggtttgacttc |

TABLE 3C-continued

Coding Sequences for CDRHs

| CloneNO: | SEQ ID NO: | Contained in Reference | Designation | Sequence |
|---|---|---|---|---|
| 9D10 | 144 | V$_H$9 | CDRH3-9 | ggtacgagctttgactac |
| 3F4 | 150 | V$_H$10 | CDRH3-10 | ggtacctcctttgactac |
| 8F9 | 144 | V$_H$11 | CDRH3-11 | ggtacgagctttgactac |

TABLE 3D

Coding Sequences for CDRLs

| CloneNO: | SEQ ID NO: | Contained in Reference | Designation | Sequence |
|---|---|---|---|---|
| 1A2 | 151 | V$_L$1 | CDRL1-1 | aggtctagtcaaagcctcgtatacagtgatggaaacacctacttgagt |
| 2G10 | 152 | V$_L$2 | CDRL1-2 | tctggaagcagctccaacattgggaataattatgtatcc |
| 14E8 | 153 | V$_L$3 | CDRL1-3 | caggcgagtcaggacattaacaattatttaaat |
| 25B10 | 155 | V$_L$5 | CDRL1-5 | ggcgtgagctctggctcagtctctactaggtactaccccagc |
| 3B4 | 156 | V$_L$6 | CDRL1-6 | aggtctagtcaaagcctcgttcactatgatggaaacacctacttgagt |
| 1B5 | 156 | V$_L$7 | CDRL1-7 | aggtctagtcaaagcctcgttcactatgatggaaacacctacttgagt |
| 10H3 | 156 | V$_L$8 | CDRL1-8 | aggtctagtcaaagcctcgttcactatgatggaaacacctacttgagt |
| 9D10 | 152 | V$_L$9 | CDRL1-9 | tctggaagcagctccaacattgggaataattatgtatcc |
| 3F4 | 152 | V$_L$10 | CDRL1-10 | tctggaagcagctccaacattgggaataattatgtatcc |
| 8F9 | 152 | V$_L$11 | CDRL1-11 | tctggaagcagctccaacattgggaataattatgtatcc |
| 1A2 | 157 | V$_L$1 | CDRL2-1 | aagatttctaaccggttctct |
| 2G10 | 158 | V$_L$2 | CDRL2-2 | gacaataataagcgaccc |
| 14E8 | 159 | V$_L$3 | CDRL2-3 | gatacatccaatttggaaaca |
| 25B10 | 161 | V$_L$5 | CDRL2-5 | agcacaaacactcgctcttct |
| 3B4 | 157 | V$_L$6 | CDRL2-6 | aagatttctaaccggttctct |
| 1B5 | 157 | V$_L$7 | CDRL2-7 | aagatttctaaccggttctct |
| 10H3 | 157 | V$_L$8 | CDRL2-8 | aagatttctaaccggttctct |
| 9D10 | 162 | V$_L$9 | CDRL2-9 | gacaataataggcgaccctca |
| 3F4 | 163 | V$_L$10 | CDRL2-10 | gacaataataaccgaccctca |
| 8F9 | 164 | V$_L$11 | CDRL2-11 | gacaataataagcgaccctca |
| 1A2 | 165 | V$_L$1 | CDRL3-1 | atgcaagctatagaatttccgtggacg |
| 2G10 | 166 | V$_L$2 | CDRL3-2 | ggaacatgggatagcagcctgagtgttgtggca |
| 14E8 | 167 | V$_L$3 | CDRL3-3 | caacagtatgataatctcttcacc |
| 25B10 | 169 | V$_L$5 | CDRL3-5 | gtgctgtatatgggtagtggcatttgggtg |
| 3B4 | 170 | V$_L$6 | CDRL3-6 | atgcaagctctagaatttccgtggacg |
| 1B5 | 170 | V$_L$7 | CDRL3-7 | atgcaagctctagaatttccgtggacg |
| 10H3 | 170 | V$_L$8 | CDRL3-8 | atgcaagctctagaatttccgtggacg |
| 9D10 | 171 | V$_L$9 | CDRL3-9 | ggaacatgggatagcagcctgagtgctgtggtg |

TABLE 3D-continued

Coding Sequences for CDRLs

| CloneNO: | SEQ ID NO: | Contained in Reference | Designation | Sequence |
|---|---|---|---|---|
| 3F4 | 172 | V$_L$10 | CDRL3-10 | gaaacatgggatagcagcctgagtgctggggtg |
| 8F9 | 173 | V$_L$11 | CDRL3-11 | ggaacttgggatagcagcctgagtgctgtggta |

The structure and properties of CDRs within a naturally occurring antigen binding proteins and antigen binding protein-FGF21 fusion antigen binding protein components (e.g., antibodies) has been described, supra. Briefly, in a traditional antibody, the CDRs are embedded within a framework in the heavy and light chain variable region where they constitute the regions responsible for antigen binding and recognition. A variable region comprises at least three heavy or light chain CDRs, (see, e.g. Kabat et al., 1991, *Sequences of Proteins of Immunological Interest*, Public Health Service N.I.H., Bethesda, Md.; see also Chothia and Lesk, 1987, *J. Mol. Biol.* 196:901-917; Chothia et al., 1989, *Nature* 342: 877-883), within a framework region (designated framework regions 1-4, FR1, FR2, FR3, and FR4, by Kabat et al., 1991, supra; see also Chothia and Lesk, 1987, supra). The CDRs provided herein, however, can not only be used to define the antigen binding domain of an antigen binding protein or antigen binding protein-FGF21 fusion antigen binding protein component, but they can be embedded in a variety of other polypeptide structures, as described herein.

In one aspect, the CDRs provided are (a) a CDRH selected from the group consisting of (i) a CDRH1 selected from the group consisting of SEQ ID NO:83-88; (ii) a CDRH2 selected from the group consisting of SEQ ID NO:89-97; (iii) a CDRH3 selected from the group consisting of SEQ ID NO:98-105; and (iv) a CDRH of (i), (ii) and (iii) that contains one or more amino acid substitutions, deletions or insertions of no more than five, four, three, two, or one amino acids; (B) a CDRL selected from the group consisting of (i) a CDRL1 selected from the group consisting of SEQ ID NO:106-111; (ii) a CDRL2 selected from the group consisting of SEQ ID NO:112-119; (iii) a CDRL3 selected from the group consisting of SEQ ID NO:120-127; and (iv) a CDRL of (i), (ii) and (iii) that contains one or more amino acid substitutions, deletions or insertions of no more than five, four, three, two, or one amino acids amino acids.

In another aspect, an antigen binding protein or antigen binding protein-FGF21 fusion antigen binding protein component includes 1, 2, 3, 4, 5, or 6 variant forms of the CDRs listed in Tables 3A and 3B, each having at least 80%, 85%, 90%, 95%, 96%, 97%, 98%, or 99% sequence identity to a CDR sequence listed in Tables 3A and 3B. Some antigen binding proteins and antigen binding protein-FGF21 fusion antigen binding protein components include 1, 2, 3, 4, 5, or 6 of the CDRs listed in Tables 3A and 3B, each differing by no more than 1, 2, 3, 4 or 5 amino acids from the CDRs listed in these tables.

In still another aspect, an antigen binding protein or antigen binding protein-FGF21 fusion antigen binding protein component includes the following associations of CDRL1, CDRL2 and CDRL3: SEQ ID NOs:106, 112 and 120; SEQ ID NOs: 107, 113, 121; SEQ ID NO: 108, 114, 122; SEQ ID NOs: 110, 116, 124; SEQ ID NOs: 111, 112, 125; SEQ ID NOs: 111, 112, 127; SEQ ID NOs: 111, 112, 125; SEQ ID NOs: 107, 117, 126; SEQ ID NOs: 107, 118, 127 and SEQ ID NOs: 107, 119, 126.

In an additional aspect, an antigen binding protein or antigen binding protein-FGF21 fusion antigen binding protein component includes the following associations of CDRH1, CDRH2 and CDRH3: SEQ ID NOs:83, 89, and 98; SEQ ID NOs 84, 90, 99; SEQ ID NOs: 85, 91, 100; SEQ ID NOs: 87, 93, 102; SEQ ID NOs:88, 89, 103; SEQ ID NOs: 88, 89, 104; SEQ ID NOs: 88, 94, 104; SEQ ID NOs: 85, 95, 105; SEQ ID NOs: 85, 96, 105; and SEQ ID NOs: 85, 97, 105.

In another aspect, an antigen binding protein or antigen binding protein-FGF21 fusion antigen binding protein component includes the following associations of CDRL1, CDRL2 and CDRL3 with CDRH1, CDRH2 and CDRH3: SEQ ID NOs:106, 112 and 120 and SEQ ID NOs:83, 89, and 98; SEQ ID NOs: 107, 113, 121 and SEQ ID NOs 84, 90, 99; SEQ ID NO: 108, 114, 122 and SEQ ID NOs: 85, 91, 100; SEQ ID NOs: 110, 116, 124 and SEQ ID NOs: 87, 93, 102; SEQ ID NOs: 111, 112, 125 and SEQ ID NOs:88, 89, 103; SEQ ID NOs: 111, 112, 127 and SEQ ID NOs: 88, 89, 104; SEQ ID NOs: 111, 112, 125 and SEQ ID NOs: 88, 94, 104; SEQ ID NOs: 107, 117, 126 and SEQ ID NOs: 85, 95, 105; SEQ ID NOs: 107, 118, 127 and SEQ ID NOs: 85, 96, 105; and SEQ ID NOs: 107, 119, 126 and SEQ ID NOs: 85, 97, 105.

Consensus Sequences

In yet another aspect, the CDRs disclosed herein include consensus sequences derived from groups of related antigen binding proteins and antigen binding protein-FGF21 fusion antigen binding protein components, particularly monoclonal antibodies. As described herein, a "consensus sequence" refers to amino acid sequences having conserved amino acids common among a number of sequences and variable amino acids that vary within a given amino acid sequences. The CDR consensus sequences provided include CDRs corresponding to each of CDRH1, CDRH2, CDRH3, CDRL1, CDRL2 and CDRL3.

Consensus sequences were determined using standard phylogenic analyses of the CDRs corresponding to the $V_H$ and $V_L$ of the disclosed antibodies, some of which specifically binds β-Klotho one of FGFR1c, FGFR2c, FGFR3c, and FGFR4. The consensus sequences were determined by keeping the CDRs contiguous within the same sequence corresponding to a $V_H$ or $V_L$.

Light Chain CDR3
Group 1

| MQA | I | EFPWT | (SEQ ID NO: 120) |
| MQA | L | EFPWT | (SEQ ID NO: 125) |
| MQA | X$_1$ | EFPWT | (SEQ ID NO: 174) | wherein X$_1$ is L or I

Group 2

| | | | | |
|---|---|---|---|---|
| GTWDSSLS | V | V | A | (SEQ ID NO: 121) |
| GTWDSSLS | A | V | V | (SEQ ID NO: 126) |
| GTWDSSLS | X₂ | V | X₃ | (SEQ ID NO: 175) | wherein $X_2$ is V or A and $X_3$ is V or A

Group 3

QQYDNLFT (SEQ ID NO: 122)

Group 4

QQYGSAPLT (SEQ ID NO: 123)

Group 5

VLYMGSGIWV (SEQ ID NO: 124)

Group 6

ETWDSSLSAGV (SEQ ID NO: 127)

Light Chain CDR2
Group 1

KISNRFS (SEQ ID NO: 112)

Group 2

| | | | | |
|---|---|---|---|---|
| DNN | K | RP | | (SEQ ID NO: 113) |
| DNN | N | RP | S | (SEQ ID NO: 118) |
| DNN | R | RP | S | (SEQ ID NO: 117) |
| DNN | X₄ | RP | X₅ | (SEQ ID NO: 176) | wherein $X_4$ is K, N or R and $X_5$ is S or absent

Group 3

DTSNLET (SEQ ID NO: 114)

Group 4

GASSRAT (SEQ ID NO: 115)

Group 5

STNTRSS (SEQ ID NO: 116)

Light Chain CDR1
Group 1

| | | | | |
|---|---|---|---|---|
| RSSQSLV | | Y | S | DGNTYLS (SEQ ID NO: 106) |
| RSSQSLV | H | Y | | DGNTYLS (SEQ ID NO: 111) |
| RSSQSLV | X₂₂ | Y | X₂₃ | DGNTYLS (SEQ ID NO: 177) | wherein $X_{22}$ is H or absent and $X_{23}$ is S or absent.

Group 2

SGSSSNIGNNYVS (SEQ ID NO: 107)

Group 3

QASQDINNYLN (SEQ ID NO: 108)

Group 4

RASQSVSGNYLA (SEQ ID NO: 109)

Group 5

GVSSGSVSTRYYPS (SEQ ID NO: 110)

Heavy CDR3
Group 1

| | |
|---|---|
| GWFD Y | (SEQ ID NO: 98) |
| GWFD I | (SEQ ID NO: 103) |
| GWFD F | (SEQ ID NO: 104) |
| GWFD X₆ | (SEQ ID NO: 178) | wherein $X_6$ is Y, I or F

Group 2

GTSFDY (SEQ ID NO: 99)

Group 3

YGGSFDY (SEQ ID NO: 100)

Group 4

MVYVLDY (SEQ ID NO: 101)

Group 5

VAGPFDF (SEQ ID NO: 102)

Heavy CDR2
Group 1

| | | | |
|---|---|---|---|
| WINP N | SGGTNSAQKFQG | | (SEQ ID NO: 89) |
| WINP N | SGGTNSAQKFQG | | (SEQ ID NO: 89) |
| WINP N | SGGTNSAQKFQG | | (SEQ ID NO: 89) |
| WINP Y | SGGTNSAQKFQG | | (SEQ ID NO: 94) |
| WINP $X_7$ | SGGTNSAQKFQG | | (SEQ ID NO: 179) | wherein $X_7$ is N or Y

Group 2

| | | | | | | | |
|---|---|---|---|---|---|---|---|
| VI | W | F | DG | R | N | Q | YYADSVKG (SEQ ID NO: 90) |
| VI | G | Y | DG | S | Y | K | YYADSVKG (SEQ ID NO: 91) |
| VI | G | Y | DG | S | Y | K | YYADSVKG (SEQ ID NO: 91) |
| VI | $X_8$ | $X_9$ | DG | $X_{10}$ | $X_{11}$ | $X_{12}$ | YYADSVKG (SEQ ID NO: 180) | wherein $X_8$ is W or G; $X_9$ is F or Y; $X_{10}$ is R or S; $X_{11}$ is N or Y and $X_{12}$ is Q or K Group 3

| | | | | | | |
|---|---|---|---|---|---|---|
| A | ISG | S | G | V | S | TYYADSVKG (SEQ ID NO: 92) |
| D | ISG | R | G | G | Y | TYYADSVKG (SEQ ID NO: 93) |
| $X_{13}$ | ISG | $X_{14}$ | G | $X_{15}$ | $X_{16}$ | TYYADSVKG (SEQ ID NO: 181) | wherein $X_{13}$ is A or D; $X_{14}$ is S or R; $X_{15}$ is V or G; and $X_{16}$ is S or Y Group 4

| | | | | | |
|---|---|---|---|---|---|
| VI | W | YDGRNEY | Y | | ADSVKG (SEQ ID NO: 95) |
| VI | S | YDGSNKY | Y | | ADSVKG (SEQ ID NO: 96) |
| VI | W | YDGRNKY | H | | ADSVKG (SEQ ID NO: 97) |
| VI | $X_{17}$ | YDGRNKY | $X_{18}$ | | ADSVKG (SEQ ID NO: 182) | wherein $X_{17}$ is W or S and $X_{18}$ is Y or H.

Heavy CDR1
Group 1

| | | | | |
|---|---|---|---|---|
| G | Y | Y | M | H (SEQ ID NO: 83) |
| R | Y | G | M | H (SEQ ID NO: 84) |
| S | Y | G | M | H (SEQ ID NO: 85) |
| T | Y | A | M | S (SEQ ID NO: 86) |
| I | Y | A | M | S (SEQ ID NO: 87) |
| A | Y | Y | M | H (SEQ ID NO: 88) |
| $X_{19}$ | Y | $X_{20}$ | M | $X_{21}$ (SEQ ID NO: 183) | wherein $X_{19}$ is A, G, R, S, T or I, $X_{20}$ is Y, G or A and $X_{21}$ is H or S.

In some cases the antigen binding protein or antigen binding protein-FGF21 fusion antigen binding protein component comprises at least one heavy chain CDR1, CDR2, or CDR3 having one of the above consensus sequences. In some cases, the antigen binding protein or antigen binding protein-FGF21 fusion antigen binding protein component comprises at least one light chain CDR1, CDR2, or CDR3 having one of the above consensus sequences. In other cases, the antigen binding protein or antigen binding protein-FGF21 fusion antigen binding protein component comprises at least two heavy chain CDRs according to the above consensus sequences, and/or at least two light chain CDRs according to the above consensus sequences. In still other cases, the antigen binding protein or antigen binding protein-FGF21 fusion antigen binding protein component comprises at least three heavy chain CDRs according to the above consensus sequences, and/or at least three light chain CDRs according to the above consensus sequences.

FGFR-Binding Peptides

Peptides that specifically bind to an FGFR, e.g., FGFR1c, FGFR2c, FGFR3c, or FGFR4 are also provided. Such peptides can form an element of a heavy chain, which in turn can form an element of an antigen binding protein, such as an antibody that specifically binds to β-Klotho. The insertion can change the antibody's specificity from specificity for a single target into the ability to associate and/or specifically bind with two or more different targets. In various embodiments, the disclosed peptides are inserted into a CH2 or CH3 loop region of an Fc region of a heavy chain, as described herein.

Peptide libraries were screened, and ELISA experiments were performed to determine binding, which resulted in a number of peptides that bind to an FGFR, e.g., FGFR1c. Table 4A discloses exemplary FGFR1c-binding peptides that were identified (also see FIG. 12):

TABLE 4A

Exemplary FGFR-binding Peptides

| Identifier | Amino Acid Sequence | SEQ ID NO |
|---|---|---|
| SR1 | TRLWKYWV | 184 |
| SR2 | RRLYIFWE | 185 |

TABLE 4A-continued

Exemplary FGFR-binding Peptides

| Identifier | Amino Acid Sequence | SEQ ID NO |
|---|---|---|
| SR3 | YKAWGYYV | 186 |
| SR4 | YQAWGYYV | 187 |
| SR5 | YQAWGYLV | 188 |
| SR6 | YQAWGYFV | 189 |
| SR7 | FTWVFWNV | 190 |
| SR8 | YQVWGYFV | 191 |
| SR9 | YKWLKWNL | 192 |
| SR10 | RRLYIFEW | 193 |
| SR11 | WAERGG | 194 |
| SR12 | GGWAVGRI | 195 |
| SR13 | YKYLVFWV | 196 |
| SR14 | YKYLSYWV | 197 |
| SR15 | YKTAWYWK | 198 |
| SR16 | YVFHKWWV | 199 |
| SR17 | YVFYLWWK | 200 |
| SR18 | YRWLHWHV | 201 |
| SR19 | YKFLFWHA | 202 |
| SR20 | RRQWGFWV | 203 |
| SR21 | YSAWSFWV | 204 |
| SR22 | LARWGFWV | 205 |
| SR23 | YDAWGYWV | 206 |
| SR24 | WRKYYHFWVS | 207 |
| SR25 | KRLYGLFWYD | 208 |
| SR26 | KKHWSSLFFE | 209 |
| SR27 | KAWPYSWEAV | 210 |
| Rm26 | EWYCGVLFNCQQ | 211 |
| Rm27 | HFGCGVIFNCVSD | 212 |
| Rm33 | WELCASGYGWCYLH | 213 |
| Rm37 | APSCKSYIGFGLYHCWDG | 214 |
| Rm40 | HFKCGMGLFECADP | 215 |

TABLE 4B

Exemplary FGFR-binding Peptide Coding Sequences

| Identifier | Coding Sequence | SEQ ID NO |
|---|---|---|
| SR1 | acgaggctttggaagtattgggtg | 216 |
| SR2 | aggaggttgtatattttttgggag | 217 |
| SR3 | tataaggcgtggggttattatgtg | 218 |
| SR4 | tattaggcgtggggttattatgtg | 219 |
| SR5 | tattaggcgtggggttatttggtg | 220 |
| SR6 | taccaggcttggggttacttcgtt | 221 |
| SR7 | ttcacttgggttttctggaacgtt | 222 |
| SR8 | taccaggcttggggttacttcgtt | 223 |
| SR9 | tacaaatggctgaaatggaacctg | 224 |
| SR10 | aggaggttgtatattttttgggag | 225 |
| SR11 | tgggcggagagggtggt | 226 |
| SR12 | gggggtgggcggttgggcgtatt | 227 |
| SR13 | tacaaatacctggttttctgggtt | 228 |
| SR14 | tacaaatacctgtcttactgggtt | 229 |
| SR15 | tacaaaactgcttggtactggaaa | 230 |
| SR16 | tatgtgtttcataagtggtgggtt | 231 |
| SR17 | tacgttttctacctgtggtggaaa | 232 |
| SR18 | taccgttggctgcattggcatgtt | 233 |

TABLE 4B-continued

Exemplary FGFR-binding Peptide Coding Sequences

| Identifier | Coding Sequence | SEQ ID NO |
|---|---|---|
| SR19 | tacaaattcctgttctggcacgct | 234 |
| SR20 | aggaggcagtgggggtttttgggtt | 235 |
| SR21 | tactctgcttggtctttctgggtt | 236 |
| SR22 | ttggctaggtggggtttttgggtt | 237 |
| SR23 | tatgatgcgtggggttattgggtg | 238 |
| SR24 | tggcgtaaatactaccatttctgggtttct | 239 |
| SR25 | aaacgtctgtacggtctgttctggtacgac | 240 |
| SR26 | aaaaaacattggtcttctctgttcttcgaa | 241 |
| SR27 | aaagcttggccgtactcttgggaagctgtt | 242 |
| Rm26 | gagtggtactgcggcgtgctgttcaactgccagcag | 243 |
| Rm27 | cattttggttgcggtgttatttttaattgtgtttctgat | 244 |
| Rm33 | tgggagctttgtgcttctggttatggttggtgctatcttcat | 245 |
| Rm37 | gctccttcttgcaagtcttatattggttttggtctttatcattgttgggatggt | 246 |
| Rm40 | cacttcaagtgcggcatgggcctgttcgagtgcgccgacccc | 247 |

Full-Length Heavy Chains Comprising a FGFR-Binding Peptide

Having provided exemplary heavy chain variable regions, in another aspect, a heavy chain of an antigen binding protein comprising a FGFR-binding peptide, such as a peptide disclosed in Table 4A, is provided. In this aspect, the FGFR-binding peptide is inserted into the primary sequence of the heavy chain and forms an integrated component of the heavy chain. The FGFR-binding peptide can be located at any point in the heavy chain; in one example the FGFR-binding peptide is located in a CH2 or CH3 loop of the heavy chain.

An FGFR-binding peptide can be flanked on the N, C or both termini by flanking residues. Flanking residues, such as glycine residues, can provide a level of flexibility that is conducive to the formation of a disulfide bond between the flanking cysteine residues. In one example, an FGFR-binding peptide, such as those shown in Table 4A, can be flanked on the N terminus by GGC residues and on the C terminus by CGG residues. Flanking sequences can comprise 1, 2, 3, 4, 5, 6, 7, 8, 9, or 10 residues.

TABLE 5A

Exemplary Antibody Heavy Chains Comprising a FGFR-binding Peptide

| Clone | FGFR-binding Peptide Identifier | FGFR-binding Peptide SEQ ID NO | Sequence Identifier | SEQ ID NO | Amino Acid Sequence |
|---|---|---|---|---|---|
| 1A2-SR4 | SR4 | 187 | H1-SR4 | 248 | QVQLVQSGAEVKKPGASVKV SCKASGYTFTGYYMHWVRQ APGQGLEWMGWINPNSGGT NSAQKFQGRVTMTRDTSISTA YMELSRLRSDDTAVYYCARD ATSGWFDYWGQGTLVTVSSA STKGPSVFPLAPSSKSTSGGTA ALGCLVKDYFPEPVTVSWNS GALTSGVHTFPAVLQSSGLYS LSSVVTVPSSSLGTQTYICNV NHKPSNTKVDKKVEPKSCDK THTCPPCPAPELLGGPSVFLFP PKPKDTLMISRTPEVTCVVVD VSHEDPEVKFNWYVDGVEV HNAKTKPREEQYQSTYRVVS VLTVLHQDWLNGKEYKCKV SNKALPAPIEKTISKAKGQPRE PQVYTLPPSRDELGGCYQAW GYYVCGGTKNQVSLTCLVKG FYPSDIAVEWESNGQPENNY |

TABLE 5A-continued

Exemplary Antibody Heavy Chains Comprising a FGFR-binding Peptide

| Clone | FGFR-binding Peptide Identifier | FGFR-binding Peptide SEQ ID NO | Sequence Identifier | SEQ ID NO | Amino Acid Sequence |
|---|---|---|---|---|---|
| | | | | | KTTPPVLDSDGSFFLYSKLTV DKSRWQQGNVFSCSVMHEA LHNHYTQKSLSLSPGK |
| 2G10-SR4 | SR4 | 187 | H2-SR4 | 249 | QVQLVESGGGVVQPGRSLRL SCAASRFSFSRYGMHWVRQA PGKGLEWVAVIWFDGRNQY YADSVKGRFTISRDNSKNTLF LQMNSLRVEDTAVYYCARD HPVVGTSFDYWGQGTLVTVS SASTKGPSVFPLAPSSKSTSGG TAALGCLVKDYFPEPVTVSW NSGALTSGVHTFPAVLQSSGL YSLSSVVTVPSSSLGTQTYICN VNHKPSNTKVDKKVEPKSCD KTHTCPPCPAPELLGGPSVFLF PPKPKDTLMISRTPEVTCVVV DVSHEDPEVKFNWYVDGVE VHNAKTKPREEQYQSTYRVV SVLTVLHQDWLNGKEYKCK VSNKALPAPIEKTISKAKGQP REPQVYTLPPSRDELGGCYQA WGYYVCGGTKNQVSLTCLV KGFYPSDIAVEWESNGQPEN NYKTTPPVLDSDGSFFLYSKL TVDKSRWQQGNVFSCSVMH EALHNHYTQKSLSLSPGK |
| 14E8-SR4 | SR4 | 187 | H3-SR4 | 250 | QVQLVESGGGVVQPGRSLRL SCAASGFTFSSYGMHWVRQA PGKGLEWVAVIGYDGSYKYY ADSVKGRFTISRDNSKNTLYL QMNSLRAEDTAVYYCARDGS NWNYGGSFDYWGQGTLVTV SSASTKGPSVFPLAPSSKSTSG GTAALGCLVKDYFPEPVTVS WNSGALTSGVHTFPAVLQSS GLYSLSSVVTVPSSSLGTQTYI CNVNHKPSNTKVDKKVEPKS CDKTHTCPPCPAPELLGGPSV FLFPPKPKDTLMISRTPEVTCV VVDVSHEDPEVKFNWYVDG VEVHNAKTKPREEQYQSTYR VVSVLTVLHQDWLNGKEYK CKVSNKALPAPIEKTISKAKG QPREPQVYTLPPSRDELGGCY QAWGYYVCGGTKNQVSLTC LVKGFYPSDIAVEWESNGQPE NNYKTTPPVLDSDGSFFLYSK LTVDKSRWQQGNVFSCSVM HEALHNHYTQKSLSLSPGK |
| 25B10-SR4 | SR4 | 187 | H5-SR4 | 252 | EVQLLESGGGLVQPEGSLRLS CAASGFTFSIYAMSWVRQAP GKGLEWVSDISGRGGYTYYA DSVKGRFTISRDNSKNTLYLQ MNSLRADDTAVYYCAKDRSI AVAGPFDFWGQGTLVTVSSA STKGPSVFPLAPSSKSTSGGTA ALGCLVKDYFPEPVTVSWNS GALTSGVHTFPAVLQSSGLYS LSSVVTVPSSSLGTQTYICNV NHKPSNTKVDKKVEPKSCDK THTCPPCPAPELLGGPSVFLFP PKPKDTLMISRTPEVTCVVVD VSHEDPEVKFNWYVDGVEV HNAKTKPREEQYQSTYRVVS VLTVLHQDWLNGKEYKCKV SNKALPAPIEKTISKAKGQPRE PQVYTLPPSRDELGGCYQAW GYYVCGGTKNQVSLTCLVKG FYPSDIAVEWESNGQPENNY |

TABLE 5A-continued

Exemplary Antibody Heavy Chains Comprising a FGFR-binding Peptide

| Clone | FGFR-binding Peptide Identifier | FGFR-binding Peptide SEQ ID NO | Sequence Identifier | SEQ ID NO | Amino Acid Sequence |
|---|---|---|---|---|---|
| | | | | | KTTPPVLDSDGSFFLYSKLTV DKSRWQQGNVFSCSVMHEA LHNHYTQKSLSLSPGK |
| 1A2-Rm26 | Rm26 | 211 | H1-Rm26 | 253 | QVQLVQSGAEVKKPGASVKV SCKASGYTFTGYYMHWVRQ APGQGLEWMGWINPNSGGT NSAQKFQGRVTMTRDTSISTA YMELSRLRSDDTAVYYCARD ATSGWFDYWGQGTLVTVSSA STKGPSVFPLAPSSKSTSGGTA ALGCLVKDYFPEPVTVSWNS GALTSGVHTFPAVLQSSGLYS LSSVVTVPSSSLGTQTYICNV NHKPSNTKVDKKVEPKSCDK THTCPPCPAPELLGGPSVFLFP PKPKDTLMISRTPEVTCVVVD VSHEDPEVKFNWYVDGVEV HNAKTKPREEQYQSTYRVVS VLTVLHQDWLNGKEYKCKV SNKALPAPIEKTISKAKGQPRE PQVYTLPPSRDELGGEWYCG VLFNCQQGGTKNQVSLTCLV KGFYPSDIAVEWESNGQPEN NYKTTPPVLDSDGSFFLYSKL TVDKSRWQQGNVFSCSVMH EALHNHYTQKSLSLSPGK |
| 1A2-Rm40 | Rm40 | 215 | H1-Rm40 | 254 | QVQLVQSGAEVKKPGASVKV SCKASGYTFTGYYMHWVRQ APGQGLEWMGWINPNSGGT NSAQKFQGRVTMTRDTSISTA YMELSRLRSDDTAVYYCARD ATSGWFDYWGQGTLVTVSSA STKGPSVFPLAPSSKSTSGGTA ALGCLVKDYFPEPVTVSWNS GALTSGVHTFPAVLQSSGLYS LSSVVTVPSSSLGTQTYICNV NHKPSNTKVDKKVEPKSCDK THTCPPCPAPELLGGPSVFLFP PKPKDTLMISRTPEVTCVVVD VSHEDPEVKFNWYVDGVEV HNAKTKPREEQYQSTYRVVS VLTVLHQDWLNGKEYKCKV SNKALPAPIEKTISKAKGQPRE PQVYTLPPSRDELGGHFKCG MGLFECADPGGTKNQVSLTC LVKGFYPSDIAVEWESNGQPE NNYKTTPPVLDSDGSFFLYSK LTVDKSRWQQGNVFSCSVM HEALHNHYTQKSLSLSPGK |
| 2G10-Rm26 | Rm26 | 211 | H2-Rm26 | 255 | QVQLVESGGGVVQPGRSLRL SCAASRFSFSRYGMHWVRQA PGKGLEWVAVIWFDGRNQY YADSVKGRFTISRDNSKNTLF LQMNSLRVEDTAVYYCARD HPVVGTSFDYWGQGTLVTVS SASTKGPSVFPLAPSSKSTSGG TAALGCLVKDYFPEPVTVSW NSGALTSGVHTFPAVLQSSGL YSLSSVVTVPSSSLGTQTYICN VNHKPSNTKVDKKVEPKSCD KTHTCPPCPAPELLGGPSVFLF PPKPKDTLMISRTPEVTCVVV DVSHEDPEVKFNWYVDGVE VHNAKTKPREEQYQSTYRVV SVLTVLHQDWLNGKEYKCK VSNKALPAPIEKTISKAKGQP REPQVYTLPPSRDELGGEWY CGVLFNCQQGGTKNQVSLTC LVKGFYPSDIAVEWESNGQPE |

TABLE 5A-continued

Exemplary Antibody Heavy Chains Comprising a FGFR-binding Peptide

| Clone | FGFR-binding Peptide Identifier | FGFR-binding Peptide SEQ ID NO | Sequence Identifier | SEQ ID NO | Amino Acid Sequence |
|---|---|---|---|---|---|
| | | | | | NNYKTTPPVLDSDGSFFLYSK LTVDKSRWQQGNVFSCSVM HEALHNHYTQKSLSLSPGK |
| 2G10-Rm40 | Rm40 | 215 | H2-Rm40 | 256 | QVQLVESGGGVVQPGRSLRL SCAASRFSFSRYGMHWVRQA PGKGLEWVAVIWFDGRNQY YADSVKGRFTISRDNSKNTLF LQMNSLRVEDTAVYYCARD HPVVGTSFDYWGQGTLVTVS SASTKGPSVFPLAPSSKSTSGG TAALGCLVKDYFPEPVTVSW NSGALTSGVHTFPAVLQSSGL YSLSSVVTVPSSSLGTQTYICN VNHKPSNTKVDKKVEPKSCD KTHTCPPCPAPELLGGPSVFLF PPKPKDTLMISRTPEVTCVVV DVSHEDPEVKFNWYVDGVE VHNAKTKPREEQYQSTYRVV SVLTVLHQDWLNGKEYKCK VSNKALPAPIEKTISKAKGQP REPQVYTLPPSRDELGGHFKC GMGLFECADPGGTKNQVSLT CLVKGFYPSDIAVEWESNGQP ENNYKTTPPVLDSDGSFFLYS KLTVDKSRWQQGNVFSCSV MHEALHNHYTQKSLSLSPGK |

TABLE 5B

Coding Sequence for Antibody Heavy Chains Comprising a FGFR-binding Peptide

| Clone | FGFR-binding Peptide Identifier | FGFR-binding Peptide DNA SEQ ID NO | Sequence Identifier | SEQ ID NO | Coding Sequence |
|---|---|---|---|---|---|
| 1A2-SR4 | SR4 | 219 | H1-SR4 | 257 | caggtgcaactggtgcagtctggggctgaggtgaa gaagcctggggcctcagtgaaggtctcctgcaagg cttctggatacaccttcaccggctactatatgcactgg gtgcgacaggcccctggacaagggcttgagtggat gggatggatcaaccctaacagtggtggcacaaact ctgcacagaagtttcagggcagggtcaccatgacc agggacacgtccatcagcacagcctacatggagct gagcaggctgagatctgacgacacggccgtgtatta ctgtgcaagagatgcgaccagtggctggtttgacta ctggggccagggaaccctggtcaccgtctctagtgc ctccaccaagggcccatcggtcttccccctggcacc ctcctccaagagcacctctgggggcacagcggccc tgggctgcctggtcaaggactacttccccgaaccgg tgacggtgtcgtggaactcaggcgccctgaccagc ggcgtgcacaccttcccggctgtcctacagtcctca ggactctactccctcagcagcgtggtgaccgtgccc tccagcagcttgggcacccagacctacatctgcaac gtgaatcacaagcccagcaacaccaaggtggacaa gaaagttgagcccaaatcttgtgacaaaactcacac atgcccaccgtgcccagcacctgaactcctggggg gaccgtcagtcttcctcttccccccaaaacccaagg acaccctcatgatctcccggacccctgaggtcacat gcgtggtggtggacgtgagccacgaagaccctga ggtcaagttcaactggtacgtggacggcgtggaggt gcataatgccaagacaaagccgcgggaggagcag taccagagcacgtaccgtgtggtcagcgtcctcacc gtcctgcaccaggactggctgaatggcaaggagta caagtgcaaggtctccaacaaagccctcccagccc ccatcgagaaaaccatctccaaagccaaagggcag ccccgagaaccacaggtgtacaccctgcccccatc |

TABLE 5B-continued

Coding Sequence for Antibody Heavy Chains Comprising a FGFR-binding Peptide

| Clone | FGFR-binding Peptide Identifier | FGFR-binding Peptide DNA SEQ ID NO | Sequence Identifier | SEQ ID NO | Coding Sequence |
|---|---|---|---|---|---|
| | | | | | ccgggatgagctgggtggttgctaccaggcctggg gctactacgtgtgcggtggtaccaagaaccaggtca gcctgacctgcctggtcaaaggcttctatcccagcg acatcgccgtggagtgggagagcaatgggcagcc ggagaacaactacaagaccacgcctcccgtgctgg actccgacggctccttcttcctctatagcaagctcacc gtggacaagagcaggtggcagcaggggaacgtct tctcatgctccgtgatgcatgaggctctgcacaacca ctacacgcagaagagcctctccctgtctccgggtaa a |
| 2G10-SR4 | SR4 | 219 | H2-SR4 | 258 | caggtgcagttggtggagtctggggggaggcgtggt ccagcctggggaggtccctgagactctcctgtgcagc gtctagattctccttcagtagatatggcatgcactggg tccgccaggctccaggcaaggggctggagtgggt ggcagttatatggtttgatggaagaaatcaatactatg cagactccgtgaaggggcgattcaccatctccaga gacaattccaagaatacgctgtttctgcaaatgaaca gcctgagagtcgaggacacggctgtgtattactgtg cgagagatcacccagtagttggtacgagctttgacta ctggggccagggaaccctggtcaccgtctctagtgc ctccaccaagggcccatcggtcttccccctggcacc ctcctccaagagcacctctggggggcacagcggcc tgggctgcctggtcaaggactacttccccgaaccgg tgacggtgtcgtggaactcaggcgccctgaccagc ggcgtgcacaccttcccggctgtcctacagtcctca ggactctactccctcagcagcgtggtgaccgtgccc tccagcagcttgggcacccagacctacatctgcaac gtgaatcacaagcccagcaacaccaaggtggacaa gaaagttgagcccaaatcttgtgacaaaactcacac atgcccaccgtgcccagcacctgaactcctggggg gaccgtcagtcttcctcttccccccaaaacccaagg acaccctcatgatctcccggacccctgaggtcacat gcgtggtggtggacgtgagccacgaagaccctga ggtcaagttcaactggtacgtggacggcgtggaggt gcataatgccaagacaaagccgcgggaggagcag taccagagcacgtaccgtgtggtcagcgtcctcacc gtcctgcaccaggactggctgaatggcaaggagta caagtgcaaggtctccaacaaagccctcccagccc ccatcgagaaaaccatctccaaagccaaagggcag ccccgagaaccacaggtgtacaccctgcccccatc ccgggatgagctgggtggttgctaccaggcctggg gctactacgtgtgcggtggtaccaagaaccaggtca gcctgacctgcctggtcaaaggcttctatcccagcg acatcgccgtggagtgggagagcaatgggcagcc ggagaacaactacaagaccacgcctcccgtgctgg actccgacggctccttcttcctctatagcaagctcacc gtggacaagagcaggtggcagcaggggaacgtct tctcatgctccgtgatgcatgaggctctgcacaacca ctacacgcagaagagcctctccctgtctccgggtaa a |
| 14E8-SR4 | SR4 | 219 | H3-SR4 | 259 | caggtgcaactggtggagtctggggggaggcgtggt ccagcctggggaggtccctgagactctcctgtgcagc gtctggattcaccttcagtagctatggcatgcactgg gtccgccaggctccaggcaaggggctggagtggg tggcagttatagggtatgatggaagttataaatactat gcagactccgtgaagggccgattcaccatctccaga gacaattccaagaacacgctatatctgcaaatgaac agcctgagagccgaggacacggctgtgtattactgt gcgagagatgggtctaactggaactacggggttct tttgactactggggccagggaaccctggtcaccgtc tctagtgcctccaccaagggcccatcggtcttccccc tggcaccctcctccaagagcacctctggggggcaca gcggccctgggctgcctggtcaaggactacttcccc gaaccggtgacggtgtcgtggaactcaggcgccct gaccagcggcgtgcacaccttcccggctgtcctaca gtcctcaggactctactccctcagcagcgtggtgac cgtgccctccagcagcttgggcacccagacctacat ctgcaacgtgaatcacaagcccagcaacaccaagg tggacaagaaagttgagcccaaatcttgtgacaaaa |

TABLE 5B-continued

Coding Sequence for Antibody Heavy Chains Comprising a FGFR-binding Peptide

| Clone | FGFR-binding Peptide Identifier | FGFR-binding Peptide DNA SEQ ID NO | Sequence Identifier | SEQ ID NO | Coding Sequence |
|---|---|---|---|---|---|
| | | | | | ctcacacatgcccaccgtgcccagcacctgaactcc tgggggaccgtcagtcttcctcttccccccaaaac ccaaggacaccctcatgatctcccggacccctgag gtcacatgcgtggtggtggacgtgagccacgaaga ccctgaggtcaagttcaactggtacgtggacggcgt ggaggtgcataatgccaagacaaagccgcgggag gagcagtaccagagcacgtaccgtgtggtcagcgt cctcaccgtcctgcaccaggactggctgaatggcaa ggagtacaagtgcaaggtctccaacaaagccctcc cagcccccatcgagaaaaccatctccaaagccaaa gggcagccccgagaaccacaggtgtacaccctgc ccccatcccgggatgagctgggtggttgctaccag gcctggggctactacgtgtgcggtggtaccaagaa ccaggtcagcctgacctgcctggtcaaaggcttctat cccagcgacatcgccgtggagtgggagagcaatg gcagccggagaacaactacaagaccacgcctcc cgtgctggactccgacggctccttcttcctctatagca agctcaccgtggacaagagcaggtggcagcaggg gaacgtcttctcatgctccgtgatgcatgaggctctg cacaaccactacacgcagaagagcctctccctgtct ccgggtaaa |
| 25B10-SR4 | SR4 | 219 | H5-SR4 | 261 | gaggtgcagctgttggagtctgggggaggcttggta cagccggaggggtccctgagactctcctgtgcagc ctctggattcacctttagcatctatgccatgagctggg tccgccaggctccagggaaggggctggagtgggt ctcagatattagtggtcgtggtggttacacatactacg cagactccgtgaagggccggttcaccatctccaga gacaattccaagaacacgctgtatctgcaaatgaac agcctgagagccgacgacacggccgtatattactgt gcgaaagatcggagtatagcagtggctggtccttttg acttctggggccagggaacccctggtcaccgtctcta gtgcctccaccaagggcccatcggtcttccccctgg caccctcctccaagagcacctctgggggcacagcg gccctgggctgcctggtcaaggactacttccccgaa ccggtgacggtgtcgtggaactcaggcgccctgac cagcggcgtgcacaccttcccggctgtcctacagtc ctcaggactctactccctcagcagcgtggtgaccgt gccctccagcagcttgggcacccagacctacatctg caacgtgaatcacaagcccagcaacaccaaggtgg acaagaaagttgagcccaaatcttgtgacaaaactc acacatgcccaccgtgcccagcacctgaactcctg gggggaccgtcagtcttcctcttccccccaaaccc aaggacaccctcatgatctcccggacccctgaggtc acatgcgtggtggtggacgtgagccacgaagaccc tgaggtcaagttcaactggtacgtggacggcgtgga ggtgcataatgccaagacaaagccgcgggaggag cagtaccagagcacgtaccgtgtggtcagcgtcctc accgtcctgcaccaggactggctgaatggcaagga gtacaagtgcaaggtctccaacaaagccctcccag ccccatcgagaaaaccatctccaaagccaaaggg cagccccgagaaccacaggtgtacaccctgccccc atcccgggatgagctgggtggttgctaccaggcctg gggctactacgtgtgcggtggtaccaagaaccagg tcagcctgacctgcctggtcaaaggcttctatcccag cgacatcgccgtggagtgggagagcaatgggcag ccggagaacaactacaagaccacgcctcccgtgct ggactccgacggctccttcttcctctatagcaagctc accgtggacaagagcaggtggcagcagggaac gtcttctcatgctccgtgatgcatgaggctctgcaca accactacacgcagaagagcctctccctgtctccgg gtaaa |
| 1A2-Rm26 | Rm26 | 243 | H1-Rm26 | 262 | caggtgcaactggtgcagtctggggctgaggtgaa gaagcctggggcctcagtgaaggtctcctgcaagg cttctggatacaccttcaccggctactatatgcactgg gtgcgacaggcccctggacaagggcttgagtggat gggatggatcaaccctaacagtggtggcacaaact ctgcacagaagtttcagggcagggtcaccatgacc agggacacgtccatcagcacagcctacatggagct gagcaggctgagatctgacgacacggccgtgtatta |

TABLE 5B-continued

Coding Sequence for Antibody Heavy Chains Comprising a FGFR-binding Peptide

| Clone | FGFR-binding Peptide Identifier | FGFR-binding Peptide DNA SEQ ID NO | Sequence Identifier | SEQ ID NO | Coding Sequence |
|---|---|---|---|---|---|
| | | | | | ctgtgcaagagatgcgaccagtggctggtttgacta ctggggccagggaaccctggtcaccgtctctagtgc ctccaccaaggcccatcggtcttcccctggcacc ctcctccaagagcacctctgggggcacagcggccc tgggctgcctggtcaaggactacttccccgaaccgg tgacggtgtcgtggaactcaggcgccctgaccagc ggcgtgcacaccttcccggctgtcctacagtcctca ggactctactccctcagcagcgtggtgaccgtgccc tccagcagcttgggcacccagacctacatctgcaac gtgaatcacaagcccagcaacaccaaggtggacaa gaaagttgagcccaaatcttgtgacaaaactcacac atgcccaccgtgcccagcacctgaactcctggggg gaccgtcagtcttcctcttccccccaaaacccaagg acaccctcatgatctcccggacccctgaggtcacat gcgtggtggtggacgtgagccacgaagaccctga ggtcaagttcaactggtacgtggacggcgtggaggt gcataatgccaagacaaagccgcggggaggagcag taccagagcacgtaccgtgtggtcagcgtcctcacc gtcctgcaccaggactggctgaatggcaaggagta caagtgcaaggtctccaacaaagcccctcccagccc ccatcgagaaaaccatctccaaagccaaagggcag ccccgagaaccacaggtgtacaccctgcccccatc ccgggatgagctgggtggtgagtggtactgcggcg tgctgttcaactgccagcagggtggtaccaagaacc aggtcagcctgacctgcctggtcaaaggcttctatcc cagcgacatcgccgtggagtgggagagcaatggg cagccggagaacaactacaagaccacgcctcccgt gctggactccgacggctccttcttcctctatagcaag ctcaccgtggacaagagcaggtggcagcagggga acgtcttctcatgctccgtgatgcatgaggctctgca caaccactacacgcagaagagcctctccctgtctcc gggtaaa |
| 1A2-Rm40 | Rm40 | 247 | H1-Rm40 | 263 | caggtgcaactggtgcagtctggggctgaggtgaa gaagcctggggcctcagtgaaggtctcctgcaagg cttctggatacaccttcaccggctactatatgcactgg gtgcgacaggcccctggacaagggcttgagtggat gggatggatcaacccctaacagtggtggcacaaact ctgcacagaagtttcagggcagggtcaccatgacc agggacacgtccatcagcacagcctatatggagct gagcaggctgagatctgacgacacggccgtgtatta ctgtgcaagagatgcgaccagtggctggtttgacta ctggggccagggaaccctggtcaccgtctctagtgc ctccaccaaggcccatcggtcttcccctggcacc ctcctccaagagcacctctgggggcacagcggccc tgggctgcctggtcaaggactacttccccgaaccgg tgacggtgtcgtggaactcaggcgccctgaccagc ggcgtgcacaccttcccggctgtcctacagtcctca ggactctactccctcagcagcgtggtgaccgtgccc tccagcagcttgggcacccagacctacatctgcaac gtgaatcacaagcccagcaacaccaaggtggacaa gaaagttgagcccaaatcttgtgacaaaactcacac atgcccaccgtgcccagcacctgaactcctggggg gaccgtcagtcttcctcttccccccaaaacccaagg acaccctcatgatctcccggacccctgaggtcacat gcgtggtggtggacgtgagccacgaagaccctga ggtcaagttcaactggtacgtggacggcgtggaggt gcataatgccaagacaaagccgcggggaggagcag taccagagcacgtaccgtgtggtcagcgtcctcacc gtcctgcaccaggactggctgaatggcaaggagta caagtgcaaggtctccaacaaagcccctcccagccc ccatcgagaaaaccatctccaaagccaaagggcag ccccgagaaccacaggtgtacaccctgcccccatc ccgggatgagctgggtggtcacttcaagtgcggcat gggcctgttcgagtgcgccgaccccggtggtacca agaaccaggtcagcctgacctgcctggtcaaaggc ttctatcccagcgacatcgccgtggagtgggagagc aatgggcagccggagaacaactacaagaccacgc ctcccgtgctggactccgacggctccttcttcctctat agcaagctcaccgtggacaagagcaggtggcagc aggggaacgtcttctcatgctccgtgatgcatgagg |

TABLE 5B-continued

Coding Sequence for Antibody Heavy Chains Comprising a FGFR-binding Peptide

| Clone | FGFR-binding Peptide Identifier | FGFR-binding Peptide DNA SEQ ID NO | Sequence Identifier | SEQ ID NO | Coding Sequence |
|---|---|---|---|---|---|
| | | | | | ctctgcacaaccactacacgcagaagagcctctccc tgtctccgggtaaa |
| 2G10-Rm26 | Rm26 | 243 | H2-Rm26 | 264 | caggtgcagttggtggagtctggggagggcgtggt ccagcctggggaggtccctgagactctcctgtgcagc gtctagattctccttcagtagatatggcatgcactggg tccgccaggctccaggcaaggggctggagtgggt ggcagttatatggtttgatggaagaaatcaatactatg cagactccgtgaaggggcgattcaccatctccaga gacaattccaagaatacgctgtttctgcaaatgaaca gcctgagagtcgaggacacggctgtgtattactgtg cgagagatcacccagtagttggtacgagctttgacta ctggggccagggaaccctggtcaccgtctctagtgc ctccaccaagggcccatcggtcttccccctggcacc ctcctccaagagcacctctggggcacagcggcc tgggctgcctggtcaaggactacttccccgaaccgg tgacggtgtcgtggaactcaggcgccctgaccagc ggcgtgcacaccttcccggctgtcctacagtcctca ggactctactccctcagcagcgtggtgaccgtgccc tccagcagcttgggcacccagacctacatctgcaac gtgaatcacaagcccagcaacaccaaggtggacaa gaaagttgagcccaaatcttgtgacaaaactcacac atgcccaccgtgcccagcacctgaactcctggggg gaccgtcagtcttcctcttccccccaaaacccaagg acaccctcatgatctcccggacccctgaggtcacat gcgtggtggtggacgtgagccacgaagaccctga ggtcaagttcaactggtacgtggacggcgtggaggt gcataatgccaagacaaagccgcgggaggagcag taccagagcacgtaccgtgtggtcagcgtcctcacc gtcctgcaccaggactggctgaatggcaaggagta caagtgcaaggtctccaacaaagccctcccagccc ccatcgagaaaaccatctccaaagccaaagggcag ccccgagaaccacaggtgtacaccctgcccccatc ccgggatgagctgggtggtgagtggtactgcggcg tgctgttcaactgccagcagggtggtaccaagaacc aggtcagcctgacctgcctggtcaaaggcttctatcc cagcgacatcgccgtggagtgggagagcaatggg cagccggagaacaactacaagaccacgcctcccgt gctggactccgacggctccttcttcctctatagcaag ctcaccgtggacaagagcaggtggcagcagggga acgtcttctcatgctccgtgatgcatgaggctctgca caaccactacacgcagaagagcctctccctgtctcc gggtaaa |
| 2G10-RM40 | Rm40 | 247 | H2-Rm40 | 265 | caggtgcagttggtggagtctggggagggcgtggt ccagcctggggaggtccctgagactctcctgtgcagc gtctagattctccttcagtagatatggcatgcactggg tccgccaggctccaggcaaggggctggagtgggt ggcagttatatggtttgatggaagaaatcaatactatg cagactccgtgaaggggcgattcaccatctccaga gacaattccaagaatacgctgtttctgcaaatgaaca gcctgagagtcgaggacacggctgtgtattactgtg cgagagatcacccagtagttggtacgagctttgacta ctggggccagggaaccctggtcaccgtctctagtgc ctccaccaagggcccatcggtcttccccctggcacc ctcctccaagagcacctctggggcacagcggcc tgggctgcctggtcaaggactacttccccgaaccgg tgacggtgtcgtggaactcaggcgccctgaccagc ggcgtgcacaccttcccggctgtcctacagtcctca ggactctactccctcagcagcgtggtgaccgtgccc tccagcagcttgggcacccagacctacatctgcaac gtgaatcacaagcccagcaacaccaaggtggacaa gaaagttgagcccaaatcttgtgacaaaactcacac atgcccaccgtgcccagcacctgaactcctggggg gaccgtcagtcttcctcttccccccaaaacccaagg acaccctcatgatctcccggacccctgaggtcfacat gcgtggtggtggacgtgagccacgaagaccctga ggtcaagttcaactggtacgtggacggcgtggaggt gcataatgccaagacaaagccgcgggaggagcag taccagagcacgtaccgtgtggtcagcgtcctcacc gtcctgcaccaggactggctgaatggcaaggagta |

TABLE 5B-continued

Coding Sequence for Antibody Heavy Chains Comprising a FGFR-binding Peptide

| Clone | FGFR-binding Peptide Identifier | FGFR-binding Peptide DNA SEQ ID NO | Sequence Identifier | SEQ ID NO | Coding Sequence |
|---|---|---|---|---|---|
| | | | | | caagtgcaaggtctccaacaaagccctcccagccc<br>ccatcgagaaaaccatctccaaagccaaagggcag<br>ccccgagaaccacaggtgtacaccctgcccccatc<br>ccgggatgagctgggtggtcacttcaagtgcggcat<br>gggcctgttcgagtgcgccgacccggtggtacca<br>agaaccaggtcagcctgacctgctggtcaaaggc<br>ttctatcccagcgacatcgccgtggagtgggagagc<br>aatgggcagccggagaacaactacaagaccacgc<br>ctcccgtgctggactccgacggctccttcttcctctat<br>agcaagctcaccgtggacaagagcaggtggcagc<br>aggggaacgtcttctcatgctccgtgatgcatgagg<br>ctctgcacaaccactacacgcagaagagcctctccc<br>tgtctccgggtaaa |

Exemplary Antigen Binding Proteins and Antigen Binding Protein-FGF21 Fusion Antigen Binding Protein Components According to one aspect, an isolated antigen binding protein comprising (A) one or more heavy chain complementarity determining regions (CDRHs) selected from the group consisting of: (i) a CDRH1 selected from the group consisting of SEQ ID NO:83-88; (ii) a CDRH2 selected from the group consisting of SEQ ID NO:89-97; (iii) a CDRH3 selected from the group consisting of SEQ ID NO: 98-105; and (iv) a CDRH of (i), (ii) and (iii) that contains one or more amino acid substitutions, deletions or insertions of no more than five, four, three, two or one amino acids; (B) one or more light chain complementary determining regions (CDRLs) selected from the group consisting of: (i) a CDRL1 selected from the group consisting of SEQ ID NO:106-111; (ii) a CDRL2 selected from the group consisting of SEQ ID NO:112-119; (iii) a CDRL3 selected from the group consisting of SEQ ID NO: 120-127; and (iv) a CDRL of (i), (ii) and (iii) that contains one or more amino acid substitutions, deletions or insertions of no more than five, four, three, two or one amino acids; or (C) one or more heavy chain CDRHs of (A) and one or more light chain CDRLs of (B).

In another embodiment, the CDRHs have at least 70%, 75%, 80%, 85%, 90%, 95%, 96%, 97%, 98% or 99% sequence identity with an amino acid sequence selected from the group consisting of SEQ ID NO: 83-105, and/or the CDRLs have at least 70%, 75%, 80%, 85%, 90%, 95%, 96%, 97%, 98% or 99% sequence identity with an amino acid sequence selected from the group consisting of SEQ ID NO: 106-127. In a further embodiment, the VHis selected from the group consisting of SEQ ID NO: 72-82, and/or the VL is selected from the group consisting of SEQ ID NO: 61-71.

According to one aspect, an isolated antigen binding protein comprising (A) one or more variable heavy chains (VHs) selected from the group consisting of: (i) SEQ ID NO: 72-82; and (ii) a VH of (i) that contains one or more amino acid substitutions, deletions or insertions of no more than five, four, three, four, two or one amino acids; (B) one or more variable light chains (VLs) selected from the group consisting of: (i) SEQ ID NO:61-71, and (ii) a VL of (i) that contains one or more amino acid substitutions, deletions or insertions of no more than five, four, three, two or one amino acids; or (C) one or more variable heavy chains of (A) and one or more variable light chains of (B).

In another embodiment, the variable heavy chain (VH) has at least 70%, 75%, 80%, 85%, 90%, 95%, 96%, 97%, 98% or 99% sequence identity with an amino acid sequence selected from the group consisting of SEQ ID NO:72-82, and/or the variable light chain (VL) has at least 70%, 75%, 80%, 85%, 90%, 95%, 96%, 97%. 98% or 99% sequence identity with an amino acid sequence selected from the group consisting of SEQ ID NO: 61-71.

In one aspect, also provided is an antigen binding protein and antigen binding protein-FGF21 fusion antigen binding protein component that associates with an eptiope comprising amino acid residues from FGFR1c, FGRF2c, FGFR3c or FGFR4, when associated with β-Klotho. In one particular embodiment the epitope comprises amino acid residues from FGFR1c.

In one aspect, also provided is an antigen binding protein and antigen binding protein-FGF21 fusion antigen binding protein component that specifically binds to an epitope comprising amino acid residues from β-Klotho.

In another aspect, also provided is an isolated antigen binding protein and antigen binding protein-FGF21 fusion antigen binding protein component that specifically binds to an epitope comprising amino acid residues from both β-Klotho and amino acid residues from FGFR1c, FGFR2c, FGFR3c, or FGFR4.

In yet another embodiment, the isolated antigen binding protein and antigen binding protein-FGF21 fusion antigen binding protein component described hereinabove comprises a first amino acid sequence comprising at least one of the CDRH consensus sequences disclosed herein, and a second amino acid sequence comprising at least one of the CDRL consensus sequences disclosed herein. In one aspect, the first amino acid sequence comprises at least two of the CDRH consensus sequences, and/or the second amino acid sequence comprises at least two of the CDRL consensus sequences.

In certain embodiments, the first and the second amino acid sequence are covalently bonded to each other.

In a further embodiment, the first amino acid sequence of the isolated antigen binding protein or antigen binding protein-FGF21 fusion antigen binding protein component includes the CDRH3 of SEQ ID NO:98, the CDRH2 of SEQ ID NO:89, and the CDRH1 of SEQ ID NO:83, and/or the second amino acid sequence of the isolated antigen binding protein or antigen binding protein-FGF21 fusion antigen binding protein component comprises the CDRL3 of SEQ ID NO:120, the CDRL2 of SEQ ID NO: 112, and the CDRL1 of SEQ ID NO:106.

In another embodiment, the first amino acid sequence of the isolated antigen binding protein or antigen binding protein-FGF21 fusion antigen binding protein component includes the CDRH3 of SEQ ID NO:99, the CDRH2 of SEQ ID NO:90, and the CDRH1 of SEQ ID NO:84, and/or the second amino acid sequence of the isolated antigen binding protein or antigen binding protein-FGF21 fusion antigen binding protein component comprises the CDRL3 of SEQ ID NO:121, the CDRL2 of SEQ ID NO:113, and the CDRL1 of SEQ ID NO:107.

In a further embodiment, the first amino acid sequence of the isolated antigen binding protein or antigen binding protein-FGF21 fusion antigen binding protein component includes the CDRH3 of SEQ ID NO:100, the CDRH2 of SEQ ID NO:91, and the CDRH1 of SEQ ID NO:85, and/or the second amino acid sequence of the isolated antigen binding protein or antigen binding protein-FGF21 fusion antigen binding protein component comprises the CDRL3 of SEQ ID NO:122, the CDRL2 of SEQ ID NO:114, and the CDRL1 of SEQ ID NO:108.

In another embodiment, the first amino acid sequence of the isolated antigen binding protein or antigen binding protein-FGF21 fusion antigen binding protein component includes the CDRH3 of SEQ ID NO:102, the CDRH2 of SEQ ID NO:93, and the CDRH1 of SEQ ID NO:87, and/or the second amino acid sequence of the isolated antigen binding protein or antigen binding protein-FGF21 fusion antigen binding protein component comprises the CDRL3 of SEQ ID NO:124, the CDRL2 of SEQ ID NO:116, and the CDRL1 of SEQ ID NO:110.

In a further embodiment, the first amino acid sequence of the isolated antigen binding protein or antigen binding protein-FGF21 fusion antigen binding protein component includes the CDRH3 of SEQ ID NO:103, the CDRH2 of SEQ ID NO:89, and the CDRH1 of SEQ ID NO:88, and/or the second amino acid sequence of the isolated antigen binding protein or antigen binding protein-FGF21 fusion antigen binding protein component comprises the CDRL3 of SEQ ID NO:125, the CDRL2 of SEQ ID NO:112, and the CDRL1 of SEQ ID NO:111.

In another embodiment, the first amino acid sequence of the isolated antigen binding protein or antigen binding protein-FGF21 fusion antigen binding protein component includes the CDRH3 of SEQ ID NO:104, the CDRH2 of SEQ ID NO:89, and the CDRH1 of SEQ ID NO:88, and/or the second amino acid sequence of the isolated antigen binding protein or antigen binding protein-FGF21 fusion antigen binding protein component comprises the CDRL3 of SEQ ID NO:127, the CDRL2 of SEQ ID NO:112, and the CDRL1 of SEQ ID NO:111.

In another embodiment, the first amino acid sequence of the isolated antigen binding protein or antigen binding protein-FGF21 fusion antigen binding protein component includes the CDRH3 of SEQ ID NO:104, the CDRH2 of SEQ ID NO:94, and the CDRH1 of SEQ ID NO:88, and/or the second amino acid sequence of the isolated antigen binding protein or antigen binding protein-FGF21 fusion antigen binding protein component comprises the CDRL3 of SEQ ID NO:125, the CDRL2 of SEQ ID NO:112, and the CDRL1 of SEQ ID NO:111.

In a further embodiment, the first amino acid sequence of the isolated antigen binding protein or antigen binding protein-FGF21 fusion antigen binding protein component includes the CDRH3 of SEQ ID NO:105, the CDRH2 of SEQ ID NO:95, and the CDRH1 of SEQ ID NO:85, and/or the second amino acid sequence of the isolated antigen binding protein or antigen binding protein-FGF21 fusion antigen binding protein component comprises the CDRL3 of SEQ ID NO:126, the CDRL2 of SEQ ID NO:117, and the CDRL1 of SEQ ID NO:107.

In another embodiment, the first amino acid sequence of the isolated antigen binding protein or antigen binding protein-FGF21 fusion antigen binding protein component includes the CDRH3 of SEQ ID NO:105, the CDRH2 of SEQ ID NO:96, and the CDRH1 of SEQ ID NO:85, and/or the second amino acid sequence of the isolated antigen binding protein or antigen binding protein-FGF21 fusion antigen binding protein component comprises the CDRL3 of SEQ ID NO:127, the CDRL2 of SEQ ID NO:118, and the CDRL1 of SEQ ID NO:107.

In another embodiment, the first amino acid sequence of the isolated antigen binding protein or antigen binding protein-FGF21 fusion antigen binding protein component includes the CDRH3 of SEQ ID NO:105, the CDRH2 of SEQ ID NO:97, and the CDRH1 of SEQ ID NO:85, and/or the second amino acid sequence of the isolated antigen binding protein or antigen binding protein-FGF21 fusion antigen binding protein component comprises the CDRL3 of SEQ ID NO:126, the CDRL2 of SEQ ID NO:119, and the CDRL1 of SEQ ID NO:107.

In a further embodiment, the antigen binding protein comprises at least one CDRH sequence of heavy chain sequences H1-H11 as shown in Table 3A, or 1A2-SR4, 2G10-SR4, 14E8-SR4, 25B10-SR4, 1A2-Rm26, 1A2-Rm40, 2G10-Rm26, 2G10-Rm40 as shown in Table 5A. In again a further embodiment, the antigen binding protein comprises at least one CDRL sequence of light chain sequences L1-L11 as shown in Table 3B.

In again a further embodiment, the antigen binding protein comprises at least two CDRH sequences of heavy chain sequences H1-H11 as shown in Table 3A, or 1A2-SR4, 2G10-SR4, 14E8-SR4, 25B10-SR4, 1A2-Rm26, 1A2-Rm40, 2G10-Rm26, 2G10-Rm40 as shown in Table 5A, and at least two CDRL sequences of light chain sequences L1-L11 as shown in Table 3B.

In again another embodiment, the antigen binding protein comprises the CDRH1, CDRH2, and CDRH3 sequences of heavy chain sequences H1-H11 as shown in Table 3A, or 1A2-SR4, 2G10-SR4, 14E8-SR4, 25B10-SR4, 1A2-Rm26, 1A2-Rm40, 2G10-Rm26, 2G10-Rm40 as shown in Table 5A. In yet another embodiment, the antigen binding protein comprises the CDRL1, CDRL2, and CDRL3 sequences of light chain sequences L1-L11 as shown in Table 3B.

In yet another embodiment, the antigen binding protein comprises all six CDRs of L1 and H1, or L2 and H2, or L3 and H3, or L4 and H4, or L5 and H5, L6 and H6, L7 and H7, L8 and H8, L9 and H9, L10 and H10 or L11 and H11 or the six CDRs of 1A2-SR4, 2G10-SR4, 14E8-SR4, 25B10-SR4, 1A2-Rm26, 1A2-Rm40, 2G10-Rm26 and 2G10-Rm40, as shown in Tables 6A, 6B and 6C.

TABLE 6A

Heavy Chain Sequences Without a FGFR-Binding Peptide

| Clone | Full Heavy (H#) | Full Heavy SEQ ID NO | Variable Heavy (VH#) | Variable Heavy SEQ ID NO | CDRH1 SEQ ID NO | CDRH2 SEQ ID NO | CDRH3 SEQ ID NO |
|---|---|---|---|---|---|---|---|
| 1A2 | H1 | 28 | $V_H1$ | 50 | 83 | 89 | 98 |
| 2G10 | H2 | 29 | $V_H2$ | 51 | 84 | 90 | 99 |
| 14E8 | H3 | 30 | $V_H3$ | 52 | 85 | 91 | 100 |
| 25B10 | H5 | 32 | $V_H5$ | 54 | 87 | 93 | 102 |
| 3B4 | H6 | 33 | $V_H6$ | 55 | 88 | 89 | 103 |
| 1B5 | H7 | 34 | $V_H7$ | 56 | 88 | 89 | 104 |
| 10H3 | H8 | 35 | $V_H8$ | 57 | 88 | 94 | 104 |
| 9D10 | H9 | 36 | $V_H9$ | 58 | 85 | 95 | 105 |
| 3F4 | H10 | 37 | $V_H10$ | 59 | 85 | 96 | 105 |
| 8F9 | H11 | 38 | $V_H11$ | 60 | 85 | 97 | 105 |

TABLE 6B

Light Chain Sequences

| CLone | Full Light (L#) | Full Light SEQ ID NO | Variable Light (VH#) | Variable Light SEQ ID NO | CDRL1 SEQ ID NO | CDRL2 SEQ ID NO | CDRL3 SEQ ID NO |
|---|---|---|---|---|---|---|---|
| 1A2 | L1 | 17 | $V_L1$ | 61 | 106 | 112 | 120 |
| 2G10 | L2 | 18 | $V_L2$ | 62 | 107 | 113 | 121 |
| 14E8 | L3 | 19 | $V_L3$ | 63 | 108 | 114 | 122 |
| 25B10 | L5 | 21 | $V_L5$ | 65 | 110 | 116 | 124 |
| 3B4 | H6 | 22 | $V_L6$ | 66 | 111 | 112 | 125 |
| 1B5 | H7 | 23 | $V_L7$ | 67 | 111 | 112 | 127 |
| 10H3 | H8 | 24 | $V_L8$ | 68 | 111 | 112 | 125 |
| 9D10 | H9 | 25 | $V_L9$ | 69 | 107 | 117 | 126 |
| 3F4 | H10 | 26 | $V_L10$ | 70 | 107 | 118 | 127 |
| 8F9 | H11 | 27 | $V_L11$ | 71 | 107 | 119 | 126 |

TABLE 6C

Heavy Chain Sequences Comprising a FGFR-binding Peptide

| Clone | FGFR-binding Peptide Identifier | Full Heavy SEQ ID NO | Variable Heavy (VH#) | Variable Heavy SEQ ID NO | CDRH1 SEQ ID NO | CDRH2 SEQ ID NO | CDRH3 SEQ ID NO |
|---|---|---|---|---|---|---|---|
| 1A2-SR4 | SR4 | 28 | $V_H1$ | 50 | 83 | 89 | 98 |
| 2G10-SR4 | SR4 | 29 | $V_H2$ | 51 | 84 | 90 | 99 |
| 14E8-SR4 | SR4 | 30 | $V_H3$ | 52 | 85 | 91 | 100 |
| 25B10-SR4 | SR4 | 32 | $V_H5$ | 54 | 87 | 93 | 102 |
| 1A2-Rm26 | Rm26 | 28 | $V_H1$ | 50 | 83 | 89 | 98 |
| 1A2-Rm40 | Rm40 | 28 | $V_H1$ | 50 | 83 | 89 | 98 |
| 2G10-Rm26 | Rm26 | 29 | $V_H2$ | 51 | 84 | 90 | 99 |
| 2G10-Rm40 | Rm40 | 29 | $V_H2$ | 51 | 84 | 90 | 99 |

In one aspect, the isolated antigen binding proteins and antigen binding protein-FGF21 fusion antigen binding protein components that specifically bind β-Klotho β-Klotho and one or more of FGFR1c, FGFR2c, FGFR3c, and FGFR4 provided herein can be a monoclonal antibody, a polyclonal antibody, a recombinant antibody, a human antibody, a humanized antibody, a chimeric antibody, a multispecific antibody, or an antibody fragment thereof.

In another embodiment, the antibody fragment of the isolated antigen-binding proteins and antigen binding protein-FGF21 fusion antigen binding protein components provided herein can be a Fab fragment, a Fab' fragment, an $F(ab')_2$ fragment, an Fv fragment, a diabody, or a single chain antibody molecule.

In a further embodiment, an isolated antigen binding protein and antigen binding protein-FGF21 fusion antigen binding protein components provided herein that specifically binds β-Klotho or β-Klotho and one or more of FGFR1c, FGFR2c, FGFR3c, and FGFR4 is a human antibody and can be of the IgG1-, IgG2-IgG3- or IgG4-type.

In another embodiment, an isolated antigen binding protein or antigen binding protein-FGF21 fusion antigen binding protein component that specifically binds β-Klotho β-Klotho and one or more of FGFR1c, FGFR2c, FGFR3c, and FGFR4 comprises just a light or a heavy chain polypeptide as set forth in Tables 1 and 5. In some embodiments, an antigen binding protein or antigen binding protein-FGF21 fusion antigen binding protein component that specifically binds β-Klotho or β-Klotho and one or more of FGFR1c, FGFR2c, FGFR3c, and FGFR4 consists just of a variable light or variable heavy domain such as those listed in Table 2. Such antigen binding proteins and antigen binding protein-FGF21 fusion antigen binding protein components can be PEGylated with one or more PEG molecules, for examples PEG molecules having a molecular weight selected from the group consisting of 5K, 10K, 20K, 40K, 50K, 60K, 80K, 100K or greater than 100K.

In yet another aspect, the isolated antigen binding proteins and antigen binding protein-FGF21 fusion antigen binding protein components that specifically bind β-Klotho or β-Klotho and one or more of FGFR1c, FGFR2c, FGFR3c, and FGFR4 provided herein can be coupled to a labeling group and can compete for binding to the extracellular portion of β-Klotho β-Klotho and one or more of FGFR1c, FGFR2c, FGFR3c, and FGFR4 with an antigen binding protein of one of the isolated antigen binding proteins and antigen binding protein-FGF21 fusion antigen binding protein components provided herein. In one embodiment, the isolated antigen binding proteins and antigen binding protein-FGF21 fusion antigen binding protein components provided herein can reduce blood glucose levels, decrease triglyceride and cholesterol levels or improve other glycemic parameters and cardiovascular risk factors when administered to a patient.

As will be appreciated, for any antigen binding protein or antigen binding protein-FGF21 fusion antigen binding protein component comprising more than one CDR from the depicted sequences, any combination of CDRs independently selected from the depicted sequences is useful. Thus, antigen binding proteins and antigen binding protein-FGF21 fusion antigen binding protein components with one, two, three, four, five or six of independently selected CDRs can be generated. However, as will be appreciated, specific embodiments generally utilize combinations of CDRs that are non-repetitive, e.g., antigen binding proteins and antigen binding protein-FGF21 fusion antigen binding protein components are generally not made with two CDRH2 regions, etc.

Some of the antigen binding proteins and antigen binding protein-FGF21 fusion antigen binding protein components that specifically bind β-Klotho or β-Klotho and one or more of FGFR1c, FGFR2c, FGFR3c, and FGFR4 that are provided herein are discussed in more detail below.

Antigen Binding Proteins and Antigen Binding Protein-FGF21 Fusion Antigen Binding Protein Components and Binding Epitopes and Binding Domains When an antigen binding protein or antigen binding protein-FGF21 fusion antigen binding protein component is said to bind an epitope on β-Klotho or β-Klotho and one or more of FGFR1c, FGFR2c, FGFR3c, and FGFR4, or the extracellular domain thereof, for example, what is meant is that the antigen binding protein or antigen binding protein-FGF21 fusion antigen binding protein component specifically binds to a specified portion of β-Klotho or a specified portion of a complex comprising β-Klotho and one or more of FGFR1c, FGFR2c, FGFR3c, and FGRR4. In some embodiments, e.g., in certain cases where the antigen binding protein or antigen binding protein-FGF21 fusion antigen binding protein component binds only β-Klotho, the antigen binding protein or antigen binding protein-FGF21 fusion antigen binding protein component can specifically bind to a polypeptide consisting of the specified residues (e.g., a specified segment of β-Klotho). In other embodiments, e.g., in certain cases where a antigen binding protein or antigen binding protein-FGF21 fusion antigen binding protein component interacts with both β-Klotho and one or more of FGFR1c, FGFR2c, FGFR3c and FGFR4, the antigen binding protein or antigen binding protein-FGF21 fusion antigen binding protein component will bind residues, sequences of residues, or regions in both β-Klotho and FGFR1c, FGFR2c, FGFR3c or FGFR4, depending on which receptor the antigen binding protein or antigen binding protein-FGF21 fusion antigen binding protein component recognizes. In still other embodiments the antigen binding protein and antigen binding protein-FGF21 fusion antigen binding protein components will bind residues, sequence or residues or regions of a complex comprising β-Klotho and FGFR1c. In any of the foregoing embodiments, such an antigen binding protein or antigen binding protein-FGF21 fusion antigen binding protein component typically does not need to contact every residue of β-Klotho and/or one or more of FGFR1c, FGFR2c, FGFR3c, and FGFR4. Nor does every single amino acid substitution or deletion within β-Klotho and/or FGFR1c, FGFR2c, FGFR3c or FGFR4, or β-Klotho and one or more of FGFR1c, FGFR2c, FGFR3c, and FGFR4, or the extracellular domain of the recited proteins or complexes necessarily significantly affect binding affinity.

Epitope specificity and the binding domain(s) of an antigen binding protein or antigen binding protein-FGF21 fusion antigen binding protein component can be determined by a variety of methods. Some methods, for example, can use truncated portions of an antigen. Other methods utilize antigen mutated at one or more specific residues, such as by employing an alanine scanning or arginine scanning-type approach or by the generation and study of chimeric proteins in which various domains, regions or amino acids are swapped between two proteins, or by protease protection assays.

Competing Antigen Binding Proteins and Antigen Binding Protein-FGF21 Fusion Antigen Binding Protein Components In another aspect, antigen binding proteins and antigen binding protein-FGF21 fusion antigen binding protein components are provided that compete with one of the exemplified antibodies or functional fragments binding to an epitope described herein for specific binding to β-Klotho or β-Klotho and one or more of FGFR1c, FGFR2c, FGFR3c, and FGFR4. Such antigen binding proteins and antigen binding protein-FGF21 fusion antigen binding protein components can also bind to the same epitope as one of the herein exemplified antigen binding proteins or antigen binding protein-FGF21 fusion antigen binding protein components, or an overlapping epitope. Antigen binding proteins and antigen binding protein-FGF21 fusion antigen binding protein components and fragments thereof that compete with or bind to the same epitope as the exemplified antigen binding proteins and antigen binding protein-FGF21 fusion antigen binding protein components are expected to show similar functional properties. The exemplified antigen binding proteins and antigen binding protein-FGF21 fusion antigen binding protein component and fragments thereof include those with the heavy and light chains, variable region domains $V_L1$-$V_L11$ and $V_H1$-$V_H11$, and the CDRs included in Tables 1 and 3, respectively. Thus, as a specific example, the antigen binding proteins and antigen binding protein-FGF21 fusion antigen binding protein components that are provided include those that compete with an antibody or fragment having:

(a) all 6 of the CDRs listed for an antibody as listed in Table 3;

(b) a $V_H$ and a $V_L$ selected from $V_L1$-$V_L11$ and $V_H1$-$V_H11$ for an antibody as listed in Table 2; or (c) two light chains and two heavy chains as specified for an antibody as listed in Tables 1 and 5.

Thus, in one embodiment, the present disclosure provides antigen binding proteins and antigen binding protein-FGF21 fusion antigen binding protein components that compete for binding to β-Klotho or β-Klotho and one or more of FGFR1c, FGFR2c, FGFR3c, and FGFR4 with a reference antibody, wherein the reference antibody comprises a combination of light chain and heavy chain variable domain sequences selected from the group consisting of L1H1, L2H2, L3H3, L4H4, L5H5, L6H6, L7H7, L8H8, L9H9, L10H0 or L11H11.

In another embodiment, the present disclosure provides human antigen binding proteins and antigen binding protein-FGF21 fusion antigen binding protein components that compete for binding to β-Klotho or β-Klotho and one or more of FGFR1c, FGFR2c, FGFR3c, and FGFR4 with a reference antibody, wherein the reference antibody is 1A2, 2G10, 14E8, 25B10, 3B4, 1B5, 10H3, 9D10, 3F4 or 8F9.

In a further embodiment, an isolated human antigen binding protein or antigen binding protein-FGF21 fusion antigen binding protein component is provided that specifically binds to β-Klotho or β-Klotho and one or more of FGFR1c, FGFR2c, FGFR3c, and FGFR4 with substantially the same Kd as a reference antibody; initiates FGF21-like signaling in an in vitro ELK-Luciferase assay to the same degree as a reference antibody; lowers blood glucose; lowers serum lipid levels; and/or competes for binding with said reference antibody to β-Klotho or β-Klotho and one or more of FGFR1c, FGFR2c, FGFR3c, and FGFR4, wherein the reference antibody is selected from the group consisting of 1A2, 2G10, 14E8, 25B10, 3B4, 1B5, 10H3, 9D10, 3F4 or 8F9.

The ability to compete with an antigen binding protein or antigen binding protein-FGF21 fusion antigen binding protein component can be determined using any suitable assay, in which 1A2, 2G10, 14E8, 25B10, 3B4, 1B5, 10H3, 9D10, 3F4, 8F9, 1A2-SR4, 2G10-SR4, 14E8-SR4, 25B10-SR4, 1A2-Rm26, 1A2-Rm40, 2G10-Rm26, or 2G10-Rm40 can be used as the reference antibody.

Monoclonal Antibodies

The antigen binding proteins and antigen binding protein-FGF21 fusion antigen binding protein components that are provided include monoclonal antibodies that bind to β-Klotho or β-Klotho and one or more of FGFR1c, FGFR2c, FGFR3c, and FGFR4, and induce FGF21-like signaling to various degrees. Monoclonal antibodies can be produced using any technique known in the art, e.g., by immortalizing spleen cells harvested from the transgenic animal after completion of the immunization schedule. The spleen cells can be immortalized using any technique known in the art, e.g., by fusing them with myeloma cells to produce hybridomas. Myeloma cells for use in hybridoma-producing fusion procedures preferably are non-antibody-producing, have high fusion efficiency, and enzyme deficiencies that render them incapable of growing in certain selective media which support the growth of only the desired fused cells (hybridomas). Examples of suitable cell lines for use in mouse fusions include Sp-20, P3-X63/Ag8, P3-X63-Ag8.653, NS1/1.Ag 4 1, Sp210-Ag14, FO, NSO/U, MPC-11, MPC11-X45-GTG 1.7 and S194/5XXO Bul; examples of cell lines used in rat fusions include R210.RCY3, Y3-Ag 1.2.3, IR983F and 4B210. Other cell lines useful for cell fusions are U-266, GM1500-GRG2, LICR-LON-HMy2 and UC729-6.

In some instances, a hybridoma cell line is produced by immunizing an animal (e.g., a transgenic animal having human immunoglobulin sequences) with a FGFR1c, β-Klotho or FGFR1c and/or β-Klotho immunogen (e.g., a soluble complex comprising the extracellular domains of FGFR1c, FGFR2c, FGFR3c or FGFR4 and/or β-Klotho as shown in Examples 2, and 3 membranes on which the extracellular domains of FGFR1c, FGFR2c, FGFR3c or FGFR4 and/or β-Klotho are expressed, as shown in Examples 1 and 3 or whole cells expressing FGFR1c and/or β-Klotho, as shown in Examples 1 and 3); harvesting spleen cells from the immunized animal; fusing the harvested spleen cells to a myeloma cell line, thereby generating hybridoma cells; establishing hybridoma cell lines from the hybridoma cells, and identifying a hybridoma cell line that produces an antibody that specifically binds to β-Klotho or β-Klotho and one or more of FGFR1c, FGFR2c, FGFR3c, and FGFR4 (e.g., as described herein) and can induce FGF21-like signaling (e.g., as described in Examples 5-7). Such hybridoma cell lines, and the monoclonal antibodies produced by them, form aspects of the present disclosure.

Monoclonal antibodies secreted by a hybridoma cell line can be purified using any technique known in the art. Hybridomas or mAbs can be further screened to identify mAbs with particular properties, such as the ability to induce FGF21-like signaling. Examples of such screens are provided herein.

Chimeric and Humanized Antigen Binding Proteins and Antigen Binding Protein-FGF21 Fusion Antigen Binding Protein Components Chimeric and humanized antigen binding proteins and antigen binding protein-FGF21 fusion antigen binding protein components (e.g., antibodies, such as monoclonal antibodies) based upon the disclosed sequences are also provided. Monoclonal antibodies for use as therapeutic agents can be modified in various ways prior to use. One example is a chimeric antibody, which is an antibody composed of protein segments from different antibodies that are covalently joined to produce functional immunoglobulin light or heavy chains or immunologically functional portions thereof. Generally, a portion of the heavy chain and/or light chain is identical with or homologous to a corresponding sequence in antibodies derived from a particular species or belonging to a particular antibody class or subclass, while the remainder of the chain(s) is/are identical with or homologous to a corresponding sequence in antibodies derived from another species or belonging to another antibody class or subclass. For methods relating to chimeric antibodies, see, for example, U.S. Pat. No. 4,816,567; and Morrison et al., 1985, Proc. Natl. Acad. Sci. USA 81:6851-6855, which are hereby incorporated by reference. CDR grafting is described, for example, in U.S. Pat. Nos. 6,180,370, 5,693, 762, 5,693,761, 5,585,089, and 5,530,101.

Generally, the goal of making a chimeric antibody is to create a chimera in which the number of amino acids from the intended patient species is maximized. One example is the "CDR-grafted" antibody, in which the antibody comprises one or more complementarity determining regions (CDRs) from a particular species or belonging to a particular antibody class or subclass, while the remainder of the antibody chain(s) is/are identical with or homologous to a corresponding sequence in antibodies derived from another species or belonging to another antibody class or subclass. For use in humans, the variable region or selected CDRs from a rodent antibody often are grafted into a human antibody, replacing the naturally-occurring variable regions or CDRs of the human antibody.

One useful type of chimeric antibody is a "humanized" antibody. Generally, a humanized antibody is produced from a monoclonal antibody raised initially in a non-human animal. Certain amino acid residues in this monoclonal antibody, typically from non-antigen recognizing portions of the antibody, are modified to be homologous to corresponding residues in a human antibody of corresponding isotype. Humanization can be performed, for example, using various methods by substituting at least a portion of a rodent variable region for the corresponding regions of a human antibody (see, e.g., U.S. Pat. No. 5,585,089, and No. 5,693,762; Jones et al., 1986, *Nature* 321:522-525; Riechmann et al., 1988, *Nature* 332:323-27; Verhoeyen et al., 1988, *Science* 239: 1534-1536).

In one aspect, the CDRs of the light and heavy chain variable regions of the antibodies provided herein (see Tables 3 and 6) are grafted to framework regions (FRs) from antibodies from the same, or a different, phylogenetic species. For example, the CDRs of the heavy and light chain variable regions $V_H1$, $V_H2$, $V_H3$, $V_H4$ or $V_H5$ and/or $V_L1$, $V_L2$, $V_L3$, $V_L4$ or $V_L5$ can be grafted to consensus human FRs. To create consensus human FRs, FRs from several human heavy chain or light chain amino acid sequences can be aligned to identify a consensus amino acid sequence. In other embodiments, the FRs of a heavy chain or light chain disclosed herein are replaced with the FRs from a different heavy chain or light chain. In one aspect, rare amino acids in the FRs of the heavy and light chains of an antigen binding protein (e.g., an antibody) that specifically binds β-Klotho or β-Klotho and one or more of FGFR1c, FGFR2c, FGFR3c, and FGFR4 are not replaced, while the rest of the FR amino acids are replaced. A "rare amino acid" is a specific amino acid that is in a position in which this particular amino acid is not usually found in an FR. Alternatively, the grafted variable regions from the one heavy or light chain can be used with a constant region that is different from the constant region of that particular heavy or light chain as disclosed herein. In other embodiments, the grafted variable regions are part of a single chain Fv antibody.

In certain embodiments, constant regions from species other than human can be used along with the human variable region(s) to produce hybrid antibodies.

Fully Human Antibodies

Fully human antibodies are also provided by the instant disclosure. Methods are available for making fully human antibodies specific for a given antigen without exposing human beings to the antigen ("fully human antibodies"). One specific means provided for implementing the production of fully human antibodies is the "humanization" of the mouse humoral immune system. Introduction of human immunoglobulin (Ig) loci into mice in which the endogenous Ig genes have been inactivated is one means of producing fully human monoclonal antibodies (mAbs) in mouse, an animal that can be immunized with any desirable antigen. Using fully human antibodies can minimize the immunogenic and allergic responses that can sometimes be caused by administering mouse or mouse-derived mAbs to humans as therapeutic agents.

Fully human antibodies can be produced by immunizing transgenic animals (typically mice) that are capable of producing a repertoire of human antibodies in the absence of endogenous immunoglobulin production. Antigens for this purpose typically have six or more contiguous amino acids, and optionally are conjugated to a carrier, such as a hapten. See, e.g., Jakobovits et al., (1993) *Proc. Natl. Acad. Sci. USA* 90:2551-2555; Jakobovits et al., (1993) *Nature* 362:255-258; and Bruggermann et al., (1993) *Year in Immunol.* 7:33. In one example of such a method, transgenic animals are produced by incapacitating the endogenous mouse immunoglobulin loci encoding the mouse heavy and light immunoglobulin chains therein, and inserting into the mouse genome large fragments of human genome DNA containing loci that encode human heavy and light chain proteins. Partially modified animals, which have less than the full complement of human immunoglobulin loci, are then cross-bred to obtain an animal having all of the desired immune system modifications. When administered an immunogen, these transgenic animals produce antibodies that are immunospecific for the immunogen but have human rather than murine amino acid sequences, including the variable regions. For further details of such methods, see, for example, WO96/33735 and WO94/02602. Additional methods relating to transgenic mice for making human antibodies are described in U.S. Pat. Nos. 5,545,807; 6,713,610; 6,673,986; 6,162,963; 5,545,807; 6,300,129; 6,255,458; 5,877,397; 5,874,299 and 5,545,806; in PCT publications WO91/10741, WO90/04036, and in EP 546073B1 and EP 546073A1.

The transgenic mice described above, referred to herein as "HuMab" mice, contain a human immunoglobulin gene minilocus that encodes unrearranged human heavy ([μ, mu] and [γ, gamma]) and [κ, kappa] light chain immunoglobulin sequences, together with targeted mutations that inactivate the endogenous μ [mu] and κ [kappa] chain loci (Lonberg et al., 1994, *Nature* 368:856-859). Accordingly, the mice exhibit reduced expression of mouse IgM or [κ, kappa] and in response to immunization, and the introduced human heavy and light chain transgenes undergo class switching and somatic mutation to generate high affinity human IgG [κ, kappa] monoclonal antibodies (Lonberg et al., supra.; Lonberg and Huszar, (1995) *Intern. Rev. Immunol.* 13: 65-93; Harding and Lonberg, (1995) *Ann. N.Y. Acad. Sci.* 764:536-546). The preparation of HuMab mice is described in detail in Taylor et al., (1992) *Nucleic Acids Research* 20:6287-6295; Chen et al., (1993) *International Immunology* 5:647-656; Tuaillon et al., (1994) *J. Immunol.* 152:2912-2920; Lonberg et al., (1994) *Nature* 368:856-859; Lonberg, (1994) *Handbook of Exp. Pharmacology* 113:49-101; Taylor et al., (1994) *International Immunology* 6:579-591; Lonberg and Huszar, (1995) *Intern. Rev. Immunol.* 13:65-93; Harding and Lonberg, (1995) *Ann. N.Y Acad. Sci.* 764:536-546; Fishwild et al., (1996) *Nature Biotechnology* 14:845-851; the foregoing references are hereby incorporated by reference in their entirety for all purposes. See, further U.S. Pat. Nos. 5,545,806; 5,569,825; 5,625,126; 5,633,425; 5,789,650; 5,877,397; 5,661,016; 5,814,318; 5,874,299; and No. 5,770,429; as well as U.S. Pat. No. 5,545,807; International Publication Nos. WO 93/1227; WO 92/22646; and WO 92/03918, the disclosures of all of which are hereby incorporated by reference in their entirety for all purposes. Technologies utilized for producing human antibodies in these transgenic mice are disclosed also in WO 98/24893, and Mendez et al., (1997) *Nature Genetics* 15:146-156, which are hereby incorporated by reference. For example, the HCo7 and HCo12 transgenic mice strains can be used to generate antigen binding proteins (e.g., antibodies) that bind to β-Klotho or β-Klotho and one or more of FGFR1c, FGFR2c, FGFR3c, and FGFR4 and induce FGF21-like signalling. Further details regarding the production of human antibodies using transgenic mice are provided in the examples herein.

Using hybridoma technology, antigen-specific human mAbs with the desired specificity can be produced and selected from the transgenic mice such as those described above. Such antibodies can be cloned and expressed using a suitable vector and host cell, or the antibodies can be harvested from cultured hybridoma cells.

Fully human antibodies can also be derived from phage-display libraries (as disclosed in Hoogenboom et al., (1991) *J. Mol. Biol.* 227:381; and Marks et al., (1991) *J. Mol. Biol.* 222:581). Phage display techniques mimic immune selection through the display of antibody repertoires on the surface of filamentous bacteriophage, and subsequent selection of phage by their binding to an antigen of choice. One such technique is described in PCT Publication No. WO 99/10494 (hereby incorporated by reference), which describes the isolation of high affinity and functional agonistic antibodies for MPL- and msk-receptors using such an approach.

Bispecific or Bifunctional Antigen Binding Proteins and Antigen Binding Protein-FGF21 Fusion Antigen Binding Protein Components The antigen binding proteins and antigen binding protein-FGF21 fusion antigen binding protein components that are provided also include bispecific and bifunctional antibodies that include one or more CDRs or one or more variable regions as described herein. A bispecific or bifunctional antibody can be, in some instances, an artificial hybrid antibody having two different heavy/light chain pairs and two different binding sites. Bispecific antibodies can be produced by a variety of methods including, but not limited to, fusion of hybridomas or linking of Fab' fragments. See, e.g., Songsivilai and Lachmann, 1990, *Clin. Exp. Immunol.* 79:315-321; Kostelny et al., 1992, *J. Immunol.* 148:1547-1553. In one embodiment, an antigen binding protein or antigen binding protein-FGF21 fusion antigen binding protein component of the instant disclosure can bind β-Klotho or β-Klotho and one or more of FGFR1c, FGFR2c, FGFR3c, and FGFR4, which can lead to the activation of FGF21-like activity as measured by the FGF21-like functional and signaling assays described in Examples 5-7.

Antigen Binding Protein-FGF21 Fusions

It has been demonstrated that the N-terminus of FGF-21 provides specificity for the FGF receptor, while the C-terminus of FGF-21 provides specificity for β-Klotho. Accordingly, antigen binding protein-FGF21 fusions can be designed that mimic the signaling ability of mature FGF21 and can comprise (a) an antigen binding protein component that has specificity for β-Klotho and (b) an FGF21 component comprising a variable length of the N-terminal end of an FGF21 polypeptide sequence that retains specificity for an FGF21 receptor. Alternatively, an antigen binding protein-FGF21 fusion can comprise (a) an antigen binding protein component that has specificity for one or more of FGFR1c, FGFR2c, FGFR3c and FGFR4 and (b) an FGF21 component comprising a variable length of the C-terminal end of an FGF21 polypeptide sequence that retains specificity β-Klotho. Optionally, linkers can be included to join the FGF21 component to the antigen binding protein component. Thus, in another aspect of the present disclosure, antigen binding protein-FGF21 fusions are provided.

In one embodiment an antigen binding protein-FGF21 fusion comprises (a) an antigen binding protein component that specifically binds β-Klotho or β-Klotho and one or more of FGFR1c, FGFR2c, FGFR3c, and FGFR4; and (b) an FGF21 component, which comprises a truncated form of FGF21. In some embodiments, the antigen binding protein-FGF21 fusion comprises an antigen binding protein component that specifically binds to human β-Klotho and is fused to an FGF21 component comprising a truncated form of human FGF21. In some embodiments, the antigen binding protein component is selected from the antigen binding proteins of Tables 1-3 and 6. In some embodiments the FGF21 component comprises between 25 and 180 amino acids of SEQ ID NO:341. In one particular embodiment the antigen binding protein component is antibody 2G10 and the FGF21 component comprises residues 1-170 of FGF21 (SEQ ID NO: 343).

The FGF21 component of a fusion can be joined directly to the antigen bnding protein component of the fusion at the N-terminus of either the heavy or the light chain of the antigen binding protein component. In other embodiments the FGF21 component of a fusion can be directly joined to the antigen binding protein component of the fusion at the C-terminus of the heavy chain of the antigen binding protein component. Optionally, a linker can be employed to join the components of a fusion together, either at the N or C-terminus of the heavy chain of an antigen binding protein or the N-terminus of the light chain of an antigen binding protein.

The disclosed antigen binding protein-FGF21 fusions may exhibit a variety of characteristics such as (i) in vivo potency similar or equal to the full length mature form of FGF21; (ii) high binding affinity and specificity to an FGF21 receptor or β-Klotho; (iii) decreased immunogenicity due to the presence of the native sequences of truncated FGF-21; and (iv) the extended half-life typical of an antibody.

The Antigen Binding Protein Component

An antigen binding protein component of an antigen binding protein-FGF21 fusion comprises a protein that specifically binds (a) β-Klotho, (b) one or more of FGFR1c, FGFR2c, FGFR3c, and FGFR4, or (c) β-Klotho and one or more of FGFR1c, FGFR2c, FGFR3c, and FGFR4. The specificity of the antigen binding protein will depend on the overall architecture of the fusion, although all designs will preferably produce a fusion that mimics the signaling activity of FGF21. Any of the antigen binding protein formats described herein can be employed in a fusion, such as antibodies, hemibodies, Fab fragments, etc. The antigen binding proteins and elements thereof (e.g., heavy chains, light chains, variable regions and CDRs) provided in Tables 1-3 and 6 can serve as antigen binding components of an antigen binding protein-FGF21 fusion.

In one embodiment the antigen binding protein component specifically binds β-Klotho. In this embodiment the FGF21 component of the fusion will specifically associate with one or more of FGFR1c, FGFR2c, FGFR3c, and FGFR4 and will comprise an N-terminally truncated form of FGF21. The antigen binding component can also bind one or more of FGFR1c, FGFR2c, FGFR3c, and FGFR4 in addition to β-Klotho.

In another embodiment the antigen binding protein component specifically binds one or more of FGFR1c, FGFR2c, FGFR3c, and FGFR4. In this embodiment that FGF21 component of the fusion will specifically associate with β-Klotho and will comprise a C-terminally truncated form of FGF21. The antigen binding protein component can also bind to β-Klotho in addition to one or more of FGFR1c, FGFR2c, FGFR3c, and FGFR4.

When the antigen binding component is an antibody, the antibody can comprise an antibody provided herein, such as those described in Tables 1-3 and 6, such as those secreted from clones 1A2, 2G10, 14E8, 25B10, 3B4, 1B5, 10H3, 9D10, 3F4, and 8F9. Antibodies comprising one or more of the disclosed CDRs, including Fab fragments and variable regions, can also be employed in an antigen binding protein component.

The FGF-21 Component

The FGF21 component of the antigen binding protein-FGF21 fusion can comprise any length of FGF21 that is at least 25 amino acids in length.

In various embodiments, the FGF21 component of an antigen binding protein comprises a fragment of FGF21 (SEQ ID NO:341), comprising between 25 and 180 amino acids, for example 180, 179, 178, 177, 176, 175, 174, 173, 172, 171, 170, 169, 168, 167, 166, 165, 160, 155, 150, 145, 140, 135, 130, 125, 120, 115, 110, 105, 100, 95, 90, 85, 80, 75, 70, 65, 60, 55, 50, 45, 40, 35, 30 or 25 amino acids. The FGF21 component can be a fragment of SEQ ID NO:341 that has been truncated from the N-terminus, C-terminus or both the C-terminus to generate the fragment comprising between 25 and 180 amino acids.

In some embodiments, the FGF21 component can comprise an FGF21 sequence (e.g., SEQ ID NO:341) which has been truncated on the C-terminal end. For example the FGF21 component can comprise residues 1-180, 1-179, 1-178, 1-177, 1-176, 1-175, 1-174, 1-173, 1-172, 1-171, 1-170, 1-169, 1-168, 1-167, 1-166, 1-165, 1-160, 1-155, 1-150, 1-145, 1-140, 1-135, 1-130, 1-125, 1-120, 1-115, 1-110, 1-105, 1-100, 1-95, 1-90, 1-85, 1-80, 1-75, 1-70, 1-65, 1-60, 1-55, 1-50, 1-45, 1-40, 1-35, 1-30 or 1-25 of SEQ ID NO:341.

In other embodiments the FGF21 component can comprise an FGF21 sequence (e.g., SEQ ID NO:341) which has been truncated on the N-terminal end. For example the FGF21 component can comprise residues 2-181, 3-181, 4-181, 5-181, 6-181, 7-181, 8-181, 9-181, 10-181, 11-181, 12-181, 13-181, 14-181, 15-181, 20-181, 25-181, 30-181, 35-181, 40-181, 45-181, 50-181, 55-181, 60-181, 65-181, 70-181, 75-181, 80-181, 85-181, 90-181, 95-181, 100-181, 105-181, 110-181, 115-181, 120-181, 125-181, 130-181, 135-181, 140-181, 145-181, 150-181, 155-181, 160-181 or 165-181.

In still other embodiments the FGF21 component can comprise an FGF21 sequence (e.g., SEQ ID NO:341) which has been truncated on both the N- and C-terminal ends. For example the FGF21 component can comprise 2-181, 3-180, 4-179, 5-178, 6-177, 7-176, 8-175, 9-174, 10-173, 11-172, 12-171, 13-170, 14-165, 15-160, 20-155, 25-150, 30-145, 35-140, 40-135, 45-130, 50-125, 55-120, 60-115, 65-110, 70-105 or 75-100.

Linkers

The antigen binding protein component of a fusion can, but need not, be associated with the FGF21 component of the fusion via a linker sequence. Examples of linkers are provided here and can comprise peptides, polysaccharides, PEG and other types of polymers. Examples of suitable peptide linkers are described in U.S. Pat. Nos. 4,751,180 and 4,935,233. In particular embodiments a peptide linker comprises a Gly-Gly-Gly-Gly-Ser (SEQ ID NO: 344) motif repeated two or more times. Thus, a linker can comprise, for example, $(G_4S)_3$ (SEQ ID NO: 336), $(G_4S)_6$ (SEQ ID NO: 337), $(G_4S)_9$ (SEQ ID NO: 338), $(G_4S)_{12}$ (SEQ ID NO: 339), or $(G_4S)_{15}$ (SEQ ID NO: 340). Other examples of polymeric linkers include PEG molecules, such as PEG 20, PEG 40 or PEG 60.

The disclosed antigen binding protein-FGF21 fusions can be expressed and purified using standard laboratory techniques as described herein, for example in Example 17. The fusions can be expressed as a single full length protein or they can be expressed in components and subsequently joined via a chemical reaction. Standard purification techniques, such as Protein A, size exclusion and ion exchange chromatography, can be employed to isolate an antigen binding protein-FGF21 fusion.

Other Forms of Antigen Binding Proteins and Antigen Binding Protein-FGF21 Fusion Antigen Binding Protein Components Some of the antigen binding proteins and antigen binding protein-FGF21 fusion antigen binding protein components that specifically binds β-Klotho or β-Klotho and one or more of FGFR1c, FGFR2c, FGFR3c, and FGFR4 that are provided can comprise variant forms of the antigen binding proteins and antigen binding protein-FGF21 fusion antigen binding protein components disclosed herein (e.g., those comprising one or more of the sequences listed in Tables 1-3 and 6).

In various embodiments, the antigen binding proteins and antigen binding protein-FGF21 fusion antigen binding protein components disclosed herein can comprise one or more non-naturally occurring amino acids. For instance, some of the antigen binding proteins and antigen binding protein-FGF21 fusion antigen binding protein components can have one or more non-naturally occurring amino acid substitutions in one or more of the heavy or light chains, variable regions or CDRs listed in Tables 1-3 and 6. Examples of non-naturally occurring amino acids (which can be substituted for any naturally-occurring amino acid found in any sequence disclosed herein, as desired) include: 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine, and other similar amino acids and imino acids (e.g., 4-hydroxyproline). In the polypeptide notation used herein, the left-hand direction is the amino terminal direction and the right-hand direction is the carboxyl-terminal direction, in accordance with standard usage and convention. A non-limiting lists of examples of non-naturally occurring amino acids that can be inserted into an antigen binding protein or antigen binding protein-FGF21 fusion antigen binding protein component primary amino acid sequence or substituted for a wild-type residue in an antigen binding protein or antigen binding protein-FGF21 fusion antigen binding protein component sequence include β-amino acids, homoamino acids, cyclic amino acids and amino acids with derivatized side chains. Examples include (in the L-form or D-form; abbreviated as in parentheses): citrulline (Cit), homocitrulline (hCit), Nα-methylcitrulline (NMeCit), Nα-methylhomocitrulline (Nα-MeHoCit), ornithine (Orn), Nα-Methylornithine (Nα-MeOrn or NMeOrn), sarcosine (Sar), homolysine (hLys or hK), homoarginine (hArg or hR), homoglutamine (hQ), Nα-methylarginine (NMeR), Nα-methylleucine (Nα-MeL or NMeL), N-methylhomolysine (NMeHoK), Nα-methylglutamine (NMeQ), norleucine (Nle), norvaline (Nva), 1,2,3,4-tetrahydroisoquinoline (Tic), Octahydroindole-2-carboxylic acid (Oic), 3-(1-naphthyl) alanine (1-Nal), 3-(2-naphthyl)alanine (2-Nal), 1,2,3,4-tetrahydroisoquinoline (Tic), 2-indanylglycine (IgI), para-iodophenylalanine (pI-Phe), para-aminophenylalanine (4AmP or 4-Amino-Phe), 4-guanidino phenylalanine (Guf), glycyllysine (abbreviated "K(Nε-glycyl)" or "K(glycyl)" or "K(gly)"), nitrophenylalanine (nitrophe), aminophenylalanine (aminophe or Amino-Phe), benzylphenylalanine (benzylphe), γ-carboxyglutamic acid (γ-carboxyglu), hydroxyproline (hydroxypro), p-carboxyl-phenylalanine (Cpa), α-aminoadipic acid (Aad), Nα-methyl valine (NMeVal), N-α-methyl leucine (NMeLeu), Nα-methylnorleucine (NMeNle), cyclopentylglycine (Cpg), cyclohexylglycine (Chg), acetylarginine (acetylarg), α, β-diaminopropionoic acid (Dpr), α,γ-diaminobutyric acid (Dab), diaminopropionic acid (Dap), cyclohexylalanine (Cha), 4-methyl-phenylalanine (MePhe),β,β-diphenyl-alanine (BiPhA), aminobutyric acid (Abu), 4-phenyl-phenylalanine (or biphenylalanine; 4Bip), α-amino-isobutyric acid (Aib), beta-alanine, beta-aminopropionic acid, piperidinic acid, aminocaprioic acid, aminoheptanoic acid, aminopimelic acid, desmosine, diaminopimelic acid, N-ethylglycine, N-ethylaspargine, hydroxylysine, allo-hydroxylysine, isodesmosine, allo-isoleucine, N-methylglycine, N-methylisoleucine, N-methylvaline, 4-hydroxyproline (Hyp), γ-carboxyglutamate, ε-N,N,N-trimethyllysine, ε-N-acetyllysine, O-phosphoserine, N-acetylserine, N-formylmethionine, 3-methylhistidine, 5-hydroxylysine, ω-methylarginine, 4-Amino-O-Phthalic Acid (4APA), and other similar amino acids, and derivatized forms of any of those specifically listed.

Additionally, the antigen binding proteins and antigen binding protein-FGF21 fusion antigen binding protein components can have one or more conservative amino acid substitutions in one or more of the heavy or light chains, variable regions or CDRs listed in Tables 1-6. Naturally-occurring amino acids can be divided into classes based on common side chain properties:
1) hydrophobic: norleucine, Met, Ala, Val, Leu, Ile;
2) neutral hydrophilic: Cys, Ser, Thr, Asn, Gln;
3) acidic: Asp, Glu;
4) basic: His, Lys, Arg;
5) residues that influence chain orientation: Gly, Pro; and
6) aromatic: Trp, Tyr, Phe.

Conservative amino acid substitutions can involve exchange of a member of one of these classes with another member of the same class. Conservative amino acid substitutions can encompass non-naturally occurring amino acid residues, which are typically incorporated by chemical peptide synthesis rather than by synthesis in biological systems. These include peptidomimetics and other reversed or inverted forms of amino acid moieties.

Non-conservative substitutions can involve the exchange of a member of one of the above classes for a member from another class. Such substituted residues can be introduced into regions of the antigen binding protein or antigen binding protein-FGF21 fusion antigen binding protein component that are homologous with human antibodies, or into the non-homologous regions of the molecule.

In making such changes, according to certain embodiments, the hydropathic index of amino acids can be considered. The hydropathic profile of a protein is calculated by assigning each amino acid a numerical value ("hydropathy index") and then repetitively averaging these values along the peptide chain. Each amino acid has been assigned a hydropathic index on the basis of its hydrophobicity and charge characteristics. They are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic profile in conferring interactive biological function on a protein is understood in the art (see, e.g., Kyte et al., 1982, J. Mol. Biol. 157:105-131). It is known that certain amino acids can be substituted for other amino acids having a similar hydropathic index or score and still retain a similar biological activity. In making changes based upon the hydropathic index, in certain embodiments, the substitution of amino acids whose hydropathic indices are within ±2 is included. In some aspects, those which are within ±1 are included, and in other aspects, those within ±0.5 are included.

It is also understood in the art that the substitution of like amino acids can be made effectively on the basis of hydrophilicity, particularly where the biologically functional protein or peptide thereby created is intended for use in immunological embodiments, as in the present case. In certain embodiments, the greatest local average hydrophilicity of a protein, as governed by the hydrophilicity of its adjacent amino acids, correlates with its immunogenicity and antigen-binding or immunogenicity, that is, with a biological property of the protein.

The following hydrophilicity values have been assigned to these amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5) and tryptophan (−3.4). In making changes based upon similar hydrophilicity values, in certain embodiments, the substitution of amino acids whose hydrophilicity values are within ±2 is included, in other embodiments, those which are within ±1 are included, and in still other embodiments, those within ±0.5 are included. In some instances, one can also identify epitopes from primary amino acid sequences on the basis of hydrophilicity. These regions are also referred to as "epitopic core regions."

Exemplary conservative amino acid substitutions are set forth in Table 7.

TABLE 7

Conservative Amino Acid Substitutions

| Original Residue | Exemplary Substitutions |
|---|---|
| Ala | Ser |
| Arg | Lys |
| Asn | Gln, His |
| Asp | Glu |
| Cys | Ser |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile |
| Phe | Met, Leu, Tyr |
| Ser | Thr |
| Thr | Ser |
| Trp | Tyr |
| Tyr | Trp, Phe |
| Val | Ile, Leu |

A skilled artisan will be able to determine suitable variants of the disclosed antigen binding proteins and antigen binding protein-FGF21 fusion antigen binding protein components as set forth herein using well-known techniques. One skilled in the art can identify suitable areas of the molecules that can be changed without destroying activity by targeting regions not believed to be important for activity. The skilled artisan also will be able to identify residues and portions of the molecules that are conserved among similar polypeptides. In further embodiments, even areas that can be important for biological activity or for structure can be subject to conservative amino acid substitutions without destroying the biological activity or without adversely affecting the polypeptide structure.

Additionally, one skilled in the art can review structure-function studies identifying residues in similar polypeptides that are important for activity or structure. In view of such a comparison, one can predict the importance of amino acid residues in a protein that correspond to amino acid residues important for activity or structure in similar proteins. One skilled in the art can opt for chemically similar amino acid substitutions for such predicted important amino acid residues.

One skilled in the art can also analyze the 3-dimensional structure and amino acid sequence in relation to that structure in similar polypeptides. In view of such information, one skilled in the art can predict the alignment of amino acid residues of an antigen binding protein or antigen binding protein-FGF21 fusion antigen binding protein component (e.g, an antibody) with respect to its three dimensional structure. One skilled in the art can choose not to make radical changes to amino acid residues predicted to be on the surface of the protein, since such residues can be involved in important interactions with other molecules. Moreover, one skilled in the art can generate test variants containing a single amino acid substitution at each desired amino acid residue. These variants can then be screened using assays for FGF21-like signaling (e.g., as described in the Examples provided herein), thus yielding information regarding which amino acids can be changed and which must not be changed. In other words, based on information gathered from such routine experiments, one skilled in the art can readily determine the amino acid positions where further substitutions should be avoided either alone or in combination with other mutations.

A number of scientific publications have been devoted to the prediction of secondary structure. See, Moult, (1996) *Curr. Op. in Biotech.* 7:422-427; Chou et al., (1974) *Biochem.* 13:222-245; Chou et al., (1974) *Biochemistry* 113:211-222; Chou et al., (1978) *Adv. Enzymol. Relat. Areas Mol. Biol.* 47:45-148; Chou et al., (1979) *Ann. Rev. Biochem.* 47:251-276; and Chou et al., (1979) *Biophys. J.* 26:367-384. Moreover, computer programs are currently available to assist with predicting secondary structure. One method of predicting secondary structure is based upon homology modeling. For example, two polypeptides or proteins that have a sequence identity of greater than 30%, or similarity greater than 40% can have similar structural topologies. The growth of the protein structural database (PDB) has provided enhanced predictability of secondary structure, including the potential number of folds within a polypeptide's or protein's structure. See, Holm et al., (1999) *Nucl. Acid. Res.* 27:244-247. It has been suggested (Brenner et al., (1997) *Curr. Op. Struct. Biol.* 7:369-376) that there are a limited number of folds in a given polypeptide or protein and that once a critical number of structures have been resolved, structural prediction will become dramatically more accurate.

Additional methods of predicting secondary structure include "threading" (Jones, (1997) *Curr. Opin. Struct. Biol.* 7:377-387; Sippl et al., (1996) *Structure* 4:15-19), "profile analysis" (Bowie et al., (1991) *Science* 253:164-170; Gribskov et al., (1990) *Meth. Enzym.* 183:146-159; Gribskov et al., (1987) *Proc. Nat. Acad. Sci.* 84:4355-4358), and "evolutionary linkage" (See, Holm, (1999) supra; and Brenner, (1997) supra).

In some embodiments, amino acid substitutions can be made in the disclosed antigen binding proteins and antigen binding protein-FGF21 fusion antigen binding protein components that: (1) reduce susceptibility to proteolysis, (2) reduce susceptibility to oxidation, (3) alter binding affinity for forming protein complexes, (4) alter ligand or antigen binding affinities, and/or (4) confer or modify other physicochemical or functional properties on such polypeptides. For example, single or multiple amino acid substitutions (in certain embodiments, conservative amino acid substitutions) can be made in the sequences disclosed herein.

In other embodiments, substitutions can be made in that portion of the disclosed antigen binding proteins and antigen binding protein-FGF21 fusion antigen binding protein components that lies outside the domain(s) forming intermolecular contacts). In such embodiments, conservative amino acid substitutions can be used that do not substantially change the structural characteristics of the parent sequence (e.g., one or more replacement amino acids that do not disrupt the secondary structure that characterizes the parent or native antigen binding protein). Examples of art-recognized polypeptide secondary and tertiary structures are described in *Proteins, Structures and Molecular Principles* (Creighton, Ed.), 1984, W. H. New York: Freeman and Company; *Introduction to Protein Structure* (Branden and Tooze, eds.), 1991, New York: Garland Publishing; and Thornton et al., (1991) *Nature* 354:105, which are each incorporated herein by reference.

Additional preferred antigen binding protein and antigen binding protein-FGF21 fusion antigen binding protein components variants include cysteine variants wherein one or more cysteine residues in the parent or native amino acid sequence are deleted from or substituted with another amino acid (e.g., serine). Cysteine variants are useful, inter alia when antibodies must be refolded into a biologically active conformation. Cysteine variants can have fewer cysteine residues than the native antibody, and typically have an even number to minimize interactions resulting from unpaired cysteines.

The heavy and light chains, variable regions domains and CDRs that are disclosed can be used to prepare polypeptides that contain an antigen binding region that can specifically bind to β-Klotho or β-Klotho and one or more of FGFR1c, FGFR2c, FGFR3c, and FGFR4 and induce FGF21-like signaling. For example, one or more of the CDRs listed in Tables 3 and 6 can be incorporated into a molecule (e.g., an antigen binding protein or antigen binding protein-FGF21 fusion antigen binding protein component) covalently or noncovalently to make an immunoadhesion. An immunoadhesion can incorporate the CDR(s) as part of a larger polypeptide chain, can covalently link the CDR(s) to another polypeptide chain, or can incorporate the CDR(s) noncovalently. The CDR(s) enable the immunoadhesion to bind specifically to a particular antigen of interest (e.g., β-Klotho or β-Klotho and one or more of FGFR1c, FGFR2c, FGFR3c, and FGFR4 or an epitope thereon).

The heavy and light chains, variable regions domains and CDRs that are disclosed can be used to prepare antigen binding proteins and antigen binding protein-FGF21 fusion antigen binding protein components that contain an antigen binding region that can specifically bind to one or more of β-Klotho or β-Klotho and one or more of FGFR1c, FGFR2c, FGFR3c, and FGFR4 and induce FGF21-like signaling. For example, one or more of the CDRs listed in Tables 3 and 6 can be incorporated into a molecule (e.g., an antigen binding protein or antigen binding protein-FGF21 fusion antigen binding protein component) that is structurally similar to a "half" antibody comprising the heavy chain, the light chain of an antigen binding protein paired with a Fc fragment so that the antigen binding region is monovalent (like a Fab fragment) but with a dimeric Fc moiety.

Mimetics (e.g., "peptide mimetics" or "peptidomimetics") based upon the variable region domains and CDRs that are described herein are also provided. These analogs can be peptides, non-peptides or combinations of peptide and non-peptide regions. See, e.g., Fauchere, 1986, *Adv. Drug Res.* 15:29; Veber and Freidinger, 1985, *TINS p.* 392; and Evans et al., 1987, *J. Med. Chem.* 30:1229, which are incorporated herein by reference for any purpose. Peptide mimetics that are structurally similar to therapeutically useful peptides can be used to produce a similar therapeutic or prophylactic effect. Such compounds are often developed with the aid of computerized molecular modeling. Generally, peptidomimetics are proteins that are structurally similar to an antibody displaying a desired biological activity, such as, in the context of the instant disclosure, the ability to specifically bind β-Klotho β-Klotho and one or more of FGFR1c, FGFR2c, FGFR3c, and FGFR4, but which have one or more peptide linkages optionally replaced by a linkage selected from: —$CH_2NH$—, —$CH_2S$—, —$CH_2$—$CH_2$—, —CH═CH-(cis and trans), —$COCH_2$—, —$CH(OH)CH_2$—, and —$CH_2SO$—, by methods well known in the art. Systematic substitution of one or more amino acids of a consensus sequence with a D-amino acid of the same type (e.g., D-lysine in place of L-lysine) can be used in certain embodiments to generate more stable proteins. In addition, constrained peptides comprising a consensus sequence or a substantially identical consensus sequence variation can be generated by methods known in the art (see, e.g., Rizo and Gierasch, 1992, *Ann. Rev. Biochem.* 61:387), incorporated herein by reference), for example, by adding internal cysteine residues capable of forming intramolecular disulfide bridges which cyclize the peptide.

Derivatives of the antigen binding proteins and antigen binding protein-FGF21 fusion antigen binding protein components that specifically bind β-Klotho or β-Klotho and one or more of FGFR1c, FGFR2c, FGFR3c, and FGFR4 that are described herein are also provided. The derivatized antigen binding proteins and antigen binding protein-FGF21 fusion antigen binding protein components can comprise any molecule or substance that imparts a desired property to the antibody or fragment, such as increased half-life in a particular use. The derivatized antigen binding protein or antigen binding protein-FGF21 fusion antigen binding protein component can comprise, for example, a detectable (or labeling) moiety (e.g., a radioactive, colorimetric, antigenic or enzymatic molecule, a detectable bead (such as a magnetic or electrodense (e.g., gold) bead), or a molecule that specifically binds to another molecule (e.g., biotin or streptavidin)), a therapeutic or diagnostic moiety (e.g., a radioactive, cytotoxic, or pharmaceutically active moiety), or a molecule that increases the suitability of the antigen binding protein or antigen binding protein-FGF21 fusion antigen binding protein component for a particular use (e.g., administration to a subject, such as a human subject, or other in vivo or in vitro uses). Examples of molecules that can be used to derivatize an antigen binding protein or antigen binding protein-FGF21 fusion antigen binding protein component include albumin (e.g., human serum albumin (HSA)) and polyethylene glycol (PEG). Albumin-linked and PEGylated derivatives of antigen binding proteins and antigen binding protein-FGF21 fusion antigen binding protein components can be prepared using techniques well known in the art. Certain antigen binding proteins and antigen binding protein-FGF21 fusion antigen binding protein components include a PEGylated single chain polypeptide as described herein. In one embodiment, the antigen binding protein or antigen binding protein-FGF21 fusion antigen binding protein component is conjugated or otherwise linked to transthyretin (TTR) or a TTR variant. The TTR or TTR variant can be chemically modified with, for example, a chemical selected from the group consisting of dextran, poly(n-vinyl pyrrolidone), polyethylene glycols, propropylene glycol homopolymers, polypropylene oxide/ethylene oxide co-polymers, polyoxyethylated polyols and polyvinyl alcohols.

Other derivatives include covalent or aggregative conjugates of the antigen binding proteins and antigen binding protein-FGF21 fusion antigen binding protein components that specifically bind β-Klotho or β-Klotho and one or more of FGFR1c, FGFR2c, FGFR3c, and FGFR4 that are disclosed herein with other proteins or polypeptides, such as by expression of recombinant fusion proteins comprising heterologous polypeptides fused to the N-terminus or C-terminus of an antigen binding protein that induce FGF21-like signaling. For example, the conjugated peptide can be a heterologous signal (or leader) polypeptide, e.g., the yeast alpha-factor leader, or a peptide such as an epitope tag. An antigen binding protein-containing fusion protein of the present disclosure can comprise peptides added to facilitate purification or identification of an antigen binding protein or antigen binding protein-FGF21 fusion antigen binding protein component that specifically binds β-Klotho or β-Klotho and one or more of FGFR1c, FGFR2c, FGFR3c, and FGFR4 (e.g., poly-His). An antigen binding protein or antigen binding protein-FGF21 fusion antigen binding protein component that specifically binds β-Klotho or β-Klotho and one or more of FGFR1c, FGFR2c, FGFR3c, and FGFR4 also can be linked to the FLAG peptide as described in Hopp et al., 1988, *Bio/Technology* 6:1204; and U.S. Pat. No. 5,011, 912. The FLAG peptide is highly antigenic and provides an epitope reversibly bound by a specific monoclonal antibody (mAb), enabling rapid assay and facile purification of expressed recombinant protein. Reagents useful for preparing fusion proteins in which the FLAG peptide is fused to a given polypeptide are commercially available (Sigma, St. Louis, Mo.).

Multimers that comprise one or more antigen binding proteins or antigen binding protein-FGF21 fusion antigen binding protein components that specifically bind β-Klotho or β-Klotho and one or more of FGFR1c, FGFR2c, FGFR3c, and FGFR4 form another aspect of the present disclosure. Multimers can take the form of covalently-linked or non-covalently-linked dimers, trimers, or higher multimers. Multimers comprising two or more antigen binding proteins or antigen binding protein-FGF21 fusion antigen binding protein components that bind β-Klotho or β-Klotho and one or more of FGFR1c, FGFR2c, FGFR3c, and FGFR4 and which induce FGF21-like signaling are contemplated for use as therapeutics, diagnostics and for other uses as well, with one example of such a multimer being a homodimer. Other exemplary multimers include heterodimers, homotrimers, heterotrimers, homotetramers, heterotetramers, etc.

One embodiment is directed to multimers comprising multiple antigen binding proteins or antigen binding protein-FGF21 fusion antigen binding protein components that specifically bind β-Klotho or β-Klotho and one or more of FGFR1c, FGFR2c, FGFR3c, and FGFR4 that are joined via covalent or non-covalent interactions between peptide moieties fused to an antigen binding protein or antigen binding protein-FGF21 fusion antigen binding protein component that specifically binds β-Klotho or β-Klotho and one or more of FGFR1c, FGFR2c, FGFR3c, and FGFR4. Such peptides can be peptide linkers (spacers), or peptides that have the property of promoting multimerization. Leucine zippers and certain polypeptides derived from antibodies are among the peptides that can promote multimerization of antigen binding proteins attached thereto, as described in more detail herein.

In particular embodiments, the multimers comprise from two to four antigen binding proteins or antigen binding protein-FGF21 fusion antigen binding protein components that bind β-Klotho or β-Klotho and one or more of FGFR1c, FGFR2c, FGFR3c, and FGFR4. The antigen binding protein or antigen binding protein-FGF21 fusion antigen binding protein components moieties of the multimer can be in any of the forms described above, e.g., variants or fragments. Preferably, the multimers comprise antigen binding proteins or antigen binding protein-FGF21 fusion antigen binding protein components that have the ability to specifically bind β-Klotho or β-Klotho and one or more of FGFR1c, FGFR2c, FGFR3c, and FGFR4.

In one embodiment, an oligomer is prepared using polypeptides derived from immunoglobulins. Preparation of fusion proteins comprising certain heterologous polypeptides fused to various portions of antibody-derived polypeptides (including the Fc domain) has been described, e.g., by Ashkenazi et al., (1991) *Proc. Natl. Acad. Sci. USA* 88:10535; Byrn et al., (1990) *Nature* 344:677; and Hollenbaugh et al., 1992 "Construction of Immunoglobulin Fusion Proteins", in Current Protocols in Immunology, Suppl. 4, pages 10.19.1-10.19.11.

One embodiment is directed to a dimer comprising two fusion proteins created by fusing an antigen binding protein or antigen binding protein-FGF21 fusion antigen binding protein component that specifically binds β-Klotho or β-Klotho and one or more of FGFR1c, FGFR2c, FGFR3c, and FGFR4 to the Fc region of an antibody. The dimer can be made by, for example, inserting a gene fusion encoding the fusion protein into an appropriate expression vector, expressing the gene fusion in host cells transformed with the recombinant expression vector, and allowing the expressed fusion protein to assemble much like antibody molecules, whereupon interchain disulfide bonds form between the Fc moieties to yield the dimer.

The term "Fc polypeptide" as used herein includes native and mutein forms of polypeptides derived from the Fc region of an antibody. Truncated forms of such polypeptides containing the hinge region that promotes dimerization also are included. Fusion proteins comprising Fc moieties (and oligomers formed therefrom) offer the advantage of facile purification by affinity chromatography over Protein A or Protein G columns.

One suitable Fc polypeptide, described in PCT application WO 93/10151 and U.S. Pat. No. 5,426,048 and U.S. Pat. No. 5,262,522, is a single chain polypeptide extending from the N-terminal hinge region to the native C-terminus of the Fc region of a human IgG1 antibody. Another useful Fc polypeptide is the Fc mutein described in U.S. Pat. No. 5,457,035, and in Baum et al., (1994) *EMBO J.* 13:3992-4001. The amino acid sequence of this mutein is identical to that of the native Fc sequence presented in WO 93/10151, except that amino acid 19 has been changed from Leu to Ala, amino acid 20 has been changed from Leu to Glu, and amino acid 22 has been changed from Gly to Ala. The mutein exhibits reduced affinity for Fc receptors.

In other embodiments, the variable portion of the heavy and/or light chains of a antigen binding protein or antigen binding protein-FGF21 fusion antigen binding protein component, such as disclosed herein, can be substituted for the variable portion of an antibody heavy and/or light chain.

Alternatively, the oligomer can be a fusion protein comprising multiple antigen binding proteins or antigen binding protein-FGF21 fusion antigen binding protein components that specifically bind β-Klotho or β-Klotho and one or more of FGFR1c, FGFR2c, FGFR3c, and FGFR4, with or without peptide linkers (spacer peptides). Among the suitable peptide linkers are those described in U.S. Pat. No. 4,751,180 and U.S. Pat. No. 4,935,233.

Another method for preparing oligomeric derivatives comprising that antigen binding proteins and antigen binding protein-FGF21 fusion antigen binding protein components that specifically bind β-Klotho or β-Klotho and one or more of FGFR1c, FGFR2c, FGFR3c, and FGFR4 involves use of a leucine zipper. Leucine zipper domains are peptides that promote oligomerization of the proteins in which they are found. Leucine zippers were originally identified in several DNA-binding proteins (Landschulz et al., (1988) *Science* 240:1759), and have since been found in a variety of different proteins. Among the known leucine zippers are naturally occurring peptides and derivatives thereof that dimerize or trimerize. Examples of leucine zipper domains suitable for producing soluble oligomeric proteins are described in PCT application WO 94/10308, and the leucine zipper derived from lung surfactant protein D (SPD) described in Hoppe et al., (1994) *FEBS Letters* 344:191, hereby incorporated by reference. The use of a modified leucine zipper that allows for stable trimerization of a heterologous protein fused thereto is described in Fanslow et al., (1994) *Semin. Immunol.* 6:267-278. In one approach, recombinant fusion proteins comprising an antigen binding protein or antigen binding protein-FGF21 fusion antigen binding protein component fragment or derivative that specifically binds β-Klotho or β-Klotho and one or more of FGFR1c, FGFR2c, FGFR3c, and FGFR4 is fused to a leucine zipper peptide are expressed in suitable host cells, and the soluble oligomeric antigen binding protein fragments or derivatives that form are recovered from the culture supernatant.

In certain embodiments, the antigen binding protein or antigen binding protein-FGF21 fusion antigen binding protein component has a $K_D$ (equilibrium binding affinity) of less than 1 pM, 10 pM, 100 pM, 1 nM, 2 nM, 5 nM, 10 nM, 25 nM or 50 nM.

Another aspect provides an antigen binding protein or antigen binding protein-FGF21 fusion antigen binding protein component (or portion thereof) having a half-life of at least one day in vitro or in vivo (e.g., when administered to a human subject). In one embodiment, the antigen binding protein or antigen binding protein-FGF21 fusion antigen binding protein component has a half-life of at least three days. In another embodiment, the antigen binding protein or antigen binding protein-FGF21 fusion antigen binding protein component (or portion thereof) has a half-life of four days or longer. In another embodiment, the antigen binding protein or antigen binding protein-FGF21 fusion antigen binding protein component (or portion thereof) has a half-life of eight days or longer. In another embodiment, the antigen binding protein or antigen binding protein-FGF21 fusion antigen binding protein component (or portion thereof) is derivatized or modified such that it has a longer half-life as compared to the underivatized or unmodified antigen binding protein. In another embodiment, an antigen binding protein or antigen binding protein-FGF21 fusion antigen binding protein component that specifically binds β-Klotho or β-Klotho and one or more of FGFR1c, FGFR2c, FGFR3c, and FGFR4 contains point mutations to increase serum half life, such as described in WO 00/09560, published Feb. 24, 2000, incorporated by reference.

Glycosylation

An antigen binding protein or antigen binding protein-FGF21 fusion antigen binding protein component that specifically binds β-Klotho or β-Klotho and one or more of FGFR1c, FGFR2c, FGFR3c, and FGFR4 can have a glycosylation pattern that is different or altered from that found in the native species. As is known in the art, glycosylation patterns can depend on both the sequence of the protein (e.g., the presence or absence of particular glycosylation amino acid residues, discussed below), or the host cell or organism in which the protein is produced. Particular expression systems are discussed below.

Glycosylation of polypeptides is typically either N-linked or O-linked. N-linked refers to the attachment of the carbohydrate moiety to the side chain of an asparagine residue. The tri-peptide sequences asparagine-X-serine and asparagine-X-threonine, where X is any amino acid except proline, are the recognition sequences for enzymatic attachment of the carbohydrate moiety to the asparagine side chain. Thus, the presence of either of these tri-peptide sequences in a polypeptide creates a potential glycosylation site. O-linked glycosylation refers to the attachment of one of the sugars N-acetylgalactosamine, galactose, or xylose, to a hydroxyamino acid, most commonly serine or threonine, although 5-hydroxyproline or 5-hydroxylysine can also be used.

Addition of glycosylation sites to the antigen binding protein is conveniently accomplished by altering the amino acid sequence such that it contains one or more of the above-described tri-peptide sequences (for N-linked glycosylation sites). The alteration can also be made by the addition of, or substitution by, one or more serine or threonine residues to the starting sequence (for O-linked glycosylation sites). For ease, the antigen binding protein or antigen binding protein-FGF21 fusion antigen binding protein component amino acid sequence can be altered through changes at the DNA level, particularly by mutating the DNA encoding the target polypeptide at preselected bases such that codons are generated that will translate into the desired amino acids.

Another means of increasing the number of carbohydrate moieties on the antigen binding protein is by chemical or enzymatic coupling of glycosides to the protein. These procedures are advantageous in that they do not require production of the protein in a host cell that has glycosylation capabilities for N- and O-linked glycosylation. Depending on the coupling mode used, the sugar(s) can be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described in WO 87/05330 and in Aplin and Wriston, (1981) *CRC Crit. Rev. Biochem.*, pp. 259-306.

Removal of carbohydrate moieties present on the starting antigen binding protein or antigen binding protein-FGF21 fusion antigen binding protein component can be accomplished chemically or enzymatically. Chemical deglycosylation requires exposure of the protein to the compound trifluoromethanesulfonic acid, or an equivalent compound. This treatment results in the cleavage of most or all sugars except the linking sugar (N-acetylglucosamine or N-acetylgalactosamine), while leaving the polypeptide intact. Chemical deglycosylation is described by Hakimuddin et al., (1987) *Arch. Biochem. Biophys.* 259:52 and by Edge et al., (1981) *Anal. Biochem.* 118:131. Enzymatic cleavage of carbohydrate moieties on polypeptides can be achieved by the use of a variety of endo- and exo-glycosidases as described by Thotakura et al., (1987) *Meth. Enzymol.* 138: 350. Glycosylation at potential glycosylation sites can be prevented by the use of the compound tunicamycin as described by Duskin et al., (1982) *J. Biol. Chem.* 257:3105. Tunicamycin blocks the formation of protein-N-glycoside linkages.

Hence, aspects of the present disclosure include glycosylation variants of antigen binding proteins NS antigen binding protein-FGF21 fusion antigen binding protein components that specifically bind β-Klotho or β-Klotho and one or more of FGFR1c, FGFR2c, FGFR3c, and FGFR4 wherein the number and/or type of glycosylation site(s) has been altered compared to the amino acid sequences of the parent polypeptide. In certain embodiments, antigen binding protein and antigen binding protein-FGF21 fusion antigen binding protein component variants comprise a greater or a lesser number of N-linked glycosylation sites than the native sequence. An N-linked glycosylation site is characterized by the sequence: Asn-X-Ser or Asn-X-Thr, wherein the amino acid residue designated as X can be any amino acid residue except proline. The substitution of amino acid residues to create this sequence provides a potential new site for the addition of an N-linked carbohydrate chain. Alternatively, substitutions that eliminate or alter this sequence will prevent addition of an N-linked carbohydrate chain present in the native polypeptide. For example, the glycosylation can be reduced by the deletion of an Asn or by substituting the Asn with a different amino acid. In other embodiments, one or more new N-linked sites are created. Antibodies typically have a N-linked glycosylation site in the Fc region.

Labels and Effector Groups

In some embodiments, an antigen binding protein that specifically binds β-Klotho or β-Klotho and one or more of FGFR1c, FGFR2c, FGFR3c, and FGFR4 comprises one or more labels. The term "labeling group" or "label" means any detectable label. Examples of suitable labeling groups include, but are not limited to, the following: radioisotopes or radionuclides (e.g., 3H, $^{14}C$, $^{15}N$, $^{35}S$, $^{90}Y$, $^{99}Tc$, $^{111}I$, $^{125}I$, $^{131}I$) fluorescent groups (e.g., FITC, rhodamine, lanthanide phosphors), enzymatic groups (e.g., horseradish peroxidase, β-galactosidase, luciferase, alkaline phosphatase), chemiluminescent groups, biotinyl groups, or predetermined polypeptide epitopes recognized by a secondary reporter (e.g., leucine zipper pair sequences, binding sites for secondary antibodies, metal binding domains, epitope tags). In some embodiments, the labeling group is coupled to the antigen binding protein or antigen binding protein-FGF21 fusion antigen binding protein component via spacer arms of various lengths to reduce potential steric hindrance. Various methods for labeling proteins are known in the art and can be used as seen fit.

The term "effector group" means any group coupled to an antigen binding protein or antigen binding protein-FGF21 fusion antigen binding protein component that specifically binds β-Klotho or β-Klotho and one or more of FGFR1c, FGFR2c, FGFR3c, and FGFR4 that acts as a cytotoxic agent. Examples for suitable effector groups are radioisotopes or radionuclides (e.g., 3H, $^{14}C$, $^{15}N$, $^{35}S$, $^{90}Y$, $^{99}Tc$, $^{111}I$, $^{125}I$, $^{131}I$). Other suitable groups include toxins, therapeutic groups, or chemotherapeutic groups. Examples of suitable groups include calicheamicin, auristatins, geldanamycin and cantansine. In some embodiments, the effector group is coupled to the antigen binding protein or antigen binding protein-FGF21 fusion antigen binding protein component via spacer arms of various lengths to reduce potential steric hindrance.

In general, labels fall into a variety of classes, depending on the assay in which they are to be detected: (a) isotopic labels, which can be radioactive or heavy isotopes; (b) magnetic labels (e.g., magnetic particles); (c) redox active moieties; (d) optical dyes; enzymatic groups (e.g. horseradish peroxidase, β-galactosidase, luciferase, alkaline phosphatase); (e) biotinylated groups; and (f) predetermined polypeptide epitopes recognized by a secondary reporter (e.g., leucine zipper pair sequences, binding sites for secondary antibodies, metal binding domains, epitope tags, etc.). In some embodiments, the labeling group is coupled to the antigen binding protein or antigen binding protein-FGF21 fusion antigen binding protein component via spacer arms of various lengths to reduce potential steric hindrance. Various methods for labeling proteins are known in the art.

Specific labels include optical dyes, including, but not limited to, chromophores, phosphors and fluorophores, with the latter being specific in many instances. Fluorophores can be either "small molecule" fluores, or proteinaceous fluores.

By "fluorescent label" is meant any molecule that can be detected via its inherent fluorescent properties. Suitable fluorescent labels include, but are not limited to, fluorescein, rhodamine, tetramethylrhodamine, eosin, erythrosin, coumarin, methyl-coumarins, pyrene, Malacite green, stilbene, Lucifer Yellow, Cascade Blue, Texas Red, IAEDANS, EDANS, BODIPY FL, LC Red 640, Cy 5, Cy 5.5, LC Red 705, Oregon green, the Alexa-Fluor dyes (Alexa Fluor 350, Alexa Fluor 430, Alexa Fluor 488, Alexa Fluor 546, Alexa Fluor 568, Alexa Fluor 594, Alexa Fluor 633, Alexa Fluor 647, Alexa Fluor 660, Alexa Fluor 680), Cascade Blue, Cascade Yellow and R-phycoerythrin (PE) (Molecular Probes, Eugene, Oreg.), FITC, Rhodamine, and Texas Red (Pierce, Rockford, Ill.), Cy5, Cy5.5, Cy7 (Amersham Life Science, Pittsburgh, Pa.). Suitable optical dyes, including fluorophores, are described in MOLECULAR PROBES HANDBOOK by Richard P. Haugland, hereby expressly incorporated by reference.

Suitable proteinaceous fluorescent labels also include, but are not limited to, green fluorescent protein, including a *Renilla, Ptilosarcus,* or *Aequorea* species of GFP (Chalfie et al., (1994) *Science* 263:802-805), EGFP (Clontech Labs., Inc., Genbank Accession Number U55762), blue fluorescent protein (BFP, Quantum Biotechnologies, Inc., Quebec, Canada; Stauber, (1998) *Biotechniques* 24:462-471; Heim et al., (1996) *Curr. Biol.* 6:178-182), enhanced yellow fluorescent protein (EYFP, Clontech Labs., Inc.), luciferase (Ichiki et al., (1993) *J. Immunol.* 150:5408-5417), γ galactosidase (Nolan et al., (1988) *Proc. Natl. Acad. Sci. U.S.A.* 85:2603-2607) and *Renilla* (WO92/15673, WO95/07463, WO98/14605, WO98/26277, WO99/49019, U.S. Pat. No. 5,292,658, No. 5418155, No. 5683888, No. 5741668, No. 5777079, No. 5804387, No. 5874304, No. 5876995, No. 5925558).

Preparation of Antigen Binding Proteins and Antigen Binding Protein-FGF21 Fusion Antigen Binding Protein Components Non-human antibodies that are provided can be, for example, derived from any antibody-producing animal, such as mouse, rat, rabbit, goat, donkey, or non-human primate (such as monkey (e.g., cynomolgus or rhesus monkey) or ape (e.g., chimpanzee)). Non-human antibodies can be used, for instance, in in vitro cell culture and cell-culture based applications, or any other application where an immune response to the antibody does not occur or is insignificant, can be prevented, is not a concern, or is desired. In certain embodiments, the antibodies can be produced by immunizing with full-length β-Klotho (Example 1), with the extracellular domain of β-Klotho (Example 2), with whole cells expressing β-Klotho, with membranes prepared from cells expressing β-Klotho (Example 1), with fusion proteins, e.g., Fc fusions comprising β-Klotho (or extracellular domains thereof) fused to Fc, or other methods known in the art, e.g., as described in the Examples presented herein. Alternatively, non-human antibodies can be raised by immunizing with amino acids which are segments of β-Klotho that form part of the epitope to which certain antibodies provided herein bind. The antibodies can be polyclonal, monoclonal, or can be synthesized in host cells by expressing recombinant DNA.

Fully human antibodies can be prepared as described herein by immunizing transgenic animals containing human immunoglobulin loci or by selecting a phage display library that is expressing a repertoire of human antibodies.

The monoclonal antibodies (mAbs) can be produced by a variety of techniques, including conventional monoclonal antibody methodology, e.g., the standard somatic cell hybridization technique of Kohler and Milstein, (1975) *Nature* 256:495. Alternatively, other techniques for producing monoclonal antibodies can be employed, for example, the viral or oncogenic transformation of B-lymphocytes. One suitable animal system for preparing hybridomas is the murine system, which is a well-established procedure. Immunization protocols and techniques for isolation of immunized splenocytes for fusion are known in the art. For such procedures, B cells from immunized mice are fused with a suitable immortalized fusion partner, such as a murine myeloma cell line. If desired, rats or other mammals besides can be immunized instead of mice and B cells from such animals can be fused with the murine myeloma cell line to form hybridomas. Alternatively, a myeloma cell line from a source other than mouse can be used. Fusion procedures for making hybridomas also are well known. SLAM technology can also be employed in the production of antibodies.

The single chain antibodies that are provided can be formed by linking heavy and light chain variable domain (Fv region) fragments via an amino acid bridge (short peptide linker), resulting in a single polypeptide chain. Such single-chain Fvs (scFvs) can be prepared by fusing DNA encoding a peptide linker between DNAs encoding the two variable domain polypeptides ($V_L$ and $V_H$). The resulting polypeptides can fold back on themselves to form antigen binding monomers, or they can form multimers (e.g., dimers, trimers, or tetramers), depending on the length of a flexible linker between the two variable domains (Kortt et al., (1997) *Prot. Eng.* 10:423; Kortt et al., (2001) *Biomol. Eng.* 18:95-108). By combining different $V_L$ and $V_H$-comprising polypeptides, one can form multimeric scFvs that bind to different epitopes (Kriangkum et al., (2001) *Biomol. Eng.* 18:31-40). Techniques developed for the production of single chain antibodies include those described in U.S. Pat. No. 4,946,778; Bird, (1988) *Science* 242:423; Huston et al., (1988) *Proc. Natl. Acad. Sci. U.S.A.* 85:5879; Ward et al., (1989) *Nature* 334:544, de Graaf et al., (2002) *Methods Mol. Biol.* 178:379-387. Single chain antibodies derived from antibodies provided herein include, but are not limited to scFvs comprising the variable domain combinations of the heavy and light chain variable regions depicted in Tables 2A-2D, or combinations of light and heavy chain variable domains which include CDRs depicted in Tables 3 and 6.

Antibodies provided herein that are of one subclass can be changed to antibodies from a different subclass using subclass switching methods. Thus, IgG antibodies can be derived from an IgM antibody, for example, and vice versa. Such techniques allow the preparation of new antibodies that possess the antigen binding properties of a given antibody (the parent antibody), but also exhibit biological properties associated with an antibody isotype or subclass different from that of the parent antibody. Recombinant DNA techniques can be employed. Cloned DNA encoding particular antibody polypeptides can be employed in such procedures, e.g., DNA encoding the constant domain of an antibody of the desired isotype. See, e.g., Lantto et al., (2002)*Methods Mol. Biol.* 178:303-316.

Accordingly, the antibodies that are provided include those comprising, for example, the variable domain combinations described, supra, having a desired isotype (for example, IgA, IgG1, IgG2, IgG3, IgG4, IgE, and IgD) as well as Fab or F(ab')$_2$ fragments thereof. Moreover, if an IgG4 is desired, it can also be desired to introduce a point mutation (CPSCP→CPPCP (SEQ ID NOS 266-267, respectively) in the hinge region as described in Bloom et al., (1997) *Protein Science* 6:407, incorporated by reference herein) to alleviate a tendency to form intra-H chain disulfide bonds that can lead to heterogeneity in the IgG4 antibodies.

Moreover, techniques for deriving antibodies having different properties (i.e., varying affinities for the antigen to which they bind) are also known. One such technique, referred to as chain shuffling, involves displaying immunoglobulin variable domain gene repertoires on the surface of filamentous bacteriophage, often referred to as phage display. Chain shuffling has been used to prepare high affinity antibodies to the hapten 2-phenyloxazol-5-one, as described by Marks et al., (1992) BioTechnology 10:779.

Conservative modifications can be made to the heavy and light chain variable regions described in Table 2, or the CDRs described in Table 3 (and corresponding modifications to the encoding nucleic acids) to produce an antigen binding protein having functional and biochemical characteristics. Methods for achieving such modifications are described above.

Antigen binding proteins and antigen binding protein-FGF21 fusion antigen binding protein components that specifically bind β-Klotho or β-Klotho and one or more of FGFR1c, FGFR2c, FGFR3c and FGFR4 can be further modified in various ways. For example, if they are to be used for therapeutic purposes, they can be conjugated with polyethylene glycol (PEGylated) to prolong the serum half-life or to enhance protein delivery. Alternatively, the V region of the subject antibodies or fragments thereof can be fused with the Fc region of a different antibody molecule. The Fc region used for this purpose can be modified so that it does not bind complement, thus reducing the likelihood of inducing cell lysis in the patient when the fusion protein is used as a therapeutic agent. In addition, the subject antigen binding proteins and antigen binding protein-FGF21 fusion antigen binding protein components or functional fragments thereof can be conjugated with human serum albumin to enhance the serum half-life of the antibody or fragment thereof. Another useful fusion partner for the antigen binding proteins and antigen binding protein-FGF21 fusion antigen binding protein components or fragments thereof is transthyretin (TTR). TTR has the capacity to form a tetramer, thus an antibody-TTR fusion protein can form a multivalent antibody which can increase its binding avidity.

Alternatively, substantial modifications in the functional and/or biochemical characteristics of the antigen binding proteins and antigen binding protein-FGF21 fusion antigen binding protein components described herein can be achieved by creating substitutions in the amino acid sequence of the heavy and light chains that differ significantly in their effect on maintaining (a) the structure of the molecular backbone in the area of the substitution, for example, as a sheet or helical conformation, (b) the charge or hydrophobicity of the molecule at the target site, or (c) the bulkiness of the side chain. A "conservative amino acid substitution" can involve a substitution of a native amino acid residue with a normative residue that has little or no effect on the polarity or charge of the amino acid residue at that position. See, Table 7, presented herein. Furthermore, any native residue in the polypeptide can also be substituted with alanine, as has been previously described for alanine scanning mutagenesis.

Amino acid substitutions (whether conservative or non-conservative) of the subject antigen binding proteins and antigen binding protein-FGF21 fusion antigen binding protein components can be implemented by those skilled in the art by applying routine techniques. Amino acid substitutions can be used to identify important residues of the antigen binding proteins provided herein, or to increase or decrease the affinity of these antigen binding proteins for β-Klotho or β-Klotho and one or more of FGFR1c, FGFR2c, FGFR3c, and FGFR4 or for modifying the binding affinity of other antigen binding proteins and antigen binding protein-FGF21 fusion antigen binding protein components described herein.

Methods of Expressing Antigen Binding Proteins and Antigen Binding Protein-FGF21 Fusion Antigen Binding Protein Components Expression systems and constructs in the form of plasmids, expression vectors, transcription or expression cassettes that comprise at least one polynucleotide as described above are also provided herein, as well as host cells comprising such expression systems or constructs.

The antigen binding proteins and antigen binding protein-FGF21 fusion antigen binding protein components provided herein can be prepared by any of a number of conventional techniques. For example, antigen binding proteins and antigen binding protein-FGF21 fusion antigen binding protein components that specifically bind β-Klotho β-Klotho and one or more of FGFR1c, FGFR2c, FGFR3c, and FGFR4 can be produced by recombinant expression systems, using any technique known in the art. See, e.g., Monoclonal Antibodies, Hybridomas: A New Dimension in Biological Analyses, Kennet et al. (eds.) Plenum Press, New York (1980); and Antibodies: A Laboratory Manual, Harlow and Lane (eds.), Cold Spring Harbor Laboratory Press, Cold Spring Harbor, N.Y. (1988).

Antigen binding proteins and antigen binding protein-FGF21 fusion antigen binding protein components can be expressed in hybridoma cell lines (e.g., in particular antibodies can be expressed in hybridomas) or in cell lines other than hybridomas. Expression constructs encoding the antigen binding proteins and antigen binding protein-FGF21 fusion antigen binding protein components can be used to transform a mammalian, insect or microbial host cell. Transformation can be performed using any known method for introducing polynucleotides into a host cell, including, for example packaging the polynucleotide in a virus or bacteriophage and transducing a host cell with the construct by transfection procedures known in the art, as exemplified by U.S. Pat. No. 4,399,216; 4,912,040; 4,740,461; 4,959,455. The optimal transformation procedure used will depend upon which type of host cell is being transformed. Methods for introduction of heterologous polynucleotides into mammalian cells are well known in the art and include, but are not limited to, dextran-mediated transfection, calcium phosphate precipitation, polybrene mediated transfection, protoplast fusion, electroporation, encapsulation of the polynucleotide(s) in liposomes, mixing nucleic acid with positively-charged lipids, and direct microinjection of the DNA into nuclei.

Recombinant expression constructs typically comprise a nucleic acid molecule encoding a polypeptide comprising one or more of the following: one or more CDRs provided herein; a light chain constant region; a light chain variable region; a heavy chain constant region (e.g., $C_H1$, $C_H2$ and/or $C_H3$); and/or another scaffold portion of an antigen binding protein or antigen binding protein-FGF21 fusion antigen binding protein component. These nucleic acid sequences are inserted into an appropriate expression vector using standard ligation techniques. In one embodiment, the heavy or light chain constant region is appended to the C-terminus of an antigen binding protein or antigen binding protein-FGF21 fusion antigen binding protein component that specifically binds to β-Klotho or β-Klotho and one or more of FGFR1c, FGFR2c, FGFR3c, and FGFR4-specific heavy or light chain variable regions and is ligated into an expression vector. The vector is typically selected to be functional in the particular host cell employed (i.e., the vector is compatible with the host cell machinery, permitting amplification and/or expression of the gene to occur). In some embodiments, vectors are used that employ protein-fragment complementation assays using protein reporters, such as dihydrofolate reductase (see, for example, U.S. Pat. No. 6,270,964, which is hereby incorporated by reference). Suitable expression vectors can be purchased, for example, from Invitrogen Life Technologies or BD Biosciences (formerly "Clontech"). Other useful vectors for cloning and expressing the antibodies and fragments include those described in Bianchi and McGrew, (2003) *Biotech. Biotechnol. Bioeng.* 84:439-44, which is hereby incorporated by reference. Additional suitable expression vectors are discussed, for example, in *Methods Enzymol.*, vol. 185 (D. V. Goeddel, ed.), 1990, New York: Academic Press.

Typically, expression vectors used in any of the host cells will contain sequences for plasmid maintenance and for cloning and expression of exogenous nucleotide sequences. Such sequences, collectively referred to as "flanking sequences" in certain embodiments will typically include one or more of the following nucleotide sequences: a promoter, one or more enhancer sequences, an origin of replication, a transcriptional termination sequence, a complete intron sequence containing a donor and acceptor splice site, a sequence encoding a leader sequence for polypeptide secretion, a ribosome binding site, a polyadenylation sequence, a polylinker region for inserting the nucleic acid encoding the polypeptide to be expressed, and a selectable marker element. Each of these sequences is discussed below.

Optionally, the vector can contain a "tag"-encoding sequence, i.e., an oligonucleotide molecule located at the 5' or 3' end of an antigen binding protein or antigen binding protein-FGF21 fusion antigen binding protein component coding sequence; the oligonucleotide sequence encodes polyHis (such as hexaHis (SEQ ID NO: 268)), or another "tag" such as FLAG®, HA (hemaglutinin influenza virus), or myc, for which commercially available antibodies exist. This tag is typically fused to the polypeptide upon expression of the polypeptide, and can serve as a means for affinity purification or detection of the antigen binding protein or antigen binding protein-FGF21 fusion antigen binding protein componens from the host cell. Affinity purification can be accomplished, for example, by column chromatography using antibodies against the tag as an affinity matrix. Optionally, the tag can subsequently be removed from the purified antigen binding protein by various means such as using certain peptidases for cleavage.

Flanking sequences can be homologous (i.e., from the same species and/or strain as the host cell), heterologous (i.e., from a species other than the host cell species or strain), hybrid (i.e., a combination of flanking sequences from more than one source), synthetic or native. As such, the source of a flanking sequence can be any prokaryotic or eukaryotic organism, any vertebrate or invertebrate organism, or any plant, provided that the flanking sequence is functional in, and can be activated by, the host cell machinery.

Flanking sequences useful in the vectors can be obtained by any of several methods well known in the art. Typically, flanking sequences useful herein will have been previously identified by mapping and/or by restriction endonuclease digestion and can thus be isolated from the proper tissue source using the appropriate restriction endonucleases. In some cases, the full nucleotide sequence of a flanking sequence can be known. Here, the flanking sequence can be synthesized using the methods described herein for nucleic acid synthesis or cloning.

Whether all or only a portion of the flanking sequence is known, it can be obtained using polymerase chain reaction (PCR) and/or by screening a genomic library with a suitable probe such as an oligonucleotide and/or flanking sequence fragment from the same or another species. Where the flanking sequence is not known, a fragment of DNA containing a flanking sequence can be isolated from a larger piece of DNA that can contain, for example, a coding sequence or even another gene or genes. Isolation can be accomplished by restriction endonuclease digestion to produce the proper DNA fragment followed by isolation using agarose gel purification, Qiagen® column chromatography (Chatsworth, Calif.), or other methods known to the skilled artisan. The selection of suitable enzymes to accomplish this purpose will be readily apparent to one of ordinary skill in the art.

An origin of replication is typically a part of those prokaryotic expression vectors purchased commercially, and the origin aids in the amplification of the vector in a host cell. If the vector of choice does not contain an origin of replication site, one can be chemically synthesized based on a known sequence, and ligated into the vector. For example, the origin of replication from the plasmid pBR322 (New England Biolabs, Beverly, Mass.) is suitable for most gram-negative bacteria, and various viral origins (e.g., SV40, polyoma, adenovirus, vesicular stomatitus virus (VSV), or papillomaviruses such as HPV or BPV) are useful for cloning vectors in mammalian cells. Generally, the origin of replication component is not needed for mammalian expression vectors (for example, the SV40 origin is often used only because it also contains the virus early promoter).

A transcription termination sequence is typically located 3' to the end of a polypeptide coding region and serves to terminate transcription. Usually, a transcription termination sequence in prokaryotic cells is a G-C rich fragment followed by a poly-T sequence. While the sequence is easily cloned from a library or even purchased commercially as part of a vector, it can also be readily synthesized using methods for nucleic acid synthesis such as those described herein.

A selectable marker gene encodes a protein necessary for the survival and growth of a host cell grown in a selective culture medium. Typical selection marker genes encode proteins that (a) confer resistance to antibiotics or other toxins, e.g., ampicillin, tetracycline, or kanamycin for prokaryotic host cells; (b) complement auxotrophic deficiencies of the cell; or (c) supply critical nutrients not available from complex or defined media. Specific selectable markers are the kanamycin resistance gene, the ampicillin resistance gene, and the tetracycline resistance gene. Advantageously, a neomycin resistance gene can also be used for selection in both prokaryotic and eukaryotic host cells.

Other selectable genes can be used to amplify the gene that will be expressed. Amplification is the process wherein genes that are required for production of a protein critical for growth or cell survival are reiterated in tandem within the chromosomes of successive generations of recombinant cells. Examples of suitable selectable markers for mammalian cells include dihydrofolate reductase (DHFR) and promoterless thymidine kinase genes. Mammalian cell transformants are placed under selection pressure wherein only the transformants are uniquely adapted to survive by virtue of the selectable gene present in the vector. Selection pressure is imposed by culturing the transformed cells under conditions in which the concentration of selection agent in the medium is successively increased, thereby leading to the amplification of both the selectable gene and the DNA that encodes another gene, such as an antigen binding protein or antigen binding protein-FGF21 fusion antigen binding protein component that specifically binds to β-Klotho or β-Klotho and one or more of FGFR1c, FGFR2c, FGFR3c, and FGFR4. As a result, increased quantities of a polypeptide such as an antigen binding protein or antigen binding protein-FGF21 fusion antigen binding protein component are synthesized from the amplified DNA.

A ribosome-binding site is usually necessary for translation initiation of mRNA and is characterized by a Shine-Dalgarno sequence (prokaryotes) or a Kozak sequence (eukaryotes). The element is typically located 3' to the promoter and 5' to the coding sequence of the polypeptide to be expressed.

In some cases, such as where glycosylation is desired in a eukaryotic host cell expression system, one can manipulate the various pre- or pro-sequences to improve glycosylation or yield. For example, one can alter the peptidase cleavage site of a particular signal peptide, or add prosequences, which also can affect glycosylation. The final protein product can have, in the −1 position (relative to the first amino acid of the mature protein), one or more additional amino acids incident to expression, which can not have been totally removed. For example, the final protein product can have one or two amino acid residues found in the peptidase cleavage site, attached to the amino-terminus. Alternatively, use of some enzyme cleavage sites can result in a slightly truncated form of the desired polypeptide, if the enzyme cuts at such area within the mature polypeptide.

Expression and cloning will typically contain a promoter that is recognized by the host organism and operably linked to the molecule encoding an antigen binding protein or antigen binding protein-FGF21 fusion antigen binding protein component that specifically binds β-Klotho or β-Klotho and one or more of FGFR1c, FGFR2c, FGFR3c, and FGFR4. Promoters are untranscribed sequences located upstream (i.e., 5') to the start codon of a structural gene (generally within about 100 to 1000 bp) that control transcription of the structural gene. Promoters are conventionally grouped into one of two classes: inducible promoters and constitutive promoters. Inducible promoters initiate increased levels of transcription from DNA under their control in response to some change in culture conditions, such as the presence or absence of a nutrient or a change in temperature. Constitutive promoters, on the other hand, uniformly transcribe a gene to which they are operably linked, that is, with little or no control over gene expression. A large number of promoters, recognized by a variety of potential host cells, are well known. A suitable promoter is operably linked to the DNA encoding heavy chain or light chain comprising an antigen binding protein or antigen binding protein-FGF21 fusion antigen binding protein component by removing the promoter from the source DNA by restriction enzyme digestion and inserting the desired promoter sequence into the vector.

Suitable promoters for use with yeast hosts are also well known in the art. Yeast enhancers are advantageously used with yeast promoters. Suitable promoters for use with mammalian host cells are well known and include, but are not limited to, those obtained from the genomes of viruses such as polyoma virus, fowlpox virus, adenovirus (such as Adenovirus 2), bovine papilloma virus, avian sarcoma virus, cytomegalovirus, retroviruses, hepatitis-B virus, and Simian Virus 40 (SV40). Other suitable mammalian promoters include heterologous mammalian promoters, for example, heat-shock promoters and the actin promoter.

Additional promoters which can be of interest include, but are not limited to: SV40 early promoter (Benoist and Chambon, (1981) *Nature* 290:304-310); CMV promoter (Thornsen et al., (1984) *Proc. Natl. Acad. U.S.A.* 81:659-663); the promoter contained in the 3' long terminal repeat of Rous sarcoma virus (Yamamoto et al., (1980) *Cell* 22:787-797); herpes thymidine kinase promoter (Wagner et al., (1981) *Proc. Natl. Acad. Sci. U.S.A.* 78:1444-1445); promoter and regulatory sequences from the metallothionine gene (Prinster et al., (1982) *Nature* 296:39-42); and prokaryotic promoters such as the beta-lactamase promoter (Villa-Kamaroff et al., (1978) *Proc. Natl. Acad. Sci. U.S.A.* 75:3727-3731); or the tac promoter (DeBoer et al., (1983) *Proc. Natl. Acad. Sci. U.S.A.* 80:21-25). Also of interest are the following animal transcriptional control regions, which exhibit tissue specificity and have been utilized in transgenic animals: the elastase I gene control region that is active in pancreatic acinar cells (Swift et al., (1984) *Cell* 38:639-646; Ornitz et al., (1986) *Cold Spring Harbor Symp. Quant. Biol.* 50:399-409; MacDonald, (1987) *Hepatology* 7:425-515); the insulin gene control region that is active in pancreatic beta cells (Hanahan, (1985) *Nature* 315:115-122); the immunoglobulin gene control region that is active in lymphoid cells (Grosschedl et al., (1984) *Cell* 38:647-658; Adames et al., (1985) *Nature* 318:533-538; Alexander et al., (1987) *Mol. Cell. Biol.* 7:1436-1444); the mouse mammary tumor virus control region that is active in testicular, breast, lymphoid and mast cells (Leder et al., (1986) *Cell* 45:485-495); the albumin gene control region that is active in liver (Pinkert et al., (1987) *Genes and Devel.* 1:268-276); the alpha-fetoprotein gene control region that is active in liver (Krumlauf et al., (1985) *Mol. Cell. Biol.* 5:1639-1648; Hammer et al., (1987) *Science* 253:53-58); the alpha 1-antitrypsin gene control region that is active in liver (Kelsey et al., (1987) *Genes and Devel.* 1:161-171); the beta-globin gene control region that is active in myeloid cells (Mogram et al., (1985) *Nature* 315:338-340; Kollias et al., (1986) *Cell* 46:89-94); the myelin basic protein gene control region that is active in oligodendrocyte cells in the brain (Readhead et al., (1987) *Cell* 48:703-712); the myosin light chain-2 gene control region that is active in skeletal muscle (Sani, (1985) *Nature*

314:283-286); and the gonadotropic releasing hormone gene control region that is active in the hypothalamus (Mason et al., (1986) *Science* 234:1372-1378).

An enhancer sequence can be inserted into the vector to increase transcription of DNA encoding light chain or heavy chain comprising an antigen binding protein or antigen binding protein-FGF21 fusion antigen binding protein component that specifically binds β-Klotho or β-Klotho and one or more of FGFR1c, FGFR2c, FGFR3c, and FGFR4 by higher eukaryotes. Enhancers are cis-acting elements of DNA, usually about 10-300 bp in length, that act on the promoter to increase transcription. Enhancers are relatively orientation and position independent, having been found at positions both 5' and 3' to the transcription unit. Several enhancer sequences available from mammalian genes are known (e.g., globin, elastase, albumin, alpha-feto-protein and insulin). Typically, however, an enhancer from a virus is used. The SV40 enhancer, the cytomegalovirus early promoter enhancer, the polyoma enhancer, and adenovirus enhancers known in the art are exemplary enhancing elements for the activation of eukaryotic promoters. While an enhancer can be positioned in the vector either 5' or 3' to a coding sequence, it is typically located at a site 5' from the promoter. A sequence encoding an appropriate native or heterologous signal sequence (leader sequence or signal peptide) can be incorporated into an expression vector, to promote extracellular secretion of the antibody. The choice of signal peptide or leader depends on the type of host cells in which the antibody is to be produced, and a heterologous signal sequence can replace the native signal sequence. Examples of signal peptides that are functional in mammalian host cells include the following: the signal sequence for interleukin-7 (IL-7) described in U.S. Pat. No. 4,965,195; the signal sequence for interleukin-2 receptor described in Cosman et al., (1984) *Nature* 312:768; the interleukin-4 receptor signal peptide described in EP Patent No. 0367 566; the type I interleukin-1 receptor signal peptide described in U.S. Pat. No. 4,968,607; the type II interleukin-1 receptor signal peptide described in EP Patent No. 0 460 846.

The expression vectors that are provided can be constructed from a starting vector such as a commercially available vector. Such vectors can, but need not, contain all of the desired flanking sequences. Where one or more of the flanking sequences described herein are not already present in the vector, they can be individually obtained and ligated into the vector. Methods used for obtaining each of the flanking sequences are well-known to one skilled in the art.

After the vector has been constructed and a nucleic acid molecule encoding light chain, a heavy chain, or a light chain and a heavy chain component(s) of an antigen binding protein or antigen binding protein-FGF21 fusion antigen binding protein component that specifically binds β-Klotho or β-Klotho and one or more of FGFR1c, FGFR2c, FGFR3c, and FGFR4 has been inserted into the proper site of the vector, the completed vector can be inserted into a suitable host cell for amplification and/or polypeptide expression. The transformation of an expression vector for an antigen binding protein or antigen binding protein-FGF21 fusion antigen binding protein component into a selected host cell can be accomplished by well-known methods including transfection, infection, calcium phosphate co-precipitation, electroporation, microinjection, lipofection, DEAE-dextran mediated transfection, or other known techniques. The method selected will in part be a function of the type of host cell to be used. These methods and other suitable methods are well-known to the skilled artisan, and are set forth, for example, in Sambrook et al., (2001), supra.

A host cell, when cultured under appropriate conditions, synthesizes an antigen binding protein or antigen binding protein-FGF21 fusion antigen binding protein component that can subsequently be collected from the culture medium (if the host cell secretes it into the medium) or directly from the host cell producing it (if it is not secreted). The selection of an appropriate host cell will depend upon various factors, such as desired expression levels, polypeptide modifications that are desirable or necessary for activity (such as glycosylation or phosphorylation) and ease of folding into a biologically active molecule.

Mammalian cell lines available as hosts for expression are well known in the art and include, but are not limited to, immortalized cell lines available from the American Type Culture Collection (ATCC), including but not limited to Chinese hamster ovary (CHO) cells, HeLa cells, baby hamster kidney (BHK) cells, monkey kidney cells (COS), human hepatocellular carcinoma cells (e.g., Hep G2), and a number of other cell lines. In certain embodiments, cell lines can be selected through determining which cell lines have high expression levels and constitutively produce antigen binding proteins and antigen binding protein-FGF21 fusion antigen binding protein components that specifically bind to β-Klotho or β-Klotho and one or more of FGFR1c, FGFR2c, FGFR3c or FGFR4. In another embodiment, a cell line from the B cell lineage that does not make its own antibody but has a capacity to make and secrete a heterologous antibody can be selected. The ability to induce FGF21-like signaling can also form a selection criterion.

Uses Of Antigen Binding Proteins and Antigen Binding Protein-FGF21 Fusions For Diagnostic And Therapeutic Purposes The antigen binding proteins and antigen binding protein-FGF21 fusions disclosed herein are useful for detecting the presence of β-Klotho or β-Klotho and one or more of FGFR1c, FGFR2c, FGFR3c, and FGFR4 in biological samples and identification of cells or tissues that produce β-Klotho or β-Klotho and one or more of FGFR1c, FGFR2c, FGFR3c, and FGFR4. For instance, the antigen binding proteins and antigen binding protein-FGF21 fusions disclosed herein can be used in diagnostic assays, e.g., binding assays to detect and/or quantify β-Klotho or β-Klotho and one or more of FGFR1c, FGFR2c, FGFR3c, and FGFR4 expressed in a tissue or cell. Antigen binding proteins and antigen binding protein-FGF21 fusions that specifically bind to β-Klotho or β-Klotho and one or more of FGFR1c, FGFR2c, FGFR3c, and FGFR4 can be used in treatment of diseases related to FGF21-like signaling in a patient in need thereof, such as type 2 diabetes, obesity, dyslipidemia, NASH, cardiovascular disease, and metabolic syndrome. By forming a signaling complex comprising an antigen binding protein or antigen binding protein-FGF21 fusions, β-Klotho and one or more of FGFR1c, FGFR2c, FGFR3c, and FGFR4, the natural in vivo activity of FGF21, which associates with an FGFR such as FGFR1c, FGFR2c, FGFR3c, FGFR4 and β-Klotho in vivo to initiate signaling, can be mimicked and/or enhanced, leading to therapeutic effects.

Indications

A disease or condition associated with human FGF21 includes any disease or condition whose onset in a patient is caused by, at least in part, the induction of FGF21-like signaling, which is initiated in vivo by the formation of a complex comprising FGFR1c, FGFR2c, FGFR3c or FGFR4, β-Klotho and FGF21. The severity of the disease or condition can also be decreased by the induction of FGF21-like signaling. Examples of diseases and conditions that can be treated with the antigen binding proteins include type 2 diabetes, obesity, dyslipidemia, NASH, cardiovascular disease, and metabolic syndrome.

The antigen binding proteins and antigen binding protein-FGF21 fusions described herein can be used to treat type 2 diabetes, obesity, dyslipidemia, NASH, cardiovascular disease, and metabolic syndrome, or can be employed as a prophylactic treatment administered, e.g., daily, weekly, biweekly, monthly, bimonthly, biannually, etc to prevent or reduce the frequency and/or severity of symptoms, e.g., elevated plasma glucose levels, elevated triglycerides and cholesterol levels, thereby providing an improved glycemic and cardiovascular risk factor profile.

Diagnostic Methods

The antigen binding proteins and antigen binding protein-FGF21 fusions described herein can be used for diagnostic purposes to detect, diagnose, or monitor diseases and/or conditions associated with FGFR1c, FGFR2c, FGFR3c, FGFR4, β-Klotho, FGF21 or combinations thereof. Also provided are methods for the detection of the presence of β-Klotho or β-Klotho and one or more of FGFR1c, FGFR2c, FGFR3c, and FGFR4 in a sample using classical immunohistological methods known to those of skill in the art (e.g., Tijssen, 1993, *Practice and Theory of Enzyme Immunoassays*, Vol 15 (Eds R. H. Burdon and P. H. van Knippenberg, Elsevier, Amsterdam); Zola, (1987) *Monoclonal Antibodies: A Manual of Techniques*, pp. 147-158 (CRC Press, Inc.); Jalkanen et al., (1985) *J. Cell. Biol.* 101:976-985; Jalkanen et al., (1987) *J. Cell Biol.* 105:3087-3096). The detection of β-Klotho or β-Klotho and one or more of FGFR1c, FGFR2c, FGFR3c, and FGFR4 can be performed in vivo or in vitro.

Diagnostic applications provided herein include use of the antigen binding proteins and antigen binding protein-FGF21 fusions to detect expression of β-Klotho or β-Klotho and one or more of FGFR1c, FGFR2c, FGFR3c, and FGFR4. Examples of methods useful in the detection of the presence of β-Klotho or β-Klotho and one or more of FGFR1c, FGFR2c, FGFR3c, and FGFR4 include immunoassays, such as the enzyme linked immunosorbent assay (ELISA) and the radioimmunoassay (RIA).

For diagnostic applications, the antigen binding protein or antigen binding protein-FGF21 fusion typically will be labeled with a detectable labeling group. Suitable labeling groups include, but are not limited to, the following: radioisotopes or radionuclides (e.g., $^{3}H$, $^{14}C$, $^{15}N$, $^{35}S$, $^{90}Y$, $^{99}Tc$, $^{111}In$, $^{125}I$, $^{131}I$), fluorescent groups (e.g., FITC, rhodamine, lanthanide phosphors), enzymatic groups (e.g., horseradish peroxidase, β-galactosidase, luciferase, alkaline phosphatase), chemiluminescent groups, biotinyl groups, or predetermined polypeptide epitopes recognized by a secondary reporter (e.g., leucine zipper pair sequences, binding sites for secondary antibodies, metal binding domains, epitope tags). In some embodiments, the labeling group is coupled to the antigen binding protein via spacer arms of various lengths to reduce potential steric hindrance. Various methods for labeling proteins are known in the art and can be used.

In another aspect, an antigen binding protein or antigen binding protein-FGF21 fusion can be used to identify a cell or cells that express β-Klotho or β-Klotho and one or more of FGFR1c, FGFR2c, FGFR3c, and FGFR4. In a specific embodiment, the antigen binding protein or antigen binding protein-FGF21 fusion is labeled with a labeling group and the binding of the labeled antigen binding protein or antigen binding protein-FGF21 fusion to β-Klotho or β-Klotho and one or more of FGFR1c, FGFR2c, FGFR3c, and FGFR4 is detected. In a further specific embodiment, the binding of the antigen binding protein or antigen binding protein-FGF21 fusion to β-Klotho or β-Klotho and one or more of FGFR1c, FGFR2c, FGFR3c, and FGFR4 detected in vivo. In a further specific embodiment, the antigen binding protein or antigen binding protein-FGF21 fusion is isolated and measured using techniques known in the art. See, for example, *Harlow and Lane*, (1988) *Antibodies: A Laboratory Manual*, New York: Cold Spring Harbor (ed. 1991 and periodic supplements); John E. Coligan, ed., (1993) *Current Protocols In Immunology* New York: John Wiley & Sons.

Another aspect provides for detecting the presence of a test molecule that competes for binding to β-Klotho or β-Klotho and one or more of FGFR1c, FGFR2c, FGFR3c, and FGFR4 with the antigen binding proteins and antigen binding protein-FGF21 fusions provided, as disclosed herein. An example of one such assay could involve detecting the amount of free antigen binding protein or antigen binding protein-FGF21 fusion in a solution containing an amount of β-Klotho or β-Klotho and one or more of FGFR1c, FGFR2c, FGFR3c, and FGFR4 in the presence or absence of the test molecule. An increase in the amount of free antigen binding protein or antigen binding protein-FGF21 fusion (i.e., the antigen binding protein or antigen binding protein-FGF21 fusion not bound to β-Klotho or β-Klotho and one or more of FGFR1c, FGFR2c, FGFR3c, and FGFR4) would indicate that the test molecule is capable of competing for binding to β-Klotho or β-Klotho and one or more of FGFR1c, FGFR2c, FGFR3c, and FGFR4 with the antigen binding protein or antigen binding protein-FGF21 fusion. In one embodiment, the antigen binding protein or antigen binding protein-FGF21 fusion is labeled with a labeling group. Alternatively, the test molecule is labeled and the amount of free test molecule is monitored in the presence and absence of an antigen binding protein or antigen binding protein-FGF21 fusion.

Methods of Treatment: Pharmaceutical Formulations, Routes of Administration

Methods of using the antigen binding proteins and antigen binding protein-FGF21 fusions are also provided. In some methods, an antigen binding protein or antigen binding protein-FGF21 fusion is provided to a patient. The antigen binding protein or antigen binding protein-FGF21 fusion induces FGF21-like signaling.

Pharmaceutical compositions that comprise a therapeutically effective amount of one or a plurality of the disclosed antigen binding proteins and antigen binding protein-FGF21 fusions and a pharmaceutically acceptable diluent, carrier, solubilizer, emulsifier, preservative, and/or adjuvant are also provided. In addition, methods of treating a patient by administering such pharmaceutical composition are included. The term "patient" includes human patients.

Acceptable formulation materials are nontoxic to recipients at the dosages and concentrations employed. In specific embodiments, pharmaceutical compositions comprising a therapeutically effective amount of human antigen binding proteins or antigen binding protein-FGF21 fusions that specifically bind β-Klotho or β-Klotho and one or more of FGFR1c, FGFR2c, FGFR3c, and FGFR4 are provided.

In certain embodiments, acceptable formulation materials preferably are nontoxic to recipients at the dosages and concentrations employed. In certain embodiments, the pharmaceutical composition can contain formulation materials for modifying, maintaining or preserving, for example, the pH, osmolarity, viscosity, clarity, color, isotonicity, odor, sterility, stability, rate of dissolution or release, adsorption or penetration of the composition. In such embodiments, suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as Pluronics, PEG, sorbitan esters, polysorbates such as polysorbate 20, polysorbate, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. See, *Remington's Pharmaceutical Sciences,* 18th Edition, (A. R. Gennaro, ed.), 1990, Mack Publishing Company.

In certain embodiments, the optimal pharmaceutical composition will be determined by one skilled in the art depending upon, for example, the intended route of administration, delivery format and desired dosage. See, for example, *Remington's Pharmaceutical Sciences,* supra. In certain embodiments, such compositions can influence the physical state, stability, rate of in vivo release and rate of in vivo clearance of the antigen binding proteins disclosed. In certain embodiments, the primary vehicle or carrier in a pharmaceutical composition can be either aqueous or non-aqueous in nature. For example, a suitable vehicle or carrier can be water for injection, physiological saline solution or artificial cerebrospinal fluid, possibly supplemented with other materials common in compositions for parenteral administration. Neutral buffered saline or saline mixed with serum albumin are further exemplary vehicles. In specific embodiments, pharmaceutical compositions comprise Tris buffer of about pH 7.0-8.5, or acetate buffer of about pH 4.0-5.5, and can further include sorbitol or a suitable substitute. In certain embodiments, compositions comprising antigen binding proteins or antigen binding protein-FGF21 fusions that specifically bind β-Klotho or β-Klotho and one or more of FGFR1c, FGFR2c, FGFR3c, and FGFR4 can be prepared for storage by mixing the selected composition having the desired degree of purity with optional formulation agents (*Remington's Pharmaceutical Sciences,* supra) in the form of a lyophilized cake or an aqueous solution. Further, in certain embodiments, an antigen binding protein or antigen binding protein-FGF21 fusion that bind β-Klotho or β-Klotho and one or more of FGFR1c, FGFR2c, FGFR3c, and FGFR4 can be formulated as a lyophilizate using appropriate excipients such as sucrose.

The pharmaceutical compositions can be selected for parenteral delivery. Alternatively, the compositions can be selected for inhalation or for delivery through the digestive tract, such as orally. Preparation of such pharmaceutically acceptable compositions is within the skill of the art.

The formulation components are present preferably in concentrations that are acceptable to the site of administration. In certain embodiments, buffers are used to maintain the composition at physiological pH or at a slightly lower pH, typically within a pH range of from about 5 to about 8.

When parenteral administration is contemplated, the therapeutic compositions can be provided in the form of a pyrogen-free, parenterally acceptable aqueous solution comprising the desired antigen binding protein or antigen binding protein-FGF21 fusion in a pharmaceutically acceptable vehicle. A particularly suitable vehicle for parenteral injection is sterile distilled water in which the antigen binding protein is formulated as a sterile, isotonic solution, properly preserved. In certain embodiments, the preparation can involve the formulation of the desired molecule with an agent, such as injectable microspheres, bio-erodible particles, polymeric compounds (such as polylactic acid or polyglycolic acid), beads or liposomes, that can provide controlled or sustained release of the product which can be delivered via depot injection. In certain embodiments, hyaluronic acid can also be used, having the effect of promoting sustained duration in the circulation. In certain embodiments, implantable drug delivery devices can be used to introduce the desired antigen binding protein or antigen binding protein-FGF21 fusion.

Certain pharmaceutical compositions are formulated for inhalation. In some embodiments, antigen binding proteins or antigen binding protein-FGF21 fusions that bind to β-Klotho or β-Klotho and one or more of FGFR1c, FGFR2c, FGFR3c, and FGFR4 are formulated as a dry, inhalable powder. In specific embodiments, antigen binding protein or antigen binding protein-FGF21 fusion inhalation solutions can also be formulated with a propellant for aerosol delivery. In certain embodiments, solutions can be nebulized. Pulmonary administration and formulation methods therefore are further described in International Patent Application No. PCT/US94/001875, which is incorporated by reference and describes pulmonary delivery of chemically modified proteins. Some formulations can be administered orally. Antigen binding proteins or antigen binding protein-FGF21 fusions that specifically bind β-Klotho or β-Klotho and one or more of FGFR1c, FGFR2c, FGFR3c, and FGFR4 that are administered in this fashion can be formulated with or without carriers customarily used in the compounding of solid dosage forms such as tablets and capsules. In certain embodiments, a capsule can be designed to release the active portion of the formulation at the point in the gastrointestinal tract when bioavailability is maximized and pre-systemic degradation is minimized. Additional agents can be included to facilitate absorption of an antigen binding protein or antigen binding protein-FGF21 fusion. Diluents, flavorings, low melting point waxes, vegetable oils, lubricants, suspending agents, tablet disintegrating agents, and binders can also be employed.

Some pharmaceutical compositions comprise an effective quantity of one or a plurality of human antigen binding proteins or antigen binding protein-FGF21 fusions that specifically bind β-Klotho or β-Klotho and one or more of FGFR1c, FGFR2c, FGFR3c, and FGFR4 in a mixture with non-toxic excipients that are suitable for the manufacture of tablets. By dissolving the tablets in sterile water, or another appropriate vehicle, solutions can be prepared in unit-dose form. Suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional pharmaceutical compositions will be evident to those skilled in the art, including formulations involving antigen binding proteins or antigen binding protein-FGF21 fusions that specifically bind β-Klotho or β-Klotho and one or more of FGFR1c, FGFR2c, FGFR3c, and FGFR4 in sustained- or controlled-delivery formulations. Techniques for formulating a variety of other sustained- or controlled-delivery means, such as liposome carriers, bio-erodible microparticles or porous beads and depot injections, are also known to those skilled in the art. See, for example, International Patent Application No. PCT/US93/00829, which is incorporated by reference and describes controlled release of porous polymeric microparticles for delivery of pharmaceutical compositions. Sustained-release preparations can include semipermeable polymer matrices in the form of shaped articles, e.g., films, or microcapsules. Sustained release matrices can include polyesters, hydrogels, polylactides (as disclosed in U.S. Pat. No. 3,773,919 and European Patent Application Publication No. EP 058481, each of which is incorporated by reference), copolymers of L-glutamic acid and gamma ethyl-L-glutamate (Sidman et al., 1983, *Biopolymers* 2:547-556), poly (2-hydroxyethyl-inethacrylate) (Langer et al., 1981, *J. Biomed. Mater. Res.* 15:167-277 and Langer, 1982, *Chem. Tech.* 12:98-105), ethylene vinyl acetate (Langer et al., 1981, supra) or poly-D(-)-3-hydroxybutyric acid (European Patent Application Publication No. EP 133,988). Sustained release compositions can also include liposomes that can be prepared by any of several methods known in the art. See, e.g., Eppstein et al., 1985, *Proc. Natl. Acad. Sci. U.S.A.* 82:3688-3692; European Patent Application Publication Nos. EP 036,676; EP 088,046 and EP 143,949, incorporated by reference.

Pharmaceutical compositions used for in vivo administration are typically provided as sterile preparations. Sterilization can be accomplished by filtration through sterile filtration membranes. When the composition is lyophilized, sterilization using this method can be conducted either prior to or following lyophilization and reconstitution. Compositions for parenteral administration can be stored in lyophilized form or in a solution. Parenteral compositions generally are placed into a container having a sterile access port, for example, an intravenous solution bag or vial having a stopper pierceable by a hypodermic injection needle.

In certain embodiments, cells expressing a recombinant antigen binding protein as disclosed herein is encapsulated for delivery (see, *Invest. Ophthalmol V is Sci* (2002) 43:3292-3298 and *Proc. Natl. Acad. Sciences USA* (2006) 103:3896-3901).

In certain formulations, an antigen binding protein or antigen binding protein-FGF21 fusion has a concentration of at least 1 mg/ml, 2 mg/ml, 3 mg/ml, 4 mg/ml, 5 mg/ml, 10 mg/ml, 20 mg/ml, 30 mg/ml, 40 mg/ml, 50 mg/ml, 60 mg/ml, 70 mg/ml, 80 mg/ml, 90 mg/ml, 100 mg/ml or 150 mg/ml. Some formulations contain a buffer, sucrose and polysorbate. An example of a formulation is one containing 50-100 mg/ml of antigen binding protein, 5-20 mM sodium acetate, 5-10% w/v sucrose, and 0.002-0.008% w/v polysorbate. Certain, formulations, for instance, contain 65-75 mg/ml of an antigen binding protein in 9-11 mM sodium acetate buffer, 8-10% w/v sucrose, and 0.005-0.006% w/v polysorbate. The pH of certain such formulations is in the range of 4.5-6. Other formulations have a pH of 5.0-5.5 (e.g., pH of 5.0, 5.2 or 5.4).

Once the pharmaceutical composition has been formulated, it can be stored in sterile vials as a solution, suspension, gel, emulsion, solid, crystal, or as a dehydrated or lyophilized powder. Such formulations can be stored either in a ready-to-use form or in a form (e.g., lyophilized) that is reconstituted prior to administration. Kits for producing a single-dose administration unit are also provided. Certain kits contain a first container having a dried protein and a second container having an aqueous formulation. In certain embodiments, kits containing single and multi-chambered pre-filled syringes (e.g., liquid syringes and lyosyringes) are provided. The therapeutically effective amount of an antigen binding protein-containing pharmaceutical composition to be employed will depend, for example, upon the therapeutic context and objectives. One skilled in the art will appreciate that the appropriate dosage levels for treatment will vary depending, in part, upon the molecule delivered, the indication for which the antigen binding protein or antigen binding protein-FGF21 fusion is being used, the route of administration, and the size (body weight, body surface or organ size) and/or condition (the age and general health) of the patient. In certain embodiments, the clinician can titer the dosage and modify the route of administration to obtain the optimal therapeutic effect.

A typical dosage can range from about 1 μg/kg to up to about 30 mg/kg or more, depending on the factors mentioned above. In specific embodiments, the dosage can range from 10 μg/kg up to about 30 mg/kg, optionally from 0.1 mg/kg up to about 30 mg/kg, alternatively from 0.3 mg/kg up to about 20 mg/kg. In some applications, the dosage is from 0.5 mg/kg to 20 mg/kg. In some instances, an antigen binding protein is dosed at 0.3 mg/kg, 0.5 mg/kg, 1 mg/kg, 3 mg/kg, 10 mg/kg, or 20 mg/kg. The dosage schedule in some treatment regimes is at a dose of 0.3 mg/kg qW, 0.5 mg/kg qW, 1 mg/kg qW, 3 mg/kg qW, 10 mg/kg qW, or 20 mg/kg qW.

Dosing frequency will depend upon the pharmacokinetic parameters of the particular antigen binding protein or antigen binding protein-FGF21 fusion in the formulation used. Typically, a clinician administers the composition until a dosage is reached that achieves the desired effect. The composition can therefore be administered as a single dose, or as two or more doses (which can or can not contain the same amount of the desired molecule) over time, or as a continuous infusion via an implantation device or catheter. Appropriate dosages can be ascertained through use of appropriate dose-response data. In certain embodiments, the antigen binding proteins or antigen binding protein-FGF21 fusions can be administered to patients throughout an extended time period. Chronic administration of an antigen binding protein or antigen binding protein-FGF21 fusion minimizes the adverse immune or allergic response commonly associated with antigen binding proteins and antigen binding protein-FGF21 fusions that are not fully human, for example an antibody raised against a human antigen in a non-human animal, for example, a non-fully human antibody or non-human antibody produced in a non-human species.

The route of administration of the pharmaceutical composition is in accord with known methods, e.g., orally, through injection by intravenous, intraperitoneal, intracerebral (intra-parenchymal), intracerebroventricular, intramuscular, intra-ocular, intraarterial, intraportal, or intralesional routes; by sustained release systems or by implantation devices. In certain embodiments, the compositions can be administered by bolus injection or continuously by infusion, or by implantation device.

The composition also can be administered locally via implantation of a membrane, sponge or another appropriate material onto which the desired molecule has been absorbed or encapsulated. In certain embodiments, where an implantation device is used, the device can be implanted into any suitable tissue or organ, and delivery of the desired molecule can be via diffusion, timed-release bolus, or continuous administration.

It also can be desirable to use antigen binding protein or antigen binding protein-FGF21 fusion pharmaceutical compositions ex vivo. In such instances, cells, tissues or organs that have been removed from the patient are exposed to antigen binding protein or antigen binding protein-FGF21 fusion pharmaceutical compositions after which the cells, tissues and/or organs are subsequently implanted back into the patient.

In particular, antigen binding proteins or antigen binding protein-FGF21 fusions that specifically bind β-Klotho or β-Klotho and one or more of FGFR1c, FGFR2c, FGFR3c, and FGFR4 can be delivered by implanting certain cells that have been genetically engineered, using methods such as those described herein, to express and secrete the polypeptide. In certain embodiments, such cells can be animal or human cells, and can be autologous, heterologous, or xenogeneic. In certain embodiments, the cells can be immortalized. In other embodiments, in order to decrease the chance of an immunological response, the cells can be encapsulated to avoid infiltration of surrounding tissues. In further embodiments, the encapsulation materials are typically biocompatible, semi-permeable polymeric enclosures or membranes that allow the release of the protein product(s) but prevent the destruction of the cells by the patient's immune system or by other detrimental factors from the surrounding tissues.

Combination Therapies

In another aspect, the present disclosure provides a method of treating a subject for diabetes with a therapeutic antigen binding protein or antigen binding protein-FGF21 fusion of the present disclosure, such as the fully human therapeutic antibodies described herein, together with one or more other treatments. In one embodiment, such a combination therapy achieves an additive or synergistic effect. The antigen binding proteins or antigen binding protein-FGF21 fusions can be administered in combination with one or more of the type 2 diabetes or obesity treatments currently available. These treatments for diabetes include biguanide (metformin), and sulfonylureas (such as glyburide, glipizide). Additional treatments directed at maintaining glucose homeostasis include PPAR gamma agonists (such as pioglitazone, rosiglitazone); glinides (such as meglitinide, repaglinide, and nateglinide); DPP-4 inhibitors (such as Januvia® and Onglyza®) and alpha glucosidase inhibitors (such as acarbose, voglibose).

Additional combination treatments for diabetes include injectable treatments such as insulin and incretin mimetics (such as Byetta®, Exenatide®), other GLP-1 (glucagon-like peptide) analogs such as liraglutide, other GLP-1R agonists and Symlin® (pramlintide). Additional treatment directed at weight loss drugs include Meridia and Xenical.

EXAMPLES

The following examples, including the experiments conducted and the results achieved, are provided for illustrative purposes only and are not to be construed as limiting.

Example 1

Preparation of FGFR1c Over Expressing Cells for Use as an Antigen

Nucleic acid sequences encoding the full length human FGFR1c polypepetide (SEQ ID NO: 305; FIGS. 1a-b) and a separate sequence encoding the full length human β-Klotho polypeptide (SEQ ID NO: 308; FIGS. 2a-c) were subcloned into suitable mammalian cell expression vectors (e.g., pcDNA3.1 Zeo, pcDNA3.1 Hyg (Invitrogen, Calsbad, Calif.) or pDSRα20). The pDSRα20 vector contains SV40 early promoter/enhancer for expressing the gene of interest and a mouse DHFR expression cassette for selection in CHO DHFR (−) host cells such as AM1 CHO (a derivative of DG44, CHO DHFR (−)).

AM-1 CHO cells were seeded at $1.5 \times 10^6$ cells per 100 mm dish. After 24 hours, the cells were co-transfected with linearized DNAs of pDSRα20/huFGFR1c and pDSRα20/huβ-Klotho with FuGene6 (Roche Applied Science). The transfected cells were trypsinized 2 days after transfection and seeded into CHO DHFR selective growth medium containing 10% dialyzed FBS and without hypoxanthine/thymidine supplement. After 2 weeks, the resulting transfected colonies were trypsinized and pooled.

HEK293T cells were transfected with the full length huFGFR1c and huβ-Klotho in pcDNA3.1 series or pTT14 (an expression vector developed by Durocher, NRCC, with CMV promoter and EBV ori, similar to pTT5 and a puromycin selection marker) based vector and selected with the corresponding drugs following similar procedure as for the CHO transfection and selection.

The FGF21R (i.e., FGFR1c and β-Klotho) transfected AM1 CHO or 293T cell pools were sorted repeatedly using Alexa 647-labeled FGF21. As a cell-surface staining reagent, FGF21 was labeled with Alexa 647-NHS following the method recommended by the manufacturer (Molecular Probes, Inc. Cat A 2006). The Alexa 647-labeled FGF21 showed specific staining of FGF21R receptor expressing cells and not the non-transfected parental cells (FIG. 3). High expressing cells were collected at the end of the final sorting, expanded and frozen into vials. The AM-1/huFGF21R cells were prepared for immunization and the 293T/huFGF21R cells were used for titering mouse sera by FACS after immunization and in binding screens of the hybridoma supernatants by FMAT (see Example 4).

Example 2

Preparation of a Soluble FGFR1c/β-Klotho Complex for Use as Antigen

Soluble FGF21 receptor constructs were generated in pTT14 or pcDNA3.1 expression vectors. The FGFR1c ECD-Fc construct (SEQ ID NO: 311, FIG. 4) comprises the N-terminal extracelluar domain of FGFR1c (amino acid residues #1-374; SEQ ID NO:5) fused to IgG1 Fc (SEQ ID NO: 20). The β-Klotho ECD-Fc construct (SEQ ID NO: 312, FIG. 5) comprises the N-terminal extracellular domain of β-Klotho (amino acid residues #1-996; SEQ ID NO:8) fused to IgG1 Fc (SEQ ID NO: 20).

HEK293 cells (293F, Invitrogen) were transfected with human FGFR1c ECD-Fc/pTT5, human β-Klotho ECD-Fc/pTT14-puro and dGFP/pcDNA3.1-Neo and selected in the presence of the corresponding drugs followed by repeated FACS sorting based on dGFP expression. Cells were grown in serum-free Dulbecco's Modified Eagle Medium (DMEM) supplemented with nonessential amino acids in HyperFlasks (Corning) for 4 days and conditioned media (CM) harvested for purification.

Figure 6:
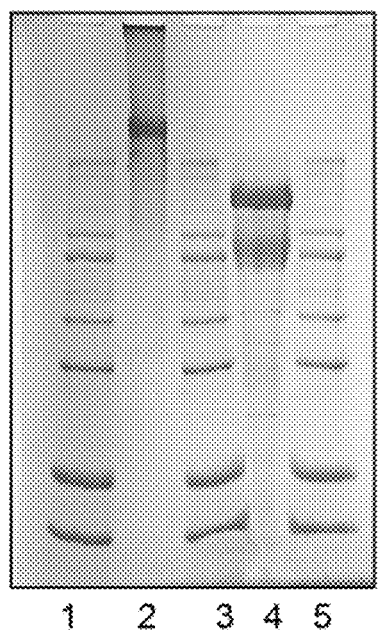
FIG. 6 is a SDS PAGE gel showing the level of purity achieved from preparations of a soluble FGF21 receptor complex comprising FGFR1c ECD-Fc and β-Klotho ECD-Fc, which was employed as an immunogen to generate antigen binding proteins.
Figure 9A:
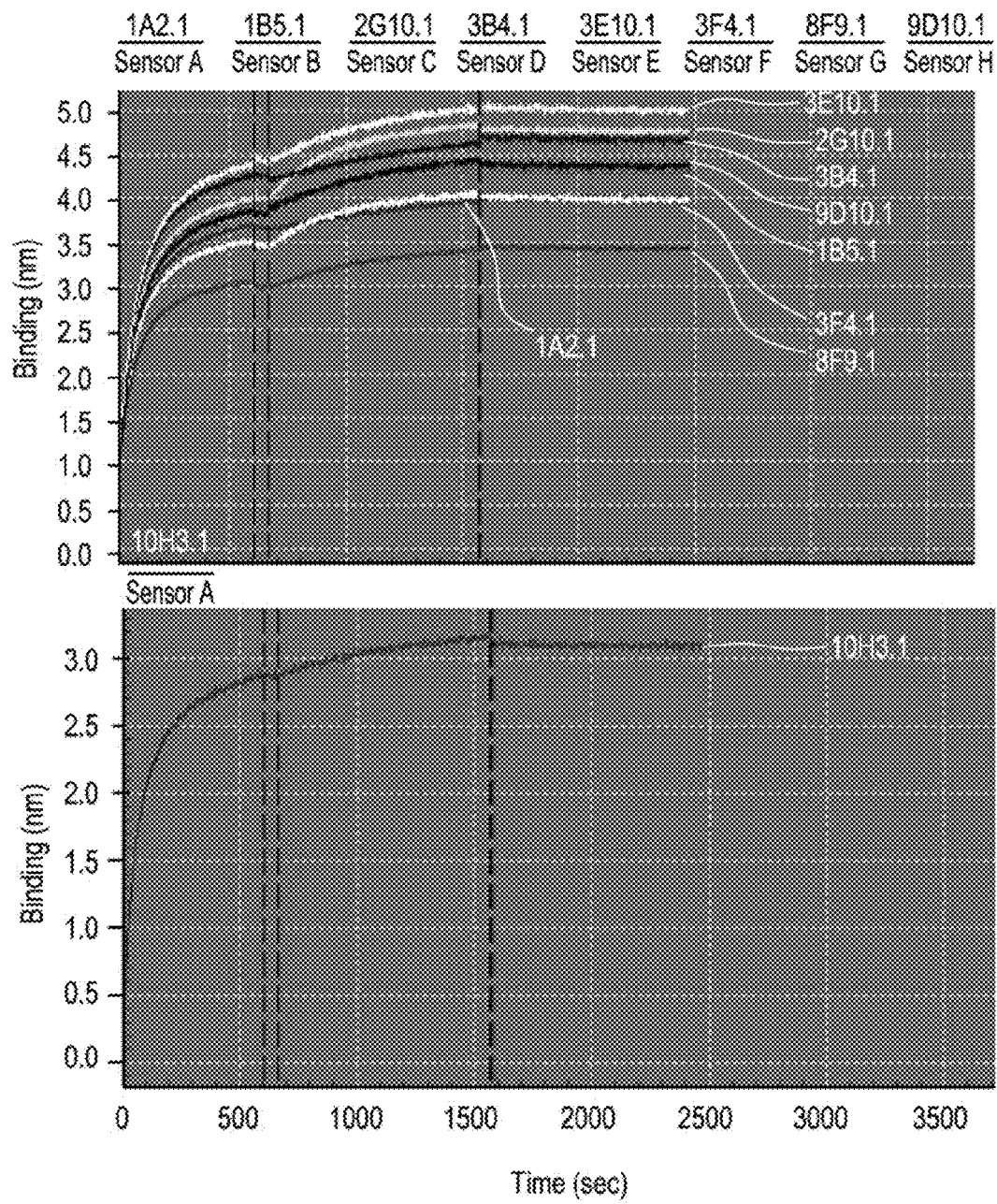
Figure 10:
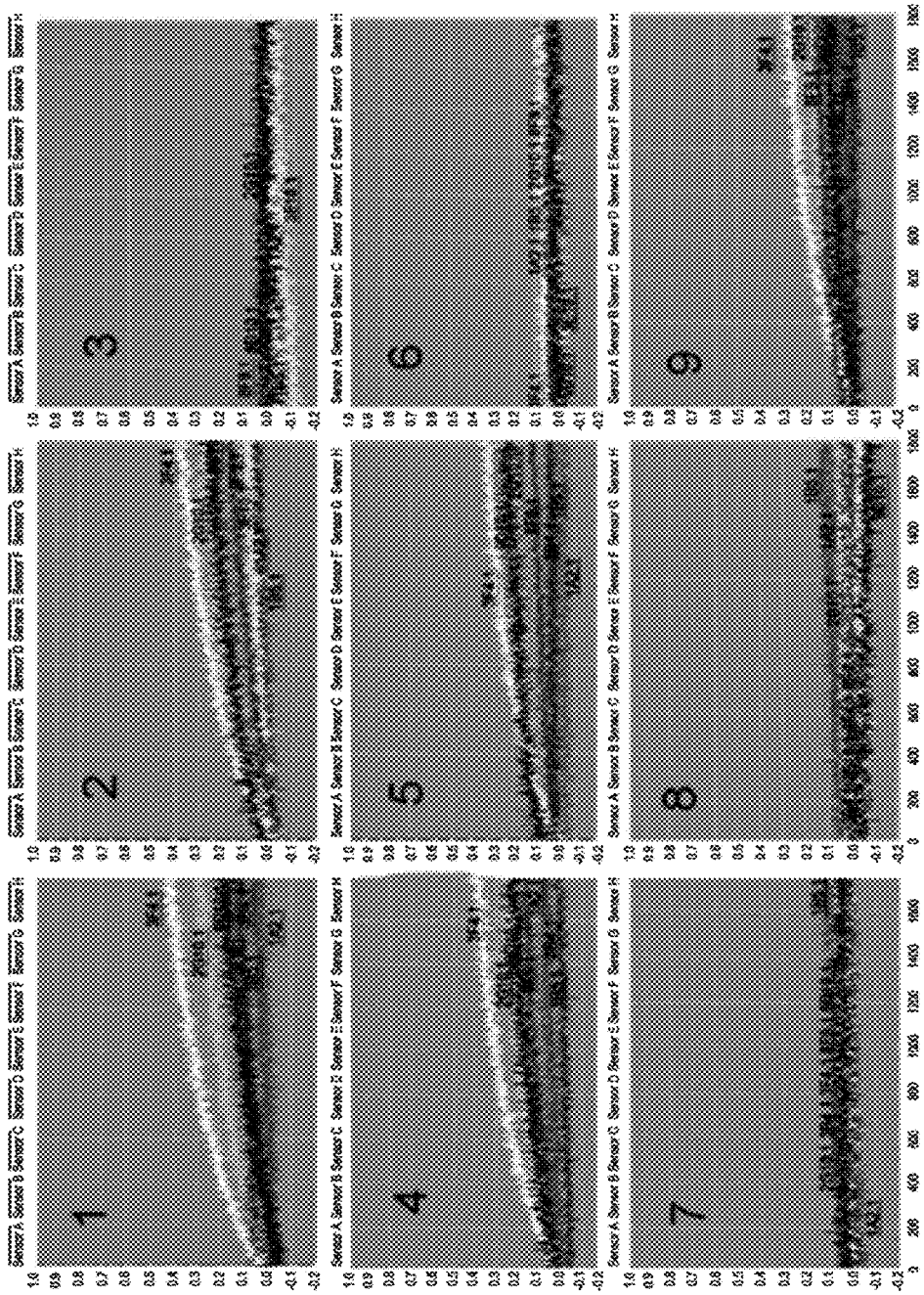
FIG. 10 is a series of traces from competitive binding assays performed using some of the disclosed β-Klotho binding proteins.

The 293 CM was concentrated 6 fold and applied to Protein A FF equilibrated in PBS. The protein was eluted with Pierce Gentle Ag/Ab elution buffer. The Protein A pool was dialyzed against 20 mM Tris-HCl, pH 7, 10 mM NaCl and applied to SP HP at pH 7.0. The FGFR1c ECD-Fc was present in the flow-through and the heterodimer was eluted with linear gradient of 0-0.4 M NaCl, 20 mM tris-HCl pH 7.0. N-terminus amino acid sequencing verified the purified soluble FGF21R to be a heterodimer composed of (1:1) ratio of FGFR1c ECD-Fc and betaKlotho ECD-Fc. The purified soluble FGF21R-Fc (FIG. 6) was used as the antigen for immunization.

Example 3

Preparation of Monoclonal Antibodies

Immunizations were conducted using one or more suitable forms of FGF21 receptor antigen, including: (1) cell bound receptor of CHO transfectants expressing full length human FGFR1c and β-Klotho at the cell surface, obtained by transfecting CHO cells with cDNA encoding a human full length FGFR1c polypeptide of SEQ ID NO: 305 (see also FIGS. 1a-b) and cDNA encoding a human β-Klotho polypeptide of SEQ ID NO: 308 (see also FIGS. 2a-c); (2) membrane extract from the aforementioned cells expressing the FGF21R receptor complex; or (3) soluble FGF21R receptor obtainable by co-expressing the N-terminal extracellular domain (ECD) of FGFR1c (SEQ ID NO: 311; see also FIG. 4) and the N-terminal extracellular domain (ECD) of β-Klotho (SEQ ID NO: 312; see also FIG. 5) or (4) combinations thereof.

A suitable amount of immunogen (i.e., 10 μgs/mouse of soluble FGF21R or 3–4×10$^6$ cells/mouse of stably transfected CHO cells or 150 μgs/mouse of purified FGF21R membranes prepared from CHO cells stably expressing FGF21R) was used for initial immunization in XenoMouse™ according to the methods disclosed in U.S. patent application Ser. No. 08/759,620, filed Dec. 3, 1996 and International Patent Application Nos. WO 98/24893, and WO 00/76310, the disclosures of which are hereby incorporated by reference. Following the initial immunization, subsequent boost immunizations of immunogen (5 μg/mouse of soluble FGF21R or 1.7×10$^6$ FGF21R transfected cells/mouse or 75 μgs of purified FGF21R membranes) were administered on a schedule and for the duration necessary to induce a suitable anti-FGF21R titer in the mice. Titers were determined by a suitable method, for example, by enzyme immunoassay, fluorescence activated cell sorting (FACS), or by other methods (including combinations of enzyme immunoassays and FACS).

Animals exhibiting suitable titers were identified, and lymphocytes were obtained from draining lymph nodes and, if necessary, pooled for each cohort. Lymphocytes were dissociated from lymphoid tissue by grinding in a suitable medium (for example, Dulbecco's Modified Eagle Medium; DMEM; obtainable from Invitrogen, Carlsbad, Calif.) to release the cells from the tissues, and suspended in DMEM. B cells were selected and/or expanded using standard methods, and fused with suitable fusion partner, for example, nonsecretory myeloma P3X63Ag8.653 cells (American Type Culture Collection CRL 1580; Kearney et al, *J. Immunol.* 123, 1979, 1548-1550), using techniques that were known in the art.

In one suitable fusion method, lymphocytes were mixed with fusion partner cells at a ratio of 1:4. The cell mixture was gently pelleted by centrifugation at 400×g for 4 minutes, the supernatant decanted, and the cell mixture gently mixed (for example, by using a 1 ml pipette). Fusion was induced with PEG/DMSO (polyethylene glycol/dimethyl sulfoxide; obtained from Sigma-Aldrich, St. Louis Mo.; 1 ml per million of lymphocytes). PEG/DMSO was slowly added with gentle agitation over one minute followed, by one minute of mixing. IDMEM (DMEM without glutamine; 2 ml per million of B cells), was then added over 2 minutes with gentle agitation, followed by additional IDMEM (8 ml per million B-cells) which was added over 3 minutes.

The fused cells were pelleted (400×g 6 minutes) and resuspended in 20 ml Selection media (for example, DMEM containing Azaserine and Hypoxanthine [HA] and other supplemental materials as necessary) per million B-cells. Cells were incubated for 20-30 minutes at 37° C. and then resuspended in 200 ml selection media and cultured for three to four days in T175 flasks prior to 96 well plating.

Cells were distributed into 96-well plates using standard techniques to maximize clonality of the resulting colonies. After several days of culture, supernatants were collected and subjected to screening assays as detailed in the examples below, including confirmation of binding to human FGF21 receptor, specificity and/or cross-species reactivity. Positive cells were further selected and subjected to standard cloning and subcloning techniques. Clonal lines were expanded in vitro, and the secreted human antibodies obtained for analysis.

In this manner, mice were immunized with either cells or membranes expressing full length FGF21R cells, or soluble FGF21R extracellular domain, with a range of 11-17 immunizations over a period of approximately one to three and one-half months. Several cell lines secreting FGF21R-specific antibodies were obtained, and the antibodies were further characterized. The sequences thereof are presented herein and in the Sequence Listing, and results of various tests using these antibodies are provided.

Example 4

Selection of Binding Antibodies by FMAT

After 14 days of culture, hybridoma supernatants were screened for FGF21R-specific monoclonal antibodies by Fluorometric Microvolume Assay Technology (FMAT) by screening against either the CHO AM1/huFGF21R cell line or recombinant HEK293 cells that were transfected with human FGF21R and counter-screening against parental CHO or HEK293 cells. Briefly, the cells in Freestyle media (Invitrogen) were seeded into 384-well FMAT plates in a volume of 50 μL/well at a density of 4,000 cells/well for the stable transfectants, and at a density of 16,000 cells/well for the parental cells, and cells were incubated overnight at 37° C. 10 μL/well of supernatant was then added, and the plates were incubated for approximately one hour at 4° C., after which 10 μL/well of anti-human IgG-Cy5 secondary antibody was added at a concentration of 2.8 μg/ml (400 ng/ml final concentration). Plates were then incubated for one hour at 4° C., and fluorescence was read using an FMAT Cellular Detection System (Applied Biosystems).

In total, over 3,000 hybridoma supernatants were identified as binding to the FGF21 receptor expressing cells but not to parental cells by the FMAT method. These supernatants were then tested in the FGF21 functional assays as described below.

Example 5

Selection of Antibodies that Induce FGF21-Like Signaling

Experiments were performed to identify functional antibodies that mimic wild-type FGF21 activity (e.g., the ability to induce FGF21-like signaling) using a suitable FGF21 reporter assay. The disclosed FGF21 reporter assay measures activation of FGFR signaling via a MAPK pathway readout. β-Klotho is a co-receptor for FGF21 signaling, and although it is believed not to have any inherent signaling capability due to its very short cytoplasmic domain, it is required for FGF21 to induce signaling through FGFRs.

5.A ELK-Luciferase Reporter Assay

ELK-luciferase assays were performed using a recombinant human 293T kidney cell or CHO cell system. Specifically, the host cells were engineered to over-express β-Klotho and luciferase reporter constructs. The reporter constructs contain sequences encoding GAL4-ELK1 and 5xUAS-Luc, a luciferase reporter driven by a promoter containing five tandem copies of the Gal4 binding site. Activation of the FGF21 receptor complex in these recombinant reporter cell lines induces intracellular signal transduction, which in turn leads to ERK and ELK phosphorylation. Luciferase activity is regulated by the level of phosphorylated ELK, and is used to indirectly monitor and quantify FGF21 activity.

In one example, CHO cells were transfected sequencially using the Lipofectamine 2000 transfection reagent (Invitrogen) according to the manufacturer's protocol with the receptor constructs expressing β-Klotho, FGFR1c and the reporter plasmids: 5xGal4-Luciferase (minimal TK promoter with 5xGal4 binding sites upstream of luciferase) and Gal4-ELK1. Gal4-ELK1 binds to the Gal4 binding sites and activates transcription when it is phosphorylated by ERK. Luciferase transcription, and thereby the corresponding enzymatic activity in this context is regulated by the level of phosphorylated ELK1, and is used to indirectly monitor and quantify FGF21 activity.

Clone 2E10 was selected as the FGF21 luciferase reporter cell line based on the optimal assay window of 10-20 fold with native FGF21 exhibiting an EC50 in the single nM range.

For the assay, the ELK-luciferase reporter cells were plated in 96 well assay plates, and serum starved overnight. FGF21 or test samples were added for 6 hours at 37 degrees. The plates were then allowed to cool to room temperature and the luciferase activity in the cell lysates was measured with Bright-Glo (Promega).

5.B ERK-Phosphorylation Assay

Alternative host cell lines, specifically a L6 (a rat myoblastic cell line), was developed and employed to identify antibodies with FGF21-like signaling activity. The rat L6 cell line is a desirable host cell line for the activity assay because it is known to express minimal levels of endogeneous FGF receptors. The L6 cells do not respond to FGF21 even when transfected with β-Klotho expression vector and therefore provides a cleaner background. (Kurosu et al., (2007) J. Biol. Chem. 282, 26687-26695).

L6 cells were maintained in Dulbecco's modified Eagle's medium supplemented with 10% fetal bovine serum and penicillin/streptomycin. Cells were transfected with plasmids expressing βKlotho and individual FGFR using the Lipofectamine 2000 transfection reagent (Invitrogen) according to the manufacturer's protocol.

Analysis of FGF signaling in L6 cells was performed as described in the literature (Kurosu et al., (2007) J. Biol. Chem. 282, 26687-26695). Cell cultures were collected 10 min after the treatment of FGF21 or test molecules and snap frozen in liquid nitrogen, homogenized in the lysis buffer and subjected to western blot analysis using an anti-phospho-p44/42 MAP kinase (ERK1/2) antibody and an anti-ERK antibody (Cell Signaling). The percent of phosphrylated ERK versus total ERK protein was determined in this way.

In addition, the factor-dependent mouse BaF3 cell-based proliferation assay used frequently for cytokine receptors can also be developed and applied.

Among the hybridoma supernatants tested in the CHO cell (clone 2E10) based human FGF21 ELK-luciferase reporter assay, over 30 were identified as positive (>5% of the activity of FGF21) when compared to 20 nM FGF21 as the positive control. Antibodies were then purified from the conditioned media of the hybridoma cultures of these positives and tested again in the CHO cell based ELK-luciferase reporter assay. (FIG. 7) showed the representative antibodies in the dose-responsive potency assay with estimated EC50 less than 1 μg/ml (or 6.7 nM). The activities were confirmed in the L6 cell based ERK1/2-phosphrylation assay (FIG. 8) with EC50 less than 10 nM which is consistent to the ELK-luciferase assay in the CHO stable cell line 2E10.

Example 6

Elisa of FGFR1c Binders

Peptides that bind to FGFR1c were identified and examined in an ELISA assay. Subsequently, human FGFR1c (hu-FGFR1c), and murine FGFR1c (mu-FGFR1c) were expressed and purified. Anti-M13-HRP was purchased from GE healthcare (Piscataway, N.J.). Maxisorp 96 well plates (Thermo Fisher Scientific; Rockford, Ill.) were coated with 2 μg/ml hu-FGFR1c and mu-FGFR1c in PBS respectively. Plates were then incubated at 4° C. overnight and blocked in 2% MPBS at room temperature for 1 h the next day. Plates were then incubated for 1 h with samples diluted in 2% MPBS and washed 3 times with PBST (Tween20) after 1 h incubation. Anti-M13-HRP was diluted 1:10000 in 2% MPBS and added to each well then incubated for 1 h. After 1 h incubation, plates were washed 3 times with 300 μl PBST Lumiglo chemiluminescent reagent (KPL; Gaithersburg, Md.) was added and luminescence was measured using Perkin Elmer Envision reader (Perkin Elmer; Waltham, Mass.).

Example 7

Construction of Bispecific FGF21 Mimetic Antigen Binding Proteins

Vector pTT5 SNS (National Research Council of Canada, Ottawa, Canada) was used for heavy chains. The N-linked glycosylation site in IgG1 was removed by overlap PCR as follows using Novagen (Darmstadt, Germany) Hot Start KOD PCR kit 71086. The reaction contained 30.5 μl $H_2O$, 2.5 μl DMSO, 5 μl 10x buffer #1, 5 μl dNTPs for final concentration of 0.2 mM, 2 μl $MgCl_2$ (catalog number 71153) for final concentration of 1 mM, 1 μl template DNA prepared by Qiagen spin Mini-prep (Valencia, Calif.), 1.5 μl each of forward and reverse oligos at 10 μmol/μl for a final concentration of 0.3 μM each, and 1 μl KOD Hot Start DNA Polymerase. The reaction was thermocycled 94° C. 2 min, then 30 cycles of [94° C. for 15 sec, 45° C. for 30 sec, and 68° C. for 3 min] Two initial PCR reactions were performed to introduce the mutation. The primer pair sequences were GGAGGAGCAGTACCAGAGCACGTACCGTGTGGTCAGCGTC (SEQ ID NO: 269) with CTTCCGAGTGAGAGACAC (SEQ ID NO: 270) and CAGCTGGCGTAATAGCGAAG (SEQ ID NO: 271) with TGCTCTGGTACTGCTCCTCCCGCGGCTTTGTCTTGGCATTATG (SEQ ID NO: 272). The PCR products were gel purified using a Qiagen spin column kit (Valencia, Calif.) and then added together in an overlap PCR reaction using primers CTTCCGAGTGAGAGACAC (SEQ ID NO: 273) and CAGCTGGCGTAATAGCGAAG (SEQ ID NO: 274). The final PCR product was gel purified and used to replace the original fragment in the pTT5 SNS vector using restriction sites BsmBI and NotI. Quick Ligase kit from New England Biolabs (Ipswich, Mass.) and TOP10 chemically competent cells from Invitrogen (Carlsbad, Calif.) were used for cloning and then the DNA constructs were purified and sequence-verified.

Heavy chain CDRs were PCRed and cloned into this vector using BssHII and BsmBI and primers AAAAAAGGCACTAGAGACGGTGACCAGGGTTCC (SEQ ID NO: 275) and TTTTTTTTGCGCGCTGTCAGGTGCAACTGGTGCAGTC (SEQ ID NO: 276) for 1A2 or primers AAAAAAGGCACTAGAGACGGTGACCAGGGTTCC (SEQ ID NO: 277) and TTTTTTTTGCGCGCTGTCAGGTGCAGTTGGTGGAGTC (SEQ ID NO: 278) for 2G10. 1A2 light chain was cloned into pTT5 Kappa using BssHII and BsiWI and primers TTTTTTTTGCGCGCTGTGATATTGTGATGACCCAGAC (SEQ ID NO: 279) and AAAAAACGTACGTTTGATTTCCACCTGGGTCC (SEQ ID NO: 280). 2G10 light chain was cloned into pTT5 Lambda using BssHII and BsmBI and primers TTTTTTTTGCGCGCTGTCAGTCTGTGTTGACGCAGCC (SEQ ID NO: 281) and TTTTTCGTCTCTGACCTAGGACGGTCAGCTTGGTCC (SEQ ID NO: 282).

All oligos (see Table 8) were diluted to 10 µM in water. 9 µl UB and LA oligos were used for 5' internal phosphorylation. A mixture (1 µl) of 90% NEB PNK buffer (Ipswich, Mass.) and 10% NEB PNK (Ipswich, Mass.) was added. The mixture was incubated at 37° C. for 10 min and then at 60° C. for 20 min (in a PCR machine). 9 µl of the complimentary oligo was then added. All oligo pairs were cycled at 95° C. for 20 sec, then decreased 0.1° C./sec to 50° C. (a 7:30 min ramp). Both pairs of oligos were mixed and "stitched" at 55° C. for 20 sec, using a 5 mM ramp to 25° C. (a 0.1° C./sec decrease). 150 µl of 5 mM Tris-HCl pH 8.5/0.1 mM EDTA was then added to the linker prep. The linker was ligated into pTT5-1A2 or 2G10 which had been digested with BsrGI and SexAI and gel purified.

TABLE 8

Oligos Used in Constructing Antigen Binding Proteins

| Oligo # | Oligo Name | Sequence | SEQ ID NO |
|---|---|---|---|
| 5412-51 | R26 UA | GTA CAC CCT GCC CCC ATC CCG GGA TGA GCT GGG TGG TGA GTG GTA CTG CGG CGT | 283 |
| 5412-52 | R26 UB | GCT GTT CAA CTG CCA GCA GGG TGG TAC CAA GAA | 284 |
| 5412-53 | R26 LB | CCT GGT TCT TGG TAC CAC CCT GCT GGC AGT TGA ACA GCA CGC GCC AGT ACC ACT C | 285 |

TABLE 8-continued

Oligos Used in Constructing Antigen Binding Proteins

| Oligo # | Oligo Name | Sequence | SEQ ID NO |
|---|---|---|---|
| 5412-54 | R26 LA | ACC ACC CAG CTC ATC CCG GGA TGG GGG CAG GGT | 286 |
| 5412-63 | R40 UA | GTA CAC CCT GCC CCC ATC CCG GGA TGA GCT GGG TGG TCA CTT CAA GTG CGG CA | 287 |
| 5412-64 | R40 UB | TGG GCC TGT TCG AGT GCG CCG ACC CCG GTG GTA CCA AGA A | 288 |
| 5412-65 | R40 LB | CCT GGT TCT TGG TAC CAC CGG GGT CGG CGC ACT CGA ACA GGC CCA TGC CGC ACT TGA AGT | 289 |
| 5412-50 | R40 LA | GAC CAC CCA GCT CAT CCC GGG ATG GGG GCA GGG T | 290 |
| 5448-38 | SR4 UA | GTA CAC CCT GCC CCC ATC CCG GGA TG AGC TGG GTG GTT GCT ACC A | 291 |
| 5448-40 | SR4 UB | GGC CTG GGG CTA CTA CGT GTG CGG TGG TAC CAA GAA | 292 |
| 5448-39 | SR4 LB | CCT GGT TCT TGG TAC CAC CGC ACA CGT AGT AGC CCC AGG CCT GGT AGC AAC CAC CCA GC | 293 |
| 4619-60 | SR4 LA | TCA TCC CGG GAT GGG GGC AGG GT | 294 |

FGFR1c binder SR4 was also added to the N-terminus of 1A2 or 2G10 as follows: A PCR reaction was done on the heavy chain plasmid using primers AAAAAAGGCACTAGAGACGGTGACCAGGGTTCC (SEQ ID NO: 295) and TCAGGCGTGGGGCTATTATGTGTGCGGAGGCGGAGGAGGCCAGGTGCAACTGGT GCAGTC (SEQ ID NO: 296). One µl of this reaction was then used as a template for PCR with primers AAAAAAGGCACTAGAGACGGTGACCAGGGTTCC (SEQ ID NO: 297) and TCAGGCGTGGGGCTATTATGTGTGCGGAGGCGGAGGAGGCCAGGTGCAGTTGGT GGAGTC (SEQ ID NO: 298). This PCR provided a SR4-CDR fragment that was then purified using a Qiagen PCR Clean Up Kit (Valencia, Calif.) and ligated into pTT5-IgG1 Aglyco BssHII to BsmBI.

SR4 was also added to the C-terminus of 1A2 or 2G10 as follows: A PCR reaction was done on pTT5-IgG1 Aglyco using primers CGGCGTGGAGGTGCATAATG (SEQ ID NO: 299) and AATAGCCCCACGCCTGATAGCAGCCTCCTCCGCCTCCTTTACCCGGAGACAGGGA GAG (SEQ ID NO: 300). One µl of this reaction was then used as a template for PCR with primers CGGCGTGGAGGTGCATAATG (SEQ ID NO: 301) and GATGTCGAGGCGGCCGCTCAGCCGCCGCACACATAATAGCCCCACGCCTGATAG (SEQ ID NO: 302). This PCR provided an IgG1-SR4 fragment that was then purified using a Qiagen PCR Clean Up Kit (Valencia, Calif.) and ligated into pTT5-IgG1 Aglyco SacII to NotI. Before ligation, the vector was dephosphorylated in a 30 min reaction using a Roche rAPid AP kit (Mannheim, Germany).

Example 8

Expression of Bispecific FGF21 Mimetic Antigen Binding Proteins

The bispecific FGF21 mimetics antigen binding proteins in the pTT5 vector were expressed transiently in serum-free suspension adapted 293-6E cells maintained in FreeStyle medium (Invitrogen Corporation, Carlsbad, Calif.) supplemented with (25 µg/ml) geneticin (Invitrogen) and 0.1% Pluronic F68 (Invitrogen). Transfections were performed as 1 L cultures. Briefly, the cell inoculum was grown to $1.1 \times 10^6$ cells/ml in a 3 L fernbach shake flask (Corning, Inc.). The shake flask culture was maintained on an Innova 2150 shaker platform (News Brunswick Scientific, Edison, N.J.) at 65 RPM which was placed in a humidified incubator maintained at 37° C. and 5% $CO_2$. At the time of transfection, the 293-6E cells were diluted to $1.0 \times 10^6$ cells/ml. The transfection complexes were formed in 100 ml FreeStyle medium. 1 mg plasmid DNA was first added to the medium followed by 3 ml of FuGene HD transfection reagent (Roche Applied Science, Indianapolis, Ind.). The transfection complex was incubated at room temperature for approximately 15 minutes and then added to the cells in the shake flask. Twenty-hour hours post transfection, 20% (w/v) of peptone TN1 (OrganoTechnie S.A., TeknieScience, QC, Canada) was added to reach a final concentration of 0.5% (w/v). The transfection/expression was performed for 4-7 days, after which the conditioned medium was harvested by centrifugation at 4,000 RPM for 60 minutes at 4° C.

Example 9

Purification of Antigen Binding Proteins from Transient Cell Culture

The FGF21 mimetic antigen binding proteins were purified from transient cell culture as follows. All purification processes were carried out at room temperature or 4° C. One purification scheme was used to purify various bispecfic FGF21 mimetic antibodies and used affinity chromatography.

9.A

Protein A Chromatography

The host cell culture fluid (CCF) was loaded onto Protein G chromatography media in the form of a column, Protein A High Performance (GE Healthcare, formerly Amersham Biosciences), equilibrated in PBS.

After loading, the Protein A column was washed with PBS until the absorbance at 280 nm of the flow-through returned to baseline. The antibodies were then eluted from the column using 10 mM Acetate, pH 3.5 and immediately neutralized by adding 80 µL of a stock solution of 1M Tris Base per mL of elution volume. The absorbance at 280 nm of the eluate was monitored and fractions containing protein were collected to make the Protein A pool.

Formulation and Concentration

Following purification, the antibodies were formulated in DPBS (8.1 mM $NaHPO_4$—$H_2O$, 138 mM $NaCl_2$, 1.2 mM $KH_2PO_4$, 2.7 mM KCL pH 7.4) by dialysis using 10,000 MWCO membranes (Pierce Slide-A-Lyzer). If measuring concentration of the antibodies were necessary, a centrifugal device (Macrocep, Pall) with a 10,000 MWCO membrane was used. Following formulation the antibodies were filtered through a sterile 0.2 µm filter and stored at 4° C. or frozen.

Example 10

ELISA of the Bispecific FGF21 Mimetics Antibodies

Biotin-hu-β-Klotho-His, biotin-mu-βKlotho-His, hu-FGFR1c-His, and mu-FGFR1c-Fc were expressed and purified. Anti-Fc-HRP was purchased from Thermo Fisher Scientific (Rockford, Ill.). Neutravidin 96 well plates (Thermo Fisher Scientific; Rockford, Ill.) were coated with 2 µg/ml biotin-hu-β-Klotho-His or biotin-mu-β-Klotho-His in PBS (Invitrogen; Carlsbad, Calif.). Maxisorp 96 well plates (Thermo Fisher Scientific; Rockford, Ill.) were coated with 2 µg/ml hu-FGFR1c-His or mu-FGFR1c-Fc in PBS. Plates were then incubated at 4° C. overnight. Plates were blocked in 2% milk-PBS at room temperature for 1 hour. Each well was then incubated 1 hour with samples diluted in 2% milk-PBS. Plates were washed 3 times with 300 µl PBS/0.1% Tween20 (Invitrogen; Carlsbad, Calif. and Sigma-Aldrich; St. Louis, Mo.). Anti-hu-Fc-HRP was diluted 1:10000 in 2% milk-PBS and added to each well. Plates were again washed 3 times with 300 µl PBS/0.1% Tween20. Lumiglo reagent (KPL; Gaithersburg, Md.) was added and luminescence was measured (Perkin Elmer; Waltham, Mass.).

Example 11

Luciferase Assays of the Bispecific FGF21 Mimetics Antibodies

AM1D cells expressing FGFR1c, Elk and Luciferase with or without βKlotho were constructed. FGF21 was expressed and purified. AM1D cells expressing FGFR1c, βKlotho, Elk, and Luciferase were maintained in DMEM media (Invitrogen; Carlsbad, Calif.) supplemented with 10% dialyzed fetal bovine serum (Invitrogen; Carlsbad, Calif.), 200 µg/ml Hygromycin B (Invitrogen; Carlsbad, Calif.), 4 µg/ml Puromycin (Invitrogen; Carlsbad, Calif.), Penicillin-Streptomycin-Glutamine (Invitrogen; Carlsbad, Calif.), Sodium Pyruvate (Invitrogen; Carlsbad, Calif.), and MEM non-essential amino acids (Invitrogen; Carlsbad, Calif.). AMID cells expressing FGFR1c, Elk, and Luciferase were maintained in DMEM media supplemented with 10% dialyzed fetal bovine serum, 400 µg/ml Hygromycin B, 6 µg/ml Puromycin, HT Supplement (Invitrogen; Carlsbad, Calif.), Penicillin-Streptomycin-Glutamine, Sodium Pyruvate, and MEM non-essential amino acids.

Cells were plated at a density of $3 \times 10^4$ cells/well in a 96 half well plate (Corning; Lowell, Mass.) in F-12 media (Invitrogen; Carlsbad, Calif.) containing 0.1% BSA (Sigma-Aldrich; St. Louis, Mo.) for a total volume of 30 µl/well. The cells were then incubated at 37° C. for 20-22 hours. Samples were diluted in PBS (Invitrogen; Carlsbad, Calif.) and 15 µl was added to each well. Cells were then incubated at 37° C. for 15 minutes. Human FGF21 was diluted in F-12 media and 5 µl was added to the cells for a final concentration of 3 nM. Cells were then incubated at 37° C. for 5-7 hours. Luciferase reagent (Perkin Elmer; Waltham, Mass.) was added and luminescence was measured (Perkin Elmer; Waltham, Mass.).

Example 12

Kinetic Study of the Anti-β-Klotho Antibodies

Biotinylated hu-β-klotho was prepared. Affinity measurement of purified anti-β-klotho antibodies was performed using Octet QK (fortéBIO Inc., Menlo Park, Calif.) following the vendor's protocol. Streptavidin High Binding FA Biosensors were incubated for 1 h with biotinylated hu-β-klotho at 100 nM in Kinetic buffer (fortéBIO Inc., Menlo Park, Calif.) for antigen coating and in Kinetic buffer for 1 min for establishing the baseline. The biosensors were incubated with a control IgG at 2 µg/ml in Kinetic buffer for 15 min to measure association, and then in Kinetic buffer for 15 min to measure dissociation. Affinity data was derived using the built-in analysis software.

Example 13

Epitope Binning of Anti-β-Klotho Antibodies

While off-line, columns of Streptavidin High Binding FA Biosensors can be incubated in biotinylated hu-β-klotho at 100 nM in Kinetic buffer (fortéBIO Inc., Menlo Park, Calif.), for 1 hour for antigen coating, then in Kinetic buffer for 2 min, followed by incubation with the anti-β-klotho antibodies, different for each column, at 11 µg/ml in Kinetic buffer for 2.5 hours. The antibodies for the first load can be Ab1 in column 1, Ab2 in column 2, etc. In the beginning, sensors in each column can be preloaded with a specific first-loaded IgG, and incubated with different test IgGs in different wells at 11 µg/ml for 30 minutes. The order for $2^{nd}$-load IgGs are Ab1 in well A, Ab2 in well B, etc. Binding signals of $2^{nd}$ IgGs can be recorded as the read out.

Example 14

Arginine Scanning

As described herein, FGF21 mimetic antigen binding proteins and antigen binding protein-FGF21 fusions that bind human β-Klotho or both β-Klotho and one of FGFR1c, FGFR2c, FGFR3c, or FGFR4, i.e., FGFR1c, were created and characterized. To determine the neutralizing determinants on human FGFR1c and/or β-Klotho that these various antigen binding proteins and antigen binding protein-FGF21 fusions bind, a number of mutant FGFR1c and/or β-Klotho proteins can be constructed having arginine substitutions at select amino acid residues of human FGFR1c and/or β-Klotho. Arginine scanning is an art-recognized method of evaluating where antibodies, or other proteins, bind to another protein, see, e.g., Nanevicz et al., (1995) *J. Biol. Chem.* 270:37, 21619-21625 and Zupnick et al., (2006) *J. Biol. Chem.* 281:29, 20464-20473. In general, the arginine sidechain is positively charged and relatively bulky as compared to other amino acids, which can disrupt antibody binding to a region of the antigen where the mutation is introduced. Arginine scanning is a method that determines if a residue is part of a neutralizing determinant and/or an epitope.

Various amino acids distributed throughout the human FGFR1c and/or β-Klotho extracellular domains can be selected for mutation to arginine. The selection can be biased towards charged or polar amino acids to maximize the possibility of the residue being on the surface and reduce the likelihood of the mutation resulting in misfolded protein. Using standard techniques known in the art, sense and anti-sense oligonucleotides containing the mutated residues can be designed based on criteria provided by Stratagene Quickchange® II protocol kit (Stratagene/Agilent, Santa Clara, Calif.). Mutagenesis of the wild-type (WT) FGFR1c and/or β-Klotho sequences can be performed using a Quickchange® II kit (Stratagene). Chimeric constructs can be engineered to encode a FLAG-histidine tag (six histidines (SEQ ID NO: 268)) on the carboxy terminus of the extracellular domain to facilitate purification via the poly-His tag.

Multiplex analysis using the Bio-Plex Workstation and software (BioRad, Hercules, Calif.) can be performed to determine neutralizing determinants on human FGFR1c and/β-Klotho by analyzing exemplary human FGFR1c and/or β-Klotho mAbs differential binding to arginine mutants versus wild-type FGFR1c and/or β-Klotho proteins. Any number of bead codes of pentaHis-coated beads ("pentaHis" disclosed as SEQ ID NO: 303) (Qiagen, Valencia, Calif.) can be used to capture histidine-tagged protein. The bead codes can allow the multiplexing of FGFR1c and/or β-Klotho arginine mutants and wild-type human FGFR1c and/or β-Klotho.

To prepare the beads, 100 µl of wild-type FGFR1c and/or β-Klotho and FGFR1c and/or β-Klotho arginine mutant supernatants from transient expression culture are bound to penta-His-coated beads ("penta-His" disclosed as SEQ ID NO: 303) overnight at 4° C. or 2 hours at room temperature with vigorous shaking. The beads are then washed as per the manufacturer's protocol and the bead set pooled and aliquoted into 2 or 3 columns of a 96-well filter plate (Millipore, Bellerica, Mass., product #MSBVN1250) for duplicate or triplicate assay points, respectively. 100 µl anti-FGFR1c and/or anti-β-Klotho antigen binding protein in 4-fold dilutions are added to the wells, incubated for 1 hour at room temperature, and washed. 100 µl of a 1:100 dilution of PE-conjugated anti-human IgG Fc (Jackson Labs., Bar Harbor, Me., product #109-116-170) is added to each well, incubated for 1 hour at room temperature and washed. Beads are resuspended in 1% BSA, shaken for 3 minutes, and read on the Bio-Plex workstation. Antibody binding to FGFR1c and/or β-Klotho arginine mutant protein is compared to antibody binding to the human FGFR1c and/or β-Klotho wild-type from the same pool. A titration of antibody over approximately a 5 log scale can be performed. Median Fluorescence Intensity (MFI) of FGFR1c and/or β-Klotho arginine mutant proteins can be graphed as a percent of maximum wild-type human FGFR1c and/or β-Klotho signal. Those mutants for which signal from all the antigen binding proteins are below a cut-off value, e.g., 30% of wild-type FGFR1c and/or β-Klotho can be deemed to be either of too low a protein concentration on the bead due to poor expression in the transient culture or possibly misfolded and can be excluded from analysis. Mutations (i.e., arginine substitutions) that increase the EC50 for the FGFR1c and/or β-Klotho antigen binding protein by a cut-off value, e.g., 3-fold or greater (as calculated by, e.g., GraphPad Prism®) can be considered to have negatively affected FGFR1c and/or β-Klotho antigen binding protein binding. Through these methods, neutralizing determinants and epitopes for various FGFR1c and/or β-Klotho antigen binding proteins can be elucidated.

Example 15

Construction of Chimeric Receptors

In another method of determining the activation determinants on human FGFR1c and/or β-Klotho that these various antigen binding proteins and antigen binding protein-FGF21 fusions bind, specific chimeric FGFR1c and/or β-Klotho proteins comprising sequences from human and mouse proteins can be constructed, expressed in transient or stable 293 or CHO cells as described before and tested. For example, a chimeric FGF21 receptor can be constructed comprising native human FGFR1c, FGFR2c, FGFR3c or FGFR4, in one example FGFR1c, paired with chimeric human or mouse β-Klotho in which selected regions or sequences on the human β-Klotho are systematically replaced by the corresponding mouse-specific residues (see, e.g., FIG. 2). Similarly, native human β-Klotho paired is with chimeric human/mouse FGFR1c, FGFR2c, FGFR3c or FGFR4, in one example FGFR1c, in which selected regions or sequences on the human FGFR1c are systematically replaced by the corresponding mouse-specific residues. The critical sequences involved in the binding and/or activity of the antigen binding proteins can be derived through binding assay or activity measurements described herein or known in the art, based on the chimeric FGF21 receptors.

Example 16

Protease Protection Analysis

Regions of the human FGF21 receptor bound by the antigen binding proteins and antigen binding protein-FGF21 fusions that bind human FGF21 receptor, e.g., FGFR1c, β-Klotho or a complex comprising FGFR1c and β-Klotho can be identified by fragmenting human FGF21 receptor into peptides with specific proteases, e.g., AspN, Lys-C, chymotrypsin or trypsin. The sequence of the resulting human FGF21 receptor peptides (i.e., both disulfide- and non-disulfide-containing peptide fragments from FGFR1c and β-Klotho portions) can then be determined. In one example, soluble forms of a human FGF21 receptor complex, e.g., a complex comprising the FGFR1c ECD-Fc and β-Klotho ECD-Fc heterodimer described herein, can be digested with AspN (which cleaves after aspartic acid and some glutamic acid residues at the amino end) by incubating about 100 µg of soluble FGF21 receptor at 1.0 mg/ml in 0.1M sodium phosphate (pH 6.5) for 20 hrs at 37° C. with 2 µg of AspN.

A peptide profile of the AspN digests can then be generated on HPLC chromatography while a control digestion with a similar amount of antibody is expected to be essentially resistant to AspN endoproteinase. A protease protection assay can then be performed to determine the proteolytic digestion of human FGF21 receptor in the presence of the antigen binding proteins. The general principle of this assay is that binding of an antigen binding protein or antigen binding protein-FGF21 fusion to the FGF21 receptor can result in protection of certain specific protease cleavage sites and this information can be used to determine the region or portion of FGF21 receptor where the antigen binding protein or antigen binding protein-FGF21 fusion binds.

Briefly, the peptide digests can be subjected to HPLC peptide mapping; the individual peaks are collected, and the peptides are identified and mapped by on-line electrospray ionization LC-MS (ESI-LC-MS) analyses and/or by N-terminal sequencing. HPLC analyses for these studies can be performed using a narrow bore reverse-phase C18 column (Agilent Technologies) for off-line analysis and using a capillary reverse phase C18 column (The Separation Group) for LC-MS. HPLC peptide mapping can be performed with a linear gradient from 0.05% trifluoroacetic acid (mobile phase A) to 90% acetonitrile in 0.05% trifluoroacetic acid. Columns can be developed at desirable flow rate for narrow bore HPLC for off-line or on-line LC-MS analyses, and for capillary HPLC for on-line LC-MS analyses.

Sequence analyses can be conducted by on-line LC-MS/MS and by Edman sequencing on the peptide peaks recovered from HPLC. On-line ESI LC-MS analyses of the peptide digest can be performed to determine the precise mass and sequence of the peptides that are separated by HPLC. The identities of selected peptides present in the peptide peaks from the protease digestion can thus be determined Example 17

Antigen Binding Protein-FGF21 Fusions

The C-terminus of FGF21 has been reported to be the critical motif for β-Klotho binding specificity (Wu, et al., *J. Biol. Chem.* 283, 33304-33309 (2008)). A cluster of highly protease-susceptible cleavage sites have been identified near the C-terminus of FGF21 based on in vivo testing, specifically between Pro171 and Ser 172. Cleavage at this cluster of resides diminishes the binding to β-Klotho and inactivated FGF21 in vivo. The series of antigen binding protein-FGF21 fusions disclosed herein were designed to replace the native β-Klotho binding motif in FGF21 with a high affinity antigen binding protein.

A series of ten antigen binding protein-FGF21 fusions were generated comprising (a) an antigen binding protein component that specifically binds β-Klotho or β-Klotho and one or more of FGFR1c, FGFR2c, FGFR3c, and FGFR4; and (b) an FGF21 component comprising FGF21 or a fragment thereof. The ten antigen binding protein-FGF21 fusions were engineered with the goal that the antigen binding protein component would specifically bind human β-Klotho and the FGF21 component would associate with FGFR1c, ultimately forming a complex that can initiate FGF21-induced signaling. Thus, the fusions were designed as FGF21 mimetics.

The fusions were tested in in vitro activity assays as described below.

17.A

Construction

Ten specific antigen binding protein fusions were generated. These fusions each comprised the anti-β-Klotho antibody 2G10 (as described in Tables 1-3 and 6) fused to residues 1-169 (SEQ ID NO: 342) or 1-170 of mature FGF21 (SEQ ID NO: 343) in various orientations via a linker (i.e., $(G_4S)_{15}$ (SEQ ID NO: 340), $(G_4S)_{12}$ (SEQ ID NO: 339), $(G_4S)_9$ (SEQ ID NO: 338), $(G_4S)_6$ (SEQ ID NO: 337), and $(G_4S)_3$ (SEQ ID NO: 336)), and are shown below.

The antigen binding protein fusions generated, which are presented from N- to C-terminus, included:
  (a) FGF21(1-169)-$(G_4S)_3$-2G10 (SEQ ID NOs:315 (coding sequence) and 316 (amino acid sequence));
  (b) FGF21(1-169)-$(G_4S)_6$-2G10 (SEQ ID NOs:319 (coding sequence) and 320 (amino acid sequence));
  (c) FGF21(1-169)-$(G_4S)_9$-2G10 (SEQ ID NOs:321 (coding sequence) and 322 (amino acid sequence));
  (d) FGF21(1-169)-$(G_4S)_{12}$-2G10 (SEQ ID NOs:323 (coding sequence) and 324 (amino acid sequence));
  (e) FGF21(1-169)-$(G_4S)_{15}$-2G10 (SEQ ID NOs:325 (coding sequence) and 326 (amino acid sequence));
  (f) 2G10-$(G_4S)_3$-FGF21(1-170) (SEQ ID NOs:317 (coding sequence) and 318 (amino acid sequence));

(g) 2G10-$(G_4S)_6$-FGF21(1-170) (SEQ ID NOs:327 (coding sequence) and 328 (amino acid sequence));

(h) 2G10-$(G_4S)_9$-FGF21(1-170) (SEQ ID NOs:329 (coding sequence) and 330 (amino acid sequence));

(i) 2G10-$(G_4S)_{12}$-FGF21(1-170) (SEQ ID NOs:331 (coding sequence) and 332 (amino acid sequence)); and (j) 2G10-$(G_4S)_{15}$-FGF21(1-170) (SEQ ID NOs:333 (coding sequence) and 334 (amino acid sequence)).

The antigen binding protein fusions were constructed as follows:

Construction of FGF21(1-169)-$(G_4S)_3$-2G10 Coding Sequence (SEQ ID NOs:316)

A nucleic acid sequence encoding amino acids 1-197 of full-length wild type human FGF21 (SEQ ID NO:2), i.e., the signal sequence and residues 1-169 of the mature form of FGF21 (SEQ ID NO:342)), was amplified with two primers, attaching a SalI restriction site as well as a Kozak sequence on the 5' end and two copies of a $(G_4S)_3$ linker (SEQ ID NO: 336) plus a BamHI restriction site on the 3' end.

The anti-β-Klotho antibody 2G10 mature form (i.e., minus signal peptide) was amplified using two primers. The first primer attached a BamHI site as well as one copy of a $(G_4S)_3$ linker (SEQ ID NO: 336) on the 5' end and the second primer added a NotI restriction site after the stop codon.

The FGF21-containing PCR fragment was digested with SalI and BamHI restriction enzymes, likewise the anti-β-Klotho antibody 2G10 PCR fragment was digested with BamHI and NotI restriction enzymes. Both fragments, as well as a pTT5 expression plasmid fragment digested with SalI and NotI, were gel purified and the resulting fragments ligated to obtain pTT5-Human FGF21 (1-197 (i.e., residues 1-169 plus the 28 residue signal sequence))-$(G_4S)_3$-anti-β-Klotho antibody 2G10.

Construction of FGF21 (1-169)-$(G_4S)_6$-2G10 (SEQ ID NO:320), FGF21 (1-169)-$(G_4S)_9$-2G10 (SEQ ID NO:322), FGF21(1-169)-$(G_4S)_{12}$-2G10 (SEQ ID NO:324), FGF21(1-169)-$(G_4S)_{15}$-2G10 (SEQ ID NO:326) Coding Sequences Using the transient expression clone pTT5-Human FGF21 (1-197)-$(G_4S)_3$-anti-β-Klotho antibody 2G10, all subsequent clones were made with larger linkers. Taking advantage of the unique BamHI restriction site within the $(G_4S)_3$ linker (SEQ ID NO: 336) as well as the overall clone, two phosphorylated and annealed oligomers coding for an additional $(G_4S)_3$ linker (SEQ ID NO: 336) were inserted. These annealed oligomers contained BamHI complatible ends that allowed ligation into a BamHI linearized fragment of pTT5-Human FGF21 (1-197)-$(G_4S)_3$-anti-β-Klotho antibody 2G10 clone. In this process, only one BamHI restriction site at one end of the annealed ligomers was regenerated, yielding pTT5-Human FGF21 (1-197)-$(G_4S)_6$-anti-β-Klotho antibody 2G10. Similarly, the pTT5-Human FGF21-$(G_4S)_6$-anti-β-Klotho antibody 2G10 clone was used to produce the $(G_4S)_9$ version. Ultimately, the $(G_4S)_{15}$ clone was produced from a $(G_4S)_{12}$ clone.

Construction of 2G10-$(G_4S)_3$-FGF21(1-170) (SEQ ID NO:318) Coding Sequence

A nucleic acid sequence encoding the full length anti-β-Klotho antibody 2G10 mature form (plus signal peptide) but lacking the terminal lysine was amplified using two primers. The first primer attached a SalI restriction site as well as a Kozak sequence on the 5' end and two copies of a $(G_4S)_3$ linker (SEQ ID NO: 336) plus a BamHI restriction site on the 3' end.

A nucleic acid sequence encoding amino acids 1-170 of the mature form of FGF21 (SEQ ID NO:343) was amplified with two primers. The first primer attached a BamHI site as well as one copy of a $(G_4S)_3$ linker (SEQ ID NO: 336) on the 5' end and the second primer added a NotI restriction site after the stop codon.

The anti-β-Klotho antibody 2G10 containing PCR fragment was digested with SalI and BamHI restriction enzymes, likewise the FGF21 PCR fragment was digested with BamHI and NotI restriction enzymes. Both fragments as well as a pTT5 expression plasmid fragment digested with SalI and NotI were gel purified and the resulting fragments ligated to obtain pTT5-anti-β-Klotho antibody 2G10-$(G_4S)_3$-human FGF21 (1-170).

Construction of 2G10-$(G_4S)$-FGF21(1-170) (SEQ ID NO:328), 2G10-$(G_4S)$-FGF21(1-170) (SEQ ID NO:330), 2G10-$(G_4S)_{12}$-FGF21 (1-170) (SEQ ID NO:332), 2G10-$(G_4S)_{15}$-FGF21 (1-170) (SEQ ID NO:334) Coding Sequences Using the transient expression clone pTT5-anti-β-Klotho antibody 2G10-$(G_4S)_3$-human FGF21 (1-170), all subsequent clones were made with larger linkers. Taking advantage of the unique BamHI restriction site within the $(G_4S)_3$ linker (SEQ ID NO: 336) as well as the overall clone, two phosphorylated and annealed oligomers coding for an additional $(G_4S)_3$ linker (SEQ ID NO: 336) were inserted. These annealed oligomers contained BamHI complatible ends that allowed ligation into a BamHI linearized fragment of pTT5-anti-β-Klotho antibody 2G10-$(G_4S)_3$-human FGF21 (1-170). In this process, only one BamHI restriction site at one end of the annealed ligomers was regenerated, yielding pTT5-anti-β-Klotho antibody 2G10-$(G_4S)_6$-human FGF21 (1-170). Similarly, the pTT5-anti-β-Klotho antibody 2G10-$(G_4S)_6$-human FGF21 (1-170) clone was used to produce the $(G45)_9$ version. Ultimately, the $(G_4S)_{15}$ clone was produced from a $(G_4S)_{12}$ clone.

17.B

Expression and Purification cDNA encoding each of the fusions proteins was generated and inserted into a pTT5 expression vector, with desK 2G10 heavy chain used in the C-terminal fusions.

The constructs were expressed in transiently transfected 293 cells. The human embryonic kidney 293 cell line stably expressing Epstein Barr virus Nuclear Antigen-1 (293-6E cells) was obtained from the National Research Council (Montreal, Canada). Cells were maintained as serum-free suspension cultures using F17 medium (Invitrogen, Carlsbad, Calif.) supplemented with 6 mM L-glutamine (Invitrogen, Carlsbad, Calif.), 1.1% F-68 Pluronic (Invitrogen, Carlsbad, Calif.) and 50 ug/ul Geneticin (Invitrogen, Carlsbad, Calif.). The suspension cell cultures were maintained in Erlenmeyer shake flask cultures. The culture flasks were shaken at 65 rpm at 37° C. in a humidified, 5% $CO_2$ atmosphere. Cells were routinely passaged by dilution to 3.0e5 viable cells/ml on Mondays and Wednesdays and to 1.5e5 viable cells/ml on Fridays for a period of three months before being replaced with a freshly thawed vial of cells.

Stock solutions (1 mg/ml) of 25-kDa linear PEImax (Polysciences, Warrington, Pa.) were prepared in water, acidified with HCl to pH 2.0 until dissolved, then neutralized with NaOH, sterilized by filtration (0.2 µm), aliquoted, and stored at −20° C. until used. Tryptone N1 was obtained from OrganoTechni S.A. (TekniScience, QC, Canada). Stock solutions (20%, w/v) were prepared in Freestyle medium (Invitrogen, Carlsbad, Calif.), sterilized by filtration through 0.2 µm filters, and stored at 4° C. until use.

For transfection, cells were diluted to 1.1e6 cells/ml. The transfection mixture of DNA and PEImax was prepared in fresh medium at 10% of the culture volume. The transfection mixtures consisted of 500 ug of DNA per ml of culture followed by 3 ug of PEImax per ug of DNA and were incubated for 10 minutes before being added to the cell culture. Cultures were typically harvested 6-7 days post-transfection.

The conditioned media was harvested and the fusions were purified using Protein A chromatography (MabSelect Sure, Millipore) at pH 3.5. The elution pools were titrated to around pH 7.0 and the buffer was then exchanged into PBS.

17.C

Binding Assays

Figure 16:
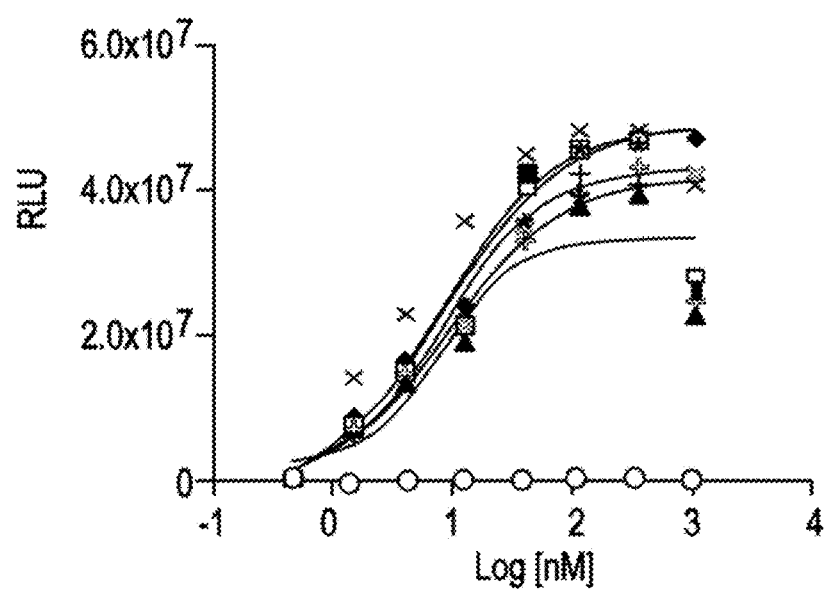
FIG. 16 is a plot depicting the results of a series of binding assays demonstrating that antigen binding protein fusions comprising the anti-β-Klotho antibody 2G10, joined via a linker, to a truncated form FGF21 comprising either residues 1-169 (SEQ ID NO: 342), when the configuration of the fusion is FGF21-linker-2G10 (from N- to C-terminus) residues or residues 1-170 (SEQ ID NO: 343) when the configuration of the fusion is 2G10-linker-FGF21 (from N- to C-terminus), bind to murine β-Klotho.
Figure 17:
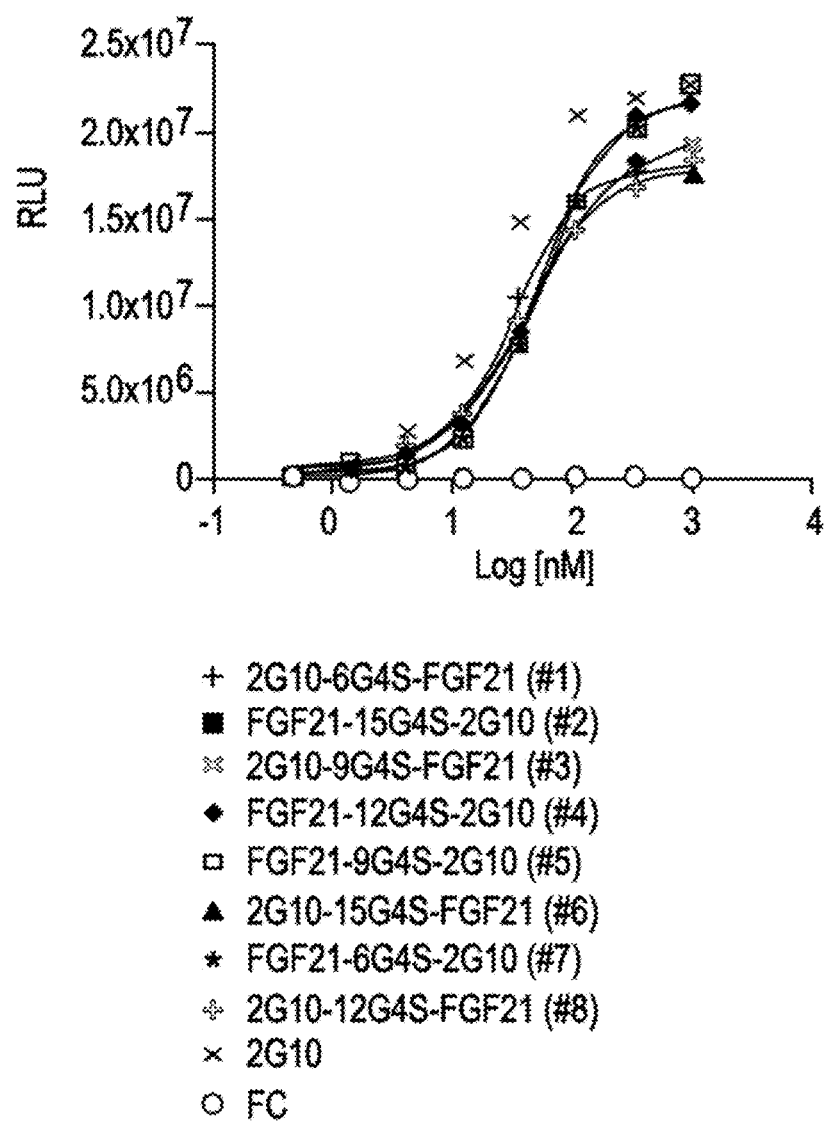
FIG. 17 is a plot depicting the results of a series of binding assays demonstrating that antigen binding protein fusions comprising the anti-β-Klotho antibody 2G10, joined via a linker, to a truncated form of FGF21 comprising either residues 1-169 (SEQ ID NO: 342), when the configuration of the fusion is FGF21-linker-2G10 (from N- to C-terminus) residues or residues 1-170 (SEQ ID NO: 343) when the configuration of the fusion is 2G10-linker-FGF21 (from N- to C-terminus), bind to human β-Klotho.

The fusions were assayed for binding to both human and mouse β-Klotho using an ELISA format. As shown in FIG. 16, all of the fusions were observed to bind to human β-Klotho, and FIG. 17 demonstrates that all of the fusions were observed to bind to murine β-Klotho. The observed binding was independent of the relative orientation of the FGF21 component with respect to the 2G10 antibody component.

17.D

In Vitro Activity Assays

Figure 18:
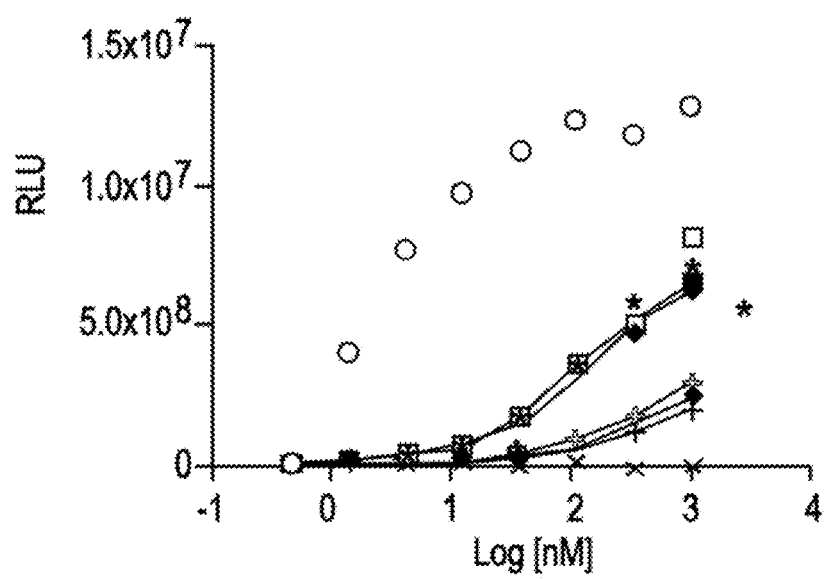
FIG. 18 is a plot depicting the results of luciferase assays demonstrating that the activity of antigen binding protein fusions comprising the anti-β-Klotho antibody 2G10, joined via a linker, to a truncated form of FGF21 comprising either residues 1-169 (SEQ ID NO: 342), when the configuration of the fusion is FGF21-linker-2G10 (from N- to C-terminus) residues or residues 1-170 (SEQ ID NO: 343) when the configuration of the fusion is 2G10-linker-FGF21 (from N- to C-terminus), is dependent on the orientation for the FGF21 component and is independent of linker length in a luciferase assay using AMID reporter cells expressing β-Klotho and FGFR1c in the absence of FGF21.

The fusions were then tested in a luciferase assay using AM1D reporter cells expressing β-Klotho and FGFR1c. FIG. 18 demonstrates that all of the fusions are active in the reporter assay. Additionally FIG. 18 demonstrates that while the observed activity is independent of linker length, the relative orientation of the FGF21 component with respect to the 2G10 antibody component of the fusion is significant. More particularly, it was observed that fusions in which the antibody component of the fusion is located at the N-terminus of the fusion showed a higher level of activity than those fusions in which the antibody component is located at the C-terminus of the overall fusion.

Figure 19:
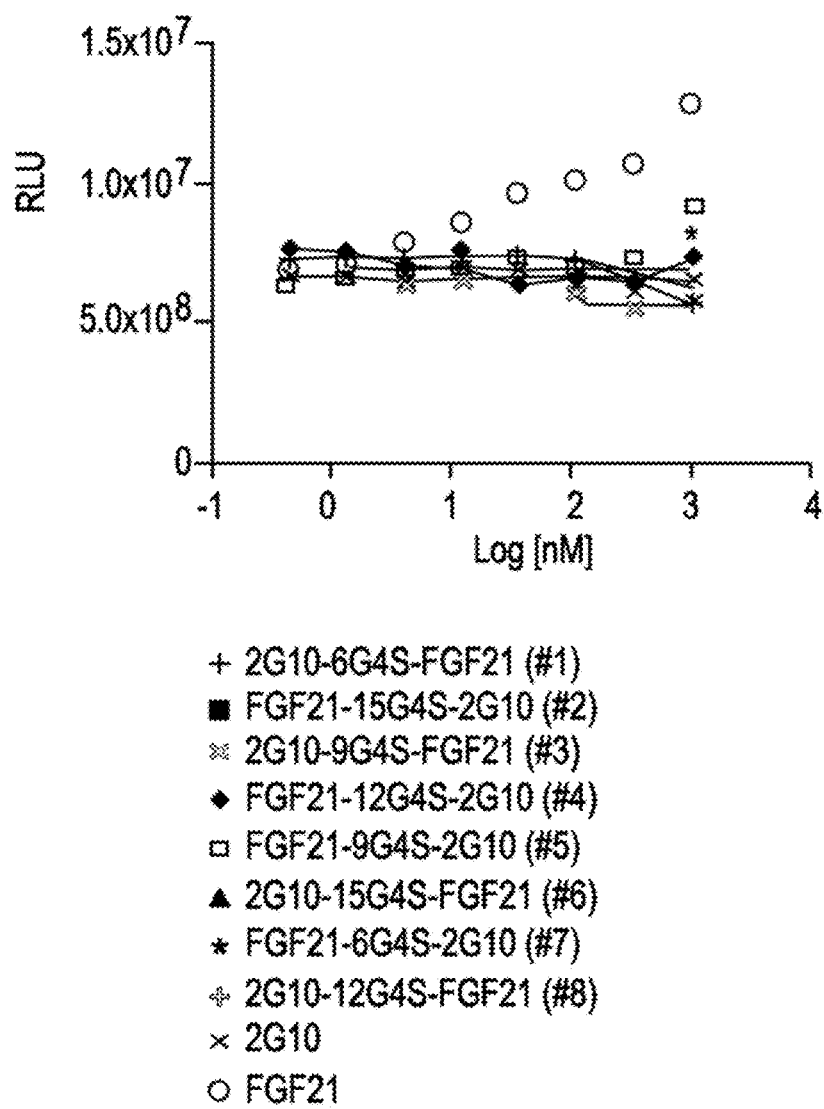
FIG. 19 is a plot depicting the results of a series of luciferase assays that demonstrate that antigen binding protein fusions comprising the anti-β-Klotho antibody 2G10, joined via a linker, to a truncated form of FGF21 comprising either residues 1-169 (SEQ ID NO: 342), when the configuration of the fusion is FGF21-linker-2G10 (from N- to C-terminus) residues or residues 1-170 (SEQ ID NO: 343) when the configuration of the fusion is 2G10-linker-FGF21 (from N- to C-terminus), show no detectable antagonistic activity in a luciferase assay using AMID reporter cells expressing β-Klotho and FGFR1c when incubated with 3 nM FGF21.
Figure 20:
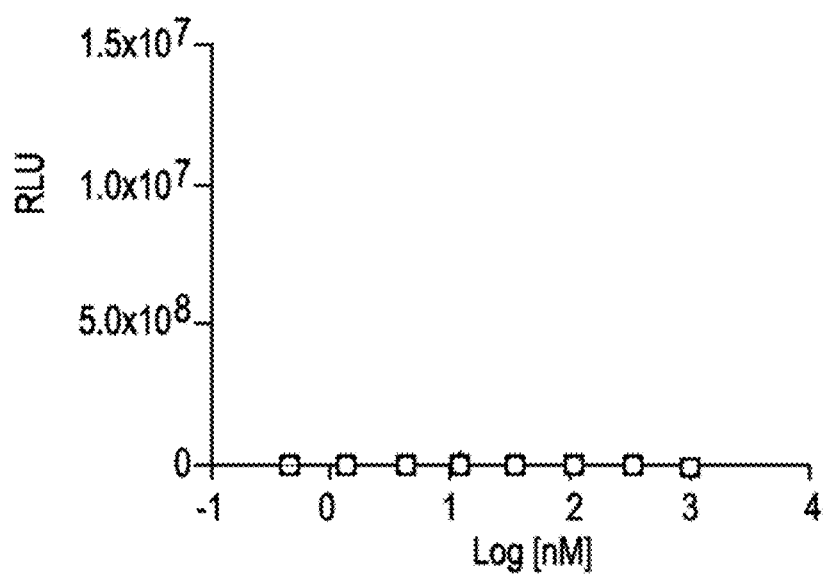
FIG. 20 is a plot depicting the results of a series of luciferase assays that demonstrate that antigen binding protein fusions comprising the anti-β-Klotho antibody 2G10, joined via a linker, to a truncated form of FGF21 comprising either residues 1-169 (SEQ ID NO: 342), when the configuration of the fusion is FGF21-linker-2G10 (from N- to C-terminus) residues or residues 1-170 (SEQ ID NO: 343) when the configuration of the fusion is 2G10-linker-FGF21 (from N- to C-terminus), show no detectable activity in a luciferase assay using AMID reporter cells expressing β-Klotho and FGFR1c when incubated with 3 nM α-Klotho in the absence of FGF21.
Figure 21:
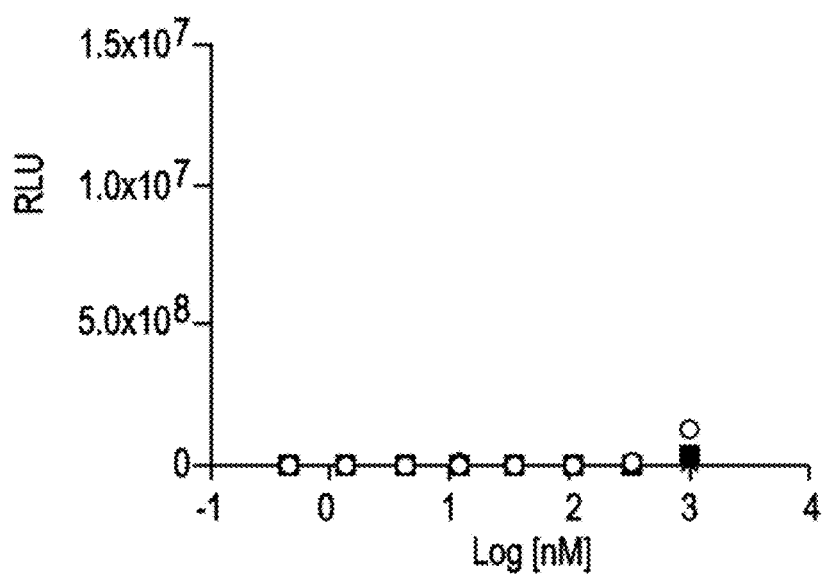
FIG. 21 is a plot depicting the results of a series of luciferase assays that demonstrate that antigen binding protein fusions comprising the anti-β-Klotho antibody 2G10, joined via a linker, to a truncated form of FGF21 comprising either residues 1-169 (SEQ ID NO: 342), when the configuration of the fusion is FGF21-linker-2G10 (from N- to C-terminus) residues or residues 1-170 (SEQ ID NO: 343) when the configuration of the fusion is 2G10-linker-FGF21 (from N- to C-terminus), show no detectable activity in a luciferase assay using AMID reporter cells expressing FGFR1c but not β-Klotho in the absence of FGF21.

The fusions were then tested in a luciferase assay using AM1D reporter cells expressing β-Klotho and FGFR1c. When the fusion proteins were incubated with 3 nM FGF21 none of the fusions demonstrated any detectable antagonistic activity, as shown in FIG. 19. Additionally, FIG. 20 demonstrates that the fusions did not interact with human α-Klotho, confirming the specificity of the fusions for β-Klotho. Moreover, no activity was detected in the luciferase assay using AM1D reporter cells expressing β-Klotho and FGFR1c in the absence of β-Klotho.

CONCLUSIONS

Summarily, the results of the experiments presented in this Example 17 indicate that the antigen binding protein-FGF21 fusions that were generated (a) specifically bind human β-Klotho and induce FGF21-mediated activity; and (b) do not induce FGF21-mediated activity in the absence of human β-Klotho.

The disclosed fusion proteins combine the benefits of natural FGF21 activity while deleting a proteolysis-sensitive region of the C-terminus, which otherwise leads to inactivation of FGF21 through degradation. The β-Klotho binding antibody provided target specific binding with a higher affinity than FGF21 alone. In particular, the binding affinity of FGF21 to β-Klotho is in the range of 10-20 nM whereas the binding affinity for β-Klotho specific antibodies is typically in the sub-nanmolar or picomolar range. This highly enhanced affinity is expected to improve the in vivo targeting efficiency. Furthermore, in contrast to the fast clearance of exogenously administered FGF21 observed in vivo ($t_{1/2}$<30 min), these antibody-based fusion proteins are expected to exhibit an extended half-life of days or weeks, reminiscent of a typical antibody in vivo. These beneficial attributes combine make the disclosed fusion proteins uniquely suited for a therapeutic role.

Each reference cited herein is incorporated by reference in its entirety for all that it teaches and for all purposes.

The present disclosure is not to be limited in scope by the specific embodiments described herein, which are intended as illustrations of individual aspects of the disclosure, and functionally equivalent methods and components form aspects of the disclosure. Indeed, various modifications of the disclosure, in addition to those shown and described herein will become apparent to those skilled in the art from the foregoing description and accompanying drawings. Such modifications are intended to fall within the scope of the appended claims.

What is claimed is:

1. An antigen binding protein comprising:
   (a) a light chain variable domain comprising; (i) a light chain CDR1 comprising an amino acid sequence of SEQ ID NO: 107; (ii) a light chain CDR2 comprising an amino acid sequence of SEQ ID NO: 113; (iii) a light chain CDR3 comprising an amino acid sequence of SEQ ID NO: 121; and
   (b) a heavy chain variable domain comprising: (i) a heavy chain CDR1 comprising an amino acid sequence of SEQ ID NO: 84; (ii) a heavy chain CDR2 comprising an amino acid sequence of SEQ ID NO: 90; and (iii) a heavy chain CDR3 comprising an amino acid sequence of SEQ ID NO: 99; wherein the antigen binding protein specifically binds β-Klotho.

2. The isolated antigen binding protein of claim 1, wherein the antigen binding protein comprises: (a) a light chain variable domain sequence comprising SEQ ID NO: 18; and (b) a heavy chain variable domain sequence comprising SEQ ID NO: 29; wherein the antigen binding protein specifically binds to β-Klotho.

3. The antigen binding protein of claim 2, wherein the antigen binding protein comprises: (a) the light chain constant sequence of SEQ ID NO: 13; (b) the light chain constant sequence of SEQ ID NO:15; (c) the heavy chain constant sequence of SEQ ID NO: 9; or (d) the light chain constant sequence of SEQ ID NO: 13 or SEQ ID NO: 15 and the heavy chain constant sequence of SEQ ID NO: 9.

4. The antigen binding protein of claim 1, wherein the antigen binding protein comprises a human antibody, a humanized antibody, chimeric antibody, a monoclonal antibody, a polyclonal antibody, a recombinant antibody, an antigen-binding antibody fragment, a single chain antibody, a diabody, a triabody, a tetrabody, a Fab fragment, an F(fa')x fragment, a domain antibody, an IgD antibody, an IgE antibody, an IgM antibody, an IgG1 antibody, an IgG2 antibody, an IgG3 antibody, an IgG4 antibody, or an IgG4 antibody having at least one mutation in the hinge region.

5. The antigen binding protein of claim 1, that, when bound to β-Klotho: (a) binds to β-Klotho with substantially the same Kd as a reference antibody; (b) induces FGF21-like signaling of 10% or greater than the signaling induced by a wild-type FGF21 standard comprising the mature form of SEQ ID NO:2 as measured in an ELK-luciferase reporter assay; (c) exhibits an EC50 of 10 nM or less of FGF21-like signaling in an assay selected from the group consisting of: (i) a FGFR1c/β-Klotho-mediated in vitro recombinant cell-based assay; (d) exhibits an EC50 of less than 10 nM of agonistic activity on FGFR1c in the presence of β-Klotho in an in vitro recombinant FGFR1c receptor mediated reporter assay; and (e) an EC50 of greater than 1 μM of agonistic activity on FGFR1c in the absence of β-Klotho in an in vitro recombinant FGFR1c receptor mediated reporter assay; and (f) competes for binding with a reference antibody to β-Klotho, wherein the reference antibody comprises one or more of the following combinations of light chain and heavy chain variable domain sequences: L1H1, L2H2, L3H3, L4H4, L5H5, L6H6, L7H7, L8H8, L9H9, L10H10 and L11H11.

6. The antigen binding protein of claim 5, that, when bound to β-Klotho: (a) lowers blood glucose in an animal model; (b) lowers serum lipid levels in an animal model; or (c) (a) and (b).

7. A pharmaceutical composition comprising the antigen binding protein of claim 1 in admixture with a pharmaceutically acceptable carrier thereof.

8. An isolated nucleic acid comprising a polynucleotide sequence encoding the light chain variable domain, the heavy chain variable domain, or both, of the antigen binding protein of claim 1.

9. An isolated nucleic acid comprising a polynucleotide sequence encoding, SEQ ID NO: 18, SEQ ID NO: 29, or both.

10. An expression vector comprising the nucleic acid of claim 9.

11. An isolated cell comprising the nucleic acid of claim 9.

12. The isolated cell of claim 11, comprising an expression vector comprising the nucleic acid.

13. A method of producing an antigen binding protein that specifically binds to β-Klotho comprising incubating the host cell of claim 12 under conditions that allow it to express the antigen binding protein.

14. An antigen binding protein of any of claims 1, 2, and 3-6, wherein the heavy chain comprises a peptide that specifically binds to one or more of FGFR1c, FGFR2c, FGFR3c, and FGFR4.

15. A heavy chain of the antigen binding protein of claim 14, wherein the peptide comprises one or more of: TRLWKYWV (SEQ ID NO: 184); RRLYIFWE (SEQ ID NO: 185); YKAWGYYV (SEQ ID NO: 186); YQAWGYYV (SEQ ID NO: 187); YQAWGYLV (SEQ ID NO: 188); YQAWGYFV (SEQ ID NO: 189); FTWVFWNV (SEQ ID NO: 190); YQVWGYFV (SEQ ID NO: 191); YKWLKWNL (SEQ ID NO: 192); RRLYIFEW (SEQ ID NO: 193); WAERGG (SEQ ID NO: 194); GGWAVGRI (SEQ ID NO: 195); YKYLVFWV (SEQ ID NO: 196); YKYLSYWV (SEQ ID NO: 197); YKTAWYWK (SEQ ID NO: 198); YVFHKWWV (SEQ ID NO: 199); YVFYLWWK (SEQ ID NO: 200); YRWLHWHV (SEQ ID NO: 201); YKFLFWHA (SEQ ID NO: 202); RRQWGFWV (SEQ ID NO: 203); YSAWSFWV (SEQ ID NO: 204); LARWGFWV (SEQ ID NO: 205); YDAWGYWV (SEQ ID NO: 206); WRKYYHFWVS (SEQ ID NO: 207); KRLYGLFWYD (SEQ ID NO: 208); KKHWSSLFFE (SEQ ID NO: 209); KAWPYSWEAV (SEQ ID NO: 210); EWYCGVLFNCQQ (SEQ ID NO: 211); HFGCGVIFNCVSD (SEQ ID NO: 212); WELCASGYGWCYLH (SEQ ID NO: 213); APSCKSYIGFGLYHCWDG (SEQ ID NO: 214); and or HFKCGMGLFECADP (SEQ ID NO: 215).

16. The antigen binding protein heavy chain of claim 15, wherein the heavy chain comprises a CH2 loop, a CH3 loop or both a CH2 and a CH3 loop.

17. The heavy chain of claim 16, wherein the heavy chain comprises a CH3 loop.

18. The heavy chain of claim 17, wherein the CH3 loop comprises the peptide.

19. The heavy chain of claim 16, wherein the heavy chain comprises a CH2 loop.

20. The heavy chain of claim 19, wherein the CH2 loop comprises the peptide.

21. An antigen binding protein comprising the heavy chain of claim 15, 18 or 20.

22. A pharmaceutical composition comprising the antigen binding protein of claim 14 in admixture with a pharmaceutically acceptable carrier thereof.

23. An isolated nucleic acid comprising a polynucleotide sequence encoding the light chain variable domain, the heavy chain variable domain, or both, of the antigen binding protein of claim 14.

24. The isolated nucleic acid of claim 23, comprising a polynucleotide sequence encoding SEQ ID NO: 18, SEQ ID NO: 29, or both.

25. An expression vector comprising the nucleic acid of claim 24.

26. An isolated cell comprising the nucleic acid of claim 24.

27. The isolated cell of claim 26, comprising an expression vector comprising the nucleic acid.

28. A method of producing an antigen binding protein that specifically binds to β-Klotho comprising incubating the host cell of claim 27 under conditions that allow it to express the antigen binding protein.

29. An antigen binding protein-FGF21 fusion comprising: (a) an antigen binding component, wherein the antigen binding component comprises an antigen binding protein of claim 1; and (b) an FGF21 component.

30. The antigen binding protein-FGF21 fusion of claim 29, wherein the FGF21 component comprises at least 25 consecutive residues of SEQ ID NO:341.

31. The antigen binding protein-FGF21 fusion of claim 30, wherein the FGF21 component comprises (a) SEQ ID NO:342 or (b) SEQ ID NO:343.

32. The antigen binding protein-FGF21 fusion of claim 29, further comprising a linker.

33. The antigen binding protein-FGF21 fusion of claim 29 or claim 31, wherein the antigen binding component comprises SEQ ID NOS:18 and 29.

34. The antigen binding protein-FGF21 fusion of claim 32, wherein the linker is selected from the group consisting of $(G_4S)_3$, (SEQ ID NO: 336) $(G_4S)_6$ (SEQ ID NO: 337), $(G_4S)_9$ (SEQ ID NO: 338), $(G_4S)_{12}$ (SEQ ID NO: 339) and $(G_4S)_{15}$ (SEQ ID NO: 340).

35. The antigen binding protein-FGF21 fusion of claim 29, wherein the FGF21 component is joined to the heavy chain of the antigen binding component.

36. The antigen binding protein-FGF21 fusion of claim 35, wherein the heavy chain comprises one or more of: SEQ ID NOs:316, 320, 322, 324, 326, 318, 328, 330, 332 and 334.

37. The antigen binding protein-FGF21 fusion of claim 29, wherein the FGF21 component is joined to the light chain of the antigen binding component.

38. The antigen binding protein of claim 29, that, when bound to β-Klotho, β-Klotho and one or more of FGFR1c, FGFR2c, FGFR3c, and FGFR4: (a) lowers blood glucose in an animal model; (b) lowers serum lipid levels in an animal model; or (c) (a) and (b).

39. A pharmaceutical composition comprising an antigen binding protein-FGF21 fusion of claim 29, further comprising a pharmaceutically acceptable carrier.

40. A method of treating a condition in a subject in need of such treatment comprising administering a therapeutically effective amount of the composition of claim 7, 22, or 39 to the subject, wherein the condition is treatable by lowering blood glucose.

41. The method of claim 40, wherein the condition is selected from type 2 diabetes, obesity, dyslipidemia, NASH, cardiovascular disease, and metabolic syndrome.

* * * * *

SEQUENCE LISTING

```
<160> NUMBER OF SEQ ID NOS: 344

<210> SEQ ID NO 1
<211> LENGTH: 630
<212> TYPE: DNA
<213> ORGANISM: Homo sapiens

<400> SEQUENCE: 1
atggactcgg acgagaccgg gttcgagcac tcaggactgt gggtttctgt gctggctggt        60
cttctgctgg gagcctgcca ggcacacccc atccctgact ccagtcctct cctgcaattc       120
gggggccaag tccggcagcg gtacctctac acagatgatg cccagcagac agaagcccac       180
ctggagatca gggaggatgg gacggtgggg ggcgctgctg accagagccc cgaaagtctc       240
ctgcagctga aagccttgaa gccgggagtt attcaaatct ggggagtcaa gacatccagg       300
ttcctgtgcc agcggccaga tggggccctg tatggatcgc tccactttga ccctgaggcc       360
```

```
tgcagcttcc gggagctgct tcttgaggac ggatacaatg tttaccagtc cgaagcccac      420
ggcctcccgc tgcacctgcc agggaacaag tccccacacc gggaccctgc accccgagga      480
ccagctcgct tcctgccact accaggcctg cccccgcac ccccggagcc acccggaatc       540 ctggccccc agcccccga tgtgggctcc tcggaccctc tgagcatggt gggaccttcc        600
cagggccgaa gccccagcta cgcttcctga                                        630

<210> SEQ ID NO 2
<211> LENGTH: 209
<212> TYPE: PRT
<213> ORGANISM: Homo sapiens

<400> SEQUENCE: 2

Met Asp Ser Asp Glu Thr Gly Phe Glu His Ser Gly Leu Trp Val Ser
1               5                   10                  15

Val Leu Ala Gly Leu Leu Leu Gly Ala Cys Gln Ala His Pro Ile Pro
                20                  25                  30

Asp Ser Ser Pro Leu Leu Gln Phe Gly Gly Gln Val Arg Gln Arg Tyr
            35                  40                  45

Leu Tyr Thr Asp Asp Ala Gln Gln Thr Glu Ala His Leu Glu Ile Arg
    50                  55                  60

Glu Asp Gly Thr Val Gly Gly Ala Ala Asp Gln Ser Pro Glu Ser Leu
65                  70                  75                  80

Leu Gln Leu Lys Ala Leu Lys Pro Gly Val Ile Gln Ile Leu Gly Val
                85                  90                  95

Lys Thr Ser Arg Phe Leu Cys Gln Arg Pro Asp Gly Ala Leu Tyr Gly
                100                 105                 110

Ser Leu His Phe Asp Pro Glu Ala Cys Ser Phe Arg Glu Leu Leu Leu
            115                 120                 125

Glu Asp Gly Tyr Asn Val Tyr Gln Ser Glu Ala His Gly Leu Pro Leu
    130                 135                 140

His Leu Pro Gly Asn Lys Ser Pro His Arg Asp Pro Ala Pro Arg Gly
145                 150                 155                 160

Pro Ala Arg Phe Leu Pro Leu Pro Gly Leu Pro Pro Ala Pro Pro Glu
                165                 170                 175

Pro Pro Gly Ile Leu Ala Pro Gln Pro Pro Asp Val Gly Ser Ser Asp
                180                 185                 190

Pro Leu Ser Met Val Gly Pro Ser Gln Gly Arg Ser Pro Ser Tyr Ala
            195                 200                 205

Ser

<210> SEQ ID NO 3
<211> LENGTH: 2469
<212> TYPE: DNA
<213> ORGANISM: Homo sapiens

<400> SEQUENCE: 3
atgtggagct ggaagtgcct cctcttctgg gctgtgctgg tcacagccac actctgcacc        60
gctaggccgt ccccgacctt gcctgaacaa gcccagccct ggggagcccc tgtggaagtg      120
gagtccttcc tggtccaccc cggtgacctg ctgcagcttc gctgtcggct gcgggacgat      180
gtgcagagca tcaactggct gcgggacggg gtgcagctgg cggaaagcaa ccgcacccgc      240
atcacagggg aggaggtgga ggtgcaggac tccgtgcccg cagactccgg cctctatgct      300
tgcgtaacca gcagcccctc gggcagtgac accacctact ctccgtcaa tgtttcagat      360
```

```
gctctcccct cctcggagga tgatgatgat gatgatgact cctcttcaga ggagaaagaa      420
acagataaca ccaaaccaaa ccgtatgccc gtagctccat attggacatc accagaaaag      480
atggaaaaga aattgcatgc agtgccggct gccaagacag tgaagttcaa atgcccttcc      540
agtgggacac caaacccaac actgcgctgg ttgaaaaatg caaagaatt caaacctgac       600 cacagaattg gaggctacaa ggtccgttat gccacctgga gcatcataat ggactctgtg      660
gtgccctctg acaagggcaa ctacacctgc attgtggaga tgagtacgg cagcatcaac       720 cacacatacc agctggatgt cgtggagcgg tcccctcacc ggcccatcct gcaagcaggg      780
ttgcccgcca acaaaacagt ggccctgggt agcaacgtgg agttcatgtg taaggtgtac      840
agtgacccgc agccgcacat ccagtggcta aagcacatcg aggtgaatgg gagcaagatt      900
ggcccagaca acctgcctta tgtccagatc ttgaagactg ctggagttaa taccaccgac      960
aaagagatgg aggtgcttca cttaagaaat gtctcctttg aggacgcagg ggagtatacg     1020
tgcttggcgg gtaactctat cggactctcc catcactctg catggttgac cgttctggaa     1080
gccctggaag agaggccggc agtgatgacc tcgcccctgt acctggagat catcatctat     1140
tgcacagggg ccttcctcat ctcctgcatg gtggggtcgg tcatcgtcta caagatgaag     1200
agtggtacca gaagagtga cttccacagc cagatggctg tgcacaagct ggccaagagc      1260
atccctctgc gcagacaggt aacagtgtct gctgactcca gtgcatccat gaactctggg     1320
gttcttctgg ttcggccatc acggctctcc tccagtggga ctcccatgct agcagggtgc     1380
tctgagtatg agcttcccga agaccctcgc tgggagctgc ctcgggacag actggtctta     1440 ggcaaaccccc tgggagaggg ctgctttggg caggtggtgt tggcagaggc tatcgggctg     1500
gacaaggaca aacccaaccg tgtgaccaaa gtggctgtga agatgttgaa gtcggacgca      1560
acagagaaag acttgtcaga cctgatctca gaaatggaga tgatgaagat gatcgggaag     1620
cataagaata tcatcaacct gctgggggcc tgcacgcagg atggtccctt gtatgtcatc     1680
gtggagtatg cctccaaggg caacctgcgg gagtacctgc aggcccggag gccccaggg     1740 ctggaatact gctacaaccc cagccacaac ccagaggagc agctctcctc caaggacctg     1800
gtgtcctgcg cctaccaggt ggcccgaggc atggagtatc tggcctccaa gaagtgcata     1860
caccgagacc tggcagccag gaatgtcctg gtgacagagg acaatgtgat gaagatagca     1920
gactttggcc tcgcacggga cattcaccac atcgactact ataaaaagac aaccaacggc     1980
cgactgcctg tgaagtggat ggcacccgag gcattatttg accggatcta caccaccag     2040 agtgatgtgt ggtctttcgg ggtgctcctg tgggagatct tcactctggg cggctcccca     2100 tacccccggtg tgcctgtgga ggaacttttc aagctgctga aggagggtca ccgcatggac     2160
aagcccagta actgcaccaa cgagctgtac atgatgatgc gggactgctg gcatgcagtg     2220
ccctcacaga gacccacctt caagcagctg gtggaagacc tggaccgcat cgtggccttg     2280
acctccaacc aggagtacct ggacctgtcc atgcccctgg accagtactc ccccagcttt     2340
cccgacaccc ggagctctac gtgctcctca ggggaggatt ccgtcttctc tcatgagccg     2400
ctgcccgagg agccctgcct gccccgacac ccagcccagc ttgccaatgg cggactcaaa     2460
cgccgctga                                                            2469
```

<210> SEQ ID NO 4
<211> LENGTH: 822
<212> TYPE: PRT
<213> ORGANISM: Homo sapiens

<400> SEQUENCE: 4

-continued

```
Met Trp Ser Trp Lys Cys Leu Leu Phe Trp Ala Val Leu Val Thr Ala
1               5                   10                  15

Thr Leu Cys Thr Ala Arg Pro Ser Pro Thr Leu Pro Glu Gln Ala Gln
            20                  25                  30

Pro Trp Gly Ala Pro Val Glu Val Glu Ser Phe Leu Val His Pro Gly
        35                  40                  45

Asp Leu Leu Gln Leu Arg Cys Arg Leu Arg Asp Asp Val Gln Ser Ile
50                  55                  60

Asn Trp Leu Arg Asp Gly Val Gln Leu Ala Glu Ser Asn Arg Thr Arg
65                  70                  75                  80

Ile Thr Gly Glu Glu Val Glu Val Gln Asp Ser Val Pro Ala Asp Ser
                85                  90                  95

Gly Leu Tyr Ala Cys Val Thr Ser Ser Pro Ser Gly Ser Asp Thr Thr
            100                 105                 110

Tyr Phe Ser Val Asn Val Ser Asp Ala Leu Pro Ser Ser Glu Asp Asp
        115                 120                 125

Asp Asp Asp Asp Asp Ser Ser Ser Glu Glu Lys Glu Thr Asp Asn Thr
130                 135                 140

Lys Pro Asn Arg Met Pro Val Ala Pro Tyr Trp Thr Ser Pro Glu Lys
145                 150                 155                 160

Met Glu Lys Lys Leu His Ala Val Pro Ala Ala Lys Thr Val Lys Phe
                165                 170                 175

Lys Cys Pro Ser Ser Gly Thr Pro Asn Pro Thr Leu Arg Trp Leu Lys
            180                 185                 190

Asn Gly Lys Glu Phe Lys Pro Asp His Arg Ile Gly Gly Tyr Lys Val
        195                 200                 205

Arg Tyr Ala Thr Trp Ser Ile Ile Met Asp Ser Val Val Pro Ser Asp
210                 215                 220

Lys Gly Asn Tyr Thr Cys Ile Val Glu Asn Glu Tyr Gly Ser Ile Asn
225                 230                 235                 240

His Thr Tyr Gln Leu Asp Val Val Glu Arg Ser Pro His Arg Pro Ile
                245                 250                 255

Leu Gln Ala Gly Leu Pro Ala Asn Lys Thr Val Ala Leu Gly Ser Asn
            260                 265                 270

Val Glu Phe Met Cys Lys Val Tyr Ser Asp Pro Gln Pro His Ile Gln
        275                 280                 285

Trp Leu Lys His Ile Glu Val Asn Gly Ser Lys Ile Gly Pro Asp Asn
290                 295                 300

Leu Pro Tyr Val Gln Ile Leu Lys Thr Ala Gly Val Asn Thr Thr Asp
305                 310                 315                 320

Lys Glu Met Glu Val Leu His Leu Arg Asn Val Ser Phe Glu Asp Ala
                325                 330                 335

Gly Glu Tyr Thr Cys Leu Ala Gly Asn Ser Ile Gly Leu Ser His His
            340                 345                 350

Ser Ala Trp Leu Thr Val Leu Glu Ala Leu Glu Glu Arg Pro Ala Val
        355                 360                 365

Met Thr Ser Pro Leu Tyr Leu Glu Ile Ile Ile Tyr Cys Thr Gly Ala
370                 375                 380

Phe Leu Ile Ser Cys Met Val Gly Ser Val Ile Val Tyr Lys Met Lys
385                 390                 395                 400

Ser Gly Thr Lys Lys Ser Asp Phe His Ser Gln Met Ala Val His Lys
                405                 410                 415
```

```
Leu Ala Lys Ser Ile Pro Leu Arg Arg Gln Val Thr Val Ser Ala Asp
            420                 425                 430

Ser Ser Ala Ser Met Asn Ser Gly Val Leu Leu Val Arg Pro Ser Arg
        435                 440                 445

Leu Ser Ser Ser Gly Thr Pro Met Leu Ala Gly Val Ser Glu Tyr Glu
450                 455                 460

Leu Pro Glu Asp Pro Arg Trp Glu Leu Pro Arg Asp Arg Leu Val Leu
465                 470                 475                 480

Gly Lys Pro Leu Gly Glu Gly Cys Phe Gly Gln Val Val Leu Ala Glu
                485                 490                 495

Ala Ile Gly Leu Asp Lys Asp Lys Pro Asn Arg Val Thr Lys Val Ala
            500                 505                 510

Val Lys Met Leu Lys Ser Asp Ala Thr Glu Lys Asp Leu Ser Asp Leu
            515                 520                 525

Ile Ser Glu Met Glu Met Met Lys Met Ile Gly Lys His Lys Asn Ile
530                 535                 540

Ile Asn Leu Leu Gly Ala Cys Thr Gln Asp Gly Pro Leu Tyr Val Ile
545                 550                 555                 560

Val Glu Tyr Ala Ser Lys Gly Asn Leu Arg Glu Tyr Leu Gln Ala Arg
                565                 570                 575

Arg Pro Pro Gly Leu Glu Tyr Cys Tyr Asn Pro Ser His Asn Pro Glu
                580                 585                 590

Glu Gln Leu Ser Ser Lys Asp Leu Val Ser Cys Ala Tyr Gln Val Ala
            595                 600                 605

Arg Gly Met Glu Tyr Leu Ala Ser Lys Lys Cys Ile His Arg Asp Leu
            610                 615                 620

Ala Ala Arg Asn Val Leu Val Thr Glu Asp Asn Val Met Lys Ile Ala
625                 630                 635                 640

Asp Phe Gly Leu Ala Arg Asp Ile His His Ile Asp Tyr Tyr Lys Lys
                645                 650                 655

Thr Thr Asn Gly Arg Leu Pro Val Lys Trp Met Ala Pro Glu Ala Leu
                660                 665                 670

Phe Asp Arg Ile Tyr Thr His Gln Ser Asp Val Trp Ser Phe Gly Val
            675                 680                 685

Leu Leu Trp Glu Ile Phe Thr Leu Gly Gly Ser Pro Tyr Pro Gly Val
690                 695                 700

Pro Val Glu Glu Leu Phe Lys Leu Leu Lys Glu Gly His Arg Met Asp
705                 710                 715                 720

Lys Pro Ser Asn Cys Thr Asn Glu Leu Tyr Met Met Met Arg Asp Cys
                725                 730                 735

Trp His Ala Val Pro Ser Gln Arg Pro Thr Phe Lys Gln Leu Val Glu
            740                 745                 750

Asp Leu Asp Arg Ile Val Ala Leu Thr Ser Asn Gln Glu Tyr Leu Asp
            755                 760                 765

Leu Ser Met Pro Leu Asp Gln Tyr Ser Pro Ser Phe Pro Asp Thr Arg
770                 775                 780

Ser Ser Thr Cys Ser Ser Gly Glu Asp Ser Val Phe Ser His Glu Pro
785                 790                 795                 800

Leu Pro Glu Glu Pro Cys Leu Pro Arg His Pro Ala Gln Leu Ala Asn
                805                 810                 815

Gly Gly Leu Lys Arg Arg
            820
```

```
<210> SEQ ID NO 5
<211> LENGTH: 374
<212> TYPE: PRT
<213> ORGANISM: Homo sapiens

<400> SEQUENCE: 5

Met Trp Ser Trp Lys Cys Leu Leu Phe Trp Ala Val Leu Val Thr Ala
1               5                   10                  15

Thr Leu Cys Thr Ala Arg Pro Ser Pro Thr Leu Pro Glu Gln Ala Gln
            20                  25                  30

Pro Trp Gly Ala Pro Val Glu Val Glu Ser Phe Leu Val His Pro Gly
        35                  40                  45

Asp Leu Leu Gln Leu Arg Cys Arg Leu Arg Asp Asp Val Gln Ser Ile
    50                  55                  60

Asn Trp Leu Arg Asp Gly Val Gln Leu Ala Glu Ser Asn Arg Thr Arg
65                  70                  75                  80

Ile Thr Gly Glu Glu Val Glu Val Gln Asp Ser Val Pro Ala Asp Ser
                85                  90                  95

Gly Leu Tyr Ala Cys Val Thr Ser Ser Pro Ser Gly Ser Asp Thr Thr
            100                 105                 110

Tyr Phe Ser Val Asn Val Ser Asp Ala Leu Pro Ser Ser Glu Asp Asp
        115                 120                 125

Asp Asp Asp Asp Asp Ser Ser Ser Glu Glu Lys Glu Thr Asp Asn Thr
    130                 135                 140

Lys Pro Asn Arg Met Pro Val Ala Pro Tyr Trp Thr Ser Pro Glu Lys
145                 150                 155                 160

Met Glu Lys Lys Leu His Ala Val Pro Ala Ala Lys Thr Val Lys Phe
                165                 170                 175

Lys Cys Pro Ser Ser Gly Thr Pro Asn Pro Thr Leu Arg Trp Leu Lys
            180                 185                 190

Asn Gly Lys Glu Phe Lys Pro Asp His Arg Ile Gly Gly Tyr Lys Val
        195                 200                 205

Arg Tyr Ala Thr Trp Ser Ile Ile Met Asp Ser Val Val Pro Ser Asp
    210                 215                 220

Lys Gly Asn Tyr Thr Cys Ile Val Glu Asn Glu Tyr Gly Ser Ile Asn
225                 230                 235                 240

His Thr Tyr Gln Leu Asp Val Val Glu Arg Ser Pro His Arg Pro Ile
                245                 250                 255

Leu Gln Ala Gly Leu Pro Ala Asn Lys Thr Val Ala Leu Gly Ser Asn
            260                 265                 270

Val Glu Phe Met Cys Lys Val Tyr Ser Asp Pro Gln Pro His Ile Gln
        275                 280                 285

Trp Leu Lys His Ile Glu Val Asn Gly Ser Lys Ile Gly Pro Asp Asn
    290                 295                 300

Leu Pro Tyr Val Gln Ile Leu Lys Thr Ala Gly Val Asn Thr Thr Asp
305                 310                 315                 320

Lys Glu Met Glu Val Leu His Leu Arg Asn Val Ser Phe Glu Asp Ala
                325                 330                 335

Gly Glu Tyr Thr Cys Leu Ala Gly Asn Ser Ile Gly Leu Ser His His
            340                 345                 350

Ser Ala Trp Leu Thr Val Leu Glu Ala Leu Glu Glu Arg Pro Ala Val
        355                 360                 365

Met Thr Ser Pro Leu Tyr
    370
```

<210> SEQ ID NO 6
<211> LENGTH: 3135
<212> TYPE: DNA
<213> ORGANISM: Homo sapiens

<400> SEQUENCE: 6

| | | | | | |
|---|---|---|---|---|---|
| atgaagccag | gctgtgcggc | aggatctcca | gggaatgaat | ggattttctt | cagcactgat | 60 |
| gaaataacca | cacgctatag | gaatacaatg | tccaacgggg | gattgcaaag | atctgtcatc | 120 |
| ctgtcagcac | ttattctgct | acgagctgtt | actggattct | ctggagatgg | aagagctata | 180 |
| tggtctaaaa | atcctaattt | tactccggta | aatgaaagtc | agctgtttct | ctatgacact | 240 |
| ttccctaaaa | acttttttctg | gggtattggg | actggagcat | tgcaagtgga | agggagttgg | 300 |
| aagaaggatg | gaaaaggacc | ttctatatgg | gatcatttca | tccacacaca | ccttaaaaat | 360 |
| gtcagcagca | cgaatggttc | cagtgacagt | tatattttc | tggaaaaaga | cttatcagcc | 420 |
| ctggatttta | taggagtttc | ttttatcaa | ttttcaattt | cctggccaag | gcttttcccc | 480 |
| gatggaatag | taacagttgc | caacgcaaaa | ggtctgcagt | actacagtac | tcttctggac | 540 |
| gctctagtgc | ttagaaacat | tgaacctata | gttactttat | accactggga | tttgcctttg | 600 |
| gcactacaag | aaaaatatgg | ggggtggaaa | atgatacca | taatagatat | cttcaatgac | 660 |
| tatgccacat | actgtttcca | gatgtttggg | gaccgtgtca | aatattggat | tacaattcac | 720 |
| aacccatatc | tagtggcttg | gcatgggtat | ggacaggta | tgcatgcccc | tggagagaag | 780 |
| ggaaatttag | cagctgtcta | cactgtggga | cacaacttga | tcaaggctca | ctcgaaagtt | 840 |
| tggcataact | acaacacaca | tttccgccca | catcagaagg | gttggttatc | gatcacgttg | 900 |
| ggatctcatt | ggatcgagcc | aaaccggtcg | gaaaacacga | tggatatatt | caaatgtcaa | 960 |
| caatccatgg | tttctgtgct | tggatggttt | gccaacccta | tccatgggga | tggcgactat | 1020 |
| ccagagggga | tgagaaagaa | gttgttctcc | gttctaccca | ttttctctga | agcagagaag | 1080 |
| catgagatga | gaggcacagc | tgatttcttt | gccttttctt | ttggacccaa | caacttcaag | 1140 |
| cccctaaaca | ccatggctaa | atgggacaa | atgtttcac | ttaatttaag | agaagcgctg | 1200 |
| aactggatta | aactggaata | caaccaaccct | cgaatcttga | ttgctgagaa | tggctggttc | 1260 |
| acagacagtc | gtgtgaaaac | agaagacacc | acggccatct | acatgatgaa | gaatttcctc | 1320 |
| agccaggtgc | ttcaagcaat | aaggttagat | gaaatacgag | tgtttggtta | tactgcctgg | 1380 |
| tctctcctgg | atggctttga | atggcaggat | gcttacacca | tccgccgagg | attattttat | 1440 |
| gtggatttta | acagtaaaca | gaaagagcgg | aaacctaagt | cttcagcaca | ctactacaaa | 1500 |
| cagatcatac | gagaaaatgg | ttttctttta | aaagagtcca | cgccagatgt | gcagggccag | 1560 |
| tttccctgtg | acttctcctg | gggtgtcact | gaatctgttc | ttaagcccga | gtctgtggct | 1620 |
| tcgtccccac | agttcagcga | tcctcatctg | tacgtgtgga | acgccactgg | caacagactg | 1680 |
| ttgcaccgag | tggaagggt | gaggctgaaa | acacgacccg | ctcaatgcac | agattttgta | 1740 |
| aacatcaaaa | aacaacttga | gatgttggca | agaatgaaag | tcacccacta | ccggtttgct | 1800 |
| ctggattggg | cctcggtcct | tcccactggc | aacctgtccg | cggtgaaccg | acaggccctg | 1860 |
| aggtactaca | ggtgcgtggt | cagtgagggg | ctgaagcttg | gcatctccgc | gatggtcacc | 1920 |
| ctgtattatc | cgacccacgc | ccacctaggc | ctccccgagc | ctctgttgca | tgccgacggg | 1980 |
| tggctgaacc | catcgacggc | cgaggccttc | caggcctacg | ctgggctgtg | cttccaggag | 2040 |
| ctgggggacc | tggtgaagct | ctggatcacc | atcaacgagc | ctaaccggct | aagtgacatc | 2100 |
| tacaaccgct | ctggcaacga | cacctacggg | gcggcgcaca | acctgctggt | ggcccacgcc | 2160 |

-continued

```
ctggcctggc gcctctacga ccggcagttc aggccctcac agcgcggggc cgtgtcgctg   2220
tcgctgcacg cggactgggc ggaacccgcc aaccccatg  ctgactcgca ctggagggcg   2280
gccgagcgct tcctgcagtt cgagatcgcc tggttcgccg agccgctctt caagaccggg   2340
gactaccccg cggccatgag ggaatacatt gcctccaagc accgacgggg gctttccagc   2400
tcggccctgc cgcgcctcac cgaggccgaa aggaggctgc tcaagggcac ggtcgacttc   2460
tgcgcgctca accacttcac cactaggttc gtgatgcacg agcagctggc cggcagccgc   2520
tacgactcgg acagggacat ccagtttctg caggacatca cccgcctgag ctcccccacg   2580
cgcctggctg tgattccctg gggggtgcgc aagctgctgc ggtgggtccg gaggaactac   2640
ggcgacatgg acatttacat caccgccagt ggcatcgacg accaggctct ggaggatgac   2700
cggctccgga gtactacct  agggaagtac cttcaggagg tgctgaaagc atacctgatt   2760
gataaagtca gaatcaaagg ctattatgca ttcaaactgg ctgaagagaa atctaaaccc   2820
agatttggat tcttcacatc tgattttaaa gctaaatcct caatacaatt ttacaacaaa   2880
gtgatcagca gcagggggctt ccctttttgag aacagtagtt ctagatgcag tcagacccaa   2940
gaaaatacag agtgcactgt ctgcttattc cttgtgcaga agaaaccact gatattcctg   3000
ggttgttgct tcttctccac cctggttcta ctcttatcaa ttgccatttt tcaaaggcag   3060
aagagaagaa agttttggaa agcaaaaaac ttacaacaca taccattaaa gaaaggcaag   3120
agagttgtta gctaa                                                    3135
```

<210> SEQ ID NO 7
<211> LENGTH: 1044
<212> TYPE: PRT
<213> ORGANISM: Homo sapiens

<400> SEQUENCE: 7

| Met | Lys | Pro | Gly | Cys | Ala | Ala | Gly | Ser | Pro | Gly | Asn | Glu | Trp | Ile | Phe |
|---|---|---|---|---|---|---|---|---|---|---|---|---|---|---|---|
| 1 | | | | 5 | | | | | 10 | | | | | 15 | |

| Phe | Ser | Thr | Asp | Glu | Ile | Thr | Thr | Arg | Tyr | Arg | Asn | Thr | Met | Ser | Asn |
| | | | 20 | | | | | 25 | | | | | 30 | | |

| Gly | Gly | Leu | Gln | Arg | Ser | Val | Ile | Leu | Ser | Ala | Leu | Ile | Leu | Leu | Arg |
| | | 35 | | | | | 40 | | | | | 45 | | | |

| Ala | Val | Thr | Gly | Phe | Ser | Gly | Asp | Gly | Arg | Ala | Ile | Trp | Ser | Lys | Asn |
| 50 | | | | | 55 | | | | | 60 | | | | | |

| Pro | Asn | Phe | Thr | Pro | Val | Asn | Glu | Ser | Gln | Leu | Phe | Leu | Tyr | Asp | Thr |
| 65 | | | | | 70 | | | | | 75 | | | | | 80 |

| Phe | Pro | Lys | Asn | Phe | Phe | Trp | Gly | Ile | Gly | Thr | Gly | Ala | Leu | Gln | Val |
| | | | | 85 | | | | | 90 | | | | | 95 | |

| Glu | Gly | Ser | Trp | Lys | Lys | Asp | Gly | Lys | Gly | Pro | Ser | Ile | Trp | Asp | His |
| | | | 100 | | | | | 105 | | | | | 110 | | |

| Phe | Ile | His | Thr | His | Leu | Lys | Asn | Val | Ser | Ser | Thr | Asn | Gly | Ser | Ser |
| | | 115 | | | | | 120 | | | | | 125 | | | |

| Asp | Ser | Tyr | Ile | Phe | Leu | Glu | Lys | Asp | Leu | Ser | Ala | Leu | Asp | Phe | Ile |
| 130 | | | | | 135 | | | | | 140 | | | | | |

| Gly | Val | Ser | Phe | Tyr | Gln | Phe | Ser | Ile | Ser | Trp | Pro | Arg | Leu | Phe | Pro |
| 145 | | | | | 150 | | | | | 155 | | | | | 160 |

| Asp | Gly | Ile | Val | Thr | Val | Ala | Asn | Ala | Lys | Gly | Leu | Gln | Tyr | Tyr | Ser |
| | | | | 165 | | | | | 170 | | | | | 175 | |

| Thr | Leu | Leu | Asp | Ala | Leu | Val | Leu | Arg | Asn | Ile | Glu | Pro | Ile | Val | Thr |
| | | | 180 | | | | | 185 | | | | | 190 | | |

-continued

```
Leu Tyr His Trp Asp Leu Pro Leu Ala Leu Gln Glu Lys Tyr Gly Gly
            195                 200                 205

Trp Lys Asn Asp Thr Ile Ile Asp Ile Phe Asn Asp Tyr Ala Thr Tyr
210                 215                 220

Cys Phe Gln Met Phe Gly Asp Arg Val Lys Tyr Trp Ile Thr Ile His
225                 230                 235                 240

Asn Pro Tyr Leu Val Ala Trp His Gly Tyr Gly Thr Gly Met His Ala
                245                 250                 255

Pro Gly Glu Lys Gly Asn Leu Ala Ala Val Tyr Thr Val Gly His Asn
                260                 265                 270

Leu Ile Lys Ala His Ser Lys Val Trp His Asn Tyr Asn Thr His Phe
            275                 280                 285

Arg Pro His Gln Lys Gly Trp Leu Ser Ile Thr Leu Gly Ser His Trp
290                 295                 300

Ile Glu Pro Asn Arg Ser Glu Asn Thr Met Asp Ile Phe Lys Cys Gln
305                 310                 315                 320

Gln Ser Met Val Ser Val Leu Gly Trp Phe Ala Asn Pro Ile His Gly
                325                 330                 335

Asp Gly Asp Tyr Pro Glu Gly Met Arg Lys Lys Leu Phe Ser Val Leu
                340                 345                 350

Pro Ile Phe Ser Glu Ala Glu Lys His Glu Met Arg Gly Thr Ala Asp
            355                 360                 365

Phe Phe Ala Phe Ser Phe Gly Pro Asn Asn Phe Lys Pro Leu Asn Thr
370                 375                 380

Met Ala Lys Met Gly Gln Asn Val Ser Leu Asn Leu Arg Glu Ala Leu
385                 390                 395                 400

Asn Trp Ile Lys Leu Glu Tyr Asn Asn Pro Arg Ile Leu Ile Ala Glu
                405                 410                 415

Asn Gly Trp Phe Thr Asp Ser Arg Val Lys Thr Glu Asp Thr Thr Ala
                420                 425                 430

Ile Tyr Met Met Lys Asn Phe Leu Ser Gln Val Leu Gln Ala Ile Arg
            435                 440                 445

Leu Asp Glu Ile Arg Val Phe Gly Tyr Thr Ala Trp Ser Leu Leu Asp
450                 455                 460

Gly Phe Glu Trp Gln Asp Ala Tyr Thr Ile Arg Arg Gly Leu Phe Tyr
465                 470                 475                 480

Val Asp Phe Asn Ser Lys Gln Lys Glu Arg Lys Pro Lys Ser Ser Ala
                485                 490                 495

His Tyr Tyr Lys Gln Ile Ile Arg Glu Asn Gly Phe Ser Leu Lys Glu
                500                 505                 510

Ser Thr Pro Asp Val Gln Gly Gln Phe Pro Cys Asp Phe Ser Trp Gly
            515                 520                 525

Val Thr Glu Ser Val Leu Lys Pro Glu Ser Val Ala Ser Ser Pro Gln
530                 535                 540

Phe Ser Asp Pro His Leu Tyr Val Trp Asn Ala Thr Gly Asn Arg Leu
545                 550                 555                 560

Leu His Arg Val Glu Gly Val Arg Leu Lys Thr Arg Pro Ala Gln Cys
                565                 570                 575

Thr Asp Phe Val Asn Ile Lys Lys Gln Leu Glu Met Leu Ala Arg Met
                580                 585                 590

Lys Val Thr His Tyr Arg Phe Ala Leu Asp Trp Ala Ser Val Leu Pro
            595                 600                 605

Thr Gly Asn Leu Ser Ala Val Asn Arg Gln Ala Leu Arg Tyr Tyr Arg
```

```
                610              615              620
Cys Val Val Ser Glu Gly Leu Lys Leu Gly Ile Ser Ala Met Val Thr
625              630              635              640

Leu Tyr Tyr Pro Thr His Ala His Leu Gly Leu Pro Glu Pro Leu Leu
                645              650              655

His Ala Asp Gly Trp Leu Asn Pro Ser Thr Ala Glu Ala Phe Gln Ala
                660              665              670

Tyr Ala Gly Leu Cys Phe Gln Glu Leu Gly Asp Leu Val Lys Leu Trp
                675              680              685

Ile Thr Ile Asn Glu Pro Asn Arg Leu Ser Asp Ile Tyr Asn Arg Ser
690              695              700

Gly Asn Asp Thr Tyr Gly Ala Ala His Asn Leu Leu Val Ala His Ala
705              710              715              720

Leu Ala Trp Arg Leu Tyr Asp Arg Gln Phe Arg Pro Ser Gln Arg Gly
                725              730              735

Ala Val Ser Leu Ser Leu His Ala Asp Trp Ala Glu Pro Ala Asn Pro
                740              745              750

Tyr Ala Asp Ser His Trp Arg Ala Ala Glu Arg Phe Leu Gln Phe Glu
                755              760              765

Ile Ala Trp Phe Ala Glu Pro Leu Phe Lys Thr Gly Asp Tyr Pro Ala
770              775              780

Ala Met Arg Glu Tyr Ile Ala Ser Lys His Arg Arg Gly Leu Ser Ser
785              790              795              800

Ser Ala Leu Pro Arg Leu Thr Glu Ala Glu Arg Arg Leu Leu Lys Gly
                805              810              815

Thr Val Asp Phe Cys Ala Leu Asn His Phe Thr Thr Arg Phe Val Met
                820              825              830

His Glu Gln Leu Ala Gly Ser Arg Tyr Asp Ser Asp Arg Asp Ile Gln
                835              840              845

Phe Leu Gln Asp Ile Thr Arg Leu Ser Ser Pro Thr Arg Leu Ala Val
                850              855              860

Ile Pro Trp Gly Val Arg Lys Leu Leu Arg Trp Val Arg Arg Asn Tyr
865              870              875              880

Gly Asp Met Asp Ile Tyr Ile Thr Ala Ser Gly Ile Asp Asp Gln Ala
                885              890              895

Leu Glu Asp Asp Arg Leu Arg Lys Tyr Tyr Leu Gly Lys Tyr Leu Gln
                900              905              910

Glu Val Leu Lys Ala Tyr Leu Ile Asp Lys Val Arg Ile Lys Gly Tyr
                915              920              925

Tyr Ala Phe Lys Leu Ala Glu Glu Lys Ser Lys Pro Arg Phe Gly Phe
930              935              940

Phe Thr Ser Asp Phe Lys Ala Lys Ser Ser Ile Gln Phe Tyr Asn Lys
945              950              955              960

Val Ile Ser Ser Arg Gly Phe Pro Phe Glu Asn Ser Ser Ser Arg Cys
                965              970              975

Ser Gln Thr Gln Glu Asn Thr Glu Cys Thr Val Cys Leu Phe Leu Val
                980              985              990

Gln Lys Lys Pro Leu Ile Phe Leu Gly Cys Cys Phe Phe Ser Thr Leu
                995             1000             1005

Val Leu Leu Leu Ser Ile Ala Ile Phe Gln Arg Gln Lys Arg Arg
                1010             1015             1020

Lys Phe Trp Lys Ala Lys Asn Leu Gln His Ile Pro Leu Lys Lys
                1025             1030             1035
```

```
Gly Lys Arg Val Val Ser
        1040

<210> SEQ ID NO 8
<211> LENGTH: 996
<212> TYPE: PRT
<213> ORGANISM: Homo sapiens

<400> SEQUENCE: 8

Met Lys Pro Gly Cys Ala Ala Gly Ser Pro Gly Asn Glu Trp Ile Phe
1               5                   10                  15

Phe Ser Thr Asp Glu Ile Thr Thr Arg Tyr Arg Asn Thr Met Ser Asn
            20                  25                  30

Gly Gly Leu Gln Arg Ser Val Ile Leu Ser Ala Leu Ile Leu Leu Arg
        35                  40                  45

Ala Val Thr Gly Phe Ser Gly Asp Gly Arg Ala Ile Trp Ser Lys Asn
    50                  55                  60

Pro Asn Phe Thr Pro Val Asn Glu Ser Gln Leu Phe Leu Tyr Asp Thr
65                  70                  75                  80

Phe Pro Lys Asn Phe Phe Trp Gly Ile Gly Thr Gly Ala Leu Gln Val
                85                  90                  95

Glu Gly Ser Trp Lys Lys Asp Gly Lys Gly Pro Ser Ile Trp Asp His
            100                 105                 110

Phe Ile His Thr His Leu Lys Asn Val Ser Ser Thr Asn Gly Ser Ser
        115                 120                 125

Asp Ser Tyr Ile Phe Leu Glu Lys Asp Leu Ser Ala Leu Asp Phe Ile
    130                 135                 140

Gly Val Ser Phe Tyr Gln Phe Ser Ile Ser Trp Pro Arg Leu Phe Pro
145                 150                 155                 160

Asp Gly Ile Val Thr Val Ala Asn Ala Lys Gly Leu Gln Tyr Tyr Ser
                165                 170                 175

Thr Leu Leu Asp Ala Leu Val Leu Arg Asn Ile Glu Pro Ile Val Thr
            180                 185                 190

Leu Tyr His Trp Asp Leu Pro Leu Ala Leu Gln Glu Lys Tyr Gly Gly
        195                 200                 205

Trp Lys Asn Asp Thr Ile Ile Asp Ile Phe Asn Asp Tyr Ala Thr Tyr
    210                 215                 220

Cys Phe Gln Met Phe Gly Asp Arg Val Lys Tyr Trp Ile Thr Ile His
225                 230                 235                 240

Asn Pro Tyr Leu Val Ala Trp His Gly Tyr Gly Thr Gly Met His Ala
                245                 250                 255

Pro Gly Glu Lys Gly Asn Leu Ala Ala Val Tyr Thr Val Gly His Asn
            260                 265                 270

Leu Ile Lys Ala His Ser Lys Val Trp His Asn Tyr Asn Thr His Phe
        275                 280                 285

Arg Pro His Gln Lys Gly Trp Leu Ser Ile Thr Leu Gly Ser His Trp
    290                 295                 300

Ile Glu Pro Asn Arg Ser Glu Asn Thr Met Asp Ile Phe Lys Cys Gln
305                 310                 315                 320

Gln Ser Met Val Ser Val Leu Gly Trp Phe Ala Asn Pro Ile His Gly
                325                 330                 335

Asp Gly Asp Tyr Pro Glu Gly Met Arg Lys Lys Leu Phe Ser Val Leu
            340                 345                 350

Pro Ile Phe Ser Glu Ala Glu Lys His Glu Met Arg Gly Thr Ala Asp
```

```
            355                 360                 365
Phe Phe Ala Phe Ser Phe Gly Pro Asn Asn Phe Lys Pro Leu Asn Thr
370                 375                 380

Met Ala Lys Met Gly Gln Asn Val Ser Leu Asn Leu Arg Glu Ala Leu
385                 390                 395                 400

Asn Trp Ile Lys Leu Glu Tyr Asn Asn Pro Arg Ile Leu Ile Ala Glu
                    405                 410                 415

Asn Gly Trp Phe Thr Asp Ser Arg Val Lys Thr Glu Asp Thr Thr Ala
                420                 425                 430

Ile Tyr Met Met Lys Asn Phe Leu Ser Gln Val Leu Gln Ala Ile Arg
                435                 440                 445

Leu Asp Glu Ile Arg Val Phe Gly Tyr Thr Ala Trp Ser Leu Leu Asp
450                 455                 460

Gly Phe Glu Trp Gln Asp Ala Tyr Thr Ile Arg Arg Gly Leu Phe Tyr
465                 470                 475                 480

Val Asp Phe Asn Ser Lys Gln Lys Glu Arg Lys Pro Lys Ser Ser Ala
                485                 490                 495

His Tyr Tyr Lys Gln Ile Ile Arg Glu Asn Gly Phe Ser Leu Lys Glu
                500                 505                 510

Ser Thr Pro Asp Val Gln Gly Gln Phe Pro Cys Asp Phe Ser Trp Gly
                515                 520                 525

Val Thr Glu Ser Val Leu Lys Pro Glu Ser Val Ala Ser Ser Pro Gln
530                 535                 540

Phe Ser Asp Pro His Leu Tyr Val Trp Asn Ala Thr Gly Asn Arg Leu
545                 550                 555                 560

Leu His Arg Val Glu Gly Val Arg Leu Lys Thr Arg Pro Ala Gln Cys
                565                 570                 575

Thr Asp Phe Val Asn Ile Lys Lys Gln Leu Glu Met Leu Ala Arg Met
                580                 585                 590

Lys Val Thr His Tyr Arg Phe Ala Leu Asp Trp Ala Ser Val Leu Pro
                595                 600                 605

Thr Gly Asn Leu Ser Ala Val Asn Arg Gln Ala Leu Arg Tyr Tyr Arg
610                 615                 620

Cys Val Val Ser Glu Gly Leu Lys Leu Gly Ile Ser Ala Met Val Thr
625                 630                 635                 640

Leu Tyr Tyr Pro Thr His Ala His Leu Gly Leu Pro Glu Pro Leu Leu
                645                 650                 655

His Ala Asp Gly Trp Leu Asn Pro Ser Thr Ala Glu Ala Phe Gln Ala
                660                 665                 670

Tyr Ala Gly Leu Cys Phe Gln Glu Leu Gly Asp Leu Val Lys Leu Trp
                675                 680                 685

Ile Thr Ile Asn Glu Pro Asn Arg Leu Ser Asp Ile Tyr Asn Arg Ser
                690                 695                 700

Gly Asn Asp Thr Tyr Gly Ala Ala His Asn Leu Leu Val Ala His Ala
705                 710                 715                 720

Leu Ala Trp Arg Leu Tyr Asp Arg Gln Phe Arg Pro Ser Gln Arg Gly
                725                 730                 735

Ala Val Ser Leu Ser Leu His Ala Asp Trp Ala Glu Pro Ala Asn Pro
                740                 745                 750

Tyr Ala Asp Ser His Trp Arg Ala Ala Glu Arg Phe Leu Gln Phe Glu
                755                 760                 765

Ile Ala Trp Phe Ala Glu Pro Leu Phe Lys Thr Gly Asp Tyr Pro Ala
                770                 775                 780
```

```
Ala Met Arg Glu Tyr Ile Ala Ser Lys His Arg Gly Leu Ser Ser
785                 790                 795                 800

Ser Ala Leu Pro Arg Leu Thr Glu Ala Glu Arg Leu Leu Lys Gly
            805                 810                 815

Thr Val Asp Phe Cys Ala Leu Asn His Phe Thr Thr Arg Phe Val Met
        820                 825                 830

His Glu Gln Leu Ala Gly Ser Arg Tyr Asp Ser Asp Arg Asp Ile Gln
        835                 840                 845

Phe Leu Gln Asp Ile Thr Arg Leu Ser Ser Pro Thr Arg Leu Ala Val
850                 855                 860

Ile Pro Trp Gly Val Arg Lys Leu Leu Arg Trp Val Arg Arg Asn Tyr
865                 870                 875                 880

Gly Asp Met Asp Ile Tyr Ile Thr Ala Ser Gly Ile Asp Asp Gln Ala
                885                 890                 895

Leu Glu Asp Asp Arg Leu Arg Lys Tyr Tyr Leu Gly Lys Tyr Leu Gln
                900                 905                 910

Glu Val Leu Lys Ala Tyr Leu Ile Asp Lys Val Arg Ile Lys Gly Tyr
            915                 920                 925

Tyr Ala Phe Lys Leu Ala Glu Glu Lys Ser Lys Pro Arg Phe Gly Phe
        930                 935                 940

Phe Thr Ser Asp Phe Lys Ala Lys Ser Ser Ile Gln Phe Tyr Asn Lys
945                 950                 955                 960

Val Ile Ser Ser Arg Gly Phe Pro Phe Glu Asn Ser Ser Arg Cys
                965                 970                 975

Ser Gln Thr Gln Glu Asn Thr Glu Cys Thr Val Cys Leu Phe Leu Val
            980                 985                 990

Gln Lys Lys Pro
        995

<210> SEQ ID NO 9
<211> LENGTH: 330
<212> TYPE: PRT
<213> ORGANISM: Homo sapiens

<400> SEQUENCE: 9

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
```

```
                145                 150                 155                 160
        Tyr Val Asp Gly Val Glu Val His Asn Ala Lys Thr Lys Pro Arg Glu
                        165                 170                 175

Glu Gln Tyr Gln Ser Thr Tyr Arg Val Val Ser Val Leu Thr Val Leu
                        180                 185                 190

His Gln Asp Trp Leu Asn Gly Lys Glu Tyr Lys Cys Lys Val Ser Asn
                        195                 200                 205

Lys Ala Leu Pro Ala Pro Ile Glu Lys Thr Ile Ser Lys Ala Lys Gly
                210                 215                 220

Gln Pro Arg Glu Pro Gln Val Tyr Thr Leu Pro Pro Ser Arg Asp Glu
        225                 230                 235                 240

Leu Thr Lys Asn Gln Val Ser Leu Thr Cys Leu Val Lys Gly Phe Tyr
                        245                 250                 255

Pro Ser Asp Ile Ala Val Glu Trp Glu Ser Asn Gly Gln Pro Glu Asn
                        260                 265                 270

Asn Tyr Lys Thr Thr Pro Pro Val Leu Asp Ser Asp Gly Ser Phe Phe
                        275                 280                 285

Leu Tyr Ser Lys Leu Thr Val Asp Lys Ser Arg Trp Gln Gln Gly Asn
                290                 295                 300

Val Phe Ser Cys Ser Val Met His Glu Ala Leu His Asn His Tyr Thr
        305                 310                 315                 320

Gln Lys Ser Leu Ser Leu Ser Pro Gly Lys
                        325                 330

<210> SEQ ID NO 10
<211> LENGTH: 978
<212> TYPE: DNA
<213> ORGANISM: Homo sapiens

<400> SEQUENCE: 10
gcctccacca agggcccatc ggtcttcccc ctggcgccct gctccaggag cacctccgag      60
agcacagcgg ccctgggctg cctggtcaag gactacttcc ccgaaccggt gacggtgtcg     120
tggaactcag gcgctctgac cagcggcgtg cacaccttcc cagctgtcct acagtcctca     180
ggactctact ccctcagcag cgtggtgacc gtgccctcca gcaacttcgg cacccagacc     240
tacacctgca acgtagatca caagcccagc aacaccaagg tggacaagac agttgagcgc     300
aaatgttgtg tcgagtgccc accgtgccca gcaccacctg tggcaggacc gtcagtcttc     360
ctcttccccc caaaacccaa ggacaccctc atgatctccc ggacccctga ggtcacgtgc     420
gtggtggtgg acgtgagcca cgaagacccc gaggtccagt tcaactggta cgtggacggc     480
gtggaggtgc ataatgccaa gacaaagcca cgggaggagc agttcaacag cacgttccgt     540
gtggtcagcg tcctcaccgt tgtgcaccag gactggctga acggcaagga gtacaagtgc     600
aaggtctcca acaaaggcct cccagccccc atcgagaaaa ccatctccaa aaccaaaggg     660
cagccccgag aaccacaggt gtacaccctg cccccatccc gggaggagat gaccaagaac     720
caggtcagcc tgacctgcct ggtcaaaggc ttctacccca gcgacatcgc cgtggagtgg     780
gagagcaatg ggcagccgga gaacaactac aagaccacac ctcccatgct ggactccgac     840
ggctccttct tcctctacag caagctcacc gtggacaaga gcaggtggca gcaggggaac     900
gtcttctcat gctccgtgat gcatgaggct ctgcacaacc actacacgca gaagagcctc     960
tccctgtctc cgggtaaa                                                   978

<210> SEQ ID NO 11
```

```
<211> LENGTH: 464
<212> TYPE: PRT
<213> ORGANISM: Homo sapiens

<400> SEQUENCE: 11

Gln Val Gln Leu Val Glu Ser Gly Gly Gly Val Val Gln Pro Gly Arg
1               5                   10                  15

Ser Leu Arg Leu Ser Cys Ala Ala Ser Arg Phe Ser Phe Ser Arg Tyr
            20                  25                  30

Gly Met His Trp Val Arg Gln Ala Pro Gly Lys Gly Leu Glu Trp Val
        35                  40                  45

Ala Val Ile Trp Phe Asp Gly Arg Asn Gln Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Val Glu Asp Thr Ala Val Tyr Tyr Cys
                85                  90                  95

Ala Arg Asp His Pro Val Val Gly Thr Ser Phe Asp Tyr Trp Gly Gln
            100                 105                 110

Gly Thr Leu Val Thr Val Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Gln Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Gly Gly Cys Tyr Gln Ala Trp
        355                 360                 365

Gly Tyr Tyr Val Cys Gly Gly Thr Lys Asn Gln Val Ser Leu Thr Cys
    370                 375                 380

Leu Val Lys Gly Phe Tyr Pro Ser Asp Ile Ala Val Glu Trp Glu Ser
```

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
            405                 410                 415

Arg Trp Gln Gln Gly Asn Val Phe Ser Cys Ser Val Met His Glu Ala
        420                 425                 430

Leu His Asn His Tyr Thr Gln Lys Ser Leu Ser Leu Ser Pro Gly Lys
    435                 440                 445

450                 455                 460

<210> SEQ ID NO 12
<211> LENGTH: 1392
<212> TYPE: DNA
<213> ORGANISM: Homo sapiens

<400> SEQUENCE: 12
caggtgcagt tggtggagtc tgggggaggc gtggtccagc ctggagggtc cctgagactc      60
tcctgtgcag cgtctagatt ctccttcagt agatatggca tgcactgggt ccgccaggct     120
ccaggcaagg ggctggagtg ggtggcagtt atatggtttg atggaagaaa tcaatactat     180
gcagactccg tgaaggggcg attcaccatc tccagagaca attccaagaa tacgctgttt     240
ctgcaaatga acagcctgag agtcgaggac acggctgtgt attactgtgc gagagatcac     300
ccagtagttg gtacgagctt tgactactgg ggccagggaa ccctggtcac cgtctctagt     360
gcctccacca agggcccatc ggtcttcccc ctggcaccct cctccaagag cacctctggg     420
ggcacagcgg ccctgggctg cctggtcaag gactacttcc ccgaaccggt gacggtgtcg     480
tggaactcag gcgccctgac cagcggcgtg cacaccttcc cggctgtcct acagtcctca     540
ggactctact ccctcagcag cgtggtgacc gtgccctcca gcagcttggg cacccagacc     600
tacatctgca acgtgaatca caagcccagc aacaccaagg tggacaagaa agttgagccc     660
aaatcttgtg acaaaactca cacatgccca ccgtgcccag cacctgaact cctgggggga     720
ccgtcagtct tcctcttccc cccaaaaccc aaggacaccc tcatgatctc ccggacccct     780
gaggtcacat gcgtggtggt ggacgtgagc cacgaagacc ctgaggtcaa gttcaactgg     840
tacgtggacg gcgtggaggt gcataatgcc aagacaaagc cgcgggagga gcagtaccag     900
agcacgtacc gtgtggtcag cgtcctcacc gtcctgcacc aggactggct gaatggcaag     960
gagtacaagt gcaaggtctc caacaaagcc ctcccagccc ccatcgagaa aaccatctcc    1020
aaagccaaag gcagccccg agaaccacag gtgtacaccc tgcccccatc ccgggatgag    1080
ctgggtggtt gctaccaggc tggggctac tacgtgtgcg gtggtaccaa gaaccaggtc    1140
agcctgacct gcctggtcaa aggcttctat cccagcgaca tcgccgtgga gtgggagagc    1200
aatgggcagc cggagaacaa ctacaagacc acgcctcccg tgctggactc cgacggctcc    1260
ttcttcctct atagcaagct caccgtggac aagagcaggt ggcagcaggg gaacgtcttc    1320
tcatgctccg tgatgcatga ggctctgcac aaccactaca cgcagaagag cctctccctg    1380
tctccgggta aa                                                        1392

<210> SEQ ID NO 13
<211> LENGTH: 107
<212> TYPE: PRT
<213> ORGANISM: Homo sapiens

<400> SEQUENCE: 13

Arg Thr Val Ala Ala Pro Ser Val Phe Ile Phe Pro Pro Ser Asp Glu

```
1               5                   10                  15
Gln Leu Lys Ser Gly Thr Ala Ser Val Val Cys Leu Leu Asn Asn Phe
            20                  25                  30
Tyr Pro Arg Glu Ala Lys Val Gln Trp Lys Val Asp Asn Ala Leu Gln
            35                  40                  45
Ser Gly Asn Ser Gln Glu Ser Val Thr Glu Gln Asp Ser Lys Asp Ser
            50                  55                  60
Thr Tyr Ser Leu Ser Ser Thr Leu Thr Leu Ser Lys Ala Asp Tyr Glu
65                  70                  75                  80
Lys His Lys Val Tyr Ala Cys Glu Val Thr His Gln Gly Leu Ser Ser
                    85                  90                  95
Pro Val Thr Lys Ser Phe Asn Arg Gly Glu Cys
                100                 105

<210> SEQ ID NO 14
<211> LENGTH: 321
<212> TYPE: DNA
<213> ORGANISM: Homo sapiens

<400> SEQUENCE: 14
cgtacggtgg ctgcaccatc tgtcttcatc ttcccgccat ctgatgagca gttgaaatct      60
ggaactgcct ctgttgtgtg cctgctgaat aacttctatc ccagagaggc caaagtacag     120
tggaaggtgg ataacgccct ccaatcgggt aactcccagg agagtgtcac agagcaggac     180
agcaaggaca gcacctacag cctcagcagc accctgacgc tgagcaaagc agactacgag     240
aaacacaaag tctacgcctg cgaagtcacc catcagggcc tgagctcgcc cgtcacaaag     300
agcttcaaca ggggagagtg t                                               321

<210> SEQ ID NO 15
<211> LENGTH: 106
<212> TYPE: PRT
<213> ORGANISM: Homo sapiens

<400> SEQUENCE: 15

Gly Gln Pro Lys Ala Asn Pro Thr Val Thr Leu Phe Pro Pro Ser Ser
1               5                   10                  15
Glu Glu Leu Gln Ala Asn Lys Ala Thr Leu Val Cys Leu Ile Ser Asp
            20                  25                  30
Phe Tyr Pro Gly Ala Val Thr Val Ala Trp Lys Ala Asp Gly Ser Pro
            35                  40                  45
Val Lys Ala Gly Val Glu Thr Thr Lys Pro Ser Lys Gln Ser Asn Asn
            50                  55                  60
Lys Tyr Ala Ala Ser Ser Tyr Leu Ser Leu Thr Pro Glu Gln Trp Lys
65                  70                  75                  80
Ser His Arg Ser Tyr Ser Cys Gln Val Thr His Glu Gly Ser Thr Val
                    85                  90                  95
Glu Lys Thr Val Ala Pro Thr Glu Cys Ser
                100                 105

<210> SEQ ID NO 16
<211> LENGTH: 318
<212> TYPE: DNA
<213> ORGANISM: Homo sapiens

<400> SEQUENCE: 16
ggtcagccca aggccaaccc cactgtcact ctgttcccgc cctcctctga ggagctccaa      60
```

```
gccaacaagg ccacactagt gtgtctgatc agtgacttct acccgggagc tgtgacagtg    120
gcctggaagg cagatggcag ccccgtcaag gcgggagtgg agaccaccaa accctccaaa    180
cagagcaaca acaagtacgc ggccagcagc tacctgagcc tgacgcccga gcagtggaag    240
tcccacagaa gctacagctg ccaggtcacg catgaaggga gcaccgtgga agacagtg     300 gcccctacag aatgttca                                                  318
```

<210> SEQ ID NO 17
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide <400> SEQUENCE: 17

```
Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asn Thr Tyr Leu Ser Trp Leu Gln Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Asp Asp Val Gly Ile Tyr Tyr Cys Met Gln Ala
                85                  90                  95

Ile Glu Phe Pro Trp Thr Phe Gly Gln Gly Thr Gln Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 18
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide <400> SEQUENCE: 18

```
Gln Ser Val Leu Thr Gln Pro Pro Ser Val Ser Ala Ala Pro Gly Gln
1               5                   10                  15

Lys Val Thr Val Ser Cys Ser Gly Ser Ser Ser Asn Ile Gly Asn Asn
            20                  25                  30
```

```
Tyr Val Ser Trp Tyr Gln Gln Leu Pro Gly Thr Ala Pro Lys Leu Leu
            35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Glu Tyr Tyr Cys Gly Thr Trp Asp Ser Ser Leu
                85                  90                  95

Ser Val Val Ala Phe Gly Gly Gly Thr Lys Leu Thr Val Leu Gly Gln
            100                 105                 110

Pro Lys Ala Asn Pro Thr Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Gly Ser Pro Val Lys
145                 150                 155                 160

Ala Gly Val Glu Thr Thr Lys Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 19
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Asn Asn Tyr
            20                  25                  30

Leu Asn Trp Tyr Gln Gln Lys Leu Gly Lys Ala Pro Lys Leu Leu Ile
        35                  40                  45

Tyr Asp Thr Ser Asn Leu Glu Thr Gly Val Pro Ser Arg Phe Ser Gly
    50                  55                  60

Ser Gly Phe Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Leu Phe Thr
                85                  90                  95

Phe Gly Gln Gly Thr Arg Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
```

```
                    165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
            195                 200                 205

Asn Arg Gly Glu Cys
    210

<210> SEQ ID NO 20
<211> LENGTH: 227
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 21
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Gln Thr Val Val Thr Gln Glu Pro Ser Phe Ser Val Ser Pro Gly Gly
```

```
1               5                   10                  15
Thr Val Thr Leu Thr Cys Gly Val Ser Ser Gly Ser Val Ser Thr Arg
                20                  25                  30

Tyr Tyr Pro Ser Trp Tyr Gln Gln Thr Pro Gly Gln Ala Pro Arg Thr
            35                  40                  45

Leu Ile Asn Ser Thr Asn Thr Arg Ser Ser Gly Val Pro Asp Arg Phe
        50                  55                  60

Ser Gly Ser Ile Leu Gly Asn Lys Ala Ala Leu Thr Ile Thr Gly Ala
65                  70                  75                  80

Gln Ala Asp Asp Glu Ser Asp Tyr Phe Cys Val Leu Tyr Met Gly Ser
                85                  90                  95

Gly Ile Trp Val Phe Gly Gly Gly Thr Lys Leu Thr Val Leu Gly Gln
                100                 105                 110

Pro Lys Ala Asn Pro Thr Val Thr Leu Phe Pro Pro Ser Ser Glu Glu
            115                 120                 125

Leu Gln Ala Asn Lys Ala Thr Leu Val Cys Leu Ile Ser Asp Phe Tyr
        130                 135                 140

Pro Gly Ala Val Thr Val Ala Trp Lys Ala Asp Gly Ser Pro Val Lys
145                 150                 155                 160

Ala Gly Val Glu Thr Thr Lys Pro Ser Lys Gln Ser Asn Asn Lys Tyr
                165                 170                 175

Ala Ala Ser Ser Tyr Leu Ser Leu Thr Pro Glu Gln Trp Lys Ser His
                180                 185                 190

Arg Ser Tyr Ser Cys Gln Val Thr His Glu Gly Ser Thr Val Glu Lys
            195                 200                 205

Thr Val Ala Pro Thr Glu Cys Ser
        210                 215

<210> SEQ ID NO 22
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val His Tyr
                20                  25                  30

Asp Gly Asn Thr Tyr Leu Ser Trp Leu Gln Gln Arg Pro Gly Gln Pro
            35                  40                  45

Pro Arg Leu Leu Ile Tyr Lys Ile Ser Asn Arg Phe Ser Gly Val Pro
        50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Ile Tyr Tyr Cys Met Gln Ala
                85                  90                  95

Leu Glu Phe Pro Trp Thr Phe Gly Gln Gly Thr Lys Val Glu Ile Lys
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140
```

```
Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 23
<211> LENGTH: 219
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 23

```
Asp Ile Val Met Thr Gln Thr Pro Leu Thr Ser Pro Val Thr Leu Gly
1               5                   10                  15

Gln Pro Ala Ser Ile Ser Cys Arg Ser Ser Gln Ser Leu Val His Tyr
            20                  25                  30

Asp Gly Asn Thr Tyr Leu Ser Trp Leu Gln Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Ile Tyr Tyr Cys Met Gln Ala
                85                  90                  95

Leu Glu Phe Pro Trp Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 24
<211> LENGTH: 219
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 24

```
Asp Ile Val Met Thr Gln Thr Pro Leu Ser Pro Val Thr Leu Gly
1               5                   10                  15

Gln Pro Ala Ser Ile Ser Cys Arg Ser Ser Gln Ser Leu Val His Tyr
            20                  25                  30

Asp Gly Asn Thr Tyr Leu Ser Trp Leu Gln Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Ala Ala Glu Asp Val Gly Ile Tyr Tyr Cys Met Gln Ala
                85                  90                  95

Leu Glu Phe Pro Trp Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 25
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Arg Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Val Val Phe Gly Gly Gly Thr Lys Leu Thr Val Leu Gly Gln
            100                 105                 110

Pro Lys Ala Asn Pro Thr Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140
```

```
Pro Gly Ala Val Thr Val Ala Trp Lys Ala Asp Gly Ser Pro Val Lys
145                 150                 155                 160

Ala Gly Val Glu Thr Thr Lys Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 26
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Asn Arg Pro Ser Gly Ile Pro Asp Arg Phe Ser
50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Glu Thr Trp Asp Ser Ser Leu
                85                  90                  95

Ser Ala Gly Val Phe Gly Gly Gly Thr Lys Leu Thr Val Leu Gly Gln
            100                 105                 110

Pro Lys Ala Asn Pro Thr Val Thr Leu Phe Pro Pro Ser Ser Glu Glu
        115                 120                 125

Leu Gln Ala Asn Lys Ala Thr Leu Val Cys Leu Ile Ser Asp Phe Tyr
130                 135                 140

Pro Gly Ala Val Thr Val Ala Trp Lys Ala Asp Gly Ser Pro Val Lys
145                 150                 155                 160

Ala Gly Val Glu Thr Thr Lys Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 27
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27
```

Gln Ser Val Leu Thr Gln Pro Pro Ser Val Ser Ala Ala Pro Gly Gln
1               5                   10                  15

Lys Val Thr Ile Ser Cys Ser Gly Ser Ser Asn Ile Gly Asn Asn
            20                  25                  30

Tyr Val Ser Trp Tyr Gln Gln Leu Pro Gly Thr Ala Pro Lys Leu Leu
            35                  40                  45

Ile Tyr Asp Asn Asn Lys Arg Pro Ser Gly Ile Pro Asp Arg Phe Ser
50                      55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Val Val Phe Gly Gly Gly Thr Lys Leu Thr Val Leu Gly Gln
            100                 105                 110

Pro Lys Ala Asn Pro Thr Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Gly Ser Pro Val Lys
145                 150                 155                 160

Ala Gly Val Glu Thr Thr Lys Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 28
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
            35                  40                  45

Gly Trp Ile Asn Pro Asn Ser Gly Gly Thr Asn Ser Ala Gln Lys Phe
50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Ala Thr Ser Gly Trp Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly

```
            130                 135                 140
Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
                180                 185                 190

Ser Leu Gly Thr Gln Thr Tyr Ile Cys Asn Val Asn His Lys Pro Ser
                195                 200                 205

Asn Thr Lys Val Asp Lys Lys Val Glu Pro Lys Ser Cys Asp Lys Thr
                210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
                275                 280                 285

Lys Thr Lys Pro Arg Glu Glu Gln Tyr Gln Ser Thr Tyr Arg Val Val
                290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Arg Asp Glu Leu Thr Lys Asn Gln Val Ser Leu Thr Cys
                355                 360                 365

Leu Val Lys Gly Phe Tyr Pro Ser Asp Ile Ala Val Glu Trp Glu Ser
                370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Lys
                435                 440                 445

<210> SEQ ID NO 29
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Gln Val Gln Leu Val Glu Ser Gly Gly Gly Val Val Gln Pro Gly Arg
1               5                   10                  15

Ser Leu Arg Leu Ser Cys Ala Ala Ser Arg Phe Ser Phe Ser Arg Tyr
                20                  25                  30

Gly Met His Trp Val Arg Gln Ala Pro Gly Lys Gly Leu Glu Trp Val
                35                  40                  45
```

```
Ala Val Ile Trp Phe Asp Gly Arg Asn Gln Tyr Tyr Ala Asp Ser Val
 50                  55                  60
Lys Gly Arg Phe Thr Ile Ser Arg Asp Asn Ser Lys Asn Thr Leu Phe
 65                  70                  75                  80
Leu Gln Met Asn Ser Leu Arg Val Glu Asp Thr Ala Val Tyr Tyr Cys
                 85                  90                  95
Ala Arg Asp His Pro Val Val Gly Thr Ser Phe Asp Tyr Trp Gly Gln
                100                 105                 110
Gly Thr Leu Val Thr Val Ser Ser Ala Ser Thr Lys Gly Pro Ser Val
                115                 120                 125
Phe Pro Leu Ala Pro Ser Ser Lys Ser Thr Ser Gly Gly Thr Ala Ala
130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
                180                 185                 190
Ser Ser Ser Leu Gly Thr Gln Thr Tyr Ile Cys Asn Val Asn His Lys
                195                 200                 205
Pro Ser Asn Thr Lys Val Asp Lys Lys Val Glu Pro Lys Ser Cys Asp
210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
                260                 265                 270
Asp Pro Glu Val Lys Phe Asn Trp Tyr Val Asp Gly Val Glu Val His
                275                 280                 285
Asn Ala Lys Thr Lys Pro Arg Glu Glu Gln Tyr Gln Ser Thr Tyr Arg
                290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
                340                 345                 350
Thr Leu Pro Pro Ser Arg Asp Glu Leu Thr Lys Asn Gln Val Ser Leu
                355                 360                 365
Thr Cys Leu Val Lys Gly Phe Tyr Pro Ser Asp Ile Ala Val Glu Trp
                370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
                420                 425                 430
Glu Ala Leu His Asn His Tyr Thr Gln Lys Ser Leu Ser Leu Ser Pro
                435                 440                 445
Gly Lys
450
```

```
<210> SEQ ID NO 30
<211> LENGTH: 452
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Gly Tyr Asp Gly Ser Tyr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Ser Asn Trp Asn Tyr Gly Gly Ser Phe Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Gln Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365
```

```
Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
                435                 440                 445

Ser Pro Gly Lys
    450

<210> SEQ ID NO 31

<400> SEQUENCE: 31

000

<210> SEQ ID NO 32
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Glu Val Gln Leu Leu Glu Ser Gly Gly Gly Leu Val Gln Pro Glu Gly
1               5                   10                  15

Ser Leu Arg Leu Ser Cys Ala Ala Ser Gly Phe Thr Phe Ser Ile Tyr
            20                  25                  30

Ala Met Ser Trp Val Arg Gln Ala Pro Gly Lys Gly Leu Glu Trp Val
        35                  40                  45

Ser Asp Ile Ser Gly Arg Gly Gly Tyr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Asp Asp Thr Ala Val Tyr Tyr Cys
                85                  90                  95

Ala Lys Asp Arg Ser Ile Ala Val Ala Gly Pro Phe Asp Phe Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Val Glu Pro Lys Ser Cys
    210                 215                 220

Asp Lys Thr His Thr Cys Pro Pro Cys Pro Ala Pro Glu Leu Leu Gly
```

225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
                260                 265                 270

Glu Asp Pro Glu Val Lys Phe Asn Trp Tyr Val Asp Gly Val Glu Val
                275                 280                 285

His Asn Ala Lys Thr Lys Pro Arg Glu Glu Gln Tyr Gln Ser Thr Tyr
            290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
                340                 345                 350

Tyr Thr Leu Pro Pro Ser Arg Asp Glu Leu Thr Lys Asn Gln Val Ser
                355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
                435                 440                 445

Pro Gly Lys
    450

<210> SEQ ID NO 33
<211> LENGTH: 444
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ala Tyr
                20                  25                  30

Tyr Met His Trp Val Arg Gln Ala Pro Gly Gln Gly Leu Glu Trp Met
            35                  40                  45

Gly Trp Ile Asn Pro Asn Ser Gly Gly Thr Asn Ser Ala Gln Lys Phe
    50                  55                  60

Gln Gly Arg Val Thr Met Thr Arg Asp Thr Ser Ile Arg Thr Ala Tyr
65                  70                  75                  80

Met Glu Leu Ser Trp Leu Arg Ser Asp Asp Thr Ala Val Tyr Tyr Cys
                85                  90                  95

Ala Arg Asp Ala Thr Ser Gly Trp Phe Asp Ile Trp Gly Gln Gly Thr
                100                 105                 110

Pro Val Thr Val Ser Ser Ala Ser Thr Lys Gly Pro Ser Val Phe Pro
            115                 120                 125

```
Leu Ala Pro Cys Ser Arg Ser Thr Ser Glu Ser Thr Ala Ala Leu Gly
            130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Asn Phe Gly Thr Gln Thr Tyr Thr Cys Asn Val Asp His Lys Pro Ser
        195                 200                 205

Asn Thr Lys Val Asp Lys Thr Val Glu Arg Lys Cys Cys Val Glu Cys
210                 215                 220

Pro Pro Cys Pro Ala Pro Pro Val Ala Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Phe Arg Val Val Ser Val Leu Thr
290                 295                 300

Val Val His Gln Asp Trp Leu Asn Gly Lys Glu Tyr Lys Cys Lys Val
305                 310                 315                 320

Ser Asn Lys Gly Leu Pro Ala Pro Ile Glu Lys Thr Ile Ser Lys Thr
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Ser Asn Gly Gln Pro
370                 375                 380

Glu Asn Tyr Lys Thr Thr Pro Pro Met Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Lys
        435                 440

<210> SEQ ID NO 34
<211> LENGTH: 444
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ala Tyr
            20                  25                  30

Tyr Met His Trp Val Arg Gln Ala Pro Gly Gln Gly Leu Glu Trp Met
        35                  40                  45
```

Gly Trp Ile Asn Pro Asn Ser Gly Thr Asn Ser Ala Gln Lys Phe
            50                  55                  60

Gln Gly Arg Val Thr Met Thr Arg Asp Thr Ser Ile Arg Thr Ala Tyr
 65                  70                  75                  80

Met Glu Leu Ser Trp Leu Arg Ser Asp Thr Ala Val Tyr Tyr Cys
                 85                  90                  95

Ala Arg Asp Ala Thr Ser Gly Trp Phe Asp Phe Trp Gly Gln Gly Thr
                100                 105                 110

Pro Val Thr Val Ser Ser Ala Ser Thr Lys Gly Pro Ser Val Phe Pro
                115                 120                 125

Leu Ala Pro Cys Ser Arg Ser Thr Ser Glu Ser Thr Ala Ala Leu Gly
                130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
                180                 185                 190

Asn Phe Gly Thr Gln Thr Tyr Thr Cys Asn Val Asp His Lys Pro Ser
                195                 200                 205

Asn Thr Lys Val Asp Lys Thr Val Glu Arg Lys Cys Cys Val Glu Cys
210                 215                 220

Pro Pro Cys Pro Ala Pro Pro Val Ala Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Gln Phe
                260                 265                 270

Asn Trp Tyr Val Asp Gly Val Glu Val His Asn Ala Lys Thr Lys Pro
                275                 280                 285

Arg Glu Glu Gln Phe Asn Ser Thr Phe Arg Val Val Ser Val Leu Thr
290                 295                 300

Val Val His Gln Asp Trp Leu Asn Gly Lys Glu Tyr Lys Cys Lys Val
305                 310                 315                 320

Ser Asn Lys Gly Leu Pro Ala Pro Ile Glu Lys Thr Ile Ser Lys Thr
                325                 330                 335

Lys Gly Gln Pro Arg Glu Pro Gln Val Tyr Thr Leu Pro Pro Ser Arg
                340                 345                 350

Glu Glu Met Thr Lys Asn Gln Val Ser Leu Thr Cys Leu Val Lys Gly
                355                 360                 365

Phe Tyr Pro Ser Asp Ile Ala Val Glu Trp Glu Ser Asn Gly Gln Pro
                370                 375                 380

Glu Asn Asn Tyr Lys Thr Thr Pro Pro Met Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
                420                 425                 430

Tyr Thr Gln Lys Ser Leu Ser Leu Ser Pro Gly Lys
                435                 440

<210> SEQ ID NO 35
<211> LENGTH: 444

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35
```

| Gln | Val | Gln | Leu | Val | Gln | Ser | Gly | Ala | Glu | Val | Arg | Lys | Pro | Gly | Ala |
|---|---|---|---|---|---|---|---|---|---|---|---|---|---|---|---|
| 1 | | | | 5 | | | | | 10 | | | | | 15 | |

| Ser | Val | Lys | Val | Ser | Cys | Lys | Ala | Ser | Gly | Tyr | Thr | Phe | Thr | Ala | Tyr |
|---|---|---|---|---|---|---|---|---|---|---|---|---|---|---|---|
| | | | 20 | | | | | 25 | | | | | 30 | | |

| Tyr | Met | His | Trp | Val | Arg | Gln | Ala | Pro | Gly | Gln | Gly | Leu | Glu | Trp | Met |
|---|---|---|---|---|---|---|---|---|---|---|---|---|---|---|---|
| | | 35 | | | | | 40 | | | | | 45 | | | |

| Gly | Trp | Ile | Asn | Pro | Tyr | Ser | Gly | Gly | Thr | Asn | Ser | Ala | Gln | Lys | Phe |
|---|---|---|---|---|---|---|---|---|---|---|---|---|---|---|---|
| | 50 | | | | | 55 | | | | | 60 | | | | |

| Gln | Gly | Arg | Val | Thr | Met | Thr | Arg | Asp | Thr | Ser | Ile | Ser | Thr | Ala | Tyr |
|---|---|---|---|---|---|---|---|---|---|---|---|---|---|---|---|
| 65 | | | | | 70 | | | | | 75 | | | | | 80 |

| Met | Glu | Leu | Ser | Trp | Leu | Arg | Ser | Asp | Asp | Thr | Ala | Val | Tyr | Tyr | Cys |
|---|---|---|---|---|---|---|---|---|---|---|---|---|---|---|---|
| | | | | 85 | | | | | 90 | | | | | 95 | |

| Ala | Arg | Asp | Ala | Thr | Ser | Gly | Trp | Phe | Asp | Phe | Trp | Gly | Gln | Gly | Thr |
|---|---|---|---|---|---|---|---|---|---|---|---|---|---|---|---|
| | | | 100 | | | | | 105 | | | | | 110 | | |

| Leu | Val | Thr | Val | Ser | Ser | Ala | Ser | Thr | Lys | Gly | Pro | Ser | Val | Phe | Pro |
|---|---|---|---|---|---|---|---|---|---|---|---|---|---|---|---|
| | | 115 | | | | | 120 | | | | | 125 | | | |

| Leu | Ala | Pro | Cys | Ser | Arg | Ser | Thr | Ser | Glu | Ser | Thr | Ala | Ala | Leu | Gly |
|---|---|---|---|---|---|---|---|---|---|---|---|---|---|---|---|
| | 130 | | | | | 135 | | | | | 140 | | | | |

| Cys | Leu | Val | Lys | Asp | Tyr | Phe | Pro | Glu | Pro | Val | Thr | Val | Ser | Trp | Asn |
|---|---|---|---|---|---|---|---|---|---|---|---|---|---|---|---|
| 145 | | | | | 150 | | | | | 155 | | | | | 160 |

| Ser | Gly | Ala | Leu | Thr | Ser | Gly | Val | His | Thr | Phe | Pro | Ala | Val | Leu | Gln |
|---|---|---|---|---|---|---|---|---|---|---|---|---|---|---|---|
| | | | | 165 | | | | | 170 | | | | | 175 | |

| Ser | Ser | Gly | Leu | Tyr | Ser | Leu | Ser | Val | Val | Thr | Val | Pro | Ser | Ser |
|---|---|---|---|---|---|---|---|---|---|---|---|---|---|---|
| | | | 180 | | | | | 185 | | | | | 190 | |

| Asn | Phe | Gly | Thr | Gln | Thr | Tyr | Thr | Cys | Asn | Val | Asp | His | Lys | Pro | Ser |
|---|---|---|---|---|---|---|---|---|---|---|---|---|---|---|---|
| | | 195 | | | | | 200 | | | | | 205 | | | |

| Asn | Thr | Lys | Val | Asp | Lys | Thr | Val | Glu | Arg | Lys | Cys | Cys | Val | Glu | Cys |
|---|---|---|---|---|---|---|---|---|---|---|---|---|---|---|---|
| | 210 | | | | | 215 | | | | | 220 | | | | |

| Pro | Pro | Cys | Pro | Ala | Pro | Pro | Val | Ala | Gly | Pro | Ser | Val | Phe | Leu | Phe |
|---|---|---|---|---|---|---|---|---|---|---|---|---|---|---|---|
| 225 | | | | | 230 | | | | | 235 | | | | | 240 |

| Pro | Pro | Lys | Pro | Lys | Asp | Thr | Leu | Met | Ile | Ser | Arg | Thr | Pro | Glu | Val |
|---|---|---|---|---|---|---|---|---|---|---|---|---|---|---|---|
| | | | | 245 | | | | | 250 | | | | | 255 | |

| Thr | Cys | Val | Val | Val | Asp | Val | Ser | His | Glu | Asp | Pro | Glu | Val | Gln | Phe |
|---|---|---|---|---|---|---|---|---|---|---|---|---|---|---|---|
| | | | | 260 | | | | | 265 | | | | | 270 | |

| Asn | Trp | Tyr | Val | Asp | Gly | Val | Glu | Val | His | Asn | Ala | Lys | Thr | Lys | Pro |
|---|---|---|---|---|---|---|---|---|---|---|---|---|---|---|---|
| | 275 | | | | | 280 | | | | | 285 | | | | |

| Arg | Glu | Glu | Gln | Phe | Asn | Ser | Thr | Phe | Arg | Val | Val | Ser | Val | Leu | Thr |
|---|---|---|---|---|---|---|---|---|---|---|---|---|---|---|---|
| | 290 | | | | | 295 | | | | | 300 | | | | |

| Val | Val | His | Gln | Asp | Trp | Leu | Asn | Gly | Lys | Glu | Tyr | Lys | Cys | Lys | Val |
|---|---|---|---|---|---|---|---|---|---|---|---|---|---|---|---|
| 305 | | | | | 310 | | | | | 315 | | | | | 320 |

| Ser | Asn | Lys | Gly | Leu | Pro | Ala | Pro | Ile | Glu | Lys | Thr | Ile | Ser | Lys | Thr |
|---|---|---|---|---|---|---|---|---|---|---|---|---|---|---|---|
| | | | | 325 | | | | | 330 | | | | | 335 | |

| Lys | Gly | Gln | Pro | Arg | Glu | Pro | Gln | Val | Tyr | Thr | Leu | Pro | Pro | Ser | Arg |
|---|---|---|---|---|---|---|---|---|---|---|---|---|---|---|---|
| | | | 340 | | | | | 345 | | | | | 350 | | |

| Glu | Glu | Met | Thr | Lys | Asn | Gln | Val | Ser | Leu | Thr | Cys | Leu | Val | Lys | Gly |
|---|---|---|---|---|---|---|---|---|---|---|---|---|---|---|---|
| | | | 355 | | | | | 360 | | | | | 365 | | |

| Phe | Tyr | Pro | Ser | Asp | Ile | Ala | Val | Glu | Trp | Glu | Ser | Asn | Gly | Gln | Pro |
|---|---|---|---|---|---|---|---|---|---|---|---|---|---|---|---|
| | | 370 | | | | | 375 | | | | | 380 | | | |

Glu Asn Asn Tyr Lys Thr Thr Pro Pro Met Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Lys
        435                 440

<210> SEQ ID NO 36
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Arg Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Arg Asn Glu Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Arg Met Asn Ser Leu Arg Ala Glu Asp Thr Ala Val Tyr Tyr Cys
                85                  90                  95

Ala Arg Asp His Pro Val Ala Gly Thr Ser Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Asn Phe Gly Thr Gln Thr Tyr Thr Cys Asn Val Asp His Lys
        195                 200                 205

Pro Ser Asn Thr Lys Val Asp Lys Thr Val Glu Arg Lys Cys Cys Val
    210                 215                 220

Glu Cys Pro Pro Cys Pro Ala Pro Pro Val Ala Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Phe Arg Val Val Ser Val

```
                290                 295                 300
Leu Thr Val Val His Gln Asp Trp Leu Asn Gly Lys Glu Tyr Lys Cys
305                 310                 315                 320

Lys Val Ser Asn Lys Gly Leu Pro Ala Pro Ile Glu Lys Thr Ile Ser
                325                 330                 335

Lys Thr Lys Gly Gln Pro Arg Glu Pro Gln Val Tyr Thr Leu Pro Pro
                340                 345                 350

Ser Arg Glu Glu Met Thr Lys Asn Gln Val Ser Leu Thr Cys Leu Val
                355                 360                 365

Lys Gly Phe Tyr Pro Ser Asp Ile Ala Val Glu Trp Glu Ser Asn Gly
                370                 375                 380

Gln Pro Glu Asn Asn Tyr Lys Thr Thr Pro Pro Met Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
                420                 425                 430

Asn His Tyr Thr Gln Lys Ser Leu Ser Leu Ser Pro Gly Lys
                435                 440                 445

<210> SEQ ID NO 37
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ile Phe Arg Ser Tyr
                20                  25                  30

Gly Met His Trp Val Arg Gln Ala Pro Gly Lys Gly Leu Glu Trp Val
                35                  40                  45

Ala Val Ile Ser Tyr Asp Gly Ser Asn Lys Tyr Tyr Ala Asp Ser Val
                50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp His Pro Val Ala Gly Thr Ser Phe Asp Tyr Trp Gly Gln
                100                 105                 110

Gly Thr Leu Val Thr Val Ser Ser Ala Ser Thr Lys Gly Pro Ser Val
                115                 120                 125

Phe Pro Leu Ala Pro Cys Ser Arg Ser Thr Ser Glu Ser Thr Ala Ala
                130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Asn Phe Gly Thr Gln Thr Tyr Thr Cys Asn Val Asp His Lys
                195                 200                 205
```

```
Pro Ser Asn Thr Lys Val Asp Lys Thr Val Glu Arg Lys Cys Cys Val
    210                 215                 220
Glu Cys Pro Pro Cys Pro Ala Pro Pro Val Ala Gly Pro Ser Val Phe
225                 230                 235                 240
Leu Phe Pro Pro Lys Pro Lys Asp Thr Leu Met Ile Ser Arg Thr Pro
                245                 250                 255
Glu Val Thr Cys Val Val Val Asp Val Ser His Glu Asp Pro Glu Val
                260                 265                 270
Gln Phe Asn Trp Tyr Val Asp Gly Val Glu Val His Asn Ala Lys Thr
            275                 280                 285
Lys Pro Arg Glu Glu Gln Phe Asn Ser Thr Phe Arg Val Val Ser Val
    290                 295                 300
Leu Thr Val Val His Gln Asp Trp Leu Asn Gly Lys Glu Tyr Lys Cys
305                 310                 315                 320
Lys Val Ser Asn Lys Gly Leu Pro Ala Pro Ile Glu Lys Thr Ile Ser
                325                 330                 335
Lys Thr Lys Gly Gln Pro Arg Glu Pro Gln Val Tyr Thr Leu Pro Pro
            340                 345                 350
Ser Arg Glu Glu Met Thr Lys Asn Gln Val Ser Leu Thr Cys Leu Val
            355                 360                 365
Lys Gly Phe Tyr Pro Ser Asp Ile Ala Val Glu Trp Glu Ser Asn Gly
    370                 375                 380
Gln Pro Glu Asn Asn Tyr Lys Thr Thr Pro Pro Met Leu Asp Ser Asp
385                 390                 395                 400
Gly Ser Phe Phe Leu Tyr Ser Lys Leu Thr Val Asp Lys Ser Arg Trp
                405                 410                 415
Gln Gln Gly Asn Val Phe Ser Cys Ser Val Met His Glu Ala Leu His
            420                 425                 430
Asn His Tyr Thr Gln Lys Ser Leu Ser Leu Ser Pro Gly Lys
            435                 440                 445

<210> SEQ ID NO 38
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Gln Val Gln Leu Val Glu Ser Gly Gly Gly Val Val Gln Pro Gly Arg
1               5                   10                  15
Ser Leu Arg Leu Ser Cys Ala Ala Ser Gly Phe Thr Phe Ser Ser Tyr
            20                  25                  30
Gly Met His Trp Val Arg Gln Ala Pro Gly Lys Gly Leu Glu Trp Val
        35                  40                  45
Ala Val Ile Trp Tyr Asp Gly Arg Asn Lys Tyr His Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Asp His Pro Val Ala Gly Thr Ser Phe Asp Tyr Trp Gly Gln
            100                 105                 110
Gly Thr Leu Val Thr Val Ser Ser Ala Ser Thr Lys Gly Pro Ser Val
        115                 120                 125
```

```
Phe Pro Leu Ala Pro Cys Ser Arg Ser Thr Ser Glu Ser Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Asn Phe Gly Thr Gln Thr Tyr Thr Cys Asn Val Asp His Lys
            195                 200                 205

Pro Ser Asn Thr Lys Val Asp Lys Thr Val Glu Arg Lys Cys Cys Val
210                 215                 220

Glu Cys Pro Pro Cys Pro Ala Pro Pro Val Ala Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Gln Phe Asn Trp Tyr Val Asp Gly Val Glu Val His Asn Ala Lys Thr
            275                 280                 285

Lys Pro Arg Glu Glu Gln Phe Asn Ser Thr Phe Arg Val Val Ser Val
290                 295                 300

Leu Thr Val Val His Gln Asp Trp Leu Asn Gly Lys Glu Tyr Lys Cys
305                 310                 315                 320

Lys Val Ser Asn Lys Gly Leu Pro Ala Pro Ile Glu Lys Thr Ile Ser
                325                 330                 335

Lys Thr Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Met Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
            435                 440                 445

<210> SEQ ID NO 39
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asn Thr Tyr Leu Ser Trp Leu Gln Gln Arg Pro Gly Gln Pro
```

```
                35                  40                  45
Pro Arg Leu Ile Tyr Lys Ile Ser Asn Arg Phe Ser Gly Val Pro
 50                  55                  60

Asp Arg Phe Ser Gly Ser Gly Ala Gly Thr Asp Phe Thr Leu Lys Ile
65                  70                  75                  80

Ser Arg Val Glu Ala Asp Asp Val Gly Ile Tyr Tyr Cys Met Gln Ala
                85                  90                  95

Ile Glu Phe Pro Trp Thr Phe Gly Gln Gly Thr Gln Val Glu Ile Lys
               100                 105                 110

Arg

<210> SEQ ID NO 40
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Gln Ser Val Leu Thr Gln Pro Pro Ser Val Ser Ala Ala Pro Gly Gln
1               5                   10                  15

Lys Val Thr Val Ser Cys Ser Gly Ser Ser Ser Asn Ile Gly Asn Asn
                20                  25                  30

Tyr Val Ser Trp Tyr Gln Gln Leu Pro Gly Thr Ala Pro Lys Leu Leu
                35                  40                  45

Ile Tyr Asp Asn Asn Lys Arg Pro Ser Gly Ile Pro Asp Arg Phe Ser
 50                 55                  60

Gly Ser Lys Ser Gly Thr Ser Ala Thr Leu Gly Ile Thr Gly Leu Gln
65                  70                  75                  80

Thr Gly Asp Glu Ala Glu Tyr Tyr Cys Gly Thr Trp Asp Ser Ser Leu
                85                  90                  95

Ser Val Val Ala Phe Gly Gly Gly Thr Lys Leu Thr Val Leu Gly
                100                 105                 110

<210> SEQ ID NO 41
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Asn Asn Tyr
                20                  25                  30

Leu Asn Trp Tyr Gln Gln Lys Leu Gly Lys Ala Pro Lys Leu Leu Ile
                35                  40                  45

Tyr Asp Thr Ser Asn Leu Glu Thr Gly Val Pro Ser Arg Phe Ser Gly
 50                 55                  60

Ser Gly Phe Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Leu Phe Thr
                85                  90                  95

Phe Gly Gln Gly Thr Arg Leu Glu Ile Lys Arg
                100                 105
```

<210> SEQ ID NO 42

<400> SEQUENCE: 42

000

<210> SEQ ID NO 43
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

```
Gln Thr Val Val Thr Gln Glu Pro Ser Phe Ser Val Ser Pro Gly Gly
1               5                   10                  15

Thr Val Thr Leu Thr Cys Gly Val Ser Gly Ser Val Ser Thr Arg
            20                  25                  30

Tyr Tyr Pro Ser Trp Tyr Gln Gln Thr Pro Gly Gln Ala Pro Arg Thr
        35                  40                  45

Leu Ile Asn Ser Thr Asn Thr Arg Ser Ser Gly Val Pro Asp Arg Phe
    50                  55                  60

Ser Gly Ser Ile Leu Gly Asn Lys Ala Ala Leu Thr Ile Thr Gly Ala
65                  70                  75                  80

Gln Ala Asp Asp Glu Ser Asp Tyr Phe Cys Val Leu Tyr Met Gly Ser
                85                  90                  95

Gly Ile Trp Val Phe Gly Gly Gly Thr Lys Leu Thr Val Leu Gly
                100                 105                 110
```

<210> SEQ ID NO 44
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

```
Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val His Tyr
            20                  25                  30

Asp Gly Asn Thr Tyr Leu Ser Trp Leu Gln Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Ile Tyr Tyr Cys Met Gln Ala
                85                  90                  95

Leu Glu Phe Pro Trp Thr Phe Gly Gln Gly Thr Lys Val Glu Ile Lys
                100                 105                 110
```

<210> SEQ ID NO 45
<211> LENGTH: 112
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 45

Asp Ile Val Met Thr Gln Thr Pro Leu Thr Ser Pro Val Thr Leu Gly
1               5                   10                  15

Gln Pro Ala Ser Ile Ser Cys Arg Ser Ser Gln Ser Leu Val His Tyr
            20                  25                  30

Asp Gly Asn Thr Tyr Leu Ser Trp Leu Gln Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Ile Tyr Tyr Cys Met Gln Ala
                85                  90                  95

Leu Glu Phe Pro Trp Thr Phe Gly Gln Gly Thr Lys Val Glu Ile Lys
            100                 105                 110

<210> SEQ ID NO 46
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val His Tyr
            20                  25                  30

Asp Gly Asn Thr Tyr Leu Ser Trp Leu Gln Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Ala Ala Glu Asp Val Gly Ile Tyr Tyr Cys Met Gln Ala
                85                  90                  95

Leu Glu Phe Pro Trp Thr Phe Gly Gln Gly Thr Lys Val Glu Ile Lys
            100                 105                 110

<210> SEQ ID NO 47
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Arg Arg Pro Ser Gly Ile Pro Asp Arg Phe Ser
    50                  55                  60

```
Gly Ser Lys Ser Gly Thr Ser Ala Thr Leu Gly Ile Thr Gly Leu Gln
 65                  70                  75                  80

Thr Gly Asp Glu Ala Asp Tyr Tyr Cys Gly Thr Trp Asp Ser Ser Leu
                 85                  90                  95

Ser Ala Val Val Phe Gly Gly Gly Thr Lys Leu Thr Val Leu
                100                 105                 110

<210> SEQ ID NO 48
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Gln Ser Val Leu Thr Gln Pro Pro Ser Val Ser Ala Ala Pro Gly Gln
  1               5                  10                  15

Lys Val Thr Ile Ser Cys Ser Gly Ser Ser Ser Asn Ile Gly Asn Asn
                 20                  25                  30

Tyr Val Ser Trp Tyr Gln Gln Leu Pro Gly Thr Ala Pro Lys Leu Leu
             35                  40                  45

Ile Tyr Asp Asn Asn Arg Pro Ser Gly Ile Pro Asp Arg Phe Ser
 50                  55                  60

Gly Ser Lys Ser Gly Thr Ser Ala Thr Leu Gly Ile Thr Gly Leu Gln
 65                  70                  75                  80

Thr Gly Asp Glu Ala Asp Tyr Tyr Cys Glu Thr Trp Asp Ser Ser Leu
                 85                  90                  95

Ser Ala Gly Val Phe Gly Gly Gly Thr Lys Leu Thr Val Leu
                100                 105                 110

<210> SEQ ID NO 49
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Gln Ser Val Leu Thr Gln Pro Pro Ser Val Ser Ala Ala Pro Gly Gln
  1               5                  10                  15

Lys Val Thr Ile Ser Cys Ser Gly Ser Ser Ser Asn Ile Gly Asn Asn
                 20                  25                  30

Tyr Val Ser Trp Tyr Gln Gln Leu Pro Gly Thr Ala Pro Lys Leu Leu
             35                  40                  45

Ile Tyr Asp Asn Asn Lys Arg Pro Ser Gly Ile Pro Asp Arg Phe Ser
 50                  55                  60

Gly Ser Lys Ser Gly Thr Ser Ala Thr Leu Gly Ile Thr Gly Leu Gln
 65                  70                  75                  80

Thr Gly Asp Glu Ala Asp Tyr Tyr Cys Gly Thr Trp Asp Ser Ser Leu
                 85                  90                  95

Ser Ala Val Val Phe Gly Gly Gly Thr Lys Leu Thr Val Leu
                100                 105                 110

<210> SEQ ID NO 50
<211> LENGTH: 118
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 50

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Ser Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Ala Thr Ser Gly Trp Phe Asp Tyr Trp Gly Gln Gly Thr
            100                 105                 110

Leu Val Thr Val Ser Ser
        115

<210> SEQ ID NO 51
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Gln Val Gln Leu Val Glu Ser Gly Gly Gly Val Val Gln Pro Gly Arg
1               5                   10                  15

Ser Leu Arg Leu Ser Cys Ala Ala Ser Arg Phe Ser Phe Ser Arg Tyr
            20                  25                  30

Gly Met His Trp Val Arg Gln Ala Pro Gly Lys Gly Leu Glu Trp Val
        35                  40                  45

Ala Val Ile Trp Phe Asp Gly Arg Asn Gln Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Val Glu Asp Thr Ala Val Tyr Tyr Cys
                85                  90                  95

Ala Arg Asp His Pro Val Val Gly Thr Ser Phe Asp Tyr Trp Gly Gln
            100                 105                 110

Gly Thr Leu Val Thr Val Ser Ser
        115                 120

<210> SEQ ID NO 52
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Gln Val Gln Leu Val Glu Ser Gly Gly Gly Val Val Gln Pro Gly Arg
1               5                   10                  15
```

```
Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Gly Tyr Asp Gly Ser Tyr Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Ser Asn Trp Asn Tyr Gly Gly Ser Phe Asp Tyr Trp
            100                 105                 110

Gly Gln Gly Thr Leu Val Thr Val Ser Ser
        115                 120
```

<210> SEQ ID NO 53

<400> SEQUENCE: 53

000

<210> SEQ ID NO 54
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

```
Glu Val Gln Leu Leu Glu Ser Gly Gly Gly Leu Val Gln Pro Glu Gly
1               5                   10                  15

Ser Leu Arg Leu Ser Cys Ala Ala Ser Gly Phe Thr Phe Ser Ile Tyr
            20                  25                  30

Ala Met Ser Trp Val Arg Gln Ala Pro Gly Lys Gly Leu Glu Trp Val
        35                  40                  45

Ser Asp Ile Ser Gly Arg Gly Gly Tyr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Asp Asp Thr Ala Val Tyr Tyr Cys
                85                  90                  95

Ala Lys Asp Arg Ser Ile Ala Val Ala Gly Pro Phe Asp Phe Trp Gly
            100                 105                 110

Gln Gly Thr Leu Val Thr Val Ser Ser
        115                 120
```

<210> SEQ ID NO 55
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ala Tyr
            20                  25                  30
```

```
Tyr Met His Trp Val Arg Gln Ala Pro Gly Gln Gly Leu Glu Trp Met
            35                  40                  45

Gly Trp Ile Asn Pro Asn Ser Gly Gly Thr Asn Ser Ala Gln Lys Phe
     50                  55                  60

Gln Gly Arg Val Thr Met Thr Arg Asp Thr Ser Ile Arg Thr Ala Tyr
 65                  70                  75                  80

Met Glu Leu Ser Trp Leu Arg Ser Asp Thr Ala Val Tyr Tyr Cys
                85                  90                  95

Ala Arg Asp Ala Thr Ser Gly Trp Phe Asp Ile Trp Gly Gln Gly Thr
            100                 105                 110

Pro Val Thr Val Ser Ser
        115
```

<210> SEQ ID NO 56
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

```
Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ala Tyr
             20                  25                  30

Tyr Met His Trp Val Arg Gln Ala Pro Gly Gln Gly Leu Glu Trp Met
            35                  40                  45

Gly Trp Ile Asn Pro Asn Ser Gly Gly Thr Asn Ser Ala Gln Lys Phe
     50                  55                  60

Gln Gly Arg Val Thr Met Thr Arg Asp Thr Ser Ile Arg Thr Ala Tyr
 65                  70                  75                  80

Met Glu Leu Ser Trp Leu Arg Ser Asp Asp Thr Ala Val Tyr Tyr Cys
                85                  90                  95

Ala Arg Asp Ala Thr Ser Gly Trp Phe Asp Phe Trp Gly Gln Gly Thr
            100                 105                 110

Pro Val Thr Val Ser Ser
        115
```

<210> SEQ ID NO 57
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

```
Gln Val Gln Leu Val Gln Ser Gly Ala Glu Val Arg Lys Pro Gly Ala
 1               5                  10                  15

Ser Val Lys Val Ser Cys Lys Ala Ser Gly Tyr Thr Phe Thr Ala Tyr
             20                  25                  30

Tyr Met His Trp Val Arg Gln Ala Pro Gly Gln Gly Leu Glu Trp Met
            35                  40                  45

Gly Trp Ile Asn Pro Tyr Ser Gly Gly Thr Asn Ser Ala Gln Lys Phe
     50                  55                  60

Gln Gly Arg Val Thr Met Thr Arg Asp Thr Ser Ile Ser Thr Ala Tyr
 65                  70                  75                  80
```

```
Met Glu Leu Ser Trp Leu Arg Ser Asp Asp Thr Ala Val Tyr Tyr Cys
                85                  90                  95

Ala Arg Asp Ala Thr Ser Gly Trp Phe Asp Phe Trp Gly Gln Gly Thr
            100                 105                 110

Leu Val Thr Val Ser Ser
        115

<210> SEQ ID NO 58
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Arg Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Arg Asn Glu Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Arg Met Asn Ser Leu Arg Ala Glu Asp Thr Ala Val Tyr Tyr Cys
                85                  90                  95

Ala Arg Asp His Pro Val Ala Gly Thr Ser Phe Asp Tyr Trp Gly Gln
            100                 105                 110

Gly Thr Leu Val Thr Val Ser Ser
        115                 120

<210> SEQ ID NO 59
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ile Phe Arg Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp His Pro Val Ala Gly Thr Ser Phe Asp Tyr Trp Gly Gln
            100                 105                 110

Gly Thr Leu Val Thr Val Ser Ser
        115                 120
```

<210> SEQ ID NO 60
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Arg Asn Lys Tyr His Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp His Pro Val Ala Gly Thr Ser Phe Asp Tyr Trp Gly Gln
            100                 105                 110

Gly Thr Leu Val Thr Val Ser Ser
        115                 120

<210> SEQ ID NO 61
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 61
gatattgtga tgacccagac tccactctcc tcacctgtca cccttggaca gccggcctcc     60
atctcctgca ggtctagtca aagcctcgta tacagtgatg gaaacaccta cttgagttgg    120
cttcagcaga ggccaggcca gcctccaaga ctcctaattt ataagatttc taaccggttc    180
tctggggtcc cagacagatt cagtggcagt ggggcaggga cagatttcac actgaaaatc    240
agcagggtgg aagctgacga tgtcgggatt tattactgca tgcaagctat agaatttccg    300
tggacgttcg gccaagggac ccaggtggaa atcaaacgt                           339

<210> SEQ ID NO 62
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 62
cagtctgtgt tgacgcagcc gccctcagtg tctgcggccc caggacagaa ggtcaccgtc     60
tcctgctctg gaagcagctc caacattggg aataattatg tatcctggta ccagcaactc    120
ccaggaacag cccccaaact cctcatttat gacaataata gcgaccctc agggattcct    180 gaccgattct ctggctccaa gtctggcacg tcagccaccc tgggcatcac cggactccag    240
actggggacg aggccgagta ttactgcgga acatgggata gcagcctgag tgttgtggca    300
ttcggcggag ggaccaagct gaccgtccta ggt          333

<210> SEQ ID NO 63
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 63
gacatccaga tgacccagtc tccatcctcc ctgtctgcat ctgtaggaga cagagtcacc    60
atcacttgcc aggcgagtca ggacattaac aattatttaa attggtatca gcagaaacta   120
gggaaagccc ctaagctcct gatctacgat acatccaatt tggaaacagg gtcccatca    180 aggttcagtg aagtggatt tgggacagat tttactttca ccatcagcag cctgcagcct    240
gaagatattg caacatatta ctgtcaacag tatgataatc tcttcacctt cggccaaggg   300
acacgactgg agattaaacg t                                             321

<210> SEQ ID NO 64

<400> SEQUENCE: 64

000

<210> SEQ ID NO 65
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 65
cagactgtgg tgacccagga gccatcgttc tcagtgtccc ctggagggac agtcacactc    60
acttgtggcg tgagctctgg ctcagtctct actaggtact accccagctg gtaccagcag   120
accccaggcc aggctccacg cacgctcatc aacagcacaa acactcgctc ttctggggtc   180
cctgatcgct tctctggctc catccttggg aacaaagctg ccctcaccat cacgggggcc   240
caggcagatg atgaatctga ttatttctgt gtgctgtata tgggtagtgg catttgggtg   300
ttcggcggag ggaccaagct gaccgtccta ggt                                333

<210> SEQ ID NO 66
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 66
gatattgtga tgacccagac tccactctcc tcacctgtca cccttggaca gccggcctcc    60
atctcctgca ggtctagtca aagcctcgtt cactatgatg gaaacaccta cttgagttgg   120
cttcagcaga ggccaggcca gcctccaaga ctcctaattt ataagatttc taaccggttc   180
tctggggtcc cagacagatt cagtggcagt ggggcaggga cagatttcac actgaaaatc   240
agcagggtgg aagctgagga tgtcgggatt tattactgca tgcaagctct agaatttccg   300
tggacgttcg gccaagggac caaggtggaa atcaaa                             336

<210> SEQ ID NO 67
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 67
gatattgtga tgacccagac tccactcacc tcacctgtca cccttggaca gccggcctcc    60
atctcctgca ggtctagtca aagcctcgtt cactatgatg gaaacaccta cttgagttgg   120
cttcagcaga ggccaggcca gcctccaaga ctcctaattt ataagatttc taaccggttc   180
tctggggtcc cagacagatt cagtggcagt ggggcaggga cagatttcac actgaaaatc   240
agcagggtgg aagctgagga tgtcgggatt tattactgca tgcaagctct agaatttccg   300
tggacgttcg gccaagggac caaggtggaa atcaaa                             336

<210> SEQ ID NO 68
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 68
gatattgtga tgacccagac tccactctcc tcacctgtca cccttggaca gccggcctcc    60
atctcctgca ggtctagtca aagcctcgtt cactatgatg gaaacaccta cttgagttgg   120
cttcagcaga ggccaggcca gcctccaaga ctcctaattt ataagatttc taaccggttc   180
tctggggtcc cagacagatt cagtggcagt ggggcaggga cagatttcac actgaaaatc   240
agcagggtgg cagctgagga tgtcgggatt tattactgca tgcaagctct agaatttccg   300
tggacgttcg gccaagggac caaggtggaa atcaaa                             336

<210> SEQ ID NO 69
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 69
cagtctgtgt tgacgcagcc gccctcagtg tctgcggccc caggacagaa ggtcaccatc    60
tcctgctctg gaagcagctc caacattggg aataattatg tatcctggta ccagcagctc   120
ccagggacag cccccaaact cctcatttat gacaataata gcgaccctc agggattcct   180 gaccgattct ctggctccaa gtctggcacg tcagccaccc tgggcatcac cggactccag   240 actgggacg aggccgatta ttactgcgga acatgggata gcagcctgag tgctgtggtg   300
ttcggcggag ggaccaagct gaccgtccta                                    330

<210> SEQ ID NO 70
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 70

```
cagtctgtgt tgacgcagcc gccctcagtg tctgcggccc caggacagaa ggtcaccatc    60
tcctgctctg gaagcagctc aacattggg aataattatg tatcctggta ccagcagctc   120
ccaggaacag cccccaaact cctcatttat gacaataata accgaccctc agggattcct   180
gaccgattct ctggctccaa gtctggcacg tcagccaccc tgggcatcac cggactccag   240
actggggacg aggccgatta ttactgcgaa acatgggata gcagcctgag tgctggggtg   300
ttcggcggag ggaccaagct gaccgtccta                                    330

<210> SEQ ID NO 71
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 71
cagtctgtgt tgacgcagcc gccctcagtg tctgcggccc caggacagaa ggtcaccatc    60
tcctgctctg gaagcagctc aacattggg aataattatg tatcctggta ccagcaactc   120
ccaggaacag cccccaaact cctcatttat gacaataata acgaccctc agggattcct    180 gaccgattct ctggctccaa gtctggcacg tcagccaccc tgggcatcac cggactccag   240
actggggacg aggccgatta ttactgcgga acttgggata gcagcctgag tgctgtggta   300
ttcggcggag ggaccaagct gaccgtccta                                    330

<210> SEQ ID NO 72
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 72
caggtgcaac tggtgcagtc tggggctgag gtgaagaagc ctggggcctc agtgaaggtc    60
tcctgcaagg cttctggata caccttcacc ggctactata tgcactgggt gcgacaggcc   120
cctggacaag gcttgagtg gatgggatgg atcaaccccta acagtggtgg cacaaactct   180
gcacagaagt ttcagggcag ggtcaccatg accagggaca cgtccatcag cacagcctac   240
atggagctga gcaggctgag atctgacgac acggccgtgt attactgtgc aagagatgcg   300
accagtggct ggtttgacta ctggggccag ggaaccctgg tcaccgtctc tagt          354

<210> SEQ ID NO 73
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 73
caggtgcagt tggtggagtc tgggggaggc gtggtccagc ctgggaggtc cctgagactc    60
tcctgtgcag cgtctagatt ctccttcagt agatatggca tgcactgggt ccgccaggct   120
ccaggcaagg ggctggagtg ggtggcagtt atatggtttg atggaagaaa tcaatactat   180
gcagactccg tgaaggggcg attcaccatc tccagagaca attccaagaa tacgctgttt   240
ctgcaaatga acagcctgag agtcgaggac acggctgtgt attactgtgc gagagatcac   300
```

```
ccagtagttg gtacgagctt tgactactgg ggccagggaa ccctggtcac cgtctctagt    360
```

<210> SEQ ID NO 74
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 74

```
caggtgcaac tggtggagtc tgggggaggc gtggtccagc ctgggaggtc cctgagactc    60
tcctgtgcag cgtctggatt caccttcagt agctatggca tgcactgggt ccgccaggct   120
ccaggcaagg ggctggagtg ggtggcagtt atagggtatg atggaagtta taaatactat   180
gcagactccg tgaagggccg attcaccatc tccagagaca attccaagaa cacgctatat   240
ctgcaaatga acagcctgag agccgaggac acggctgtgt attactgtgc gagagatggg   300
tctaactgga actacggggg ttcttttgac tactggggcc agggaaccct ggtcaccgtc   360
tctagt                                                              366
```

<210> SEQ ID NO 75

<400> SEQUENCE: 75

000

<210> SEQ ID NO 76
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 76

```
gaggtgcagc tgttggagtc tgggggaggc ttggtacagc cggaggggtc cctgagactc    60
tcctgtgcag cctctggatt cacctttagc atctatgcca tgagctgggt ccgccaggct   120
ccagggaagg ggctggagtg ggtctcagat attagtggtc gtggtggtta cacatactac   180
gcagactccg tgaagggccg gttcaccatc tccagagaca attccaagaa cacgctgtat   240
ctgcaaatga acagcctgag agccgacgac acggccgtat attactgtgc gaaagatcgg   300
agtatagcag tggctggtcc ttttgacttc tggggccagg gaaccctggt caccgtctct   360
agt                                                                 363
```

<210> SEQ ID NO 77
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 77

```
caggtgcagc tggtgcagtc tggggctgag gtgaagaagc ctggggcctc agtgaaggtc    60
tcctgcaagg cttctggata caccttcacc gcctactata tgcactgggt gcgacaggcc   120
cctggacaag gcttgagtg gatgggatgg atcaaccctaacagtggtgg cacaaactct    180
gcacagaagt tcagggcag ggtcaccatg accagggaca cgtccatcag aacagcctac    240
```

```
atggagttga gctggctgag atctgacgac acggccgtgt attattgtgc gagagatgcg      300
accagtggct ggtttgacat ctggggccag ggaaccccgg tcaccgtctc ctca            354
```

<210> SEQ ID NO 78
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 78

```
caggtgcagc tggtgcagtc tggggctgag gtgaagaagc ctggggcctc agtgaaggtc      60
tcctgcaagg cttctggata caccttcacc gcctactata tgcactgggt gcgacaggcc     120
cctggacaag gcttgagtg gatgggatgg atcaaccta acagtggtgg cacaaactct       180
gcacagaagt tcagggcag gtcaccatg accagggaca cgtccatcag aacagcctac       240
atggagttga gctggctgag atctgacgac acggccgtgt attactgtgc gagagatgcg     300
accagtggct ggtttgactt ctggggccag ggaaccccgg tcaccgtctc ctca            354
```

<210> SEQ ID NO 79
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 79

```
caggtgcagc tggtgcagtc tggggctgag gtgaggaagc ctggggcctc agtgaaggtc      60
tcctgcaagg cttctggata caccttcacc gcctactata tgcactgggt gcgacaggcc     120
cctggacaag gcttgagtg gatgggatgg atcaaccctt acagtggtgg cacaaactct      180
gcacagaagt tcagggcag gtcaccatg accagggaca cgtccatcag cacagcctac       240
atggagttga gctggctgag atctgacgac acggccgtgt attactgtgc gagagatgcg     300
accagtggct ggtttgactt ctggggccag ggaaccctgg tcaccgtctc ctca            354
```

<210> SEQ ID NO 80
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 80

```
caggtgcagc tggtggagtc tgggggaggc gtggtccagc ctgggaggtc cctgagactc      60
tcctgcgcag cgtctggatt caccttcaga agctatggca tgcactgggt ccgccaggct     120
ccaggcaagg gctggagtg ggtggcagtt atatggtatg atggaaggaa tgaatactat      180
gcagactccg tgaagggccg attcaccatc tccagagaca attccaagaa tacgctgtat    240
ctgcgaatga acagtctgag agccgaggac acggctgtgt attactgtgc gagagatcac     300
ccagtagctg gtacgagctt tgactactgg ggccagggaa ccctggtcac cgtctcctca     360
```

<210> SEQ ID NO 81
<211> LENGTH: 360
<212> TYPE: DNA
<213> ORGANISM: Artificial Sequence
<220> FEATURE:

<223> OTHER INFORMATION: Description of Artificial Sequence: Synthetic
polynucleotide

<400> SEQUENCE: 81

```
caggtgcagc tggtggagtc tgggggcggc gtggtccagc ctgggaggtc cctgagactc    60
tcctgtgcag cctctggatt catcttcagg agctatggca tgcactgggt ccgccaggct   120
ccaggcaagg ggctggagtg ggtggcagtt atatcatatg atggaagtaa taaatactat   180
gcagactccg tgaagggccg attcaccatc tccagagaca attccaagaa cacgctgtat   240
ctgcaaatga acagcctgag agctgaggac acggctgtct attactgtgc gagagatcac   300
ccagtggctg gtacctcctt tgactactgg ggccagggaa ccctggtcac cgtctcctca   360
```

<210> SEQ ID NO 82
<211> LENGTH: 360
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 82

```
caggtgcagc tggtggagtc tgggggaggc gtggtccagc ctgggaggtc cctgagactc    60
tcctgtgcag cgtctggatt caccttcagt agctatggca tgcactgggt ccgccaggct   120
ccaggcaagg ggctggagtg ggtggcagtc atatggtatg atggaagaaa taaataccat   180
gcagactccg tgaagggccg attcaccatc tccagagaca attccaagaa cacgctatat   240
ctgcaaatga acagcctgag agccgaggac acggctgtgt attactgtgc gagagatcac   300
ccagtagctg gtacgagctt tgactactgg ggccaggaa ccctggtcac cgtctcctca   360
```

<210> SEQ ID NO 83
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 83

Gly Tyr Tyr Met His
1               5

<210> SEQ ID NO 84
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 84

Arg Tyr Gly Met His
1               5

<210> SEQ ID NO 85
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 85

Ser Tyr Gly Met His
1               5

<210> SEQ ID NO 86

<400> SEQUENCE: 86

000

<210> SEQ ID NO 87
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Ile Tyr Ala Met Ser
1               5

<210> SEQ ID NO 88
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Ala Tyr Tyr Met His
1               5

<210> SEQ ID NO 89
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Trp Ile Asn Pro Asn Ser Gly Gly Thr Asn Ser Ala Gln Lys Phe Gln
1               5                   10                  15

Gly

<210> SEQ ID NO 90
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Val Ile Trp Phe Asp Gly Arg Asn Gln Tyr Tyr Ala Asp Ser Val Lys
1               5                   10                  15

Gly

<210> SEQ ID NO 91
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 91

Val Ile Gly Tyr Asp Gly Ser Tyr Lys Tyr Tyr Ala Asp Ser Val Lys
1               5                   10                  15

Gly

<210> SEQ ID NO 92

<400> SEQUENCE: 92

000

<210> SEQ ID NO 93
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Asp Ile Ser Gly Arg Gly Gly Tyr Thr Tyr Tyr Ala Asp Ser Val Lys
1               5                   10                  15

Gly

<210> SEQ ID NO 94
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Trp Ile Asn Pro Tyr Ser Gly Gly Thr Asn Ser Ala Gln Lys Phe Gln
1               5                   10                  15

Gly

<210> SEQ ID NO 95
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Val Ile Trp Tyr Asp Gly Arg Asn Glu Tyr Tyr Ala Asp Ser Val Lys
1               5                   10                  15

Gly

<210> SEQ ID NO 96
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Val Ile Ser Tyr Asp Gly Ser Asn Lys Tyr Tyr Ala Asp Ser Val Lys
1               5                   10                  15

Gly
```

```
<210> SEQ ID NO 97
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Val Ile Trp Tyr Asp Gly Arg Asn Lys Tyr His Ala Asp Ser Val Lys
1               5                   10                  15

Gly

<210> SEQ ID NO 98
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Gly Trp Phe Asp Tyr
1               5

<210> SEQ ID NO 99
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Gly Thr Ser Phe Asp Tyr
1               5

<210> SEQ ID NO 100
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Tyr Gly Gly Ser Phe Asp Tyr
1               5

<210> SEQ ID NO 101

<400> SEQUENCE: 101

000

<210> SEQ ID NO 102
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Val Ala Gly Pro Phe Asp Phe
1               5
```

```
<210> SEQ ID NO 103
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Gly Trp Phe Asp Ile
1               5

<210> SEQ ID NO 104
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Gly Trp Phe Asp Phe
1               5

<210> SEQ ID NO 105
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Gly Thr Ser Phe Asp Tyr
1               5

<210> SEQ ID NO 106
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Arg Ser Ser Gln Ser Leu Val Tyr Ser Asp Gly Asn Thr Tyr Leu Ser
1               5                   10                  15

<210> SEQ ID NO 107
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Ser Gly Ser Ser Ser Asn Ile Gly Asn Asn Tyr Val Ser
1               5                   10

<210> SEQ ID NO 108
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108
```

Gln Ala Ser Gln Asp Ile Asn Asn Tyr Leu Asn
1               5                   10

<210> SEQ ID NO 109

<400> SEQUENCE: 109

000

<210> SEQ ID NO 110
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Gly Val Ser Ser Gly Ser Val Ser Thr Arg Tyr Tyr Pro Ser
1               5                   10

<210> SEQ ID NO 111
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Arg Ser Ser Gln Ser Leu Val His Tyr Asp Gly Asn Thr Tyr Leu Ser
1               5                   10                  15

<210> SEQ ID NO 112
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Lys Ile Ser Asn Arg Phe Ser
1               5

<210> SEQ ID NO 113
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Asp Asn Asn Lys Arg Pro
1               5

<210> SEQ ID NO 114
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Asp Thr Ser Asn Leu Glu Thr

```
<210> SEQ ID NO 115

<400> SEQUENCE: 115

000

<210> SEQ ID NO 116
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Ser Thr Asn Thr Arg Ser Ser
1               5

<210> SEQ ID NO 117
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Asp Asn Asn Arg Arg Pro Ser
1               5

<210> SEQ ID NO 118
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Asp Asn Asn Asn Arg Pro Ser
1               5

<210> SEQ ID NO 119
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Asp Asn Asn Lys Arg Pro Ser
1               5

<210> SEQ ID NO 120
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Met Gln Ala Ile Glu Phe Pro Trp Thr
1               5
```

```
<210> SEQ ID NO 121
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Gly Thr Trp Asp Ser Ser Leu Ser Val Val Ala
1               5                   10

<210> SEQ ID NO 122
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Gln Gln Tyr Asp Asn Leu Phe Thr
1               5

<210> SEQ ID NO 123

<400> SEQUENCE: 123

000

<210> SEQ ID NO 124
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Val Leu Tyr Met Gly Ser Gly Ile Trp Val
1               5                   10

<210> SEQ ID NO 125
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Met Gln Ala Leu Glu Phe Pro Trp Thr
1               5

<210> SEQ ID NO 126
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Gly Thr Trp Asp Ser Ser Leu Ser Ala Val Val
1               5                   10

<210> SEQ ID NO 127
```

```
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Glu Thr Trp Asp Ser Ser Leu Ser Ala Gly Val
1               5                   10

<210> SEQ ID NO 128
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 128
ggctactata tgcac                                                    15

<210> SEQ ID NO 129
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 129
agatatggca tgcac                                                    15

<210> SEQ ID NO 130
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 130
agctatggca tgcac                                                    15

<210> SEQ ID NO 131

<400> SEQUENCE: 131

000

<210> SEQ ID NO 132
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 132
atctatgcca tgagc                                                    15

<210> SEQ ID NO 133
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 133
gcctactata tgcac                                                             15

<210> SEQ ID NO 134
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 134
tggatcaacc ctaacagtgg tggcacaaac tctgcacaga agtttcaggg c                     51

<210> SEQ ID NO 135
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 135
ttatatggtt tgatggaaga aatcaatact atgcagactc cgtgaagggg                       50

<210> SEQ ID NO 136
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 136
gttatagggt atgatggaag ttataaatac tatgcagact ccgtgaaggg c                     51

<210> SEQ ID NO 137

<400> SEQUENCE: 137

000

<210> SEQ ID NO 138
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 138
gatattagtg gtcgtggtgg ttacacatac tacgcagact ccgtgaaggg c                     51

<210> SEQ ID NO 139
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 139
tggatcaacc cttacagtgg tggcacaaac tctgcacaga agtttcaggg c                     51

<210> SEQ ID NO 140

```
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 140
gttatatggt atgatggaag gaatgaatac tatgcagact ccgtgaaggg c       51

<210> SEQ ID NO 141
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 141
gttatatcat atgatggaag taataaatac tatgcagact ccgtgaaggg c       51

<210> SEQ ID NO 142
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 142
gtcatatggt atgatggaag aaataaatac catgcagact ccgtgaaggg c       51

<210> SEQ ID NO 143
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 143
ggctggtttg actac                                               15

<210> SEQ ID NO 144
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 144
ggtacgagct ttgactac                                            18

<210> SEQ ID NO 145
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 145
tacgggggtt cttttgacta c                                        21

<210> SEQ ID NO 146
```

```
<400> SEQUENCE: 146

000

<210> SEQ ID NO 147
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 147
gtggctggtc cttttgactt c                                            21

<210> SEQ ID NO 148
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 148
ggctggtttg acatc                                                   15

<210> SEQ ID NO 149
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 149
ggctggtttg acttc                                                   15

<210> SEQ ID NO 150
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 150
ggtacctcct ttgactac                                                18

<210> SEQ ID NO 151
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 151
aggtctagtc aaagcctcgt atacagtgat ggaaacacct acttgagt               48

<210> SEQ ID NO 152
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 152
```
tctggaagca gctccaacat tgggaataat tatgtatcc         39

<210> SEQ ID NO 153
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 153
caggcgagtc aggacattaa caattattta aat         33

<210> SEQ ID NO 154

<400> SEQUENCE: 154

000

<210> SEQ ID NO 155
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 155
ggcgtgagct ctggctcagt ctctactagg tactacccca gc         42

<210> SEQ ID NO 156
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 156
aggtctagtc aaagcctcgt tcactatgat ggaaacacct acttgagt         48

<210> SEQ ID NO 157
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 157
aagatttcta accggttctc t         21

<210> SEQ ID NO 158
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 158
gacaataata agcgaccc         18

<210> SEQ ID NO 159
<211> LENGTH: 21
<212> TYPE: DNA

```
<213> ORGANISM: Artificial Sequence
<220> FEATURE:
<223> OTHER INFORMATION: Description of Artificial Sequence: Synthetic
      oligonucleotide

<400> SEQUENCE: 159
gatacatcca atttggaaac a                                              21

<210> SEQ ID NO 160

<400> SEQUENCE: 160

000

<210> SEQ ID NO 161
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 161
agcacaaaca ctcgctcttc t                                              21

<210> SEQ ID NO 162
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 162
gacaataata ggcgaccctc a                                              21

<210> SEQ ID NO 163
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 163
gacaataata accgaccctc a                                              21

<210> SEQ ID NO 164
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 164
gacaataata agcgaccctc a                                              21

<210> SEQ ID NO 165
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 165
```
atgcaagcta tagaatttcc gtggacg                                           27

<210> SEQ ID NO 166
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 166
ggaacatggg atagcagcct gagtgttgtg gca                                    33

<210> SEQ ID NO 167
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 167
caacagtatg ataatctctt cacc                                              24

<210> SEQ ID NO 168

<400> SEQUENCE: 168

000

<210> SEQ ID NO 169
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 169
gtgctgtata tgggtagtgg catttgggtg                                        30

<210> SEQ ID NO 170
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 170
atgcaagctc tagaatttcc gtggacg                                           27

<210> SEQ ID NO 171
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 171
ggaacatggg atagcagcct gagtgctgtg gtg                                    33

<210> SEQ ID NO 172
<211> LENGTH: 33
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 172
gaaacatggg atagcagcct gagtgctggg gtg                              33

<210> SEQ ID NO 173
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 173
ggaacttggg atagcagcct gagtgctgtg gta                              33

<210> SEQ ID NO 174
<211> LENGTH: 9
<212> TYPE: PRT
<213> ORGANISM: Artificial Sequence
<220> FEATURE:
<223> OTHER INFORMATION: Description of Artificial Sequence: Synthetic
      consensus peptide
<220> FEATURE:
<221> NAME/KEY: MOD_RES
<222> LOCATION: (4)..(4)
<223> OTHER INFORMATION: Leu or Ile

<400> SEQUENCE: 174

Met Gln Ala Xaa Glu Phe Pro Trp Thr
1               5

<210> SEQ ID NO 175
<211> LENGTH: 11
<212> TYPE: PRT
<213> ORGANISM: Artificial Sequence
<220> FEATURE:
<223> OTHER INFORMATION: Description of Artificial Sequence: Synthetic
      consensus peptide
<220> FEATURE:
<221> NAME/KEY: MOD_RES
<222> LOCATION: (9)..(9)
<223> OTHER INFORMATION: Val or Ala
<220> FEATURE:
<221> NAME/KEY: MOD_RES
<222> LOCATION: (11)..(11)
<223> OTHER INFORMATION: Val or Ala

<400> SEQUENCE: 175

Gly Thr Trp Asp Ser Ser Leu Ser Xaa Val Xaa
1               5                   10

<210> SEQ ID NO 176
<211> LENGTH: 7
<212> TYPE: PRT
<213> ORGANISM: Artificial Sequence
<220> FEATURE:
<223> OTHER INFORMATION: Description of Artificial Sequence: Synthetic
      consensus peptide
<220> FEATURE:
<221> NAME/KEY: MOD_RES
<222> LOCATION: (4)..(4)
<223> OTHER INFORMATION: Lys, Asn or Arg
<220> FEATURE:
<221> NAME/KEY: MOD_RES
<222> LOCATION: (7)..(7)
<223> OTHER INFORMATION: Ser or absent

<400> SEQUENCE: 176
```

```
Asp Asn Asn Xaa Arg Pro Xaa
1               5
```

<210> SEQ ID NO 177
<211> LENGTH: 17
<212> TYPE: PRT
<213> ORGANISM: Artificial Sequence
<220> FEATURE:
<223> OTHER INFORMATION: Description of Artificial Sequence: Synthetic
      consensus peptide
<220> FEATURE:
<221> NAME/KEY: MOD_RES
<222> LOCATION: (8)..(8)
<223> OTHER INFORMATION: His or absent
<220> FEATURE:
<221> NAME/KEY: MOD_RES
<222> LOCATION: (10)..(10)
<223> OTHER INFORMATION: Ser or absent

<400> SEQUENCE: 177

```
Arg Ser Ser Gln Ser Leu Val Xaa Tyr Xaa Asp Gly Asn Thr Tyr Leu
1               5                   10                  15

Ser
```

<210> SEQ ID NO 178
<211> LENGTH: 5
<212> TYPE: PRT
<213> ORGANISM: Artificial Sequence
<220> FEATURE:
<223> OTHER INFORMATION: Description of Artificial Sequence: Synthetic
      consensus peptide
<220> FEATURE:
<221> NAME/KEY: MOD_RES
<222> LOCATION: (5)..(5)
<223> OTHER INFORMATION: Tyr, Ile or Phe

<400> SEQUENCE: 178

```
Gly Trp Phe Asp Xaa
1               5
```

<210> SEQ ID NO 179
<211> LENGTH: 17
<212> TYPE: PRT
<213> ORGANISM: Artificial Sequence
<220> FEATURE:
<223> OTHER INFORMATION: Description of Artificial Sequence: Synthetic
      consensus peptide
<220> FEATURE:
<221> NAME/KEY: MOD_RES
<222> LOCATION: (5)..(5)
<223> OTHER INFORMATION: Asn or Tyr

<400> SEQUENCE: 179

```
Trp Ile Asn Pro Xaa Ser Gly Gly Thr Asn Ser Ala Gln Lys Phe Gln
1               5                   10                  15

Gly
```

<210> SEQ ID NO 180
<211> LENGTH: 17
<212> TYPE: PRT
<213> ORGANISM: Artificial Sequence
<220> FEATURE:
<223> OTHER INFORMATION: Description of Artificial Sequence: Synthetic
      consensus peptide
<220> FEATURE:
<221> NAME/KEY: MOD_RES
<222> LOCATION: (3)..(3)
<223> OTHER INFORMATION: Trp or Gly
<220> FEATURE:

```
<221> NAME/KEY: MOD_RES
<222> LOCATION: (4)..(4)
<223> OTHER INFORMATION: Phe or Tyr
<220> FEATURE:
<221> NAME/KEY: MOD_RES
<222> LOCATION: (7)..(7)
<223> OTHER INFORMATION: Arg or Ser
<220> FEATURE:
<221> NAME/KEY: MOD_RES
<222> LOCATION: (8)..(8)
<223> OTHER INFORMATION: Asn or Tyr
<220> FEATURE:
<221> NAME/KEY: MOD_RES
<222> LOCATION: (9)..(9)
<223> OTHER INFORMATION: Gln or Lys

<400> SEQUENCE: 180

Val Ile Xaa Xaa Asp Gly Xaa Xaa Xaa Tyr Tyr Ala Asp Ser Val Lys
1               5                   10                  15
Gly

<210> SEQ ID NO 181
<211> LENGTH: 17
<212> TYPE: PRT
<213> ORGANISM: Artificial Sequence
<220> FEATURE:
<223> OTHER INFORMATION: Description of Artificial Sequence: Synthetic
      consensus peptide
<220> FEATURE:
<221> NAME/KEY: MOD_RES
<222> LOCATION: (1)..(1)
<223> OTHER INFORMATION: Ala or Asp
<220> FEATURE:
<221> NAME/KEY: MOD_RES
<222> LOCATION: (5)..(5)
<223> OTHER INFORMATION: Ser or Arg
<220> FEATURE:
<221> NAME/KEY: MOD_RES
<222> LOCATION: (7)..(7)
<223> OTHER INFORMATION: Val or Gly
<220> FEATURE:
<221> NAME/KEY: MOD_RES
<222> LOCATION: (8)..(8)
<223> OTHER INFORMATION: Ser or Tyr

<400> SEQUENCE: 181

Xaa Ile Ser Gly Xaa Gly Xaa Xaa Thr Tyr Tyr Ala Asp Ser Val Lys
1               5                   10                  15
Gly

<210> SEQ ID NO 182
<211> LENGTH: 17
<212> TYPE: PRT
<213> ORGANISM: Artificial Sequence
<220> FEATURE:
<223> OTHER INFORMATION: Description of Artificial Sequence: Synthetic
      consensus peptide
<220> FEATURE:
<221> NAME/KEY: MOD_RES
<222> LOCATION: (3)..(3)
<223> OTHER INFORMATION: Trp or Ser
<220> FEATURE:
<221> NAME/KEY: MOD_RES
<222> LOCATION: (11)..(11)
<223> OTHER INFORMATION: Tyr or His

<400> SEQUENCE: 182

Val Ile Xaa Tyr Asp Gly Arg Asn Lys Tyr Xaa Ala Asp Ser Val Lys
1               5                   10                  15
Gly
```

```
<210> SEQ ID NO 183
<211> LENGTH: 5
<212> TYPE: PRT
<213> ORGANISM: Artificial Sequence
<220> FEATURE:
<223> OTHER INFORMATION: Description of Artificial Sequence: Synthetic
      consensus peptide
<220> FEATURE:
<221> NAME/KEY: MOD_RES
<222> LOCATION: (1)..(1)
<223> OTHER INFORMATION: Ala, Gly, Arg, Ser, Thr or Ile
<220> FEATURE:
<221> NAME/KEY: MOD_RES
<222> LOCATION: (3)..(3)
<223> OTHER INFORMATION: Tyr, Gly or Ala
<220> FEATURE:
<221> NAME/KEY: MOD_RES
<222> LOCATION: (5)..(5)
<223> OTHER INFORMATION: His or Ser

<400> SEQUENCE: 183

Xaa Tyr Xaa Met Xaa
1               5

<210> SEQ ID NO 184
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

Thr Arg Leu Trp Lys Tyr Trp Val
1               5

<210> SEQ ID NO 185
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

Arg Arg Leu Tyr Ile Phe Trp Glu
1               5

<210> SEQ ID NO 186
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

Tyr Lys Ala Trp Gly Tyr Tyr Val
1               5

<210> SEQ ID NO 187
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187
```

Tyr Gln Ala Trp Gly Tyr Tyr Val
1               5

<210> SEQ ID NO 188
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

Tyr Gln Ala Trp Gly Tyr Leu Val
1               5

<210> SEQ ID NO 189
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 189

Tyr Gln Ala Trp Gly Tyr Phe Val
1               5

<210> SEQ ID NO 190
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

Phe Thr Trp Val Phe Trp Asn Val
1               5

<210> SEQ ID NO 191
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191

Tyr Gln Val Trp Gly Tyr Phe Val
1               5

<210> SEQ ID NO 192
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

Tyr Lys Trp Leu Lys Trp Asn Leu
1               5

<210> SEQ ID NO 193
<211> LENGTH: 8
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 193

Arg Arg Leu Tyr Ile Phe Glu Trp
1               5

<210> SEQ ID NO 194
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

Trp Ala Glu Arg Gly Gly
1               5

<210> SEQ ID NO 195
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 195

Gly Gly Trp Ala Val Gly Arg Ile
1               5

<210> SEQ ID NO 196
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 196

Tyr Lys Tyr Leu Val Phe Trp Val
1               5

<210> SEQ ID NO 197
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 197

Tyr Lys Tyr Leu Ser Tyr Trp Val
1               5

<210> SEQ ID NO 198
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 198

Tyr Lys Thr Ala Trp Tyr Trp Lys
1               5
```

```
<210> SEQ ID NO 199
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 199

Tyr Val Phe His Lys Trp Trp Val
1               5

<210> SEQ ID NO 200
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 200

Tyr Val Phe Tyr Leu Trp Trp Lys
1               5

<210> SEQ ID NO 201
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 201

Tyr Arg Trp Leu His Trp His Val
1               5

<210> SEQ ID NO 202
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 202

Tyr Lys Phe Leu Phe Trp His Ala
1               5

<210> SEQ ID NO 203
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 203

Arg Arg Gln Trp Gly Phe Trp Val
1               5

<210> SEQ ID NO 204
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 204
```

```
Tyr Ser Ala Trp Ser Phe Trp Val
1               5

<210> SEQ ID NO 205
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 205

Leu Ala Arg Trp Gly Phe Trp Val
1               5

<210> SEQ ID NO 206
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 206

Tyr Asp Ala Trp Gly Tyr Trp Val
1               5

<210> SEQ ID NO 207
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 207

Trp Arg Lys Tyr Tyr His Phe Trp Val Ser
1               5                   10

<210> SEQ ID NO 208
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208

Lys Arg Leu Tyr Gly Leu Phe Trp Tyr Asp
1               5                   10

<210> SEQ ID NO 209
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 209

Lys Lys His Trp Ser Ser Leu Phe Phe Glu
1               5                   10

<210> SEQ ID NO 210
<211> LENGTH: 10
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 210

Lys Ala Trp Pro Tyr Ser Trp Glu Ala Val
1               5                   10

<210> SEQ ID NO 211
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 211

Glu Trp Tyr Cys Gly Val Leu Phe Asn Cys Gln Gln
1               5                   10

<210> SEQ ID NO 212
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 212

His Phe Gly Cys Gly Val Ile Phe Asn Cys Val Ser Asp
1               5                   10

<210> SEQ ID NO 213
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 213

Trp Glu Leu Cys Ala Ser Gly Tyr Gly Trp Cys Tyr Leu His
1               5                   10

<210> SEQ ID NO 214
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 214

Ala Pro Ser Cys Lys Ser Tyr Ile Gly Phe Gly Leu Tyr His Cys Trp
1               5                   10                  15

Asp Gly

<210> SEQ ID NO 215
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 215

His Phe Lys Cys Gly Met Gly Leu Phe Glu Cys Ala Asp Pro
```

```
<210> SEQ ID NO 216
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 216
acgaggcttt ggaagtattg ggtg                                              24

<210> SEQ ID NO 217
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 217
aggaggttgt atatttttg ggag                                               24

<210> SEQ ID NO 218
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 218
tataaggcgt ggggttatta tgtg                                              24

<210> SEQ ID NO 219
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 219
tattaggcgt ggggttatta tgtg                                              24

<210> SEQ ID NO 220
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 220
tattaggcgt ggggttattt ggtg                                              24

<210> SEQ ID NO 221
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 221
taccaggctt ggggttactt cgtt                                              24
```

<210> SEQ ID NO 222
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 222
ttcacttggg ttttctggaa cgtt                                              24

<210> SEQ ID NO 223
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 223
taccaggttt ggggttactt cgtt                                              24

<210> SEQ ID NO 224
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 224
tacaaatggc tgaaatggaa cctg                                              24

<210> SEQ ID NO 225
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 225
aggaggttgt atattttttg ggag                                              24

<210> SEQ ID NO 226
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 226
tgggcggaga ggggtggt                                                     18

<210> SEQ ID NO 227
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 227 gggggggtggg cggttgggcg tatt                                             24

<210> SEQ ID NO 228
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 228
tacaaatacc tggttttctg ggtt                                              24

<210> SEQ ID NO 229
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 229
tacaaatacc tgtcttactg ggtt                                              24

<210> SEQ ID NO 230
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 230
tacaaaactg cttggtactg gaaa                                              24

<210> SEQ ID NO 231
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 231
tatgtgtttc ataagtggtg ggtt                                              24

<210> SEQ ID NO 232
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 232
tacgttttct acctgtggtg gaaa                                              24

<210> SEQ ID NO 233
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 233
taccgttggc tgcattggca tgtt                                              24

```
<210> SEQ ID NO 234
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 234
tacaaattcc tgttctggca cgct                                              24

<210> SEQ ID NO 235
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 235
aggaggcagt gggggttttg ggtt                                              24

<210> SEQ ID NO 236
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 236
tactctgctt ggtctttctg ggtt                                              24

<210> SEQ ID NO 237
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 237
ttggctaggt gggggttttg ggtt                                              24

<210> SEQ ID NO 238
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 238
tatgatgcgt ggggttattg ggtg                                              24

<210> SEQ ID NO 239
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 239
tggcgtaaat actaccattt ctgggtttct                                        30

<210> SEQ ID NO 240
```

```
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 240
aaacgtctgt acggtctgtt ctggtacgac                                    30

<210> SEQ ID NO 241
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 241
aaaaaacatt ggtcttctct gttcttcgaa                                    30

<210> SEQ ID NO 242
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 242
aaagcttggc cgtactcttg ggaagctgtt                                    30

<210> SEQ ID NO 243
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 243
gagtggtact gcggcgtgct gttcaactgc cagcag                             36

<210> SEQ ID NO 244
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 244
cattttggtt gcggtgttat ttttaattgt gtttctgat                          39

<210> SEQ ID NO 245
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 245
tgggagcttt gtgcttctgg ttatggttgg tgctatcttc at                      42

<210> SEQ ID NO 246
<211> LENGTH: 54
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 246
gctccttctt gcaagtctta tattggtttt ggtctttatc attgttggga tggt          54

<210> SEQ ID NO 247
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 247
cacttcaagt gcggcatggg cctgttcgag tgcgccgacc cc                       42

<210> SEQ ID NO 248
<211> LENGTH: 462
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 248
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Ser Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Ala Thr Ser Gly Trp Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser His Glu Asp Pro
        260                 265                 270

Glu Val Lys Phe Asn Trp Tyr Val Asp Gly Val Glu Val His Asn Ala
    275                 280                 285

Lys Thr Lys Pro Arg Glu Glu Gln Tyr Gln Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Gly Gly Cys Tyr Gln Ala Trp Gly Tyr
        355                 360                 365

Tyr Val Cys Gly Gly Thr Lys Asn Gln Val Ser Leu Thr Cys Leu Val
    370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Lys Leu Thr Val Asp Lys Ser Arg Trp
            420                 425                 430

Gln Gln Gly Asn Val Phe Ser Cys Ser Val Met His Glu Ala Leu His
        435                 440                 445

Asn His Tyr Thr Gln Lys Ser Leu Ser Leu Ser Pro Gly Lys
    450                 455                 460

<210> SEQ ID NO 249
<211> LENGTH: 464
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 249

Gln Val Gln Leu Val Glu Ser Gly Gly Gly Val Val Gln Pro Gly Arg
1               5                   10                  15

Ser Leu Arg Leu Ser Cys Ala Ala Ser Arg Phe Ser Phe Ser Arg Tyr
            20                  25                  30

Gly Met His Trp Val Arg Gln Ala Pro Gly Lys Gly Leu Glu Trp Val
        35                  40                  45

Ala Val Ile Trp Phe Asp Gly Arg Asn Gln Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Val Glu Asp Thr Ala Val Tyr Tyr Cys
                85                  90                  95

Ala Arg Asp His Pro Val Val Gly Thr Ser Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Gln Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Gly Gly Cys Tyr Gln Ala Trp
        355                 360                 365

Gly Tyr Tyr Val Cys Gly Gly Thr Lys Asn Gln Val Ser Leu Thr Cys
    370                 375                 380

Leu Val Lys Gly Phe Tyr Pro Ser Asp Ile Ala Val Glu Trp Glu Ser
385                 390                 395                 400

Asn Gly Gln Pro Glu Asn Asn Tyr Lys Thr Thr Pro Pro Val Leu Asp
                405                 410                 415

Ser Asp Gly Ser Phe Phe Leu Tyr Ser Lys Leu Thr Val Asp Lys Ser
            420                 425                 430

Arg Trp Gln Gln Gly Asn Val Phe Ser Cys Ser Val Met His Glu Ala
        435                 440                 445

Leu His Asn His Tyr Thr Gln Lys Ser Leu Ser Leu Ser Pro Gly Lys
    450                 455                 460

<210> SEQ ID NO 250
<211> LENGTH: 466
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 250

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val

```
                35                  40                  45
Ala Val Ile Gly Tyr Asp Gly Ser Tyr Lys Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Gly Ser Asn Trp Asn Tyr Gly Gly Ser Phe Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Gln Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Gly Gly Cys Tyr Gln
        355                 360                 365

Ala Trp Gly Tyr Tyr Val Cys Gly Gly Thr Lys Asn Gln Val Ser Leu
    370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Tyr Ser Lys Leu Thr Val Asp
            420                 425                 430

Lys Ser Arg Trp Gln Gln Gly Asn Val Phe Ser Cys Ser Val Met His
        435                 440                 445

Glu Ala Leu His Asn His Tyr Thr Gln Lys Ser Leu Ser Leu Ser Pro
    450                 455                 460
```

Gly Lys
465

<210> SEQ ID NO 251

<400> SEQUENCE: 251

000

<210> SEQ ID NO 252
<211> LENGTH: 465
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 252

Glu Val Gln Leu Leu Glu Ser Gly Gly Gly Leu Val Gln Pro Glu Gly
1               5                   10                  15

Ser Leu Arg Leu Ser Cys Ala Ala Ser Gly Phe Thr Phe Ser Ile Tyr
            20                  25                  30

Ala Met Ser Trp Val Arg Gln Ala Pro Gly Lys Gly Leu Glu Trp Val
        35                  40                  45

Ser Asp Ile Ser Gly Arg Gly Gly Tyr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Asp Asp Thr Ala Val Tyr Tyr Cys
                85                  90                  95

Ala Lys Asp Arg Ser Ile Ala Val Ala Gly Pro Phe Asp Phe Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Gln Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Gly Gly Cys Tyr Gln Ala
                355                 360                 365

Trp Gly Tyr Tyr Val Cys Gly Gly Thr Lys Asn Gln Val Ser Leu Thr
    370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Val Leu
                405                 410                 415

Asp Ser Asp Gly Ser Phe Phe Leu Tyr Ser Lys Leu Thr Val Asp Lys
                420                 425                 430

Ser Arg Trp Gln Gln Gly Asn Val Phe Ser Cys Ser Val Met His Glu
                435                 440                 445

Ala Leu His Asn His Tyr Thr Gln Lys Ser Leu Ser Leu Ser Pro Gly
    450                 455                 460

Lys
465

<210> SEQ ID NO 253
<211> LENGTH: 464
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 253

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Tyr Met His Trp Val Arg Gln Ala Pro Gly Gln Gly Leu Glu Trp Met
            35                  40                  45

Gly Trp Ile Asn Pro Asn Ser Gly Gly Thr Asn Ser Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Thr Ala Val Tyr Tyr Cys
                85                  90                  95

Ala Arg Asp Ala Thr Ser Gly Trp Phe Asp Tyr Trp Gly Gln Gly Thr
            100                 105                 110

Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

```
Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Gln Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Gly Gly Glu Trp Tyr Cys Gly Val Leu
        355                 360                 365

Phe Asn Cys Gln Gln Gly Gly Thr Lys Asn Gln Val Ser Leu Thr Cys
    370                 375                 380

Leu Val Lys Gly Phe Tyr Pro Ser Asp Ile Ala Val Glu Trp Glu Ser
385                 390                 395                 400

Asn Gly Gln Pro Glu Asn Asn Tyr Lys Thr Thr Pro Pro Val Leu Asp
                405                 410                 415

Ser Asp Gly Ser Phe Phe Leu Tyr Ser Lys Leu Thr Val Asp Lys Ser
            420                 425                 430

Arg Trp Gln Gln Gly Asn Val Phe Ser Cys Ser Val Met His Glu Ala
        435                 440                 445

Leu His Asn His Tyr Thr Gln Lys Ser Leu Ser Leu Ser Pro Gly Lys
    450                 455                 460

<210> SEQ ID NO 254
<211> LENGTH: 466
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 254

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Tyr Met His Trp Val Arg Gln Ala Pro Gly Gln Gly Leu Glu Trp Met
            35                  40                  45

Gly Trp Ile Asn Pro Asn Ser Gly Gly Thr Asn Ser Ala Gln Lys Phe
        50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
```

```
                        85                  90                  95
Ala Arg Asp Ala Thr Ser Gly Trp Phe Asp Tyr Trp Gly Gln Gly Thr
                100                 105                 110

Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Gln Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Gly Gly His Phe Lys Cys Gly Met Gly
        355                 360                 365

Leu Phe Glu Cys Ala Asp Pro Gly Gly Thr Lys Asn Gln Val Ser Leu
        370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Tyr Ser Lys Leu Thr Val Asp
            420                 425                 430

Lys Ser Arg Trp Gln Gln Gly Asn Val Phe Ser Cys Ser Val Met His
        435                 440                 445

Glu Ala Leu His Asn His Tyr Thr Gln Lys Ser Leu Ser Leu Ser Pro
        450                 455                 460

Gly Lys
465

<210> SEQ ID NO 255
<211> LENGTH: 466
<212> TYPE: PRT
<213> ORGANISM: Artificial Sequence
```

-continued

```
<220> FEATURE:
<223> OTHER INFORMATION: Description of Artificial Sequence: Synthetic
      polypeptide

<400> SEQUENCE: 255

Gln Val Gln Leu Val Glu Ser Gly Gly Val Val Gln Pro Gly Arg
1               5                   10                  15

Ser Leu Arg Leu Ser Cys Ala Ala Ser Arg Phe Ser Phe Ser Arg Tyr
            20                  25                  30

Gly Met His Trp Val Arg Gln Ala Pro Gly Lys Gly Leu Glu Trp Val
        35                  40                  45

Ala Val Ile Trp Phe Asp Gly Arg Asn Gln Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Val Glu Asp Thr Ala Val Tyr Tyr Cys
                85                  90                  95

Ala Arg Asp His Pro Val Val Gly Thr Ser Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Gln Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Gly Gly Glu Trp Tyr Cys Gly
        355                 360                 365

Val Leu Phe Asn Cys Gln Gln Gly Gly Thr Lys Asn Gln Val Ser Leu
    370                 375                 380

Thr Cys Leu Val Lys Gly Phe Tyr Pro Ser Asp Ile Ala Val Glu Trp
```

```
                385                 390                 395                 400
Glu Ser Asn Gly Gln Pro Glu Asn Asn Tyr Lys Thr Thr Pro Pro Val
                405                 410                 415

Leu Asp Ser Asp Gly Ser Phe Phe Leu Tyr Ser Lys Leu Thr Val Asp
                420                 425                 430

Lys Ser Arg Trp Gln Gln Gly Asn Val Phe Ser Cys Ser Val Met His
                435                 440                 445

Glu Ala Leu His Asn His Tyr Thr Gln Lys Ser Leu Ser Leu Ser Pro
                450                 455                 460

Gly Lys
465

<210> SEQ ID NO 256
<211> LENGTH: 468
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 256

Gln Val Gln Leu Val Glu Ser Gly Gly Gly Val Val Gln Pro Gly Arg
1               5                   10                  15

Ser Leu Arg Leu Ser Cys Ala Ala Ser Arg Phe Ser Phe Ser Arg Tyr
                20                  25                  30

Gly Met His Trp Val Arg Gln Ala Pro Gly Lys Gly Leu Glu Trp Val
                35                  40                  45

Ala Val Ile Trp Phe Asp Gly Arg Asn Gln Tyr Tyr Ala Asp Ser Val
                50                  55                  60

Lys Gly Arg Phe Thr Ile Ser Arg Asp Asn Ser Lys Asn Thr Leu Phe
65              70                  75                  80

Leu Gln Met Asn Ser Leu Arg Val Glu Asp Thr Ala Val Tyr Tyr Cys
                85                  90                  95

Ala Arg Asp His Pro Val Val Gly Thr Ser Phe Asp Tyr Trp Gly Gln
                100                 105                 110

Gly Thr Leu Val Thr Val Ser Ser Ala Ser Thr Lys Gly Pro Ser Val
                115                 120                 125

Phe Pro Leu Ala Pro Ser Ser Lys Ser Thr Ser Gly Gly Thr Ala Ala
                130                 135                 140

Leu Gly Cys Leu Val Lys Asp Tyr Phe Pro Glu Pro Val Thr Val Ser
145             150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
                195                 200                 205

Pro Ser Asn Thr Lys Val Asp Lys Lys Val Glu Pro Lys Ser Cys Asp
                210                 215                 220

Lys Thr His Thr Cys Pro Pro Cys Pro Ala Pro Glu Leu Leu Gly Gly
225             230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270
```

```
Asp Pro Glu Val Lys Phe Asn Trp Tyr Val Asp Gly Val Glu Val His
            275                 280                 285

Asn Ala Lys Thr Lys Pro Arg Glu Glu Gln Tyr Gln Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Gly Gly His Phe Lys Cys Gly
        355                 360                 365

Met Gly Leu Phe Glu Cys Ala Asp Pro Gly Gly Thr Lys Asn Gln Val
    370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
            420                 425                 430

Val Asp Lys Ser Arg Trp Gln Gln Gly Asn Val Phe Ser Cys Ser Val
        435                 440                 445

Met His Glu Ala Leu His Asn His Tyr Thr Gln Lys Ser Leu Ser Leu
    450                 455                 460

Ser Pro Gly Lys
465

<210> SEQ ID NO 257
<211> LENGTH: 1386
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 257
caggtgcaac tggtgcagtc tggggctgag gtgaagaagc ctggggcctc agtgaaggtc      60
tcctgcaagg cttctggata caccttcacc ggctactata tgcactgggt gcgacaggcc     120
cctggacaag ggcttgagtg gatgggatgg atcaaccct a acagtggtgg cacaaactct     180
gcacagaagt tcagggcag g gtcaccatg accagggaca cgtccatcag cacagcctac     240
atggagctga gcaggctgag atctgacgac acggccgtgt attactgtgc aagagatgcg     300
accagtggct ggtttgacta ctggggccag ggaaccctgg tcaccgtctc tagtgcctcc     360
accaagggcc catcggtctt ccccctggca ccctcctcca gagcacctc tgggggcaca     420 gcggccctgg gctgcctggt caaggactac ttccccgaac cggtgacggt gtcgtggaac     480
tcaggcgccc tgaccagcgg cgtgcacacc ttcccggctg tcctacagtc ctcaggactc     540
tactccctca gcagcgtggt gaccgtgccc tccagcagct gggcaccca gacctacatc     600 tgcaacgtga atcacaagcc cagcaacacc aaggtggaca gaaagttga gcccaaatct     660 tgtgacaaaa ctcacacatg cccaccgtgc ccagcacctg aactcctggg gggaccgtca     720
gtcttcctct tccccccaaa acccaaggac accctcatga tctcccggac ccctgaggtc     780
acatgcgtgt ggtggacgt gagccacgaa gaccctgagg tcaagttcaa ctggtacgtg     840
gacggcgtgg aggtgcataa tgccaagaca aagccgcggg aggagcagta ccagagcacg     900
```

```
taccgtgtgg tcagcgtcct caccgtcctg caccaggact ggctgaatgg caaggagtac    960
aagtgcaagg tctccaacaa agccctccca gcccccatcg agaaaaccat ctccaaagcc   1020
aaagggcagc cccgagaacc acaggtgtac accctgcccc catcccggga tgagctgggt   1080
ggttgctacc aggcctgggg ctactacgtg tgcggtggta ccaagaacca ggtcagcctg   1140
acctgcctgg tcaaaggctt ctatcccagc gacatcgccg tggagtggga gagcaatggg   1200
cagccggaga caactacaa gaccacgcct cccgtgctgg actccgacgg ctccttcttc    1260
ctctatagca agctcaccgt ggacaagagc aggtggcagc aggggaacgt cttctcatgc   1320
tccgtgatgc atgaggctct gcacaaccac tacacgcaga gagcctctc cctgtctccg    1380 ggtaaa                                                              1386

<210> SEQ ID NO 258
<211> LENGTH: 1392
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 258
caggtgcagt tggtggagtc tgggggaggc gtggtccagc ctgggaggtc cctgagactc     60
tcctgtgcag cgtctagatt ctccttcagt agatatggca tgcactgggt ccgccaggct    120
ccaggcaagg ggctggagtg ggtggcagtt atatggtttg atggaagaaa tcaatactat    180
gcagactccg tgaaggggcg attcaccatc tccagagaca attccaagaa tacgctgttt    240
ctgcaaatga acagcctgag agtcgaggac acggctgtgt attactgtgc gagagatcac    300
ccagtagttg gtacgagctt tgactactgg ggccagggaa ccctggtcac cgtctctagt    360
gcctccacca agggcccatc ggtcttcccc ctggcaccct cctccaagag cacctctggg    420
ggcacagcgg ccctgggctg cctggtcaag gactacttcc ccgaaccggt gacggtgtcg    480
tggaactcag gcgccctgac cagcggcgtg cacaccttcc cggctgtcct acagtcctca    540
ggactctact ccctcagcag cgtggtgacc gtgccctcca gcagcttggg cacccagacc    600
tacatctgca acgtgaatca caagcccagc aacaccaagg tggacaagaa agttgagccc    660
aaatcttgtg acaaaactca cacatgccca ccgtgcccag cacctgaact cctggggggga   720 ccgtcagtct tcctcttccc cccaaaaccc aaggacaccc tcatgatctc ccggacccct    780
gaggtcacat gcgtggtggt ggacgtgagc cacgaagacc ctgaggtcaa gttcaactgg    840
tacgtggacg gcgtggaggt gcataatgcc aagacaaagc cgcgggagga gcagtaccag    900
agcacgtacc gtgtggtcag cgtcctcacc gtcctgcacc aggactggct gaatggcaag    960
gagtacaagt gcaaggtctc caacaaagcc ctcccagccc catcgagaaa accatctcc   1020 aaagccaaag gcagccccg agaaccacag gtgtacaccc tgcccccatc ccggatgag    1080 ctgggtggtt gctaccaggc ctggggctac tacgtgtgcg gtggtaccaa gaaccaggtc   1140
agcctgacct gcctggtcaa aggcttctat cccagcgaca tcgccgtgga gtgggagagc   1200
aatgggcagc cggagaacaa ctacaagacc acgcctcccg tgctggactc cgacggctcc   1260
ttcttcctct atagcaagct caccgtggac aagagcaggt ggcagcaggg gaacgtcttc   1320
tcatgctccg tgatgcatga ggctctgcac aaccactaca cgcagaagag cctctccctg   1380
tctccgggta aa                                                      1392
```

<210> SEQ ID NO 259
<211> LENGTH: 1398
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 259

```
caggtgcaac tggtggagtc tgggggaggc gtggtccagc ctgggaggtc cctgagactc    60
tcctgtgcag cgtctggatt caccttcagt agctatggca tgcactgggt ccgccaggct   120
ccaggcaagg ggctggagtg ggtggcagtt atagggtatg atggaagtta taaatactat   180
gcagactccg tgaagggccg attcaccatc tccagagaca attccaagaa cacgctatat   240
ctgcaaatga acagcctgag agccgaggac acggctgtgt attactgtgc gagagatggg   300
tctaactgga actacggggg ttcttttgac tactggggcc agggaaccct ggtcaccgtc   360
tctagtgcct ccaccaaggg cccatcggtc ttccccctgg cacccctcct caagagcacc   420
tctgggggca gcggccct gggctgcctg gtcaaggact acttccccga accggtgacg      480
gtgtcgtgga actcaggcgc cctgaccagc ggcgtgcaca ccttcccggc tgtcctacag   540
tcctcaggac tctactccct cagcagcgtg gtgaccgtgc cctccagcag cttgggcacc   600
cagacctaca tctgcaacgt gaatcacaag cccagcaaca ccaaggtgga caagaaagtt   660
gagcccaaat cttgtgacaa aactcacaca tgcccaccgt gcccagcacc tgaactcctg   720
gggggaccgt cagtcttcct cttccccca aaacccaagg acaccctcat gatctcccgg    780
acccctgagg tcacatgcgt ggtggtggac gtgagccacg aagaccctga ggtcaagttc   840
aactggtacg tggacggcgt ggaggtgcat aatgccaaga caaagccgcg ggaggagcag   900
taccagagca cgtaccgtgt ggtcagcgtc ctcaccgtcc tgcaccagga ctggctgaat   960
ggcaaggagt acaagtgcaa ggtctccaac aaagccctcc cagcccccat cgagaaaacc  1020
atctccaaag ccaaagggca gccccgagaa ccacaggtgt acaccctgcc cccatcccgg  1080
gatgagctgg tggttgcta ccaggcctgg ggctactacg tgtgcggtgg taccaagaac   1140
caggtcagcc tgacctgcct ggtcaaaggc ttctatccca gcgacatcgc cgtggagtgg  1200
gagagcaatg ggcagccgga gaacaactac aagaccacgc ctcccgtgct ggactccgac  1260
ggctccttct tcctctatag caagctcacc gtggacaaga gcaggtggca gcaggggaac  1320
gtcttctcat gctccgtgat gcatgaggct ctgcacaacc actacacgca gaagagcctc  1380
tccctgtctc cgggtaaa                                                1398
```

<210> SEQ ID NO 260

<400> SEQUENCE: 260

000

<210> SEQ ID NO 261
<211> LENGTH: 1395
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 261

```
gaggtgcagc tgttggagtc tgggggaggc ttggtacagc cggaggggtc cctgagactc    60
tcctgtgcag cctctggatt caccttttagc atctatgcca tgagctgggt ccgccaggct  120
```

```
ccagggaagg ggctggagtg ggtctcagat attagtggtc gtggtggtta cacatactac      180
gcagactccg tgaagggccg gttcaccatc tccagagaca attccaagaa cacgctgtat      240
ctgcaaatga acagcctgag agccgacgac acggccgtat attactgtgc gaaagatcgg      300
agtatagcag tggctggtcc ttttgacttc tggggccagg gaaccctggt caccgtctct      360
agtgcctcca ccaagggccc atcggtcttc cccctggcac cctcctccaa gagcacctct      420
gggggcacag cggccctggg ctgcctggtc aaggactact tccccgaacc ggtgacggtg      480
tcgtggaact caggcgccct gaccagcggc gtgcacacct tcccggctgt cctacagtcc      540
tcaggactct actccctcag cagcgtggtg accgtgccct ccagcagctt gggcacccag      600
acctacatct gcaacgtgaa tcacaagccc agcaacacca aggtggacaa gaaagttgag      660
cccaaatctt gtgacaaaac tcacacatgc ccaccgtgcc cagcacctga actcctgggg      720
ggaccgtcag tcttcctctt ccccccaaaa cccaaggaca cctcatgat ctcccggacc       780 cctgaggtca catgcgtggt ggtggacgtg agccacgaag accctgaggt caagttcaac      840
tggtacgtgg acggcgtgga ggtgcataat gccaagacaa agccgcggga ggagcagtac      900
cagagcacgt accgtgtggt cagcgtcctc accgtcctgc accaggactg gctgaatggc      960
aaggagtaca agtgcaaggt ctccaacaaa gccctcccag cccccatcga gaaaaccatc     1020
tccaaagcca agggcagcc ccgagaacca caggtgtaca ccctgccccc atcccgggat      1080
gagctgggtg gttgctacca ggcctgggc tactacgtgt gcggtggtac caagaaccag      1140
gtcagcctga cctgcctggt caaaggcttc tatcccagcg acatcgccgt ggagtgggag     1200
agcaatgggc agccggagaa caactacaag accacgcctc ccgtgctgga ctccgacggc     1260
tccttcttcc tctatagcaa gctcaccgtg gacaagagca ggtggcagca ggggaacgtc     1320
ttctcatgct ccgtgatgca tgaggctctg cacaaccact acacgcagaa gagcctctcc     1380
ctgtctccgg gtaaa                                                      1395
```

<210> SEQ ID NO 262  
<211> LENGTH: 1392  
<212> TYPE: DNA  
<213> ORGANISM: Artificial Sequence  
<220> FEATURE:  
<223> OTHER INFORMATION: Description of Artificial Sequence: Synthetic polynucleotide

<400> SEQUENCE: 262

```
caggtgcaac tggtgcagtc tggggctgag gtgaagaagc ctggggcctc agtgaaggtc       60
tcctgcaagg cttctggata caccttcacc ggctactata tgcactgggt gcgacaggcc      120
cctggacaag gcttgagtg gatgggatgg atcaacccta acagtggtgg cacaaactct      180
gcacagaagt tcagggcag ggtcaccatg accagggaca cgtccatcag cacagcctac       240
atggagctga gcaggctgag atctgacgac acggccgtgt attactgtgc aagagatgcg      300
accagtggct ggtttgacta ctgggccag ggaaccctgg tcaccgtctc tagtgcctcc       360
accaagggcc catcggtctt ccccctggca cctcctcca agagcacctc tggggcaca        420 gcggccctgg gctgcctggt caaggactac ttccccgaac cggtgacggt gtcgtggaac      480
tcaggcgccc tgaccagcgg cgtgcacacc ttcccggctg tcctacagtc ctcaggactc      540
tactccctca gcagcgtggt gaccgtgccc tccagcagct tggcaccca gacctacatc       600 tgcaacgtga atcacaagcc cagcaacacc aaggtggaca agaaagttga gcccaaatct      660
tgtgacaaaa ctcacacatg cccaccgtgc ccagcacctg aactcctggg gggaccgtca      720
```

```
gtcttcctct tcccccaaa acccaaggac accctcatga tctcccggac ccctgaggtc    780
acatgcgtgg tggtggacgt gagccacgaa gaccctgagg tcaagttcaa ctggtacgtg    840
gacggcgtgg aggtgcataa tgccaagaca aagccgcggg aggagcagta ccagagcacg    900
taccgtgtgg tcagcgtcct caccgtcctg caccaggact ggctgaatgg caaggagtac    960
aagtgcaagg tctccaacaa agccctccca gcccccatcg agaaaaccat ctccaaagcc   1020
aaagggcagc cccgagaacc acaggtgtac accctgcccc catcccggga tgagctgggt   1080
ggtgagtggt actgcggcgt gctgttcaac tgccagcagg tggtaccaa gaaccaggtc    1140 agcctgacct gcctggtcaa aggcttctat cccagcgaca tcgccgtgga gtgggagagc   1200
aatgggcagc cggagaacaa ctacaagacc acgcctcccg tgctggactc cgacggctcc   1260
ttcttcctct atagcaagct caccgtggac aagagcaggt ggcagcaggg gaacgtcttc   1320
tcatgctccg tgatgcatga ggctctgcac aaccactaca cgcagaagag cctctccctg   1380
tctccgggta aa                                                       1392
```

<210> SEQ ID NO 263
<211> LENGTH: 1398
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 263

```
caggtgcaac tggtgcagtc tggggctgag gtgaagaagc ctggggcctc agtgaaggtc      60
tcctgcaagg cttctggata caccttcacc ggctactata tgcactgggt gcgacaggcc     120
cctggacaag gcttgagtg gatgggatgg atcaaccctaa acagtggtgg cacaaactct     180
gcacagaagt ttcagggcag ggtcaccatg accagggaca cgtccatcag cacagcctac     240
atggagctga gcaggctgag atctgacgac acggccgtgt attactgtgc aagagatgcg     300
accagtggct ggtttgacta ctggggccag ggaaccctgg tcaccgtctc tagtgcctcc     360
accaagggcc catcggtctt ccccctggca ccctcctcca agagcacctc tgggggcaca     420
gcggccctgg gctgcctggt caaggactac ttccccgaac cggtgacggt gtcgtggaac     480
tcaggcgccc tgaccagcgg cgtgcacacc ttcccggctg tcctacagtc ctcaggactc     540
tactccctca gcagcgtggt gaccgtgccc tccagcagct gggcaccca gacctacatc     600 tgcaacgtga atcacaagcc cagcaacacc aaggtggaca gaaagttga gcccaaatct     660 tgtgacaaaa ctcacacatg cccaccgtgc ccagcacctg aactcctggg gggaccgtca     720
gtcttcctct tccccccaaa acccaaggac accctcatga tctcccggac ccctgaggtc     780
acatgcgtgg tggtggacgt gagccacgaa gaccctgagg tcaagttcaa ctggtacgtg     840
gacggcgtgg aggtgcataa tgccaagaca aagccgcggg aggagcagta ccagagcacg     900
taccgtgtgg tcagcgtcct caccgtcctg caccaggact ggctgaatgg caaggagtac     960
aagtgcaagg tctccaacaa agccctccca gcccccatcg agaaaaccat ctccaaagcc    1020
aaagggcagc cccgagaacc acaggtgtac accctgcccc catcccggga tgagctgggt   1080
ggtcacttca gtgcggcat gggcctgttc gagtgcgccg accccggtgg taccaagaac    1140
caggtcagcc tgacctgcct ggtcaaaggc ttctatccca gcgacatcgc cgtggagtgg    1200
gagagcaatg gcagccgga gaacaactac aagaccacgc ctcccgtgct ggactccgac    1260
ggctccttct tcctctatag caagctcacc gtggacaaga gcaggtggca gcaggggaac    1320
```

```
gtcttctcat gctccgtgat gcatgaggct ctgcacaacc actacacgca gaagagcctc    1380
tccctgtctc cgggtaaa                                                  1398

<210> SEQ ID NO 264
<211> LENGTH: 1398
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 264
caggtgcagt tggtggagtc tgggggaggc gtggtccagc ctgggaggtc cctgagactc      60
tcctgtgcag cgtctagatt ctccttcagt agatatggca tgcactgggt ccgccaggct     120
ccaggcaagg ggctggagtg ggtggcagtt atatggtttg atggaagaaa tcaatactat     180
gcagactccg tgaaggggcg attcaccatc tccagagaca attccaagaa tacgctgttt     240
ctgcaaatga acagcctgag agtcgaggac acggctgtgt attactgtgc gagagatcac     300
ccagtagttg gtacgagctt tgactactgg ggccagggaa ccctggtcac cgtctctagt     360
gcctccacca agggcccatc ggtcttcccc ctggcaccct cctccaagag cacctctggg     420
ggcacagcgg ccctgggctg cctggtcaag gactacttcc ccgaaccggt gacggtgtcg     480
tggaactcag gcgccctgac cagcggcgtg cacaccttcc cggctgtcct acagtcctca     540
ggactctact ccctcagcag cgtggtgacc gtgccctcca gcagcttggg cacccagacc     600
tacatctgca acgtgaatca caagcccagc aacaccaagg tggacaagaa agttgagccc     660
aaatcttgtg acaaaactca cacatgccca ccgtgcccag cacctgaact cctggggggga    720 ccgtcagtct tcctcttccc cccaaaaccc aaggacaccc tcatgatctc ccggacccct     780
gaggtcacat gcgtggtggt ggacgtgagc cacgaagacc ctgaggtcaa gttcaactgg     840
tacgtggacg gcgtggaggt gcataatgcc aagacaaagc cgcgggagga gcagtaccag     900
agcacgtacc gtgtggtcag cgtcctcacc gtcctgcacc aggactggct gaatggcaag     960
gagtacaagt gcaaggtctc caacaaagcc ctcccagccc ccatcgagaa aaccatctcc    1020
aaagccaaag ggcagccccg agaaccacag gtgtacaccc tgcccccatc ccgggatgag    1080
ctgggtggtg agtggtactg cggcgtgctg ttcaactgcc agcagggtgg taccaagaac    1140
caggtcagcc tgacctgcct ggtcaaaggc ttctatccca gcgacatcgc cgtggagtgg    1200
gagagcaatg ggcagccgga gaacaactac aagaccacgc ctcccgtgct ggactccgac    1260
ggctccttct tcctctatag caagctcacc gtggacaaga gcaggtggca gcaggggaac    1320
gtcttctcat gctccgtgat gcatgaggct ctgcacaacc actacacgca gaagagcctc    1380
tccctgtctc cgggtaaa                                                  1398

<210> SEQ ID NO 265
<211> LENGTH: 1404
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 265
caggtgcagt tggtggagtc tgggggaggc gtggtccagc ctgggaggtc cctgagactc      60
tcctgtgcag cgtctagatt ctccttcagt agatatggca tgcactgggt ccgccaggct     120
```

```
ccaggcaagg ggctggagtg ggtggcagtt atatggtttg atggaagaaa tcaatactat      180
gcagactccg tgaaggggcg attcaccatc tccagagaca attccaagaa tacgctgttt      240
ctgcaaatga acagcctgag agtcgaggac acggctgtgt attactgtgc gagagatcac      300
ccagtagttg gtacgagctt tgactactgg ggccagggaa ccctggtcac cgtctctagt      360
gcctccacca agggcccatc ggtcttcccc ctggcaccct cctccaagag cacctctggg      420
ggcacagcgg ccctgggctg cctggtcaag gactacttcc ccgaaccggt gacggtgtcg      480
tggaactcag gcgccctgac cagcggcgtg cacaccttcc cggctgtcct acagtcctca      540
ggactctact ccctcagcag cgtggtgacc gtgccctcca gcagcttggg cacccagacc      600
tacatctgca acgtgaatca caagcccagc aacaccaagg tggacaagaa agttgagccc      660
aaatcttgtg acaaaactca cacatgccca ccgtgcccag cacctgaact cctgggggga      720
ccgtcagtct tcctcttccc cccaaaaccc aaggacaccc tcatgatctc ccggacccct      780
gaggtcacat gcgtggtggt ggacgtgagc cacgaagacc ctgaggtcaa gttcaactgg      840
tacgtggacg gcgtggaggt gcataatgcc aagacaaagc cgcgggagga gcagtaccag      900
agcacgtacc gtgtggtcag cgtcctcacc gtcctgcacc aggactggct gaatggcaag      960
gagtacaagt gcaaggtctc caacaaagcc ctcccagccc ccatcgagaa aaccatctcc     1020
aaagccaaag ggcagccccg agaaccacag gtgtacaccc tgcccccatc ccgggatgag     1080
ctgggtggtc acttcaagtg cggcatgggc ctgttcgagt gcgccgaccc cggtggtacc     1140
aagaaccagg tcagcctgac ctgcctggtc aaaggcttct atcccagcga catcgccgtg     1200
gagtgggaga gcaatgggca gccggagaac aactacaaga ccacgcctcc cgtgctggac     1260
tccgacggct ccttcttcct ctatagcaag ctcaccgtgg acaagagcag gtggcagcag     1320
gggaacgtct tctcatgctc cgtgatgcat gaggctctgc acaaccacta cacgcagaag     1380
agcctctccc tgtctccggg taaa                                             1404
```

<210> SEQ ID NO 266
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 266

Cys Pro Ser Cys Pro
1               5

<210> SEQ ID NO 267
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 267

Cys Pro Pro Cys Pro
1               5

<210> SEQ ID NO 268
<211> LENGTH: 6
<212> TYPE: PRT
<213> ORGANISM: Artificial Sequence
<220> FEATURE:
<223> OTHER INFORMATION: Description of Artificial Sequence: Synthetic

```
                6xHis tag

<400> SEQUENCE: 268

His His His His His His
1               5

<210> SEQ ID NO 269
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 269
ggaggagcag taccagagca cgtaccgtgt ggtcagcgtc                          40

<210> SEQ ID NO 270
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 270
cttccgagtg agagacac                                                  18

<210> SEQ ID NO 271
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 271
cagctggcgt aatagcgaag                                                20

<210> SEQ ID NO 272
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 272
tgctctggta ctgctcctcc cgcggctttg tcttggcatt atg                      43

<210> SEQ ID NO 273
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 273
cttccgagtg agagacac                                                  18

<210> SEQ ID NO 274
<211> LENGTH: 20
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 274
cagctggcgt aatagcgaag                                              20

<210> SEQ ID NO 275
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 275
aaaaaaggca ctagagacgg tgaccagggt tcc                               33

<210> SEQ ID NO 276
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 276
ttttttttgc gcgctgtcag gtgcaactgg tgcagtc                           37

<210> SEQ ID NO 277
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 277
aaaaaaggca ctagagacgg tgaccagggt tcc                               33

<210> SEQ ID NO 278
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 278
ttttttttgc gcgctgtcag gtgcagttgg tggagtc                           37

<210> SEQ ID NO 279
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 279
ttttttttgc gcgctgtgat attgtgatga cccagac                           37

<210> SEQ ID NO 280
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 280
aaaaaacgta cgtttgattt ccacctgggt cc                                         32

<210> SEQ ID NO 281
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 281 tttttttgc gcgctgtcag tctgtgttga cgcagcc                                     37

<210> SEQ ID NO 282
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 282 tttttcgtc tctgacctag gacggtcagc ttggtcc                                     37

<210> SEQ ID NO 283
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 283
gtacaccctg cccccatccc gggatgagct gggtggtgag tggtactgcg gcgt                 54

<210> SEQ ID NO 284
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 284
gctgttcaac tgccagcagg gtggtaccaa gaa                                        33

<210> SEQ ID NO 285
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 285
cctggttctt ggtaccaccc tgctggcagt tgaacagcac gccgcagtac cactc               55

<210> SEQ ID NO 286
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 286
accacccagc tcatcccggg atgggggcag ggt                               33

<210> SEQ ID NO 287
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 287
gtacaccctg cccccatccc gggatgagct gggtggtcac ttcaagtgcg gca         53

<210> SEQ ID NO 288
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 288
tgggcctgtt cgagtgcgcc gaccccggtg gtaccaagaa                        40

<210> SEQ ID NO 289
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 289
cctggttctt ggtaccaccg gggtcggcgc actcgaacag gcccatgccg cacttgaagt  60

<210> SEQ ID NO 290
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 290
gaccacccag ctcatcccgg gatgggggca gggt                              34

<210> SEQ ID NO 291
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 291
gtacaccctg cccccatccc gggatgagct gggtggttgc tacca                  45

<210> SEQ ID NO 292
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 292
```

```
ggcctggggc tactacgtgt gcggtggtac caagaa                                36
```

<210> SEQ ID NO 293
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 293

```
cctggttctt ggtaccaccg cacacgtagt agccccaggc ctggtagcaa ccacccagc      59
```

<210> SEQ ID NO 294
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 294

```
tcatcccggg atgggggcag ggt                                             23
```

<210> SEQ ID NO 295
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 295

```
aaaaaaggca ctagagacgg tgaccagggt tcc                                  33
```

<210> SEQ ID NO 296
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 296

```
tcaggcgtgg ggctattatg tgtgcggagg cggaggaggc caggtgcaac tggtgcagtc     60
```

<210> SEQ ID NO 297
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 297

```
aaaaaaggca ctagagacgg tgaccagggt tcc                                  33
```

<210> SEQ ID NO 298
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 298
tcaggcgtgg ggctattatg tgtgcggagg cggaggaggc caggtgcagt tggtggagtc        60

<210> SEQ ID NO 299
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 299
cggcgtggag gtgcataatg                                                   20

<210> SEQ ID NO 300
<211> LENGTH: 58
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 300
aatagcccca cgcctgatag cagcctcctc cgcctccttt acccggagac agggagag        58

<210> SEQ ID NO 301
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 301
cggcgtggag gtgcataatg                                                   20

<210> SEQ ID NO 302
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 302
gatgtcgagg cggccgctca gccgccgcac acataatagc cccacgcctg atag            54

<210> SEQ ID NO 303
<211> LENGTH: 5
<212> TYPE: PRT
<213> ORGANISM: Artificial Sequence
<220> FEATURE:
<223> OTHER INFORMATION: Description of Artificial Sequence: Synthetic
      5xHis tag

<400> SEQUENCE: 303

His His His His His
1               5

<210> SEQ ID NO 304
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 304

```
Gly Gly Gly Gly Gly
1               5

<210> SEQ ID NO 305
<211> LENGTH: 822
<212> TYPE: PRT
<213> ORGANISM: Homo sapiens

<400> SEQUENCE: 305

Met Trp Ser Trp Lys Cys Leu Leu Phe Trp Ala Val Leu Val Thr Ala
1               5                   10                  15

Thr Leu Cys Thr Ala Arg Pro Ser Pro Thr Leu Pro Glu Gln Ala Gln
                20                  25                  30

Pro Trp Gly Ala Pro Val Glu Val Glu Ser Phe Leu Val His Pro Gly
            35                  40                  45

Asp Leu Leu Gln Leu Arg Cys Arg Leu Arg Asp Asp Val Gln Ser Ile
        50                  55                  60

Asn Trp Leu Arg Asp Gly Val Gln Leu Ala Glu Ser Asn Arg Thr Arg
65                  70                  75                  80

Ile Thr Gly Glu Glu Val Glu Val Gln Asp Ser Val Pro Ala Asp Ser
                85                  90                  95

Gly Leu Tyr Ala Cys Val Thr Ser Ser Pro Ser Gly Ser Asp Thr Thr
            100                 105                 110

Tyr Phe Ser Val Asn Val Ser Asp Ala Leu Pro Ser Ser Glu Asp Asp
        115                 120                 125

Asp Asp Asp Asp Asp Ser Ser Ser Glu Glu Lys Glu Thr Asp Asn Thr
    130                 135                 140

Lys Pro Asn Arg Met Pro Val Ala Pro Tyr Trp Thr Ser Pro Glu Lys
145                 150                 155                 160

Met Glu Lys Lys Leu His Ala Val Pro Ala Ala Lys Thr Val Lys Phe
                165                 170                 175

Lys Cys Pro Ser Ser Gly Thr Pro Asn Pro Thr Leu Arg Trp Leu Lys
            180                 185                 190

Asn Gly Lys Glu Phe Lys Pro Asp His Arg Ile Gly Gly Tyr Lys Val
        195                 200                 205

Arg Tyr Ala Thr Trp Ser Ile Ile Met Asp Ser Val Val Pro Ser Asp
    210                 215                 220

Lys Gly Asn Tyr Thr Cys Ile Val Glu Asn Glu Tyr Gly Ser Ile Asn
225                 230                 235                 240

His Thr Tyr Gln Leu Asp Val Val Glu Arg Ser Pro His Arg Pro Ile
                245                 250                 255

Leu Gln Ala Gly Leu Pro Ala Asn Lys Thr Val Ala Leu Gly Ser Asn
            260                 265                 270

Val Glu Phe Met Cys Lys Val Tyr Ser Asp Pro Gln Pro His Ile Gln
        275                 280                 285

Trp Leu Lys His Ile Glu Val Asn Gly Ser Lys Ile Gly Pro Asp Asn
    290                 295                 300

Leu Pro Tyr Val Gln Ile Leu Lys Thr Ala Gly Val Asn Thr Thr Asp
305                 310                 315                 320

Lys Glu Met Glu Val Leu His Leu Arg Asn Val Ser Phe Glu Asp Ala
                325                 330                 335

Gly Glu Tyr Thr Cys Leu Ala Gly Asn Ser Ile Gly Leu Ser His His
            340                 345                 350

Ser Ala Trp Leu Thr Val Leu Glu Ala Leu Glu Glu Arg Pro Ala Val
        355                 360                 365
```

```
Met Thr Ser Pro Leu Tyr Leu Glu Ile Ile Tyr Cys Thr Gly Ala
    370                 375                 380

Phe Leu Ile Ser Cys Met Val Gly Ser Val Ile Val Tyr Lys Met Lys
385                 390                 395                 400

Ser Gly Thr Lys Lys Ser Asp Phe His Ser Gln Met Ala Val His Lys
                405                 410                 415

Leu Ala Lys Ser Ile Pro Leu Arg Arg Gln Val Thr Val Ser Ala Asp
            420                 425                 430

Ser Ser Ala Ser Met Asn Ser Gly Val Leu Leu Val Arg Pro Ser Arg
        435                 440                 445

Leu Ser Ser Ser Gly Thr Pro Met Leu Ala Gly Val Ser Glu Tyr Glu
    450                 455                 460

Leu Pro Glu Asp Pro Arg Trp Glu Leu Pro Arg Asp Arg Leu Val Leu
465                 470                 475                 480

Gly Lys Pro Leu Gly Glu Gly Cys Phe Gly Gln Val Val Leu Ala Glu
                485                 490                 495

Ala Ile Gly Leu Asp Lys Asp Lys Pro Asn Arg Val Thr Lys Val Ala
            500                 505                 510

Val Lys Met Leu Lys Ser Asp Ala Thr Glu Lys Asp Leu Ser Asp Leu
        515                 520                 525

Ile Ser Glu Met Glu Met Met Lys Met Ile Gly Lys His Lys Asn Ile
    530                 535                 540

Ile Asn Leu Leu Gly Ala Cys Thr Gln Asp Gly Pro Leu Tyr Val Ile
545                 550                 555                 560

Val Glu Tyr Ala Ser Lys Gly Asn Leu Arg Glu Tyr Leu Gln Ala Arg
                565                 570                 575

Arg Pro Pro Gly Leu Glu Tyr Cys Tyr Asn Pro Ser His Asn Pro Glu
            580                 585                 590

Glu Gln Leu Ser Ser Lys Asp Leu Val Ser Cys Ala Tyr Gln Val Ala
        595                 600                 605

Arg Gly Met Glu Tyr Leu Ala Ser Lys Lys Cys Ile His Arg Asp Leu
    610                 615                 620

Ala Ala Arg Asn Val Leu Val Thr Glu Asp Asn Val Met Lys Ile Ala
625                 630                 635                 640

Asp Phe Gly Leu Ala Arg Asp Ile His His Ile Asp Tyr Tyr Lys Lys
                645                 650                 655

Thr Thr Asn Gly Arg Leu Pro Val Lys Trp Met Ala Pro Glu Ala Leu
            660                 665                 670

Phe Asp Arg Ile Tyr Thr His Gln Ser Asp Val Trp Ser Phe Gly Val
        675                 680                 685

Leu Leu Trp Glu Ile Phe Thr Leu Gly Gly Ser Pro Tyr Pro Gly Val
    690                 695                 700

Pro Val Glu Glu Leu Phe Lys Leu Leu Lys Glu Gly His Arg Met Asp
705                 710                 715                 720

Lys Pro Ser Asn Cys Thr Asn Glu Leu Tyr Met Met Arg Asp Cys
                725                 730                 735

Trp His Ala Val Pro Ser Gln Arg Pro Thr Phe Lys Gln Leu Val Glu
            740                 745                 750

Asp Leu Asp Arg Ile Val Ala Leu Thr Ser Asn Gln Glu Tyr Leu Asp
        755                 760                 765

Leu Ser Met Pro Leu Asp Gln Tyr Ser Pro Ser Phe Pro Asp Thr Arg
    770                 775                 780
```

-continued

Ser Ser Thr Cys Ser Ser Gly Glu Asp Ser Val Phe Ser His Glu Pro
785                 790                 795                 800

Leu Pro Glu Glu Pro Cys Leu Pro Arg His Pro Ala Gln Leu Ala Asn
        805                 810                 815

Gly Gly Leu Lys Arg Arg
            820

<210> SEQ ID NO 306
<211> LENGTH: 822
<212> TYPE: PRT
<213> ORGANISM: Mus musculus

<400> SEQUENCE: 306

Met Trp Gly Trp Lys Cys Leu Leu Phe Trp Ala Val Leu Val Thr Ala
1               5                   10                  15

Thr Leu Cys Thr Ala Arg Pro Ala Pro Thr Leu Pro Glu Gln Ala Gln
            20                  25                  30

Pro Trp Gly Val Pro Val Glu Val Glu Ser Leu Leu Val His Pro Gly
        35                  40                  45

Asp Leu Leu Gln Leu Arg Cys Arg Leu Arg Asp Asp Val Gln Ser Ile
    50                  55                  60

Asn Trp Leu Arg Asp Gly Val Gln Leu Val Glu Ser Asn Arg Thr Arg
65                  70                  75                  80

Ile Thr Gly Glu Glu Val Glu Val Arg Asp Ser Ile Pro Ala Asp Ser
                85                  90                  95

Gly Leu Tyr Ala Cys Val Thr Ser Ser Pro Ser Gly Ser Asp Thr Thr
            100                 105                 110

Tyr Phe Ser Val Asn Val Ser Asp Ala Leu Pro Ser Ser Glu Asp Asp
        115                 120                 125

Asp Asp Asp Asp Asp Ser Ser Ser Glu Glu Lys Glu Thr Asp Asn Thr
    130                 135                 140

Lys Pro Asn Arg Arg Pro Val Ala Pro Tyr Trp Thr Ser Pro Glu Lys
145                 150                 155                 160

Met Glu Lys Lys Leu His Ala Val Pro Ala Ala Lys Thr Val Lys Phe
                165                 170                 175

Lys Cys Pro Ser Ser Gly Thr Pro Asn Pro Thr Leu Arg Trp Leu Lys
            180                 185                 190

Asn Gly Lys Glu Phe Lys Pro Asp His Arg Ile Gly Gly Tyr Lys Val
        195                 200                 205

Arg Tyr Ala Thr Trp Ser Ile Ile Met Asp Ser Val Val Pro Ser Asp
    210                 215                 220

Lys Gly Asn Tyr Thr Cys Ile Val Glu Asn Glu Tyr Gly Ser Ile Asn
225                 230                 235                 240

His Thr Tyr Gln Leu Asp Val Val Glu Arg Ser Pro His Arg Pro Ile
                245                 250                 255

Leu Gln Ala Gly Leu Pro Ala Asn Lys Thr Val Ala Leu Gly Ser Asn
            260                 265                 270

Val Glu Phe Met Cys Lys Val Tyr Ser Asp Pro Gln Pro His Ile Gln
        275                 280                 285

Trp Leu Lys His Ile Glu Val Asn Gly Ser Lys Ile Gly Pro Asp Asn
    290                 295                 300

Leu Pro Tyr Val Gln Ile Leu Lys Thr Ala Gly Val Asn Thr Thr Asp
305                 310                 315                 320

Lys Glu Met Glu Val Leu His Leu Arg Asn Val Ser Phe Glu Asp Ala
                325                 330                 335

```
Gly Glu Tyr Thr Cys Leu Ala Gly Asn Ser Ile Gly Leu Ser His His
            340                 345                 350

Ser Ala Trp Leu Thr Val Leu Glu Ala Leu Glu Arg Pro Ala Val
            355                 360                 365

Met Thr Ser Pro Leu Tyr Leu Glu Ile Ile Tyr Cys Thr Gly Ala
370             375                 380

Phe Leu Ile Ser Cys Met Leu Gly Ser Val Ile Tyr Lys Met Lys
385             390                 395                 400

Ser Gly Thr Lys Lys Ser Asp Phe His Ser Gln Met Ala Val His Lys
                405                 410                 415

Leu Ala Lys Ser Ile Pro Leu Arg Arg Gln Val Thr Val Ser Ala Asp
                420                 425                 430

Ser Ser Ala Ser Met Asn Ser Gly Val Leu Leu Val Arg Pro Ser Arg
                435                 440                 445

Leu Ser Ser Ser Gly Thr Pro Met Leu Ala Gly Val Ser Glu Tyr Glu
            450                 455                 460

Leu Pro Glu Asp Pro Arg Trp Glu Leu Pro Arg Asp Arg Leu Val Leu
465                 470                 475                 480

Gly Lys Pro Leu Gly Glu Gly Cys Phe Gly Gln Val Val Leu Ala Glu
                485                 490                 495

Ala Ile Gly Leu Asp Lys Asp Lys Pro Asn Arg Val Thr Lys Val Ala
            500                 505                 510

Val Lys Met Leu Lys Ser Asp Ala Thr Glu Lys Asp Leu Ser Asp Leu
            515                 520                 525

Ile Ser Glu Met Glu Met Met Lys Met Ile Gly Lys His Lys Asn Ile
            530                 535                 540

Ile Asn Leu Leu Gly Ala Cys Thr Gln Asp Gly Pro Leu Tyr Val Ile
545                 550                 555                 560

Val Glu Tyr Ala Ser Lys Gly Asn Leu Arg Glu Tyr Leu Gln Ala Arg
                565                 570                 575

Arg Pro Pro Gly Leu Glu Tyr Cys Tyr Asn Pro Ser His Asn Pro Glu
                580                 585                 590

Glu Gln Leu Ser Ser Lys Asp Leu Val Ser Cys Ala Tyr Gln Val Ala
            595                 600                 605

Arg Gly Met Glu Tyr Leu Ala Ser Lys Lys Cys Ile His Arg Asp Leu
610                 615                 620

Ala Ala Arg Asn Val Leu Val Thr Glu Asp Asn Val Met Lys Ile Ala
625                 630                 635                 640

Asp Phe Gly Leu Ala Arg Asp Ile His His Ile Asp Tyr Tyr Lys Lys
                645                 650                 655

Thr Thr Asn Gly Arg Leu Pro Val Lys Trp Met Ala Pro Glu Ala Leu
            660                 665                 670

Phe Asp Arg Ile Tyr Thr His Gln Ser Asp Val Trp Ser Phe Gly Val
            675                 680                 685

Leu Leu Trp Glu Ile Phe Thr Leu Gly Gly Ser Pro Tyr Pro Gly Val
            690                 695                 700

Pro Val Glu Glu Leu Phe Lys Leu Leu Lys Glu Gly His Arg Met Asp
705                 710                 715                 720

Lys Pro Ser Asn Cys Thr Asn Glu Leu Tyr Met Met Met Arg Asp Cys
                725                 730                 735

Trp His Ala Val Pro Ser Gln Arg Pro Thr Phe Lys Gln Leu Val Glu
            740                 745                 750
```

```
Asp Leu Asp Arg Ile Val Ala Leu Thr Ser Asn Gln Glu Tyr Leu Asp
        755                 760                 765

Leu Ser Ile Pro Leu Asp Gln Tyr Ser Pro Ser Phe Pro Asp Thr Arg
    770                 775                 780

Ser Ser Thr Cys Ser Ser Gly Glu Asp Ser Val Phe Ser His Glu Pro
785                 790                 795                 800

Leu Pro Glu Glu Pro Cys Leu Pro Arg His Pro Thr Gln Leu Ala Asn
            805                 810                 815

Ser Gly Leu Lys Arg Arg
            820

<210> SEQ ID NO 307
<211> LENGTH: 822
<212> TYPE: PRT
<213> ORGANISM: Artificial Sequence
<220> FEATURE:
<223> OTHER INFORMATION: Description of Artificial Sequence: Synthetic
      consensus polypeptide
<220> FEATURE:
<221> NAME/KEY: MOD_RES
<222> LOCATION: (3)..(3)
<223> OTHER INFORMATION: Ser or Gly
<220> FEATURE:
<221> NAME/KEY: MOD_RES
<222> LOCATION: (36)..(36)
<223> OTHER INFORMATION: Ala or Val
<220> FEATURE:
<221> NAME/KEY: MOD_RES
<222> LOCATION: (43)..(43)
<223> OTHER INFORMATION: Phe or Leu
<220> FEATURE:
<221> NAME/KEY: MOD_RES
<222> LOCATION: (74)..(74)
<223> OTHER INFORMATION: Ala or Val
<220> FEATURE:
<221> NAME/KEY: MOD_RES
<222> LOCATION: (89)..(89)
<223> OTHER INFORMATION: Gln or Arg
<220> FEATURE:
<221> NAME/KEY: MOD_RES
<222> LOCATION: (149)..(149)
<223> OTHER INFORMATION: Met or Arg
<220> FEATURE:
<221> NAME/KEY: MOD_RES
<222> LOCATION: (812)..(812)
<223> OTHER INFORMATION: Ala or Thr
<220> FEATURE:
<221> NAME/KEY: MOD_RES
<222> LOCATION: (817)..(817)
<223> OTHER INFORMATION: Gly or Ser

<400> SEQUENCE: 307

Met Trp Xaa Trp Lys Cys Leu Leu Phe Trp Ala Val Leu Val Thr Ala
1               5                   10                  15

Thr Leu Cys Thr Ala Arg Pro Ala Pro Thr Leu Pro Gly Gln Ala Gln
            20                  25                  30

Pro Trp Gly Xaa Pro Val Glu Val Glu Ser Xaa Leu Val His Pro Gly
        35                  40                  45

Asp Leu Leu Gln Leu Arg Cys Arg Leu Arg Asp Asp Val Gln Ser Ile
    50                  55                  60

Asn Trp Leu Arg Asp Gly Val Gln Leu Xaa Glu Ser Asn Arg Thr Arg
65                  70                  75                  80

Ile Thr Gly Glu Glu Val Glu Val Xaa Asp Ser Ile Pro Ala Asp Ser
            85                  90                  95

Gly Leu Tyr Ala Cys Val Thr Ser Ser Pro Ser Gly Ser Asp Thr Thr
        100                 105                 110
```

-continued

Tyr Phe Ser Val Asn Val Ser Asp Ala Leu Pro Ser Glu Asp Asp
            115                 120                 125

Asp Asp Asp Asp Asp Ser Ser Ser Glu Glu Lys Glu Thr Asp Asn Thr
130                 135                 140

Lys Pro Asn Arg Xaa Pro Val Ala Pro Tyr Trp Thr Ser Pro Glu Lys
145                 150                 155                 160

Met Glu Lys Lys Leu His Ala Val Pro Ala Ala Lys Thr Val Lys Phe
            165                 170                 175

Lys Cys Pro Ser Ser Gly Thr Pro Asn Pro Thr Leu Arg Trp Leu Lys
            180                 185                 190

Asn Gly Lys Glu Phe Lys Pro Asp His Arg Ile Gly Gly Tyr Lys Val
            195                 200                 205

Arg Tyr Ala Thr Trp Ser Ile Ile Met Asp Ser Val Val Pro Ser Asp
            210                 215                 220

Lys Gly Asn Tyr Thr Cys Ile Val Glu Asn Glu Tyr Gly Ser Ile Asn
225                 230                 235                 240

His Thr Tyr Gln Leu Asp Val Val Glu Arg Ser Pro His Arg Pro Ile
            245                 250                 255

Leu Gln Ala Gly Leu Pro Ala Asn Lys Thr Val Ala Leu Gly Ser Asn
            260                 265                 270

Val Glu Phe Met Cys Lys Val Tyr Ser Asp Pro Gln Pro His Ile Gln
            275                 280                 285

Trp Leu Lys His Ile Glu Val Asn Gly Ser Lys Ile Gly Pro Asp Asn
            290                 295                 300

Leu Pro Tyr Val Gln Ile Leu Lys Thr Ala Gly Val Asn Thr Thr Asp
305                 310                 315                 320

Lys Glu Met Glu Val Leu His Leu Arg Asn Val Ser Phe Glu Asp Ala
            325                 330                 335

Gly Glu Tyr Thr Cys Leu Ala Gly Asn Ser Ile Gly Leu Ser His His
            340                 345                 350

Ser Ala Trp Leu Thr Val Leu Glu Ala Leu Glu Arg Pro Ala Val
            355                 360                 365

Met Thr Ser Pro Leu Tyr Leu Glu Ile Ile Tyr Cys Thr Gly Ala
            370                 375                 380

Phe Leu Ile Ser Cys Met Leu Gly Ser Val Ile Ile Tyr Lys Met Lys
385                 390                 395                 400

Ser Gly Thr Lys Lys Ser Asp Phe His Ser Gln Met Ala Val His Lys
            405                 410                 415

Leu Ala Lys Ser Ile Pro Leu Arg Arg Gln Val Thr Val Ser Ala Asp
            420                 425                 430

Ser Ser Ala Ser Met Asn Ser Gly Val Leu Leu Val Arg Pro Ser Arg
            435                 440                 445

Leu Ser Ser Ser Gly Thr Pro Met Leu Ala Gly Val Ser Glu Tyr Glu
            450                 455                 460

Leu Pro Glu Asp Pro Arg Trp Glu Leu Pro Arg Asp Arg Leu Val Leu
465                 470                 475                 480

Gly Lys Pro Leu Gly Glu Gly Cys Phe Gly Gln Val Val Leu Ala Glu
            485                 490                 495

Ala Ile Gly Leu Asp Lys Asp Lys Pro Asn Arg Val Thr Lys Val Ala
            500                 505                 510

Val Lys Met Leu Lys Ser Asp Ala Thr Glu Lys Asp Leu Ser Asp Leu
            515                 520                 525

Ile Ser Glu Met Glu Met Met Lys Met Ile Gly Lys His Lys Asn Ile

```
                530             535             540
Ile Asn Leu Leu Gly Ala Cys Thr Gln Asp Gly Pro Leu Tyr Val Ile
545                 550                 555                 560

Val Glu Tyr Ala Ser Lys Gly Asn Leu Arg Glu Tyr Leu Gln Ala Arg
                565                 570                 575

Arg Pro Pro Gly Leu Glu Tyr Cys Tyr Asn Pro Ser His Asn Pro Glu
            580                 585                 590

Glu Gln Leu Ser Ser Lys Asp Leu Val Ser Cys Ala Tyr Gln Val Ala
        595                 600                 605

Arg Gly Met Glu Tyr Leu Ala Ser Lys Lys Cys Ile His Arg Asp Leu
    610                 615                 620

Ala Ala Arg Asn Val Leu Val Thr Glu Asp Asn Val Met Lys Ile Ala
625                 630                 635                 640

Asp Phe Gly Leu Ala Arg Asp Ile His His Ile Asp Tyr Tyr Lys Lys
                645                 650                 655

Thr Thr Asn Gly Arg Leu Pro Val Lys Trp Met Ala Pro Glu Ala Leu
            660                 665                 670

Phe Asp Arg Ile Tyr Thr His Gln Ser Asp Val Trp Ser Phe Gly Val
        675                 680                 685

Leu Leu Trp Glu Ile Phe Thr Leu Gly Gly Ser Pro Tyr Pro Gly Val
    690                 695                 700

Pro Val Glu Glu Leu Phe Lys Leu Leu Lys Glu Gly His Arg Met Asp
705                 710                 715                 720

Lys Pro Ser Asn Cys Thr Asn Glu Leu Tyr Met Met Met Arg Asp Cys
                725                 730                 735

Trp His Ala Val Pro Ser Gln Arg Pro Thr Phe Lys Gln Leu Val Glu
            740                 745                 750

Asp Leu Asp Arg Ile Val Ala Leu Thr Ser Asn Gln Glu Tyr Leu Asp
        755                 760                 765

Leu Ser Ile Pro Leu Asp Gln Tyr Ser Pro Ser Phe Pro Asp Thr Arg
    770                 775                 780

Ser Ser Thr Cys Ser Ser Gly Glu Asp Ser Val Phe Ser His Glu Pro
785                 790                 795                 800

Leu Pro Glu Glu Pro Cys Leu Pro Arg His Pro Xaa Gln Leu Ala Asn
                805                 810                 815

Xaa Gly Leu Lys Arg Arg
            820

<210> SEQ ID NO 308
<211> LENGTH: 1044
<212> TYPE: PRT
<213> ORGANISM: Homo sapiens

<400> SEQUENCE: 308

Met Lys Pro Gly Cys Ala Ala Gly Ser Pro Gly Asn Glu Trp Ile Phe
1               5                   10                  15

Phe Ser Thr Asp Glu Ile Thr Thr Arg Tyr Arg Asn Thr Met Ser Asn
                20                  25                  30

Gly Gly Leu Gln Arg Ser Val Ile Leu Ser Ala Leu Ile Leu Leu Arg
            35                  40                  45

Ala Val Thr Gly Phe Ser Gly Asp Gly Arg Ala Ile Trp Ser Lys Asn
        50                  55                  60

Pro Asn Phe Thr Pro Val Asn Glu Ser Gln Leu Phe Leu Tyr Asp Thr
65                  70                  75                  80
```

-continued

```
Phe Pro Lys Asn Phe Phe Trp Gly Ile Gly Thr Gly Ala Leu Gln Val
                85                  90                  95

Glu Gly Ser Trp Lys Lys Asp Gly Lys Gly Pro Ser Ile Trp Asp His
            100                 105                 110

Phe Ile His Thr His Leu Lys Asn Val Ser Ser Thr Asn Gly Ser Ser
        115                 120                 125

Asp Ser Tyr Ile Phe Leu Glu Lys Asp Leu Ser Ala Leu Asp Phe Ile
    130                 135                 140

Gly Val Ser Phe Tyr Gln Phe Ser Ile Ser Trp Pro Arg Leu Phe Pro
145                 150                 155                 160

Asp Gly Ile Val Thr Val Ala Asn Ala Lys Gly Leu Gln Tyr Tyr Ser
                165                 170                 175

Thr Leu Leu Asp Ala Leu Val Leu Arg Asn Ile Glu Pro Ile Val Thr
            180                 185                 190

Leu Tyr His Trp Asp Leu Pro Leu Ala Leu Gln Glu Lys Tyr Gly Gly
        195                 200                 205

Trp Lys Asn Asp Thr Ile Ile Asp Ile Phe Asn Asp Tyr Ala Thr Tyr
    210                 215                 220

Cys Phe Gln Met Phe Gly Asp Arg Val Lys Tyr Trp Ile Thr Ile His
225                 230                 235                 240

Asn Pro Tyr Leu Val Ala Trp His Gly Tyr Gly Thr Gly Met His Ala
                245                 250                 255

Pro Gly Glu Lys Gly Asn Leu Ala Ala Val Tyr Thr Val Gly His Asn
            260                 265                 270

Leu Ile Lys Ala His Ser Lys Val Trp His Asn Tyr Asn Thr His Phe
        275                 280                 285

Arg Pro His Gln Lys Gly Trp Leu Ser Ile Thr Leu Gly Ser His Trp
    290                 295                 300

Ile Glu Pro Asn Arg Ser Glu Asn Thr Met Asp Ile Phe Lys Cys Gln
305                 310                 315                 320

Gln Ser Met Val Ser Val Leu Gly Trp Phe Ala Asn Pro Ile His Gly
                325                 330                 335

Asp Gly Asp Tyr Pro Glu Gly Met Arg Lys Lys Leu Phe Ser Val Leu
            340                 345                 350

Pro Ile Phe Ser Glu Ala Glu Lys His Glu Met Arg Gly Thr Ala Asp
        355                 360                 365

Phe Phe Ala Phe Ser Phe Gly Pro Asn Asn Phe Lys Pro Leu Asn Thr
    370                 375                 380

Met Ala Lys Met Gly Gln Asn Val Ser Leu Asn Leu Arg Glu Ala Leu
385                 390                 395                 400

Asn Trp Ile Lys Leu Glu Tyr Asn Asn Pro Arg Ile Leu Ile Ala Glu
                405                 410                 415

Asn Gly Trp Phe Thr Asp Ser Arg Val Lys Thr Glu Asp Thr Thr Ala
            420                 425                 430

Ile Tyr Met Met Lys Asn Phe Leu Ser Gln Val Leu Gln Ala Ile Arg
        435                 440                 445

Leu Asp Glu Ile Arg Val Phe Gly Tyr Thr Ala Trp Ser Leu Leu Asp
    450                 455                 460

Gly Phe Glu Trp Gln Asp Ala Tyr Thr Ile Arg Arg Gly Leu Phe Tyr
465                 470                 475                 480

Val Asp Phe Asn Ser Lys Gln Lys Glu Arg Lys Pro Lys Ser Ser Ala
                485                 490                 495

His Tyr Tyr Lys Gln Ile Ile Arg Glu Asn Gly Phe Ser Leu Lys Glu
```

```
                500             505             510
Ser Thr Pro Asp Val Gln Gly Gln Phe Pro Cys Asp Phe Ser Trp Gly
            515             520             525

Val Thr Glu Ser Val Leu Lys Pro Glu Ser Val Ala Ser Ser Pro Gln
            530             535             540

Phe Ser Asp Pro His Leu Tyr Val Trp Asn Ala Thr Gly Asn Arg Leu
545             550             555             560

Leu His Arg Val Glu Gly Val Arg Leu Lys Thr Arg Pro Ala Gln Cys
                565             570             575

Thr Asp Phe Val Asn Ile Lys Lys Gln Leu Glu Met Leu Ala Arg Met
            580             585             590

Lys Val Thr His Tyr Arg Phe Ala Leu Asp Trp Ala Ser Val Leu Pro
            595             600             605

Thr Gly Asn Leu Ser Ala Val Asn Arg Gln Ala Leu Arg Tyr Tyr Arg
            610             615             620

Cys Val Val Ser Glu Gly Leu Lys Leu Gly Ile Ser Ala Met Val Thr
625             630             635             640

Leu Tyr Tyr Pro Thr His Ala His Leu Gly Leu Pro Glu Pro Leu Leu
                645             650             655

His Ala Asp Gly Trp Leu Asn Pro Ser Thr Ala Glu Ala Phe Gln Ala
            660             665             670

Tyr Ala Gly Leu Cys Phe Gln Glu Leu Gly Asp Leu Val Lys Leu Trp
            675             680             685

Ile Thr Ile Asn Glu Pro Asn Arg Leu Ser Asp Ile Tyr Asn Arg Ser
            690             695             700

Gly Asn Asp Thr Tyr Gly Ala Ala His Asn Leu Leu Val Ala His Ala
705             710             715             720

Leu Ala Trp Arg Leu Tyr Asp Arg Gln Phe Arg Pro Ser Gln Arg Gly
                725             730             735

Ala Val Ser Leu Ser Leu His Ala Asp Trp Ala Glu Pro Ala Asn Pro
            740             745             750

Tyr Ala Asp Ser His Trp Arg Ala Ala Glu Arg Phe Leu Gln Phe Glu
            755             760             765

Ile Ala Trp Phe Ala Glu Pro Leu Phe Lys Thr Gly Asp Tyr Pro Ala
            770             775             780

Ala Met Arg Glu Tyr Ile Ala Ser Lys His Arg Arg Gly Leu Ser Ser
785             790             795             800

Ser Ala Leu Pro Arg Leu Thr Glu Ala Glu Arg Arg Leu Leu Lys Gly
                805             810             815

Thr Val Asp Phe Cys Ala Leu Asn His Phe Thr Thr Arg Phe Val Met
            820             825             830

His Glu Gln Leu Ala Gly Ser Arg Tyr Asp Ser Asp Arg Asp Ile Gln
            835             840             845

Phe Leu Gln Asp Ile Thr Arg Leu Ser Ser Pro Thr Arg Leu Ala Val
            850             855             860

Ile Pro Trp Gly Val Arg Lys Leu Leu Arg Trp Val Arg Arg Asn Tyr
865             870             875             880

Gly Asp Met Asp Ile Tyr Ile Thr Ala Ser Gly Ile Asp Asp Gln Ala
                885             890             895

Leu Glu Asp Asp Arg Leu Arg Lys Tyr Tyr Leu Gly Lys Tyr Leu Gln
            900             905             910

Glu Val Leu Lys Ala Tyr Leu Ile Asp Lys Val Arg Ile Lys Gly Tyr
            915             920             925
```

```
Tyr Ala Phe Lys Leu Ala Glu Glu Lys Ser Lys Pro Arg Phe Gly Phe
        930                 935                 940

Phe Thr Ser Asp Phe Lys Ala Lys Ser Ser Ile Gln Phe Tyr Asn Lys
945                 950                 955                 960

Val Ile Ser Ser Arg Gly Phe Pro Phe Glu Asn Ser Ser Arg Cys
                965                 970                 975

Ser Gln Thr Gln Glu Asn Thr Glu Cys Thr Val Cys Leu Phe Leu Val
                980                 985                 990

Gln Lys Lys Pro Leu Ile Phe Leu Gly Cys Cys Phe Phe Ser Thr Leu
        995                 1000                1005

Val Leu Leu Leu Ser Ile Ala Ile Phe Gln Arg Gln Lys Arg Arg
        1010                1015                1020

Lys Phe Trp Lys Ala Lys Asn Leu Gln His Ile Pro Leu Lys Lys
        1025                1030                1035

Gly Lys Arg Val Val Ser
        1040
```

<210> SEQ ID NO 309
<211> LENGTH: 1043
<212> TYPE: PRT
<213> ORGANISM: Mus musculus

<400> SEQUENCE: 309

```
Met Lys Thr Gly Cys Ala Ala Gly Ser Pro Gly Asn Glu Trp Ile Phe
1               5                   10                  15

Phe Ser Ser Asp Glu Arg Asn Thr Arg Ser Arg Lys Thr Met Ser Asn
                20                  25                  30

Arg Ala Leu Gln Arg Ser Ala Val Leu Ser Ala Phe Val Leu Leu Arg
            35                  40                  45

Ala Val Thr Gly Phe Ser Gly Asp Gly Lys Ala Ile Trp Asp Lys Lys
        50                  55                  60

Gln Tyr Val Ser Pro Val Asn Pro Ser Gln Leu Phe Leu Tyr Asp Thr
65                  70                  75                  80

Phe Pro Lys Asn Phe Ser Trp Gly Val Gly Thr Gly Ala Phe Gln Val
                85                  90                  95

Glu Gly Ser Trp Lys Thr Asp Gly Arg Gly Pro Ser Ile Trp Asp Arg
                100                 105                 110

Tyr Val Tyr Ser His Leu Arg Gly Val Asn Gly Thr Asp Arg Ser Thr
            115                 120                 125

Asp Ser Tyr Ile Phe Leu Glu Lys Asp Leu Leu Ala Leu Asp Phe Leu
        130                 135                 140

Gly Val Ser Phe Tyr Gln Phe Ser Ile Ser Trp Pro Arg Leu Phe Pro
145                 150                 155                 160

Asn Gly Thr Val Ala Ala Val Asn Ala Gln Gly Leu Arg Tyr Tyr Arg
                165                 170                 175

Ala Leu Leu Asp Ser Leu Val Leu Arg Asn Ile Glu Pro Ile Val Thr
            180                 185                 190

Leu Tyr His Trp Asp Leu Pro Leu Thr Leu Gln Glu Glu Tyr Gly Gly
        195                 200                 205

Trp Lys Asn Ala Thr Met Ile Asp Leu Phe Asn Asp Tyr Ala Thr Tyr
        210                 215                 220

Cys Phe Gln Thr Phe Gly Asp Arg Val Lys Tyr Trp Ile Thr Ile His
225                 230                 235                 240

Asn Pro Tyr Leu Val Ala Trp His Gly Phe Gly Thr Gly Met His Ala
```

```
                    245                 250                 255
Pro Gly Glu Lys Gly Asn Leu Thr Ala Val Tyr Thr Val Gly His Asn
                260                 265                 270

Leu Ile Lys Ala His Ser Lys Val Trp His Asn Tyr Asp Lys Asn Phe
            275                 280                 285

Arg Pro His Gln Lys Gly Trp Leu Ser Ile Thr Leu Gly Ser His Trp
        290                 295                 300

Ile Glu Pro Asn Arg Thr Asp Asn Met Glu Asp Val Ile Asn Cys Gln
305                 310                 315                 320

His Ser Met Ser Ser Val Leu Gly Trp Phe Ala Asn Pro Ile His Gly
                325                 330                 335

Asp Gly Asp Tyr Pro Glu Phe Met Lys Thr Gly Ala Met Ile Pro Glu
            340                 345                 350

Phe Ser Glu Ala Glu Lys Glu Val Arg Gly Thr Ala Asp Phe Phe
        355                 360                 365

Ala Phe Ser Phe Gly Pro Asn Asn Phe Arg Pro Ser Asn Thr Val Val
    370                 375                 380

Lys Met Gly Gln Asn Val Ser Leu Asn Leu Arg Gln Val Leu Asn Trp
385                 390                 395                 400

Ile Lys Leu Glu Tyr Asp Asp Pro Gln Ile Leu Ile Ser Glu Asn Gly
                405                 410                 415

Trp Phe Thr Asp Ser Tyr Ile Lys Thr Glu Asp Thr Thr Ala Ile Tyr
            420                 425                 430

Met Met Lys Asn Phe Leu Asn Gln Val Leu Gln Ala Ile Lys Phe Asp
        435                 440                 445

Glu Ile Arg Val Phe Gly Tyr Thr Ala Trp Thr Leu Leu Asp Gly Phe
    450                 455                 460

Glu Trp Gln Asp Ala Tyr Thr Thr Arg Arg Gly Leu Phe Tyr Val Asp
465                 470                 475                 480

Phe Asn Ser Glu Gln Lys Glu Arg Lys Pro Lys Ser Ser Ala His Tyr
                485                 490                 495

Tyr Lys Gln Ile Ile Gln Asp Asn Gly Phe Pro Leu Lys Glu Ser Thr
            500                 505                 510

Pro Asp Met Lys Gly Arg Phe Pro Cys Asp Phe Ser Trp Gly Val Thr
        515                 520                 525

Glu Ser Val Leu Lys Pro Glu Phe Thr Val Ser Ser Pro Gln Phe Thr
    530                 535                 540

Asp Pro His Leu Tyr Val Trp Asn Val Thr Gly Asn Arg Leu Leu Tyr
545                 550                 555                 560

Arg Val Glu Gly Val Arg Leu Lys Thr Arg Pro Ser Gln Cys Thr Asp
                565                 570                 575

Tyr Val Ser Ile Lys Lys Arg Val Glu Met Leu Ala Lys Met Lys Val
            580                 585                 590

Thr His Tyr Gln Phe Ala Leu Asp Trp Thr Ser Ile Leu Pro Thr Gly
        595                 600                 605

Asn Leu Ser Lys Val Asn Arg Gln Val Leu Arg Tyr Tyr Arg Cys Val
    610                 615                 620

Val Ser Glu Gly Leu Lys Leu Gly Val Phe Pro Met Val Thr Leu Tyr
625                 630                 635                 640

His Pro Thr His Ser His Leu Gly Leu Pro Leu Pro Leu Leu Ser Ser
                645                 650                 655

Gly Gly Trp Leu Asn Met Asn Thr Ala Lys Ala Phe Gln Asp Tyr Ala
            660                 665                 670
```

```
Glu Leu Cys Phe Arg Glu Leu Gly Asp Leu Val Lys Leu Trp Ile Thr
            675                 680                 685

Ile Asn Glu Pro Asn Arg Leu Ser Asp Met Tyr Asn Arg Thr Ser Asn
    690                 695                 700

Asp Thr Tyr Arg Ala Ala His Asn Leu Met Ile Ala His Ala Gln Val
705                 710                 715                 720

Trp His Leu Tyr Asp Arg Gln Tyr Arg Pro Val Gln His Gly Ala Val
                725                 730                 735

Ser Leu Ser Leu His Cys Asp Trp Ala Glu Pro Ala Asn Pro Phe Val
            740                 745                 750

Asp Ser His Trp Lys Ala Ala Glu Arg Phe Leu Gln Phe Glu Ile Ala
        755                 760                 765

Trp Phe Ala Asp Pro Leu Phe Lys Thr Gly Asp Tyr Pro Ser Val Met
770                 775                 780

Lys Glu Tyr Ile Ala Ser Lys Asn Gln Arg Gly Leu Ser Ser Ser Val
785                 790                 795                 800

Leu Pro Arg Phe Thr Ala Lys Glu Ser Arg Leu Val Lys Gly Thr Val
                805                 810                 815

Asp Phe Tyr Ala Leu Asn His Phe Thr Thr Arg Phe Val Ile His Lys
            820                 825                 830

Gln Leu Asn Thr Asn Arg Ser Val Ala Asp Arg Asp Val Gln Phe Leu
        835                 840                 845

Gln Asp Ile Thr Arg Leu Ser Ser Pro Ser Arg Leu Ala Val Thr Pro
850                 855                 860

Trp Gly Val Arg Lys Leu Leu Ala Trp Ile Arg Arg Asn Tyr Arg Asp
865                 870                 875                 880

Arg Asp Ile Tyr Ile Thr Ala Asn Gly Ile Asp Asp Leu Ala Leu Glu
                885                 890                 895

Asp Asp Gln Ile Arg Lys Tyr Tyr Leu Glu Lys Tyr Val Gln Glu Ala
            900                 905                 910

Leu Lys Ala Tyr Leu Ile Asp Lys Val Lys Ile Lys Gly Tyr Tyr Ala
        915                 920                 925

Phe Lys Leu Thr Glu Glu Lys Ser Lys Pro Arg Phe Gly Phe Phe Thr
930                 935                 940

Ser Asp Phe Arg Ala Lys Ser Ser Val Gln Phe Tyr Ser Lys Leu Ile
945                 950                 955                 960

Ser Ser Ser Gly Leu Pro Ala Glu Asn Arg Ser Pro Ala Cys Gly Gln
                965                 970                 975

Pro Ala Glu Asp Thr Asp Cys Thr Ile Cys Ser Phe Leu Val Glu Lys
            980                 985                 990

Lys Pro Leu Ile Phe Phe Gly Cys Cys Phe Ile Ser Thr Leu Ala Val
        995                 1000                1005

Leu Leu Ser Ile Thr Val Phe His His Gln Lys Arg Arg Lys Phe
    1010                1015                1020

Gln Lys Ala Arg Asn Leu Gln Asn Ile Pro Leu Lys Lys Gly His
    1025                1030                1035

Ser Arg Val Phe Ser
    1040

<210> SEQ ID NO 310
<211> LENGTH: 1045
<212> TYPE: PRT
<213> ORGANISM: Artificial Sequence
<220> FEATURE:
```

```
<223> OTHER INFORMATION: Description of Artificial Sequence: Synthetic
      consensus sequence
<220> FEATURE:
<221> NAME/KEY: MOD_RES
<222> LOCATION: (3)..(3)
<223> OTHER INFORMATION: Pro or Thr
<220> FEATURE:
<221> NAME/KEY: MOD_RES
<222> LOCATION: (22)..(22)
<223> OTHER INFORMATION: Ile or Arg
<220> FEATURE:
<221> NAME/KEY: MOD_RES
<222> LOCATION: (23)..(23)
<223> OTHER INFORMATION: Thr or Asn
<220> FEATURE:
<221> NAME/KEY: MOD_RES
<222> LOCATION: (26)..(26)
<223> OTHER INFORMATION: Tyr or Ser
<220> FEATURE:
<221> NAME/KEY: MOD_RES
<222> LOCATION: (28)..(28)
<223> OTHER INFORMATION: Asn or Lys
<220> FEATURE:
<221> NAME/KEY: MOD_RES
<222> LOCATION: (33)..(33)
<223> OTHER INFORMATION: Gly or Arg
<220> FEATURE:
<221> NAME/KEY: MOD_RES
<222> LOCATION: (39)..(39)
<223> OTHER INFORMATION: Val or Ala
<220> FEATURE:
<221> NAME/KEY: MOD_RES
<222> LOCATION: (44)..(44)
<223> OTHER INFORMATION: Leu or Phe
<220> FEATURE:
<221> NAME/KEY: MOD_RES
<222> LOCATION: (62)..(62)
<223> OTHER INFORMATION: Ser or Asp
<220> FEATURE:
<221> NAME/KEY: MOD_RES
<222> LOCATION: (64)..(64)
<223> OTHER INFORMATION: Asn or Lys
<220> FEATURE:
<221> NAME/KEY: MOD_RES
<222> LOCATION: (65)..(65)
<223> OTHER INFORMATION: Pro or Gln
<220> FEATURE:
<221> NAME/KEY: MOD_RES
<222> LOCATION: (66)..(66)
<223> OTHER INFORMATION: Asn or Tyr
<220> FEATURE:
<221> NAME/KEY: MOD_RES
<222> LOCATION: (67)..(67)
<223> OTHER INFORMATION: Phe or Val
<220> FEATURE:
<221> NAME/KEY: MOD_RES
<222> LOCATION: (72)..(72)
<223> OTHER INFORMATION: Glu or Pro
<220> FEATURE:
<221> NAME/KEY: MOD_RES
<222> LOCATION: (86)..(86)
<223> OTHER INFORMATION: Phe or Ser
<220> FEATURE:
<221> NAME/KEY: MOD_RES
<222> LOCATION: (94)..(94)
<223> OTHER INFORMATION: Leu or Phe
<220> FEATURE:
<221> NAME/KEY: MOD_RES
<222> LOCATION: (102)..(102)
<223> OTHER INFORMATION: Lys or Thr
<220> FEATURE:
<221> NAME/KEY: MOD_RES
<222> LOCATION: (112)..(112)
<223> OTHER INFORMATION: His or Arg
<220> FEATURE:
<221> NAME/KEY: MOD_RES
<222> LOCATION: (120)..(120)
<223> OTHER INFORMATION: Asn or Gly
<220> FEATURE:
```

```
<221> NAME/KEY: MOD_RES
<222> LOCATION: (122)..(122)
<223> OTHER INFORMATION: Ser or Asn
<220> FEATURE:
<221> NAME/KEY: MOD_RES
<222> LOCATION: (123)..(123)
<223> OTHER INFORMATION: Ser or Gly
<220> FEATURE:
<221> NAME/KEY: MOD_RES
<222> LOCATION: (125)..(125)
<223> OTHER INFORMATION: Asn or Asp
<220> FEATURE:
<221> NAME/KEY: MOD_RES
<222> LOCATION: (126)..(126)
<223> OTHER INFORMATION: Gly or Arg
<220> FEATURE:
<221> NAME/KEY: MOD_RES
<222> LOCATION: (139)..(139)
<223> OTHER INFORMATION: Ser or Leu
<220> FEATURE:
<221> NAME/KEY: MOD_RES
<222> LOCATION: (161)..(161)
<223> OTHER INFORMATION: Asp or Asn
<220> FEATURE:
<221> NAME/KEY: MOD_RES
<222> LOCATION: (163)..(163)
<223> OTHER INFORMATION: Ile or Thr
<220> FEATURE:
<221> NAME/KEY: MOD_RES
<222> LOCATION: (165)..(165)
<223> OTHER INFORMATION: Thr or Ala
<220> FEATURE:
<221> NAME/KEY: MOD_RES
<222> LOCATION: (166)..(167)
<223> OTHER INFORMATION: Val or Ala
<220> FEATURE:
<221> NAME/KEY: MOD_RES
<222> LOCATION: (170)..(170)
<223> OTHER INFORMATION: Lys or Gln
<220> FEATURE:
<221> NAME/KEY: MOD_RES
<222> LOCATION: (173)..(173)
<223> OTHER INFORMATION: Gln or Arg
<220> FEATURE:
<221> NAME/KEY: MOD_RES
<222> LOCATION: (176)..(176)
<223> OTHER INFORMATION: Ser or Arg
<220> FEATURE:
<221> NAME/KEY: MOD_RES
<222> LOCATION: (177)..(177)
<223> OTHER INFORMATION: Thr or Ala
<220> FEATURE:
<221> NAME/KEY: MOD_RES
<222> LOCATION: (201)..(201)
<223> OTHER INFORMATION: Ala or Thr
<220> FEATURE:
<221> NAME/KEY: MOD_RES
<222> LOCATION: (205)..(205)
<223> OTHER INFORMATION: Lys or Glu
<220> FEATURE:
<221> NAME/KEY: MOD_RES
<222> LOCATION: (212)..(212)
<223> OTHER INFORMATION: Asp or Ala
<220> FEATURE:
<221> NAME/KEY: MOD_RES
<222> LOCATION: (228)..(228)
<223> OTHER INFORMATION: Met or Thr
<220> FEATURE:
<221> NAME/KEY: MOD_RES
<222> LOCATION: (264)..(264)
<223> OTHER INFORMATION: Ala or Thr
<220> FEATURE:
<221> NAME/KEY: MOD_RES
<222> LOCATION: (285)..(285)
<223> OTHER INFORMATION: Asn or Asp
<220> FEATURE:
<221> NAME/KEY: MOD_RES
<222> LOCATION: (286)..(286)
<223> OTHER INFORMATION: Thr or Lys
```

-continued

```
<220> FEATURE:
<221> NAME/KEY: MOD_RES
<222> LOCATION: (287)..(287)
<223> OTHER INFORMATION: His or Asn
<220> FEATURE:
<221> NAME/KEY: MOD_RES
<222> LOCATION: (313)..(313)
<223> OTHER INFORMATION: Thr or Met
<220> FEATURE:
<221> NAME/KEY: MOD_RES
<222> LOCATION: (314)..(314)
<223> OTHER INFORMATION: Met or Glu
<220> FEATURE:
<221> NAME/KEY: MOD_RES
<222> LOCATION: (317)..(317)
<223> OTHER INFORMATION: Phe or Ile
<220> FEATURE:
<221> NAME/KEY: MOD_RES
<222> LOCATION: (318)..(318)
<223> OTHER INFORMATION: Lys or Asn
<220> FEATURE:
<221> NAME/KEY: MOD_RES
<222> LOCATION: (321)..(321)
<223> OTHER INFORMATION: Gln or His
<220> FEATURE:
<221> NAME/KEY: MOD_RES
<222> LOCATION: (324)..(324)
<223> OTHER INFORMATION: Val or Ser
<220> FEATURE:
<221> NAME/KEY: MOD_RES
<222> LOCATION: (343)..(343)
<223> OTHER INFORMATION: Gly or Phe
<220> FEATURE:
<221> NAME/KEY: MOD_RES
<222> LOCATION: (346)..(346)
<223> OTHER INFORMATION: Lys or Thr
<220> FEATURE:
<221> NAME/KEY: MOD_RES
<222> LOCATION: (347)..(347)
<223> OTHER INFORMATION: Lys or Gly
<220> FEATURE:
<221> NAME/KEY: MOD_RES
<222> LOCATION: (348)..(348)
<223> OTHER INFORMATION: Leu or absent
<220> FEATURE:
<221> NAME/KEY: MOD_RES
<222> LOCATION: (349)..(349)
<223> OTHER INFORMATION: Phe or absent
<220> FEATURE:
<221> NAME/KEY: MOD_RES
<222> LOCATION: (354)..(354)
<223> OTHER INFORMATION: Ile or Glu
<220> FEATURE:
<221> NAME/KEY: MOD_RES
<222> LOCATION: (361)..(361)
<223> OTHER INFORMATION: His or Glu
<220> FEATURE:
<221> NAME/KEY: MOD_RES
<222> LOCATION: (382)..(382)
<223> OTHER INFORMATION: Leu or Ser
<220> FEATURE:
<221> NAME/KEY: MOD_RES
<222> LOCATION: (386)..(386)
<223> OTHER INFORMATION: Ala or Val
<220> FEATURE:
<221> NAME/KEY: MOD_RES
<222> LOCATION: (398)..(398)
<223> OTHER INFORMATION: Glu or Gln
<220> FEATURE:
<221> NAME/KEY: MOD_RES
<222> LOCATION: (399)..(399)
<223> OTHER INFORMATION: Ala or Val
<220> FEATURE:
<221> NAME/KEY: MOD_RES
<222> LOCATION: (408)..(409)
<223> OTHER INFORMATION: Asn or Asp
<220> FEATURE:
<221> NAME/KEY: MOD_RES
<222> LOCATION: (411)..(411)
```

```
<223> OTHER INFORMATION: Arg or Gln
<220> FEATURE:
<221> NAME/KEY: MOD_RES
<222> LOCATION: (424)..(424)
<223> OTHER INFORMATION: Arg or Tyr
<220> FEATURE:
<221> NAME/KEY: MOD_RES
<222> LOCATION: (441)..(441)
<223> OTHER INFORMATION: Ser or Asn
<220> FEATURE:
<221> NAME/KEY: MOD_RES
<222> LOCATION: (449)..(449)
<223> OTHER INFORMATION: Leu or Phe
<220> FEATURE:
<221> NAME/KEY: MOD_RES
<222> LOCATION: (474)..(474)
<223> OTHER INFORMATION: Ile or Thr
<220> FEATURE:
<221> NAME/KEY: MOD_RES
<222> LOCATION: (486)..(486)
<223> OTHER INFORMATION: Lys or Glu
<220> FEATURE:
<221> NAME/KEY: MOD_RES
<222> LOCATION: (504)..(504)
<223> OTHER INFORMATION: Arg or Gln
<220> FEATURE:
<221> NAME/KEY: MOD_RES
<222> LOCATION: (509)..(509)
<223> OTHER INFORMATION: Ser or Pro
<220> FEATURE:
<221> NAME/KEY: MOD_RES
<222> LOCATION: (518)..(518)
<223> OTHER INFORMATION: Gln or Lys
<220> FEATURE:
<221> NAME/KEY: MOD_RES
<222> LOCATION: (520)..(520)
<223> OTHER INFORMATION: Gln or Arg
<220> FEATURE:
<221> NAME/KEY: MOD_RES
<222> LOCATION: (538)..(538)
<223> OTHER INFORMATION: Ser or Phe
<220> FEATURE:
<221> NAME/KEY: MOD_RES
<222> LOCATION: (539)..(539)
<223> OTHER INFORMATION: Val or Thr
<220> FEATURE:
<221> NAME/KEY: MOD_RES
<222> LOCATION: (540)..(540)
<223> OTHER INFORMATION: Ala or Val
<220> FEATURE:
<221> NAME/KEY: MOD_RES
<222> LOCATION: (555)..(555)
<223> OTHER INFORMATION: Ala or Val
<220> FEATURE:
<221> NAME/KEY: MOD_RES
<222> LOCATION: (581)..(581)
<223> OTHER INFORMATION: Asn or Ser
<220> FEATURE:
<221> NAME/KEY: MOD_RES
<222> LOCATION: (585)..(585)
<223> OTHER INFORMATION: Gln or Arg
<220> FEATURE:
<221> NAME/KEY: MOD_RES
<222> LOCATION: (598)..(598)
<223> OTHER INFORMATION: Arg or Gln
<220> FEATURE:
<221> NAME/KEY: MOD_RES
<222> LOCATION: (604)..(604)
<223> OTHER INFORMATION: Ala or Thr
<220> FEATURE:
<221> NAME/KEY: MOD_RES
<222> LOCATION: (614)..(614)
<223> OTHER INFORMATION: Ala or Lys
<220> FEATURE:
<221> NAME/KEY: MOD_RES
<222> LOCATION: (619)..(619)
<223> OTHER INFORMATION: Ala or Val
<220> FEATURE:
<221> NAME/KEY: MOD_RES
```

-continued

```
<222> LOCATION: (636)..(636)
<223> OTHER INFORMATION: Ser or Phe
<220> FEATURE:
<221> NAME/KEY: MOD_RES
<222> LOCATION: (637)..(637)
<223> OTHER INFORMATION: Ala or Pro
<220> FEATURE:
<221> NAME/KEY: MOD_RES
<222> LOCATION: (653)..(653)
<223> OTHER INFORMATION: Glu or Leu
<220> FEATURE:
<221> NAME/KEY: MOD_RES
<222> LOCATION: (657)..(657)
<223> OTHER INFORMATION: His or Ser
<220> FEATURE:
<221> NAME/KEY: MOD_RES
<222> LOCATION: (659)..(659)
<223> OTHER INFORMATION: Asp or Gly
<220> FEATURE:
<221> NAME/KEY: MOD_RES
<222> LOCATION: (664)..(664)
<223> OTHER INFORMATION: Pro or Met
<220> FEATURE:
<221> NAME/KEY: MOD_RES
<222> LOCATION: (665)..(665)
<223> OTHER INFORMATION: Ser or Asn
<220> FEATURE:
<221> NAME/KEY: MOD_RES
<222> LOCATION: (668)..(668)
<223> OTHER INFORMATION: Glu or Lys
<220> FEATURE:
<221> NAME/KEY: MOD_RES
<222> LOCATION: (672)..(672)
<223> OTHER INFORMATION: Ala or Asp
<220> FEATURE:
<221> NAME/KEY: MOD_RES
<222> LOCATION: (675)..(675)
<223> OTHER INFORMATION: Gly or Glu
<220> FEATURE:
<221> NAME/KEY: MOD_RES
<222> LOCATION: (679)..(679)
<223> OTHER INFORMATION: Gln or Arg
<220> FEATURE:
<221> NAME/KEY: MOD_RES
<222> LOCATION: (705)..(705)
<223> OTHER INFORMATION: Gly or Ser
<220> FEATURE:
<221> NAME/KEY: MOD_RES
<222> LOCATION: (710)..(710)
<223> OTHER INFORMATION: Gly or Arg
<220> FEATURE:
<221> NAME/KEY: MOD_RES
<222> LOCATION: (721)..(721)
<223> OTHER INFORMATION: Leu or Gln
<220> FEATURE:
<221> NAME/KEY: MOD_RES
<222> LOCATION: (722)..(722)
<223> OTHER INFORMATION: Ala or Val
<220> FEATURE:
<221> NAME/KEY: MOD_RES
<222> LOCATION: (724)..(724)
<223> OTHER INFORMATION: Arg or His
<220> FEATURE:
<221> NAME/KEY: MOD_RES
<222> LOCATION: (733)..(733)
<223> OTHER INFORMATION: Ser or Val
<220> FEATURE:
<221> NAME/KEY: MOD_RES
<222> LOCATION: (735)..(735)
<223> OTHER INFORMATION: Arg or His
<220> FEATURE:
<221> NAME/KEY: MOD_RES
<222> LOCATION: (744)..(744)
<223> OTHER INFORMATION: Ala or Cys
<220> FEATURE:
<221> NAME/KEY: MOD_RES
<222> LOCATION: (754)..(754)
<223> OTHER INFORMATION: Ala or Val
<220> FEATURE:
```

```
<221> NAME/KEY: MOD_RES
<222> LOCATION: (785)..(785)
<223> OTHER INFORMATION: Ala or Val
<220> FEATURE:
<221> NAME/KEY: MOD_RES
<222> LOCATION: (794)..(794)
<223> OTHER INFORMATION: His or Asn
<220> FEATURE:
<221> NAME/KEY: MOD_RES
<222> LOCATION: (795)..(795)
<223> OTHER INFORMATION: Arg or Gln
<220> FEATURE:
<221> NAME/KEY: MOD_RES
<222> LOCATION: (802)..(802)
<223> OTHER INFORMATION: Ala or Val
<220> FEATURE:
<221> NAME/KEY: MOD_RES
<222> LOCATION: (806)..(806)
<223> OTHER INFORMATION: Leu or Phe
<220> FEATURE:
<221> NAME/KEY: MOD_RES
<222> LOCATION: (808)..(808)
<223> OTHER INFORMATION: Glu or Ala
<220> FEATURE:
<221> NAME/KEY: MOD_RES
<222> LOCATION: (809)..(809)
<223> OTHER INFORMATION: Ala or Lys
<220> FEATURE:
<221> NAME/KEY: MOD_RES
<222> LOCATION: (811)..(811)
<223> OTHER INFORMATION: Arg or Ser
<220> FEATURE:
<221> NAME/KEY: MOD_RES
<222> LOCATION: (821)..(821)
<223> OTHER INFORMATION: Cys or Tyr
<220> FEATURE:
<221> NAME/KEY: MOD_RES
<222> LOCATION: (834)..(834)
<223> OTHER INFORMATION: Glu or Lys
<220> FEATURE:
<221> NAME/KEY: MOD_RES
<222> LOCATION: (837)..(837)
<223> OTHER INFORMATION: Ala or Asn
<220> FEATURE:
<221> NAME/KEY: MOD_RES
<222> LOCATION: (838)..(838)
<223> OTHER INFORMATION: Gly or Thr
<220> FEATURE:
<221> NAME/KEY: MOD_RES
<222> LOCATION: (839)..(839)
<223> OTHER INFORMATION: Ser or Asn
<220> FEATURE:
<221> NAME/KEY: MOD_RES
<222> LOCATION: (841)..(841)
<223> OTHER INFORMATION: Tyr or Ser
<220> FEATURE:
<221> NAME/KEY: MOD_RES
<222> LOCATION: (842)..(842)
<223> OTHER INFORMATION: Asp or Val
<220> FEATURE:
<221> NAME/KEY: MOD_RES
<222> LOCATION: (865)..(865)
<223> OTHER INFORMATION: Ile or Thr
<220> FEATURE:
<221> NAME/KEY: MOD_RES
<222> LOCATION: (874)..(874)
<223> OTHER INFORMATION: Arg or Ala
<220> FEATURE:
<221> NAME/KEY: MOD_RES
<222> LOCATION: (881)..(881)
<223> OTHER INFORMATION: Gly or Arg
<220> FEATURE:
<221> NAME/KEY: MOD_RES
<222> LOCATION: (883)..(883)
<223> OTHER INFORMATION: Met or Arg
<220> FEATURE:
<221> NAME/KEY: MOD_RES
<222> LOCATION: (890)..(890)
<223> OTHER INFORMATION: Ser or Asn
```

-continued

```
<220> FEATURE:
<221> NAME/KEY: MOD_RES
<222> LOCATION: (895)..(895)
<223> OTHER INFORMATION: Gln or Leu
<220> FEATURE:
<221> NAME/KEY: MOD_RES
<222> LOCATION: (901)..(901)
<223> OTHER INFORMATION: Arg or Gln
<220> FEATURE:
<221> NAME/KEY: MOD_RES
<222> LOCATION: (908)..(908)
<223> OTHER INFORMATION: Gly or Glu
<220> FEATURE:
<221> NAME/KEY: MOD_RES
<222> LOCATION: (914)..(914)
<223> OTHER INFORMATION: Val or Ala
<220> FEATURE:
<221> NAME/KEY: MOD_RES
<222> LOCATION: (934)..(934)
<223> OTHER INFORMATION: Ala or Thr
<220> FEATURE:
<221> NAME/KEY: MOD_RES
<222> LOCATION: (959)..(959)
<223> OTHER INFORMATION: Asn or Ser
<220> FEATURE:
<221> NAME/KEY: MOD_RES
<222> LOCATION: (965)..(965)
<223> OTHER INFORMATION: Arg or Ser
<220> FEATURE:
<221> NAME/KEY: MOD_RES
<222> LOCATION: (967)..(967)
<223> OTHER INFORMATION: Phe or Leu
<220> FEATURE:
<221> NAME/KEY: MOD_RES
<222> LOCATION: (969)..(969)
<223> OTHER INFORMATION: Phe or Ala
<220> FEATURE:
<221> NAME/KEY: MOD_RES
<222> LOCATION: (972)..(972)
<223> OTHER INFORMATION: Ser or Arg
<220> FEATURE:
<221> NAME/KEY: MOD_RES
<222> LOCATION: (974)..(974)
<223> OTHER INFORMATION: Ser or Pro
<220> FEATURE:
<221> NAME/KEY: MOD_RES
<222> LOCATION: (975)..(975)
<223> OTHER INFORMATION: Arg or Ala
<220> FEATURE:
<221> NAME/KEY: MOD_RES
<222> LOCATION: (977)..(977)
<223> OTHER INFORMATION: Ser or Gly
<220> FEATURE:
<221> NAME/KEY: MOD_RES
<222> LOCATION: (979)..(979)
<223> OTHER INFORMATION: Thr or Pro
<220> FEATURE:
<221> NAME/KEY: MOD_RES
<222> LOCATION: (980)..(980)
<223> OTHER INFORMATION: Gln or Ala
<220> FEATURE:
<221> NAME/KEY: MOD_RES
<222> LOCATION: (982)..(982)
<223> OTHER INFORMATION: Asn or Asp
<220> FEATURE:
<221> NAME/KEY: MOD_RES
<222> LOCATION: (989)..(989)
<223> OTHER INFORMATION: Leu or Ser
<220> FEATURE:
<221> NAME/KEY: MOD_RES
<222> LOCATION: (993)..(993)
<223> OTHER INFORMATION: Gln or Glu
<220> FEATURE:
<221> NAME/KEY: MOD_RES
<222> LOCATION: (1000)..(1000)
<223> OTHER INFORMATION: Leu or Phe
<220> FEATURE:
<221> NAME/KEY: MOD_RES
<222> LOCATION: (1005)..(1005)
```

```
<223> OTHER INFORMATION: Phe or Ile
<220> FEATURE:
<221> NAME/KEY: MOD_RES
<222> LOCATION: (1009)..(1009)
<223> OTHER INFORMATION: Val or Ala
<220> FEATURE:
<221> NAME/KEY: MOD_RES
<222> LOCATION: (1015)..(1015)
<223> OTHER INFORMATION: Ala or Thr
<220> FEATURE:
<221> NAME/KEY: MOD_RES
<222> LOCATION: (1018)..(1018)
<223> OTHER INFORMATION: Gln or His
<220> FEATURE:
<221> NAME/KEY: MOD_RES
<222> LOCATION: (1019)..(1019)
<223> OTHER INFORMATION: Arg or His
<220> FEATURE:
<221> NAME/KEY: MOD_RES
<222> LOCATION: (1026)..(1026)
<223> OTHER INFORMATION: Trp or Gln
<220> FEATURE:
<221> NAME/KEY: MOD_RES
<222> LOCATION: (1033)..(1033)
<223> OTHER INFORMATION: His or Asn
<220> FEATURE:
<221> NAME/KEY: MOD_RES
<222> LOCATION: (1040)..(1040)
<223> OTHER INFORMATION: Lys or His
<220> FEATURE:
<221> NAME/KEY: MOD_RES
<222> LOCATION: (1041)..(1041)
<223> OTHER INFORMATION: Arg or Ser
<220> FEATURE:
<221> NAME/KEY: MOD_RES
<222> LOCATION: (1042)..(1042)
<223> OTHER INFORMATION: Val or Arg
<220> FEATURE:
<221> NAME/KEY: MOD_RES
<222> LOCATION: (1044)..(1044)
<223> OTHER INFORMATION: Ser or Phe
<220> FEATURE:
<221> NAME/KEY: MOD_RES
<222> LOCATION: (1045)..(1045)
<223> OTHER INFORMATION: Ser or absent

<400> SEQUENCE: 310

Met Lys Xaa Gly Cys Ala Ala Gly Ser Pro Gly Asn Glu Trp Ile Phe
1               5                   10                  15

Phe Ser Ser Asp Glu Xaa Xaa Thr Arg Xaa Arg Xaa Thr Met Ser Asn
                20                  25                  30

Xaa Ala Leu Gln Arg Ser Xaa Ile Leu Ser Ala Xaa Ile Leu Leu Arg
            35                  40                  45

Ala Val Thr Gly Phe Ser Gly Asp Gly Lys Ala Ile Trp Xaa Lys Xaa
        50                  55                  60

Xaa Xaa Xaa Ser Pro Val Asn Xaa Ser Gln Leu Phe Leu Tyr Asp Thr
65                  70                  75                  80

Phe Pro Lys Asn Phe Xaa Trp Gly Ile Gly Thr Gly Ala Xaa Gln Val
                85                  90                  95

Glu Gly Ser Trp Lys Xaa Asp Gly Lys Gly Pro Ser Ile Trp Asp Xaa
            100                 105                 110

Phe Ile His Ser His Leu Lys Xaa Val Xaa Xaa Thr Xaa Xaa Ser Ser
        115                 120                 125

Asp Ser Tyr Ile Phe Leu Glu Lys Asp Leu Xaa Ala Leu Asp Phe Ile
    130                 135                 140

Gly Val Ser Phe Tyr Gln Phe Ser Ile Ser Trp Pro Arg Leu Phe Pro
145                 150                 155                 160

Xaa Gly Xaa Val Xaa Xaa Xaa Asn Ala Xaa Gly Leu Xaa Tyr Tyr Xaa
```

```
                    165                 170                 175
Xaa Leu Leu Asp Ala Leu Val Leu Arg Asn Ile Glu Pro Ile Val Thr
                180                 185                 190

Leu Tyr His Trp Asp Leu Pro Leu Xaa Leu Gln Glu Xaa Tyr Gly Gly
                195                 200                 205

Trp Lys Asn Xaa Thr Ile Ile Asp Ile Phe Asn Asp Tyr Ala Thr Tyr
                210                 215                 220

Cys Phe Gln Xaa Phe Gly Asp Arg Val Lys Tyr Trp Ile Thr Ile His
225                 230                 235                 240

Asn Pro Tyr Leu Val Ala Trp His Gly Phe Gly Thr Gly Met His Ala
                245                 250                 255

Pro Gly Glu Lys Gly Asn Leu Xaa Ala Val Tyr Thr Val Gly His Asn
                260                 265                 270

Leu Ile Lys Ala His Ser Lys Val Trp His Asn Tyr Xaa Xaa Xaa Phe
                275                 280                 285

Arg Pro His Gln Lys Gly Trp Leu Ser Ile Thr Leu Gly Ser His Trp
                290                 295                 300

Ile Glu Pro Asn Arg Ser Asp Asn Xaa Xaa Asp Ile Xaa Xaa Cys Gln
305                 310                 315                 320

Xaa Ser Met Xaa Ser Val Leu Gly Trp Phe Ala Asn Pro Ile His Gly
                325                 330                 335

Asp Gly Asp Tyr Pro Glu Xaa Met Lys Xaa Xaa Xaa Ala Met Ile
                340                 345                 350

Pro Xaa Phe Ser Glu Ala Glu Lys Xaa Glu Met Arg Gly Thr Ala Asp
                355                 360                 365

Phe Phe Ala Phe Ser Phe Gly Pro Asn Asn Phe Lys Pro Xaa Asn Thr
                370                 375                 380

Met Xaa Lys Met Gly Gln Asn Val Ser Leu Asn Leu Arg Xaa Xaa Leu
385                 390                 395                 400

Asn Trp Ile Lys Leu Glu Tyr Xaa Xaa Pro Xaa Ile Leu Ile Ala Glu
                405                 410                 415

Asn Gly Trp Phe Thr Asp Ser Xaa Ile Lys Thr Glu Asp Thr Thr Ala
                420                 425                 430

Ile Tyr Met Met Lys Asn Phe Leu Xaa Gln Val Leu Gln Ala Ile Lys
                435                 440                 445

Xaa Asp Glu Ile Arg Val Phe Gly Tyr Thr Ala Trp Ser Leu Leu Asp
                450                 455                 460

Gly Phe Glu Trp Gln Asp Ala Tyr Thr Xaa Arg Arg Gly Leu Phe Tyr
465                 470                 475                 480

Val Asp Phe Asn Ser Xaa Gln Lys Glu Arg Lys Pro Lys Ser Ser Ala
                485                 490                 495

His Tyr Tyr Lys Gln Ile Ile Xaa Asp Asn Gly Phe Xaa Leu Lys Glu
                500                 505                 510

Ser Thr Pro Asp Met Xaa Gly Xaa Phe Pro Cys Asp Phe Ser Trp Gly
                515                 520                 525

Val Thr Glu Ser Val Leu Lys Pro Glu Xaa Xaa Xaa Ser Ser Pro Gln
                530                 535                 540

Phe Ser Asp Pro His Leu Tyr Val Trp Asn Xaa Thr Gly Asn Arg Leu
545                 550                 555                 560

Leu His Arg Val Glu Gly Val Arg Leu Lys Thr Arg Pro Ala Gln Cys
                565                 570                 575

Thr Asp Phe Val Xaa Ile Lys Lys Xaa Leu Glu Met Leu Ala Lys Met
                580                 585                 590
```

```
Lys Val Thr His Tyr Xaa Phe Ala Leu Asp Trp Xaa Ser Ile Leu Pro
            595                 600                 605

Thr Gly Asn Leu Ser Xaa Val Asn Arg Gln Xaa Leu Arg Tyr Tyr Arg
        610                 615                 620

Cys Val Ser Glu Gly Leu Lys Leu Gly Ile Xaa Xaa Met Val Thr
625                 630                 635                 640

Leu Tyr His Pro Thr His Ala His Leu Gly Leu Pro Xaa Pro Leu Leu
                645                 650                 655

Xaa Ala Xaa Gly Trp Leu Asn Xaa Xaa Thr Ala Xaa Ala Phe Gln Xaa
            660                 665                 670

Tyr Ala Xaa Leu Cys Phe Xaa Glu Leu Gly Asp Leu Val Lys Leu Trp
            675                 680                 685

Ile Thr Ile Asn Glu Pro Asn Arg Leu Ser Asp Ile Tyr Asn Arg Ser
            690                 695                 700

Xaa Asn Asp Thr Tyr Xaa Ala Ala His Asn Leu Leu Ile Ala His Ala
705                 710                 715                 720

Xaa Xaa Trp Xaa Leu Tyr Asp Arg Gln Phe Arg Pro Xaa Gln Xaa Gly
            725                 730                 735

Ala Val Ser Leu Ser Leu His Xaa Asp Trp Ala Glu Pro Ala Asn Pro
            740                 745                 750

Phe Xaa Asp Ser His Trp Lys Ala Ala Glu Arg Phe Leu Gln Phe Glu
        755                 760                 765

Ile Ala Trp Phe Ala Asp Pro Leu Phe Lys Thr Gly Asp Tyr Pro Ala
        770                 775                 780

Xaa Met Lys Glu Tyr Ile Ala Ser Lys Xaa Xaa Arg Gly Leu Ser Ser
785                 790                 795                 800

Ser Xaa Leu Pro Arg Xaa Thr Xaa Xaa Glu Xaa Arg Leu Leu Lys Gly
        805                 810                 815

Thr Val Asp Phe Xaa Ala Leu Asn His Phe Thr Thr Arg Phe Val Ile
            820                 825                 830

His Xaa Gln Leu Xaa Xaa Xaa Arg Xaa Xaa Ala Asp Arg Asp Ile Gln
    835                 840                 845

Phe Leu Gln Asp Ile Thr Arg Leu Ser Ser Pro Ser Arg Leu Ala Val
    850                 855                 860

Xaa Pro Trp Gly Val Arg Lys Leu Leu Xaa Trp Ile Arg Arg Asn Tyr
865                 870                 875                 880

Xaa Asp Xaa Asp Ile Tyr Ile Thr Ala Xaa Gly Ile Asp Asp Xaa Ala
            885                 890                 895

Leu Glu Asp Asp Xaa Ile Arg Lys Tyr Tyr Leu Xaa Lys Tyr Leu Gln
            900                 905                 910

Glu Xaa Leu Lys Ala Tyr Leu Ile Asp Lys Val Lys Ile Lys Gly Tyr
    915                 920                 925

Tyr Ala Phe Lys Leu Xaa Glu Glu Lys Ser Lys Pro Arg Phe Gly Phe
        930                 935                 940

Phe Thr Ser Asp Phe Lys Ala Lys Ser Ser Ile Gln Phe Tyr Xaa Lys
945                 950                 955                 960

Leu Ile Ser Ser Xaa Gly Xaa Pro Xaa Glu Asn Xaa Ser Xaa Xaa Cys
            965                 970                 975

Xaa Gln Xaa Xaa Glu Xaa Thr Asp Cys Thr Ile Cys Xaa Phe Leu Val
        980                 985                 990

Xaa Lys Lys Pro Leu Ile Phe Xaa  Gly Cys Cys Phe Xaa  Ser Thr Leu
        995                 1000                 1005
```

```
Xaa Leu Leu Leu Ser Ile Xaa Ile Phe Xaa Xaa Gln Lys Arg Arg
    1010                1015                1020

Lys Phe Xaa Lys Ala Lys Asn Leu Gln Xaa Ile Pro Leu Lys Lys
        1025                1030                1035

Gly Xaa Xaa Xaa Val Xaa Xaa
        1040            1045

<210> SEQ ID NO 311
<211> LENGTH: 585
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 311

Asp Pro Ser Pro Thr Leu Pro Glu Gln Ala Gln Pro Trp Gly Ala Pro
1               5                   10                  15

Val Glu Val Glu Ser Phe Leu Val His Pro Gly Asp Leu Leu Gln Leu
            20                  25                  30

Arg Cys Arg Leu Arg Asp Asp Val Gln Ser Ile Asn Trp Leu Arg Asp
        35                  40                  45

Gly Val Gln Leu Ala Glu Ser Asn Arg Thr Arg Ile Thr Gly Glu Glu
    50                  55                  60

Val Glu Val Gln Asp Ser Val Pro Ala Asp Ser Gly Leu Tyr Ala Cys
65                  70                  75                  80

Val Thr Ser Ser Pro Ser Gly Ser Asp Thr Thr Tyr Phe Ser Val Asn
                85                  90                  95

Val Ser Asp Ala Leu Pro Ser Ser Glu Asp Asp Asp Asp Asp Asp Asp
            100                 105                 110

Ser Ser Ser Glu Glu Lys Glu Thr Asp Asn Thr Lys Pro Asn Arg Met
        115                 120                 125

Pro Val Ala Pro Tyr Trp Thr Ser Pro Glu Lys Met Glu Lys Lys Leu
    130                 135                 140

His Ala Val Pro Ala Ala Lys Thr Val Lys Phe Lys Cys Pro Ser Ser
145                 150                 155                 160

Gly Thr Pro Asn Pro Thr Leu Arg Trp Leu Lys Asn Gly Lys Glu Phe
                165                 170                 175

Lys Pro Asp His Arg Ile Gly Gly Tyr Lys Val Arg Tyr Ala Thr Trp
            180                 185                 190

Ser Ile Ile Met Asp Ser Val Val Pro Ser Asp Lys Gly Asn Tyr Thr
        195                 200                 205

Cys Ile Val Glu Asn Glu Tyr Gly Ser Ile Asn His Thr Tyr Gln Leu
    210                 215                 220

Asp Val Val Glu Arg Ser Pro His Arg Pro Ile Leu Gln Ala Gly Leu
225                 230                 235                 240

Pro Ala Asn Lys Thr Val Ala Leu Gly Ser Asn Val Glu Phe Met Cys
                245                 250                 255

Lys Val Tyr Ser Asp Pro Gln Pro His Ile Gln Trp Leu Lys His Ile
            260                 265                 270

Glu Val Asn Gly Ser Lys Ile Gly Pro Asp Asn Leu Pro Tyr Val Gln
        275                 280                 285

Ile Leu Lys Thr Ala Gly Val Asn Thr Thr Asp Lys Glu Met Glu Val
    290                 295                 300

Leu His Leu Arg Asn Val Ser Phe Glu Asp Ala Gly Glu Tyr Thr Cys
305                 310                 315                 320
```

```
Leu Ala Gly Asn Ser Ile Gly Leu Ser His His Ser Ala Trp Leu Thr
            325                 330                 335

Val Leu Glu Ala Leu Glu Arg Pro Ala Val Met Thr Ser Pro Leu
        340                 345                 350

Tyr Gly Gly Gly Gly Asp Lys Thr His Thr Cys Pro Pro Cys Pro
        355                 360                 365

Ala Pro Glu Leu Leu Gly Gly Pro Ser Val Phe Leu Phe Pro Pro Lys
370                 375                 380

Pro Lys Asp Thr Leu Met Ile Ser Arg Thr Pro Glu Val Thr Cys Val
385                 390                 395                 400

Val Val Asp Val Ser His Glu Asp Pro Glu Val Lys Phe Asn Trp Tyr
                405                 410                 415

Val Asp Gly Val Glu Val His Asn Ala Lys Thr Lys Pro Arg Glu Glu
                420                 425                 430

Gln Tyr Asn Ser Thr Tyr Arg Val Val Ser Val Leu Thr Val Leu His
            435                 440                 445

Gln Asp Trp Leu Asn Gly Lys Glu Tyr Lys Cys Lys Val Ser Asn Lys
450                 455                 460

Ala Leu Pro Ala Pro Ile Glu Lys Thr Ile Ser Lys Ala Lys Gly Gln
465                 470                 475                 480

Pro Arg Glu Pro Gln Val Tyr Thr Leu Pro Pro Ser Arg Asp Glu Leu
                485                 490                 495

Thr Lys Asn Gln Val Ser Leu Thr Cys Leu Val Lys Gly Phe Tyr Pro
            500                 505                 510

Ser Asp Ile Ala Val Glu Trp Glu Ser Asn Gly Gln Pro Glu Asn Asn
            515                 520                 525

Tyr Lys Thr Thr Pro Pro Val Leu Asp Ser Asp Gly Ser Phe Phe Leu
            530                 535                 540

Tyr Ser Lys Leu Thr Val Asp Lys Ser Arg Trp Gln Gln Gly Asn Val
545                 550                 555                 560

Phe Ser Cys Ser Val Met His Glu Ala Leu His Asn His Tyr Thr Gln
                565                 570                 575

Lys Ser Leu Ser Leu Ser Pro Gly Lys
            580                 585

<210> SEQ ID NO 312
<211> LENGTH: 1176
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 312

Phe Ser Gly Asp Gly Arg Ala Ile Trp Ser Lys Asn Pro Asn Phe Thr
1               5                   10                  15

Pro Val Asn Glu Ser Gln Leu Phe Leu Tyr Asp Thr Phe Pro Lys Asn
            20                  25                  30

Phe Phe Trp Gly Ile Gly Thr Gly Ala Leu Gln Val Glu Gly Ser Trp
        35                  40                  45

Lys Lys Asp Gly Lys Gly Pro Ser Ile Trp Asp His Phe Ile His Thr
    50                  55                  60

His Leu Lys Asn Val Ser Ser Thr Asn Gly Ser Ser Asp Ser Tyr Ile
65                  70                  75                  80

Phe Leu Glu Lys Asp Leu Ser Ala Leu Asp Phe Ile Gly Val Ser Phe
```

```
                85                  90                  95
Tyr Gln Phe Ser Ile Ser Trp Pro Arg Leu Phe Pro Asp Gly Ile Val
            100                 105                 110

Thr Val Ala Asn Ala Lys Gly Leu Gln Tyr Tyr Ser Thr Leu Leu Asp
            115                 120                 125

Ala Leu Val Leu Arg Asn Ile Glu Pro Ile Val Thr Leu Tyr His Trp
130                 135                 140

Asp Leu Pro Leu Ala Leu Gln Glu Lys Tyr Gly Gly Trp Lys Asn Asp
145                 150                 155                 160

Thr Ile Ile Asp Ile Phe Asn Asp Tyr Ala Thr Tyr Cys Phe Gln Met
                165                 170                 175

Phe Gly Asp Arg Val Lys Tyr Trp Ile Thr Ile His Asn Pro Tyr Leu
                180                 185                 190

Val Ala Trp His Gly Tyr Gly Thr Gly Met His Ala Pro Gly Glu Lys
                195                 200                 205

Gly Asn Leu Ala Ala Val Tyr Thr Val Gly His Asn Leu Ile Lys Ala
            210                 215                 220

His Ser Lys Val Trp His Asn Tyr Asn Thr His Phe Arg Pro His Gln
225                 230                 235                 240

Lys Gly Trp Leu Ser Ile Thr Leu Gly Ser His Trp Ile Glu Pro Asn
                245                 250                 255

Arg Ser Glu Asn Thr Met Asp Ile Phe Lys Cys Gln Gln Ser Met Val
            260                 265                 270

Ser Val Leu Gly Trp Phe Ala Asn Pro Ile His Gly Asp Gly Asp Tyr
            275                 280                 285

Pro Glu Gly Met Arg Lys Lys Leu Phe Ser Val Leu Pro Ile Phe Ser
290                 295                 300

Glu Ala Glu Lys His Glu Met Arg Gly Thr Ala Asp Phe Phe Ala Phe
305                 310                 315                 320

Ser Phe Gly Pro Asn Asn Phe Lys Pro Leu Asn Thr Met Ala Lys Met
                325                 330                 335

Gly Gln Asn Val Ser Leu Asn Leu Arg Glu Ala Leu Asn Trp Ile Lys
            340                 345                 350

Leu Glu Tyr Asn Asn Pro Arg Ile Leu Ile Ala Glu Asn Gly Trp Phe
            355                 360                 365

Thr Asp Ser Arg Val Lys Thr Glu Asp Thr Thr Ala Ile Tyr Met Met
370                 375                 380

Lys Asn Phe Leu Ser Gln Val Leu Gln Ala Ile Arg Leu Asp Glu Ile
385                 390                 395                 400

Arg Val Phe Gly Tyr Thr Ala Trp Ser Leu Leu Asp Gly Phe Glu Trp
                405                 410                 415

Gln Asp Ala Tyr Thr Ile Arg Arg Gly Leu Phe Tyr Val Asp Phe Asn
                420                 425                 430

Ser Lys Gln Lys Glu Arg Lys Pro Lys Ser Ser Ala His Tyr Tyr Lys
            435                 440                 445

Gln Ile Ile Arg Glu Asn Gly Phe Ser Leu Lys Glu Ser Thr Pro Asp
            450                 455                 460

Val Gln Gly Gln Phe Pro Cys Asp Phe Ser Trp Gly Val Thr Glu Ser
465                 470                 475                 480

Val Leu Lys Pro Glu Ser Val Ala Ser Ser Pro Gln Phe Ser Asp Pro
                485                 490                 495

His Leu Tyr Val Trp Asn Ala Thr Gly Asn Arg Leu Leu His Arg Val
                500                 505                 510
```

```
Glu Gly Val Arg Leu Lys Thr Arg Pro Ala Gln Cys Thr Asp Phe Val
            515                 520                 525

Asn Ile Lys Lys Gln Leu Glu Met Leu Ala Arg Met Lys Val Thr His
    530                 535                 540

Tyr Arg Phe Ala Leu Asp Trp Ala Ser Val Leu Pro Thr Gly Asn Leu
545                 550                 555                 560

Ser Ala Val Asn Arg Gln Ala Leu Arg Tyr Tyr Arg Cys Val Val Ser
                565                 570                 575

Glu Gly Leu Lys Leu Gly Ile Ser Ala Met Val Thr Leu Tyr Tyr Pro
            580                 585                 590

Thr His Ala His Leu Gly Leu Pro Glu Pro Leu Leu His Ala Asp Gly
        595                 600                 605

Trp Leu Asn Pro Ser Thr Ala Glu Ala Phe Gln Ala Tyr Ala Gly Leu
        610                 615                 620

Cys Phe Gln Glu Leu Gly Asp Leu Val Lys Leu Trp Ile Thr Ile Asn
625                 630                 635                 640

Glu Pro Asn Arg Leu Ser Asp Ile Tyr Asn Arg Ser Gly Asn Asp Thr
                645                 650                 655

Tyr Gly Ala Ala His Asn Leu Leu Val Ala His Ala Leu Ala Trp Arg
            660                 665                 670

Leu Tyr Asp Arg Gln Phe Arg Pro Ser Gln Arg Gly Ala Val Ser Leu
        675                 680                 685

Ser Leu His Ala Asp Trp Ala Glu Pro Ala Asn Pro Tyr Ala Asp Ser
        690                 695                 700

His Trp Arg Ala Ala Glu Arg Phe Leu Gln Phe Glu Ile Ala Trp Phe
705                 710                 715                 720

Ala Glu Pro Leu Phe Lys Thr Gly Asp Tyr Pro Ala Ala Met Arg Glu
                725                 730                 735

Tyr Ile Ala Ser Lys His Arg Arg Gly Leu Ser Ser Ser Ala Leu Pro
            740                 745                 750

Arg Leu Thr Glu Ala Glu Arg Leu Leu Lys Gly Thr Val Asp Phe
        755                 760                 765

Cys Ala Leu Asn His Phe Thr Thr Arg Phe Val Met His Glu Gln Leu
770                 775                 780

Ala Gly Ser Arg Tyr Asp Ser Asp Arg Asp Ile Gln Phe Leu Gln Asp
785                 790                 795                 800

Ile Thr Arg Leu Ser Ser Pro Thr Arg Leu Ala Val Ile Pro Trp Gly
                805                 810                 815

Val Arg Lys Leu Leu Arg Trp Val Arg Arg Asn Tyr Gly Asp Met Asp
            820                 825                 830

Ile Tyr Ile Thr Ala Ser Gly Ile Asp Asp Gln Ala Leu Glu Asp Asp
        835                 840                 845

Arg Leu Arg Lys Tyr Tyr Leu Gly Lys Tyr Leu Gln Glu Val Leu Lys
        850                 855                 860

Ala Tyr Leu Ile Asp Lys Val Arg Ile Lys Gly Tyr Tyr Ala Phe Lys
865                 870                 875                 880

Leu Ala Glu Glu Lys Ser Lys Pro Arg Phe Gly Phe Phe Thr Ser Asp
                885                 890                 895

Phe Lys Ala Lys Ser Ser Ile Gln Phe Tyr Asn Lys Val Ile Ser Ser
            900                 905                 910

Arg Gly Phe Pro Phe Glu Asn Ser Ser Ser Arg Cys Ser Gln Thr Gln
        915                 920                 925
```

Glu Asn Thr Glu Cys Thr Val Cys Leu Phe Leu Val Gln Lys Lys Pro
930                 935                 940

Gly Gly Gly Gly Gly Asp Lys Thr His Thr Cys Pro Pro Cys Pro Ala
945                 950                 955                 960

Pro Glu Leu Leu Gly Gly Pro Ser Val Phe Leu Phe Pro Pro Lys Pro
                965                 970                 975

Lys Asp Thr Leu Met Ile Ser Arg Thr Pro Glu Val Thr Cys Val Val
                980                 985                 990

Val Asp Val Ser His Glu Asp Pro Glu Val Lys Phe Asn Trp Tyr Val
                995                 1000                1005

Asp Gly Val Glu Val His Asn Ala Lys Thr Lys Pro Arg Glu Glu
    1010                1015                1020

Gln Tyr Asn Ser Thr Tyr Arg Val Val Ser Val Leu Thr Val Leu
    1025                1030                1035

His Gln Asp Trp Leu Asn Gly Lys Glu Tyr Lys Cys Lys Val Ser
    1040                1045                1050

Asn Lys Ala Leu Pro Ala Pro Ile Glu Lys Thr Ile Ser Lys Ala
    1055                1060                1065

Lys Gly Gln Pro Arg Glu Pro Gln Val Tyr Thr Leu Pro Pro Ser
    1070                1075                1080

Arg Asp Glu Leu Thr Lys Asn Gln Val Ser Leu Thr Cys Leu Val
    1085                1090                1095

Lys Gly Phe Tyr Pro Ser Asp Ile Ala Val Glu Trp Glu Ser Asn
    1100                1105                1110

Gly Gln Pro Glu Asn Asn Tyr Lys Thr Thr Pro Pro Val Leu Asp
    1115                1120                1125

Ser Asp Gly Ser Phe Phe Leu Tyr Ser Lys Leu Thr Val Asp Lys
    1130                1135                1140

Ser Arg Trp Gln Gln Gly Asn Val Phe Ser Cys Ser Val Met His
    1145                1150                1155

Glu Ala Leu His Asn His Tyr Thr Gln Lys Ser Leu Ser Leu Ser
    1160                1165                1170

Pro Gly Lys
    1175

<210> SEQ ID NO 313
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 313

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
                20                  25                  30

Tyr Val Ser Trp Tyr Gln Gln Leu Pro Gly Thr Ala Pro Lys Leu Leu
            35                  40                  45

Ile Tyr Asp Asn Asp Lys Arg Pro Ser Gly Ile Pro Asp Arg Phe Ser
        50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Val Val Phe Gly Gly Gly Thr Lys Leu Thr Val Leu
            100                 105                 110

<210> SEQ ID NO 314
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (86)..(86)
<223> OTHER INFORMATION: Any amino acid

<400> SEQUENCE: 314

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Arg Asn Lys Tyr His Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Xaa Arg Ala Glu Asp Thr Ala Val Tyr Tyr Cys
                85                  90                  95

Ala Arg Asp His Pro Val Ala Gly Thr Ser Phe Asp Phe Trp Gly Gln
            100                 105                 110

Gly Thr Leu Val Thr Val Ser Ser
        115                 120

<210> SEQ ID NO 315
<211> LENGTH: 1989
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 315
atggactcgg acgagaccgg gttcgagcac tcagggctgt gggtttctgt gctggctggt      60
cttctgctgg agcctgcca ggcacacccc atccctgact ccagtcctct cctgcaattc     120
gggggccaag tccggcagcg gtacctctac acagatgatg cccagcagac agaagcccac    180
ctggagatca gggaggatgg gacggtgggg ggcgctgctg accagagccc cgaaagtctc    240
ctgcagctga aagccttgaa gccgggagtt attcaaatct gggagtcaa gacatccagg     300 ttcctgtgcc agcggccaga tgggccctg tatggatcgc tccactttga ccctgaggcc    360
tgcagcttcc gggagctgct tcttgaggac ggatacaatg tttaccagtc cgaagcccac    420
ggcctcccgc tgcacctgcc agggaacaag tccccacacc gggaccctgc accccgagga    480
ccagctcgct tcctgccact accaggcctg ccccccgcac cccggagcc acccggaatc    540 ctggcccccc agcccccga tgtgggctcc tcggaccctc tgagcatggt gggaggcggc    600
ggttccgggg gcggtggatc cggtggcggg ggaagccagg tgcagttggt ggagtctggg    660
ggaggcgtgg tccagcctgg gaggtccctg agactctcct gtgcagcgtc tagattctcc    720
ttcagtagat atggcatgca ctgggtccgc caggctccag gcaaggggct ggagtgggtg    780

```
gcagttatat ggtttgatgg aagaaatcaa tactatgcag actccgtgaa ggggcgattc      840
accatctcca gagacaattc caagaatacg ctgtttctgc aaatgaacag cctgagagtc      900
gaggacacgg ctgtgtatta ctgtgcgaga gatcacccag tagttggtac gagctttgac      960
tactggggcc agggaaccct ggtcaccgtc tctagtgcct ccaccaaggg cccatcggtc     1020
ttccccctgg caccctcctc caagagcacc tctgggggca gcggccct gggctgcctg       1080 gtcaaggact acttccccga accggtgacg gtgtcgtgga actcaggcgc cctgaccagc     1140
ggcgtgcaca ccttcccggc tgtcctacag tcctcaggac tctactccct cagcagcgtg     1200
gtgaccgtgc cctccagcag cttgggcacc cagacctaca tctgcaacgt gaatcacaag     1260
cccagcaaca ccaaggtgga caagaaagtt gagcccaaat cttgtgacaa aactcacaca     1320
tgcccaccgt gcccagcacc tgaactcctg ggggaccgt cagtcttcct cttcccccca      1380
aaacccaagg acaccctcat gatctcccgg acccctgagg tcacatgcgt ggtggtggac     1440
gtgagccacg aagaccctga ggtcaagttc aactggtacg tggacggcgt ggaggtgcat     1500
aatgccaaga caaagccgcg ggaggagcag taccagagca cgtaccgtgt ggtcagcgtc     1560
ctcaccgtcc tgcaccagga ctggctgaat ggcaaggagt acaagtgcaa ggtctccaac     1620
aaagccctcc cagccccat cgagaaaacc atctccaaag ccaagggca ccccgagaa        1680 ccacaggtgt acaccctgcc cccatcccgg gatgagctga ccaagaacca ggtcagcctg     1740
acctgcctgg tcaaaggctt ctatcccagc gacatcgccg tggagtggga gagcaatggg     1800
cagccggaga caactacaa gaccacgcct cccgtgctgg actccgacgg ctccttcttc      1860
ctctatagca agctcaccgt ggacaagagc aggtggcagc aggggaacgt cttctcatgc     1920
tccgtgatgc atgaggctct gcacaaccac tacacgcaga gagcctctc cctgtctccg      1980 ggtaaatag                                                             1989
```

<210> SEQ ID NO 316
<211> LENGTH: 662
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 316

Met Asp Ser Asp Glu Thr Gly Phe Glu His Ser Gly Leu Trp Val Ser
1               5                   10                  15

Val Leu Ala Gly Leu Leu Leu Gly Ala Cys Gln Ala His Pro Ile Pro
            20                  25                  30

Asp Ser Ser Pro Leu Leu Gln Phe Gly Gly Gln Val Arg Gln Arg Tyr
        35                  40                  45

Leu Tyr Thr Asp Asp Ala Gln Gln Thr Glu Ala His Leu Glu Ile Arg
    50                  55                  60

Glu Asp Gly Thr Val Gly Gly Ala Ala Asp Gln Ser Pro Glu Ser Leu
65                  70                  75                  80

Leu Gln Leu Lys Ala Leu Lys Pro Gly Val Ile Gln Ile Leu Gly Val
                85                  90                  95

Lys Thr Ser Arg Phe Leu Cys Gln Arg Pro Asp Gly Ala Leu Tyr Gly
            100                 105                 110

Ser Leu His Phe Asp Pro Glu Ala Cys Ser Phe Arg Glu Leu Leu Leu
        115                 120                 125

Glu Asp Gly Tyr Asn Val Tyr Gln Ser Glu Ala His Gly Leu Pro Leu

```
            130                 135                 140
His Leu Pro Gly Asn Lys Ser Pro His Arg Asp Pro Ala Pro Arg Gly
145                 150                 155                 160

Pro Ala Arg Phe Leu Pro Leu Pro Gly Leu Pro Pro Ala Pro Pro Glu
                165                 170                 175

Pro Pro Gly Ile Leu Ala Pro Gln Pro Pro Asp Val Gly Ser Ser Asp
                180                 185                 190

Pro Leu Ser Met Val Gly Gly Gly Ser Gly Gly Gly Ser Gly
            195                 200                 205

Gly Gly Gly Ser Gln Val Gln Leu Val Glu Ser Gly Gly Gly Val Val
            210                 215                 220

Gln Pro Gly Arg Ser Leu Arg Leu Ser Cys Ala Ala Ser Arg Phe Ser
225                 230                 235                 240

Phe Ser Arg Tyr Gly Met His Trp Val Arg Gln Ala Pro Gly Lys Gly
                245                 250                 255

Leu Glu Trp Val Ala Val Ile Trp Phe Asp Gly Arg Asn Gln Tyr Tyr
                260                 265                 270

Ala Asp Ser Val Lys Gly Arg Phe Thr Ile Ser Arg Asp Asn Ser Lys
            275                 280                 285

Asn Thr Leu Phe Leu Gln Met Asn Ser Leu Arg Val Glu Asp Thr Ala
290                 295                 300

Val Tyr Tyr Cys Ala Arg Asp His Pro Val Val Gly Thr Ser Phe Asp
305                 310                 315                 320

Tyr Trp Gly Gln Gly Thr Leu Val Thr Val Ser Ser Ala Ser Thr Lys
                325                 330                 335

Gly Pro Ser Val Phe Pro Leu Ala Pro Ser Ser Lys Ser Thr Ser Gly
                340                 345                 350

Gly Thr Ala Ala Leu Gly Cys Leu Val Lys Asp Tyr Phe Pro Glu Pro
            355                 360                 365

Val Thr Val Ser Trp Asn Ser Gly Ala Leu Thr Ser Gly Val His Thr
                370                 375                 380

Phe Pro Ala Val Leu Gln Ser Ser Gly Leu Tyr Ser Leu Ser Ser Val
385                 390                 395                 400

Val Thr Val Pro Ser Ser Ser Leu Gly Thr Gln Thr Tyr Ile Cys Asn
                405                 410                 415

Val Asn His Lys Pro Ser Asn Thr Lys Val Asp Lys Lys Val Glu Pro
                420                 425                 430

Lys Ser Cys Asp Lys Thr His Thr Cys Pro Pro Cys Pro Ala Pro Glu
            435                 440                 445

Leu Leu Gly Gly Pro Ser Val Phe Leu Phe Pro Pro Lys Pro Lys Asp
450                 455                 460

Thr Leu Met Ile Ser Arg Thr Pro Glu Val Thr Cys Val Val Val Asp
465                 470                 475                 480

Val Ser His Glu Asp Pro Glu Val Lys Phe Asn Trp Tyr Val Asp Gly
                485                 490                 495

Val Glu Val His Asn Ala Lys Thr Lys Pro Arg Glu Glu Gln Tyr Gln
            500                 505                 510

Ser Thr Tyr Arg Val Val Ser Val Leu Thr Val Leu His Gln Asp Trp
            515                 520                 525

Leu Asn Gly Lys Glu Tyr Lys Cys Lys Val Ser Asn Lys Ala Leu Pro
530                 535                 540

Ala Pro Ile Glu Lys Thr Ile Ser Lys Ala Lys Gly Gln Pro Arg Glu
545                 550                 555                 560
```

```
Pro Gln Val Tyr Thr Leu Pro Pro Ser Arg Asp Glu Leu Thr Lys Asn
                565                 570                 575

Gln Val Ser Leu Thr Cys Leu Val Lys Gly Phe Tyr Pro Ser Asp Ile
            580                 585                 590

Ala Val Glu Trp Glu Ser Asn Gly Gln Pro Glu Asn Asn Tyr Lys Thr
        595                 600                 605

Thr Pro Pro Val Leu Asp Ser Asp Gly Ser Phe Phe Leu Tyr Ser Lys
    610                 615                 620

Leu Thr Val Asp Lys Ser Arg Trp Gln Gln Gly Asn Val Phe Ser Cys
625                 630                 635                 640

Ser Val Met His Glu Ala Leu His Asn His Tyr Thr Gln Lys Ser Leu
            645                 650                 655

Ser Leu Ser Pro Gly Lys
            660

<210> SEQ ID NO 317
<211> LENGTH: 1971
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 317
atggacatga gggtgcccgc tcagctcctg gggctcctgc tgctgtggct gagaggtgcg      60
cgctgtcagg tgcagttggt ggagtctggg ggaggcgtgg tccagcctgg gaggtccctg     120
agactctcct gtgcagcgtc tagattctcc ttcagtagat atggcatgca ctgggtccgc     180
caggctccag gcaaggggct ggagtgggtg gcagttatat ggtttgatgg aagaaatcaa     240
tactatgcag actccgtgaa gggccgattc accatctcca gagacaattc caagaatacg     300
ctgtttctgc aaatgaacag cctgagagtc gaggacacgg ctgtgtatta ctgtgcgaga     360
gatcacccag tagttggtac gagctttgac tactggggcc agggaaccct ggtcaccgtc     420
tctagtgcct ccaccaaggg cccatcggtc ttccccctgg cacccctcct caagagcacc     480
tctgggggca gcggccct gggctgcctg gtcaaggact acttccccga accggtgacg     540
gtgtcgtgga actcaggcgc cctgaccagc ggcgtgcaca ccttcccggc tgtcctacag     600
tcctcaggac tctactccct cagcagcgtg gtgaccgtgc cctccagcag cttgggcacc     660
cagacctaca tctgcaacgt gaatcacaag cccagcaaca ccaaggtgga caagaaagtt     720
gagcccaaat cttgtgacaa aactcacaca tgcccaccgt gcccagcacc tgaactcctg     780
gggggaccgt cagtcttcct cttccccccca aaacccaagg acaccctcat gatctcccgg     840
acccctgagg tcacatgcgt ggtggtggac gtgagccacg aagaccctga ggtcaagttc     900
aactggtacg tggacggcgt ggaggtgcat aatgccaaga caaagccgcg ggaggagcag     960
taccagagca cgtaccgtgt ggtcagcgtc ctcaccgtcc tgcaccagga ctggctgaat    1020
ggcaaggagt acaagtgcaa ggtctccaac aaagccctcc cagcccccat cgagaaaacc    1080
atctccaaag ccaaagggca gccccgagaa ccacaggtgt acaccctgcc cccatcccgg    1140
gatgagctga ccaagaacca ggtcagcctg acctgcctgg tcaaaggctt ctatcccagc    1200
gacatcgccg tggagtggga gagcaatggg cagccggaga acaactacaa gaccacgcct    1260
cccgtgctgg actccgacgg ctccttcttc ctctatagca agctcaccgt ggacaagagc    1320
aggtggcagc aggggaacgt cttctcatgc tccgtgatgc atgaggctct gcacaaccac    1380
```

```
tacacgcaga agagcctctc cctgtctccg ggtggaggcg gcggttccgg gggcggtgga      1440
tccggtggcg ggggaagcca ccccatccct gactccagtc ctctcctgca attcgggggc      1500
caagtccggc agcggtacct ctacacagat gatgcccagc agacagaagc ccacctggag      1560
atcagggagg atgggacggt gggggggcgct gctgaccaga gccccgaaag tctcctgcag      1620
ctgaaagcct tgaagccggg agttattcaa atcttggag tcaagacatc caggttcctg       1680
tgccagcggc cagatgggc cctgtatgga tcgctccact ttgaccctga ggcctgcagc       1740
ttccgggagc tgcttcttga ggacggatac aatgtttacc agtccgaagc ccacggcctc      1800
ccgctgcacc tgccagggaa caagtcccca caccgggacc ctgcaccccg aggaccagct      1860
cgcttcctgc cactaccagg cctgcccccc gcaccccgg agccaccgg aatcctggcc        1920 ccccagcccc ccgatgtggg ctcctcggac cctctgagca tggtgggatg a               1971
```

<210> SEQ ID NO 318
<211> LENGTH: 656
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 318

```
Met Asp Met Arg Val Pro Ala Gln Leu Leu Gly Leu Leu Leu Leu Trp
1               5                   10                  15

Leu Arg Gly Ala Arg Cys Gln Val Gln Leu Val Glu Ser Gly Gly Gly
            20                  25                  30

Val Val Gln Pro Gly Arg Ser Leu Arg Leu Ser Cys Ala Ala Ser Arg
        35                  40                  45

Phe Ser Phe Ser Arg Tyr Gly Met His Trp Val Arg Gln Ala Pro Gly
    50                  55                  60

Lys Gly Leu Glu Trp Val Ala Val Ile Trp Phe Asp Gly Arg Asn Gln
65                  70                  75                  80

Tyr Tyr Ala Asp Ser Val Lys Gly Arg Phe Thr Ile Ser Arg Asp Asn
                85                  90                  95

Ser Lys Asn Thr Leu Phe Leu Gln Met Asn Ser Leu Arg Val Glu Asp
            100                 105                 110

Thr Ala Val Tyr Tyr Cys Ala Arg Asp His Pro Val Val Gly Thr Ser
        115                 120                 125

Phe Asp Tyr Trp Gly Gln Gly Thr Leu Val Thr Val Ser Ser Ala Ser
    130                 135                 140

Thr Lys Gly Pro Ser Val Phe Pro Leu Ala Pro Ser Ser Lys Ser Thr
145                 150                 155                 160

Ser Gly Gly Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
        195                 200                 205

Ser Val Val Thr Val Pro Ser Ser Ser Leu Gly Thr Gln Thr Tyr Ile
    210                 215                 220

Cys Asn Val Asn His Lys Pro Ser Asn Thr Lys Val Asp Lys Lys Val
225                 230                 235                 240

Glu Pro Lys Ser Cys Asp Lys Thr His Thr Cys Pro Pro Cys Pro Ala
                245                 250                 255
```

```
Pro Glu Leu Leu Gly Gly Pro Ser Val Phe Leu Phe Pro Pro Lys Pro
                260                 265                 270

Lys Asp Thr Leu Met Ile Ser Arg Thr Pro Glu Val Thr Cys Val Val
            275                 280                 285

Val Asp Val Ser His Glu Asp Pro Glu Val Lys Phe Asn Trp Tyr Val
        290                 295                 300

Asp Gly Val Glu Val His Asn Ala Lys Thr Lys Pro Arg Glu Glu Gln
305                 310                 315                 320

Tyr Gln Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Ala
            340                 345                 350

Leu Pro Ala Pro Ile Glu Lys Thr Ile Ser Lys Ala Lys Gly Gln Pro
        355                 360                 365

Arg Glu Pro Gln Val Tyr Thr Leu Pro Pro Ser Arg Asp Glu Leu Thr
370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Pro Pro Val Leu Asp Ser Asp Gly Ser Phe Phe Leu Tyr
            420                 425                 430

Ser Lys Leu Thr Val Asp Lys Ser Arg Trp Gln Gln Gly Asn Val Phe
        435                 440                 445

Ser Cys Ser Val Met His Glu Ala Leu His Asn His Tyr Thr Gln Lys
450                 455                 460

Ser Leu Ser Leu Ser Pro Gly Gly Gly Gly Ser Gly Gly Gly Gly
465                 470                 475                 480

Ser Gly Gly Gly Gly Ser His Pro Ile Pro Asp Ser Ser Pro Leu Leu
                485                 490                 495

Gln Phe Gly Gly Gln Val Arg Gln Arg Tyr Leu Tyr Thr Asp Asp Ala
            500                 505                 510

Gln Gln Thr Glu Ala His Leu Glu Ile Arg Glu Asp Gly Thr Val Gly
        515                 520                 525

Gly Ala Ala Asp Gln Ser Pro Glu Ser Leu Leu Gln Leu Lys Ala Leu
530                 535                 540

Lys Pro Gly Val Ile Gln Ile Leu Gly Val Lys Thr Ser Arg Phe Leu
545                 550                 555                 560

Cys Gln Arg Pro Asp Gly Ala Leu Tyr Gly Ser Leu His Phe Asp Pro
                565                 570                 575

Glu Ala Cys Ser Phe Arg Glu Leu Leu Leu Glu Asp Gly Tyr Asn Val
            580                 585                 590

Tyr Gln Ser Glu Ala His Gly Leu Pro Leu His Leu Pro Gly Asn Lys
        595                 600                 605

Ser Pro His Arg Asp Pro Ala Pro Arg Gly Pro Ala Arg Phe Leu Pro
610                 615                 620

Leu Pro Gly Leu Pro Pro Ala Pro Pro Glu Pro Pro Gly Ile Leu Ala
625                 630                 635                 640

Pro Gln Pro Pro Asp Val Gly Ser Ser Asp Pro Leu Ser Met Val Gly
                645                 650                 655

<210> SEQ ID NO 319
<211> LENGTH: 2034
<212> TYPE: DNA
```

<213> ORGANISM: Artificial Sequence
<220> FEATURE:
<223> OTHER INFORMATION: Description of Artificial Sequence: Synthetic polynucleotide

<400> SEQUENCE: 319

| | | | | | |
|---|---|---|---|---|---|
| atggactcgg | acgagaccgg | gttcgagcac | tcagggctgt | gggtttctgt | gctggctggt | 60 |
| cttctgctgg | agcctgcca | ggcacacccc | atccctgact | ccagtcctct | cctgcaattc | 120 |
| gggggccaag | tccggcagcg | gtacctctac | acagatgatg | cccagcagac | agaagcccac | 180 |
| ctggagatca | gggaggatgg | gacggtgggg | ggcgctgctg | accagagccc | cgaaagtctc | 240 |
| ctgcagctga | aagccttgaa | gccgggagtt | attcaaatct | gggagtcaa | gacatccagg | 300 |
| ttcctgtgcc | agcggccaga | tggggccctg | tatggatcgc | tccactttga | ccctgaggcc | 360 |
| tgcagcttcc | gggagctgct | tcttgaggac | ggatacaatg | tttaccagtc | cgaagcccac | 420 |
| ggcctcccgc | tgcacctgcc | agggaacaag | tccccacacc | gggaccctgc | accccgagga | 480 |
| ccagctcgct | tcctgccact | accaggcctg | cccccgcac | cccgagcc | acccggaatc | 540 |
| ctggcccccc | agcccccga | tgtgggctcc | tcggaccctc | tgagcatggt | gggaggcggc | 600 |
| ggttccgggg | gcggtggatc | tggtggcggg | ggaagcggag | gcggcggttc | cggggcggt | 660 |
| ggatccggtg | gcggggaag | ccaggtgcag | ttggtggagt | ctgggggagg | cgtggtccag | 720 |
| cctgggaggt | ccctgagact | ctcctgtgca | gcgtctagat | tctccttcag | tagatatggc | 780 |
| atgcactggg | tccgccaggc | tccaggcaag | gggctggagt | gggtggcagt | tatatggttt | 840 |
| gatggaagaa | atcaatacta | tgcagactcc | gtgaaggggc | gattcaccat | ctccagagac | 900 |
| aattccaaga | tacgctgtt | tctgcaaatg | aacagcctga | gagtcgagga | cacggctgtg | 960 |
| tattactgtg | cgagagatca | cccagtagtt | ggtacgagct | ttgactactg | gggccaggga | 1020 |
| accctggtca | ccgtctctag | tgcctccacc | aagggcccat | cggtcttccc | cctggcaccc | 1080 |
| tcctccaaga | gcacctctgg | gggcacagcg | gccctgggct | gcctggtcaa | ggactacttc | 1140 |
| cccgaaccgg | tgacggtgtc | gtggaactca | ggcgccctga | ccagcggcgt | gcacaccttc | 1200 |
| ccggctgtcc | tacagtcctc | aggactctac | tccctcagca | gcgtggtgac | cgtgccctcc | 1260 |
| agcagcttgg | gcacccagac | ctacatctgc | aacgtgaatc | acaagcccag | caacaccaag | 1320 |
| gtggacaaga | aagttgagcc | caaatcttgt | gacaaaactc | acacatgccc | accgtgccca | 1380 |
| gcacctgaac | tcctgggggg | accgtcagtc | ttcctcttcc | ccccaaaacc | caaggacacc | 1440 |
| ctcatgatct | cccggacccc | tgaggtcaca | tgcgtggtgg | tggacgtgag | ccacgaagac | 1500 |
| cctgaggtca | agttcaactg | gtacgtggac | ggcgtggagg | tgcataatgc | caagacaaag | 1560 |
| ccgcgggagg | agcagtacca | gagcacgtac | cgtgtggtca | gcgtcctcac | cgtcctgcac | 1620 |
| caggactggc | tgaatggcaa | ggagtacaag | tgcaaggtct | ccaacaaagc | cctcccagcc | 1680 |
| cccatcgaga | aaaccatctc | caaagccaaa | gggcagcccc | gagaaccaca | ggtgtacacc | 1740 |
| ctgccccat | cccgggatga | gctgaccaag | aaccaggtca | gcctgacctg | cctggtcaaa | 1800 |
| ggcttctatc | ccagcgacat | cgccgtggag | tgggagagca | atgggcagcc | ggagaacaac | 1860 |
| tacaagacca | cgcctcccgt | gctggactcc | gacggctcct | tcttcctcta | tagcaagctc | 1920 |
| accgtggaca | agagcaggtg | gcagcagggg | aacgtcttct | catgctccgt | gatgcatgag | 1980 |
| gctctgcaca | accactacac | gcagaagagc | ctctccctgt | ctccgggtaa | atag | 2034 |

<210> SEQ ID NO 320
<211> LENGTH: 677
<212> TYPE: PRT

<213> ORGANISM: Artificial Sequence
<220> FEATURE:
<223> OTHER INFORMATION: Description of Artificial Sequence: Synthetic polypeptide

<400> SEQUENCE: 320

```
Met Asp Ser Asp Glu Thr Gly Phe Glu His Ser Gly Leu Trp Val Ser
1               5                   10                  15

Val Leu Ala Gly Leu Leu Leu Gly Ala Cys Gln Ala His Pro Ile Pro
            20                  25                  30

Asp Ser Ser Pro Leu Leu Gln Phe Gly Gly Gln Val Arg Gln Arg Tyr
        35                  40                  45

Leu Tyr Thr Asp Asp Ala Gln Gln Thr Glu Ala His Leu Glu Ile Arg
50                  55                  60

Glu Asp Gly Thr Val Gly Gly Ala Ala Asp Gln Ser Pro Glu Ser Leu
65                  70                  75                  80

Leu Gln Leu Lys Ala Leu Lys Pro Gly Val Ile Gln Ile Leu Gly Val
                85                  90                  95

Lys Thr Ser Arg Phe Leu Cys Gln Arg Pro Asp Gly Ala Leu Tyr Gly
            100                 105                 110

Ser Leu His Phe Asp Pro Glu Ala Cys Ser Phe Arg Glu Leu Leu Leu
        115                 120                 125

Glu Asp Gly Tyr Asn Val Tyr Gln Ser Glu Ala His Gly Leu Pro Leu
130                 135                 140

His Leu Pro Gly Asn Lys Ser Pro His Arg Asp Pro Ala Pro Arg Gly
145                 150                 155                 160

Pro Ala Arg Phe Leu Pro Leu Pro Gly Leu Pro Pro Ala Pro Pro Glu
                165                 170                 175

Pro Pro Gly Ile Leu Ala Pro Gln Pro Pro Asp Val Gly Ser Ser Asp
            180                 185                 190

Pro Leu Ser Met Val Gly Gly Gly Ser Gly Gly Gly Gly Ser Gly Gly
        195                 200                 205

Gly Gly Gly Ser Gly Gly Gly Gly Ser Gly Gly Gly Gly Ser Gly Gly
        210                 215                 220

Gly Gly Ser Gln Val Gln Leu Val Glu Ser Gly Gly Gly Val Val Gln
225                 230                 235                 240

Pro Gly Arg Ser Leu Arg Leu Ser Cys Ala Ala Ser Arg Phe Ser Phe
                245                 250                 255

Ser Arg Tyr Gly Met His Trp Val Arg Gln Ala Pro Gly Lys Gly Leu
            260                 265                 270

Glu Trp Val Ala Val Ile Trp Phe Asp Gly Arg Asn Gln Tyr Tyr Ala
        275                 280                 285

Asp Ser Val Lys Gly Arg Phe Thr Ile Ser Arg Asp Asn Ser Lys Asn
290                 295                 300

Thr Leu Phe Leu Gln Met Asn Ser Leu Arg Val Glu Asp Thr Ala Val
305                 310                 315                 320

Tyr Tyr Cys Ala Arg Asp His Pro Val Val Gly Thr Ser Phe Asp Tyr
                325                 330                 335

Trp Gly Gln Gly Thr Leu Val Thr Val Ser Ser Ala Ser Thr Lys Gly
            340                 345                 350

Pro Ser Val Phe Pro Leu Ala Pro Ser Ser Lys Ser Thr Ser Gly Gly
        355                 360                 365

Thr Ala Ala Leu Gly Cys Leu Val Lys Asp Tyr Phe Pro Glu Pro Val
370                 375                 380
```

```
Thr Val Ser Trp Asn Ser Gly Ala Leu Thr Ser Gly Val His Thr Phe
385                 390                 395                 400

Pro Ala Val Leu Gln Ser Ser Gly Leu Tyr Ser Leu Ser Ser Val Val
            405                 410                 415

Thr Val Pro Ser Ser Ser Leu Gly Thr Gln Thr Tyr Ile Cys Asn Val
        420                 425                 430

Asn His Lys Pro Ser Asn Thr Lys Val Asp Lys Val Glu Pro Lys
            435                 440                 445

Ser Cys Asp Lys Thr His Thr Cys Pro Pro Cys Ala Pro Glu Leu
    450                 455                 460

Leu Gly Gly Pro Ser Val Phe Leu Phe Pro Pro Lys Pro Lys Asp Thr
465                 470                 475                 480

Leu Met Ile Ser Arg Thr Pro Glu Val Thr Cys Val Val Val Asp Val
                485                 490                 495

Ser His Glu Asp Pro Glu Val Lys Phe Asn Trp Tyr Val Asp Gly Val
            500                 505                 510

Glu Val His Asn Ala Lys Thr Lys Pro Arg Glu Glu Gln Tyr Gln Ser
        515                 520                 525

Thr Tyr Arg Val Val Ser Val Leu Thr Val Leu His Gln Asp Trp Leu
    530                 535                 540

Asn Gly Lys Glu Tyr Lys Cys Lys Val Ser Asn Lys Ala Leu Pro Ala
545                 550                 555                 560

Pro Ile Glu Lys Thr Ile Ser Lys Ala Lys Gly Gln Pro Arg Glu Pro
                565                 570                 575

Gln Val Tyr Thr Leu Pro Pro Ser Arg Asp Glu Leu Thr Lys Asn Gln
            580                 585                 590

Val Ser Leu Thr Cys Leu Val Lys Gly Phe Tyr Pro Ser Asp Ile Ala
        595                 600                 605

Val Glu Trp Glu Ser Asn Gly Gln Pro Glu Asn Asn Tyr Lys Thr Thr
    610                 615                 620

Pro Pro Val Leu Asp Ser Asp Gly Ser Phe Phe Leu Tyr Ser Lys Leu
625                 630                 635                 640

Thr Val Asp Lys Ser Arg Trp Gln Gln Gly Asn Val Phe Ser Cys Ser
                645                 650                 655

Val Met His Glu Ala Leu His Asn His Tyr Thr Gln Lys Ser Leu Ser
            660                 665                 670

Leu Ser Pro Gly Lys
        675

<210> SEQ ID NO 321
<211> LENGTH: 2079
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 321
atggactcgg acgagaccgg gttcgagcac tcagggctgt gggtttctgt gctggctggt      60
cttctgctgg agcctgcca ggcacacccc atccctgact ccagtcctct cctgcaattc     120 ggggccaag tccggcagcg gtacctctac acagatgatg cccagcagac agaagcccac     180
ctggagatca ggaggatgg gacggtgggg ggcgctgctg accagagccc cgaaagtctc     240
ctgcagctga aagccttgaa gccgggagtt attcaaatct ggggagtcaa gacatccagg     300
ttcctgtgcc agcggccaga tgggccctg tatggatcgc tccactttga ccctgaggcc     360
```

```
tgcagcttcc gggagctgct tcttgaggac ggatacaatg tttaccagtc cgaagcccac    420
ggcctcccgc tgcacctgcc agggaacaag tccccacacc gggaccctgc accccgagga    480
ccagctcgct tcctgccact accaggcctg cccccgcac ccccggagcc acccggaatc     540
ctggcccccc agcccccga tgtgggctcc tcggaccctc tgagcatggt gggaggcggc     600
ggttccgggg gcggtggatc tggtggcggg ggaagcggag gcggcggttc gggggcggt     660
ggatctggtg gcggggaag cggaggcggc ggttccgggg gcggtggatc cggtggcggg    720
ggaagccagg tgcagttggt ggagtctggg ggaggcgtgg tccagcctgg gaggtccctg    780
agactctcct gtgcagcgtc tagattctcc ttcagtagat atggcatgca ctgggtccgc    840
caggctccag gcaaggggct ggagtgggtg gcagttatat ggtttgatgg aagaaatcaa    900
tactatgcag actccgtgaa ggggcgattc accatctcca gagacaattc caagaatacg    960
ctgtttctgc aaatgaacag cctgagagtc gaggacacgg ctgtgtatta ctgtgcgaga   1020
gatcacccag tagttggtac gagctttgac tactggggcc agggaaccct ggtcaccgtc   1080
tctagtgcct ccaccaaggg cccatcggtc ttccccctgg cacctcctc caagagcacc    1140
tctgggggca gcggccct gggctgcctg gtcaaggact acttccccga accggtgacg     1200
gtgtcgtgga actcaggcgc cctgaccagc ggcgtgcaca ccttcccggc tgtcctacag   1260
tcctcaggac tctactccct cagcagcgtg gtgaccgtgc cctccagcag cttgggcacc   1320
cagacctaca tctgcaacgt gaatcacaag cccagcaaca ccaaggtgga caagaaagtt   1380
gagcccaaat cttgtgacaa aactcacaca tgcccaccgt gcccagcacc tgaactcctg   1440
gggggaccgt cagtcttcct cttccccca aaacccaagg acaccctcat gatctcccgg    1500
accctgagg tcacatgcgt ggtggtggac gtgagccacg aagaccctga ggtcaagttc     1560
aactggtacg tggacggcgt ggaggtgcat aatgccaaga caaagccgcg ggaggagcag   1620
taccagagca cgtaccgtgt ggtcagcgtc ctcaccgtcc tgcaccagga ctggctgaat   1680
ggcaaggagt acaagtgcaa ggtctccaac aaagccctcc cagcccccat cgagaaaacc   1740
atctccaaag ccaaagggca gccccgagaa ccacaggtgt acaccctgcc cccatcccgg   1800
gatgagctga ccaagaacca ggtcagcctg acctgcctgg tcaaaggctt ctatcccagc   1860
gacatcgccg tggagtggga gagcaatggg cagccggaga acaactacaa gaccacgcct   1920
cccgtgctgg actccgacgg ctccttcttc tctctatagca agctcaccgt ggacaagagc   1980
aggtggcagc aggggaacgt cttctcatgc tccgtgatgc atgaggctct gcacaaccac   2040
tacacgcaga gagcctctc cctgtctccg ggtaaatag                           2079
```

<210> SEQ ID NO 322
<211> LENGTH: 692
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 322

Met Asp Ser Asp Glu Thr Gly Phe Glu His Ser Gly Leu Trp Val Ser
1               5                   10                  15

Val Leu Ala Gly Leu Leu Gly Ala Cys Gln Ala His Pro Ile Pro
            20                  25                  30

Asp Ser Ser Pro Leu Leu Gln Phe Gly Gly Gln Val Arg Gln Arg Tyr
        35                  40                  45

```
Leu Tyr Thr Asp Asp Ala Gln Gln Thr Glu Ala His Leu Glu Ile Arg
    50                  55                  60

Glu Asp Gly Thr Val Gly Gly Ala Ala Asp Gln Ser Pro Glu Ser Leu
65                  70                  75                  80

Leu Gln Leu Lys Ala Leu Lys Pro Gly Val Ile Gln Ile Leu Gly Val
                85                  90                  95

Lys Thr Ser Arg Phe Leu Cys Gln Arg Pro Asp Gly Ala Leu Tyr Gly
            100                 105                 110

Ser Leu His Phe Asp Pro Glu Ala Cys Ser Phe Arg Glu Leu Leu Leu
        115                 120                 125

Glu Asp Gly Tyr Asn Val Tyr Gln Ser Glu Ala His Gly Leu Pro Leu
130                 135                 140

His Leu Pro Gly Asn Lys Ser Pro His Arg Asp Pro Ala Pro Arg Gly
145                 150                 155                 160

Pro Ala Arg Phe Leu Pro Leu Pro Gly Leu Pro Pro Ala Pro Pro Glu
                165                 170                 175

Pro Pro Gly Ile Leu Ala Pro Gln Pro Pro Asp Val Gly Ser Ser Asp
            180                 185                 190

Pro Leu Ser Met Val Gly Gly Gly Ser Gly Gly Gly Gly Ser Gly
            195                 200                 205

Gly Gly Gly Ser Gly Gly Gly Gly Ser Gly Gly Gly Gly Ser Gly Gly
        210                 215                 220

Gly Gly Ser Gly Gly Gly Gly Ser Gly Gly Gly Gly Ser Gly Gly Gly
225                 230                 235                 240

Gly Ser Gln Val Gln Leu Val Glu Ser Gly Gly Val Val Gln Pro
            245                 250                 255

Gly Arg Ser Leu Arg Leu Ser Cys Ala Ala Ser Arg Phe Ser Phe Ser
        260                 265                 270

Arg Tyr Gly Met His Trp Val Arg Gln Ala Pro Gly Lys Gly Leu Glu
            275                 280                 285

Trp Val Ala Val Ile Trp Phe Asp Gly Arg Asn Gln Tyr Tyr Ala Asp
290                 295                 300

Ser Val Lys Gly Arg Phe Thr Ile Ser Arg Asp Asn Ser Lys Asn Thr
305                 310                 315                 320

Leu Phe Leu Gln Met Asn Ser Leu Arg Val Glu Asp Thr Ala Val Tyr
                325                 330                 335

Tyr Cys Ala Arg Asp His Pro Val Val Gly Thr Ser Phe Asp Tyr Trp
            340                 345                 350

Gly Gln Gly Thr Leu Val Thr Val Ser Ser Ala Ser Thr Lys Gly Pro
        355                 360                 365

Ser Val Phe Pro Leu Ala Pro Ser Ser Lys Ser Thr Ser Gly Gly Thr
370                 375                 380

Ala Ala Leu Gly Cys Leu Val Lys Asp Tyr Phe Pro Glu Pro Val Thr
385                 390                 395                 400

Val Ser Trp Asn Ser Gly Ala Leu Thr Ser Gly Val His Thr Phe Pro
                405                 410                 415

Ala Val Leu Gln Ser Ser Gly Leu Tyr Ser Leu Ser Ser Val Val Thr
            420                 425                 430

Val Pro Ser Ser Ser Leu Gly Thr Gln Thr Tyr Ile Cys Asn Val Asn
        435                 440                 445

His Lys Pro Ser Asn Thr Lys Val Asp Lys Lys Val Glu Pro Lys Ser
450                 455                 460

Cys Asp Lys Thr His Thr Cys Pro Pro Cys Pro Ala Pro Glu Leu Leu
```

```
                465                 470                 475                 480
Gly Gly Pro Ser Val Phe Leu Phe Pro Pro Lys Pro Lys Asp Thr Leu
            485                 490                 495

Met Ile Ser Arg Thr Pro Glu Val Thr Cys Val Val Val Asp Val Ser
            500                 505                 510

His Glu Asp Pro Glu Val Lys Phe Asn Trp Tyr Val Asp Gly Val Glu
            515                 520                 525

Val His Asn Ala Lys Thr Lys Pro Arg Glu Glu Gln Tyr Gln Ser Thr
530                 535                 540

Tyr Arg Val Val Ser Val Leu Thr Val Leu His Gln Asp Trp Leu Asn
545                 550                 555                 560

Gly Lys Glu Tyr Lys Cys Lys Val Ser Asn Lys Ala Leu Pro Ala Pro
                565                 570                 575

Ile Glu Lys Thr Ile Ser Lys Ala Lys Gly Gln Pro Arg Glu Pro Gln
            580                 585                 590

Val Tyr Thr Leu Pro Pro Ser Arg Asp Glu Leu Thr Lys Asn Gln Val
            595                 600                 605

Ser Leu Thr Cys Leu Val Lys Gly Phe Tyr Pro Ser Asp Ile Ala Val
            610                 615                 620

Glu Trp Glu Ser Asn Gly Gln Pro Glu Asn Asn Tyr Lys Thr Thr Pro
625                 630                 635                 640

Pro Val Leu Asp Ser Asp Gly Ser Phe Phe Leu Tyr Ser Lys Leu Thr
                645                 650                 655

Val Asp Lys Ser Arg Trp Gln Gln Gly Asn Val Phe Ser Cys Ser Val
            660                 665                 670

Met His Glu Ala Leu His Asn His Tyr Thr Gln Lys Ser Leu Ser Leu
            675                 680                 685

Ser Pro Gly Lys
        690

<210> SEQ ID NO 323
<211> LENGTH: 2124
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 323
atggactcgg acgagaccgg gttcgagcac tcagggctgt gggtttctgt gctggctggt      60
cttctgctgg agcctgcca ggcacacccc atccctgact ccagtcctct cctgcaattc     120
gggggccaag tccggcagcg gtacctctac acagatgatg cccagcagac agaagcccac     180
ctggagatca ggaggatgg gacggtgggg ggcgctgctg accagagccc cgaaagtctc     240
ctgcagctga aagccttgaa gccgggagtt attcaaatct gggagtcaa gacatccagg     300 ttcctgtgcc agcggccaga tggggccctg tatggatcgc tccactttga ccctgaggcc     360
tgcagcttcc gggagctgct tcttgaggac ggatacaatg tttaccagtc gaagcccac     420 ggcctcccgc tgcacctgcc agggaacaag tccccacacc gggaccctgc accccgagga     480
ccagctcgct tcctgccact accaggcctg ccccccgcac cccggagcc acccggaatc     540 ctggccccc agccccccga tgtgggctcc tcggaccctc tgagcatggt gggaggcggc     600
ggttccgggg gcgtggatc tggtggcggg gaagcggag gcggcggttc gggggcggt     660 ggatctggtg gcggggaag cggaggcggc ggttccgggg gcgtggatc tggtggcggg     720
```

```
ggaagcggag gcggcggttc cggggggcggt ggatccggtg gcgggggaag ccaggtgcag   780
ttggtggagt ctgggggagg cgtggtccag cctgggaggt ccctgagact ctcctgtgca   840
gcgtctagat tctccttcag tagatatggc atgcactggg tccgccaggc tccaggcaag   900
gggctggagt gggtggcagt tatatggttt gatggaagaa atcaatacta tgcagactcc   960 gtgaagggc gattcaccat ctccagagac aattccaaga atacgctgtt tctgcaaatg   1020
aacagcctga gagtcgagga cacggctgtg tattactgtg cgagagatca cccagtagtt   1080
ggtacgagct ttgactactg gggccaggga accctggtca ccgtctctag tgcctccacc   1140
aagggcccat cggtcttccc cctggcaccc tcctccaaga gcacctctgg ggcacagcg   1200 gccctgggct gcctggtcaa ggactacttc cccgaaccgg tgacggtgtc gtggaactca   1260
ggcgccctga ccagcggcgt gcacaccttc ccggctgtcc tacagtcctc aggactctac   1320
tccctcagca gcgtggtgac cgtgccctcc agcagcttgg gcacccagac ctacatctgc   1380
aacgtgaatc acaagcccag caacaccaag gtggacaaga agttgagcc caaatcttgt   1440 gacaaaactc acacatgccc accgtgccca gcacctgaac tcctgggggg accgtcagtc   1500
ttcctcttcc ccccaaaacc caaggacacc ctcatgatct cccggacccc tgaggtcaca   1560
tgcgtggtgg tggacgtgag ccacgaagac cctgaggtca agttcaactg gtacgtggac   1620
ggcgtggagg tgcataatgc caagacaaag ccgcgggagg agcagtacca gagcacgtac   1680
cgtgtggtca gcgtcctcac cgtcctgcac caggactggc tgaatggcaa ggagtacaag   1740
tgcaaggtct ccaacaaagc cctcccagcc cccatcgaga aaaccatctc caaagccaaa   1800
gggcagcccc gagaaccaca ggtgtacacc ctgcccccat cccgggatga gctgaccaag   1860
aaccaggtca gcctgacctg cctggtcaaa ggcttctatc ccagcgacat cgccgtggag   1920
tgggagagca atgggcagcc ggagaacaac tacaagacca cgcctcccgt gctggactcc   1980
gacggctcct tcttcctcta tagcaagctc accgtggaca agagcaggtg gcagcagggg   2040
aacgtcttct catgctccgt gatgcatgag gctctgcaca accactacac gcagaagagc   2100
ctctccctgt ctccgggtaa atag                                         2124
```

<210> SEQ ID NO 324
<211> LENGTH: 707
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 324

```
Met Asp Ser Asp Glu Thr Gly Phe Glu His Ser Gly Leu Trp Val Ser
1               5                   10                  15

Val Leu Ala Gly Leu Leu Gly Ala Cys Gln Ala His Pro Ile Pro
            20                  25                  30

Asp Ser Ser Pro Leu Leu Gln Phe Gly Gly Gln Val Arg Gln Arg Tyr
        35                  40                  45

Leu Tyr Thr Asp Asp Ala Gln Gln Thr Glu Ala His Leu Glu Ile Arg
    50                  55                  60

Glu Asp Gly Thr Val Gly Gly Ala Ala Asp Gln Ser Pro Glu Ser Leu
65                  70                  75                  80

Leu Gln Leu Lys Ala Leu Lys Pro Gly Val Ile Gln Ile Leu Gly Val
                85                  90                  95

Lys Thr Ser Arg Phe Leu Cys Gln Arg Pro Asp Gly Ala Leu Tyr Gly
            100                 105                 110
```

```
Ser Leu His Phe Asp Pro Glu Ala Cys Ser Phe Arg Glu Leu Leu Leu
            115                 120                 125

Glu Asp Gly Tyr Asn Val Tyr Gln Ser Glu Ala His Gly Leu Pro Leu
    130                 135                 140

His Leu Pro Gly Asn Lys Ser Pro His Arg Asp Pro Ala Pro Arg Gly
145                 150                 155                 160

Pro Ala Arg Phe Leu Pro Leu Pro Gly Leu Pro Pro Ala Pro Pro Glu
                165                 170                 175

Pro Pro Gly Ile Leu Ala Pro Gln Pro Pro Asp Val Gly Ser Ser Asp
                180                 185                 190

Pro Leu Ser Met Val Gly Gly Gly Ser Gly Gly Gly Gly Ser Gly Gly
            195                 200                 205

Gly Gly Gly Ser Gly Gly Gly Gly Ser Gly Gly Gly Ser Gly Gly Gly
            210                 215                 220

Gly Gly Ser Gly Gly Gly Ser Gly Gly Gly Ser Gly Gly Gly Gly Gly
225                 230                 235                 240

Gly Ser Gly Gly Gly Gly Ser Gly Gly Gly Ser Gly Gly Gly Gly Gly
                245                 250                 255

Ser Gln Val Gln Leu Val Glu Ser Gly Gly Gly Val Val Gln Pro Gly
            260                 265                 270

Arg Ser Leu Arg Leu Ser Cys Ala Ala Ser Arg Phe Ser Phe Ser Arg
    275                 280                 285

Tyr Gly Met His Trp Val Arg Gln Ala Pro Gly Lys Gly Leu Glu Trp
    290                 295                 300

Val Ala Val Ile Trp Phe Asp Gly Arg Asn Gln Tyr Tyr Ala Asp Ser
305                 310                 315                 320

Val Lys Gly Arg Phe Thr Ile Ser Arg Asp Asn Ser Lys Asn Thr Leu
                325                 330                 335

Phe Leu Gln Met Asn Ser Leu Arg Val Glu Asp Thr Ala Val Tyr Tyr
                340                 345                 350

Cys Ala Arg Asp His Pro Val Val Gly Thr Ser Phe Asp Tyr Trp Gly
            355                 360                 365

Gln Gly Thr Leu Val Thr Val Ser Ser Ala Ser Thr Lys Gly Pro Ser
    370                 375                 380

Val Phe Pro Leu Ala Pro Ser Ser Lys Ser Thr Ser Gly Gly Thr Ala
385                 390                 395                 400

Ala Leu Gly Cys Leu Val Lys Asp Tyr Phe Pro Glu Pro Val Thr Val
                405                 410                 415

Ser Trp Asn Ser Gly Ala Leu Thr Ser Gly Val His Thr Phe Pro Ala
                420                 425                 430

Val Leu Gln Ser Ser Gly Leu Tyr Ser Leu Ser Ser Val Val Thr Val
            435                 440                 445

Pro Ser Ser Ser Leu Gly Thr Gln Thr Tyr Ile Cys Asn Val Asn His
    450                 455                 460

Lys Pro Ser Asn Thr Lys Val Asp Lys Lys Val Glu Pro Lys Ser Cys
465                 470                 475                 480

Asp Lys Thr His Thr Cys Pro Pro Cys Pro Ala Pro Glu Leu Leu Gly
                485                 490                 495

Gly Pro Ser Val Phe Leu Phe Pro Pro Lys Pro Lys Asp Thr Leu Met
                500                 505                 510

Ile Ser Arg Thr Pro Glu Val Thr Cys Val Val Val Asp Val Ser His
            515                 520                 525
```

| | | | | | | | | | | | | |
|---|---|---|---|---|---|---|---|---|---|---|---|---|
|Glu|Asp|Pro|Glu|Val|Lys|Phe|Asn|Trp|Tyr|Val|Asp|Gly|Val|Glu|Val|
| |530| | | |535| | | |540| | | | | | |

His Asn Ala Lys Thr Lys Pro Arg Glu Glu Gln Tyr Gln Ser Thr Tyr
545                 550                 555                 560

Arg Val Val Ser Val Leu Thr Val Leu His Gln Asp Trp Leu Asn Gly
                565                 570                 575

Lys Glu Tyr Lys Cys Lys Val Ser Asn Lys Ala Leu Pro Ala Pro Ile
            580                 585                 590

Glu Lys Thr Ile Ser Lys Ala Lys Gly Gln Pro Arg Glu Pro Gln Val
        595                 600                 605

Tyr Thr Leu Pro Pro Ser Arg Asp Glu Leu Thr Lys Asn Gln Val Ser
610                 615                 620

Leu Thr Cys Leu Val Lys Gly Phe Tyr Pro Ser Asp Ile Ala Val Glu
625                 630                 635                 640

Trp Glu Ser Asn Gly Gln Pro Glu Asn Asn Tyr Lys Thr Thr Pro Pro
                645                 650                 655

Val Leu Asp Ser Asp Gly Ser Phe Phe Leu Tyr Ser Lys Leu Thr Val
            660                 665                 670

Asp Lys Ser Arg Trp Gln Gln Gly Asn Val Phe Ser Cys Ser Val Met
        675                 680                 685

His Glu Ala Leu His Asn His Tyr Thr Gln Lys Ser Leu Ser Leu Ser
690                 695                 700

Pro Gly Lys
705

<210> SEQ ID NO 325
<211> LENGTH: 2169
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 325

```
atggactcgg acgagaccgg gttcgagcac tcagggctgt gggtttctgt gctggctggt      60
cttctgctgg agcctgcca ggcacacccc atccctgact ccagtcctct cctgcaattc     120
gggggccaag tccggcagcg gtacctctac acagatgatg cccagcagac agaagcccac     180
ctggagatca ggaggatgg gacggtgggg gcgctgctg accagagccc cgaaagtctc      240
ctgcagctga agccttgaa gccgggagtt attcaaatct tgggagtcaa gacatccagg     300
ttcctgtgcc agcggccaga tggggccctg tatggatcgc tccactttga ccctgaggcc     360
tgcagcttcc gggagctgct tcttgaggac ggatacaatg tttaccagtc gaagcccac      420 ggcctcccgc tgcacctgcc agggaacaag tccccacacc gggaccctgc accccgagga     480
ccagctcgct tcctgccact accaggcctg ccccccgcac cccggagcc acccggaatc      540 ctggccccc agcccccga tgtgggctcc tcggaccctc tgagcatggt gggaggcggc      600
ggttccgggg gcggtggatc tggtggcggg ggaagcggag gcggcggttc cggggcggt      660 ggatctggtg gcggggaag cggaggcggc ggttccgggg gcggtggatc tggtggcggg     720
ggaagcggag gcggcggttc cggggcggt ggatctggtg gcggggaag cggaggcggc      780 ggttccgggg gcggtggatc cggtggcggg ggaagccagg tgcagttggt ggagtctggg     840
ggaggcgtgg tccagcctgg gaggtccctg agactctcct gtgcagcgtc tagattctcc     900
ttcagtagat atggcatgca ctgggtccgc caggctccag gcaaggggct ggagtgggtg     960
```

```
gcagttatat ggtttgatgg aagaaatcaa tactatgcag actccgtgaa ggggcgattc    1020
accatctcca gagacaattc caagaatacg ctgtttctgc aaatgaacag cctgagagtc    1080
gaggacacgg ctgtgtatta ctgtgcgaga gatcacccag tagttggtac gagctttgac    1140
tactggggcc agggaaccct ggtcaccgtc tctagtgcct ccaccaaggg cccatcggtc    1200
ttccccctgg cacctcctc caagagcacc tctgggggca cagcggccct gggctgcctg    1260
gtcaaggact acttccccga accggtgacg gtgtcgtgga actcaggcgc cctgaccagc    1320
ggcgtgcaca ccttcccggc tgtcctacag tcctcaggac tctactccct cagcagcgtg    1380
gtgaccgtgc cctccagcag cttgggcacc cagacctaca tctgcaacgt gaatcacaag    1440
cccagcaaca ccaaggtgga caagaaagtt gagcccaaat cttgtgacaa aactcacaca    1500
tgcccaccgt gcccagcacc tgaactcctg gggggaccgt cagtcttcct cttccccca    1560 aaacccaagg acaccctcat gatctcccgg acccctgagg tcacatgcgt ggtggtggac    1620
gtgagccacg aagaccctga ggtcaagttc aactggtacg tggacggcgt ggaggtgcat    1680
aatgccaaga caaagccgcg ggaggagcag taccagagca cgtaccgtgt ggtcagcgtc    1740
ctcaccgtcc tgcaccagga ctggctgaat ggcaaggagt acaagtgcaa ggtctccaac    1800
aaagccctcc cagcccccat cgagaaaacc atctccaaag ccaagggca gccccgagaa    1860 ccacaggtgt acaccctgcc cccatcccgg gatgagctga ccaagaacca ggtcagcctg    1920
acctgcctgg tcaaaggctt ctatcccagc gacatcgccg tggagtggga gagcaatggg    1980
cagccggaga caactacaa gaccacgcct cccgtgctgg actccgacgg ctccttcttc    2040
ctctatagca agctcaccgt ggacaagagc aggtggcagc aggggaacgt cttctcatgc    2100
tccgtgatgc atgaggctct gcacaaccac tacacgcaga agagcctctc cctgtctccg    2160
ggtaaatag                                                             2169
```

<210> SEQ ID NO 326
<211> LENGTH: 722
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 326

Met Asp Ser Asp Glu Thr Gly Phe Glu His Ser Gly Leu Trp Val Ser
1               5                   10                  15

Val Leu Ala Gly Leu Leu Leu Gly Ala Cys Gln Ala His Pro Ile Pro
            20                  25                  30

Asp Ser Ser Pro Leu Leu Gln Phe Gly Gly Gln Val Arg Gln Arg Tyr
        35                  40                  45

Leu Tyr Thr Asp Asp Ala Gln Gln Thr Glu Ala His Leu Glu Ile Arg
    50                  55                  60

Glu Asp Gly Thr Val Gly Gly Ala Ala Asp Gln Ser Pro Glu Ser Leu
65                  70                  75                  80

Leu Gln Leu Lys Ala Leu Lys Pro Gly Val Ile Gln Ile Leu Gly Val
                85                  90                  95

Lys Thr Ser Arg Phe Leu Cys Gln Arg Pro Asp Gly Ala Leu Tyr Gly
            100                 105                 110

Ser Leu His Phe Asp Pro Glu Ala Cys Ser Phe Arg Glu Leu Leu Leu
        115                 120                 125

Glu Asp Gly Tyr Asn Val Tyr Gln Ser Glu Ala His Gly Leu Pro Leu
    130                 135                 140

```
His Leu Pro Gly Asn Lys Ser Pro His Arg Asp Pro Ala Pro Arg Gly
145                 150                 155                 160

Pro Ala Arg Phe Leu Pro Leu Pro Gly Leu Pro Ala Pro Pro Glu
            165                 170                 175

Pro Pro Gly Ile Leu Ala Pro Gln Pro Pro Asp Val Gly Ser Ser Asp
                180                 185                 190

Pro Leu Ser Met Val Gly Gly Gly Ser Gly Gly Gly Ser Gly
            195                 200                 205

Gly Gly Gly Ser Gly Gly Gly Ser Gly Gly Gly Ser Gly Gly
        210              215              220

Gly Gly Ser Gly Gly Gly Ser Gly Gly Gly Ser Gly Gly Gly
225             230              235                  240

Gly Ser Gly Gly Gly Ser Gly Gly Gly Ser Gly Gly Gly Gly
            245              250              255

Ser Gly Gly Gly Ser Gly Gly Gly Ser Gly Gly Gly Ser
        260              265              270

Gln Val Gln Leu Val Glu Ser Gly Gly Val Val Gln Pro Gly Arg
    275                 280                 285

Ser Leu Arg Leu Ser Cys Ala Ala Ser Arg Phe Ser Phe Ser Arg Tyr
    290                 295                 300

Gly Met His Trp Val Arg Gln Ala Pro Gly Lys Gly Leu Glu Trp Val
305                 310                 315                 320

Ala Val Ile Trp Phe Asp Gly Arg Asn Gln Tyr Tyr Ala Asp Ser Val
                325                 330                 335

Lys Gly Arg Phe Thr Ile Ser Arg Asp Asn Ser Lys Asn Thr Leu Phe
            340                 345                 350

Leu Gln Met Asn Ser Leu Arg Val Glu Asp Thr Ala Val Tyr Tyr Cys
        355                 360                 365

Ala Arg Asp His Pro Val Val Gly Thr Ser Phe Asp Tyr Trp Gly Gln
    370                 375                 380

Gly Thr Leu Val Thr Val Ser Ser Ala Ser Thr Lys Gly Pro Ser Val
385                 390                 395                 400

Phe Pro Leu Ala Pro Ser Ser Lys Ser Thr Ser Gly Gly Thr Ala Ala
                405                 410                 415

Leu Gly Cys Leu Val Lys Asp Tyr Phe Pro Glu Pro Val Thr Val Ser
            420                 425                 430

Trp Asn Ser Gly Ala Leu Thr Ser Gly Val His Thr Phe Pro Ala Val
        435                 440                 445

Leu Gln Ser Ser Gly Leu Tyr Ser Leu Ser Ser Val Val Thr Val Pro
    450                 455                 460

Ser Ser Ser Leu Gly Thr Gln Thr Tyr Ile Cys Asn Val Asn His Lys
465                 470                 475                 480

Pro Ser Asn Thr Lys Val Asp Lys Lys Val Glu Pro Lys Ser Cys Asp
                485                 490                 495

Lys Thr His Thr Cys Pro Pro Cys Pro Ala Pro Glu Leu Leu Gly Gly
            500                 505                 510

Pro Ser Val Phe Leu Phe Pro Pro Lys Pro Lys Asp Thr Leu Met Ile
        515                 520                 525

Ser Arg Thr Pro Glu Val Thr Cys Val Val Val Asp Val Ser His Glu
    530                 535                 540

Asp Pro Glu Val Lys Phe Asn Trp Tyr Val Asp Gly Val Glu Val His
545                 550                 555                 560
```

Asn Ala Lys Thr Lys Pro Arg Glu Glu Gln Tyr Gln Ser Thr Tyr Arg
            565                 570                 575

Val Val Ser Val Leu Thr Val Leu His Gln Asp Trp Leu Asn Gly Lys
        580                 585                 590

Glu Tyr Lys Cys Lys Val Ser Asn Lys Ala Leu Pro Ala Pro Ile Glu
        595                 600                 605

Lys Thr Ile Ser Lys Ala Lys Gly Gln Pro Arg Glu Pro Gln Val Tyr
        610                 615                 620

Thr Leu Pro Pro Ser Arg Asp Glu Leu Thr Lys Asn Gln Val Ser Leu
625                 630                 635                 640

Thr Cys Leu Val Lys Gly Phe Tyr Pro Ser Asp Ile Ala Val Glu Trp
            645                 650                 655

Glu Ser Asn Gly Gln Pro Glu Asn Asn Tyr Lys Thr Thr Pro Pro Val
            660                 665                 670

Leu Asp Ser Asp Gly Ser Phe Phe Leu Tyr Ser Lys Leu Thr Val Asp
        675                 680                 685

Lys Ser Arg Trp Gln Gln Gly Asn Val Phe Ser Cys Ser Val Met His
        690                 695                 700

Glu Ala Leu His Asn His Tyr Thr Gln Lys Ser Leu Ser Leu Ser Pro
705                 710                 715                 720

Gly Lys

<210> SEQ ID NO 327
<211> LENGTH: 2016
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 327
atggacatga gggtgcccgc tcagctcctg gggctcctgc tgctgtggct gagaggtgcg      60
cgctgtcagg tgcagttggt ggagtctggg ggaggcgtgg tccagcctgg gaggtccctg     120
agactctcct gtgcagcgtc tagattctcc ttcagtagat atggcatgca ctgggtccgc     180
caggctccag gcaaggggct ggagtgggtg gcagttatat ggtttgatgg aagaaatcaa     240
tactatgcag actccgtgaa ggggcgattc accatctcca gagacaattc caagaatacg     300
ctgtttctgc aaatgaacag cctgagagtc gaggacacgg ctgtgtatta ctgtgcgaga     360
gatcacccag tagttggtac gagctttgac tactggggcc agggaaccct ggtcaccgtc     420
tctagtgcct ccaccaaggg cccatcggtc ttccccctgg caccctcctc caagagcacc     480
tctgggggca gcgcggccct gggctgcctg gtcaaggact acttccccga accggtgacg     540
gtgtcgtgga actcaggcgc cctgaccagc ggcgtgcaca ccttcccggc tgtcctacag     600
tcctcaggac tctactcccc cagcagcgtg gtgaccgtgc cctccagcag cttgggcacc     660
cagacctaca tctgcaacgt gaatcacaag cccagcaaca ccaaggtgga caagaaagtt     720
gagcccaaat cttgtgacaa aactcacaca tgcccaccgt gcccagcacc tgaactcctg     780
gggggaccgt cagtcttcct cttcccccca aaacccaagg acaccctcat gatctcccgg     840
acccctgagg tcacatgcgt ggtggtggac gtgagccacg aagaccctga ggtcaagttc     900
aactggtacg tggacggcgt ggaggtgcat aatgccaaga caaagccgcg ggaggagcag     960
taccagagca cgtaccgtgt ggtcagcgtc ctcaccgtcc tgcaccagga ctggctgaat    1020
ggcaaggagt acaagtgcaa ggtctccaac aaagccctcc cagcccccat cgagaaaacc    1080

-continued

```
atctccaaag ccaaagggca gccccgagaa ccacaggtgt acaccctgcc ccatcccgg     1140 gatgagctga ccaagaacca ggtcagcctg acctgcctgg tcaaaggctt ctatcccagc    1200
gacatcgccg tggagtggga gagcaatggg cagccggaga caactacaa gaccacgcct     1260 cccgtgctgg actccgacgg ctccttcttc ctctatagca agctcaccgt ggacaagagc    1320
aggtggcagc aggggaacgt cttctcatgc tccgtgatgc atgaggctct gcacaaccac    1380
tacacgcaga gagcctctc cctgtctccg ggtggaggcg gcggttccgg gggcggtgga     1440
tctggtggcg ggggaagcgg aggcggcggt tccggggggcg gtggatccgg tggcgggggga  1500 agccacccca tccctgactc cagtcctctc ctgcaattcg ggggccaagt ccggcagcgg    1560
tacctctaca cagatgatgc ccagcagaca gaagcccacc tggagatcag ggaggatggg    1620
acggtggggg gcgctgctga ccagagcccc gaaagtctcc tgcagctgaa agccttgaag    1680
ccgggagtta ttcaaatctt gggagtcaag acatccaggt tcctgtgcca gcggccagat    1740 ggggcccctgt atggatcgct ccactttgac cctgaggcct gcagcttccg ggagctgctt    1800
cttgaggacg gatacaatgt ttaccagtcc gaagcccacg gcctcccgct gcacctgcca    1860
gggaacaagt ccccacaccg ggaccctgca ccccgaggac cagctcgctt cctgccacta    1920
ccaggcctgc ccccgcacc cccggagcca cccggaatcc tggcccccca gcccccgat     1980 gtgggctcct cggaccctct gagcatggtg ggatga                             2016
```

<210> SEQ ID NO 328
<211> LENGTH: 671
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 328

```
Met Asp Met Arg Val Pro Ala Gln Leu Leu Gly Leu Leu Leu Leu Trp
1               5                   10                  15

Leu Arg Gly Ala Arg Cys Gln Val Gln Leu Val Glu Ser Gly Gly Gly
            20                  25                  30

Val Val Gln Pro Gly Arg Ser Leu Arg Leu Ser Cys Ala Ala Ser Arg
        35                  40                  45

Phe Ser Phe Ser Arg Tyr Gly Met His Trp Val Arg Gln Ala Pro Gly
    50                  55                  60

Lys Gly Leu Glu Trp Val Ala Val Ile Trp Phe Asp Gly Arg Asn Gln
65                  70                  75                  80

Tyr Tyr Ala Asp Ser Val Lys Gly Arg Phe Thr Ile Ser Arg Asp Asn
                85                  90                  95

Ser Lys Asn Thr Leu Phe Leu Gln Met Asn Ser Leu Arg Val Glu Asp
            100                 105                 110

Thr Ala Val Tyr Tyr Cys Ala Arg Asp His Pro Val Val Gly Thr Ser
        115                 120                 125

Phe Asp Tyr Trp Gly Gln Gly Thr Leu Val Thr Val Ser Ser Ala Ser
    130                 135                 140

Thr Lys Gly Pro Ser Val Phe Pro Leu Ala Pro Ser Ser Lys Ser Thr
145                 150                 155                 160

Ser Gly Gly Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190
```

-continued

```
His Thr Phe Pro Ala Val Leu Gln Ser Ser Gly Leu Tyr Ser Leu Ser
            195                 200                 205

Ser Val Val Thr Val Pro Ser Ser Leu Gly Thr Gln Thr Tyr Ile
    210                 215                 220

Cys Asn Val Asn His Lys Pro Ser Asn Thr Lys Val Asp Lys Lys Val
225                 230                 235                 240

Glu Pro Lys Ser Cys Asp Lys Thr His Thr Cys Pro Pro Cys Pro Ala
                245                 250                 255

Pro Glu Leu Leu Gly Gly Pro Ser Val Phe Leu Phe Pro Pro Lys Pro
            260                 265                 270

Lys Asp Thr Leu Met Ile Ser Arg Thr Pro Glu Val Thr Cys Val Val
            275                 280                 285

Val Asp Val Ser His Glu Asp Pro Glu Val Lys Phe Asn Trp Tyr Val
    290                 295                 300

Asp Gly Val Glu Val His Asn Ala Lys Thr Lys Pro Arg Glu Glu Gln
305                 310                 315                 320

Tyr Gln Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Ala
            340                 345                 350

Leu Pro Ala Pro Ile Glu Lys Thr Ile Ser Lys Ala Lys Gly Gln Pro
            355                 360                 365

Arg Glu Pro Gln Val Tyr Thr Leu Pro Pro Ser Arg Asp Glu Leu Thr
            370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Pro Pro Val Leu Asp Ser Asp Gly Ser Phe Phe Leu Tyr
            420                 425                 430

Ser Lys Leu Thr Val Asp Lys Ser Arg Trp Gln Gln Gly Asn Val Phe
            435                 440                 445

Ser Cys Ser Val Met His Glu Ala Leu His Asn His Tyr Thr Gln Lys
450                 455                 460

Ser Leu Ser Leu Ser Pro Gly Gly Gly Gly Ser Gly Gly Gly Gly
465                 470                 475                 480

Ser Gly Gly Gly Gly Ser Gly Gly Gly Gly Ser Gly Gly Gly Gly Ser
                485                 490                 495

Gly Gly Gly Gly Ser His Pro Ile Pro Asp Ser Ser Pro Leu Leu Gln
            500                 505                 510

Phe Gly Gly Gln Val Arg Gln Arg Tyr Leu Tyr Thr Asp Asp Ala Gln
            515                 520                 525

Gln Thr Glu Ala His Leu Glu Ile Arg Glu Asp Gly Thr Val Gly Gly
            530                 535                 540

Ala Ala Asp Gln Ser Pro Glu Ser Leu Leu Gln Leu Lys Ala Leu Lys
545                 550                 555                 560

Pro Gly Val Ile Gln Ile Leu Gly Val Lys Thr Ser Arg Phe Leu Cys
                565                 570                 575

Gln Arg Pro Asp Gly Ala Leu Tyr Gly Ser Leu His Phe Asp Pro Glu
                580                 585                 590

Ala Cys Ser Phe Arg Glu Leu Leu Leu Glu Asp Gly Tyr Asn Val Tyr
            595                 600                 605

Gln Ser Glu Ala His Gly Leu Pro Leu His Leu Pro Gly Asn Lys Ser
```

Pro His Arg Asp Pro Ala Pro Arg Gly Pro Ala Arg Phe Leu Pro Leu
625                 630                 635                 640

Pro Gly Leu Pro Pro Ala Pro Pro Glu Pro Pro Gly Ile Leu Ala Pro
            645                 650                 655

Gln Pro Pro Asp Val Gly Ser Ser Asp Pro Leu Ser Met Val Gly
        660                 665                 670

<210> SEQ ID NO 329
<211> LENGTH: 2061
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 329

| | |
|---|---|
| atggacatga gggtgcccgc tcagctcctg gggctcctgc tgctgtggct gagaggtgcg | 60 |
| cgctgtcagg tgcagttggt ggagtctggg ggaggcgtgg tccagcctgg gaggtccctg | 120 |
| agactctcct gtgcagcgtc tagattctcc ttcagtagat atggcatgca ctgggtccgc | 180 |
| caggctccag gcaaggggct ggagtgggtg gcagttatat ggtttgatgg aagaaatcaa | 240 |
| tactatgcag actccgtgaa ggggcgattc accatctcca gagacaattc caagaatacg | 300 |
| ctgtttctgc aaatgaacag cctgagagtc gaggacacgg ctgtgtatta ctgtgcgaga | 360 |
| gatcacccag tagttggtac gagctttgac tactggggcc agggaaccct ggtcaccgtc | 420 |
| tctagtgcct ccaccaaggg cccatcggtc ttccccctgg cacccctctc caagagcacc | 480 |
| tctgggggca cagcggccct gggctgcctg gtcaaggact acttccccga accggtgacg | 540 |
| gtgtcgtgga actcaggcgc cctgaccagc ggcgtgcaca ccttcccggc tgtcctacag | 600 |
| tcctcaggac tctactccct cagcagcgtg gtgaccgtgc cctccagcag cttgggcacc | 660 |
| cagacctaca tctgcaacgt gaatcacaag cccagcaaca ccaaggtgga caagaaagtt | 720 |
| gagcccaaat cttgtgacaa aactcacaca tgcccaccgt gcccagcacc tgaactcctg | 780 |
| gggggaccgt cagtcttcct cttcccccca aaacccaagg acaccctcat gatctcccgg | 840 |
| acccctgagg tcacatgcgt ggtggtggac gtgagccacg aagaccctga ggtcaagttc | 900 |
| aactggtacg tggacggcgt ggaggtgcat aatgccaaga caaagccgcg ggaggagcag | 960 |
| taccagagca cgtaccgtgt ggtcagcgtc ctcaccgtcc tgcaccagga ctggctgaat | 1020 |
| ggcaaggagt acaagtgcaa ggtctccaac aaagccctcc cagcccccat cgagaaaacc | 1080 |
| atctccaaag ccaaagggca gccccgagaa ccacaggtgt acaccctgcc cccatcccgg | 1140 |
| gatgagctga ccaagaacca ggtcagcctg acctgcctgg tcaaaggctt ctatcccagc | 1200 |
| gacatcgccg tggagtggga gagcaatggg cagccggaga caactacaa gaccacgcct | 1260 |
| cccgtgctgg actccgacgg ctccttcttc ctctatagca agctcaccgt ggacaagagc | 1320 |
| aggtggcagc aggggaacgt cttctcatgc tccgtgatgc atgaggctct gcacaaccac | 1380 |
| tacacgcaga agagcctctc cctgtctccg ggtgaggcg gcggttccgg ggcggtgga | 1440 |
| tctggtggcg gggaagcgg aggcggcggt tccggggggcg gtggatctgg tggcggggga | 1500 |
| agcggaggcg gcggttccgg gggcggtgga tccggtggcg gggaagcca cccatccct | 1560 |
| gactccagtc ctctcctgca attcggggc caagtccggc agcggtacct ctacacagat | 1620 |
| gatgcccagc agacagaagc ccacctggag atcaggagg atgggacggt gggggcgct | 1680 |
| gctgaccaga gccccgaaag tctcctgcag ctgaaagcct tgaagccggg agttattcaa | 1740 |

-continued

```
atcttgggag tcaagacatc caggttcctg tgccagcggc cagatggggc cctgtatgga    1800
tcgctccact ttgaccctga ggcctgcagc ttccggagc tgcttcttga ggacggatac    1860
aatgtttacc agtccgaagc ccacggcctc ccgctgcacc tgccagggaa caagtcccca    1920
caccgggacc ctgcaccccg aggaccagct cgcttcctgc cactaccagg cctgccccca    1980 gcaccccgg agccacccgg aatcctggcc ccccagcccc ccgatgtggg ctcctcggac    2040
cctctgagca tggtgggatg a                                             2061
```

<210> SEQ ID NO 330
<211> LENGTH: 686
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 330

```
Met Asp Met Arg Val Pro Ala Gln Leu Leu Gly Leu Leu Leu Leu Trp
1               5                   10                  15

Leu Arg Gly Ala Arg Cys Gln Val Gln Leu Val Glu Ser Gly Gly Gly
            20                  25                  30

Val Val Gln Pro Gly Arg Ser Leu Arg Leu Ser Cys Ala Ala Ser Arg
        35                  40                  45

Phe Ser Phe Ser Arg Tyr Gly Met His Trp Val Arg Gln Ala Pro Gly
    50                  55                  60

Lys Gly Leu Glu Trp Val Ala Val Ile Trp Phe Asp Gly Arg Asn Gln
65                  70                  75                  80

Tyr Tyr Ala Asp Ser Val Lys Gly Arg Phe Thr Ile Ser Arg Asp Asn
                85                  90                  95

Ser Lys Asn Thr Leu Phe Leu Gln Met Asn Ser Leu Arg Val Glu Asp
            100                 105                 110

Thr Ala Val Tyr Tyr Cys Ala Arg Asp His Pro Val Val Gly Thr Ser
        115                 120                 125

Phe Asp Tyr Trp Gly Gln Gly Thr Leu Val Thr Val Ser Ser Ala Ser
    130                 135                 140

Thr Lys Gly Pro Ser Val Phe Pro Leu Ala Pro Ser Ser Lys Ser Thr
145                 150                 155                 160

Ser Gly Gly Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
        195                 200                 205

Ser Val Val Thr Val Pro Ser Ser Ser Leu Gly Thr Gln Thr Tyr Ile
    210                 215                 220

Cys Asn Val Asn His Lys Pro Ser Asn Thr Lys Val Asp Lys Lys Val
225                 230                 235                 240

Glu Pro Lys Ser Cys Asp Lys Thr His Thr Cys Pro Pro Cys Pro Ala
                245                 250                 255

Pro Glu Leu Leu Gly Gly Pro Ser Val Phe Leu Phe Pro Pro Lys Pro
            260                 265                 270

Lys Asp Thr Leu Met Ile Ser Arg Thr Pro Glu Val Thr Cys Val Val
        275                 280                 285

Val Asp Val Ser His Glu Asp Pro Glu Val Lys Phe Asn Trp Tyr Val
```

```
            290                 295                 300
Asp Gly Val Glu Val His Asn Ala Lys Thr Lys Pro Arg Glu Gln
305                 310                 315                 320

Tyr Gln Ser Thr Tyr Arg Val Ser Val Leu Thr Val Leu His Gln
                325                 330                 335

Asp Trp Leu Asn Gly Lys Glu Tyr Lys Cys Lys Val Ser Asn Lys Ala
                340                 345                 350

Leu Pro Ala Pro Ile Glu Lys Thr Ile Ser Lys Ala Lys Gly Gln Pro
                355                 360                 365

Arg Glu Pro Gln Val Tyr Thr Leu Pro Pro Ser Arg Asp Glu Leu Thr
370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Pro Pro Val Leu Asp Ser Asp Gly Ser Phe Phe Leu Tyr
                420                 425                 430

Ser Lys Leu Thr Val Asp Lys Ser Arg Trp Gln Gln Gly Asn Val Phe
                435                 440                 445

Ser Cys Ser Val Met His Glu Ala Leu His Asn His Tyr Thr Gln Lys
                450                 455                 460

Ser Leu Ser Leu Ser Pro Gly Gly Gly Gly Ser Gly Gly Gly Gly
465                 470                 475                 480

Ser Gly Gly Gly Gly Ser Gly Gly Gly Gly Ser Gly Gly Gly Gly Ser
                485                 490                 495

Gly Gly Gly Gly Ser Gly Gly Gly Ser Gly Gly Gly Gly Ser Gly
                500                 505                 510

Gly Gly Gly Ser His Pro Ile Pro Asp Ser Ser Pro Leu Leu Gln Phe
                515                 520                 525

Gly Gly Gln Val Arg Gln Arg Tyr Leu Tyr Thr Asp Asp Ala Gln Gln
                530                 535                 540

Thr Glu Ala His Leu Glu Ile Arg Glu Asp Gly Thr Val Gly Gly Ala
545                 550                 555                 560

Ala Asp Gln Ser Pro Glu Ser Leu Leu Gln Leu Lys Ala Leu Lys Pro
                565                 570                 575

Gly Val Ile Gln Ile Leu Gly Val Lys Thr Ser Arg Phe Leu Cys Gln
                580                 585                 590

Arg Pro Asp Gly Ala Leu Tyr Gly Ser Leu His Phe Asp Pro Glu Ala
                595                 600                 605

Cys Ser Phe Arg Glu Leu Leu Leu Glu Asp Gly Tyr Asn Val Tyr Gln
610                 615                 620

Ser Glu Ala His Gly Leu Pro Leu His Leu Pro Gly Asn Lys Ser Pro
625                 630                 635                 640

His Arg Asp Pro Ala Pro Arg Gly Pro Ala Arg Phe Leu Pro Leu Pro
                645                 650                 655

Gly Leu Pro Pro Ala Pro Pro Glu Pro Pro Gly Ile Leu Ala Pro Gln
                660                 665                 670

Pro Pro Asp Val Gly Ser Ser Asp Pro Leu Ser Met Val Gly
                675                 680                 685

<210> SEQ ID NO 331
<211> LENGTH: 2106
<212> TYPE: DNA
<213> ORGANISM: Artificial Sequence
```

<220> FEATURE:
<223> OTHER INFORMATION: Description of Artificial Sequence: Synthetic polynucleotide

<400> SEQUENCE: 331

```
atggacatga gggtgcccgc tcagctcctg gggctcctgc tgctgtggct gagaggtgcg      60
cgctgtcagg tgcagttggt ggagtctggg ggaggcgtgg tccagcctgg gaggtccctg     120
agactctcct gtgcagcgtc tagattctcc ttcagtagat atggcatgca ctgggtccgc     180
caggctccag gcaaggggct ggagtgggtg gcagttatat ggtttgatgg aagaaatcaa     240
tactatgcag actccgtgaa ggggcgattc accatctcca gagacaattc caagaatacg     300
ctgtttctgc aaatgaacag cctgagagtc gaggacacgg ctgtgtatta ctgtgcgaga     360
gatcacccag tagttggtac gagctttgac tactggggcc agggaaccct ggtcaccgtc     420
tctagtgcct ccaccaaggg cccatcggtc ttccccctgg cacctcctc caagagcacc      480
tctgggggca gcggccct gggctgcctg gtcaaggact acttccccga accggtgacg       540
gtgtcgtgga actcaggcgc cctgaccagc ggcgtgcaca ccttcccggc tgtcctacag     600
tcctcaggac tctactccct cagcagcgtg gtgaccgtgc cctccagcag cttgggcacc     660
cagacctaca tctgcaacgt gaatcacaag cccagcaaca ccaaggtgga caagaaagtt     720
gagcccaaat cttgtgacaa aactcacaca tgcccaccgt gcccagcacc tgaactcctg     780
gggggaccgt cagtcttcct cttcccccca aaacccaagg acaccctcat gatctcccgg     840
acccctgagg tcacatgcgt ggtggtggac gtgagccacg aagaccctga ggtcaagttc     900
aactggtacg tggacggcgt ggaggtgcat aatgccaaga caaagccgcg ggaggagcag     960
taccagagca cgtaccgtgt ggtcagcgtc ctcaccgtcc tgcaccagga ctggctgaat    1020
ggcaaggagt acaagtgcaa ggtctccaac aaagccctcc cagcccccat cgagaaaacc    1080
atctccaaag ccaaagggca gccccgagaa ccacaggtgt acaccctgcc cccatcccgg    1140
gatgagctga ccaagaacca ggtcagcctg acctgcctgg tcaaaggctt ctatcccagc    1200
gacatcgccg tggagtggga gagcaatggg cagccggaga caactacaa gaccacgcct    1260
cccgtgctga ctccgacgg ctccttcttc ctctatagca agctcaccgt ggacaagagc     1320
aggtggcagc aggggaacgt cttctcatgc tccgtgatgc atgaggctct gcacaaccac    1380
tacacgcaga agagcctctc cctgtctccg ggtggaggcg gcggttccgg gggcggtgga    1440
tctggtggcg ggggaagcgg aggcggcggt tccggggggcg gtggatctgg tggcggggga    1500
agcggaggcg gcggttccgg gggcggtgga tctggtggcg ggggaagcgg aggcggcggt    1560
tccgggggcg gtggatccgg tggcggggga agccacccca tccctgactc cagtcctctc    1620
ctgcaattcg ggggccaagt ccggcagcgg tacctctaca cagatgatgc ccagcagaca    1680
gaagcccacc tggagatcag ggaggatggg acggtggggg gcgctgctga ccagagcccc    1740
gaaagtctcc tgcagctgaa agccttgaag ccgggagtta ttcaaatctt gggagtcaag    1800
acatccaggt tcctgtgcca gcggccagat ggggccctgt atggatcgct ccactttgac    1860
cctgaggcct gcagcttccg ggagctgctt cttgaggacg gatacaatgt ttaccagtcc    1920
gaagcccacg gcctcccgct gcacctgcca gggaacaagt ccccacaccg ggaccctgca    1980
ccccgaggac cagctcgctt cctgccacta ccaggcctgc ccccgcacc cccggagcca     2040
cccggaatcc tggccccca gcccccgat gtgggctcct cggaccctct gagcatggtg      2100
ggatga                                                                2106
```

```
<210> SEQ ID NO 332
<211> LENGTH: 701
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 332

Met Asp Met Arg Val Pro Ala Gln Leu Leu Gly Leu Leu Leu Leu Trp
1               5                   10                  15

Leu Arg Gly Ala Arg Cys Gln Val Gln Leu Val Glu Ser Gly Gly Gly
            20                  25                  30

Val Val Gln Pro Gly Arg Ser Leu Arg Leu Ser Cys Ala Ala Ser Arg
        35                  40                  45

Phe Ser Phe Ser Arg Tyr Gly Met His Trp Val Arg Gln Ala Pro Gly
    50                  55                  60

Lys Gly Leu Glu Trp Val Ala Val Ile Trp Phe Asp Gly Arg Asn Gln
65                  70                  75                  80

Tyr Tyr Ala Asp Ser Val Lys Gly Arg Phe Thr Ile Ser Arg Asp Asn
                85                  90                  95

Ser Lys Asn Thr Leu Phe Leu Gln Met Asn Ser Leu Arg Val Glu Asp
            100                 105                 110

Thr Ala Val Tyr Tyr Cys Ala Arg Asp His Pro Val Val Gly Thr Ser
        115                 120                 125

Phe Asp Tyr Trp Gly Gln Gly Thr Leu Val Thr Val Ser Ser Ala Ser
    130                 135                 140

Thr Lys Gly Pro Ser Val Phe Pro Leu Ala Pro Ser Ser Lys Ser Thr
145                 150                 155                 160

Ser Gly Gly Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
        195                 200                 205

Ser Val Val Thr Val Pro Ser Ser Leu Gly Thr Gln Thr Tyr Ile
    210                 215                 220

Cys Asn Val Asn His Lys Pro Ser Asn Thr Lys Val Asp Lys Lys Val
225                 230                 235                 240

Glu Pro Lys Ser Cys Asp Lys Thr His Thr Cys Pro Pro Cys Pro Ala
                245                 250                 255

Pro Glu Leu Leu Gly Gly Pro Ser Val Phe Leu Phe Pro Pro Lys Pro
            260                 265                 270

Lys Asp Thr Leu Met Ile Ser Arg Thr Pro Glu Val Thr Cys Val Val
        275                 280                 285

Val Asp Val Ser His Glu Asp Pro Glu Val Lys Phe Asn Trp Tyr Val
    290                 295                 300

Asp Gly Val Glu Val His Asn Ala Lys Thr Lys Pro Arg Glu Glu Gln
305                 310                 315                 320

Tyr Gln Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Ala
            340                 345                 350

Leu Pro Ala Pro Ile Glu Lys Thr Ile Ser Lys Ala Lys Gly Gln Pro
        355                 360                 365
```

Arg Glu Pro Gln Val Tyr Thr Leu Pro Pro Ser Arg Asp Glu Leu Thr
370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
            405                 410                 415

Lys Thr Thr Pro Pro Val Leu Asp Ser Asp Gly Ser Phe Phe Leu Tyr
        420                 425                 430

Ser Lys Leu Thr Val Asp Lys Ser Arg Trp Gln Gln Gly Asn Val Phe
    435                 440                 445

Ser Cys Ser Val Met His Glu Ala Leu His Asn His Tyr Thr Gln Lys
450                 455                 460

Ser Leu Ser Leu Ser Pro Gly Gly Gly Gly Ser Gly Gly Gly Gly
465                 470                 475                 480

Ser Gly Gly Gly Gly Ser Gly Gly Gly Ser Gly Gly Gly Gly Ser
            485                 490                 495

Gly Gly Gly Gly Ser Gly Gly Gly Ser Gly Gly Gly Gly Ser Gly
        500                 505                 510

Gly Gly Gly Ser Gly Gly Gly Ser Gly Gly Gly Gly Ser Gly Gly
    515                 520                 525

Gly Gly Ser His Pro Ile Pro Asp Ser Ser Pro Leu Leu Gln Phe Gly
530                 535                 540

Gly Gln Val Arg Gln Arg Tyr Leu Tyr Thr Asp Asp Ala Gln Gln Thr
545                 550                 555                 560

Glu Ala His Leu Glu Ile Arg Glu Asp Gly Thr Val Gly Gly Ala Ala
            565                 570                 575

Asp Gln Ser Pro Glu Ser Leu Leu Gln Leu Lys Ala Leu Lys Pro Gly
        580                 585                 590

Val Ile Gln Ile Leu Gly Val Lys Thr Ser Arg Phe Leu Cys Gln Arg
    595                 600                 605

Pro Asp Gly Ala Leu Tyr Gly Ser Leu His Phe Asp Pro Glu Ala Cys
610                 615                 620

Ser Phe Arg Glu Leu Leu Leu Glu Asp Gly Tyr Asn Val Tyr Gln Ser
625                 630                 635                 640

Glu Ala His Gly Leu Pro Leu His Leu Pro Gly Asn Lys Ser Pro His
            645                 650                 655

Arg Asp Pro Ala Pro Arg Gly Pro Ala Arg Phe Leu Pro Leu Pro Gly
        660                 665                 670

Leu Pro Pro Ala Pro Pro Glu Pro Pro Gly Ile Leu Ala Pro Gln Pro
    675                 680                 685

Pro Asp Val Gly Ser Ser Asp Pro Leu Ser Met Val Gly
690                 695                 700

<210> SEQ ID NO 333
<211> LENGTH: 2151
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 333
atggacatga gggtgcccgc tcagctcctg gggctcctgc tgctgtggct gagaggtgcg      60
cgctgtcagg tgcagttggt ggagtctggg ggaggcgtgg tccagcctgg gaggtccctg    120
agactctcct gtgcagcgtc tagattctcc ttcagtagat atggcatgca ctgggtccgc    180

```
caggctccag gcaaggggct ggagtgggtg gcagttatat ggtttgatgg aagaaatcaa    240
tactatgcag actccgtgaa ggggcgattc accatctcca gagacaattc caagaatacg    300
ctgtttctgc aaatgaacag cctgagagtc gaggacacgg ctgtgtatta ctgtgcgaga    360
gatcacccag tagttggtac gagctttgac tactggggcc agggaaccct ggtcaccgtc    420
tctagtgcct ccaccaaggg cccatcggtc ttccccctgg caccctcctc caagagcacc    480
tctgggggca gcgggccct gggctgcctg gtcaaggact acttccccga accggtgacg    540
gtgtcgtgga actcaggcgc cctgaccagc ggcgtgcaca ccttcccggc tgtcctacag    600
tcctcaggac tctactccct cagcagcgtg gtgaccgtgc cctccagcag cttgggcacc    660
cagacctaca tctgcaacgt gaatcacaag cccagcaaca ccaaggtgga caagaaagtt    720
gagcccaaat cttgtgacaa aactcacaca tgcccaccgt gcccagcacc tgaactcctg    780
ggggaccgt cagtcttcct cttccccca aaacccaagg acaccctcat gatctcccgg    840
accccctgagg tcacatgcgt ggtggtggac gtgagccacg aagaccctga ggtcaagttc    900
aactggtacg tggacggcgt ggaggtgcat aatgccaaga caaagccgcg ggaggagcag    960
taccagagca cgtaccgtgt ggtcagcgtc ctcaccgtcc tgcaccagga ctggctgaat   1020
ggcaaggagt acaagtgcaa ggtctccaac aaagccctcc cagcccccat cgagaaaacc   1080
atctccaaag ccaaagggca gccccgagaa ccacaggtgt acaccctgcc cccatcccgg   1140
gatgagctga ccaagaacca ggtcagcctg acctgcctgg tcaaaggctt ctatcccagc   1200
gacatcgccg tggagtggga gagcaatggg cagccggaga acaactacaa gaccacgcct   1260
cccgtgctgg actccgacgg ctccttcttc ctctatagca agctcaccgt ggacaagagc   1320
aggtggcagc aggggaacgt cttctcatgc tccgtgatgc atgaggctct gcacaaccac   1380
tacacgcaga agagcctctc cctgtctccg ggtggaggcg gcggttccgg gggcggtgga   1440
tctggtggcg ggggaagcgg aggcggcggt tccgggggcg gtggatctgg tggcggggga   1500
agcggaggcg gcggttccgg gggcggtgga tctggtggcg ggggaagcgg aggcggcggt   1560
tccgggggcg gtggatctgg tggcggggga agcggaggcg gcggttccgg gggcggtgga   1620
tccggtggcg ggggaagcca ccccatccct gactccagtc ctctcctgca attcgggggc   1680
caagtccggc agcggtacct ctacacagat gatgcccagc agacagaagc ccacctggag   1740
atcagggagg atgggacggt gggggggcgct gctgaccaga gccccgaaag tctcctgcag   1800
ctgaaagcct tgaagccggg agttattcaa atcttgggag tcaagacatc caggttcctg   1860
tgccagcggc cagatggggc cctgtatgga tcgctccact tgacccctga ggcctgcagc   1920
ttccgggagc tgcttcttga ggacggatac aatgtttacc agtccgaagc ccacggcctc   1980
ccgctgcacc tgccagggaa caagtcccca caccggggacc ctgcacccg aggaccagct   2040
cgcttcctgc cactaccagg cctgccccc gcacccccgg agccacccgg aatcctggcc   2100
ccccagcccc ccgatgtggg ctcctcggac cctctgagca tggtgggatg a            2151
```

<210> SEQ ID NO 334
<211> LENGTH: 716
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 334

Met Asp Met Arg Val Pro Ala Gln Leu Leu Gly Leu Leu Leu Leu Trp

-continued

```
  1               5                   10                  15
Leu Arg Gly Ala Arg Cys Gln Val Gln Leu Val Glu Ser Gly Gly
             20                  25                  30
Val Val Gln Pro Gly Arg Ser Leu Arg Leu Ser Cys Ala Ala Ser
             35                  40                  45
Phe Ser Phe Ser Arg Tyr Gly Met His Trp Val Arg Gln Ala Pro Gly
             50                  55                  60
Lys Gly Leu Glu Trp Val Ala Val Ile Trp Phe Asp Gly Arg Asn Gln
 65                  70                  75                  80
Tyr Tyr Ala Asp Ser Val Lys Gly Arg Phe Thr Ile Ser Arg Asp Asn
                 85                  90                  95
Ser Lys Asn Thr Leu Phe Leu Gln Met Asn Ser Leu Arg Val Glu Asp
                100                 105                 110
Thr Ala Val Tyr Tyr Cys Ala Arg Asp His Pro Val Val Gly Thr Ser
                115                 120                 125
Phe Asp Tyr Trp Gly Gln Gly Thr Leu Val Thr Val Ser Ser Ala Ser
            130                 135                 140
Thr Lys Gly Pro Ser Val Phe Pro Leu Ala Pro Ser Ser Lys Ser Thr
145                 150                 155                 160
Ser Gly Gly Thr Ala Ala Leu Gly Cys Leu Val Lys Asp Tyr Phe Pro
                165                 170                 175
Glu Pro Val Thr Val Ser Trp Asn Ser Gly Ala Leu Thr Ser Gly Val
            180                 185                 190
His Thr Phe Pro Ala Val Leu Gln Ser Ser Gly Leu Tyr Ser Leu Ser
            195                 200                 205
Ser Val Val Thr Val Pro Ser Ser Ser Leu Gly Thr Gln Thr Tyr Ile
210                 215                 220
Cys Asn Val Asn His Lys Pro Ser Asn Thr Lys Val Asp Lys Lys Val
225                 230                 235                 240
Glu Pro Lys Ser Cys Asp Lys Thr His Thr Cys Pro Pro Cys Pro Ala
                245                 250                 255
Pro Glu Leu Leu Gly Gly Pro Ser Val Phe Leu Phe Pro Pro Lys Pro
            260                 265                 270
Lys Asp Thr Leu Met Ile Ser Arg Thr Pro Glu Val Thr Cys Val Val
            275                 280                 285
Val Asp Val Ser His Glu Asp Pro Glu Val Lys Phe Asn Trp Tyr Val
            290                 295                 300
Asp Gly Val Glu Val His Asn Ala Lys Thr Lys Pro Arg Glu Glu Gln
305                 310                 315                 320
Tyr Gln Ser Thr Tyr Arg Val Val Ser Val Leu Thr Val Leu His Gln
                325                 330                 335
Asp Trp Leu Asn Gly Lys Glu Tyr Lys Cys Lys Val Ser Asn Lys Ala
            340                 345                 350
Leu Pro Ala Pro Ile Glu Lys Thr Ile Ser Lys Ala Lys Gly Gln Pro
            355                 360                 365
Arg Glu Pro Gln Val Tyr Thr Leu Pro Pro Ser Arg Asp Glu Leu Thr
            370                 375                 380
Lys Asn Gln Val Ser Leu Thr Cys Leu Val Lys Gly Phe Tyr Pro Ser
385                 390                 395                 400
Asp Ile Ala Val Glu Trp Glu Ser Asn Gly Gln Pro Glu Asn Asn Tyr
                405                 410                 415
Lys Thr Thr Pro Pro Val Leu Asp Ser Asp Gly Ser Phe Phe Leu Tyr
            420                 425                 430
```

```
Ser Lys Leu Thr Val Asp Lys Ser Arg Trp Gln Gln Gly Asn Val Phe
        435                 440                 445

Ser Cys Ser Val Met His Glu Ala Leu His Asn His Tyr Thr Gln Lys
    450                 455                 460

Ser Leu Ser Leu Ser Pro Gly Gly Gly Gly Ser Gly Gly Gly Gly
465             470                 475                 480

Ser Gly Gly Gly Gly Ser Gly Gly Gly Gly Ser Gly Gly Gly Gly Ser
                485                 490                 495

Gly Gly Gly Gly Ser Gly Gly Gly Ser Gly Gly Gly Ser Gly
                500                 505                 510

Gly Gly Gly Ser Gly Gly Gly Ser Gly Gly Gly Ser Gly Gly
            515                 520                 525

Gly Gly Ser Gly Gly Gly Ser Gly Gly Gly Ser Gly Gly Gly
        530                 535                 540

Gly Ser His Pro Ile Pro Asp Ser Ser Pro Leu Leu Gln Phe Gly Gly
545                 550                 555                 560

Gln Val Arg Gln Arg Tyr Leu Tyr Thr Asp Ala Gln Thr Glu
                565                 570                 575

Ala His Leu Glu Ile Arg Glu Asp Gly Thr Val Gly Gly Ala Ala Asp
            580                 585                 590

Gln Ser Pro Glu Ser Leu Leu Gln Leu Lys Ala Leu Lys Pro Gly Val
        595                 600                 605

Ile Gln Ile Leu Gly Val Lys Thr Ser Arg Phe Leu Cys Gln Arg Pro
610                 615                 620

Asp Gly Ala Leu Tyr Gly Ser Leu His Phe Asp Pro Glu Ala Cys Ser
625                 630                 635                 640

Phe Arg Glu Leu Leu Leu Glu Asp Gly Tyr Asn Val Tyr Gln Ser Glu
                645                 650                 655

Ala His Gly Leu Pro Leu His Leu Pro Gly Asn Lys Ser Pro His Arg
            660                 665                 670

Asp Pro Ala Pro Arg Gly Pro Ala Arg Phe Leu Pro Leu Pro Gly Leu
        675                 680                 685

Pro Pro Ala Pro Pro Glu Pro Pro Gly Ile Leu Ala Pro Gln Pro Pro
    690                 695                 700

Asp Val Gly Ser Ser Asp Pro Leu Ser Met Val Gly
705                 710                 715

<210> SEQ ID NO 335
<211> LENGTH: 240
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(15)
<223> OTHER INFORMATION: This region may encompass 1-15 repeating 'Gly'
      residues
<220> FEATURE:
<221> NAME/KEY: MOD_RES
<222> LOCATION: (17)..(31)
<223> OTHER INFORMATION: This region may encompass 1-15 repeating 'Gly'
      residues
<220> FEATURE:
<221> NAME/KEY: MOD_RES
<222> LOCATION: (33)..(47)
<223> OTHER INFORMATION: This region may encompass 1-15 repeating 'Gly'
      residues
<220> FEATURE:
```

```
<221> NAME/KEY: MOD_RES
<222> LOCATION: (49)..(63)
<223> OTHER INFORMATION: This region may encompass 1-15 repeating 'Gly'
      residues
<220> FEATURE:
<221> NAME/KEY: MOD_RES
<222> LOCATION: (65)..(79)
<223> OTHER INFORMATION: This region may encompass 1-15 repeating 'Gly'
      residues
<220> FEATURE:
<221> NAME/KEY: MOD_RES
<222> LOCATION: (81)..(95)
<223> OTHER INFORMATION: This region may encompass 1-15 repeating 'Gly'
      residues
<220> FEATURE:
<221> NAME/KEY: MOD_RES
<222> LOCATION: (97)..(111)
<223> OTHER INFORMATION: This region may encompass 1-15 repeating 'Gly'
      residues
<220> FEATURE:
<221> NAME/KEY: MOD_RES
<222> LOCATION: (113)..(127)
<223> OTHER INFORMATION: This region may encompass 1-15 repeating 'Gly'
      residues
<220> FEATURE:
<221> NAME/KEY: MOD_RES
<222> LOCATION: (129)..(143)
<223> OTHER INFORMATION: This region may encompass 1-15 repeating 'Gly'
      residues
<220> FEATURE:
<221> NAME/KEY: MOD_RES
<222> LOCATION: (145)..(159)
<223> OTHER INFORMATION: This region may encompass 1-15 repeating 'Gly'
      residues
<220> FEATURE:
<221> NAME/KEY: MOD_RES
<222> LOCATION: (161)..(175)
<223> OTHER INFORMATION: This region may encompass 1-15 repeating 'Gly'
      residues
<220> FEATURE:
<221> NAME/KEY: MOD_RES
<222> LOCATION: (177)..(191)
<223> OTHER INFORMATION: This region may encompass 1-15 repeating 'Gly'
      residues
<220> FEATURE:
<221> NAME/KEY: MOD_RES
<222> LOCATION: (193)..(207)
<223> OTHER INFORMATION: This region may encompass 1-15 repeating 'Gly'
      residues
<220> FEATURE:
<221> NAME/KEY: MOD_RES
<222> LOCATION: (209)..(223)
<223> OTHER INFORMATION: This region may encompass 1-15 repeating 'Gly'
      residues
<220> FEATURE:
<221> NAME/KEY: MOD_RES
<222> LOCATION: (225)..(239)
<223> OTHER INFORMATION: This region may encompass 1-15 repeating 'Gly'
      residues
<220> FEATURE:
<221> NAME/KEY: misc_feature
<222> LOCATION: (1)..(240)
<223> OTHER INFORMATION: This sequence may encompass 1-15 repeating
      'Gly-Gly-Gly-Gly-Gly-Gly-Gly-Gly-Gly-Gly-Gly-Gly-Gly-Gly-Ser'
      units

<400> SEQUENCE: 335

Gly Gly Gly Gly Gly Gly Gly Gly Gly Gly Gly Gly Gly Gly Ser
1               5                   10                  15

Gly Gly Gly Gly Gly Gly Gly Gly Gly Gly Gly Gly Gly Gly Ser
            20                  25                  30

Gly Gly Gly Gly Gly Gly Gly Gly Gly Gly Gly Gly Gly Gly Ser
        35                  40                  45

Gly Gly Gly Gly Gly Gly Gly Gly Gly Gly Gly Gly Gly Gly Ser
    50                  55                  60
```

```
Gly Gly Gly Gly Gly Gly Gly Gly Gly Gly Gly Gly Gly Gly Gly Ser
 65                  70                  75                  80

Gly Gly Gly Gly Gly Gly Gly Gly Gly Gly Gly Gly Gly Gly Gly Ser
                 85                  90                  95

Gly Gly Gly Gly Gly Gly Gly Gly Gly Gly Gly Gly Gly Gly Gly Ser
            100                 105                 110

Gly Gly Gly Gly Gly Gly Gly Gly Gly Gly Gly Gly Gly Gly Gly Ser
        115                 120                 125

Gly Gly Gly Gly Gly Gly Gly Gly Gly Gly Gly Gly Gly Gly Gly Ser
    130                 135                 140

Gly Gly Gly Gly Gly Gly Gly Gly Gly Gly Gly Gly Gly Gly Gly Ser
145                 150                 155                 160

Gly Gly Gly Gly Gly Gly Gly Gly Gly Gly Gly Gly Gly Gly Gly Ser
                165                 170                 175

Gly Gly Gly Gly Gly Gly Gly Gly Gly Gly Gly Gly Gly Gly Gly Ser
            180                 185                 190

Gly Gly Gly Gly Gly Gly Gly Gly Gly Gly Gly Gly Gly Gly Gly Ser
        195                 200                 205

Gly Gly Gly Gly Gly Gly Gly Gly Gly Gly Gly Gly Gly Gly Gly Ser
    210                 215                 220

Gly Gly Gly Gly Gly Gly Gly Gly Gly Gly Gly Gly Gly Gly Gly Ser
225                 230                 235                 240

<210> SEQ ID NO 336
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 336

Gly Gly Gly Gly Ser Gly Gly Gly Gly Ser Gly Gly Gly Gly Ser
1               5                   10                  15

<210> SEQ ID NO 337
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 337

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30

<210> SEQ ID NO 338
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 338

Gly Gly Gly Gly Ser Gly Gly Gly Gly Ser Gly Gly Gly Gly Ser Gly
1               5                   10                  15
```

```
Gly Gly Gly Ser Gly Gly Gly Ser Gly Gly Gly Ser Gly Gly
        20                  25                  30

Gly Gly Ser Gly Gly Gly Ser Gly Gly Gly Ser
        35                  40                  45

<210> SEQ ID NO 339
<211> LENGTH: 60
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 339

Gly Gly Gly Gly Ser Gly Gly Gly Ser Gly Gly Gly Gly Ser Gly
1               5                   10                  15

Gly Gly Gly Ser Gly Gly Gly Ser Gly Gly Gly Ser Gly Gly
        20                  25                  30

Gly Gly Ser Gly Gly Gly Gly Ser Gly Gly Gly Ser Gly Gly
        35                  40                  45

Gly Ser Gly Gly Gly Gly Ser Gly Gly Gly Ser
        50                  55                  60

<210> SEQ ID NO 340
<211> LENGTH: 75
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 340

Gly Gly Gly Gly Ser Gly Gly Gly Gly Ser Gly Gly Gly Ser Gly
1               5                   10                  15

Gly Gly Gly Ser Gly Gly Gly Gly Ser Gly Gly Gly Ser Gly Gly
        20                  25                  30

Gly Gly Ser Gly Gly Gly Gly Ser Gly Gly Gly Ser Gly Gly Gly
        35                  40                  45

Gly Ser Gly Gly Gly Gly Ser Gly Gly Gly Ser Gly Gly Gly Gly
        50                  55                  60

Ser Gly Gly Gly Gly Ser Gly Gly Gly Ser
65                  70                  75

<210> SEQ ID NO 341
<211> LENGTH: 181
<212> TYPE: PRT
<213> ORGANISM: Homo sapiens

<400> SEQUENCE: 341

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Thr Glu Ala His
        20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
        50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
```

```
                    85                  90                  95

Glu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Pro Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Pro Ser Tyr Ala Ser
            180

<210> SEQ ID NO 342
<211> LENGTH: 169
<212> TYPE: PRT
<213> ORGANISM: Homo sapiens

<400> SEQUENCE: 342

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Pro Pro Glu Pro Pro Gly Ile Leu Ala Pro Gln Pro Pro Asp Val
145                 150                 155                 160

Gly Ser Ser Asp Pro Leu Ser Met Val
                165

<210> SEQ ID NO 343
<211> LENGTH: 170
<212> TYPE: PRT
<213> ORGANISM: Homo sapiens

<400> SEQUENCE: 343

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
```

```
                   50                  55                  60
Ile Leu Gly Val Lys Thr Ser Arg Phe Leu Cys Gln Arg Pro Asp Gly
 65                  70                  75                  80

Ala Leu Tyr Gly Ser Leu His Phe Asp Pro Glu Ala Cys Ser Phe Arg
                 85                  90                  95

Glu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Pro Pro Glu Pro Pro Gly Ile Leu Ala Pro Gln Pro Pro Asp Val
145                 150                 155                 160

Gly Ser Ser Asp Pro Leu Ser Met Val Gly
                165                 170

<210> SEQ ID NO 344
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(10)
<223> OTHER INFORMATION: This sequence may encompass 1-2 repeating
      'Gly-Gly-Gly-Gly-Ser' units

<400> SEQUENCE: 344

Gly Gly Gly Gly Ser Gly Gly Gly Gly Ser
1               5                  10
```